United States Patent
Kulyk et al.

(10) Patent No.: US 12,145,948 B2
(45) Date of Patent: Nov. 19, 2024

(54) COMPOUNDS AND METHODS FOR MODULATING HER2

(71) Applicant: IAMBIC THERAPEUTICS, INC., Los Angeles, CA (US)

(72) Inventors: Svitlana Kulyk, San Diego, CA (US); Shawn Wright, San Diego, CA (US); Joseph Dennis, San Diego, CA (US); Wallace Derricotte, Atlanta, GA (US); Iriny Botrous, San Diego, CA (US); Laurent Gomez, San Diego, CA (US)

(73) Assignee: IAMBIC THERAPEUTICS, INC., Los Angeles, CA (US)

( * ) Notice: Subject to any disclaimer, the term of this patent is extended or adjusted under 35 U.S.C. 154(b) by 0 days.

(21) Appl. No.: 18/526,935

(22) Filed: Dec. 1, 2023

(65) Prior Publication Data

US 2024/0182494 A1 Jun. 6, 2024

Related U.S. Application Data

(63) Continuation of application No. PCT/US2023/072623, filed on Aug. 22, 2023.

(60) Provisional application No. 63/507,357, filed on Jun. 9, 2023, provisional application No. 63/373,172, filed on Aug. 22, 2022, provisional application No. 63/399,989, filed on Aug. 22, 2022.

(51) Int. Cl.
*C07D 519/00* (2006.01)
*A61P 35/00* (2006.01)

(52) U.S. Cl.
CPC ............ *C07D 519/00* (2013.01); *A61P 35/00* (2018.01)

(58) Field of Classification Search
CPC .................................................. C07D 519/00
See application file for complete search history.

(56) References Cited

U.S. PATENT DOCUMENTS

| | | | |
|---|---|---|---|
| 4,150,949 | A | 4/1979 | Smith |
| 4,568,649 | A | 2/1986 | Bertoglio-Matte |
| 4,626,513 | A | 12/1986 | Burton et al. |
| 2004/0077595 | A1 | 4/2004 | Cheng et al. |
| 2011/0039838 | A1* | 2/2011 | Fink .................... A61P 17/06 514/233.2 |

FOREIGN PATENT DOCUMENTS

| | | |
|---|---|---|
| EP | 0154734 A1 | 9/1985 |
| EP | 3792263 A1 | 3/2021 |
| WO | WO-03091229 A1 | 11/2003 |
| WO | WO-2005065266 A2 | 7/2005 |
| WO | WO-2006007468 A1 | 1/2006 |
| WO | WO-2006069395 A2 | 6/2006 |
| WO | WO-2008057402 A2 | 5/2008 |
| WO | WO-2009117157 A1 | 9/2009 |
| WO | WO-2019214651 A1 | 11/2019 |
| WO | WO-2021088987 A1 | 5/2021 |
| WO | WO-2021156178 A1 | 8/2021 |
| WO | WO-2021156180 A1 | 8/2021 |
| WO | WO-2021213800 A1 | 10/2021 |

OTHER PUBLICATIONS

Awale et al.: 3D-QSAR CoMFA analysis of C5 substituted pyrrolotriazines as HER2 (erbB2) inhibitors. Journal of Molecular Graphics and Modelling. 26:1169-1178 (2008).
Bagshawe, Kenneth D.: Antibody-directed enzyme prodrug therapy: A review. Drug Development Research. 34(2):220-230 (1995).
Batrakova et al.: Using exosomes, naturally-equipped nanocarriers, for drug delivery. J Control Release. 219:396-405 (2015).
Berge et al.: Pharmaceutical Salts. J. Pharmaceutical Sciences 66(1):1-19 (1977).
Bertolini et al. A New Rational Hypothesis for the Pharmacophore of the Active Metabolite of Leflunomide, a Potent Immunosuppressive Drug. J Med Chem 40(13):2011-2016 (Jun. 20, 1997).
Checovich et al.: Fluorescence polarization—a new tool for cell and molecular biology. Nature 375:254-256 (1995).
Co-pending U.S. Application No. 202318453798, inventors Kulyk; Svitlana et al., filed on Aug. 22, 2023.
Dandliker et al.: Equilibrium and Kinetic Inhibition Assays Based upon Fluorescence Polarization. Methods in Enzymology. 74:3-28 (1981).
Hanselman et al.: A cDNA-dependent scintillation proximity assay for quantifying apolipoprotein A-1. Journal of Lipid Research. 38:2365-2373 (1997).

(Continued)

*Primary Examiner* — Rei Tsang Shiao
(74) *Attorney, Agent, or Firm* — Wilson Sonsini Goodrich & Rosati

(57) ABSTRACT

Disclosed are compounds of Formula (I):

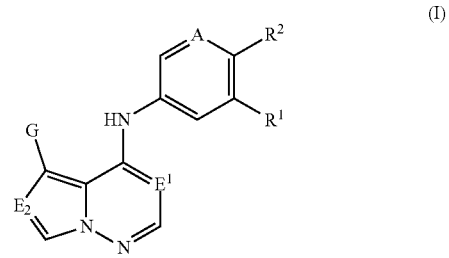

or a pharmaceutically acceptable salt, a tautomer, a stereoisomer, or a deuterated analog thereof, wherein $R^1$, $R^2$, A, $E^1$, $E^2$, and G are as described in any of the embodiments described in this disclosure; compositions thereof; and uses thereof.

27 Claims, No Drawings

(56) References Cited

OTHER PUBLICATIONS

Heim, et al., Engineering Green Fluorescent Protein for Improved Brightness, Longer Wavelengths and Fluorescence Resonance Energy Transfer. Current Biology 6(2):178-182 (1996).

Kahl et al.: A Multiple-Approach Scintillation Proximity Assay to Measure the Association between Ras and Raf. Anal. Biochem. 243:282-283 (1996).

Mitra et al.: Fluorescence resonance energy transfer between blue-emitting and red-shifted excitation derivatives of the green fluorescent protein. Gene 173(1):13-17 (1996).

Nichols et al.: Development of a Scintillation Proximity Assay for Peroxisome Proliferator-Activated Receptor γ Ligand Binding Domain. Anal. Biochem. 257:112-119 (1998).

Parker et al., Development of high throughput screening assays using fluorescence polarization: nuclear receptor-ligand-binding and kinase/phosphatase assays, J Biomol Screen, 5(2): 77-88 (2000).

PCT/US2023/072623 International Search Report and Written Opinion Oct. 31, 2023.

Selvin, Paul R.: Fluorescence Resonance Energy Transfer: Meth. in Enzymol. 246:300-345 (1995).

Shan et al. Prodrug Strategies Based on Intramolecular Cyclization Reactions. J Pharm Sci 86(7):765-767 (Jul. 1997).

Undenfriend et al.: Scintillation Proximity Assay: A Sensitive and Continuous Isotopic Method for Monitoring Ligand/Receptor and Antigen/Antibody Interactions. Anal. Biochem. 161:494-500 (1987).

Voronov et al.: Fluorescence Polarization Studies of Different Forms of Angiotensin-Converting Enzyme. Biochemistry (Moscow) 66:788-794 (2001).

Zalloum et al.: Discovery of new human epidermal growth factor receptor-2 (HER2) inhibitors for potential use as anticancer agents via ligand-based pharmacophore modeling. Journal of Molecular Graphics and Modeling. 61:61-84 (2015).

* cited by examiner

COMPOUNDS AND METHODS FOR MODULATING HER2

CROSS-REFERENCE TO RELATED APPLICATIONS

This application is a Continuation of International Application No. PCT/US2023/072623 filed on Aug. 22, 2023, which claims the benefit of U.S. Provisional Patent Application No. 63/373,172 filed on Aug. 22, 2022, U.S. Provisional Patent Application No. 63/507,357 filed on Jun. 9, 2023, and U.S. Provisional Patent Application No. 63/399,989 filed on Aug. 22, 2022, which are incorporated by reference herein in their entirety.

FIELD

The present disclosure relates to compounds useful for modulating Her2, compositions thereof, and uses thereof.

BACKGROUND

Her2 (also referred to herein as HER2) belongs to the epidermal growth factor receptor (EGFR) family. This family is composed of four HER receptors: human epidermal growth factor receptor 1 (Her1) (also termed EGFR), Her2, human epidermal growth factor receptor 3 (Her3), and human epidermal growth factor receptor 4 (Her4). The Her2 receptor is a 185 kDa transmembrane protein that is encoded by the Her2 (also known as erb-b2 receptor tyrosine kinase 2 [ERBB2]) gene. Her2 is normally expressed on cell membranes of epithelial cells of several organs like the lungs, breast and the skin, as well as gastrointestinal, reproductive, and urinary tract. Her2 in normal cells is expressed at low levels, whereas in Her2-positive cancer cells, there is an increase in the number of Her2 gene copies (gene amplification) and Her2 receptors with up to 40-to-100-fold increase in protein overexpression. The increased amount of cell surface Her2 receptors associated with Her2 overexpression leads to increased receptor-receptor interactions, provoking a sustained tyrosine phosphorylation of the kinase domain and therefore constant activation of the signaling pathways.

Tumors driven by Her2 mutations or Her2 wild type over expression may benefit from tyrosine kinase inhibitors that target Her2. HER2+ mutations in NSCLC predominantly affect the tyrosine kinase domain of Her2 and cluster in exon 20 of the ERBB2 gene. About 4% of lung cancer patients are estimated to carry activating mutations in Her2 exon 20. Clinically approved ERBB targeting tyrosine kinase inhibitors are not efficacious in these patients, as they are limited by EGFR wild type-mediated dose limiting toxicity. Afatinib and other pan-ERBB blockers have shown limited efficacy in HER2 exon 20 mutated NSCLC patients, mainly due to limitations in reaching an efficacious dose. In particular, EGFR wild type mediated toxicity limits efficacious dosing. Pan-ERBB inhibitors of mutant Her2 exon 20 include allitinib, ibrutinib, neratinib, poziotinib and pyrotinib all are limited by EGFR wild type mediated toxicity limits.

Current irreversible Her2 tyrosine kinase inhibitors in clinical development include Poziotinib and Pyrotinib that both lack selectivity for Her2 mutated tumors vs. EGFR and have adverse event profiles consistent with EGFR-related toxicities. Specifically, patients receiving poziotinib experienced Grade 3 skin rash, among other Grade 3 adverse events, that was difficult to tolerate, leading to significant dose reductions. In addition, patients receiving pyrotinib also experienced various Grade 3 adverse events including an increase of 7 or more stools a day which usually requires hospitalization.

Furthermore, Her2 YVMA insertion mutations make up about 65% of the insertion mutations in NSCLC. To date, there is currently no approved tyrosine kinase approved for the treatment of non-small cell lung cancer with an Her2 mutation.

There is therefore an unmet medical need for novel compounds that target Her2, and there is even a higher degree of urgency for novel Her2 inhibitors that are more potent against wild type Her2 and/or YVMA Her2 exon20 insertion mutations over EGFR wild type to overcome EGFR wild type mediated dose limiting toxicity.

SUMMARY

This disclosure provides novel compounds that modulate wild-type and/or mutant Her2 such as YVMA Her2 exon20 insertion mutations. In another embodiment, this disclosure provides novel compounds that inhibit wild-type and/or Her2 by irreversibly irrevbinding to the tyrosine kinase domain. In another embodiment, the compounds of this disclosure selectively inhibit wild-type Her2 and/or mutant Her2 over wild-type EGFR and therefore have less EGFR-related toxicity liabilities. In another embodiment, the compounds of this disclosure selectively inhibit YVMA Her2 exon20 insertion mutations over wild type EGFR and therefore have less EGFR-related toxicity liabilities.

One embodiment of the disclosure relates to novel compounds, as described in any of the embodiments herein, or a pharmaceutically acceptable salt, a tautomer, a stereoisomer or a deuterated analog thereof, wherein these novel compounds can modulate Her2 (which is the same as HER2 for purposes of this disclosure). Another embodiment of the disclosure relates to novel compounds, as described in any of the embodiments herein, or a pharmaceutically acceptable salt, a tautomer, a stereoisomer or a deuterated analog thereof, wherein these novel compounds can modulate Her2 with mutations such as the YVMA Her2 exon20 insertion mutations (also referred to herein as Her2 YVMA insertion mutations). Another embodiment of the disclosure relates to novel compounds, as described in any of the embodiments herein, or a pharmaceutically acceptable salt, a tautomer, a stereoisomer or a deuterated analog thereof, wherein these novel compounds can selectively inhibit wild-type Her2 and/or mutant Her2 (such as Her2 YVMA insertion mutations) over wild-type EGFR. Another embodiment of this disclosure relates to a compound of Formula (I):

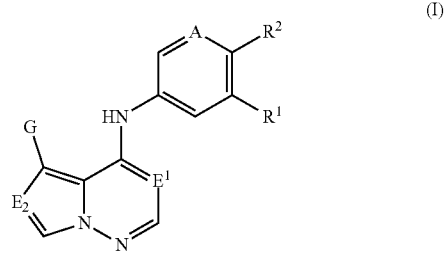

or a pharmaceutically acceptable salt, a tautomer, a stereoisomer, or a deuterated analog thereof, wherein $R^1$, $R^2$, A, $E^1$, $E^2$ and G are as described in any of the embodiments (including any of the sub embodiments thereof) in this disclosure.

Other embodiments and sub-embodiments of Formula (I) are further described herein in this disclosure.

Another embodiment of the disclosure relates to a pharmaceutical composition comprising a compound according to Formula (I) or any embodiment and sub-embodiment of Formula (I) described herein in this disclosure, or a pharmaceutically acceptable salt, a tautomer, a stereoisomer or a deuterated analog of any of these compounds, and a pharmaceutically acceptable carrier or excipient.

Another embodiment of the disclosure relates to a pharmaceutical composition comprising a compound according to Formula (I), or any embodiment of Formula (I) described herein in this disclosure, or a pharmaceutically acceptable salt, a tautomer, a stereoisomer or a deuterated analog of any of these compounds, and another therapeutic agent.

Another embodiment of this disclosure relates to a method for treating a subject with a disease or condition mediated, at least in part, Her2 (e.g., Her2 wild-type tumors, Her2 mutated tumors including Her2 with YVMA insertion mutations), said method comprising administering to the subject an effective amount of a compound according to Formula (I), or any embodiment of Formula (I) described in this disclosure, or a pharmaceutically acceptable salt, a tautomer, a stereoisomer or a deuterated analog of any of these compounds, or a pharmaceutical composition of any of the compounds as described in this disclosure. Also provided herein is the use of a compound according to Formula (I), or any embodiment of Formula (I) described in this disclosure, or a pharmaceutically acceptable salt, a tautomer, a stereoisomer or a deuterated analog of any of these compounds, or a pharmaceutical composition of any of the compounds as described in this disclosure, for the treatment of a disease or condition mediated by Her2.

Additional embodiments are further described in the Detailed Description of this disclosure.

DETAILED DESCRIPTION

I. Definitions

As used herein the following definitions apply unless clearly indicated otherwise:

It is noted here that as used herein and the appended claims, the singular forms "a," "an," and "the" include plural reference unless the context clearly dictates otherwise.

Unless a point of attachment indicates otherwise, the chemical moieties listed in the definitions of the variables of Formula (I) of this disclosure, and all the embodiments thereof, are to be read from left to right, wherein the right-hand side is directly attached to the parent structure as defined. However, if a point of attachment (e.g., a dash "-") is shown on the left-hand side of the chemical moiety (e.g., $-C_1-C(alkyl-N(R^6)_2)$, then the left-hand side of this chemical moiety is attached directly to the parent moiety as defined.

It is assumed that when considering generic descriptions of compounds described herein for the purpose of constructing a compound, such construction results in the creation of a stable structure. That is, one of ordinary skill in the art would recognize that, theoretically, some constructs would not normally be considered as stable compounds (that is, sterically practical and/or synthetically feasible).

"Alkyl," by itself, or as part of another substituent, means, unless otherwise stated, a straight or branched chain hydrocarbon, having the number of carbon atoms designated (i.e. $C_1-C_6$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, heterocycloalkylalkyl, heteroarylalkyl, etc.), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_1-C_6$alkyl refers to a straight or branched hydrocarbon having 1, 2, 3, 4, 5 or 6 carbon atoms and includes, but is not limited to, $-CH_3$, $C_2$alkyl, $C_3$alkyl, $C_4$alkyl, $C_5$alkyl, $C_6$alkyl, $C_1-C_2$alkyl, $C_2$alkyl, $C_3$alkyl, $C_1-C_3$alkyl, $C_1-C_4$alkyl, $C_1-C_5$alkyl, $C_1-C_6$alkyl, $C_2-C_3$alkyl, $C_2-C_4$alkyl, $C_2-C_5$alkyl, $C_2-C_6$alkyl, $C_3-C_4$alkyl, $C_3-C_5$alkyl, $C_3-C_6$alkyl, $C_4-C_5$alkyl, $C_4-C_6$alkyl, $C_5-C_6$alkyl and $C_6$alkyl. It is understood that substitutions are attached at any available atom to produce a stable compound.

"Alkylene" by itself or as part of another substituent means a linear or branched saturated divalent hydrocarbon moiety derived from an alkane having the number of carbon atoms indicated in the prefix. For example, (i.e., $C_1-C_6$ means one to six carbons; $C_1-C_6$alkylene is meant to include methylene, ethylene, propylene, 2-methylpropylene, pentylene, hexylene and the like). $C_1-C_4$ alkylene includes methylene $-CH_2-$, ethylene $-CH_2CH_2-$, propylene $-CH_2CH_2CH_2-$, and isopropylene $-CH(CH_3)CH_2-$, $-CH_2CH(CH_3)-$, $-CH_2-(CH_2)_2CH_2-$, $-CH_2-CH(CH_3)CH_2-$, $-CH_2-C(CH_3)_2-CH_2-CH_2CH(CH_3)-$. Typically, an alkyl (or alkylene) group will have from 1 to 24 carbon atoms, with those groups having 10 or fewer, 8 or fewer, or 6 or fewer carbon atoms. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms, or 4 or fewer main chain carbon atoms, or 3 or fewer main chain carbon atoms, or 2 or fewer main chain carbon atoms, or 1 carbon atom.

"Alkoxy" or "alkoxyl" refers to a $-O$-alkyl group, where alkyl is as defined herein. By way of example, "$C_1-C_6$alkoxy" refers to a $-O-C_1-C_6$alkyl group, where alkyl is as defined herein. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Amino" or "amine" denotes the group $NH_2$.

"Aryl" by itself, or as part of another substituent, unless otherwise stated, refers to a monocyclic, bicyclic or polycyclic polyunsaturated aromatic hydrocarbon radical containing 6 to 14 ring carbon atoms, which can be a single ring or multiple rings (up to three rings) which are fused together or linked covalently. Aryl, however, does not encompass or overlap in any way with heteroaryl defined below. If one or more aryl rings are fused with a heteroaryl ring, the resulting ring system is heteroaryl. Non-limiting examples of unsubstituted aryl groups include phenyl, 1-naphthyl and 2-naphthyl. The term "arylene" refers to a divalent aryl, wherein the aryl is as defined herein.

"Cycloalkyl" or "Carbocycle" or "Carbocyclic" by itself, or as part of another substituent, unless otherwise stated, refers to saturated or partially unsaturated, nonaromatic monocyclic ring, bridged rings, spiro rings, fused rings (e.g., bicyclic or tricyclic carbon ring systems), or cubane, having the number of carbon atoms indicated in the prefix or if unspecified having 3-6, also 4-6, and also 5-6 ring members per ring, such as cyclopropyl, cyclopentyl, cyclohexyl, where one or two ring carbon atoms may optionally be replaced by a carbonyl. Further, the term cycloalkyl is intended to encompass ring systems fused to an aromatic ring (e.g., of an aryl or heteroaryl), regardless of the point of attachment to the remainder of the molecule. Cycloalkyl refers to hydrocarbon rings having the indicated number of ring atoms (e.g., $C_3$-$C_6$ cycloalkyl and 3-6 membered cycloalkyl both mean three to six ring carbon atoms). The term "cycloalkenyl" refers to a cycloalkyl having at least one unit of unsaturation. A substituent of a cycloalkyl or cycloalkenyl may be at the point of attachment of the cycloalkyl or cycloalkenyl group, forming a quaternary center.

"Halogen" or "halo" refers to all halogens, that is, chloro (Cl), fluoro (F), bromo (Br), or iodo (I).

"Heteroatom" is meant to include oxygen (O), nitrogen (N), and sulfur (S).

"Heteroaryl" refers to a monocyclic or bicyclic aromatic ring radical containing 5-9 ring atoms (also referred to in this disclosure as a 5-9 membered heteroaryl, including monocyclic aromatic ring radicals containing 5 or 6 ring atoms (also referred to in this disclosure as a 5-6 membered heteroaryl), containing one or more, 14, 13, or 12, heteroatoms independently selected from the group consisting of O, S, and N. Any aromatic ring or ring system containing at least one heteroatom is a heteroaryl regardless of the point of attachment (i.e., through any one of the fused rings). Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalazinyl, benzotriazinyl, benzimidazolyl, benzopyrazolyl, benzotriazolyl, benzisoxazolyl, isobenzofuryl, isoindolyl, indolizinyl, benzotriazinyl, thienopyridyl, thienopyrimidinyl, pyrazolopyrimidinyl, imidazopyridines, benzothiaxolyl, benzothienyl, quinolyl, isoquinolyl, indazolyl, pteridinyl, thiadiazolyl, triazolopyridinyl, imidazotriazinyl, and pyrrolotriazinyl. "Nitrogen containing heteroaryl" refers to heteroaryl wherein at least one of the ring heteroatoms is N.

The term "heteroarylalkyl" refers to an alkyl group substituted with a heteroaryl group, where both terms are as defined herein.

The terms "heterocycle" or "heterocyclic ring" are interchangeable and comprise heterocycloalkyl rings, heterocycloalkenyl rings, and heteroaryl rings as they are defined herein. A heterocycle may be a saturated, unsaturated, or aromatic ring comprising one or more heteroatoms. Exemplary heteroatoms include N, O, P, and S atoms. Heterocycles include 3- to 10-membered monocyclic rings, 6- to 12-membered bicyclic rings, 5- to 12-membered spiro bicycles, and 5- to 12-membered bridged rings. A bicyclic heterocycle includes any combination of saturated, unsaturated and aromatic bicyclic rings, as valence permits.

The term "spirocyclic" or "spirocyclic group" refers to a group with two or more rings wherein two rings are joined together by a single atom. A spirocyclic group may comprise carbocycles and heterocycles. In some embodiments, spirocyclic groups may include 6- to 12-members between 2 or more rings. In some embodiments spirocyclic groups may include 6-12 atoms (i.e. $C_{6-12}$ spirocyclic cycloalkyl and 6-12 membered spirocyclic heterocycloalkyl) In some embodiments, spirocyclic groups may include 7-11 atoms (i.e. 7-11 membered spirocyclic cycloalkyl or 7-11 membered spirocyclic heterocycloalkyl) In some embodiments spirocyclic groups may be bicyclic or tricyclic. Non-limiting examples of spirocyclic groups include: spiro[2,2]pentyl, spiro[3,2]hexyl, spiro[3,3,heptyl], spiro[4,3]octyl, spiro[4,2] heptyl, spiro[5,5,]undecanyl, spiro[6,3]decanyl, spiro[6,5] dodecanyl, azaspiro[3.3]heptanyl, 5-azaspiro[2.4]heptanyl, diazaspiro[3.3]heptanyl, diazaspiro[3.4]octane, azaspiro [3.5]nonanyl, oxaspiro[3.5]nonanyl, thiaspiro[3.5]nonanyl, azaspiro[4.5]decanyl, and diazaspiro[5.5]undecanyl. The term "spiro group" may also be used herein to describe a cyclic substituent that is connected to another cyclic substituent such that a spirocycle is formed.

The term "heterocycloalkyl" refers to a saturated or unsaturated non-aromatic cycloalkyl group that contains from one to five heteroatoms selected from N, O, S (including S(O) and S(O)$_2$), or P (including phosphine oxide) wherein the nitrogen, sulfur, and phosphorous atoms are optionally oxidized, and the nitrogen atom(s) are optionally quarternized, the remaining ring atoms being C, where one or two C atoms may optionally be present as a carbonyl. A heterocycloalkyl group can have one or more carbon-carbon double bonds or carbon-heteroatom double bonds in the ring as long as the ring is not rendered aromatic by their presence. Further, the term heterocycloalkyl is intended to encompass any ring or ring system containing at least one heteroatom that is not a heteroaryl, regardless of the point of attachment to the remainder of the molecule. Heterocycloalkyl groups include those having a ring with a formally charge-separated aromatic resonance structure, for example, N-methylpyridonyl. The heterocycloalkyl may be substituted with one or two oxo groups, and can include sulfone and sulfoxide derivatives. The heterocycloalkyl may be a monocyclic, a bridged ring system, a fused bicyclic or a fused polycyclic ring system of 3 to 12, 4 to 10, 5 to 10, or 5 to 6 ring atoms in which one to five ring atoms are heteroatoms selected from —N═, —N—, —O—, —S—, —S(O)—, or —S(O)$_2$— and further wherein one or two ring atoms are optionally replaced by a —C(O)— group. As an example, a 4-9 membered heterocycloalkyl is a heterocycloalkyl with 4-9 ring members having at least one heteroatom. The heterocycloalkyl can also be a heterocyclic alkyl ring fused with a cycloalkyl. Non limiting examples of heterocycloalkyl groups include pyrrolidine, piperidine, morpholine, pyridone, pyrrolidine, azepane, 1,4-diazepane, azetidine, 8-azabicyclo[3.2.1]octane, 8-azabicylo[3.2.1]octene, and 3,9-diazabicyclo[4.2.1]nonane and the like. A heterocycloalkyl group can be attached to the remainder of the molecule through a ring carbon or a heteroatom. "Heterocycloalkenyl" refers to a heterocycloalkyl having at least one unit of unsaturation. A substituent of a heterocycloalkyl or heterocycloalkenyl may be at the point of attachment of the heterocycloalkyl or heterocycloalkenyl group, forming a quaternary center.

The term "heterocycloalkylalkyl" refers to an alkyl group substituted with a heterocycloalkyl group. Examples include, but are not limited to, azetidinylmethyl, morpholinomethyl, and the like.

The term "$C_1$-$C_6$haloalkyl" refers to $C_1$-$C_6$ alkyl as defined herein that is substituted with one or more halogen atoms.

The term "—$C_1$-$C_4$alkylene-$NR^aR^b$" refers to a "—$C_1$-$C_4$alkylene- that is attached to the parent moiety, and which substituted with $NR^aR^b$.

The term "$C_1$-$C_6$hydroxyalkyl" refers to $C_1$-$C_6$ alkyl as defined herein that is substituted with one or more hydroxy groups as defined herein.

The term "—$C_0$-$C_4$alkylene-$C_3$-$C_7$cycloalkyl" refers to —$C_0$-$C_4$alkylene- that is attached to the parent moiety, and which is substituted with a $C_3$-$C_7$cycloalkyl group as defined herein.

The term "oxo" refers to C(=O) or (O). In some embodiments, two possible points of attachment on a carbon form an oxo group "Hydroxyl" or "hydroxy" refers to the group OH. The term "hydroxyalkyl" or "hydroxyalkylene" refers to an alkyl group or alkylene group, respectively as defined herein, substituted with 1-5 hydroxy groups.

The term "substituent" is an atom or group of atoms substituted in place of hydrogen atom(s) of the parent molecule. Non-limiting examples of substituents in this disclosure include $J^4$ which can include monovalent or divalent substituents. Monovalent substituents are bonded to the parent moiety by replacing one hydrogen atom of the parent moiety through a single bond. The hydrogen atom that the monovalent substituent replaces may be an available hydrogen atom from a carbon or nitrogen atom of the parent moiety. Divalent substituents are bonded to the parent moiety by replacing two available hydrogen atoms of the parent moiety through a double bond. It is understood that substituents described in this disclosure cannot be attached to a parent moiety in a way that would result in an unstable molecule.

"Optional substituents" or "optionally substituted" as used throughout the disclosure means that the substitution on a compound may or may not occur, and that the description includes instances where the substitution occurs and instances in which the substitution does not. For example, the phrase "optionally substituted with 1-3 $J^1$ groups" means that the $J^1$ group may but need not be present. It is assumed in this disclosure that optional substitution on a compound occurs in a way that would result in a stable compound.

As used herein in connection with compounds of the disclosure, the term "synthesizing" and like terms means chemical synthesis from one or more precursor materials.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. Such salts can be derived from pharmaceutically acceptable inorganic or organic bases and from pharmaceutically-acceptable inorganic or organic acids, depending on the particular substituents found on the compounds described herein.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

When compounds of the present disclosure contain relatively acidic functionalities, base addition salts can be obtained by contacting the neutral form of such compounds with a sufficient amount of the desired base (i.e. a primary, secondary, tertiary, quaternary, or cyclic amine; an alkali metal hydroxide; alkaline earth metal hydroxide; or the like), either neat or in a suitable inert solvent. The desired acid can be, for example, a pyranosidyl acid (such as glucuronic acid or galacturonic acid), an alpha-hydroxy acid (such as citric acid or tartaric acid), an amino acid (such as aspartic acid or glutamic acid), an aromatic acid (such as benzoic acid or cinnamic acid), a sulfonic acid (such as p-toluenesulfonic acid or ethanesulfonic acid), or the like. In some embodiments, salts can be derived from pharmaceutically acceptable acids such as acetic, trifluoroacetic, propionic, ascorbic, benzenesulfonic, benzoic, camphorsulfonic, citric, ethanesulfonic, fumaric, glycolic, gluconic, glucoronic, glutamic, hippuric, hydrobromic, hydrochloric, isethionic, lactic, lactobionic, maleic, malic, malonic, mandelic, oxalic, methanesulfonic, mucic, naphthalenesulfonic, nicotinic, nitric, pamoic, pantothenic, phosphoric, succinic, sulfuric, sulfamic, hydroiodic, carbonic, tartaric, p-toluenesulfonic, pyruvic, aspartic, benzoic, cinnamic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylsulfamic, cyclohexylaminosulfonic, quinic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al., "Pharmaceutical Salts," J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

The term "deuterated" as used herein alone or as part of a group, means substituted deuterium atoms. The term "deuterated analog" as used herein alone or as part of a group, means substituted deuterium atoms in place of hydrogen. The deuterated analog of the disclosure may be a fully or partially deuterium substituted derivative. In some embodiments, the deuterium substituted derivative of the disclosure holds a fully or partially deuterium substituted alkyl, aryl or heteroaryl group.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. All isotopic variations of the compounds of the present disclosure, whether radioactive or not, are intended to be encompassed within the scope of the present disclosure. Examples of isotopes that can be incorporated into compounds of the disclosure include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Unless otherwise stated, when a position is designated specifically as "H" or "hydrogen," the position is understood to have hydrogen at its natural abundance isotopic composition or its isotopes, such as deuterium (D) or tritium ($^3$H). Certain isotopically-labeled compounds of the present disclosure (e.g., those labeled with $^3$H and $^{14}$C) are useful in compound and/or substrate tissue distribution assays. Tritiated (i.e., $^3$H) and carbon-14 (i.e., $^4$C) and fluorine-18 ($^{18}$F) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those described in the Schemes and in the Examples herein below, by substituting an isotopically labeled reagent for a non-isotopically labeled reagent.

"Prodrugs" means any compound which releases an active parent drug according to Formula (I) in vivo when such prodrug is administered to a subject. Prodrugs of a compound of Formula (I) are prepared by modifying functional groups present in the compound of Formula (I) in such a way, either in routine manipulation or in vivo, that the modifications may be cleaved in vivo to release the parent compound. Prodrugs may proceed from prodrug form to active form in a single step or may have one or more intermediate forms which may themselves have activity or may be inactive. Some prodrugs are activated enzymatically to yield the active compound, or a compound which, upon further chemical reaction, yields the active compound. Prodrugs include compounds of Formula (I) wherein a hydroxy, amino, carboxyl or sulfhydryl group in a compound of Formula (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula (I), and the like. Other examples of prodrugs include, without limitation, carbonates, ureides, solvates, or hydrates of the active compound. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety. As described in The Practice of Medicinal Chemistry, Ch. 31-32 (Ed. Wermuth, Academic Press, San Diego, CA, 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

(1) Oxidative reactions: Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

(2) Reductive reactions: Reductive reactions are exemplified without limitation to reactions such as reduction of carbonyl functionalities, reduction of alcohol functionalities and carbon-carbon double bonds, reduction of nitrogen-containing functional groups, and other reduction reactions.

(3) Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols.

The term "carrier" is also meant to include microspheres, liposomes, micelles, nanoparticles (naturally-equipped nanocarriers, for example, exosomes), and the like. It is known that exosomes can be highly effective drug carriers, and there are various ways in which drugs can be loaded into exosomes, including those techniques described in J Control Release. 2015 Dec. 10; 219: 396-405, the contents of which are incorporated by reference in its entirety.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, J. Med. Chem., 40:2011-2016; Shan et al., 1997, J Pharm Sci 86(7):756-757; Bagshawe, 1995, Drug Dev. Res., 34:220-230.

"Tautomer" means compounds produced by the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds that have identical molecular Formulae but differ in the nature or sequence of bonding of their atoms or in the arrangement of their atoms in space. Isomers that differ in the arrangement of their atoms in space are termed "stereoisomers."

"Stereoisomer" and "stereoisomers" refer to compounds that exist in different stereoisomeric forms, for example, if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, an atom such as carbon bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." As another example, stereoisomers include geometric isomers, such as cis- or trans-orientation of substituents on adjacent carbons of a double bond. Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as those described herein. Generally a ligand or modulator will be a small molecule, where "small molecule refers to a compound with a molecular weight of 1500 Daltons or less, 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. In some embodiments, a binding compound interacts with a specified target with a dissociation constant ($K_D$) of 10 mM or less, 1,000 μM or less, 5000 nM or less, 3000 nM or less, 1500 nM or less, 1,000 nM or less, 500 nM or less, 200 nM or less, 100 nM or less, 50 nM or less, or 25 nM or less. The term "selective" indicates that the compound binds more tightly than a reference compound, or than the same compound in a reference condition, i.e., with a lower dissociation constant. Certain compounds of this disclosure selectively inhibit wild-type Her2 and/or mutant Her to over wild-type EGFR thereby reducing EGFR dose-limiting toxicities.

In some embodiments, the greater affinity of one or more compounds in Table 1 is at least 1.5, 2, 3, 4, 5, 8, 10, 50, 100, 200, 400, 500, 1000, or 10,000-fold greater affinity. Certain compounds of this disclosure selectively inhibit wild-type Her2 and/or mutant Her to over wild-type EGFR thereby reducing EGFR dose-limiting toxicities.

The terms "modulate," "modulation," and the like refer to the ability of a compound to increase or decrease the function and/or expression of a target, such as the interaction between Her2 (including mutated forms thereof), where such function may include transcription regulatory activity and/or binding. Modulation may occur in vitro or in vivo. Modulation, as described herein, includes the inhibition, antagonism, partial antagonism, activation, agonism or partial agonism of a function or characteristic associated with Her2, either directly or indirectly, and/or the upregulation or downregulation of the expression Her2, either directly or indirectly. In another embodiment, the modulation is direct. Inhibitors or antagonists are compounds that, e.g., bind to, partially or totally block stimulation, decrease, prevent, inhibit, delay activation, inactivate, desensitize, or down-regulate signal transduction. Activators or agonists are compounds that, e.g., bind to, stimulate, increase, open, activate, facilitate, enhance activation, activate, sensitize or upregulate signal transduction. In another example, compounds that modulate Her2 can do so by inhibiting Her2 by way of irreversible or covalent binding to the Her2 tyrosine kinase. In another example, compounds that modulate Her2 can do so by inhibiting Her2 by way of reversible or non-covalent binding to the Her2 tyrosine kinase.

As used herein, the terms "treat," "treating," "therapy," "therapies," and like terms refer to the administration of material, e.g., any one or more compound(s) as described herein in an amount effective to inhibit Her2, including wild-type Her2 and mutant Her2 such as Her2 with YVMA insertion mutations. In other embodiments of this disclosure, these terms apply to the administration of the compounds of this disclosure to subjects that have disease states associated with Her2 overexpression and/or HER2 amplification. In other embodiments, the terms "treat," "treating," "therapy," "therapies," and like terms refer to the administration of material, e.g., any one or more compound(s) as described herein is an amount effective to prevent, alleviate, or ameliorate one or more symptoms of a disease or condition, i.e., indication, and/or to prolong the survival of the subject being treated. In other embodiments of this disclosure, these terms apply to the administration of the compounds of this disclosure to subjects that have disease states associated with Her2 overexpression and/or HER2 amplification.

The terms "prevent," "preventing," "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or requiring a disorder or condition or one or more of its attendant symptoms.

As used herein, the term "subject," "animal subject," and the like refers to a living organism including, but not limited to, human and non-human vertebrates, e.g. any mammal, such as a human, other primates, sports animals and animals of commercial interest such as cattle, horses, ovines, or porcines, rodents, or pets such as dogs and cats.

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

In the present context, the term "therapeutically effective" or "effective amount" indicates that a compound or material or amount of the compound or material when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

As used herein, the term "Her2 mediated disease or condition" (which is also meant to mean "Her2 mediated disease or condition" as well as "wild-type Her2 and/or mutant Her2 mediated disease or condition") refers to a disease or condition in which the biological function of Her2 affect the development and/or course of the disease or condition, and/or in which modulation of the interaction of Her2 alters the development, course, and/or symptoms. A of Her2 mediated disease or condition includes a disease or condition for which the disruption Her2 interactions (for example, by inhibiting Her2 with YVMA insertion mutations) provides a therapeutic benefit, e.g. wherein treatment with Her2 inhibitors, including compounds described herein, provides a therapeutic benefit to the subject suffering from or at risk of the disease or condition. A Her2 mediated disease or condition is intended to include a cancer or tumor that harbors loss of function mutations in Her2, or a cancer where there is activation of Her2. In other embodiments of this disclosure, Her2 mediated diseases or conditions are associated with Her2 overexpression and/or Her2 amplification. A Her2 mediated disease or condition is also intended to include various human carcinomas, including those of the lung, breast, stomach, ovary, colon, bladder, lung, uterine cervix, head and neck, gastric and esophageal cancer as well as uterine serous endometrial carcinoma, as well any associated comorbidities such as pulmonary disorder, hypertension, hypercholesterolemia, cardiovascular disease, renal function disorder, thyroid disorder, obesity, depression anxiety, osteoporosis, liver disorder, autoimmune disease, dementia, Alzheimer's disease.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of Her2 or Her2+ mutations. In particular embodiments, the greater specificity is at least 2, 3, 4, 5, 8, 10, 20, 50, 100, 200, 400, 500, or 1000-fold greater specificity.

As used herein in connection with binding compounds or ligands, the terms "specific for Her2," (which is intended to include either wild-type Her2, mutant Her2, or both wild-type Her2 and mutant Her2) and terms of like import mean that a particular compound binds to Her2 to a statistically greater extent than to other targets that may be present in a particular sample such as wild-type EGFR. Also, where biological activity other than binding is indicated, the terms "specific for Her2" indicates that a particular compound has greater biological effect associated with binding Her2 than to other enzymes, e.g., enzyme activity inhibition.

The term "first line cancer therapy" refers to therapy administered to a subject as an initial regimen to reduce the number of cancer cells. First line therapy is also referred to as induction therapy, primary therapy and primary treatment. First-line therapy can be an administered combination with one or more agents. A summary of currently accepted approaches to first line treatment for certain disease can be found in the NCI guidelines for such diseases.

The term "second line cancer therapy" refers to a cancer treatment that is administered to a subject who does not respond to first line therapy, that is, often first line therapy is administered or who has a recurrence of cancer after being in remission. In certain embodiments, second line therapy that may be administered includes a repeat of the initial successful cancer therapy, which may be any of the treatments described under "first line cancer therapy." A summary of the currently accepted approaches to second line treatment for certain diseases is described in the NCI guidelines for such diseases.

The term "refractory" refers to wherein a subject fails to respond or is otherwise resistant to cancer therapy or treatment. The cancer therapy may be first-line, second-line or any subsequently administered treatment. In certain embodiments, refractory refers to a condition where a subject fails to achieve complete remission after two induction attempts. A subject may be refractory due to a cancer cell's intrinsic resistance to a particular therapy, or the subject may be refractory due to an acquired resistance that develops during the course of a particular therapy.

In addition, abbreviations as used herein have respective meanings as follows:

| | |
|---|---|
| ACN, MeCN | Acetonitrile |
| ° C. | Degree Celsius |
| BOC | tert-butoxy carbonyl |
| DBU | 1,8-Diazabicyclo[5.4.0]undec-7-ene |
| DCE | Dichloroethane |
| DCM | Dichloromethane |
| DIEA or DIPEA | Diisopropylethylamine |
| DMF | Dimethylformamide |
| DMSO | Dimethylsulfoxide |
| EA, ETOAc, ETAC | Ethyl acetate |
| EDC, EDAC or EDCI | 1-Ethyl-3-(3-dimethylaminopropyl)carbodiimide |
| ESI | Electrospray ionization |
| HATU | Hexafluorophosphate Azabenzotriazole Tetramethyl Uronium |
| HOBt | Hydroxybenzotriazole |
| HPLC | High Performance Liquid Chromatography |
| $IC_{50}$ | Half minimal (50%) inhibitory concentration |
| LCMS | Liquid Chromatography Mass Spectrometry |
| [M + H+]+ or (MH)+ | Mass peak plus hydrogen |
| [M − H−]− or (MH)− | Mass peak minus hydrogen |
| Me | Methyl |
| MeOH | Methanol |
| MS | Mass spectrometry |
| N | Normal |
| PMB | (4-methoxyphenyl)methanamine or para-methoxy benzyl |
| PyBroP | bromotri(pyrrolidino)phosphonium hexafluorophosphate |
| RP | Reverse phase |
| RT or rt | Room temperature |
| TLC | Thin-layer chromatography |
| THF | Tetrahydrofuran |
| TFA | Trifluoroacetic acid |

II. Compounds

Embodiment 1 of this disclosure relates to a compound having Formula (I):

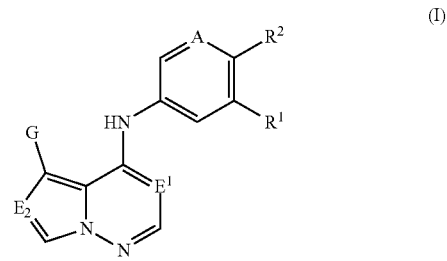

or a pharmaceutically acceptable salt, a tautomer, a stereoisomer, or a deuterated analog thereof, wherein:
A is N or CH;
$E^1$ is N or C(CN);
$E^2$ is $C(R^4)$ or N;
$R^1$ is alkyl, haloalkyl or halogen;
$R^2$ is —O-alkyl, —O-aryl, —O-heteroaryl, —O-cycloalkyl, —O-heterocycloalkyl, —O— heteroaryl-alkylene-aryl, —NH-alkyl, —NH-aryl, or —NH-heteroaryl, wherein each of the alkyl, aryl, heteroaryl, cycloalkyl or heterocycloalkyl moieties are optionally substituted with 1-4 $J^1$ groups;
or $R^1$ and $R^2$ join with the carbon atoms to which they are attached to form a saturated or unsaturated carbocyclic or heterocyclic ring, wherein the saturated or unsaturated carbocyclic or heterocyclic ring is optionally substituted with 1-4 $J^1$ groups;

G is -$L^1$-$R^3$, $L^{1a}$-$R^{3a}$, or —W—X—Y;

$L^1$ is a bond, —C(O)—, —S(O)$_2$—, —N($R^c$)—, alkylene, aryl, heteroaryl, heterocycloalkyl, or cycloalkyl, wherein the alkylene, aryl, heteroaryl, heterocycloalkyl, or cycloalkyl are each optionally substituted with 1-4 $J^2$ groups, provided that when $L^1$ is CH$_2$, $L^1$ is not attached to carbon or nitrogen of a saturated ring;

$L^{1a}$ is —C$_0$-C$_6$alkylene-C(O)N(H)—, —C$_0$-C$_6$alkylene-S(O)$_2$N(H)—;

$R^3$ is a 4-9 membered heterocyclic ring containing at least one nitrogen ring atom, wherein $R^3$ is optionally substituted with 1-4 $J^3$ groups, and wherein one nitrogen atom of $R^3$ is substituted with -$L^2$-R;

or $R^3$ is a 7-11 membered spirocyclic group containing at least one nitrogen ring atom, wherein the 7-11 membered spirocyclic group containing at least one nitrogen ring atom is optionally substituted with 1-4 $J^3$ groups, and wherein one nitrogen atom of the 7-11 membered spirocyclic group is substituted with -$L^2$-R;

$R^{3a}$ is C$_1$-C$_6$alkylene-NR$^a$R$^b$ optionally substituted with 1-4 $J^2$ groups;

W is a bond, —C(O)— or —S(O)$_2$—;

X is aryl, heteroaryl, heterocycloalkyl, or cycloalkyl, each of which is optionally substituted with 1-4 $J^2$ groups;

Y is —C$_0$-C$_4$alkylene-N(R)-$L^2$-R, —C(O)-4-7 membered heterocycloalkyl containing at least one nitrogen atom and substituted with 1-2 oxo groups, -4-7 membered heterocycloalkyl-$L^2$R, —C$_0$-C$_4$alkylene-1-yl-1H-pyrrole-2,5-dione, —C$_0$-C$_4$alkylene-C(H)═C(O)—NH$_2$, —C$_0$-C$_4$alkylene-C(H)═C(H)—C(O)—O-alkyl, —C$_0$-C$_4$alkylene-ethynylene-C(O)—O-alkyl, —C$_0$-C$_4$alkylene-C(H)═C(H)—CN, —C$_0$-C$_4$alkylene-N═C═S, —C$_0$-C$_4$-ethynyl, —C$_0$-C$_4$alkylene-ethynyl, —C$_0$-C$_4$alkylene-CN, —C$_0$-C$_4$alkylene-C(H)═N—N(H)Boc, —C$_0$-C$_4$alkylene-C(O)—CH$_2$—Br, —C$_0$-C$_4$alkylene-CH$_2$—Cl, —C$_0$-C$_4$alkylene-oxiranyl, —C$_0$-C$_4$alkylene-SH, —C$_0$-C$_4$alkylene-F, and —C$_0$-C$_4$alkylene-C(H)═O, wherein the C$_0$-C$_4$alkylene moiety is optionally substituted with 1-4 groups independently selected from halogen, cycloalkyl, alkoxy alkoxyalkyl, or hydroxy;

$R^4$ is H, halo, alkyl, or —O-alkyl;

$L^2$ is —SO$_2$— or —C(O)—;

R is ethenyl optionally substituted with 1-3 Q groups, ethynyl optionally substituted with Q, C$_1$-C$_4$ alkylene-NR$^a$R$^b$, —CH$_2$—CN, or haloalkyl wherein one halogen of haloalkyl is on the carbon atom adjacent to $L^2$, each Q is independently selected from the group consisting of halogen, haloalkyl, alkyl, —C$_1$-C$_6$alkylene-NR$^a$R$^b$, cyano, hydroxyalkyl, —C$_1$-C$_6$alkylene-C(O)OH, —C$_1$-C$_6$(alkylene-C(O)O-alkyl, alkoxyalkyl, —C$_0$-C$_4$alkylene-cycloalkyl optionally substituted with 1-3 $J^4$ groups, —C$_0$-C$_4$alkylene-cycloalkenyl optionally substituted with 1-3 $J^4$ groups, —C$_0$-C$_4$alkylene-7-11 membered spirocyclic group optionally substituted with 1-3 $J^4$ groups, —C$_0$-C$_4$alkylene-7-11 membered spirocyclic group optionally substituted with 1-3 $J^4$ groups, —C$_0$-C$_4$alkylene-heterocycloalkyl optionally substituted with 1-3 $J^4$ groups, and —C$_0$-C$_4$alkylene-heterocycloalkenyl optionally substituted with 1-3 $J^4$ groups;

or -$L^2$-R is —C═N—OH;

each $J^1$ is independently selected from the group consisting of halogen, alkyl, haloalkyl, hydroxy, hydroxyalkyl, —C$_0$-C$_4$alkylene-N(H)R$^c$, alkoxy, and alkoxyalkyl;

each $J^2$ is independently selected from the group consisting of halogen, alkyl, haloalkyl, hydroxy, hydroxyalkyl, alkoxy, and alkoxyalkyl;

each $J^3$ is attached to a carbon atom and is independently selected from the group consisting of halogen, haloalkyl, CN, alkyl, hydroxy, hydroxyalkyl, alkoxy, and alkoxyalkyl, or two of the optional 1-4 $J^3$ groups form an oxo group or a 3-6 membered spiro group, or two of the optional 1-4 $J^3$ groups are on different ring carbon and join to form a 1-3 carbon bridge;

each $J^4$ is independently selected from the group consisting of halogen, alkyl, haloalkyl, hydroxy, hydroxyalkyl, alkoxy, alkoxyalkyl, oxo, and —C$_0$-C$_4$alkylene-NR$^a$R$^b$, provided that $J^4$ groups can only include up to two oxo groups and up to one —C$_0$-C$_4$alkylene-NR$^a$R$^b$ group;

R$^a$ and R$^b$ each are independently selected from the group consisting of H, alkyl, haloalkyl, hydroxyalkyl, alkoxyalkyl, and —C$_0$-C$_3$alkylene-alkynyl optionally substituted with alkyl, haloalkyl, hydroxyalkyl, or alkoxyalkyl; and R$^c$ is selected from the group consisting of H, alkyl, haloalkyl, hydroxyalkyl, alkoxyalkyl, cycloalkyl, heterocycloalkyl, aryl, and heteroaryl, wherein the cycloalkyl, heterocycloalkyl, aryl, and heteroaryl groups are each optionally substituted with 1-3 groups selected from the group consisting of halogen, alkyl, alkoxy and alkoxyalkyl; and R$^d$ is selected from the group consisting of H, alkyl, and haloalkyl.

Embodiment 1(a) of this disclosure relates to the compound according to Embodiment 1, wherein G is -$L^1$-$R^3$.

Embodiment 1(b) of this disclosure relates to the compound according to Embodiment 1, wherein G is -$L^{1a}$-$R^{3a}$. In other embodiment of Embodiment 1(b), $L^{1a}$ is C$_0$-C$_3$alkylene-C(O)N(H)—. In other aspect of Embodiment 1(b), $R^3$ is —C$_1$-C$_4$alkylene-NR$^a$R$^b$ wherein R$^a$ and R$^b$ each are independently selected from the group consisting of C$_1$-C$_6$alkyl, C$_1$-C$_6$haloalkyl, and C$_1$-C$_6$hydroxyalkyl. In other aspect of Embodiment 1(b), $R^3$ is —C$_1$-C$_3$alkylene-NR$^a$R$^b$ wherein: R$^a$ and R$^b$ each are C$_1$-C$_3$alkyl.

Embodiment 1(c) of this disclosure relates to the compound according to Embodiment 1, wherein G is —W—X—Y Embodiment 2 of this disclosure relates to the compound according to Embodiment 1, wherein:

$R^1$ is C$_1$-C$_4$alkyl, C$_1$-C$_4$haloalkyl or halogen;

$R^2$ is —O-(5-10 membered) aryl, —O-(5-10 membered) heteroaryl, —O-(4-7 membered) cycloalkyl, —O-(4-7 membered) heterocycloalkyl, —O-(5-10 membered) heteroaryl-C$_1$-C$_4$alkylene-phenyl, —NH-(5-10 membered) aryl, or —NH-(5-10 membered) heteroaryl, wherein each of the aryl, heteroaryl, cycloalkyl and heterocycloalkyl moieties are optionally substituted with 1-3 $J^1$ groups;

or $R^1$ and $R^2$ join with the carbon atoms to which they are attached to form a ring selected from the group consisting of 5-10 membered aryl, 5-10 membered heteroaryl, 4-7 membered cycloalkyl, and 4-7 membered heterocycloalkyl, wherein each ring is optionally substituted with 1-3 $J^1$ groups;

G is -$L^1$-$R^3$ or —W—X—Y;

$L^1$ is a bond, —C(O)—, —S(O)$_2$—, —N(H)—, —N(C$_1$-C$_6$alkyl)-, C$_1$-C$_3$alkylene, 5-10 membered aryl, 5-10 membered heteroaryl, 4-7 membered heterocycloalkyl, or 4-7 membered cycloalkyl, wherein C$_1$-C$_3$alkylene, 5-10 membered aryl, 5-10 membered heteroaryl, 5-7 membered heterocycloalkyl, and 5-7 membered cycloalkyl are each optionally substituted with 1-3 $J^2$ groups, provided that when $L^1$ is CH$_2$, $L^1$ is not attached to carbon or nitrogen of a saturated ring;

$R^3$ is a 4-7 membered heterocyclic ring containing at least one nitrogen ring atom, wherein the 4-7 membered heterocyclic ring containing at least one nitrogen ring atom is optionally substituted with 1-4 $J^3$ groups, and wherein one nitrogen atom of the 4-7 membered heterocyclic ring is substituted with -$L^2$-R;

or $R^3$ is a 7-11 membered spirocyclic group containing at least one nitrogen ring atom, wherein the 7-11 membered spirocyclic group is optionally substituted with 1-4 $J^3$ groups, and wherein one nitrogen atom of $R^3$ is substituted with -$L^2$-R;

W is a bond, —C(O)— or —S(O)$_2$—;

X is 5-10 membered aryl, 5-10 membered heteroaryl, 5-7 membered heterocycloalkyl, or 5-7 membered cycloalkyl, wherein the -10 membered aryl, 5-10 membered heteroaryl, 5-7 membered heterocycloalkyl, and 5-7 membered cycloalkyl are optionally substituted with 1-3 $J^2$ groups;

Y is —C$_0$-C$_4$alkylene-N(R$^d$)-$L^2$-R, —C(O)-4-6 membered heterocycloalkyl containing one nitrogen atom and substituted with 1-2 oxo groups, -4-7 membered heterocycloalkyl-$L^2$R, —C$_0$-C$_4$alkylene-1-yl-1H-pyrrole-2,5-dione, —C$_0$-C$_4$alkylene-C(H)=C(O)—NH$_2$, —C$_0$-C$_4$alkylene-C(H)=C(H)—C(O)—O-alkyl, —C$_0$-C$_4$alkylene-ethynylene-C(O)—O-alkyl, —C$_0$-C$_4$alkylene-C(H)=C(H)—CN, —C$_0$-C$_4$alkylene-N=C=S, —C$_0$-C$_4$-etheyny, —C$_0$-C$_4$alkylene-ethynyl, —C$_0$-C$_4$alkylene-CN, —C$_0$-C$_4$alkylene-C(H)=N—N(H)Boc, —C$_0$-C$_4$alkylene-C(O)—CH$_2$—Br, —C$_0$-C$_4$alkylene-CH$_2$—Cl, —C$_0$-C$_4$alkylene-oxiranyl, —C$_0$-C$_4$alkylene-SH, —C$_0$-C$_4$alkylene-F, and —C$_0$-C$_4$alkylene-C(H)=O, wherein the —C$_0$-C$_4$alkylene moiety is optionally substituted with 1-4 groups independently selected from the group consisting of halogen, C$_3$-C$_6$cycloalkyl, C$_1$-C$_6$alkoxy —C$_1$-C$_6$alkyl-C$_1$-C$_6$alkoxy, or hydroxy;

$R^4$ is H, halo, C$_0$-C$_4$alkyl, or —O—C$_0$-C$_4$alkyl;

$L^2$ is —SO$_2$— or —C(O)—;

R is ethenyl optionally substituted with 1-3 Q groups, ethynyl optionally substituted with Q, C$_1$-C$_4$ alkylene-NR$^a$R$^b$, —CH$_2$—CN, or C$_1$-C$_6$haloalkyl, wherein one halogen of C$_1$-C$_6$haloalkyl is on the carbon atom adjacent to $L^2$;

each Q is independently selected from the group consisting of halogen, C$_1$-C$_6$haloalkyl, C$_1$-C$_6$alkyl, —C$_1$-C$_4$alkylene-NR$^a$R$^b$, cyano, C$_1$-C$_6$hydroxyalkyl, —C$_1$-C$_6$alkylene-C(O)OH, —C$_1$-C$_6$alkylene-C(O)O—C$_1$-C$_6$alkyl, —C$_1$-C$_4$alkylene-C$_1$-C$_6$alkoxy, —C$_0$-C$_4$alkylene-C$_3$-C$_7$cycloalkyl optionally substituted with 1-3 $J^4$ groups, —C$_0$-C$_4$alkylene-C$_3$-C$_7$cycloalkenyl optionally substituted with 1-3 $J^4$ groups, —C$_0$-C$_4$alkylene-7-11 membered spirocyclic heterocycloalkyl optionally substituted with 1-3 $J^4$ groups, —C$_0$-C$_4$alkylene-4-7 membered heterocloalkyl optionally substituted with 1-3 $J^4$ groups, and —C$_0$-C$_4$alkylene-4-7 membered heterocycloalkenyl optionally substituted with 1-3 $J^4$ groups; or -$L^2$-R is —C=N—OH;

each $J^1$ is independently selected from the group consisting of halogen, C$_1$-C$_6$alkyl, C$_1$-C$_6$haloalkyl, hydroxy, C$_1$-C$_6$hydroxyalkyl, —C$_0$-C$_4$alkylene-N(H)R$^c$, C$_1$-C$_6$alkoxy, and —C$_1$-C$_6$alkyl-C$_1$-C$_6$alkoxy;

each $J^2$ is independently selected from the group consisting of halogen, C$_1$-C$_6$alkyl, C$_1$-C$_6$haloalkyl, hydroxy, C$_1$-C$_6$hydroxyalkyl, C$_1$-C$_6$alkoxy, and —C$_1$-C$_6$alkyl-C$_1$-C$_6$alkoxy;

each $J^3$ is attached to a carbon atom of $R^3$ and is independently selected from the group consisting of halogen, —C$_1$-C$_6$haloalkyl, CN, C$_1$-C$_6$alkyl, hydroxy, C$_1$-C$_6$hydroxyalkyl, C$_1$-C$_6$alkoxy, and —C$_1$-C$_6$alkyl-C$_1$-C$_6$alkoxy, or two of the optional 1-4 $J^3$ groups form an oxo group or a 3-6 membered spiro group, or two of the optional 1-4 $J^3$ groups are on different ring carbon and join to form a 1-3 carbon bridge;

each $J^4$ is independently selected from the group consisting of halogen, C$_1$-C$_6$alkyl, C$_1$-C$_6$haloalkyl, hydroxy, C$_1$-C$_6$hydroxyalkyl, C$_1$-C$_6$alkoxy, —C$_1$-C$_6$alkyl-C$_1$-C$_6$alkoxy, oxo, and —C$_0$-C$_4$alkylene-NR$^a$R$^b$, provided that $J^4$ groups can only include up to two oxo groups and up to one —C$_0$-C$_4$alkylene-NR$^a$R$^b$ group;

$R^a$ and $R^b$ each are independently selected from the group consisting of H, C$_1$-C$_6$alkyl, C$_1$-C$_6$haloalkyl, C$_1$-C$_6$hydroxyalkyl, —C$_1$-C$_6$alkyl-C$_1$-C$_6$alkoxy, and C$_0$-C$_3$alkylene-C$_2$-C$_6$alkynyl optionally substituted with alkyl, C$_1$-C$_6$haloalkyl, C$_1$-C$_6$hydroxyalkyl, or —C$_1$-C$_6$alkoxy C$_1$-C$_6$alkyl; and $R^c$ is selected from the group consisting of H, C$_1$-C$_6$alkyl, C$_1$-C$_6$haloalkyl, C$_1$-C$_6$hydroxyalkyl, —C$_1$-C$_6$alkyl-C$_1$-C$_6$alkoxy, C$_3$-C$_7$cycloalkyl, 4-7 membered heterocycloalkyl, 6-10 membered aryl, and 5-10 membered heteroaryl, wherein the C$_3$-C$_7$cycloalkyl, 4-7 membered heterocycloalkyl, 6-10 membered aryl, and 5-10 membered heteroaryl groups are each optionally substituted with 1-3 groups selected from the group consisting of halogen, C$_1$-C$_6$alkyl, C$_1$-C$_6$alkoxy and C$_1$-C$_6$alkoxy-C$_1$-C$_6$alkyl; and $R^d$ is selected from the group consisting of H, C$_1$-C$_6$alkyl, and C$_1$-C$_6$haloalkyl.

Embodiment 3 of this disclosure relates to the compound according to any one of Embodiments 1, 1(a), 1(b), 1(c) or 2 having one of the following formulae:

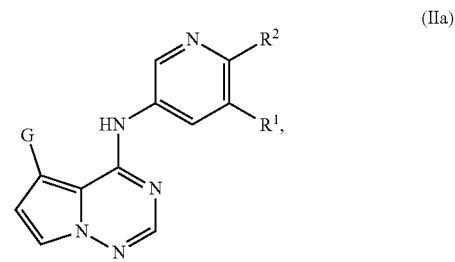

(IIa)

(IIb) 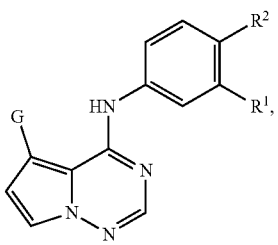

(IIc) 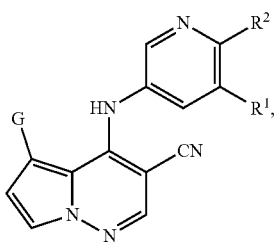

(IId) 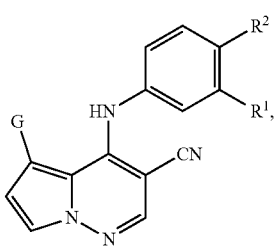

(IIe) 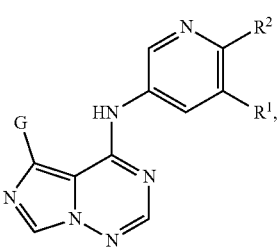

(IIf) 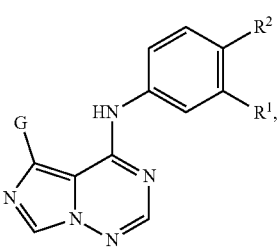

(IIg) 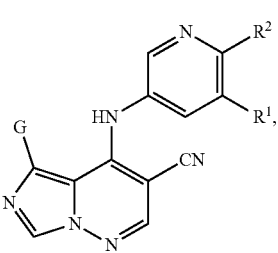

(IIh) 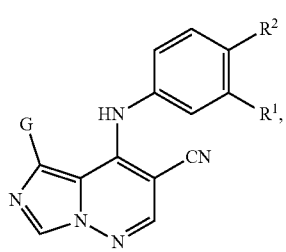

or a pharmaceutically acceptable salt, a tautomer, a stereoisomer, or a deuterated analog of any of the above compounds. Another aspect of Embodiment 3 of this disclosure relates to the compound according to any one of Embodiments 1 or 2 having one of formulae (IIa), (IIb), (IIc), (IId), (IIe), (IIf), (IIg), (IIh), or a pharmaceutically acceptable salt, a tautomer, a stereoisomer, or a deuterated analog thereof. Embodiment 4 of this disclosure relates to Embodiment 3 having Formula (IIa) or (IIb), or a pharmaceutically acceptable salt, a tautomer, a stereoisomer, or a deuterated analog of Formula (IIa) or (IIb).

Embodiment 4(a) of this disclosure relates to Embodiment 4 having Formula (IIa) or a pharmaceutically acceptable salt, a tautomer, a stereoisomer, or a deuterated analog of Formula (IIa).

Embodiment 4(b) of this disclosure relates to Embodiment 4 having Formula (IIb) or a pharmaceutically acceptable salt, a tautomer, a stereoisomer, or a deuterated analog of Formula (IIb).

Embodiment 5 of this disclosure relates to the compound according to any one Embodiments 1, 1(a), 1(b), 1(c), or 2 having one of the following formulae:

(IIIa) 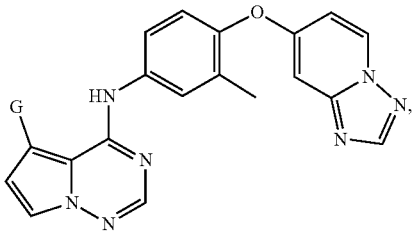

(IIIb) 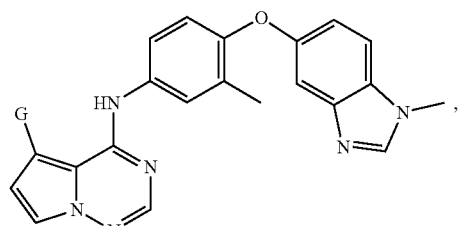

(IIIc) 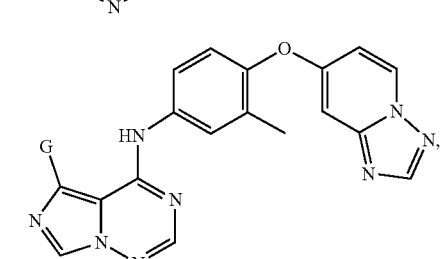

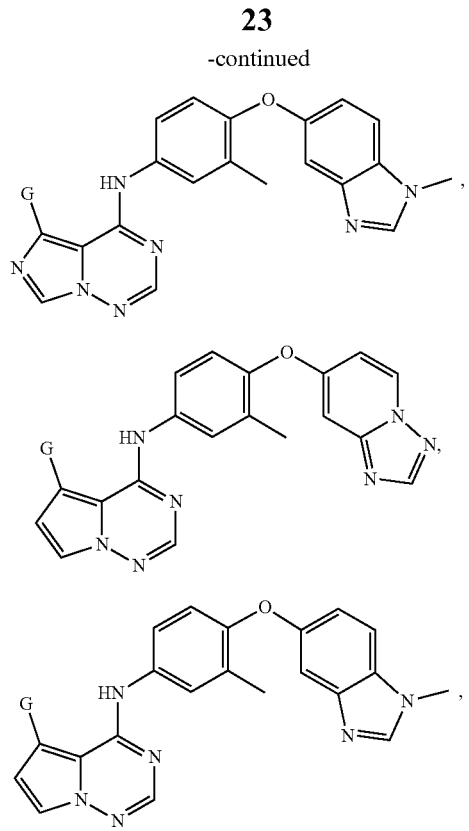

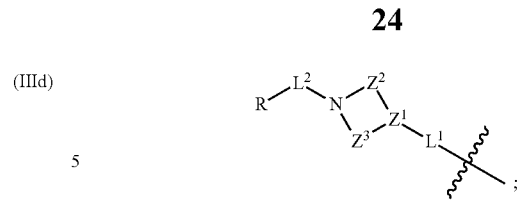

or a pharmaceutically acceptable salt, a tautomer, a stereoisomer, or a deuterated analog of any of the above compounds. Another aspect of Embodiment 5 of this disclosure relates to the compound according to any one of Embodiments 1 or 2 having one of formulae (IIIa), (IIIb), (IIIc), (IIId), (IIIe), (IIIf), or a pharmaceutically acceptable salt, a tautomer, a stereoisomer, or a deuterated analog thereof.

Embodiment 5(a) of this disclosure relates to the compound according to any one Embodiments 1, 1(a), 1(b), 1(c), or 2 having formulae (IIIa).

Embodiment 5(b) of this disclosure relates to the compound according to any one Embodiments 1, 1(a), 1(b), 1(c), or 2 having formulae (IIIb).

Embodiment 5(c) of this disclosure relates to the compound according to any one Embodiments 1, 1(a), 1(b), 1(c), or 2 having formulae (IIIc).

Embodiment 5(d) of this disclosure relates to the compound according to any one Embodiments 1, 1(a), 1(b), 1(c), or 2 having formulae (IIId).

Embodiment 5(e) of this disclosure relates to the compound according to any one Embodiments 1, 1(a), 1(b), 1(c), or 2 having formulae (IIIe).

Embodiment 5(f) of this disclosure relates to the compound according to any one Embodiments 1, 1(a), 1(b), 1(c), or 2 having formulae (IIIf).

Embodiment 6 of this disclosure relates to the compound according to any one of Embodiments 1, 2, 3, 4, 4(a), 4(b), 5, 5(a), 5(b), 5(c), 5(d), 5(e), or 5(f) wherein G is -$L^1$-$R^3$. Another aspect of Embodiment 6 of this disclosure relates to any one of Embodiments 1, 2, 3, 4, or 5, wherein G is -$L^1$-$R^3$. Embodiment 7 of this disclosure relates to the compound according to any one of Embodiments 1, 2, 3, 4, 4(a), 4(b), 5, 5(a), 5(b), 5(c), 5(d), 5(e), 5(f), or 6, wherein G is wherein:

$L^1$ is a bond, —C(O)—, —S(O)$_2$—, $C_1$-$C_3$alkylene, phenyl, 5-6 membered heteroaryl, 4-6 membered heterocycloalkyl, or 4-6 membered cycloalkyl, wherein $C_1$-$C_2$alkylene, phenyl, 5-6 membered heteroaryl, 4-6 membered heterocycloalkyl, or 4-6 membered cycloalkyl are each optionally substituted with 1-2 $J^2$ groups, provided that when $L^1$ is $CH_2$, $Z^1$ is not $CH_2$ or N;

$L^2$ is —SO$_2$— or —C(O)—;

$Z^1$ is —N(H)—, —C($R^5$)—, or a 4-7 membered spiro group optionally containing 1-2 nitrogen atoms;

$R^5$ is H, halogen, $C_1$-$C_3$alkyl or CN;

$Z^2$ and $Z^3$ are each independently —$C_1$-$C_3$alkylene or —$C_2$-$C_3$alkenylene, wherein —$C_1$-$C_3$alkylene and —$C_2$-$C_3$alkenylene are each optionally substituted with 1-4 $J^3$ groups;

R is ethenyl optionally substituted with 1-3 Q groups, ethynyl optionally substituted with Q groups, $C_1$-$C_4$ alkylene-NR$^a$R$^b$, —CH$_2$—CN, or $C_1$-$C_4$haloalkyl, wherein one halogen of $C_1$-$C_4$haloalkyl is on the carbon atom adjacent to $L^2$;

each Q is independently selected from the group consisting of halogen, $C_1$-$C_4$haloalkyl, $C_1$-$C_4$alkyl, —$C_1$-$C_4$alkylene-NR$^a$R$^b$, —$C_1$-$C_4$alkylene-cyano, $C_1$-$C_4$hydroxyalkyl, —$C_1$-$C_4$alkylene-C(O)OH, —$C_1$-$C_4$alkylene-C(O)O—$C_1$-$C_4$alkyl, —$C_1$-$C_3$alkylene-$C_1$-$C_4$alkoxy, —$C_0$-$C_4$alkylene-$C_3$-$C_7$cycloalkyl optionally substituted with 1-3 $J^4$ groups, —$C_0$-$C_4$alkylene-$C_3$-$C_7$cycloalkenyl optionally substituted with 1-3 $J^4$ groups, —$C_0$-$C_4$alkylene-7-11 membered spirocyclic heterocycloalkyl optionally substituted with 1-3 $J^4$ groups, —$C_0$-$C_4$alkylene-4-7 membered heterocycloalkyl optionally substituted with 1-3 $J^4$ groups, and —$C_0$-$C_4$alkylene-4-7 membered heterocycloalkenyl optionally substituted with 1-3 $J^4$ groups;

each $J^2$ is independently selected from the group consisting of halogen, $C_1$-$C_4$alkyl, $C_1$-$C_4$haloalkyl, hydroxy, $C_1$-$C_4$hydroxyalkyl, $C_1$-$C_4$alkoxy, and —$C_1$-$C_4$alkyl-$C_1$-$C_4$alkoxy;

each $J^3$ is independently selected from the group consisting of halogen, —$C_1$-$C_4$haloalkyl, CN, $C_1$-$C_4$alkyl, hydroxy, $C_1$-$C_4$hydroxyalkyl, $C_1$-$C_4$alkoxy, and —$C_1$-$C_4$alkyl-$C_1$-$C_4$alkoxy, or two of the optional 1-4 $J^3$ groups form an oxo group or a 3-6 membered spiro group, or two of the optional 1-4 $J^3$ groups are on different ring carbon atoms and join to form a 1-3 carbon bridge; and each $J^4$ is independently selected from the group consisting of halogen, $C_1$-$C_4$alkyl, $C_1$-$C_4$haloalkyl, hydroxy, $C_1$-$C_4$hydroxyalkyl, $C_1$-$C_4$alkoxy, —$C_1$-$C_4$alkyl-$C_1$-$C_4$alkoxy, oxo, and —$C_0$-$C_4$alkylene-NR$^a$R$^b$, provided that $J^4$ groups can only include up to two oxo groups and up to one —$C_0$-$C_4$alkylene-NR$^a$R$^b$ group. Another aspect of Embodiment 7 of this disclosure relates to any one of Embodiments 1, 2, 3, 4, 5, or 6, wherein G is

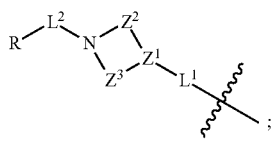

wherein:
L¹ is a bond, —C(O)—, —S(O)₂—, C₁-C₃alkylene, phenyl, 5-6 membered heteroaryl, 4-6 membered heterocycloalkyl, or 4-6 membered cycloalkyl, wherein C₁-C₂alkylene, phenyl, 5-6 membered heteroaryl, 4-6 membered heterocycloalkyl, or 4-6 membered cycloalkyl are each optionally substituted with 1-2 $J^2$ groups, provided that when L¹ is CH₂, Z¹ is not CH₂ or N;

L² is —SO₂— or —C(O)—;

Z¹ is —N(H)—, —C(R⁵)—, or a 4-7 membered spiro group optionally containing 1-2 nitrogen atoms;

R⁵ is H, halogen, C₁-C₃alkyl or CN;

Z² and Z³ are each independently —C₁-C₃alkylene or —C₂-C₃alkenylene, wherein —C₁-C₃alkylene and —C₂-C₃alkenylene are each optionally substituted with 1-4 $J^3$ groups;

R is ethenyl optionally substituted with 1-3 Q groups, ethynyl optionally substituted with Q groups, —CH₂—CN, or C₁-C₄haloalkyl, wherein one halogen of C₁-C₄haloalkyl is on the carbon atom adjacent to L²;

each Q is independently selected from the group consisting of halogen, C₁-C₄haloalkyl, C₁-C₄alkyl, —C₁-C₄alkylene-NR$^a$R$^b$, —C₁-C₄alkylene-cyano, C₁-C₄hydroxyalkyl, —C₁-C₄alkylene-C(O)OH, —C₁-C₄alkylene-C(O)O—C₁-C₄alkyl, —C₁-C₃alkylene-C₁-C₄alkoxy, —C₀-C₄alkylene-C₃-C₇cycloalkyl optionally substituted with 1-3 $J^4$ groups, —C₀-C₄alkylene-C₃-C₇cycloalkenyl optionally substituted with 1-3 $J^4$ groups, —C₀-C₄alkylene-4-7 membered heterocycloalkyl optionally substituted with 1-3 $J^4$ groups, and —C₀-C₄alkylene-4-7 membered heterocycloalkenyl optionally substituted with 1-3 $J^4$ groups;

each $J^2$ is independently selected from the group consisting of halogen, C₁-C₄alkyl, C₁-C₄haloalkyl, hydroxy, C₁-C₄hydroxyalkyl, C₁-C₄alkoxy, and —C₁-C₄alkyl-C₁-C₄alkoxy; each $J^3$ is independently selected from the group consisting of halogen, —C₁-C₄haloalkyl, CN, C₁-C₄alkyl, hydroxy, C₁-C₄hydroxyalkyl, C₁-C₄alkoxy, and —C₁-C₄alkyl-C₁-C₄alkoxy, or two of the optional 1-4 $J^3$ groups form an oxo group or a 3-6 membered spiro group, or two of the optional 1-4 $J^3$ groups are on different ring carbon atoms and join to form a 1-3 carbon bridge; and each $J^4$ is independently selected from the group consisting of halogen, C₁-C₄alkyl, C₁-C₄haloalkyl, hydroxy, C₁-C₄hydroxyalkyl, C₁-C₄alkoxy, —C₁-C₄alkyl-C₁-C₄alkoxy, oxo, and —C₀-C₄alkylene-NR$^a$R$^b$, provided that $J^4$ groups can only include up to two oxo groups and up to one —C₀-C₄alkylene-NR$^a$R$^b$ group.

Embodiment 8 of this disclosure relates to the compound according to Embodiment 7, wherein G is

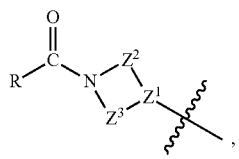

wherein:
Z¹ is —N(H)—, —C(R⁵)—, or a 4-6 membered spiro group optionally containing 1-2 nitrogen atoms;

R⁵ is H, halogen, C₁-C₃alkyl or CN;

Z² is —C₁-C₃alkylene or —C₂-C₃alkenylene, each of which is optionally substituted with 1-2 J groups;

Z³ is —C₁-C₂alkylene optionally substituted with 1-2 $J^3$ groups; R is ethenyl optionally substituted with 1-3 Q groups, ethynyl optionally substituted with Q, C₁-C₄alkylene-NR$^a$R$^b$, —CH₂—CN, or C₁-C₃haloalkyl, wherein one halogen of C₁-C₃haloalkyl is on the carbon atom adjacent to —C(O)—;

each Q is independently selected from the group consisting of halogen, C₁-C₃haloalkyl, C₁-C₃alkyl, —C₁-C₃alkylene-NR$^a$R$^b$, —C₁-C₃alkylene-cyano, C₁-C₃hydroxyalkyl, —C(O)OH, —C₁-C₃alkylene-C(O)O—C₁-C₃alkyl, —C₀-C₃alkylene-C₁-C₃alkoxy, —C₀-C₃alkylene-C₃-C₆cycloalkyl optionally substituted with 1-3 $J^4$ groups, —C₀-C₃alkylene-C₃-C₆cycloalkenyl optionally substituted with 1-3 $J^4$ groups, —C₀-C₄alkylene-7-11 membered spirocyclic heterocycloalkyl optionally substituted with 1-3 $J^4$ groups, —C₀-C₃alkylene-4-6 membered heterocycloalkyl optionally substituted with 1-3 $J^4$ groups, and —C₀-C₃alkylene-4-6 membered heterocycloalkenyl optionally substituted with 1-3 $J^4$ groups;

each $J^2$ is independently selected from the group consisting of halogen, C₁-C₃alkyl, C₁-C₃haloalkyl, hydroxy, C₁-C₃hydroxyalkyl, C₁-C₃alkoxy, and —C₁-C₃alkyl-C₁-C₃alkoxy;

each $J^3$ is independently selected from the group consisting of halogen, —C₁-C₃haloalkyl, CN, C₁-C₃alkyl, hydroxy, C₁-C₃hydroxyalkyl, C₁-C₃alkoxy, and —C₁-C₃alkyl-C₁-C₃alkoxy, or two of the optional $J^3$ groups are on different ring carbon atoms and join to form a 1-2 carbon bridge and each $J^4$ is independently selected from the group consisting of halogen, C₁-C₃alkyl, C₁-C₃haloalkyl, hydroxy, C₁-C₃hydroxyalkyl, C₁-C₃alkoxy, —C₁-C₃alkyl-C₁-C₃alkoxy, oxo, and —C₀-C₃alkylene-NR$^a$R$^b$, provided that $J^4$ groups can only include up to two oxo groups and up to one —C₀-C₃alkylene-NR$^a$R$^b$ group.

Embodiment 9 of this disclosure relates to the compound according to any one of Embodiments 1, 2, 3, 4, 4(a), 4(b), 5, 5(a), 5(b), 5(c), 5(d), 5(e), 5(f), or 6, wherein R³ is

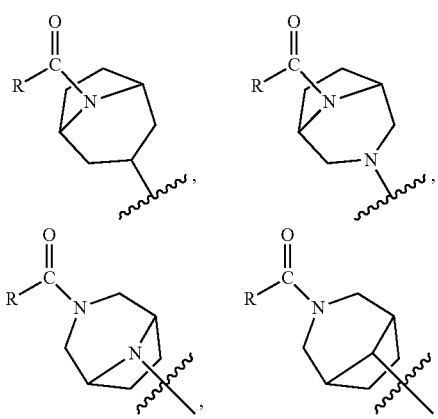

-continued

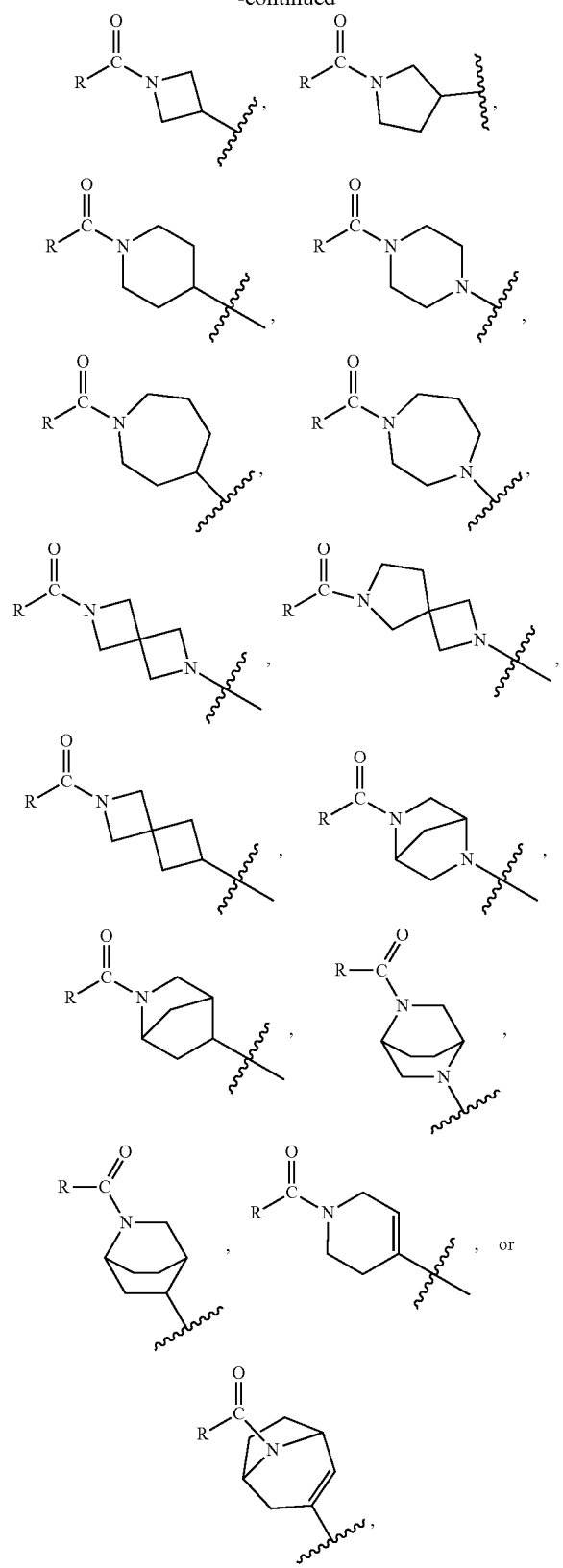

wherein the heterocyclic ring containing at least one nitrogen ring atom of $R^3$ is optionally substituted with 1-3 $J^3$ groups; and each $J^3$ is independently selected from the group consisting of halogen, —$C_1$-$C_3$haloalkyl, CN, $C_1$-$C_3$alkyl, hydroxy, $C_1$-$C_3$hydroxyalkyl, $C_1$-$C_3$alkoxy, and —$C_1$-$C_3$alkyl-$C_1$-$C_3$alkoxy.

Another aspect of Embodiment 9 relates to the compound according to any one of Embodiments 1-6, wherein $R^3$ is

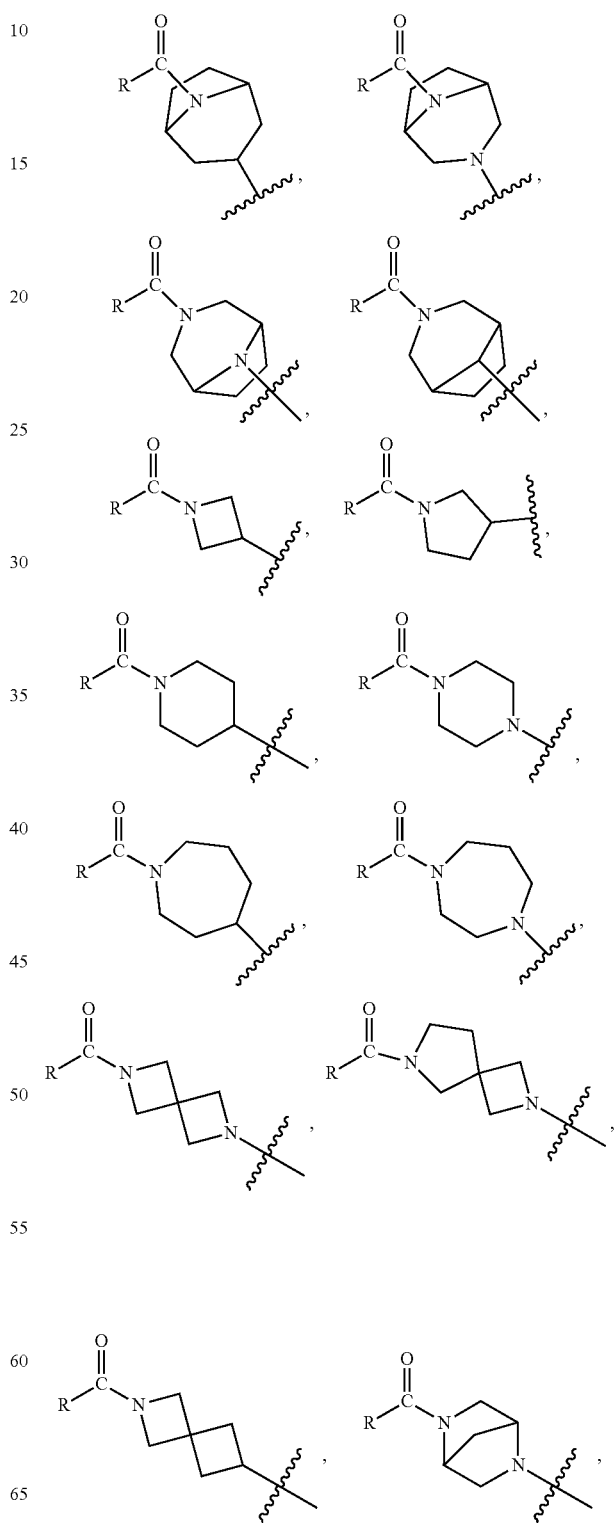

-continued

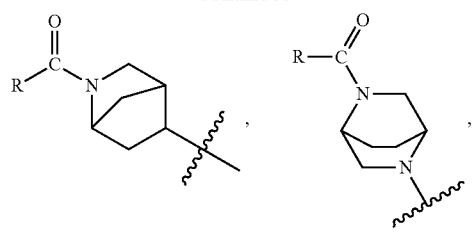

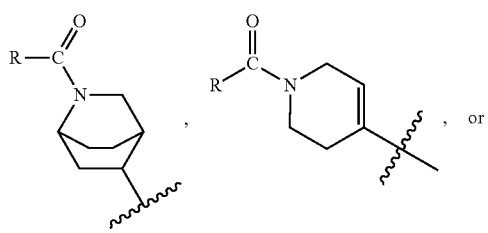

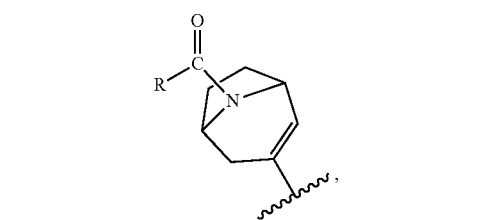

wherein the heterocyclic ring containing at least one nitrogen ring atom of $R^3$ is optionally substituted with 1-3 $J^3$ groups; and each $J^3$ is independently selected from the group consisting of halogen, —$C_1$-$C_3$haloalkyl, CN, $C_1$-$C_3$alkyl, hydroxy, $C_1$-$C_3$hydroxyalkyl, $C_1$-$C_3$alkoxy, and —$C_1$-$C_3$alkyl-$C_1$-$C_3$alkoxy.

Embodiment 9(a) of this disclosure relates to the compound according to Embodiment 9, wherein $R^3$ is

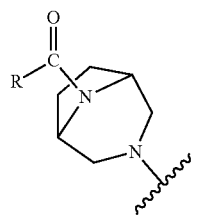

Embodiment 9(b) of this disclosure relates to the compound according to Embodiment 9, wherein $R^3$ is

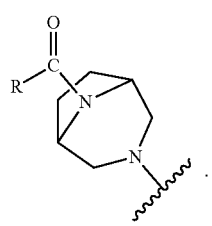

Embodiment 9(c) of this disclosure relates to the compound according to Embodiment 9, wherein $R^3$ is

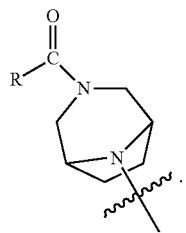

Embodiment 9(d) of this disclosure relates to the compound according to Embodiment 9, wherein $R^3$ is

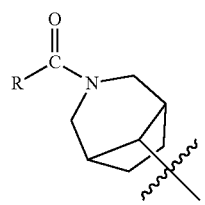

Embodiment 9(e) of this disclosure relates to the compound according to Embodiment 9, wherein $R^3$ is

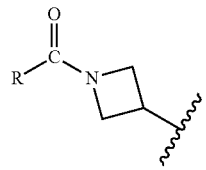

Embodiment 9(f) of this disclosure relates to the compound according to Embodiment 9, wherein $R^3$ is

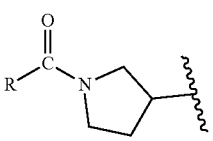

Embodiment 9(g) of this disclosure relates to the compound according to Embodiment 9, wherein $R^3$ is

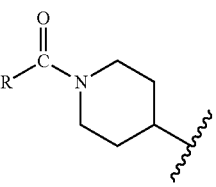

Embodiment 9(h) of this disclosure relates to the compound according to Embodiment 9, wherein R³ is

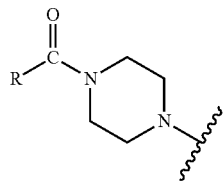

Embodiment 9(i) of this disclosure relates to the compound according to Embodiment 9, wherein R³ is

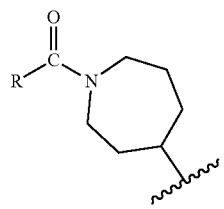

Embodiment 9(j) of this disclosure relates to the compound according to Embodiment 9, wherein R³ is

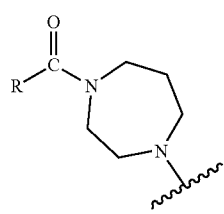

Embodiment 9(k) of this disclosure relates to the compound according to Embodiment 9, wherein R³ is

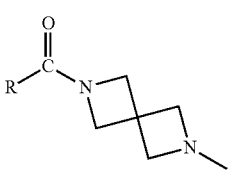

Embodiment 9(l) of this disclosure relates to the compound according to Embodiment 9, wherein R³ is

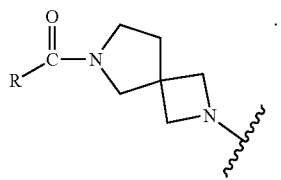

Embodiment 9(m) of this disclosure relates to the compound according to Embodiment 9, wherein R³ is

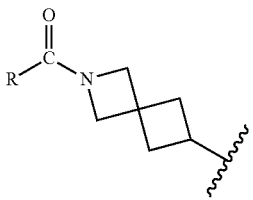

Embodiment 9(n) of this disclosure relates to the compound according to Embodiment 9, wherein R³ is

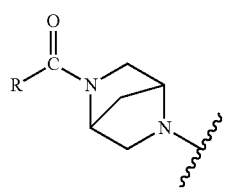

Embodiment 9(o) of this disclosure relates to the compound according to Embodiment 9, wherein R³ is

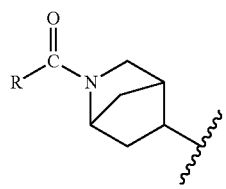

Embodiment 9(p) of this disclosure relates to the compound according to Embodiment 9, wherein R³ is

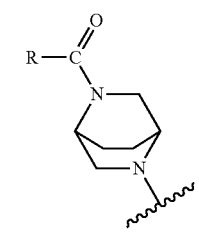

Embodiment 9(q) of this disclosure relates to the compound according to Embodiment 9, wherein R³ is

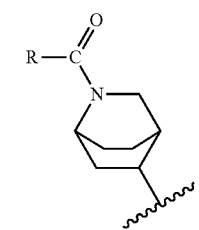

Embodiment 9(s) of this disclosure relates to the compound according to Embodiment 9, wherein $R^3$ is

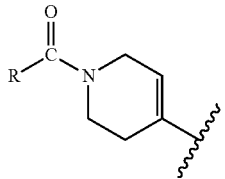

Embodiment 9(t) of this disclosure relates to the compound according to Embodiment 9, wherein $R^3$ is

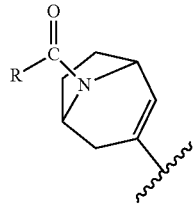

Embodiment 10 of this disclosure relates to the compound according to any one of Embodiments 1-5, wherein G is —X—Y.

Embodiment 11 of this disclosure relates to the compound according to Embodiment 10, wherein X is a 5-10 membered heteroaryl optionally substituted with 1-3 $J^2$ groups and Y is —$C_0$-$C_4$alkylene-N(H)-$L^2$-R.

Embodiment 12 of this disclosure relates to the compound according to any one of Embodiments 1, 2, 3, 4, 4(a), 4(b), 5, 5(a), 5(b), 5(c), 5(d), 5(e), 5(f), 6, 7, 8, 9, 9(a), 9(b), 9(c), 9(d), 9(e), 9(f), 9(g), 9(h), 9(i), 9(j), 9(k), 9(l), 9(m), 9(n), 9(o), 9(p), 9(q), 9(r), 9(s), 9(t), or 11, wherein R is ethenyl optionally substituted with 1-2 groups independently selected from the group consisting of halogen, $C_1$-$C_3$haloalkyl, $C_1$-$C_3$alkyl, —$C_1$-$C_3$alkylene-NR$^a$R$^b$, —$C_1$-$C_3$alkylene-cyano, $C_1$-$C_3$hydroxyalkyl, —$C_1$-$C_3$alkylene-C(O)O—$C_1$-$C_3$alkyl, —$C_1$-$C_3$alkylene-$C_1$-$C_3$alkoxy, —$C_1$-$C_3$alkylene-$C_3$-$C_6$cycloalkyl optionally substituted with 1-3 $J^4$ groups, —$C_1$-$C_3$alkylene-$C_3$-$C_6$cycloalkenyl optionally substituted with 1-3 $J^4$ groups, —$C_1$-$C_3$alkylene-4-6 membered heterocycloalkyl optionally substituted with 1-3 $J^4$ groups, and —$C_1$-$C_3$alkylene-4-6 membered heterocycloalkenyl optionally substituted with 1-3 $J^4$ groups. Another aspect of Embodiment 12 of this disclosure relates to the compound according to any one of Embodiments 1, 2, 3, 4, 4, 5, 6, 7, 8, 9, or 11, wherein R is ethenyl optionally substituted with 1-2 groups independently selected from the group consisting of halogen, $C_1$-$C_3$haloalkyl, $C_1$-$C_3$alkyl, —$C_1$-$C_3$alkylene-NR$^a$R$^b$, —$C_1$-$C_3$alkylene-cyano, $C_1$-$C_3$hydroxyalkyl, —$C_1$-$C_3$alkylene-C(O)O—$C_1$-$C_3$alkyl, —$C_1$-$C_3$alkylene-$C_1$-$C_3$alkoxy, —$C_1$-$C_3$alkylene-$C_3$-$C_6$cycloalkyl optionally substituted with 1-3 $J^4$ groups, —$C_1$-$C_3$alkylene-$C_3$-$C_6$cycloalkenyl optionally substituted with 1-3 $J^4$ groups, —$C_1$-$C_3$alkylene-4-6 membered heterocycloalkyl optionally substituted with 1-3 $J^4$ groups, and —$C_1$-$C_3$alkylene-4-6 membered heterocycloalkenyl optionally substituted with 1-3 $J^4$ groups.

Embodiment 13 of this disclosure relates to the compound according to any one of Embodiments 1, 2, 3, 4, 4(a), 4(b), 5, 5(a), 5(b), 5(c), 5(d), 5(e), 5(f), 6, 7, 8, 9, 9(a), 9(b), 9(c), 9(d), 9(e), 9(f), 9(g), 9(h), 9(i), 9(j), 9(k), 9(l), 9(m), 9(n), 9(o), 9(p), 9(q), 9(r), 9(s), 9(t), or 11, wherein R is

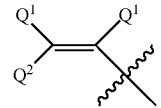

wherein:
each $Q^1$ is independently selected from the group consisting of H, F, and Cl; and
$Q^2$ is i selected from the group consisting of H, $C_1$-$C_6$haloalkyl, $C_1$-$C_6$alkyl, —$C_1$-$C_4$alkylene-NR$^a$R$^b$, —$C_0$-$C_4$alkylene-4-7 membered heterocycloalkyl optionally substituted with 1-3 $J^4$ groups, and —$C_0$-$C_4$alkylene-4-7 membered heterocycloalkenyl optionally substituted with 1-3 $J^4$ groups.

Another aspect of Embodiment 13 of this disclosure relates to the compound according to any one of Embodiments 1-9 or 11, wherein R is

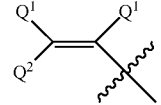

wherein:
each $Q^1$ is independently selected from the group consisting of H, F, and Cl; and
$Q^2$ is selected from the group consisting of H, $C_1$-$C_6$haloalkyl, $C_1$-$C_6$alkyl, —$C_1$-$C_4$alkylene-NR$^a$R$^b$, —$C_0$-$C_4$alkylene-4-7 membered heterocycloalkyl optionally substituted with 1-3 $J^4$ groups, and —$C_0$-$C_4$alkylene-4-7 membered heterocycloalkenyl optionally substituted with 1-3 $J^4$ groups.

Embodiment 13(a) of this disclosure relates to the compound according to Embodiment 13, wherein $Q^2$ is H.

Embodiment 13(b) of this disclosure relates to the compound according to Embodiment 13, wherein $Q^2$ is $C_1$-$C_6$haloalkyl.

Embodiment 13(c) of this disclosure relates to the compound according to Embodiment 13, wherein $Q^2$ is $C_1$-$C_6$alkyl.

Embodiment 13(d) of this disclosure relates to the compound according to Embodiment 13, wherein $Q^2$ is $C_1$-$C_4$alkylene-NR$^a$R$^b$.

Embodiment 13(e) of this disclosure relates to the compound according to Embodiment 13, wherein $Q^2$ is —$C_0$-$C_4$alkylene-4-7 membered heterocycloalkyl optionally substituted with 1-3 $J^4$ groups Embodiment 13(f) of this disclosure relates to the compound according to Embodiment 13, wherein $Q^2$ is —CO—$C_4$alkylene-4-7 membered heterocycloalkenyl optionally substituted with 1-3 $J^4$ groups.

Embodiment 14 of this disclosure relates to the compound according to any one of the preceding Embodiments, wherein $R^2$ is —O-heteroaryl, —O-heterocycloalkyl, —NH-heteroaryl or, —N(H)-heterocycloalkyl, wherein the heteroaryl or heterocycloalkyl moieties are optionally substituted with 1-3 $J^P$ groups.

Embodiment 15 of this disclosure relates to the compound according to one of the preceding Embodiments, wherein $R^2$ is —O-(5-10 membered) heteroaryl containing at least one nitrogen atom and optionally substituted with 1-2 $J^1$ groups.

Embodiment 16 of this disclosure relates to the compound according to any one of the preceding Embodiments, wherein $R^2$ is

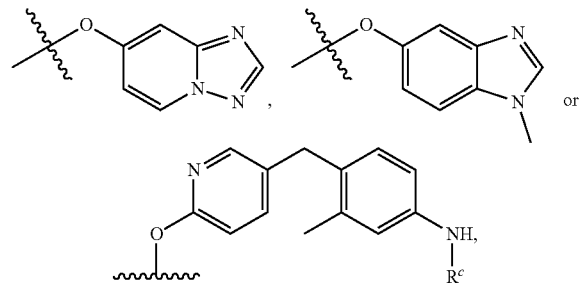

each of which is optionally substituted with 1-2 $J^1$ groups.

Embodiment 17 of this disclosure relates to the compound according to any one of the preceding Embodiments, wherein $R^2$ is

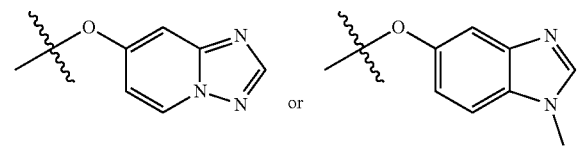 [SMILES: *Oc1ccn2ncnc2c1 ; *Oc1ccc2c(c1)ncn2C]

each of which is optionally substituted with 1-2 $J^1$ groups, wherein:
each $J^1$ is independently selected from the group consisting of halogen, $C_1$-$C_3$alkyl, $C_1$-$C_3$haloalkyl, hydroxy, $C_1$-$C_3$hydroxyalkyl, —$C_0$-$C_3$alkylene-N(H)$R^c$, $C_1$-$C_6$alkoxy, and —$C_1$-$C_6$alkyl-$C_1$-$C_6$alkoxy; and
$R^c$ is selected from the group consisting of H, $C_1$-$C_6$alkyl, $C_1$-$C_3$haloalkyl, $C_1$-$C_3$hydroxyalkyl, —$C_1$-$C_6$alkyl-$C_1$-$C_6$alkoxy, $C_3$-$C_7$cycloalkyl, 4-7 membered heterocycloalkyl, 6-10 membered aryl, and 5-10 membered heteroaryl, wherein the $C_3$-$C_7$cycloalkyl, 4-7 membered heterocycloalkyl, 6-10 membered aryl, and 5-10 membered heteroaryl groups are each optionally substituted with 1-3 groups selected from the group consisting of halogen, $C_1$-$C_6$alkyl, $C_1$-$C_6$alkoxy and $C_1$-$C_6$alkoxy-$C_1$-$C_6$alkyl.

Embodiment 18 of this disclosure relates to the compound according to any one of the preceding Embodiments, wherein $R^2$ is

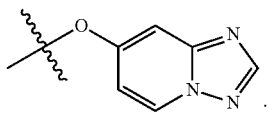 [SMILES: *Oc1ccn2ncnc2c1]

Embodiment 19 of this disclosure relates to the compound according to Embodiment 1 having one of the following formulae:

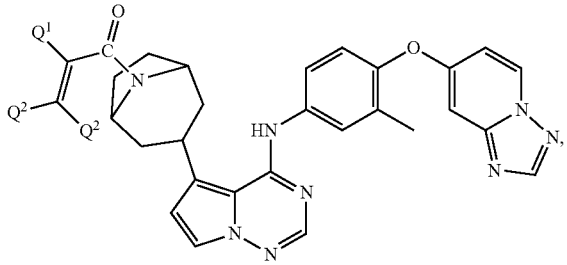

(IVa)

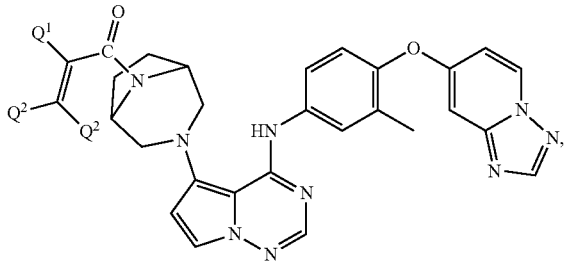

(IVb)

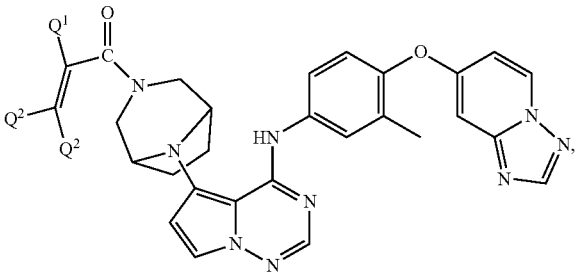

(IVc)

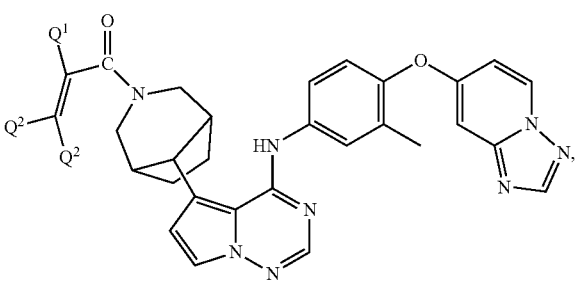

(IVd)

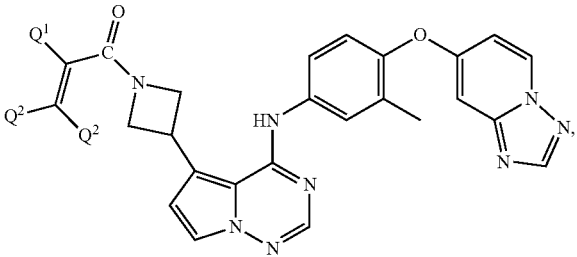

(IVe)

(IVf)
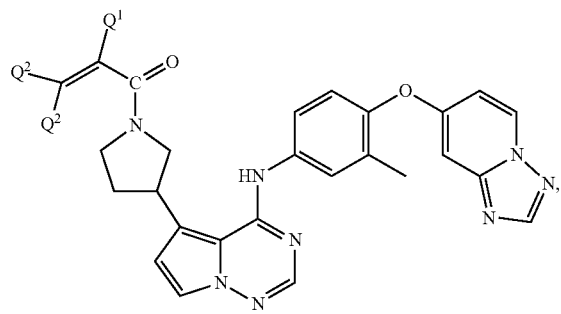
(IVg)
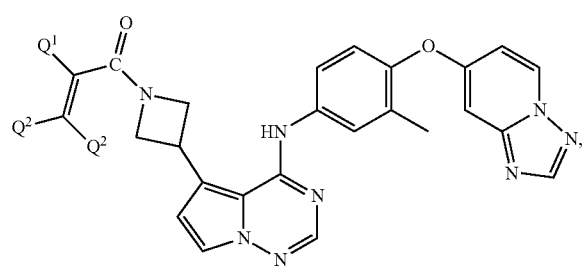
(IVh)
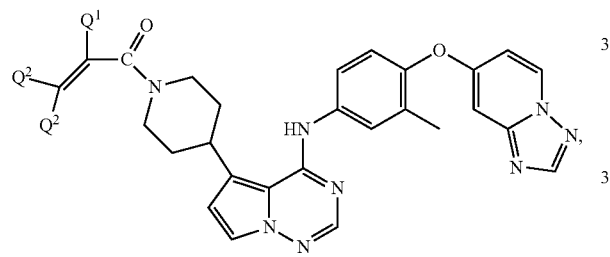
(IVi)
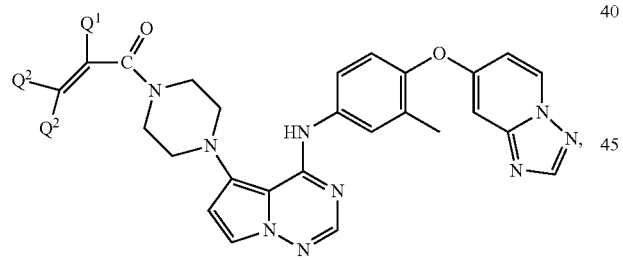
(IVj)
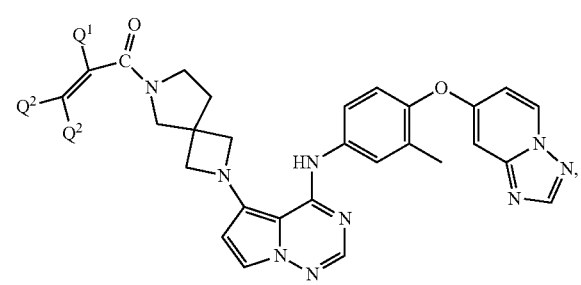
(IVk)
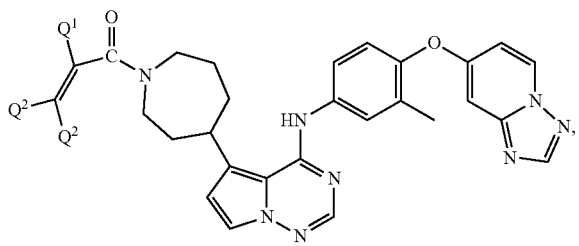
(IVl)
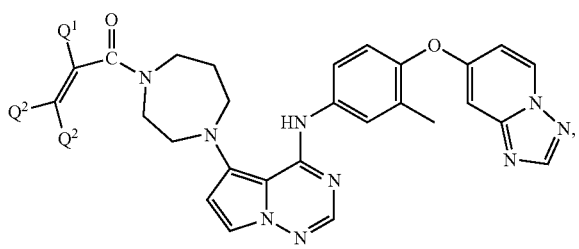
(IVm)
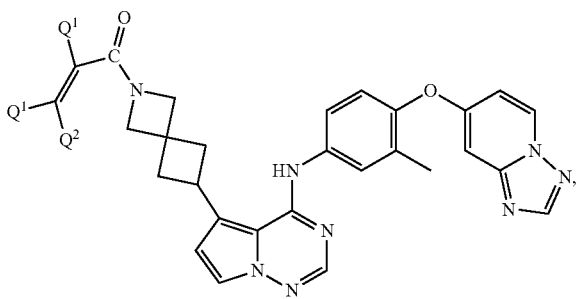
(IVn)
(IVo)
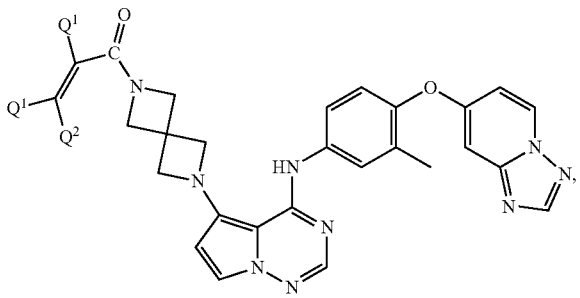

(IVp)

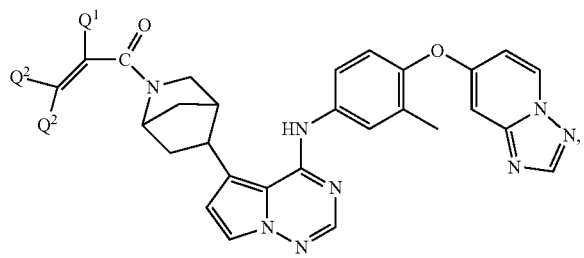

or a pharmaceutically acceptable salt, a tautomer, a stereoisomer, or a deuterated analog thereof, wherein:

each $Q^1$ is independently selected from the group consisting of H, F, and Cl; and $Q^2$ is independently selected from the group consisting of H, $C_1$-$C_6$haloalkyl, $C_1$-$C_6$alkyl, —$C_1$-$C_3$alkylene-$NR^aR^b$, —$C_0$-$C_3$alkylene-4-7 membered heterocycloalkyl optionally substituted with 1-3 $J^4$ groups, and —$C_0$-$C_3$alkylene-4-7 membered heterocycloalkenyl optionally substituted with 1-3 $J^4$ groups or a pharmaceutically acceptable salt, a tautomer, a stereoisomer, or a deuterated analog thereof, wherein each $Q^1$ is independently selected from the group consisting of H, F, and Cl; and $Q^2$ is independently selected from the group consisting of H, $C_1$-$C_6$haloalkyl, $C_1$-$C_6$alkyl, —$C_1$-$C_3$alkylene-$NR^aR^b$, —$C_0$-$C_3$alkylene-4-7 membered heterocycloalkyl optionally substituted with 1-3 $J^4$ groups, and —CO—$C_3$alkylene-4-7 membered heterocycloalkenyl optionally substituted with 1-3 $J^4$ groups.

Embodiment 20 of this disclosure relates to the compound according to Embodiment 1 having one of the following formulae:

(Va)

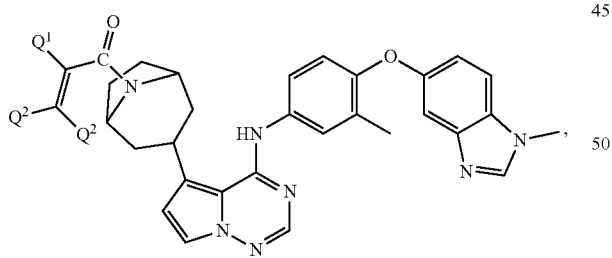

(Vb)

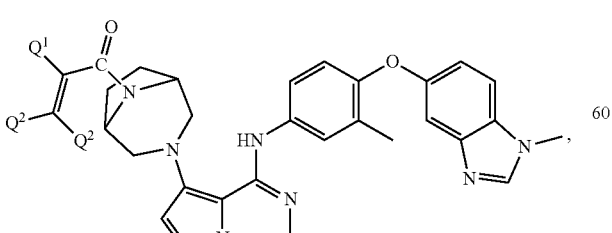

(Vc)

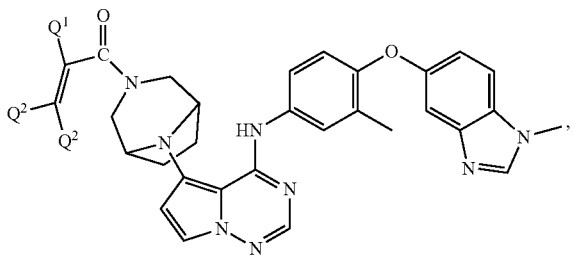

(Vd)

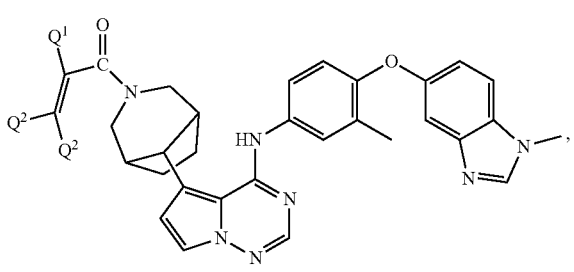

(Ve)

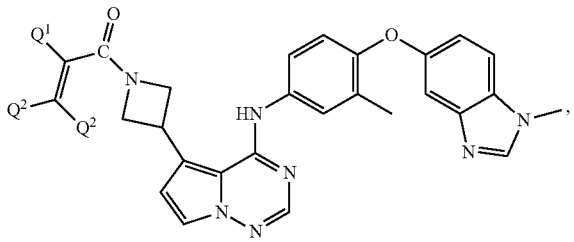

(Vf)

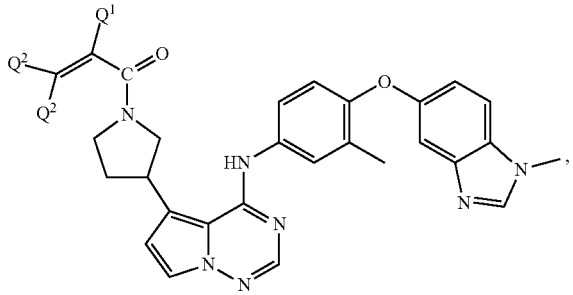

(Vg)

(Vh)
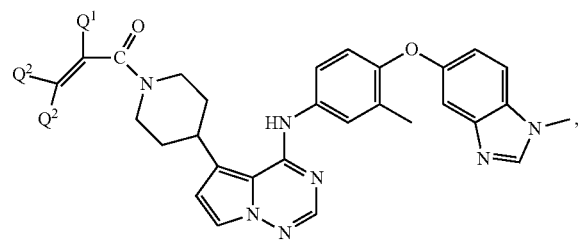
(Vi)
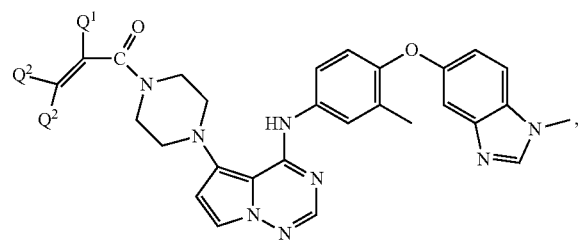
(Vj)
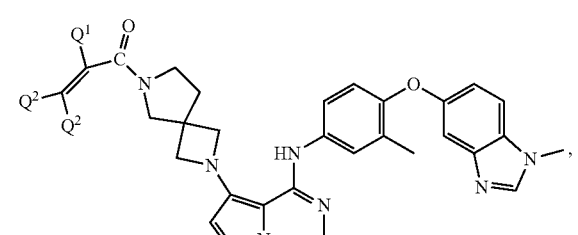
(Vk)
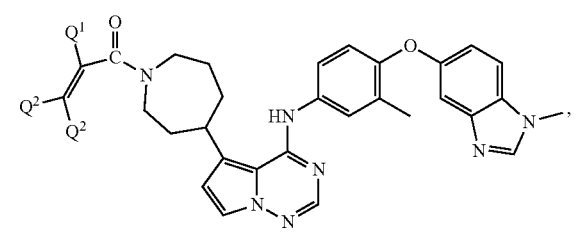
(Vl)
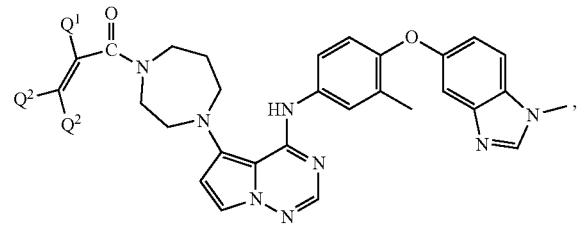
(Vm)
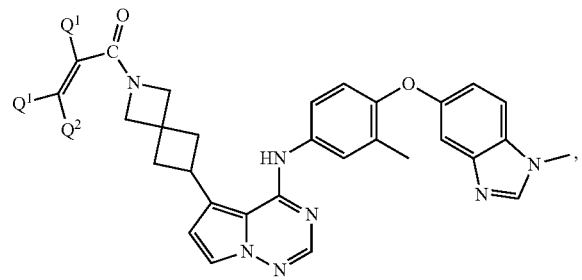
(Vn)
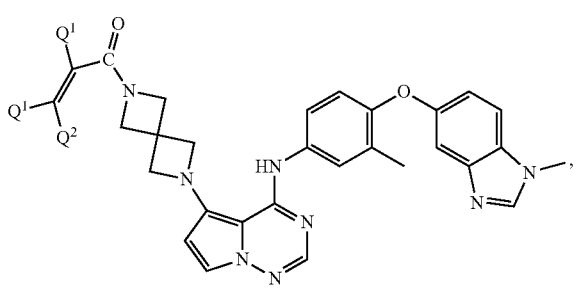
(Vo)
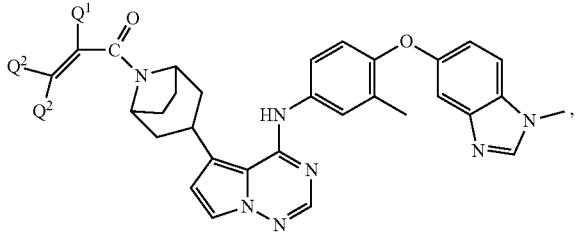
(Vp)
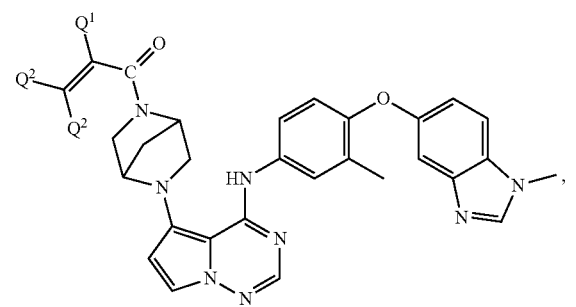
(Vq)
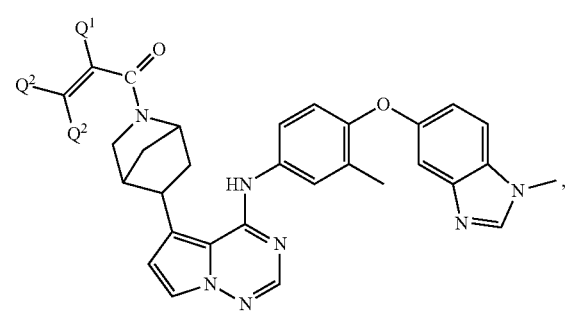
(Vr)
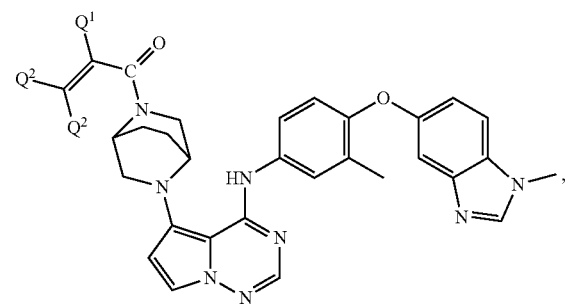

-continued (Vs)

or a pharmaceutically acceptable salt, a tautomer, a stereoisomer, or a deuterated analog thereof, wherein each $Q^1$ is independently selected from the group consisting of H, F, and Cl; and $Q^2$ is selected from the group consisting of H, $C_1$-$C_6$haloalkyl, $C_1$-$C_6$alkyl, —$C_1$-$C_3$alkylene-NR$^a$R$^b$, —$C_0$-$C_3$alkylene-4-7 membered heterocycloalkyl optionally substituted with 1-3 $J^4$ groups, and —$C_0$-$C_3$alkylene-4-7 membered heterocycloalkenyl optionally substituted with 1-3 $J^4$ groups.

Embodiment 21 of this disclosure relates to the compound according to any one of Embodiments 19 or 20, wherein at least one $Q^2$ is H.

Embodiment 22 of this disclosure relates to the compound according to any one of Embodiments 19 or 20, wherein one $Q^2$ is —$C_1$-$C_3$alkylene-NR$^a$R$^b$.

Embodiment 23 of this disclosure relates to the compound according to any one of Embodiments 19 or 20, wherein one $Q^2$ is $C_0$-$C_3$alkylene-4-7 membered heterocycloalkyl optionally substituted with 1-3 $J^4$ groups.

Embodiment 24 of this disclosure relates to the compound according to Embodiment 1 selected from Table 1, or a pharmaceutically acceptable salt thereof.

Other embodiments of this disclosure relate to any one of the preceding embodiments, wherein the compounds are selected from Table 1.

Embodiments P1-P14

Embodiment P1 of this disclosure relates to a compound having Formula (I):

(I)

or a pharmaceutically acceptable salt, a tautomer, a stereoisomer, or a deuterated analog thereof, wherein:
A is N or CH;
$E^1$ is N or C(CN);
$E^2$ is C($R^4$) or N;
$R^1$ is alkyl, haloalkyl or halogen;

$R^2$ is —O-alkyl, —O-aryl, —O-heteroaryl, —O-cycloalkyl, —O-heterocycloalkyl, —NH-alkyl, —NH-aryl, or —NH-heteroaryl, wherein each of the alkyl, aryl, heteroaryl, cycloalkyl or heterocycloalkyl moieties are optionally substituted with 1-4 $J^1$ groups;

or $R^1$ and $R^2$ join with the carbon atoms to which they are attached to form a saturated or unsaturated carbocyclic or heterocyclic ring, wherein the saturated or unsaturated carbocyclic or heterocyclic ring is optionally substituted with 1-4 $J^1$ groups;

G is -$L^1$-$R^3$ or X—Y;

$L^1$ is a bond, —C(O)—, —S(O)$_2$—, alkylene, aryl, heteroaryl, heterocycloalkyl, or cycloalkyl, wherein the alkylene, aryl, heteroaryl, heterocycloalkyl, or cycloalkyl are each optionally substituted with 0-4 $J^2$ groups, provided that when $L^1$ is CH$_2$, $L^1$ is not attached to carbon or nitrogen of a saturated ring;

$R^3$ is a 4-8 membered heterocyclic ring containing at least one nitrogen ring atom, wherein $R^3$ is optionally substituted with 1-4 $J^3$ groups, and wherein one nitrogen atom of $R^3$ is substituted with -$L^2$-R;

or $R^3$ is a 7-11 membered spirocyclic group containing at least one nitrogen ring atom, wherein the 7-11 membered spirocyclic group containing at least one nitrogen ring atom is optionally substituted with 1-4 $J^3$ groups, and wherein one nitrogen atom of the 7-11 membered spirocyclic group is substituted with -$L^2$-R;

X is aryl, heteroaryl, heterocycloalkyl, or cycloalkyl, each of which is optionally substituted with 1-4 $J^2$ groups;

Y is —$C_0$-$C_4$alkylene-N(H)-$L^2$-R, —$C_0$-$C_4$alkylene-O—C(O)—C(H)=CH$_2$, —$C_0$-$C_4$alkylene-O—C(O)-ethynyl, —$C_0$-$C_4$alkylene-C(H)=C(CN)—C(O)—NH$_2$, -4-7 membered heterocycloalkyl-$L^2$R, —$C_0$-$C_4$alkylene-1-yl-1H-pyrrole-2,5-dione, —$C_0$-$C_4$alkylene-C(H)=C(O)—NH$_2$, —$C_0$-$C_4$alkylene-C(H)=C(H)—C(O)—O-alkyl, —$C_0$-$C_4$alkylene-ethynylene-C(O)—O-alkyl, —$C_0$-$C_4$alkylene-C(H)=C(H)—CN, —$C_0$-$C_4$alkylene-N=C=S, —$C_0$-$C_4$-etheyny, —$C_0$-$C_4$alkylene-ethynyl, —$C_0$-$C_4$alkylene-CN, —$C_0$-$C_4$alkylene-C(H)=N—N(H)Boc, —$C_0$-$C_4$alkylene-C(O)—CH$_2$—Br, —$C_0$-$C_4$alkylene-CH$_2$—Cl, —$C_0$-$C_4$alkylene-oxiranyl, —$C_0$-$C_4$alkylene-SH, —$C_0$-$C_4$alkylene-F, and —$C_0$-$C_4$alkylene-C(H)=O, wherein the $C_0$-$C_4$alkylene moiety is optionally substituted with 1-4 groups independently selected from halogen, cycloalkyl, alkoxy alkoxyalkyl, or hydroxy;

$R^4$ is H, halo, alkyl, or —O-alkyl;

$L^2$ is —SO$_2$— or —C(O)—;

R is ethenyl, ethynyl, —CH$_2$—CN, or haloalkyl wherein one halogen of haloalkyl is on the carbon atom adjacent to $L^2$, and wherein the ethenyl and ethynyl are each optionally substituted with 1-3 groups independently selected from the group consisting of halogen, haloalkyl, alkyl, —$C_1$-$C_6$alkylene-NR$^a$R$^b$, cyano, hydroxyalkyl, —$C_1$-$C_6$alkylene-C(O)OH, —$C_1$-$C_6$alkylene-C(O)O-alkyl, alkoxyalkyl, —$C_0$-$C_4$alkylene-cycloalkyl optionally substituted with 0-3 $J^4$ groups, —$C_0$-$C_4$alkylene-cycloalkenyl optionally substituted with 0-3 $J^4$ groups, —$C_0$-$C_4$alkylene-heterocycloalkyl optionally substituted with 0-3 $J^4$ groups, and —$C_0$-$C_4$alkylene-heterocycloalkenyl optionally substituted with 0-3 $J^4$ groups;

or -$L^2$-R is —C=N—OH;

each $J^1$ is independently selected from the group consisting of halogen, alkyl, haloalkyl, hydroxy, hydroxyalkyl, —$C_0$-$C_4$alkylene-N(H)R$^c$, alkoxy, and alkoxyalkyl;

each $J^2$ is independently selected from the group consisting of halogen, alkyl, haloalkyl, hydroxy, hydroxyalkyl, alkoxy, and alkoxyalkyl;

each $J^3$ is independently selected from the group consisting of halogen, haloalkyl, CN, alkyl, hydroxy, hydroxyalkyl, and alkoxy, and alkoxyalkyl, provided that $J^3$ is attached to carbon;

each $J^4$ is independently selected from the group consisting of halogen, alkyl, haloalkyl, hydroxy, hydroxyalkyl, alkoxy, alkoxyalkyl, oxo, and —$C_0$-$C_4$alkylene-$NR^aR^b$, provided that $J^4$ groups can only include up to two oxo groups and up to one —$C_0$-$C_4$alkylene-$NR^aR^b$ group;

$R^a$ and $R^b$ each are independently selected from the group consisting of H, alkyl, haloalkyl, hydroxyalkyl, alkoxyalkyl, and —$C_0$-$C_3$alkylene-alkynyl optionally substituted with alkyl, haloalkyl, hydroxyalkyl, or alkoxyalkyl; and $R^c$ is selected from the group consisting of H, alkyl, haloalkyl, hydroxyalkyl, alkoxyalkyl, cycloalkyl, heterocycloalkyl, aryl, and heteroaryl, wherein the cycloalkyl, heterocycloalkyl, aryl, and heteroaryl groups are each optionally substituted with 1-3 groups selected from the group consisting of halogen, alkyl, alkoxy and alkoxyalkyl.

Embodiment P2 of this disclosure relates to the compound according to Embodiment P1, wherein:

$R^1$ is $C_1$-$C_4$alkyl, $C_1$-$C_4$haloalkyl or halogen;

$R^2$ is —O-(5-10 membered) aryl, —O-(5-10 membered) heteroaryl, —O-(4-7 membered) cycloalkyl, —O-(4-7 membered) heterocycloalkyl, —NH-(5-10 membered) aryl, or —NH-(5-10 membered) heteroaryl, wherein each of the aryl, heteroaryl, cycloalkyl and heterocycloalkyl moieties are optionally substituted with 1-3 $J^1$ groups;

or $R^1$ and $R^2$ join with the carbon atoms to which they are attached to form a ring selected from the group consisting of 5-10 membered aryl, 5-10 membered heteroaryl, 4-7 membered cycloalkyl, and 4-7 membered heterocycloalkyl, wherein each ring is optionally substituted with 1-3 $J^1$ groups;

G is -$L^1$-$R^3$ or X—Y;

$L^1$ is a bond, —C(O)—, —S(O)$_2$—, $C_1$-$C_3$alkylene, 5-10 membered aryl, 5-10 membered heteroaryl, 4-7 membered heterocycloalkyl, or 4-7 membered cycloalkyl, wherein $C_1$-$C_3$alkylene, 5-10 membered aryl, 5-10 membered heteroaryl, 5-7 membered heterocycloalkyl, and 5-7 membered cycloalkyl are each optionally substituted with 0-3 $J^2$ groups, provided that when $L^1$ is CH$_2$, $L^1$ is not attached to carbon or nitrogen of a saturated ring;

$R^3$ is a 4-7 membered heterocyclic ring containing at least one nitrogen ring atom, wherein the 4-7 membered heterocyclic ring containing at least one nitrogen ring atom is optionally substituted with 1-4 $J^3$ groups, and wherein one nitrogen atom of the 4-7 membered heterocyclic ring is substituted with -$L^2$-R;

or $R^3$ is a 7-11 membered spirocyclic group containing at least one nitrogen ring atom, wherein the 7-11 membered spirocyclic group is optionally substituted with 1-4 $J^3$ groups, and wherein one nitrogen atom of $R^3$ is substituted with -$L^2$-R;

X is 5-10 membered aryl, 5-10 membered heteroaryl, 5-7 membered heterocycloalkyl, or 5-7 membered cycloalkyl, wherein the -10 membered aryl, 5-10 membered heteroaryl, 5-7 membered heterocycloalkyl, and 5-7 membered cycloalkyl are optionally substituted with 1-3 $J^2$ groups;

Y is —$C_0$-$C_4$alkylene-N(H)-$L^2$-R, —$C_0$-$C_4$alkylene-O—C(O)—C(H)=CH$_2$, —$C_0$-$C_4$alkylene-O—C(O)-ethynyl, —$C_0$-$C_4$alkylene-C(H)=C(CN)—C(O)—NH$_2$, -4-7 membered heterocycloalkyl-$L^2$R, —$C_0$-$C_4$alkylene-1-yl-1H-pyrrole-2,5-dione, —$C_0$-$C_4$alkylene-C(H)=C(O)—NH$_2$, —$C_0$-$C_4$alkylene-C(H)=C(H)—C(O)—O-alkyl, —$C_0$-$C_4$alkylene-ethynylene-C(O)—O-alkyl, —$C_0$-$C_4$alkylene-C(H)=C(H)—CN, —$C_0$-$C_4$alkylene-N=C=S, —$C_0$-$C_4$etheyny, —$C_0$-$C_4$alkylene-ethynyl, —$C_0$-$C_4$alkylene-CN, —$C_0$-$C_4$alkylene-C(H)=N—N(H)Boc, —$C_0$-$C_4$alkylene-C(O)—CH$_2$—Br, —$C_0$-$C_4$alkylene-CH$_2$—Cl, —$C_0$-$C_4$alkylene-oxiranyl, —$C_0$-$C_4$alkylene-SH, —$C_0$-$C_4$alkylene-F, and —$C_0$-$C_4$alkylene-C(H)=O, wherein the —$C_0$-$C_4$alkylene moiety is optionally substituted with 1-4 groups independently selected from the group consisting of halogen, $C_3$-$C_6$cycloalkyl, $C_1$-$C_6$alkoxy, —$C_1$-$C_6$alkyl-$C_1$-$C_6$alkoxy, or hydroxy;

$R^4$ is H, halo, $C_0$-$C_4$alkyl, or —O—$C_0$-$C_4$alkyl;

$L^2$ is —SO$_2$— or —C(O)—;

R is ethenyl, ethynyl, —CH$_2$—CN, or $C_1$-$C_6$haloalkyl, wherein one halogen of $C_1$-$C_6$haloalkyl is on the carbon atom adjacent to $L^2$, and wherein the ethenyl and ethynyl are each optionally substituted with 1-3 groups independently selected from the group consisting of halogen, $C_1$-$C_6$haloalkyl, $C_1$-$C_6$alkyl, —$C_1$-$C_4$alkylene-$NR^aR^b$, cyano, $C_1$-$C_6$hydroxyalkyl, —$C_1$-$C_6$alkylene-C(O)OH, —$C_1$-$C_6$alkylene-C(O)O—$C_1$-$C_6$alkyl, —$C_1$-$C_4$alkylene-$C_1$-$C_6$alkoxy, —$C_0$-$C_4$alkylene-$C_3$-$C_7$cycloalkyl optionally substituted with 0-3 $J^4$ groups, —$C_0$-$C_4$alkylene-$C_3$-$C_7$cycloalkenyl optionally substituted with 0-3 $J^4$ groups, —$C_0$-$C_4$alkylene-4-7 membered heterocycloalkyl optionally substituted with 0-3 $J^4$ groups, and —$C_0$-$C_4$alkylene-4-7 membered heterocycloalkenyl optionally substituted with 0-3 $J^4$ groups;

or -$L^2$-R is —C=N—OH;

each $J^1$ is independently selected from the group consisting of halogen, $C_1$-$C_6$alkyl, $C_1$-$C_6$haloalkyl, hydroxy, $C_1$-$C_6$hydroxyalkyl, —$C_0$-$C_4$alkylene-N(H)$R^c$, $C_1$-$C_6$alkoxy, and —$C_1$-$C_6$alkyl-$C_1$-$C_6$alkoxy;

each $J^2$ is independently selected from the group consisting of halogen, $C_1$-$C_6$alkyl, $C_1$-$C_6$haloalkyl, hydroxy, $C_1$-$C_6$hydroxyalkyl, $C_1$-$C_6$alkoxy, and —$C_1$-$C_6$alkyl-$C_1$-$C_6$alkoxy;

each $J^3$ is independently selected from the group consisting of halogen, —$C_1$-$C_6$haloalkyl, CN, $C_1$-$C_6$alkyl, hydroxy, $C_1$-$C_6$hydroxyalkyl, $C_1$-$C_6$alkoxy, and —$C_1$-$C_6$alkyl-$C_1$-$C_6$alkoxy, provided that $J^3$ is attached to carbon;

each $J^4$ is independently selected from the group consisting of halogen, $C_1$-$C_6$alkyl, $C_1$-$C_6$haloalkyl, hydroxy, $C_1$-$C_6$hydroxyalkyl, $C_1$-$C_6$alkoxy, —$C_1$-$C_6$alkyl-$C_1$-$C_6$alkoxy, oxo, and —$C_0$-$C_4$alkylene-$NR^aR^b$, provided that $J^4$ groups can only include up to two oxo groups and up to one —$C_0$-$C_4$alkylene-$NR^aR^b$ group;

$R^a$ and $R^b$ each are independently selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, and $C_0$-$C_3$alkylene-$C_2$-$C_6$alkynyl optionally substituted with alkyl, $C_1$-$C_6$haloalkyl, $C_1$-$C_6$hydroxyalkyl, or —$C_1$-$C_6$alkoxy $C_1$-$C_6$alkyl; and $R^c$ is selected from the group consisting of H, $C_1$-$C_6$alkyl, $C_1$-$C_6$haloalkyl, $C_1$-$C_6$hydroxyalkyl, —$C_1$-$C_6$alkyl- C₁-C₆alkoxy, C₃-C₇cycloalkyl, 4-7 membered heterocycloalkyl, 6-10 membered aryl, and 5-10 membered heteroaryl, wherein the C₃-C₇cycloalkyl, 4-7 membered heterocycloalkyl, 6-10 membered aryl, and 5-10 membered heteroaryl groups are each optionally substituted with 1-3 groups selected from the group consisting of halogen, C₁-C₆alkyl, C₁-C₆alkoxy and C₁-C₆alkoxy-C₁-C₆alkyl.

Embodiment P3 of this disclosure relates to the compound according to any one of Embodiments P1 or P2 having one of the following formulae:

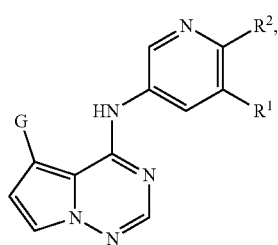
(IIa)

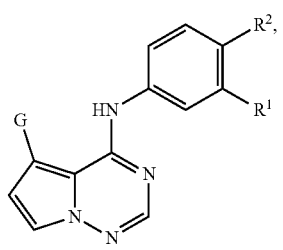
(IIb)

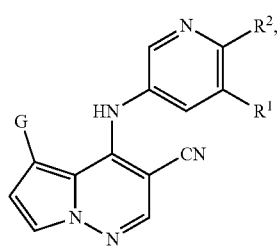
(IIc)

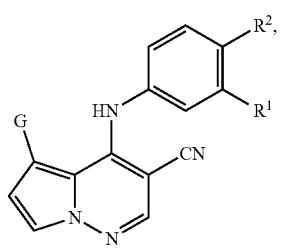
(IId)

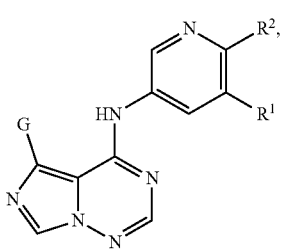
(IIe)

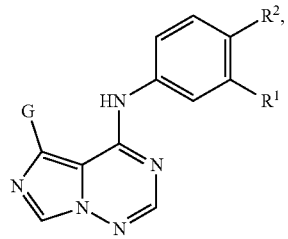
(IIf)

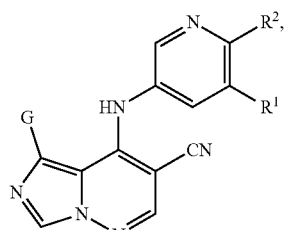
(IIg)

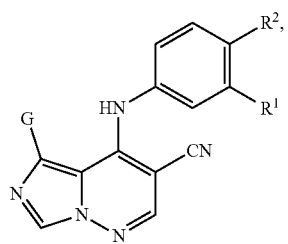
(IIh)

or a pharmaceutically acceptable salt, a tautomer, a stereoisomer, or a deuterated analog of any of the above compounds.

Embodiment P4 of this disclosure relates to Embodiment P3 having Formula (IIa) or (IIb), or a pharmaceutically acceptable salt, a tautomer, a stereoisomer, or a deuterated analog of Formula (IIa) or (IIb).

Embodiment P5 of this disclosure relates to the compound according to any one of Embodiments P1-P5 wherein G is -L¹-R³.

Embodiment P6 of this disclosure relates to the compound according to any one of the preceding embodiments wherein R³ is

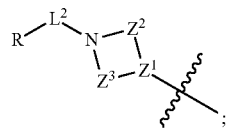
;

wherein:

L¹ is a bond, —C(O)—, —S(O)₂—, C₁-C₃alkylene, phenyl, 5-6 membered heteroaryl, 4-6 membered heterocycloalkyl, or 4-6 membered cycloalkyl, wherein C₁-C₂alkylene, phenyl, 5-6 membered heteroaryl, 4-6 membered heterocycloalkyl, or 4-6 membered cycloalkyl are each optionally substituted with 0-2 J² groups, provided that when L¹ is CH₂, Z¹ is not CH₂ or N;

L² is —SO₂— or —C(O)—;

Z¹ is —N(H)—, —C(R⁵)—, or a 4-7 membered spiro group optionally containing 1-2 nitrogen atoms;

R⁵ is H, halogen, C₁-C₃alkyl or CN;

$Z^2$ and $Z^3$ are each independently —$C_1$-$C_3$alkylene or —$C_2$-$C_3$alkenylene, wherein —$C_1$-$C_3$alkylene and -2-$C_3$alkenylene are each optionally substituted with 1-4 $J^3$ groups;

R is ethenyl, ethynyl, —$CH_2$—CN, or $C_1$-$C_4$haloalkyl, wherein one halogen of $C_1$-$C_4$haloalkyl is on the carbon atom adjacent to $L^2$, and wherein the ethenyl and ethynyl are optionally substituted with 1-3 groups each of which is independently selected from the group consisting of halogen, $C_1$-$C_4$haloalkyl, $C_1$-$C_4$alkyl, —$C_1$-$C_4$alkylene-$NR^aR^b$, —$C_1$-$C_4$alkylene-cyano, $C_1$-$C_4$hydroxyalkyl, —$C_1$-$C_4$alkylene-C(O)OH, —$C_1$-$C_4$alkylene-C(O)O—$C_1$-$C_4$alkyl, —$C_1$-$C_3$alkylene-$C_1$-$C_4$alkoxy, —$C_0$-$C_4$alkylene-$C_3$-$C_7$cycloalkyl optionally substituted with 0-3 $J^4$ groups, —$C_0$-$C_4$alkylene-$C_3$-$C_7$cycloalkenyl optionally substituted with 0-3 $J^4$ groups, —$C_0$-$C_4$alkylene-4-7 membered heterocycloalkyl optionally substituted with 0-3 $J^4$ groups, and —$C_0$-$C_4$alkylene-4-7 membered heterocycloalkenyl optionally substituted with 0-3 $J^4$ groups;

each $J^2$ is independently selected from the group consisting of halogen, $C_1$-$C_4$alkyl, $C_1$-$C_4$haloalkyl, hydroxy, $C_1$-$C_4$hydroxyalkyl, $C_1$-$C_4$alkoxy, and —$C_1$-$C_4$alkyl-$C_1$-$C_4$alkoxy;

each $J^3$ is independently selected from the group consisting of halogen, —$C_1$-$C_4$haloalkyl, CN, $C_1$-$C_4$alkyl, hydroxy, $C_1$-$C_4$hydroxyalkyl, $C_1$-$C_4$alkoxy, and —$C_1$-$C_4$alkyl-$C_1$-$C_4$alkoxy, provided that $J^3$ is attached to carbon; and each $J^4$ is independently selected from the group consisting of halogen, $C_1$-$C_4$alkyl, $C_1$-$C_4$haloalkyl, hydroxy, $C_1$-$C_4$hydroxyalkyl, $C_1$-$C_4$alkoxy, —$C_1$-$C_4$alkyl-$C_1$-$C_4$alkoxy, oxo, and —$C_0$-$C_4$alkylene-$NR^aR^b$, provided that $J^4$ groups can only include up to two oxo groups and up to one —$C_0$-$C_4$alkylene-$NR^aR^b$ group.

Embodiment P7 of this disclosure relates to the compound according to Embodiment P6, wherein $R^3$ is

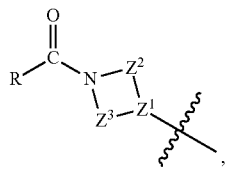

wherein:
$Z^1$ is —N(H)—, —$C(R^5)$—, or a 4-6 membered spiro group optionally containing 1-2 nitrogen atoms;
$R^5$ is H, halogen, $C_1$-$C_3$alkyl or CN;
$Z^2$ is —$C_1$-$C_3$alkylene or —$C_2$-$C_3$alkenylene, each of which is optionally substituted with 1-2 $J^3$ groups;
$Z^3$ is —$C_1$-$C_2$alkylene optionally substituted with 1-2 $J^3$ groups;
R is ethenyl, ethynyl, —$CH_2$—CN, or $C_1$-$C_3$haloalkyl, wherein one halogen of $C_1$-$C_3$haloalkyl is on the carbon atom adjacent to —C(O)—, and wherein the ethenyl and ethynyl are optionally substituted with 1-3 groups each of which is independently selected from the group consisting of halogen, $C_1$-$C_3$haloalkyl, $C_1$-$C_3$alkyl, —$C_1$-$C_3$alkylene-$NR^aR^b$, —$C_1$-$C_3$alkylene-cyano, $C_1$-$C_3$hydroxyalkyl, —C(O)OH, —$C_1$-$C_3$alkylene-C(O)O—$C_1$-$C_3$alkyl, —$C_0$-$C_3$alkylene-$C_1$-$C_3$alkoxy, —$C_0$-$C_3$alkylene-$C_3$-$C_6$cycloalkyl optionally substituted with 0-3 $J^4$ groups, —CO—$C_3$alkylene-$C_3$-$C_6$cycloalkenyl optionally substituted with 0-3 $J^4$ groups, —$C_0$-$C_3$alkylene-4-6 membered heterocycloalkyl optionally substituted with 0-3 $J^4$ groups, and —$C_0$-$C_3$alkylene-4-6 membered heterocycloalkenyl optionally substituted with 0-3 $J^4$ groups;

each $J^2$ is independently selected from the group consisting of halogen, $C_1$-$C_3$alkyl, $C_1$-$C_3$haloalkyl, hydroxy, $C_1$-$C_3$hydroxyalkyl, $C_1$-$C_3$alkoxy, and —$C_1$-$C_3$alkyl-$C_1$-$C_3$alkoxy;

each $J^3$ is independently selected from the group consisting of halogen, —$C_1$-$C_3$haloalkyl, CN, $C_1$-$C_3$alkyl, hydroxy, $C_1$-$C_3$hydroxyalkyl, $C_1$-$C_3$alkoxy, and —$C_1$-$C_3$alkyl-$C_1$-$C_3$alkoxy, provided that $J^3$ is attached to carbon; and each $J^4$ is independently selected from the group consisting of halogen, $C_1$-$C_3$alkyl, $C_1$-$C_3$haloalkyl, hydroxy, $C_1$-$C_3$hydroxyalkyl, $C_1$-$C_3$alkoxy, —$C_1$-$C_3$alkyl-$C_1$-$C_3$alkoxy, oxo, and —$C_0$-$C_3$alkylene-$NR^aR^b$, provided that $J^4$ groups can only include up to two oxo groups and up to one —$C_0$-$C_3$alkylene-$NR^aR^b$ group.

Embodiment P8 of this disclosure relates to a compound according to any one of Embodiments P1-P7, wherein R is ethenyl optionally substituted with 1-2 groups independently selected from the group consisting of halogen, $C_1$-$C_3$haloalkyl, $C_1$-$C_3$alkyl, —$C_1$-$C_3$alkylene-$NR^aR^b$, —$C_1$-$C_3$alkylene-cyano, $C_1$-$C_3$hydroxyalkyl, —$C_1$-$C_3$alkylene-C(O)O—$C_1$-$C_3$alkyl, —$C_1$-$C_3$alkylene-$C_1$-$C_3$alkoxy, —$C_1$-$C_3$alkylene-$C_3$-$C_6$cycloalkyl optionally substituted with 0-3 $J^4$ groups, —$C_1$-$C_3$alkylene-$C_3$-$C_6$cycloalkenyl optionally substituted with 0-3 $J^4$ groups, —$C_1$-$C_3$alkylene-4-6 membered heterocycloalkyl optionally substituted with 0-3 J groups, and —$C_1$-$C_3$alkylene-4-6 membered heterocycloalkenyl optionally substituted with 0-3 $J^4$ groups.

Embodiment P9 of this disclosure relates to a compound according to any one of Embodiments P1-P4, wherein G is —X—Y.

Embodiment P10 of this disclosure relates to a compound according to any one of Embodiments P1-P4 and P9, wherein is X is a 5-10 membered heteroaryl optionally substituted with 1-3 $J^2$ groups and Y is —$C_0$-$C_4$alkylene-N(H)-$L^2$-R, Embodiment P11 of this disclosure relates to a compound according to any one of Embodiments P1-P10, wherein $R^2$ is —O-heteroaryl, —O-heterocycloalkyl, —NH-heteroaryl or, —N(H)-heterocycloalkyl, wherein the heteroaryl or heterocycloalkyl moieties are optionally substituted with 1-3 $J^1$ groups.

Embodiment P12 of this disclosure relates to a compound according to any one of Embodiments P1-P11, wherein $R^2$ is —O-(5-10 membered) heteroaryl containing at least one nitrogen atom and optionally substituted with 1-2 $J^1$ groups.

Embodiment P13 of this disclosure relates to a compound according to any one of Embodiments P1-P12, wherein $R^2$ is

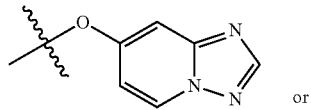

or

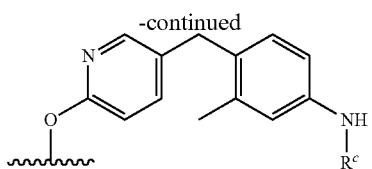

each of which is optionally substituted with 1-2 $J^1$ groups.

Embodiment P14 of this disclosure relates to a compound according to any one of Embodiments P1-P13, wherein $R^2$ is

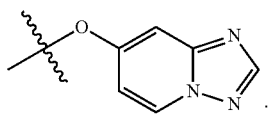 [SMILES: *Oc1ccn2ncnc2c1]

Embodiment 101 of this disclosure relates to a compound of Formula (I):

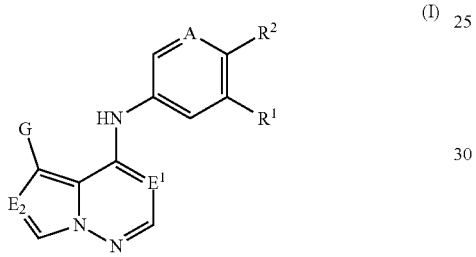

or a pharmaceutically acceptable salt, a tautomer, a stereoisomer, or a deuterated analog thereof, wherein:

A is N or CH;
$E^1$ is N or C(CN);
$E^2$ is C($R^4$) or N;
$R^1$ is alkyl, haloalkyl or halogen;
$R^2$ is —O-alkyl, —O-aryl, —O-heteroaryl, —O-cycloalkyl, —O-heterocycloalkyl, —NH-alkyl, —NH-aryl, or —NH-heteroaryl, wherein each of the alkyl, aryl, heteroaryl, cycloalkyl or heterocycloalkyl moieties are optionally substituted with 1-4 J, groups;
or $R^1$ and $R^2$ join with the carbon atoms to which they are attached to form a saturated or unsaturated carbocyclic or heterocyclic ring, wherein the saturated or unsaturated carbocyclic or heterocyclic ring is optionally substituted with 1-4 $J^1$ groups;
G is -$L^1$-$R^3$ or X—Y;
L is a bond, —C(O)—, —S(O)$_2$—, alkylene, aryl, heteroaryl, heterocycloalkyl, or cycloalkyl, wherein the alkylene, aryl, heteroaryl, heterocycloalkyl, or cycloalkyl are each optionally substituted with 0-4 $J^2$ groups, provided that when $L^1$ is CH$_2$, $L^1$ is not attached to carbon or nitrogen of a saturated ring;
$R^3$ is a 4-8 membered heterocyclic ring containing at least one nitrogen ring atom, wherein $R^3$ is optionally substituted with 1-4 $J^3$ groups, and wherein one nitrogen atom of $R^3$ is substituted with -$L^2$-R;
or $R^3$ is a 7-11 membered spirocyclic group containing at least one nitrogen ring atom, wherein the 7-11 membered spirocyclic group containing at least one nitrogen ring atom is optionally substituted with 1-4 $J^3$ groups, and wherein one nitrogen atom of the 7-11 membered spirocyclic group is substituted with -$L^2$-R;

X is aryl, heteroaryl, heterocycloalkyl, or cycloalkyl, each of which is optionally substituted with 1-4 $J^2$ groups;

Y is —$C_0$-$C_4$alkylene-N(H)-$L^2$-R, —$C_0$-$C_4$alkylene-O—C(O)—C(H)=CH$_2$, —$C_0$-$C_4$alkylene-O—C(O)-ethynyl, —$C_0$-$C_4$alkylene-C(H)=C(CN)—C(O)—NH$_2$, —$C_0$-$C_4$alkylene-1-yl-1H-pyrrole-2,5-dione, —$C_0$-$C_4$alkylene-C(H)=C(O)—NH$_2$, —$C_0$-$C_4$alkylene-C(H)=C(H)—C(O)—O-alkyl, —$C_0$-$C_4$alkylene-ethynylene-C(O)—O-alkyl, —$C_0$-$C_4$alkylene-C(H)=C(H)—CN, —$C_0$-$C_4$alkylene-N=C=S, —$C_0$-$C_4$-etheyny, —$C_0$-$C_4$alkylene-ethynyl, —$C_0$-$C_4$alkylene-CN, —$C_0$-$C_4$alkylene-C(H)=N—N(H)Boc, —$C_0$-$C_4$alkylene-C(O)—CH$_2$—Br, —$C_0$-$C_4$alkylene-CH$_2$—Cl, —$C_0$-$C_4$alkylene-oxiranyl, —$C_0$-$C_4$alkylene-SH, —$C_0$-$C_4$alkylene-F, and —$C_0$-$C_4$alkylene-C(H)=O, wherein the $C_0$-$C_4$alkylene moiety is optionally substituted with 1-4 groups independently selected from halogen, cycloalkyl, alkoxy alkoxyalkyl, or hydroxy;

$R^4$ is H, alkyl, or —O-alkyl;
$L^2$ is —SO$_2$— or —C(O)—;
R is ethenyl, ethynyl, —CH$_2$—CN, or haloalkyl wherein one halogen of haloalkyl is on the carbon atom adjacent to $L^2$, and wherein the ethenyl and ethynyl are each optionally substituted with 1-3 groups independently selected from the group consisting of halogen, haloalkyl, alkyl, —$C_1$-$C_6$alkylene-NR$^a$R$^b$, cyano, hydroxyalkyl, —$C_1$-$C_6$alkylene-C(O)OH, —$C_1$-$C_6$alkylene-C(O)O-alkyl, alkoxyalkyl, —$C_0$-$C_4$alkylene-cycloalkyl optionally substituted with 0-3 $J^4$ groups, —$C_0$-$C_4$alkylene-cycloalkenyl optionally substituted with 0-3 $J^4$ groups, —$C_0$-$C_4$alkylene-heterocycloalkyl optionally substituted with 0-3 $J^4$ groups, and —$C_0$-$C_4$alkylene-heterocycloalkenyl optionally substituted with 0-3 $J^4$ groups;
or -$L^2$-R is —C=N—OH;

each $J^1$ is independently selected from the group consisting of halogen, alkyl, haloalkyl, hydroxy, hydroxyalkyl, —$C_0$-$C_4$alkylene-N(H)R$^c$, alkoxy, and alkoxyalkyl;

each $J^2$ is independently selected from the group consisting of halogen, alkyl, haloalkyl, hydroxy, hydroxyalkyl, alkoxy, and alkoxyalkyl;

each $J^3$ is independently selected from the group consisting of halogen, haloalkyl, CN, alkyl, hydroxy, hydroxyalkyl, and alkoxy, and alkoxyalkyl, provided that $J^3$ is attached to carbon;

each $J^4$ is independently selected from the group consisting of halogen, alkyl, haloalkyl, hydroxy, hydroxyalkyl, alkoxy, alkoxyalkyl, oxo, and —$C_0$-$C_4$alkylene-NR$^a$R$^b$, provided that $J^4$ groups can only include up to two oxo groups and up to one —$C_0$-$C_4$alkylene-NR$^a$R$^b$ group;

$R^a$ and $R^b$ each are independently selected from the group consisting of H, alkyl, haloalkyl, hydroxyalkyl, alkoxyalkyl, and —$C_0$-$C_3$alkylene-alkynyl optionally substituted with alkyl, haloalkyl, hydroxyalkyl, or alkoxyalkyl; and $R^c$ is selected from the group consisting of H, alkyl, haloalkyl, hydroxyalkyl, alkoxyalkyl, cycloalkyl, heterocycloalkyl, aryl, and heteroaryl, wherein the cycloalkyl, heterocycloalkyl, aryl, and heteroaryl groups are each optionally substituted with 1-3 groups selected from the group consisting of halogen, alkyl, alkoxy and alkoxyalkyl.

Embodiment 102 of this disclosure relates to a compound according to Embodiment 101, wherein:

$R^1$ is $C_1$-$C_4$alkyl, $C_1$-$C_4$haloalkyl or halogen;

$R^2$ is —O-(5-10 membered) aryl, —O-(5-10 membered) heteroaryl, —O-(4-7 membered) cycloalkyl, —O-(4-7 membered) heterocycloalkyl, —NH-(5-10 membered) aryl, or —NH-(5-10 membered) heteroaryl, wherein each of the aryl, heteroaryl, cycloalkyl and heterocycloalkyl moieties are optionally substituted with 1-3 $J^1$ groups;

or $R^1$ and $R^2$ join with the carbon atoms to which they are attached to form a ring selected from the group consisting of 5-10 membered aryl, 5-10 membered heteroaryl, 4-7 membered cycloalkyl, and 4-7 membered heterocycloalkyl, wherein each ring is optionally substituted with 1-3 $J^1$ groups;

G is -$L^1$-$R^3$ or X—Y;

$L^1$ is a bond, —C(O)—, —S(O)$_2$—, $C_1$-$C_3$alkylene, 5-10 membered aryl, 5-10 membered heteroaryl, 4-7 membered heterocycloalkyl, or 4-7 membered cycloalkyl, wherein $C_1$-$C_3$alkylene, 5-10 membered aryl, 5-10 membered heteroaryl, 5-7 membered heterocycloalkyl, and 5-7 membered cycloalkyl are each optionally substituted with 0-3 $J^2$ groups, provided that when $L^1$ is $CH_2$, $L^1$ is not attached to carbon or nitrogen of a saturated ring;

$R^3$ is a 4-7 membered heterocyclic ring containing at least one nitrogen ring atom, wherein the 4-7 membered heterocyclic ring containing at least one nitrogen ring atom is optionally substituted with 1-4 $J^3$ groups, and wherein one nitrogen atom of the 4-7 membered heterocyclic ring is substituted with -$L^2$-R;

or $R^3$ is a 7-11 membered spirocyclic group containing at least one nitrogen ring atom, wherein the 7-11 membered spirocyclic group is optionally substituted with 1-4 $J^3$ groups, and wherein one nitrogen atom of $R^3$ is substituted with -$L^2$-R;

X is 5-10 membered aryl, 5-10 membered heteroaryl, 5-7 membered heterocycloalkyl, or 5-7 membered cycloalkyl, wherein the -10 membered aryl, 5-10 membered heteroaryl, 5-7 membered heterocycloalkyl, and 5-7 membered cycloalkyl are optionally substituted with 1-3 $J^2$ groups;

Y is —$C_0$-$C_4$alkylene-N(H)-$L^2$-R, —$C_0$-$C_4$alkylene-O—C(O)—C(H)=$CH_2$, —$C_0$-$C_4$alkylene-O—C(O)-ethynyl, —$C_0$-$C_4$alkylene-C(H)=C(CN)—C(O)—$NH_2$, —$C_0$-$C_4$alkylene-1-yl-1H-pyrrole-2,5-dione, —$C_0$-$C_4$alkylene-C(H)=C(O)—$NH_2$, —$C_0$-$C_4$alkylene-C(H)=C(H)—C(O)—O— alkyl, —$C_0$-$C_4$alkylene-ethynylene-C(O)—O-alkyl, —$C_0$-$C_4$alkylene-C(H)=C(H)—CN, —$C_0$-$C_4$alkylene-N=C=S, —$C_0$-$C_4$-etheyny, —$C_0$-$C_4$alkylene-ethynyl, —$C_0$-$C_4$alkylene-CN, —$C_0$-$C_4$alkylene-C(H)=N—N(H)Boc, —$C_0$-$C_4$alkylene-C(O)—$CH_2$—Br, —$C_0$-$C_4$alkylene-$CH_2$—Cl, —$C_0$-$C_4$alkylene-oxiranyl, —$C_0$-$C_4$alkylene-SH, —$C_0$-$C_4$alkylene-F, and —$C_0$-$C_4$alkylene-C(H)=O, wherein the —$C_0$-$C_4$alkylene moiety is optionally substituted with 1-4 groups independently selected from the group consisting of halogen, $C_3$-$C_6$cycloalkyl, $C_1$-$C_6$alkoxy —$C_1$-$C_6$alkyl-$C_1$-$C_6$alkoxy, or hydroxy;

$R^4$ is H, $C_0$-$C_4$alkyl, or —O—$C_0$-$C_4$alkyl;

$L^2$ is —$SO_2$— or —C(O)—;

R is ethenyl, ethynyl, —$CH_2$—CN, or $C_1$-$C_6$haloalkyl, wherein one halogen of $C_1$-$C_6$haloalkyl is on the carbon atom adjacent to $L^2$, and wherein the ethenyl and ethynyl are each optionally substituted with 1-3 groups independently selected from the group consisting of halogen, $C_1$-$C_6$haloalkyl, $C_1$-$C_6$alkyl, —$C_1$-$C_4$alkylene-$NR^aR^b$, cyano, $C_1$-$C_6$hydroxyalkyl, —$C_1$-$C_6$alkylene-C(O)OH, —$C_1$-$C_6$alkylene-C(O)O—$C_1$-$C_6$alkyl, —$C_1$-$C_4$alkylene-$C_1$-$C_6$alkoxy, —CO—$C_4$alkylene-$C_3$-$C_7$cycloalkyl optionally substituted with 0-3 $J^4$ groups, —$C_0$-$C_4$alkylene-$C_3$-$C_7$cycloalkenyl optionally substituted with 0-3 $J^4$ groups, —$C_0$-$C_4$alkylene-4-7 membered heterocycloalkyl optionally substituted with 0-3 $J^4$ groups, and —$C_0$-$C_4$alkylene-4-7 membered heterocycloalkenyl optionally substituted with 0-3 $J^4$ groups;

or -$L^2$-R is —C≡N—OH;

each $J^1$ is independently selected from the group consisting of halogen, $C_1$-$C_6$alkyl, $C_1$-$C_6$haloalkyl, hydroxy, $C_1$-$C_6$hydroxyalkyl, —$C_0$-$C_4$alkylene-N(H)$R^c$, $C_1$-$C_6$alkoxy, and —$C_1$-$C_6$alkyl-$C_1$-$C_6$alkoxy;

each $J^2$ is independently selected from the group consisting of halogen, $C_1$-$C_6$alkyl, $C_1$-$C_6$haloalkyl, hydroxy, $C_1$-$C_6$hydroxyalkyl, $C_1$-$C_6$alkoxy, and —$C_1$-$C_6$alkyl-$C_1$-$C_6$alkoxy;

each $J^3$ is independently selected from the group consisting of halogen, —$C_1$-$C_6$haloalkyl, CN, $C_1$-$C_6$alkyl, hydroxy, $C_1$-$C_6$hydroxyalkyl, $C_1$-$C_6$alkoxy, and —$C_1$-$C_6$alkyl-$C_6$-$C_6$alkoxy, provided that $J^3$ is attached to carbon;

each $J^4$ is independently selected from the group consisting of halogen, $C_1$-$C_6$alkyl, $C_1$-$C_6$haloalkyl, hydroxy, $C_1$-$C_6$hydroxyalkyl, $C_1$-$C_6$alkoxy, —$C_1$-$C_6$alkyl-$C_1$-$C_6$alkoxy, oxo, and —$C_0$-$C_4$alkylene-$NR^aR^b$, provided that $J^4$ groups can only include up to two oxo groups and up to one —$C_0$-$C_4$alkylene-$NR^aR^b$ group;

$R^a$ and $R^b$ each are independently selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, and $C_0$-$C_3$alkylene-$C_2$-$C_6$alkynyl optionally substituted with alkyl, $C_1$-$C_6$haloalkyl, $C_1$-$C_6$hydroxyalkyl, or —$C_1$-$C_6$alkoxy $C_1$-$C_6$alkyl; and $R^c$ is selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, $C_3$-$C_7$cycloalkyl, 4-7 membered heterocycloalkyl, 6-10 membered aryl, and 5-10 membered heteroaryl, wherein the $C_3$-$C_7$cycloalkyl, 4-7 membered heterocycloalkyl, 6-10 membered aryl, and 5-10 membered heteroaryl groups are each optionally substituted with 1-3 groups selected from the group consisting of halogen, $C_1$-$C_6$alkyl, $C_1$-$C_6$alkoxy and $C_1$-$C_6$alkoxy-$C_1$-$C_6$alkyl.

Embodiment 103 of this disclosure relates to a compound according to any one of Embodiments 101 or 102 having one of the following formulae:

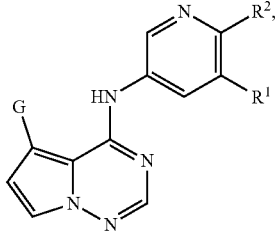
(IIa)

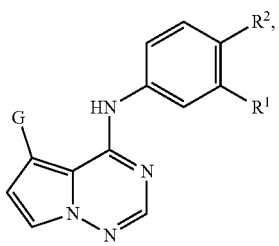
(IIb)

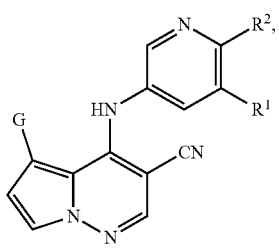
(IIc)

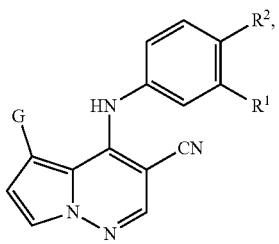
(IId)

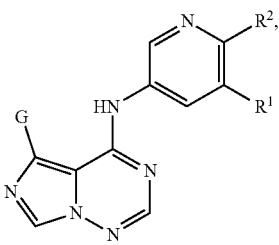
(IIe)

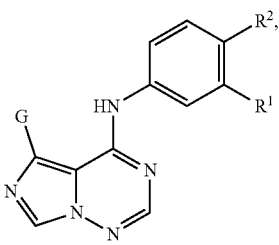
(IIf)

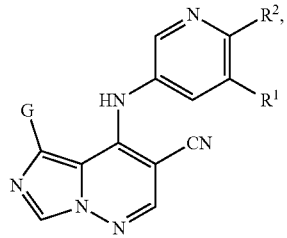
(IIg)

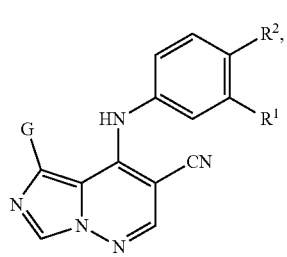
(IIh)

or a pharmaceutically acceptable salt, a tautomer, a stereoisomer, or a deuterated analog of any of the above compounds.

Embodiment 104 of this disclosure relates to a compound according to Embodiment 103 having Formula (IIa) or (IIb), or or a pharmaceutically acceptable salt, a tautomer, a stereoisomer, or a deuterated analog of Formula (IIa) or (IIb).

Embodiment 105 of this disclosure relates to a compound according to any one of the preceding Embodiments wherein G is -$L^1$-$R^3$.

Embodiment 106 of this disclosure relates to a compound according to any one of the preceding Embodiments wherein $R^3$ is

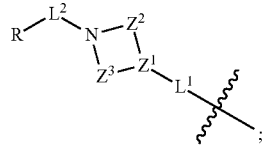

wherein:
$L^1$ is a bond, —C(O)—, —S(O)$_2$—, $C_1$-$C_3$alkylene, phenyl, 5-6 membered heteroaryl, 4-6 membered heterocycloalkyl, or 4-6 membered cycloalkyl, wherein $C_1$-$C_2$alkylene, phenyl, 5-6 membered heteroaryl, 4-6 membered heterocycloalkyl, or 4-6 membered cycloalkyl are each optionally substituted with 0-2 $J^2$ groups, provided that when $L^1$ is CH$_2$, $Z^1$ is not CH$_2$ or N;
$L^2$ is —SO$_2$— or —C(O)—; $Z^1$ is —N(H)—, —C($R^5$)—, or a 4-7 membered spiro group optionally containing 1-2 nitrogen atoms;
$R^5$ is H, halogen, $C_1$-$C_3$alkyl or CN;
$Z^2$ and $Z^3$ are each independently —$C_1$-$C_3$alkylene or —$C_2$-$C_3$alkenylene, wherein —$C_1$-$C_3$alkylene and -2-$C_3$alkenylene are each optionally substituted with 1-4 $J^3$ groups;
R is ethenyl, ethynyl, —CH$_2$—CN, or $C_1$-$C_4$haloalkyl, wherein one halogen of $C_1$-$C_4$haloalkyl is on the carbon atom adjacent to $L^2$, and wherein the ethenyl and ethynyl are optionally substituted with 1-3 groups each of which is independently selected from the group consisting of halogen, $C_1$-$C_4$haloalkyl, $C_1$-$C_4$alkyl, —$C_1$-$C_4$alkylene-NR$^a$R$^b$, —$C_1$-$C_4$alkylene-cyano, $C_1$-$C_4$hydroxyalkyl, —$C_1$-$C_4$alkylene-C(O)OH, —$C_1$-$C_4$alkylene-C(O)O—$C_1$-$C_4$alkyl, —$C_1$-$C_3$alkylene-$C_1$-$C_4$alkoxy, —CO—$C_4$alkylene-$C_3$-$C_7$cycloalkyl optionally substituted with 0-3 $J^4$ groups, —CO—$C_4$alkylene-$C_3$-$C_7$cycloalkenyl optionally substituted with 0-3 $J^4$ groups, —$C_0$-$C_4$alkylene-4-7 membered heterocycloalkyl optionally substituted with 0-3 $J^4$ groups, and —$C_0$-$C_4$alkylene-4-7 membered heterocycloalkenyl optionally substituted with 0-3 $J^4$ groups;

each $J^2$ is independently selected from the group consisting of halogen, $C_1$-$C_4$alkyl, $C_1$-$C_4$haloalkyl, hydroxy, $C_1$-$C_4$hydroxyalkyl, $C_1$-$C_4$alkoxy, and —$C_1$-$C_4$alkyl-$C_1$-$C_4$alkoxy;

each $J^3$ is independently selected from the group consisting of halogen, —$C_1$-$C_4$haloalkyl, CN, $C_1$-$C_4$alkyl, hydroxy, $C_1$-$C_4$hydroxyalkyl, $C_1$-$C_4$alkoxy, and —$C_1$-$C_4$alkyl-$C_1$-$C_4$alkoxy, provided that $J^3$ is attached to carbon; and each $J^4$ is independently selected from the group consisting of halogen, $C_1$-$C_4$alkyl, $C_1$-$C_4$haloalkyl, hydroxy, $C_1$-$C_4$hydroxyalkyl, $C_1$-$C_4$alkoxy, —$C_1$-$C_4$alkyl-$C_1$-$C_4$alkoxy, oxo, and —$C_0$-$C_4$alkylene-NR$^a$R$^b$, provided that $J^4$ groups can only include up to two oxo groups and up to one —$C_0$-$C_4$alkylene-NR$^a$R$^b$ group.

Embodiment 107 of this disclosure relates to a compound according to Embodiment 106, wherein $R^3$ is

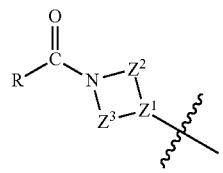

wherein:
$Z^1$ is —N(H)—, —C($R^5$)—, or a 4-6 membered spiro group optionally containing 1-2 nitrogen atoms;
$R^5$ is H, halogen, $C_1$-$C_3$alkyl or CN;
$Z^2$ is —$C_1$-$C_3$alkylene or —$C_2$-$C_3$alkenylene, each of which is optionally substituted with 1-2 $J^3$ groups;
$Z^3$ is —$C_1$-$C_2$alkylene optionally substituted with 1-2 $J^3$ groups;
R is ethenyl, ethynyl, —$CH_2$—CN, or $C_1$-$C_3$haloalkyl, wherein one halogen of $C_1$-$C_3$haloalkyl is on the carbon atom adjacent to —C(O)—, and wherein the ethenyl and ethynyl are optionally substituted with 1-3 groups each of which is independently selected from the group consisting of halogen, $C_1$-$C_3$haloalkyl, $C_1$-$C_3$alkyl, —$C_1$-$C_3$alkylene-NR$^a$R$^b$, —$C_1$-$C_3$alkylene-cyano, $C_1$-$C_3$hydroxyalkyl, —C(O)OH, —$C_1$-$C_3$alkylene-C(O)O—$C_1$-$C_3$alkyl, —$C_0$-$C_3$alkylene-$C_1$-$C_3$alkoxy, —CO—$C_3$alkylene-$C_3$-$C_6$cycloalkyl optionally substituted with 0-3 J groups, —$C_0$-$C_3$alkylene-$C_3$-$C_6$cycloalkenyl optionally substituted with 0-3 $J^4$ groups, —$C_0$-$C_3$alkylene-4-6 membered heterocycloalkyl optionally substituted with 0-3 $J^4$ groups, and —$C_0$-$C_3$alkylene-4-6 membered heterocycloalkenyl optionally substituted with 0-3 $J^4$ groups;

each $J^2$ is independently selected from the group consisting of halogen, $C_1$-$C_3$alkyl, $C_1$-$C_3$haloalkyl, hydroxy, $C_1$-$C_3$hydroxyalkyl, $C_1$-$C_3$alkoxy, and —$C_1$-$C_3$alkyl-$C_1$-$C_3$alkoxy;

each $J^3$ is independently selected from the group consisting of halogen, —$C_1$-$C_3$haloalkyl, CN, $C_1$-$C_3$alkyl, hydroxy, $C_1$-$C_3$hydroxyalkyl, $C_1$-$C_3$alkoxy, and —$C_1$-$C_3$alkyl-$C_1$-$C_3$alkoxy, provided that $J^3$ is attached to carbon; and each $J^4$ is independently selected from the group consisting of halogen, $C_1$-$C_3$alkyl, $C_1$-$C_3$haloalkyl, hydroxy, $C_1$-$C_3$hydroxyalkyl, $C_1$-$C_3$alkoxy, —$C_1$-$C_3$alkyl-$C_1$-$C_3$alkoxy, oxo, and —$C_0$-$C_3$alkylene-NR$^a$R$^b$, provided that $J^4$ groups can only include up to two oxo groups and up to one —$C_0$-$C_3$alkylene-NR$^a$R$^b$ group.

Embodiment 108 of this disclosure relates to a compound according to any one of the preceding Embodiments, wherein R is ethenyl optionally substituted with 1-2 groups independently selected from the group consisting of halogen, $C_1$-$C_3$haloalkyl, $C_1$-$C_3$alkyl, —$C_1$-$C_3$alkylene-NR$^a$R$^b$, —$C_1$-$C_3$alkylene-cyano, $C_1$-$C_3$hydroxyalkyl, —$C_1$-$C_3$alkylene-C(O)O—$C_1$-$C_3$alkyl, —$C_1$-$C_3$alkylene-$C_1$-$C_3$alkoxy, —$C_1$-$C_3$alkylene-$C_3$-$C_6$cycloalkyl optionally substituted with 0-3 $J^4$ groups, —$C_1$-$C_3$alkylene-$C_3$-$C_6$cycloalkenyl optionally substituted with 0-3 $J^4$ groups, —$C_1$-$C_3$alkylene-4-6 membered heterocycloalkyl optionally substituted with 0-3 $J^4$ groups, and —$C_1$-$C_3$alkylene-4-6 membered heterocycloalkenyl optionally substituted with 0-3 $J^4$ groups.

Embodiment 109 of this disclosure relates to a compound according to any one of the preceding Embodiments, wherein G is —X—Y.

Embodiment 110 of this disclosure relates to a compound according to any one of Embodiments 101-104 and 109 wherein is X is a 5-10 membered heteroaryl optionally substituted with 1-3 $J^2$ groups and Y is —$C_0$-$C_4$alkylene-N(H)-$L^1$-R.

Embodiment 111 of this disclosure relates to a compound according to any one of the preceding Embodiments, wherein $R^2$ is —O-heteroaryl, —O-heterocycloalkyl, —NH— heteroaryl or, —N(H)-heterocycloalkyl, wherein the heteroaryl or heterocycloalkyl moieties are optionally substituted with 1-3 $J^1$ groups.

Embodiment 112 of this disclosure relates to a compound according to any one of the preceding Embodiments, wherein $R^2$ is —O-(5-10 membered) heteroaryl containing at least one nitrogen atom and optionally substituted with 1-2 $J^1$ groups.

Embodiment 113 of this disclosure relates to a compound according to any one of the preceding Embodiments, wherein $R^2$ is

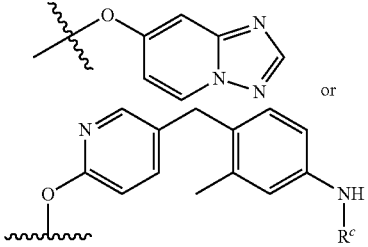

each of which is optionally substituted with 1-2 J groups.

Embodiment 114 of this disclosure relates to a compound according to any one of the preceding Embodiments, wherein $R^2$ is

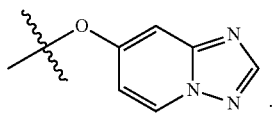 [SMILES: *Oc1ccn2ncnc2c1]

Embodiment 115 of this disclosure relates to a compound selected from Table 1, or a pharmaceutically acceptable salt thereof.

Embodiment 116 of this disclosure relates to a pharmaceutical composition comprising a compound in any one of the preceding Embodiments, and a pharmaceutically acceptable carrier.

Embodiment 117 of this disclosure relates to a pharmaceutical composition of Embodiment 113, further comprising a second pharmaceutical agent.

Embodiment 118 of this disclosure relates to a method for treating a subject with a disease or condition mediated by Her2, said method comprising administering to the subject an effective amount of a compound in any one of Embodiments 1-15, or a pharmaceutically acceptable salt, deuterated analog, a tautomer or a stereoisomer thereof, or a pharmaceutical composition in any one of Embodiments 16-17.

Embodiment 119 of this disclosure relates to a method according to Embodiment 118, wherein the disease or condition is a cancer with a Her2 YVMA insertion mutation.

Embodiment 120 of this disclosure relates to a method for treatment of a disease or condition according to Embodiment 118, wherein the disease or condition is a cancer selected from the group consisting of lung cancer, breast cancer, stomach cancer, ovarian cancer, colon cancer, bladder cancer, lung cancer, uterine cervical cancer, head and neck cancer, gastric and esophageal cancer, and uterine serous endometrial carcinoma.

Embodiment 121 of this disclosure relates to a method for treatment of a disease or condition according to any one of Embodiments 118-120, wherein the disease or condition is non-small lung cancer.

Embodiment 122 of this disclosure relates to a method according to any one of Embodiments 118-121, further comprising administering one or more additional therapeutic agents.

Embodiment 123 of this disclosure relates to a method according to Embodiment 122, wherein the one or more additional therapeutic agents is one or more of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an immune checkpoint agent selected from a PD-1 inhibitor, a PD-L1 inhibitor, and a CTLA4 inhibitor; v) and antibody drug conjugate selected from ado-trastuzumab emtansine and trastuzumab deruxtecan; vi) a hormone or hormone antagonist selected from enzalutamide, abiraterone, anastrozole, androgens, buserelin, diethylstilbestrol, exemestane, flutamide, fulvestrant, goserelin, idoxifene, letrozole, leuprolide, magestrol, raloxifene, tamoxifen, and toremifene; vii) a taxane selected from DJ-927, docetaxel, TPI 287, paclitaxel and DHA-paclitaxel; viii) a retinoid selected from alitretinoin, bexarotene, fenretinide, isotretinoin, and tretinoin; ix) an alkaloid selected from etoposide, homoharringtonine, teniposide, vinblastine, vincristine, vindesine, and vinorelbine; x) an antiangiogenic agent selected from AE-941 (GW786034, Neovastat), ABT-510, 2-methoxyestradiol, lenalidomide, and thalidomide; xi) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xii) a kinase inhibitor selected from erlotinib, gefitinib, flavopiridol, imatinib mesylate, lapatinib, sorafenib, sunitinib malate, 7-hydroxystaurosporine, and vatalanib; xiii) a targeted signal transduction inhibitor selected from bortezomib, geldanamycin, and rapamycin; xiv) a biological response modifier selected from imiquimod, interferon-α and interleukin-2; xv) an IDO inhibitor; xvi) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate, ixabepilone, lonidamine, masoprocol, mitoguanazone, oblimersen, sulindac, testolactone, tiazofurin, an mTOR inhibitor, a PI3K inhibitor, a Cdk4 inhibitor, an Akt inhibitor, a Hsp90 inhibitor, a farnesyltransferase inhibitor and an aromatase inhibitor (anastrozole letrozole exemestane); xvii) a BRAF inhibitor; xviii) a Mek inhibitor; xix) c-Kit mutant inhibitor, xx) an EGFR inhibitor, xxi) an epigenetic modulator; xxii) other adenosine axis blockade agents selected from CD39, CD38, A2AR and A2BR; or xxiii) agonists of TNFA super family member; and xxiv) an anti-ErbB2 mAb.

Embodiment 124 of this disclosure relates to a method according to Embodiment 122, wherein the one or more additional therapeutic agents is ado-trastuzumab emtansine or trastuzumab deruxtecan.

Embodiment 201 of this disclosure relates to a compound of Formula (I):

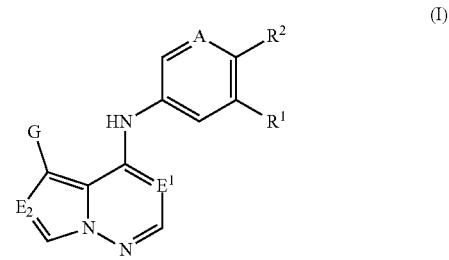

or a pharmaceutically acceptable salt, a tautomer, a stereoisomer, or a deuterated analog thereof, wherein:

A is N or CH;

$E^1$ is N or C(CN);

$E^2$ is C($R^4$) or N;

$R^1$ is alkyl, haloalkyl or halogen;

$R^2$ is —O-alkyl, —O-aryl, —O-heteroaryl, —O-cycloalkyl, —O-heterocycloalkyl, —O— heteroaryl-alkylene-aryl, —NH-alkyl, —NH-aryl, or —NH-heteroaryl, wherein each of the alkyl, aryl, heteroaryl, cycloalkyl or heterocycloalkyl moieties are optionally substituted with 1-4 $J^1$ groups;

or $R^1$ and $R^2$ join with the carbon atoms to which they are attached to form a saturated or unsaturated carbocyclic or heterocyclic ring, wherein the saturated or unsaturated carbocyclic or heterocyclic ring is optionally substituted with 1-4 $J^1$ groups;

G is -$L^1$-$R^3$ or —W—X—Y;

$L^1$ is a bond, —C(O)—, —S(O)$_2$—, —N($R^c$)—, alkylene, aryl, heteroaryl, heterocycloalkyl, or cycloalkyl, wherein the alkylene, aryl, heteroaryl, heterocycloalkyl, or cycloalkyl are each optionally substituted with 1-4 $J^2$ groups, provided that when $L^1$ is CH$_2$, $L^1$ is not attached to carbon or nitrogen of a saturated ring;

$R^3$ is a 4-9 membered heterocyclic ring containing at least one nitrogen ring atom, wherein $R^3$ is optionally substituted with 1-4 $J^3$ groups, and wherein one nitrogen atom of $R^3$ is substituted with -$L^2$-R;

or $R^3$ is a 7-11 membered spirocyclic group containing at least one nitrogen ring atom, wherein the 7-11 membered spirocyclic group containing at least one nitrogen ring atom is optionally substituted with 1-4 $J^3$ groups, and wherein one nitrogen atom of the 7-11 membered spirocyclic group is substituted with -$L^2$-R;

W is a bond, —C(O)— or —S(O)$_2$—;

X is aryl, heteroaryl, heterocycloalkyl, or cycloalkyl, each of which is optionally substituted with 1-4 $J^2$ groups;

Y is —C$_0$-C$_4$alkylene-N($R^d$)-$L^2$-R, —C(O)-4-7 membered heterocycloalkyl containing at least one nitrogen atom and substituted with 1-2 oxo groups, —C$_0$-C$_4$alkylene-1-yl-1H-pyrrole-2,5-dione, —C$_0$-C$_4$alkylene-C(H)=C(O)—NH$_2$, —C$_0$-C$_4$alkylene-C(H)=C(H)—C(O)—O— alkyl, —C$_0$-C$_4$alkylene-ethynylene-C(O)—O-alkyl, —C$_0$-C$_4$alkylene-C(H)=C(H)—CN, —C$_0$-C$_4$alkylene-N=C=S, —C$_0$-C$_4$-etheyny, —C$_0$-C$_4$alkylene-ethynyl, —C$_0$-C$_4$alkylene-CN, —C$_0$-C$_4$alkylene-C(H)=N—N(H)Boc, —C$_0$-C$_4$alkylene-C(O)—CH$_2$—Br, —C$_0$-C$_4$alkylene-CH$_2$—Cl, —C$_0$-C$_4$alkylene-oxiranyl, —C$_0$-C$_4$alkylene-SH, —C$_0$-C$_4$alkylene-F, and —C$_0$-C$_4$alkylene-C(H)=O, wherein the C$_0$-C$_4$alkylene moiety is optionally substituted with 1-4 groups independently selected from halogen, cycloalkyl, alkoxy alkoxyalkyl, or hydroxy;

$R^4$ is H, alkyl, or —O-alkyl;

$L^2$ is —SO$_2$— or —C(O)—;

R is ethenyl optionally substituted with 1-3 Q groups, ethynyl optionally substituted with Q, —CH$_2$—CN, or haloalkyl wherein one halogen of haloalkyl is on the carbon atom adjacent to $L^2$, each Q is independently selected from the group consisting of halogen, haloalkyl, alkyl, alkene, alkyne, —C$_1$-C$_6$alkylene-NR$^a$R$^b$, —C$_1$-C$_6$alkylene-OR$^c$, cyano, hydroxyalkyl, —C$_0$-C$_6$alkylene-C(O)OH, —C$_1$-C$_6$alkylene-C(O)O-alkyl, alkoxyalkyl, —C$_0$-C$_4$alkylene-cycloalkyl optionally substituted with 1-3 $J^4$ groups, —C$_0$-C$_4$alkylene-cycloalkenyl optionally substituted with 1-3 $J^4$ groups, —C$_0$-C$_4$alkylene-7-11 membered spirocyclic cycloalkyl or heterocycloalkyl optionally substituted with 1-3 $J^4$ groups, —C$_0$-C$_4$alkylene-heterocycloalkyl optionally substituted with 1-3 $J^4$ groups, and —C$_0$-C$_4$alkylene-heterocycloalkenyl optionally substituted with 1-3 $J^4$ groups;

or -$L^2$-R is —C=N—OH;

each $J^1$ is independently selected from the group consisting of halogen, alkyl, haloalkyl, hydroxy, hydroxyalkyl, —C$_0$-C$_4$alkylene-N(H)$R^c$, alkoxy, and alkoxyalkyl;

each $J^2$ is independently selected from the group consisting of halogen, alkyl, haloalkyl, hydroxy, hydroxyalkyl, alkoxy, and alkoxyalkyl;

each $J^3$ is attached to a carbon atom and is independently selected from the group consisting of halogen, haloalkyl, CN, alkyl, hydroxy, hydroxyalkyl, alkoxy, and alkoxyalkyl, or two of the optional 1-4 $J^3$ groups form an oxo group or a 3-6 membered spiro group, or two of the optional 1-4 $J^3$ groups are on different ring carbon and join to form a 1-3 carbon bridge;

each $J^4$ is independently selected from the group consisting of halogen, alkyl, haloalkyl, hydroxy, hydroxyalkyl, alkoxy, alkoxyalkyl, oxo, and —C$_0$-C$_4$alkylene-NR$^a$R$^b$, provided that $J^4$ groups can only include up to two oxo groups and up to one —C$_0$-C$_4$alkylene-NR$^a$R$^b$ group;

$R^a$ and $R^b$ each are independently selected from the group consisting of H, alkyl, alkenyl, alkynyl, haloalkyl, hydroxyalkyl, alkoxyalkyl, and —C$_0$-C$_3$alkylene-alkynyl optionally substituted with alkyl, alkenyl, alkynyl, haloalkyl, hydroxyalkyl, or alkoxyalkyl; and $R^c$ is selected from the group consisting of H, alkyl, haloalkyl, hydroxyalkyl, alkoxyalkyl, cycloalkyl, heterocycloalkyl, aryl, and heteroaryl, wherein the cycloalkyl, heterocycloalkyl, aryl, and heteroaryl groups are each optionally substituted with 1-3 groups selected from the group consisting of halogen, alkyl, alkoxy and alkoxyalkyl; and $R^d$ is selected from the group consisting of H, alkyl, and haloalkyl.

Embodiment 202 of this disclosure relates to a compound according to Embodiment 201, wherein:

$R^1$ is C$_1$-C$_4$alkyl, C$_1$-C$_4$haloalkyl or halogen;

$R^2$ is —O-(5-10 membered) aryl, —O-(5-10 membered) heteroaryl, —O-(4-7 membered) cycloalkyl, —O-(4-7 membered) heterocycloalkyl, —O-(5-10 membered) heteroaryl-C$_1$-C$_4$alkylene-phenyl, —NH-(5-10 membered) aryl, or —NH-(5-10 membered) heteroaryl, wherein each of the aryl, heteroaryl, cycloalkyl and heterocycloalkyl moieties are optionally substituted with 1-3 $J^1$ groups;

or $R^1$ and $R^2$ join with the carbon atoms to which they are attached to form a ring selected from the group consisting of 5-10 membered aryl, 5-10 membered heteroaryl, 4-7 membered cycloalkyl, and 4-7 membered heterocycloalkyl, wherein each ring is optionally substituted with 1-3 $J^1$ groups;

G is -$L^1$-$R^3$ or —W—X—Y;

$L^1$ is a bond, —C(O)—, —S(O)$_2$—, —N(H)—, —N(C$_1$-C$_6$alkyl)-, C$_1$-C$_3$alkylene, 5-10 membered aryl, 5-10 membered heteroaryl, 4-7 membered heterocycloalkyl, or 4-7 membered cycloalkyl, wherein $C_1$-$C_3$alkylene, 5-10 membered aryl, 5-10 membered heteroaryl, 5-7 membered heterocycloalkyl, and 5-7 membered cycloalkyl are each optionally substituted with 1-3 $J^2$ groups, provided that when $L^1$ is $CH_2$, $L^1$ is not attached to carbon or nitrogen of a saturated ring;

$R^3$ is a 4-7 membered heterocyclic ring containing at least one nitrogen ring atom, wherein the 4-7 membered heterocyclic ring containing at least one nitrogen ring atom is optionally substituted with 1-4 $J^3$ groups, and wherein one nitrogen atom of the 4-7 membered heterocyclic ring is substituted with -$L^2$-R;

or $R^3$ is a 7-11 membered spirocyclic group containing at least one nitrogen ring atom, wherein the 7-11 membered spirocyclic group is optionally substituted with 1-4 $J^3$ groups, and wherein one nitrogen atom of $R^3$ is substituted with -$L^2$-R;

W is 9a bond, —C(O)— or —S(O)$_2$—;

X is 5-10 membered aryl, 5-10 membered heteroaryl, 5-7 membered heterocycloalkyl, or 5-7 membered cycloalkyl, wherein the -10 membered aryl, 5-10 membered heteroaryl, 5-7 membered heterocycloalkyl, and 5-7 membered cycloalkyl are optionally substituted with 1-3 $J^2$ groups;

Y is —$C_0$-$C_4$alkylene-N(R)-$L^2$-R, —C(O)-4-6 membered heterocycloalkyl containing one nitrogen atom and substituted with 1-2 oxo groups, —$C_0$-$C_4$alkylene-1-yl-1H-pyrrole-2,5-dione, —$C_0$-$C_4$alkylene-C(H)=C(O)—NH$_2$, —$C_0$-$C_4$alkylene-C(H)=C(H)—C(O)—O-alkyl, —$C_0$-$C_4$alkylene-ethynylene-C(O)—O-alkyl, —$C_0$-$C_4$alkylene-C(H)=C(H)—CN, —$C_0$-$C_4$alkylene-N=C=S, —$C_0$-$C_4$-etheyny, —$C_0$-$C_4$alkylene-ethynyl, —$C_0$-$C_4$alkylene-CN, —$C_0$-$C_4$alkylene-C(H)=N—N(H)Boc, —$C_0$-$C_4$alkylene-C(O)—CH$_2$—Br, —$C_0$-$C_4$alkylene-CH$_2$—Cl, —$C_0$-$C_4$alkylene-oxiranyl, —$C_0$-$C_4$alkylene-SH, —$C_0$-$C_4$alkylene-F, and —$C_0$-$C_4$alkylene-C(H)=O, wherein the —$C_0$-$C_4$alkylene moiety is optionally substituted with 1-4 groups independently selected from the group consisting of halogen, $C_3$-$C_6$cycloalkyl, $C_1$-$C_6$alkoxy —$C_1$-$C_6$alkyl-$C_1$-$C_6$alkoxy, or hydroxy;

$R^4$ is H, $C_0$-$C_4$alkyl, or —O-$C_0$-$C_4$alkyl;

$L^2$ is —SO$_2$— or —C(O)—;

R is ethenyl optionally substituted with 1-3 Q groups, ethynyl optionally substituted with Q, —CH$_2$—CN, or $C_1$-$C_6$haloalkyl, wherein one halogen of $C_1$-$C_6$haloalkyl is on the carbon atom adjacent to $L^2$;

each Q is independently selected from the group consisting of halogen, $C_1$-$C_6$haloalkyl, $C_1$-$C_6$alkyl, —$C_1$-$C_4$alkylene-NR$^a$R$^b$, cyano, $C_1$-$C_6$hydroxyalkyl, —$C_1$-$C_6$alkylene-C(O)OH, —$C_1$-$C_6$alkylene-C(O)O—$C_1$-$C_6$alkyl, —$C_1$-$C_4$alkylene-$C_1$-$C_6$alkoxy, —$C_0$-$C_4$alkylene-$C_3$-$C_6$cycloalkyl optionally substituted with 1-3 $J^4$ groups, —$C_0$-$C_4$alkylene-$C_3$-$C_7$cycloalkenyl optionally substituted with 1-3 $J^4$ groups, —$C_0$-$C_4$alkylene-4-7 membered heterocycloalkyl optionally substituted with 1-3 $J^4$ groups, and —$C_0$-$C_4$alkylene-4-7 membered heterocycloalkenyl optionally substituted with 1-3 $J^4$ groups;

or -$L^2$-R is —C=N—OH;

each $J^1$ is independently selected from the group consisting of halogen, $C_1$-$C_6$alkyl, $C_1$-$C_6$haloalkyl, hydroxy, $C_1$-$C_6$hydroxyalkyl, —$C_0$-$C_4$alkylene-N(H)R$^c$, $C_1$-$C_6$alkoxy, and —$C_1$-$C_6$alkyl-$C_1$-$C_6$alkoxy;

each $J^2$ is independently selected from the group consisting of halogen, $C_1$-$C_6$alkyl, $C_1$-$C_6$haloalkyl, hydroxy, $C_1$-$C_6$hydroxyalkyl, $C_1$-$C_6$alkoxy, and —$C_1$-$C_6$alkyl-$C_1$-$C_6$alkoxy;

each $J^3$ is attached to a carbon atom of $R^3$ and is independently selected from the group consisting of halogen, —$C_1$-$C_6$haloalkyl, CN, $C_1$-$C_6$alkyl, hydroxy, $C_1$-$C_6$hydroxyalkyl, $C_1$-$C_6$alkoxy, and —$C_1$-$C_6$alkyl-$C_1$-$C_6$alkoxy, or two of the optional 1-4 $J^3$ groups form an oxo group or a 3-6 membered spiro group, or two of the optional 1-4 $J^3$ groups are on different ring carbon and join to form a 1-3 carbon bridge;

each $J^4$ is independently selected from the group consisting of halogen, $C_1$-$C_6$alkyl, $C_1$-$C_6$haloalkyl, hydroxy, $C_1$-$C_6$hydroxyalkyl, $C_1$-$C_6$alkoxy, —$C_1$-$C_6$alkyl-$C_1$-$C_6$alkoxy, oxo, and —$C_0$-$C_4$alkylene-NR$^a$R$^b$, provided that $J^4$ groups can only include up to two oxo groups and up to one —$C_0$-$C_4$alkylene-NR$^a$R$^b$ group;

$R^a$ and $R^b$ each are independently selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, and $C_0$-$C_3$alkylene-$C_2$-$C_6$alkynyl optionally substituted with alkyl, $C_1$-$C_6$haloalkyl, $C_1$-$C_6$hydroxyalkyl, or —$C_1$-$C_6$alkoxy $C_1$-$C_6$alkyl; and $R^c$ is selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, $C_3$-$C_7$cycloalkyl, 4-7 membered heterocycloalkyl, 6-10 membered aryl, and 5-10 membered heteroaryl, wherein the $C_3$-$C_7$cycloalkyl, 4-7 membered heterocycloalkyl, 6-10 membered aryl, and 5-10 membered heteroaryl groups are each optionally substituted with 1-3 groups selected from the group consisting of halogen, $C_1$-$C_6$alkyl, $C_1$-$C_6$alkoxy and $C_1$-$C_6$alkoxy-$C_1$-$C_6$alkyl; and $R^d$ is selected from the group consisting of H, $C_1$-$C_6$alkyl, and $C_1$-$C_6$haloalkyl.

Embodiment 203 of this disclosure relates to a compound according to any one of Embodiments 201 or 202 having one of the following formulae:

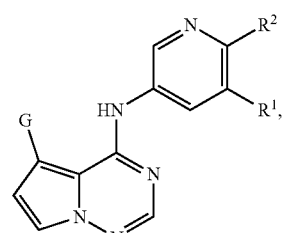

(IIa)

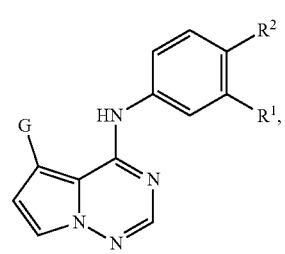

(IIb)

-continued

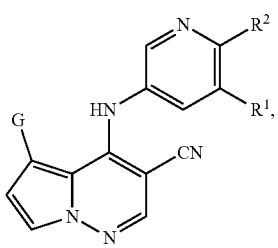
(IIc)

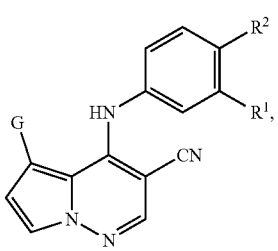
(IId)

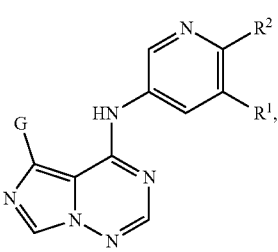
(IIe)

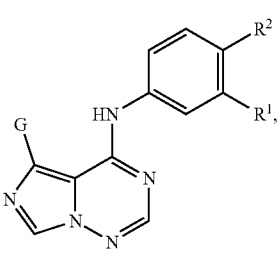
(IIf)

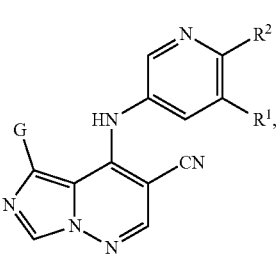
(IIg)

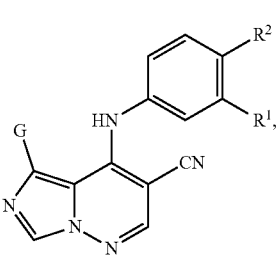
(IIh)

or a pharmaceutically acceptable salt, a tautomer, a stereoisomer, or a deuterated analog of any of the above compounds.

Embodiment 204 of this disclosure relates to a compound according to Embodiment 203 having Formula (IIa) or (IIb), or a pharmaceutically acceptable salt, a tautomer, a stereoisomer, or a deuterated analog of Formula (IIa) or (IIb).

Embodiment 205 of this disclosure relates to a compound according to any one of Embodiments 201 or 202 having one of the following formulae:

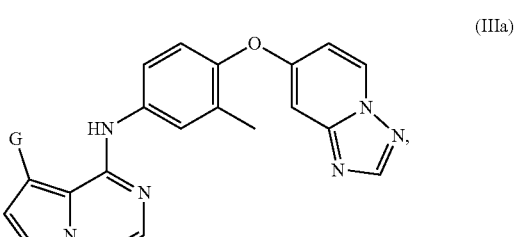
(IIIa)

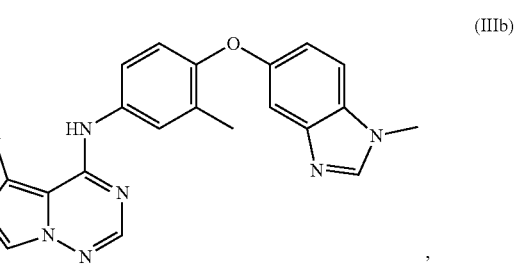
(IIIb)

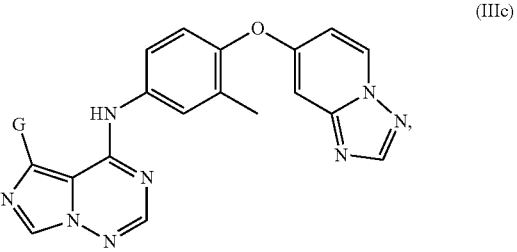
(IIIc)

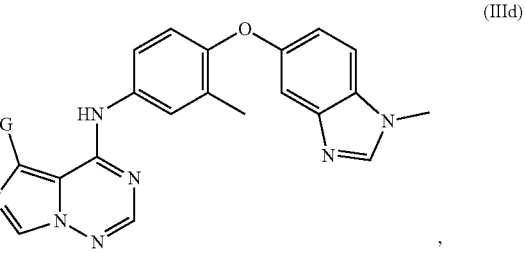
(IIId)

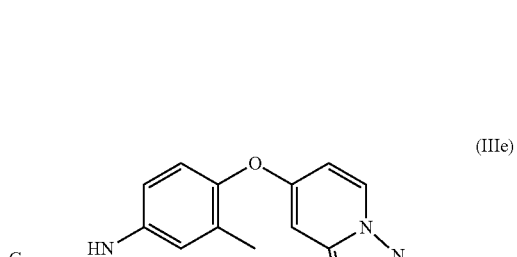
(IIIe)

-continued

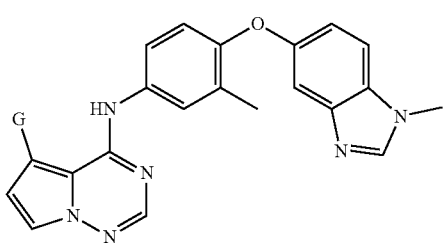
(IIIf)

or a pharmaceutically acceptable salt, a tautomer, a stereoisomer, or a deuterated analog of any of the above compounds.

Embodiment 286 of this disclosure relates to a compound according to any one of the preceding Embodiments wherein G is -$L^1$-$R^3$.

Embodiment 207 of this disclosure relates to a compound according to any one of the preceding Embodiments wherein G is

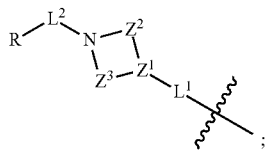
;

wherein:
$L^1$ is a bond, —C(O)—, —S(O)$_2$—, $C_1$-$C_3$alkylene, phenyl, 5-6 membered heteroaryl, 4-6 membered heterocycloalkyl, or 4-6 membered cycloalkyl, wherein $C_1$-$C_2$alkylene, phenyl, 5-6 membered heteroaryl, 4-6 membered heterocycloalkyl, or 4-6 membered cycloalkyl are each optionally substituted with 1-2 $J^2$ groups, provided that when $L^1$ is $CH_2$, $Z^1$ is not $CH_2$ or N;
$L^2$ is —SO$_2$— or —C(O)—;
$Z^1$ is —N(H)—, —C($R^5$)—, or a 4-7 membered spiro group optionally containing 1-2 nitrogen atoms;
$R^5$ is H, halogen, $C_1$-$C_3$alkyl or CN;
$Z^2$ and $Z^3$ are each independently —$C_1$-$C_3$alkylene or —$C_2$-$C_3$alkenylene, wherein —$C_1$-$C_3$alkylene and —$C_2$-$C_3$alkenylene are each optionally substituted with 1-4 $J^3$ groups;
R is ethenyl optionally substituted with 1-3 Q groups, ethynyl optionally substituted with Q groups, —CH$_2$—CN, or $C_1$-$C_4$haloalkyl, wherein one halogen of $C_1$-$C_4$haloalkyl is on the carbon atom adjacent to $L^2$;
each Q is independently selected from the group consisting of halogen, $C_1$-$C_4$haloalkyl, $C_1$-$C_4$alkyl, —$C_1$-$C_4$alkylene-NR$^a$R$^b$, —$C_1$-$C_4$alkylene-cyano, $C_1$-$C_4$hydroxyalkyl, —$C_1$-$C_4$alkylene-C(O)OH, —$C_1$-$C_4$alkylene-C(O)O—$C_1$-$C_4$alkyl, —$C_1$-$C_3$alkylene-$C_1$-$C_4$alkoxy, —$C_0$-$C_4$alkylene-$C_3$-$C_7$cycloalkyl optionally substituted with 1-3 J groups, —$C_0$-$C_4$alkylene-$C_3$-$C_7$cycloalkenyl optionally substituted with 1-3 $J^4$ groups, —$C_0$-$C_4$alkylene-4-7 membered heterocycloalkyl optionally substituted with 1-3 $J^4$ groups, and —$C_0$-$C_4$alkylene-4-7 membered heterocycloalkenyl optionally substituted with 1-3 $J^4$ groups;
each $J^2$ is independently selected from the group consisting of halogen, $C_1$-$C_4$alkyl, $C_1$-$C_4$haloalkyl, hydroxy, $C_1$-$C_4$hydroxyalkyl, $C_1$-$C_4$alkoxy, and —$C_1$-$C_4$alkyl-$C_1$-$C_4$alkoxy;
each $J^3$ is independently selected from the group consisting of halogen, —$C_1$-$C_4$haloalkyl, CN, $C_1$-$C_4$alkyl, hydroxy, $C_1$-$C_4$hydroxyalkyl, $C_1$-$C_4$alkoxy, and —$C_1$-$C_4$alkyl-$C_1$-$C_4$alkoxy, or two of the optional 1-4 $J^3$ groups form an oxo group or a 3-6 membered spiro group, or two of the optional 1-4 $J^3$ groups are on different ring carbon atoms and join to form a 1-3 carbon bridge; and
each $J^4$ is independently selected from the group consisting of halogen, $C_1$-$C_4$alkyl, $C_1$-$C_4$haloalkyl, hydroxy, $C_1$-$C_4$hydroxyalkyl, $C_1$-$C_4$alkoxy, —$C_1$-$C_4$alkyl-$C_1$-$C_4$alkoxy, oxo, and —$C_0$-$C_4$alkylene-NR$^a$R$^b$, provided that $J^4$ groups can only include up to two oxo groups and up to one —$C_0$-$C_4$alkylene-NR$^a$R$^b$ group.

Embodiment 208 of this disclosure relates to a compound according to Embodiment 207, wherein G is

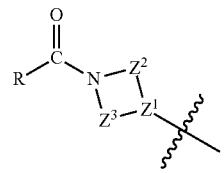
, wherein:
$Z^1$ is —N(H)—, —C($R^5$)—, or a 4-6 membered spiro group optionally containing 1-2 nitrogen atoms;
$R^5$ is H, halogen, $C_1$-$C_3$alkyl or CN;
$Z^2$ is —$C_1$-$C_3$alkylene or —$C_2$-$C_3$alkenylene, each of which is optionally substituted with 1-2 $J^3$ groups;
$Z^3$ is —$C_1$-$C_2$alkylene optionally substituted with 1-2 $J^3$ groups;
R is ethenyl optionally substituted with 1-3 Q groups, ethynyl optionally substituted with Q, —CH$_2$—CN, or $C_1$-$C_3$haloalkyl, wherein one halogen of $C_1$-$C_3$haloalkyl is on the carbon atom adjacent to —C(O)—;
each Q is independently selected from the group consisting of halogen, $C_1$-$C_3$haloalkyl, $C_1$-$C_3$alkyl, —$C_1$-$C_3$alkylene-NR$^a$R$^b$, —$C_1$-$C_3$alkylene-cyano, $C_1$-$C_3$hydroxyalkyl, —C(O)OH, —$C_1$-$C_3$alkylene-C(O)O—$C_1$-$C_3$alkyl, —$C_0$-$C_3$alkylene-$C_1$-$C_3$alkoxy, —$C_0$-$C_3$alkylene-$C_3$-$C_6$cycloalkyl optionally substituted with 1-3 $J^4$ groups, —$C_0$-$C_3$alkylene-$C_3$-$C_6$cycloalkenyl optionally substituted with 1-3 $J^4$ groups, —$C_0$-$C_3$alkylene-4-6 membered heterocycloalkyl optionally substituted with 1-3 $J^4$ groups, and —$C_0$-$C_3$alkylene-4-6 membered heterocycloalkenyl optionally substituted with 1-3 $J^4$ groups;
each $J^2$ is independently selected from the group consisting of halogen, $C_1$-$C_3$alkyl, $C_1$-$C_3$haloalkyl, hydroxy, $C_1$-$C_3$hydroxyalkyl, $C_1$-$C_3$alkoxy, and —$C_1$-$C_3$alkyl-$C_1$-$C_3$alkoxy;
each $J^3$ is independently selected from the group consisting of halogen, —$C_1$-$C_3$haloalkyl, CN, $C_1$-$C_3$alkyl, hydroxy, $C_1$-$C_3$hydroxyalkyl, $C_1$-$C_3$alkoxy, and —$C_1$-$C_3$alkyl-$C_1$-$C_3$alkoxy, or two of the optional $J^3$ groups are on different ring carbon atoms and join to form a 1-2 carbon bridge and
each $J^4$ is independently selected from the group consisting of halogen, $C_1$-$C_3$alkyl, $C_1$-$C_3$haloalkyl, hydroxy, $C_1$-$C_3$hydroxyalkyl, $C_1$-$C_3$alkoxy, —$C_1$-$C_3$alkyl-$C_1$-$C_3$alkoxy, oxo, and —$C_0$-$C_3$alkylene-NR$^a$R$^b$, provided that $J^4$ groups can only include up to two oxo groups and up to one —$C_0$-$C_3$alkylene-NR$^a$R$^b$ group.

Embodiment 209 of this disclosure relates to a compound according to any one of Embodiments 201-206 wherein $R^3$ is

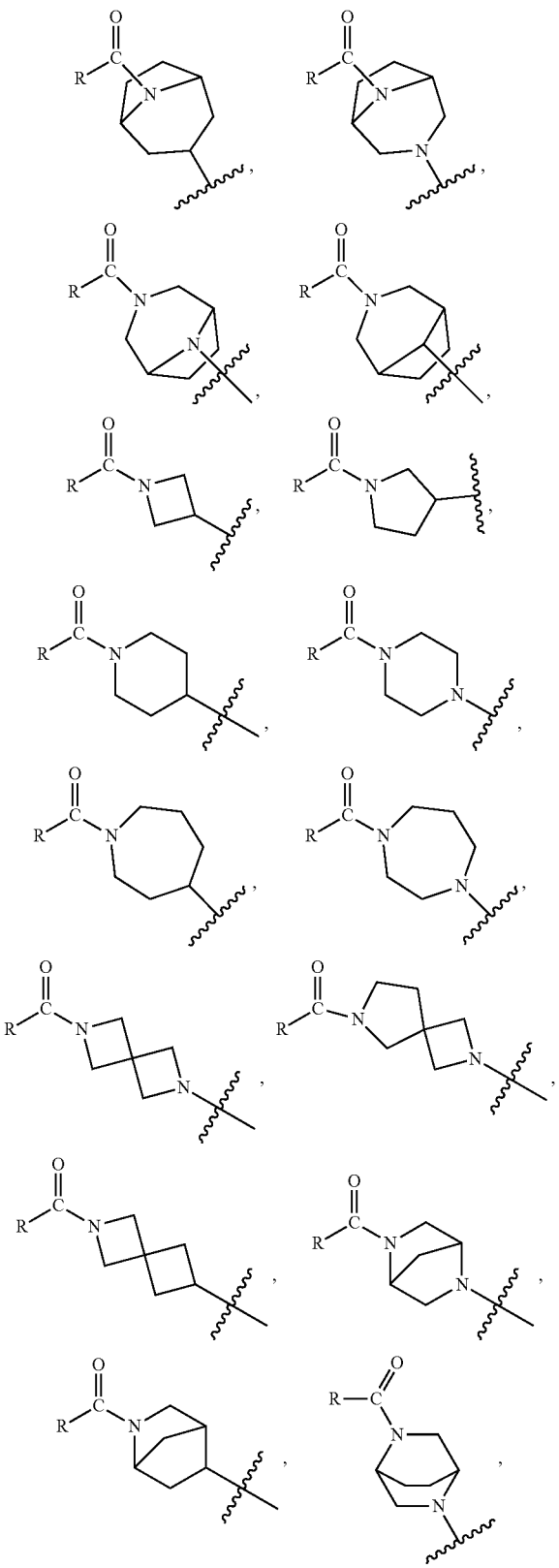

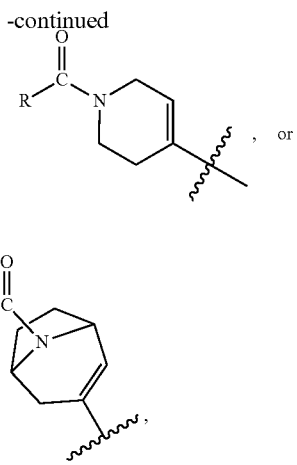

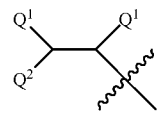

wherein the heterocyclic ring containing at least one nitrogen ring atom of $R^3$ is optionally substituted with 1-3 $J^3$ groups; and each $J^3$ is independently selected from the group consisting of halogen, —$C_1$-$C_3$haloalkyl, CN, $C_1$-$C_3$alkyl, hydroxy, $C_1$-$C_3$hydroxyalkyl, $C_1$-$C_3$alkoxy, and —$C_1$-$C_3$alkyl-$C_1$-$C_3$alkoxy.

Embodiment 210 of this disclosure relates to a compound according to any one of Embodiments 201-205, wherein G is —X—Y.

Embodiment 211 of this disclosure relates to a compound according to Embodiment 210 wherein X is a 5-10 membered heteroaryl optionally substituted with 1-3 $J^1$ groups and Y is —$C_0$-$C_4$alkylene-N(H)-$L^2$-R.

Embodiment 212 of this disclosure relates to a compound according to any one Embodiments 201-209 and 211, wherein R is ethenyl optionally substituted with 1-2 groups independently selected from the group consisting of halogen, $C_1$-$C_3$haloalkyl, $C_1$-$C_3$alkyl, —$C_1$-$C_3$alkylene-$NR^aR^b$, —$C_1$-$C_3$alkylene-cyano, $C_1$-$C_3$hydroxyalkyl, —$C_1$-$C_3$alkylene-C(O)O—$C_1$-$C_3$alkyl, —$C_1$-$C_3$alkylene-$C_1$-$C_3$alkoxy, —$C_1$-$C_3$alkylene-$C_3$-$C_6$cycloalkyl optionally substituted with 1-3 $J^4$ groups, —$C_1$-$C_3$alkylene-$C_3$-$C_6$cycloalkenyl optionally substituted with 1-3 $J^4$ groups, —$C_1$-$C_3$alkylene-4-6 membered heterocycloalkyl optionally substituted with 1-3 J groups, and —$C_1$-$C_3$alkylene-4-6 membered heterocycloalkenyl optionally substituted with 1-3 $J^4$ groups.

Embodiment 213 of this disclosure relates to a compound according to any one of Embodiments 201-209 and 211, wherein R is

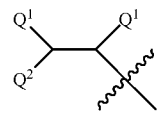

wherein:
each $Q^1$ is independently selected from the group consisting of H, F, and Cl; and
$Q^2$ is independently selected from the group consisting of H, $C_1$-$C_6$haloalkyl, $C_1$-$C_6$alkyl, —$C_1$-$C_4$alkylene-$NR^aR^b$, —$C_0$-$C_4$alkylene-4-7 membered heterocycloalkyl optionally substituted with 1-3 $J^4$ groups, and —C₀-C₄alkylene-4-7 membered heterocycloalkenyl optionally substituted with 1-3 J⁴ groups.

Embodiment 214 of this disclosure relates to a compound according to any one of the preceding Embodiments, wherein R² is —O-heteroaryl, —O-heterocycloalkyl, —NH— heteroaryl or, —N(H)-heterocycloalkyl, wherein the heteroaryl or heterocycloalkyl moieties are optionally substituted with 1-3 J groups.

Embodiment 215 of this disclosure relates to a compound according to any one of the preceding Embodiments, wherein R² is —O-(5-10 membered) heteroaryl containing at least one nitrogen atom and optionally substituted with 1-2 J¹ groups. Embodiment 216 of this disclosure relates to a compound according to any one of the preceding Embodiments, wherein R² is

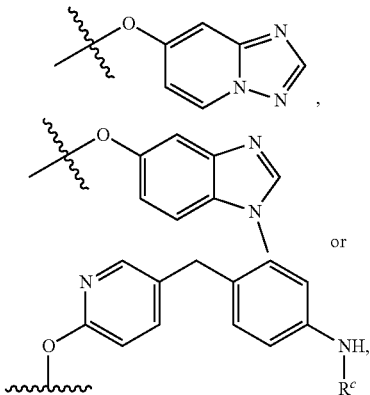

each of which is optionally substituted with 1-2 J¹ groups.

Embodiment 217 of this disclosure relates to a compound according to any one of the preceding Embodiments, wherein R² is

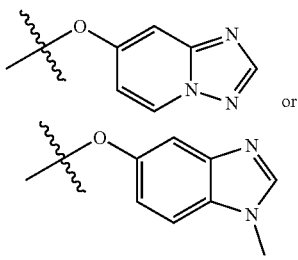

each of which is optionally substituted with 1-2 J¹ groups, wherein:

each J¹ is independently selected from the group consisting of halogen, $C_1$-$C_3$alkyl, $C_1$-$C_3$haloalkyl, hydroxy, $C_1$-$C_3$hydroxyalkyl, —$C_0$-$C_3$alkylene-N(H)R$^c$, $C_1$-$C_3$alkoxy, and —$C_1$-$C_6$alkyl-$C_1$-$C_6$alkoxy; and R$^c$ is selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, $C_3$-$C_7$cycloalkyl, 4-7 membered heterocycloalkyl, 6-10 membered aryl, and 5-10 membered heteroaryl, wherein the $C_3$-$C_7$cycloalkyl, 4-7 membered heterocycloalkyl, 6-10 membered aryl, and 5-10 membered heteroaryl groups are each optionally substituted with 1-3 groups selected from the group consisting of halogen, $C_1$-$C_6$alkyl, $C_1$-$C_6$alkoxy and $C_1$-$C_6$alkoxy-$C_1$-$C_6$alkyl.

Embodiment 218 of this disclosure relates to a compound according to any one of the preceding Embodiments, wherein R² is

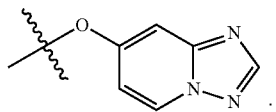 [SMILES: *Oc1ccn2ncnc2c1]

Embodiment 219 of this disclosure relates to a compound according to Embodiment 201 having one of the following formulae:

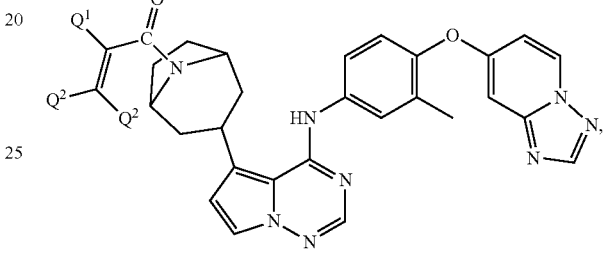

(IVa)

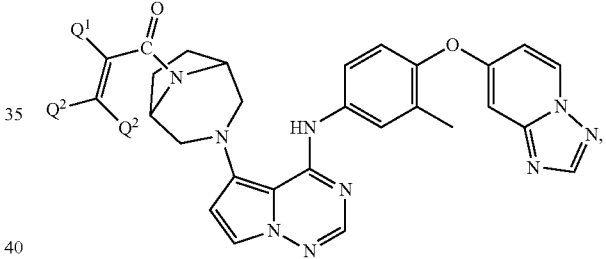

(IVb)

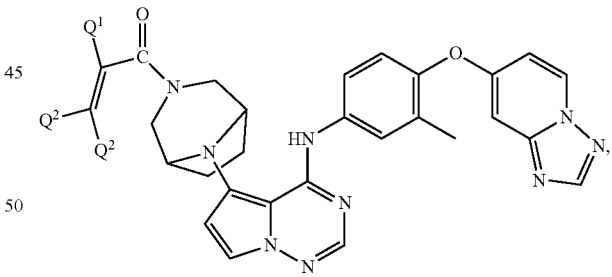

(IVc)

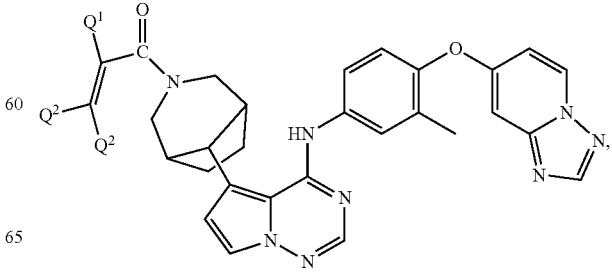

(IVd)

(IVe)
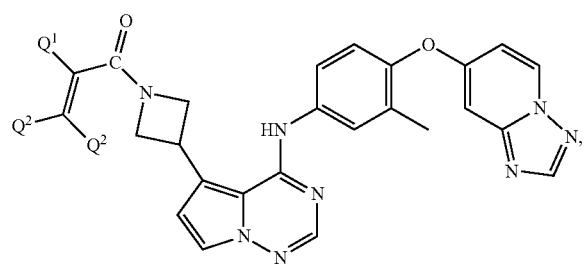
(IVf)
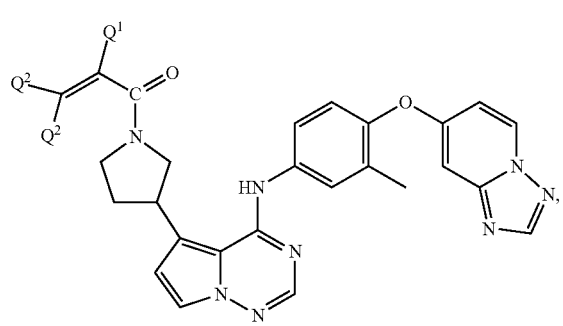
(IVg)
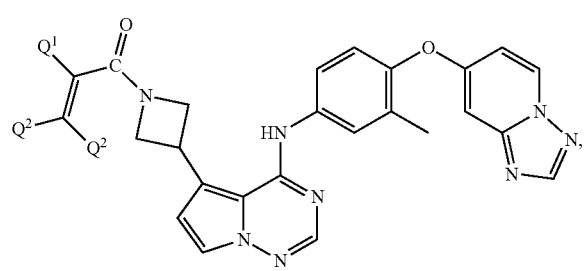
(IVh)
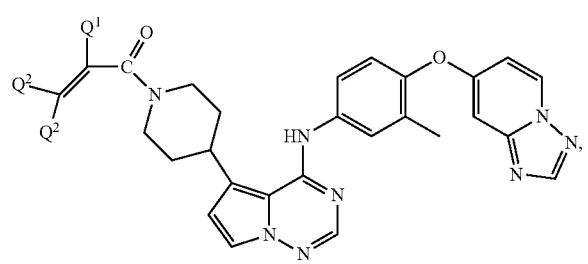
(IVi)
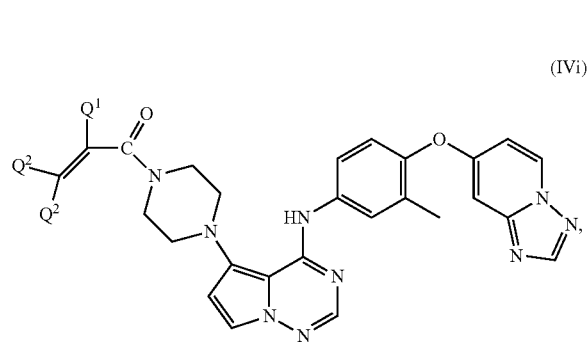
(IVj)
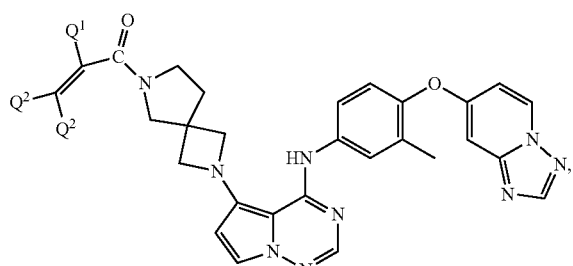
(IVk)
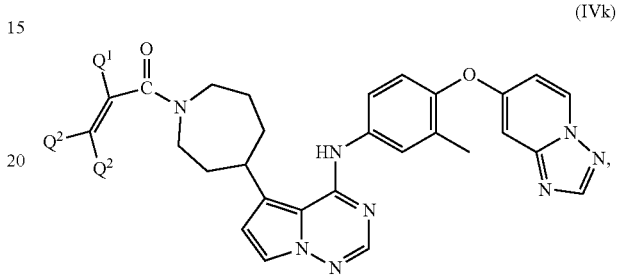
(IVl)
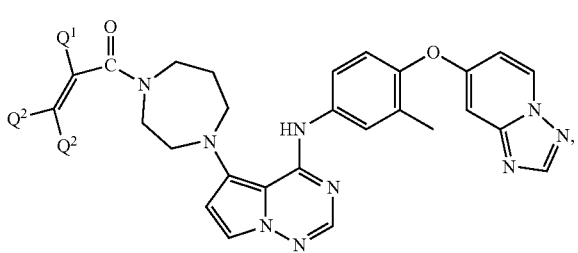
(IVm)
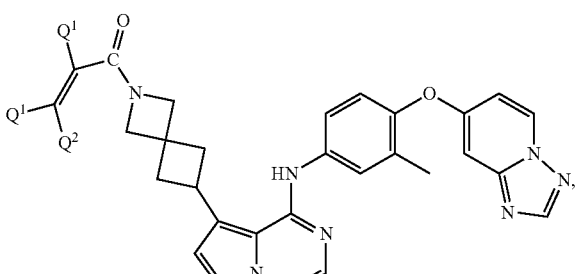
(IVn)
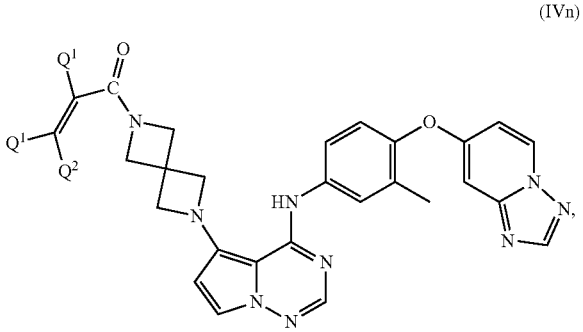

-continued

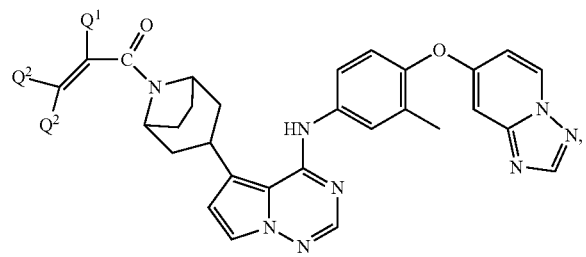
(IVo)

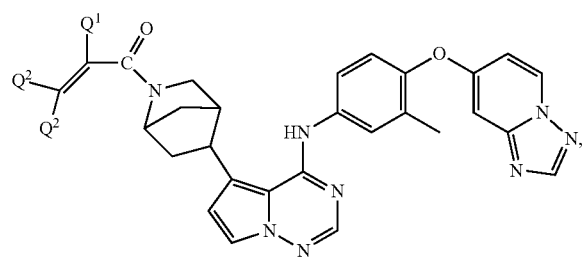
(IVo)

or a pharmaceutically acceptable salt, a tautomer, a stereoisomer, or a deuterated analog thereof, wherein:

each $Q^1$ is independently selected from the group consisting of H, F, and Cl; and $Q^2$ is independently selected from the group consisting of H, $C_1$-$C_6$haloalkyl, $C_1$-$C_6$alkyl, —$C_1$-$C_6$alkylene-$NR^aR^b$, —$C_0$-$C_6$alkylene-4-7 membered heterocycloalkyl optionally substituted with 1-3 $J^4$ groups, and —$C_0$-$C_6$alkylene-4-7 membered heterocycloalkenyl optionally substituted with 1-3 $J^4$ groups or a pharmaceutically acceptable salt, a tautomer, a stereoisomer, or a deuterated analog thereof, wherein each $Q^1$ is independently selected from the group consisting of H, F, and Cl; and $Q^2$ is independently selected from the group consisting of H, $C_1$-$C_6$haloalkyl, $C_1$-$C_6$alkyl, —$C_1$-$C_3$alkylene-$NR^aR^b$, —$C_0$-$C_3$alkylene-4-7 membered heterocycloalkyl optionally substituted with 1-3 $J^4$ groups, and —$C_0$-$C_3$alkylene-4-7 membered heterocycloalkenyl optionally substituted with 1-3 $J^4$ groups.

Embodiment 220 of this disclosure relates to a compound according to Embodiment 201 having one of the following formulae:

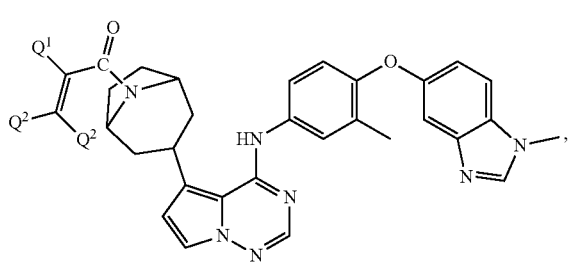
(Va)

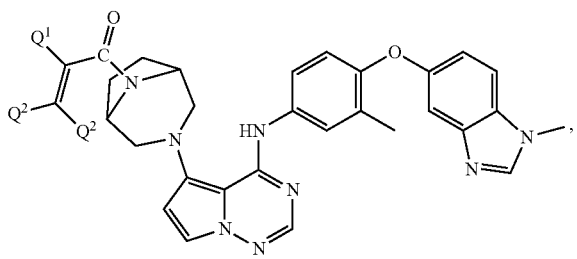
(Vb)

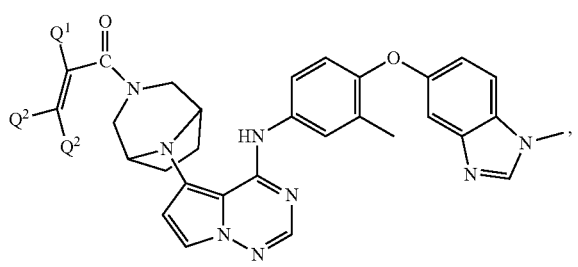
(Vc)

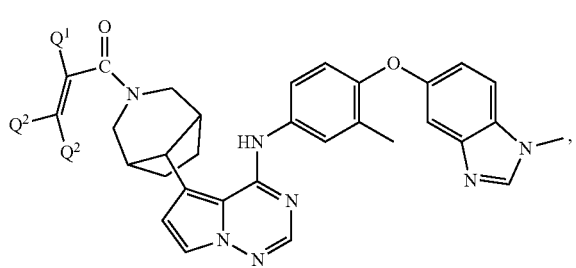
(Vd)

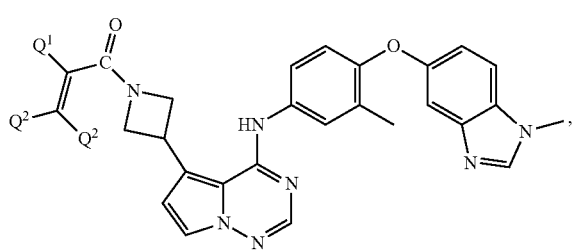
(Ve)

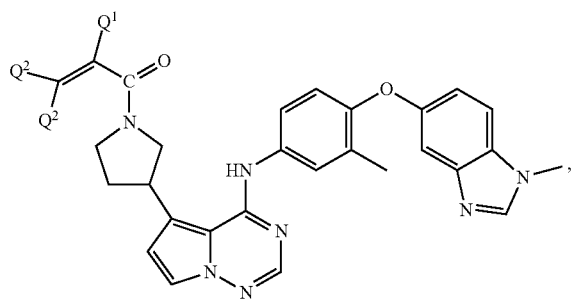
(Vf)

(Vg)
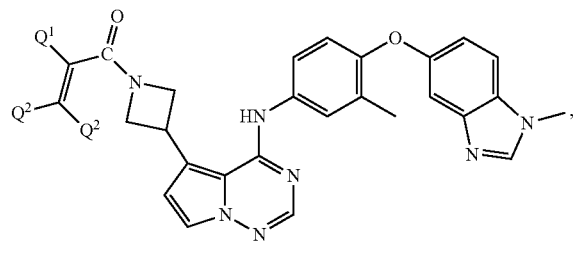
(Vh)
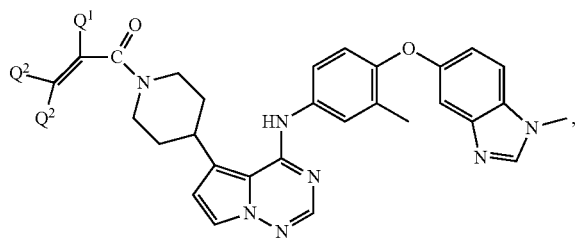
(Vi)
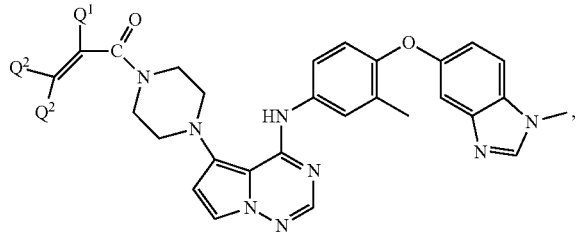
(Vj)
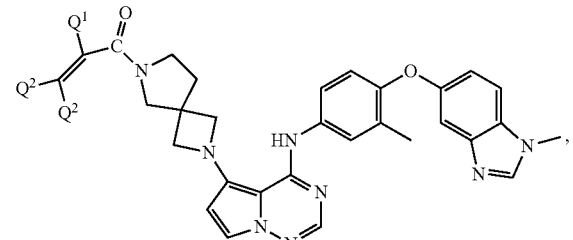
(Vk)
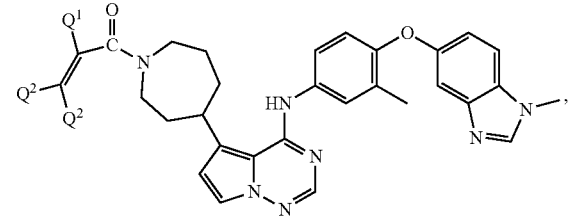
(Vl)
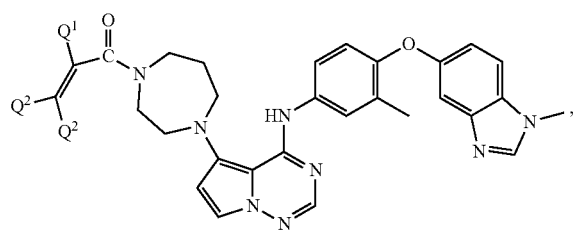
(Vm)
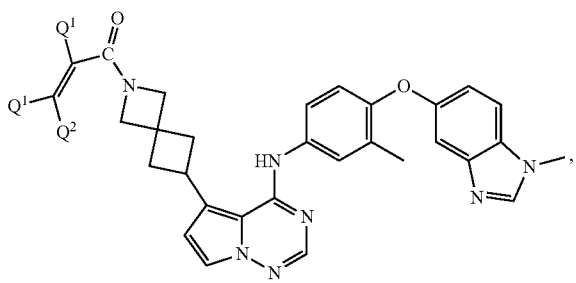
(Vn)
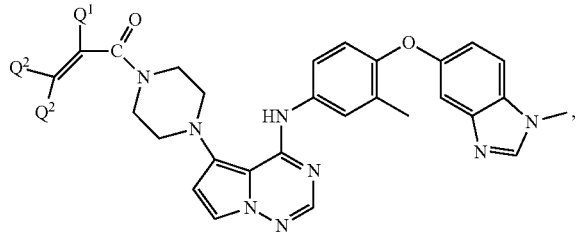
(Vo)
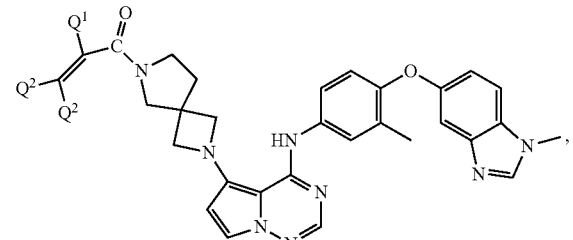
(Vp)
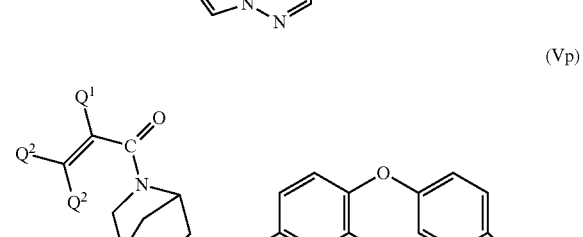
(Vq)
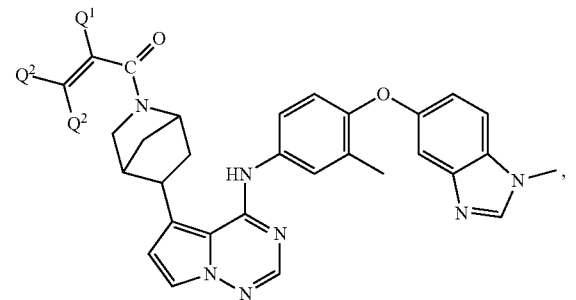

-continued

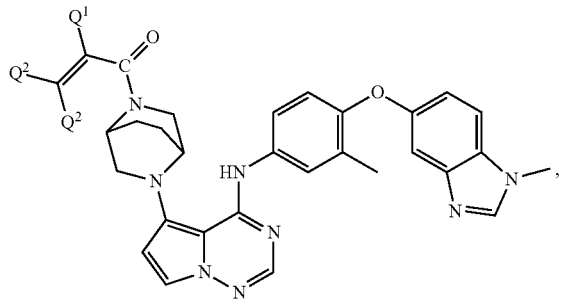

(Vr)

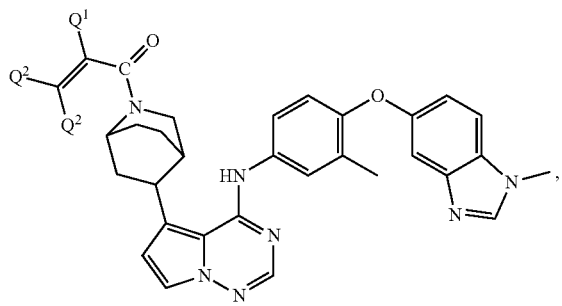

(Vs)

or a pharmaceutically acceptable salt, a tautomer, a stereoisomer, or a deuterated analog thereof, wherein:
each $Q^1$ is independently selected from the group consisting of H, F, and Cl; and
$Q^2$ is independently selected from the group consisting of H, $C_1$-$C_6$haloalkyl, $C_1$-$C_6$alkyl, —$C_1$-$C_3$alkylene-$NR^aR^b$, —$C_0$-$C_3$alkylene-4-7 membered heterocycloalkyl optionally substituted with 1-3 $J^4$ groups, and —$C_0$-$C_3$alkylene-4-7 membered heterocycloalkenyl optionally substituted with 1-3 $J^4$ groups or a pharmaceutically acceptable salt, a tautomer, a stereoisomer, or a deuterated analog thereof, wherein
each $Q^1$ is independently selected from the group consisting of H, F, and Cl; and
$Q^2$ is independently selected from the group consisting of H, $C_1$-$C_6$haloalkyl, $C_1$-$C_6$alkyl, —$C_1$-$C_3$alkylene-$NR^aR^b$, —$C_0$-$C_3$alkylene-4-7 membered heterocycloalkyl optionally substituted with 1-3 $J^4$ groups, and —$C_0$-$C_3$alkylene-4-7 membered heterocycloalkenyl optionally substituted with 1-3 $J^4$ groups.

Embodiment 221 of this disclosure relates to a compound according to any one of Embodiments 219 or 220, wherein $Q^2$ is H.

Embodiment 222 of this disclosure relates to a compound according to any one of Embodiments 219 or 220, wherein $Q^2$ is —$C_1$-$C_3$alkylene-$NR^aR^b$.

Embodiment 223 of this disclosure relates to a compound according to any one of Embodiments 219 or 220, wherein $Q^2$ is $C_0$-$C_3$alkylene-4-7 membered heterocycloalkyl optionally substituted with 1-3 $J^4$ groups.

Embodiment 224 of this disclosure relates to a compound according to Embodiment 201 selected from Table 1, or a pharmaceutically acceptable salt thereof.

Embodiment 225 of this disclosure relates to a pharmaceutical composition comprising the compound in any one of the preceding Embodiments, and a pharmaceutically acceptable carrier.

Embodiment 226 of this disclosure relates to a pharmaceutical composition according to Embodiment 225, further comprising a second pharmaceutical agent.

Embodiment 227 of this disclosure relates to a method for treating a subject with a disease or condition mediated by Her2, said method comprising administering to the subject an effective amount of a compound in any one of Embodiments 201-224, or a pharmaceutically acceptable salt, deuterated analog, a tautomer or a stereoisomer thereof, or a pharmaceutical composition in any one of Embodiments 225-226.

Embodiment 228 of this disclosure relates to a method according to Embodiment 227, wherein the disease or condition is a cancer with a Her2 YVMA insertion mutation.

Embodiment 229 of this disclosure relates to a method according to Embodiment 227, wherein the disease or condition is a cancer selected from the group consisting of lung cancer, breast cancer, stomach cancer, ovarian cancer, colon cancer, bladder cancer, lung cancer, uterine cervical cancer, head and neck cancer, gastric and esophageal cancer, and uterine serous endometrial carcinoma.

Embodiment 230 of this disclosure relates to a method for treatment of a disease or condition according to any one of Embodiments 227-229, wherein the disease or condition is non-small lung cancer.

Embodiment 231 of this disclosure relates to a method according to any one of Embodiments 227-230, further comprising administering one or more additional therapeutic agents.

Embodiment 232 of this disclosure relates to a method according to Embodiment 231, wherein the one or more additional therapeutic agents is one or more of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an immune checkpoint agent selected from a PD-1 inhibitor, a PD-L1 inhibitor, and a CTLA4 inhibitor; v) and antibody drug conjugate selected from ado-trastuzumab emtansine and trastuzumab deruxtecan; vi) a hormone or hormone antagonist selected from enzalutamide, abiraterone, anastrozole, androgens, buserelin, diethylstilbestrol, exemestane, flutamide, fulvestrant, goserelin, idoxifene, letrozole, leuprolide, magestrol, raloxifene, tamoxifen, and toremifene; vii) a taxane selected from DJ-927, docetaxel, TPI 287, paclitaxel and DHA-paclitaxel; viii) a retinoid selected from alitretinoin, bexarotene, fenretinide, isotretinoin, and tretinoin; ix) an alkaloid selected from etoposide, homoharringtonine, teniposide, vinblastine, vincristine, vindesine, and vinorelbine; x) an antiangiogenic agent selected from AE-941 (GW786034, Neovastat), ABT-510, 2-methoxyestradiol, lenalidomide, and thalidomide; xi) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xii) a kinase inhibitor selected from erlotinib, gefitinib, flavopiridol, imatinib mesylate, lapatinib, sorafenib, sunitinib malate, 7-hydroxystaurosporine, and vatalanib; xiii) a targeted signal transduction inhibitor selected from bortezonib, geldanamycin, and rapamycin; xiv) a biological response modifier selected from imiquimod, interferon-α and interleukin-2; xv) an IDO inhibitor; xvi) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate, ixabepilone, lonidamine, masoprocol, mitoguanazone, oblimersen, sulindac, testolactone, tiazofurin, an mTOR inhibitor, a PI3K inhibitor, a Cdk4 inhibitor, an Akt inhibitor, a Hsp90 inhibitor, a farnesyltransferase inhibitor and an aromatase inhibitor (anastrozole letrozole exemestane); xvii) a BRAF inhibitor; xviii) a Mek inhibitor; xix) c-Kit mutant inhibitor, xx) an EGFR inhibitor, xxi) an epigenetic modulator; xxii) other adenosine axis blockade agents selected from CD39, CD38, A2AR and A2BR; or xxiii) agonists of TNFA super family member; and xxiv) an anti-ErbB2 mAb.

Embodiment 233 of this disclosure relates to a method according to Embodiment 232, wherein the one or more additional therapeutic agents is ado-trastuzumab emtansine or trastuzumab deruxtecan.

Embodiment 234 of this disclosure relates to a method according to Embodiment 232, wherein the one or more additional therapeutic agents is pembrolizumab or nivolumab.

Embodiment 301 of this disclosure relates to a compound of Formula (I):

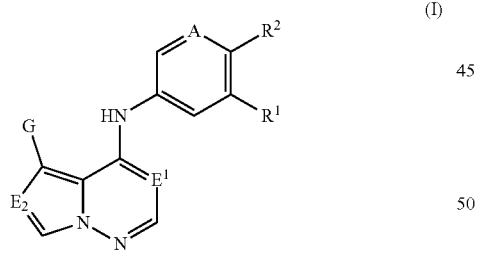

or a pharmaceutically acceptable salt, a tautomer, a stereoisomer, or a deuterated analog thereof, wherein:

A is N or CH;

$E^1$ is N or C(CN);

$E^2$ is $C(R^4)$ or N;

$R^1$ is alkyl, haloalkyl or halogen;

$R^2$ is —O-alkyl, —O-aryl, —O-heteroaryl, —O-cycloalkyl, —O-heterocycloalkyl, —NH-alkyl, —NH-aryl, or —NH-heteroaryl, wherein each of the alkyl, aryl, heteroaryl, cycloalkyl or heterocycloalkyl moieties are optionally substituted with 1-4 $J^1$ groups;

or $R^1$ and $R^2$ join with the carbon atoms to which they are attached to form a saturated or unsaturated carbocyclic or heterocyclic ring, wherein the saturated or unsaturated carbocyclic or heterocyclic ring is optionally substituted with 1-4 $J^1$ groups;

G is -$L^1$-$R^3$;

$L^1$ is —$C_0$-$C_6$alkylene-C(O)N(H)—, or —$C_0$-$C_6$alkylene-S(O)$_2$N(H)—;

$R^3$ is —$C_1$-$C_6$alkylene-NR$^a$R$^b$ optionally substituted with 1-4 $J^2$ groups;

$R^4$ is H, alkyl, or —O-alkyl;

each $J^1$ is independently selected from the group consisting of halogen, alkyl, haloalkyl, hydroxy, hydroxyalkyl, —$C_0$-$C_4$alkylene-N(H)R$^c$, alkoxy, and alkoxyalkyl;

each $J^2$ is independently selected from the group consisting of halogen, haloalkyl, CN, alkyl, hydroxy, hydroxyalkyl, and alkoxy, and alkoxyalkyl, provided that $J^3$ is attached to carbon; and $R^a$ and $R^b$ each are independently selected from the group consisting of H, alkyl, haloalkyl, hydroxyalkyl, alkoxyalkyl, and —$C_0$-$C_3$alkylene-alkynyl optionally substituted with alkyl, haloalkyl, hydroxyalkyl, or alkoxyalkyl; and Embodiment 302 of this disclosure relates to a compound according to Embodiment 301, wherein:

$R^1$ is $C_1$-$C_4$alkyl, $C_1$-$C_4$haloalkyl or halogen;

$R^2$ is —O-(5-10 membered) aryl, —O-(5-10 membered) heteroaryl, —O-(4-7 membered) cycloalkyl, —O-(4-7 membered) heterocycloalkyl, —NH-(5-10 membered) aryl, or —NH-(5-10 membered) heteroaryl, wherein each of the aryl, heteroaryl, cycloalkyl and heterocycloalkyl moieties are optionally substituted with 1-3 $J^1$ groups;

or $R^1$ and $R^2$ join with the carbon atoms to which they are attached to form a ring selected from the group consisting of 5-10 membered aryl, 5-10 membered heteroaryl, 4-7 membered cycloalkyl, and 4-7 membered heterocycloalkyl, wherein each ring is optionally substituted with 1-3 $J^1$ groups;

$L^1$ is —$C_0$-$C_3$alkylene-C(O)N(H)—, or —$C_0$-$C_3$alkylene-S(O)$_2$N(H)—;

$R^3$ is —$C_1$-$C_4$alkylene-NR$^a$R$^b$ optionally substituted with 1-2 $J^2$ groups;

$R^4$ is H, $C_0$-$C_4$alkyl, or —O—$C_0$-$C_4$alkyl;

each $J^1$ is independently selected from the group consisting of halogen, $C_1$-$C_6$alkyl, $C_1$-$C_6$haloalkyl, hydroxy, $C_1$-$C_6$hydroxyalkyl, —$C_0$-$C_4$alkylene-N(H)R$^c$, $C_1$-$C_6$alkoxy, and —$C_1$-$C_6$alkoxy-$C_1$-$C_6$alkyl;

each $J^2$ is independently selected from the group consisting of halogen, —$C_1$-$C_6$haloalkyl, CN, $C_1$-$C_6$alkyl, hydroxy, $C_1$-$C_6$hydroxyalkyl, $C_1$-$C_6$alkoxy, and —$C_1$-$C_6$alkoxy-$C_1$-$C_6$alkyl, provided that $J^2$ is attached to carbon; and $R^a$ and $R^b$ each are independently selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, and $C_0$-$C_3$alkylene-$C_2$-$C_6$alkynyl optionally substituted with alkyl, $C_1$-$C_6$haloalkyl, $C_1$-$C_6$hydroxyalkyl, or —$C_1$-$C_6$alkoxy $C_1$-$C_6$alkyl.

Embodiment 303 of this disclosure relates to a compound according to any one of Embodiments 301 or 302 having one of the following formulae:

(IIa)

(IIb)

(IIc)

(IId)

(IIe)

(IIf)

(IIg)

(IIh)

or a pharmaceutically acceptable salt, a tautomer, a stereoisomer, or a deuterated analog of any of the above compounds.

Embodiment 304 of this disclosure relates to a compound according to Embodiment 303 having Formula (IIa) or (IIb), or or a pharmaceutically acceptable salt, a tautomer, a stereoisomer, or a deuterated analog of Formula (IIa) or (IIb).

Embodiment 305 of this disclosure relates to a compound according to any one of the preceding Embodiments wherein $L^1$ is —$C_0$-$C_3$alkylene-C(O)N(H)—.

Embodiment 306 of this disclosure relates to a compound according to any one of the preceding Embodiments wherein $R^3$ is —$C_1$-$C_4$alkylene-NR$^a$R$^b$ wherein:

R$^a$ and R$^b$ each are independently selected from the group consisting of $C_1$-$C_6$alkyl, $C_1$-$C_6$haloalkyl, and $C_1$-$C_6$hydroxyalkyl.

Embodiment 307 of this disclosure relates to a compound according Embodiment 306, wherein $R^3$ is —$C_1$-$C_3$alkylene-NR$^a$R$^b$ wherein: R$^a$ and R$^b$ each are $C_1$-$C_3$alkyl.

Embodiment 308 of this disclosure relates to a compound according to any one of the preceding Embodiments, wherein $R^2$ is —O-heteroaryl, —O-heterocycloalkyl, —NH— heteroaryl or, —N(H)-heterocycloalkyl, wherein the heteroaryl or heterocycloalkyl moieties are optionally substituted with 1-3 $J^1$ groups.

Embodiment 309 of this disclosure relates to a compound according to any one of the preceding Embodiments, wherein $R^2$ is —O-(5-10 membered) heteroaryl containing at least one nitrogen atom and optionally substituted with 1-2 J groups.

Embodiment 310 of this disclosure relates to a compound according to any one of the preceding Embodiments, wherein $R^2$ is or -continued

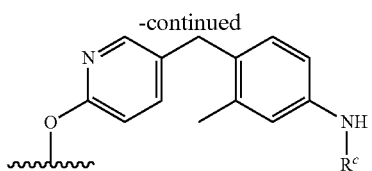

each of which is optionally substituted with 1-2 $J^1$ groups.

Embodiment 311 of this disclosure relates to a compound according to any one of the preceding Embodiments, wherein $R^2$ is

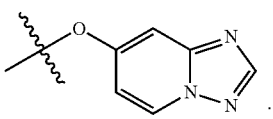

Embodiment 312 of this disclosure relates to a compound selected from Table 1, or a pharmaceutically acceptable salt thereof.

Embodiment 313 of this disclosure relates to a pharmaceutical composition comprising a compound in any one of the preceding Embodiments, and a pharmaceutically acceptable carrier.

Embodiment 314 of this disclosure relates to a pharmaceutical composition of Embodiment 313, further comprising a second pharmaceutical agent.

Embodiment 315 of this disclosure relates to a method for treating a subject with a disease or condition mediated by Her2, said method comprising administering to the subject an effective amount of a compound in any one of Embodiments 301-312, or a pharmaceutically acceptable salt, deuterated analog, a tautomer or a stereoisomer thereof, or a pharmaceutical composition in any one of Embodiments 313-314.

Embodiment 316 of this disclosure relates to a method according to Embodiment 315, wherein the disease or condition is a cancer with a Her2 YVMA insertion mutation.

Embodiment 317 of this disclosure relates to a method for treatment of a disease or condition according to Embodiment 315, wherein the disease or condition is a cancer selected from the group consisting of lung cancer, breast cancer, stomach cancer, ovarian cancer, colon cancer, bladder cancer, lung cancer, uterine cervical cancer, head and neck cancer, gastric and esophageal cancer, and uterine serous endometrial carcinoma.

Embodiment 318 of this disclosure relates to a method for treatment of a disease or condition according to any one of Embodiments 315-317, wherein the disease or condition is non-small lung cancer.

Embodiment 319 of this disclosure relates to a method according to any one of Embodiments 315-318, further comprising administering one or more additional therapeutic agents.

Embodiment 320 of this disclosure relates to a method according to Embodiment 319, wherein the one or more additional therapeutic agents is one or more of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an immune checkpoint agent selected from a PD-1 inhibitor, a PD-L1 inhibitor, and a CTLA4 inhibitor; v) and antibody drug conjugate selected from ado-trastuzumab emtansine and trastuzumab deruxtecan; vi) a hormone or hormone antagonist selected from enzalutamide, abiraterone, anastrozole, androgens, buserelin, diethylstilbestrol, exemestane, flutamide, fulvestrant, goserelin, idoxifene, letrozole, leuprolide, magestrol, raloxifene, tamoxifen, and toremifene; vii) a taxane selected from DJ-927, docetaxel, TPI 287, paclitaxel and DHA-paclitaxel; viii) a retinoid selected from alitretinoin, bexarotene, fenretinide, isotretinoin, and tretinoin; ix) an alkaloid selected from etoposide, homoharringtonine, teniposide, vinblastine, vincristine, vindesine, and vinorelbine; x) an antiangiogenic agent selected from AE-941 (GW786034, Neovastat), ABT-510, 2-methoxyestradiol, lenalidomide, and thalidomide; xi) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xii) a kinase inhibitor selected from erlotinib, gefitinib, flavopiridol, imatinib mesylate, lapatinib, sorafenib, sunitinib malate, 7-hydroxystaurosporine, and vatalanib; xiii) a targeted signal transduction inhibitor selected from bortezomib, geldanamycin, and rapamycin; xiv) a biological response modifier selected from imiquimod, interferon-α and interleukin-2; xv) an IDO inhibitor; xvi) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate, ixabepilone, lonidamine, masoprocol, mitoguanazone, oblimersen, sulindac, testolactone, tiazofurin, an mTOR inhibitor, a PI3K inhibitor, a Cdk4 inhibitor, an Akt inhibitor, a Hsp90 inhibitor, a farnesyltransferase inhibitor and an aromatase inhibitor (anastrozole letrozole exemestane); xvii) a BRAF inhibitor; xviii) a Mek inhibitor; xix) c-Kit mutant inhibitor, xx) an EGFR inhibitor, xxi) an epigenetic modulator; xxii) other adenosine axis blockade agents selected from CD39, CD38, A2AR and A2BR; or xxiii) agonists of TNFA super family member; and xxiv) an anti-ErbB2 mAb.

Embodiment 321 of this disclosure relates to a method according to Embodiment 319, wherein the one or more additional therapeutic agents is ado-trastuzumab emtansine or trastuzumab deruxtecan.

Compounds contemplated herein are described with reference to both generic formulae and specific compounds. In addition, the compounds described herein may exist in a number of different forms or derivatives, all within the scope of the present disclosure. These include, for example, tautomers, stereoisomers, racemic mixtures, regioisomers, salts, prodrugs (e.g. carboxylic acid esters), and active metabolites.

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present disclosure may exist as stereoisomers as defined herein. All such single stereoisomers, racemates and mixtures thereof are intended to be within the scope of the present disclosure. Unless specified to the contrary, all such stereoisomeric forms are included within the formulae provided herein. In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present disclosure includes both such regioisomers.

In addition to the present formulae and compounds described herein, the disclosure also includes prodrugs (generally pharmaceutically acceptable prodrugs), active metabolic derivatives (active metabolites), and their pharmaceutically acceptable salts.

Unless specified to the contrary, specification of a compound herein includes pharmaceutically acceptable salts of such compound.

In some embodiments, compounds of the disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

III. Formulations and Administration

Embodiment 25 of this disclosure relates to a pharmaceutical composition comprising the compound in any one of the preceding Embodiments, and a pharmaceutically acceptable carrier.

Embodiment 26 of this disclosure relates to the pharmaceutical composition according to Embodiment 25, further comprising a second pharmaceutical agent.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art and include considerations such as toxicity and dosage forms that retard the compound or composition from exerting its effects. Techniques and formulations generally may be found in The Science and Practice of Pharmacy, $21^{st}$ edition, Lippincott, Williams and Wilkins, Philadelphia, P A, 2005 (hereby incorporated by reference herein).

Compounds of the present disclosure (i.e. any of the compounds described in Embodiments 1-24, including any of the sub embodiments thereof) can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, the compounds can be administered by oral administration. For oral administration, for example, the compounds can be formulated into conventional oral dosage forms such as capsules, tablets, and liquid preparations such as syrups, elixirs, and concentrated drops.

For inhalants, compounds of the disclosure may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the disclosure may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin;

muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum-100-yridi, talc, poly-vinylpyrrolidone,-100-yridine gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the disclosure are formulated in sterile liquid solutions, such as in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

The compounds of the disclosure may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present disclosure, or at the same time as a compound of the disclosure. Use in combination also includes use with a therapy or medical procedure that is administered once or infrequently, such as surgery, along with a compound of the disclosure administered within a short time or longer time before or after the other therapy or procedure. In some embodiments, the present disclosure provides for delivery of compounds of the disclosure and one or more other drug therapeutics delivered by a different route of administration or by the same route of administration. The use in combination for any route of administration includes delivery of compounds of the disclosure and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the disclosure. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the disclosure and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

IV. Methods of Use

Disease Indications and Modulations Her2
Exemplary Diseases Associated with Her2

Her2 overexpression has been reported in various tumors, including lung, breast, stomach, ovary, colon, bladder, lung, uterine cervix, head and neck, gastric and esophageal cancer as well as uterine serous endometrial carcinoma [1]. Further, comorbidities that can be associated with Her2 mediated tumors, such as stage IV WT NSCLC, include pulmonary disorder, hypertension, hypercholesterolemia, cardiovascular disease, renal function disorder, thyroid disorder, obesity, depression anxiety, osteoporosis, liver disorder, autoimmune disease, dementia, and Alzheimer's disease. It is contemplated that such comorbidities can also be treated by Her2 inhibitors such as the compounds of this disclosure. The methods and compounds will typically be used in therapy for human subjects. However, they may also be used to treat similar or identical indications in other animal subjects.
References:
1. Iqbal N, Iqbal N. Human Epidermal Growth Factor Receptor 2 (HER2) in cancers: Overexpression and therapeutic implications. Molecular Biology International. 2014; 852748:2014

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the therapeutically effective amount used in the methods provided herein is at least 10 mg per day. In certain embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, or 2500 mg per day. In other embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, or 5000 mg per day or more. In certain embodiments, the 104-yridined is administered continuously.

In certain embodiments, provided herein is a method for treating a diseases or condition mediated by Her2 by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, or 5000 mg per day of any of the compounds described in a compound in one of Embodiments 1-24, or any of the sub embodiments thereof, or a pharmaceutically acceptable salt, deuterated analog, a tautomer or a stereoisomer thereof, or a pharmaceutical composition in one of Embodiments 25-26., and wherein the compound is administered on an empty stomach.

Embodiment 27 of this disclosure relates to a method for treating a subject with a disease or condition mediated by Her2, said method comprising administering to the subject an effective amount of a compound in any one of Embodiments 1-24, or any sub-embodiments thereof, or a pharmaceutically acceptable salt, deuterated analog, a tautomer or a stereoisomer thereof, or a pharmaceutical composition in any one of Embodiments 25-26.

Embodiment 28 of this disclosure relates to the method according to Embodiment 27, wherein the disease or condition is a cancer with a Her2 YVMA insertion mutation.

Embodiment 29 of this disclosure relates to the method according to Embodiment 27, wherein the disease or condition is a cancer selected from the group consisting of lung cancer, breast cancer, stomach cancer, ovarian cancer, colon cancer, bladder cancer, lung cancer, uterine cervical cancer, head and neck cancer, gastric and esophageal cancer, and uterine serous endometrial carcinoma.

Embodiment 30 of this disclosure relates to the method according to any one of Embodiments 27-29, wherein the disease or condition is non-small lung cancer.

V. Combination Therapy

Her2 modulators may be usefully combined with another pharmacologically active compound, or with two or more other pharmacologically active compounds, particularly in the treatment of cancer. In one embodiment, the combinations includes any one or more compound(s) as described herein along with one or more compounds that are therapeutically effective for the same disease indication, wherein the compounds have a synergistic effect on the disease indication. In one embodiment, the combination includes any one or more compound(s) as described herein effective in treating a cancer and one or more other compounds that are effective in treating the same cancer, further wherein the compounds are synergistically effective in treating the cancer.

Embodiment 31 of this disclosure relates to the method according to any one of Embodiments 27-29, further comprising administering one or more additional therapeutic agents.

Embodiment 32 of this disclosure relates to the method according to Embodiment 31, wherein the one or more additional therapeutic agents is one or more of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an immune checkpoint agent selected from a PD-1 inhibitor, a PD-L1 inhibitor, and a CTLA4 inhibitor; v) and antibody drug conjugate selected from ado-trastuzumab emtansine and trastuzumab deruxtecan; vi) a hormone or hormone antagonist selected from enzalutamide, abiraterone, anastrozole, androgens, buserelin, diethylstilbestrol, exemestane, flutamide, fulvestrant, goserelin, idoxifene, letrozole, leuprolide, magestrol, raloxifene, tamoxifen, and toremifene; vii) a taxane selected from DJ-927, docetaxel, TPI 287, paclitaxel and DHA-paclitaxel; viii) a retinoid selected from alitretinoin, bexarotene, fenretinide, isotretinoin, and tretinoin; ix) an alkaloid selected from etoposide, homoharringtonine, teniposide, vinblastine, vincristine, vindesine, and vinorelbine; x) an antiangiogenic agent selected from AE-941 (GW786034, Neovastat), ABT-510, 2-methoxyestradiol, lenalidomide, and thalidomide; xi) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xii) a kinase inhibitor selected from erlotinib, gefitinib, flavopiridol, imatinib mesylate, lapatinib, sorafenib, sunitinib malate, 7-hydroxystaurosporine, and vatalanib; xiii) a targeted signal transduction inhibitor selected from bortezomib, geldanamycin, and rapamycin; xiv) a biological response modifier selected from imiquimod, interferon-α and interleukin-2; xv) an IDO inhibitor; xvi) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate, ixabepilone, lonidamine, masoprocol, mitoguanazone, oblimersen, sulindac, testolactone, tiazofurin, an mTOR inhibitor, a PI3K inhibitor, a Cdk4 inhibitor, an Akt inhibitor, a Hsp90 inhibitor, a farnesyltransferase inhibitor and an aromatase inhibitor (anastrozole letrozole exemestane); xvii) a BRAF inhibitor; xviii) a Mek inhibitor; xix) c-Kit mutant inhibitor, xx) an EGFR inhibitor, xxi) an epigenetic modulator; xxii) other adenosine axis blockade agents selected from CD39, CD38, A2AR and A2BR; or xxiii) agonists of TNFA super family member; and xxiv) an anti-ErbB2 mAb. Her2 ubiquitination and internalization are key mechanisms underlying endocytosis and consequent efficacy of the anti-Her2 antibody-drug conjugates (ADC). Non-limiting examples of anti-HER2 ADCs include Kadcycla® (ado-trastuzumab emtansine) (T-DM1) that is approved for patients with Her2-positive, metastatic breast cancer and Her2-positive early breast cancer. Another ADC is Enhertu® (trastuzumab deruxtecan) (T-DXd)—that is currently in Phase 2 for pre-treated Her-mutated NSCLC and currently approved for (1) unresectable or metastatic HER2-positive breast cancer, (2) unresectable or metastatic HER2-low breast cancer, (3) unresectable or metastatic non-small cell lung cancer, and (4) locally advanced or metastatic HER2-positive gastric or gastroesophageal junction adenocarcinoma Irreversible Her2 kinase inhibitors of this disclosure can enhance Her2 ubiquitination and internalization likely by interrupting Her2:HSP90 chaperone interaction, leading to degradation of the Her2 receptor. It follows that Her2 kinase inhibitors of this disclosure may increase the efficacy of these ADC drugs, which require co-internalization with Her2 into the lysosome to release the tumor cell killing payload.

Embodiment 33 of this disclosure relates to the method according to Embodiment 32, wherein the one or more additional therapeutic agents is ado-trastuzumab emtansine or trastuzumab deruxtecan.

Embodiment 34 of this disclosure relates to the method according to Embodiment 32, wherein the one or more additional therapeutic agents is pembrolizumab or nivolumab.

Embodiment 34 of this disclosure relates to the method according to Embodiment 32, wherein the one or more additional therapeutic agents is pembrolizumab.

Non-limiting examples of a PD-1 inhibitors that can be combined with the compounds of this disclosure for the methods of treatments of this disclosure include pembrolizumab (KEYTRUDA®), nivolumab, cemiplimab. Non-limiting examples of PD-L1 inhibitor that can be combined with the compounds of this disclosure include atezolizumab, avelumab, and durvalumab. Non-limiting examples CTLA4 inhibitors that can be combined with the compounds of this disclosure include ipilimumab.

In another embodiment, the compounds of this disclosure are combined with docetaxel or gemcitabine in the methods of treatments of this disclosure.

In another embodiment, the present disclosure provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, gamma-ray, or electron, proton, neutron, or alpha-particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexatin lutetium), surgery, or bone marrow and stem cell transplantation.

VI. Kits

In another aspect, the present disclosure provides kits that include one or more compounds as described in any one of a compound in one of Embodiments 1-15, or a pharmaceutically acceptable salt, deuterated analog, a tautomer or a stereoisomer thereof, or a pharmaceutical composition in one of Embodiments 16-17. In some embodiments, the compound or composition is packaged, e.g., in a vial, bottle, flask, which may be further packaged, e.g., within a box, envelope, or bag. The compound or composition may be approved by the U.S. Food and Drug Administration or similar regulatory agency for administration to a mammal, e.g., a human. The compound or composition may be approved for administration to a mammal, e.g., a human, for a Her2 mediated disease or condition. The kits described herein may include written instructions for use and/or other indication that the compound or composition is suitable or approved for administration to a mammal, e.g., a human, for a Her2 mediated disease or condition. The compound or composition may be packaged in unit dose or single dose form, e.g., single dose pills, capsules, or the like.

VII. Binding Assays

The methods of the present disclosure can involve assays that are able to detect the binding of compounds to a target molecule. Such binding is at a statistically significant level, with a confidence level of at least 90%, or at least 95, 97, 98, 99% or greater confidence level that the assay signal represents binding to the target molecule, i.e., is distinguished from background. In some embodiments, controls are used to distinguish target binding from non-specific binding. A large variety of assays indicative of binding are known for different target types and can be used for this disclosure.

Binding compounds can be characterized by their effect on the activity of the target molecule. Thus, a "low activity" compound has an inhibitory concentration ($IC_{50}$) or effective concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Measuring Enzymatic and Binding Reactions During Screening Assays

Techniques for measuring the progression of enzymatic and binding reactions, e.g., in multicontainer carriers, are known in the art and include, but are not limited to, the following. Spectrophotometric and spectrofluorometric assays are well known in the art. Examples of such assays include the use of colorimetric assays for the detection of peroxides, as described in Gordon, A. J. and Ford, R. A., (1972) The Chemist's Companion: A Handbook Of Practical Data, Techniques, And References, John Wiley and Sons, N.Y., Page 437. Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) Spectrophotometry and Spectrofluorometry: A Practical Approach, pp. 91-114, IRL Press Ltd.; and Bell, (1981) Spectroscopy In Biochemistry, Vol. I, pp. 155-194, CRC Press.

In spectrofluorometric methods, enzymes are exposed to substrates that change their intrinsic fluorescence when processed by the target enzyme. Typically, the substrate is nonfluorescent and is converted to a fluorophore through one or more reactions. As a non-limiting example, Smase activity can be detected using the Amplex® Red reagent (Molecular Probes, Eugene, OR). In order to measure sphingomyelinase activity using Amplex® Red, the following reactions occur. First, Smase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry. Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, OR) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan. Exemplary normal-and-polarized fluorescence readers include the POLARION® fluorescence polarization system (Tecan AG, Hombrechtikon, Switzerland). General multiwell plate readers for other assays are available, such as the VERSAMAX® reader and the SPECTRAMAX multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, MA).

The target molecule can be bound to the scintillator plates by a variety of well-known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

VIII. General Synthesis

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

The compounds of this disclosure may contain one or more asymmetric or chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromatography, chiral seed crystals, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

It will also be appreciated that in each of the schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

Compounds of the present disclosure may be synthesized in accordance with the schemes and examples described below. The examples may be altered by substitution of the starting materials with other materials having similar structures to result in corresponding products. The structure of the desired product will generally make apparent to a person of skill in the art the required starting materials.

General Scheme 1

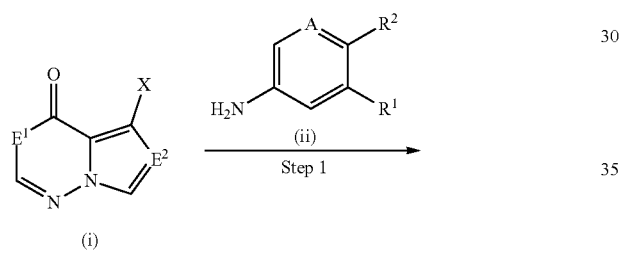

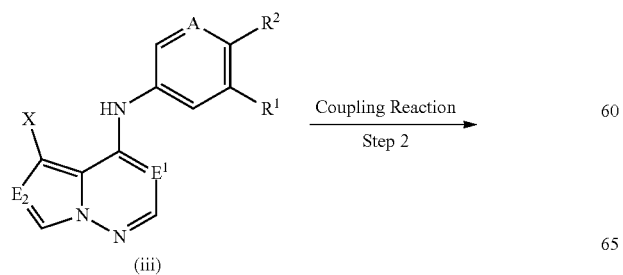

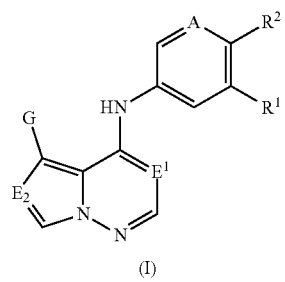

Step 1: Compound (i) can be converted to Compound (ii) through the application of a peptide coupling reagent such as PyBroP (by way of example) in appropriate reaction conditions which may be in the presence of a tertiary amine such as triethylamine. The reaction can take place in an appropriate solvent which may be aprotic solvent such as THF but may vary depending on the starting materials or intermediate compounds. Variables E1, E2, A, G, R1, and R2 in General Scheme 1 are as defined in this disclosure. Variable X in General Scheme 1 is an appropriate leaving group such as Br or Cl.

Step 2: Compound (ii) can be converted to Compound I by cross-coupling reactions by way of example such as palladium catalyzed Suzuki coupling with an organoborate such as

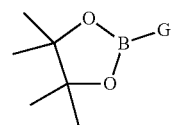

by way of example to arrive at Compound 1. Variable G can be further modified one or more times by techniques described in this disclosure or by techniques known in the art.

General Scheme 2

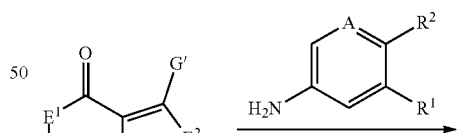

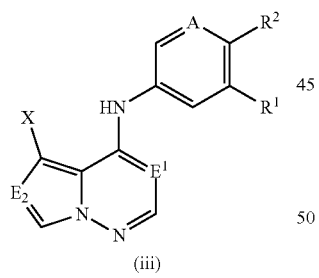

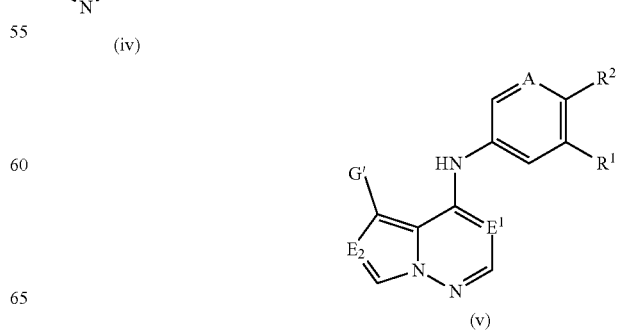

101

-continued

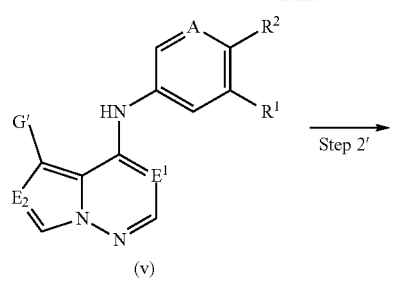

(v)

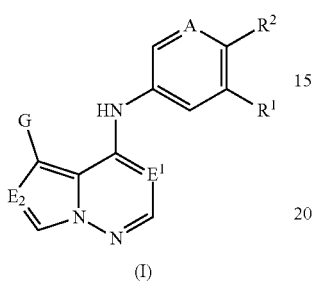

(I)

Step 1': Compound (iv) can be converted to Compound (v) through the application of a peptide coupling reagent such as PyBroP by way of example in the presence of a tertiary amine such as triethylamine. The reaction can take place in an aprotic solvent such as THF. Variables E1, E2, A, R1, and R2 in General Scheme 1 are as defined in this disclosure. Variable G' in General Scheme 1 can be a BOC-protected G group or another precursor that can be modified one or more times by techniques described in this disclosure or by techniques known in the art. G' can also the same as variable G as described in this disclosure in which there would be no Step 2' to modify variable G'.

Step 2': Compound (v) can be converted to Compound I by one or more techniques described in this disclosure or known in the art. Such on re s de techniques may include by way of example BOC deprotection, peptide coupling reactions with HATU, amide formation with HOBt, or nucleophilic substitution.

Synthesis of Intermediate A

Intermediate A

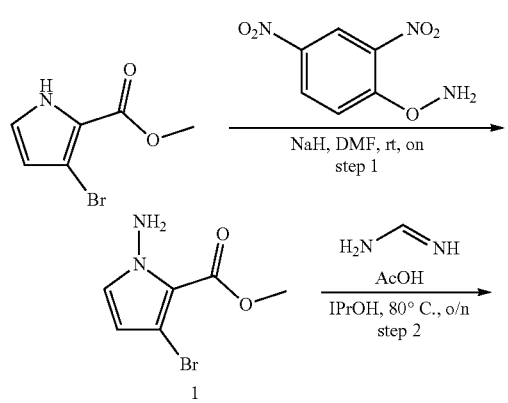

102

-continued

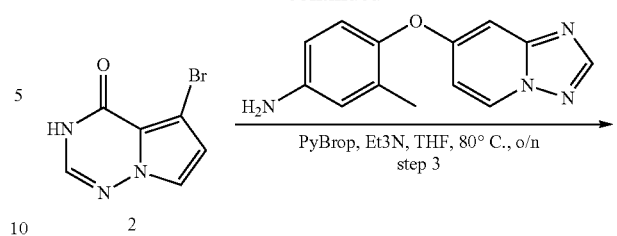

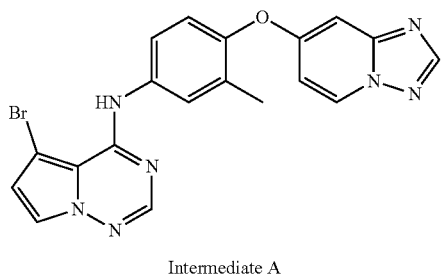

Intermediate A

Step 1. Methyl 1-amino-3-bromo-1H-pyrrole-2-carboxylate

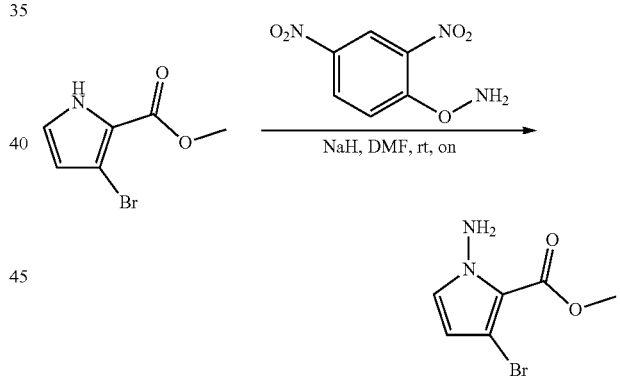

A solution of methyl 3-bromo-1H-pyrrole-2-carboxylate (25 g, 122.53 mmol) in DMF (200 mL) and THF (1000 mL) was treated with NaH (60% in mineral oil, 6.37 g, 159.25 mmol) for 1 hour at 0° C. followed by the addition of O-(2,4-dinitrophenyl)hydroxylamine (29.28 g, 147.04 mmol) at 0° C. and the mixture was stirred for 16 hours at room temperature. The reaction was quenched by the addition of saturated ammonium chloride aqueous solution (500 ml) at 0° C. The resulting mixture was diluted with water (1 L) and extracted with ethyl acetate (1.5 L×2). The combined organic layers were washed with brine (1.5 L×2), dried over anhydrous sodium sulfate, concentrated under reduced pressure. The residue was purified by silica gel column chromatography (0-20% ethyl acetate in hexanes) to provide methyl 1-amino-3-bromo-1H-pyrrole-2-carboxylate (22 g, 81.97%). LCMS (ESI-MS) m/z=219.0 [M+H]$^+$

Step 2. 5-bromopyrrolo[2,1-f][1,2,4]triazin-4(3H)-one

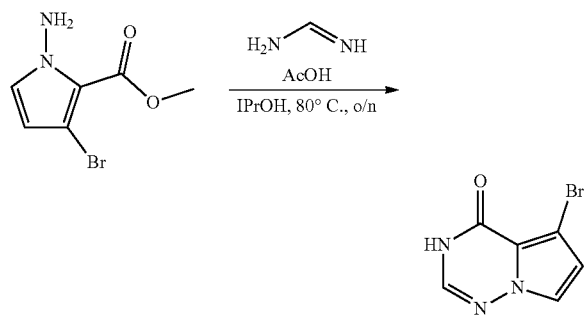

To a stirred solution of methyl 1-amino-3-bromo-1H-pyrrole-2-carboxylate (22 g, 100.43 mmol) in iPrOH (150 mL) was added formimidamide acetate (20.91 g, 200.87 mmol). The mixture was stirred at 80° C. overnight. The resulting mixture was diluted with water (300 ml). The precipitated solids were collected by filtration and washed with water (100 ml×3) and petroleum ether (200 ml) to afford 5-bromopyrrolo[2,1-f][1,2,4]triazin-4(3H)-one (13.2 g crude). LCMS (ESI-MS) m/z=214.0 [M+H]$^+$.

Step 3. N-(4-([1,2,4]triazolo[1,5-a]pyridin-7-yloxy)-3-methylphenyl)-5-bromopyrrolo[2,1-f][1,2,4]triazin-4-amine

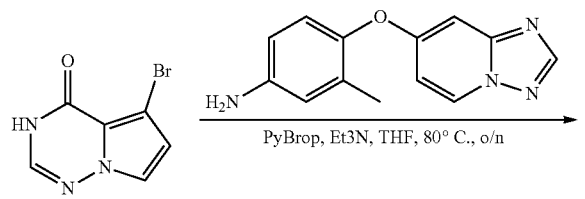

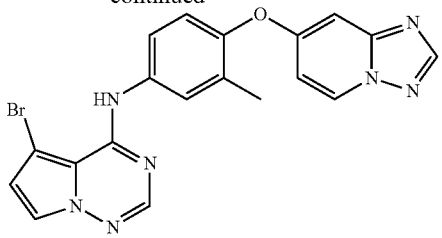

A solution of 5-bromopyrrolo[2,1-f][1,2,4]triazin-4(3H)-one (13.2 g, 61.97 mmol), 4-([1,2,4]triazolo[1,5-a]pyridin-7-yloxy)-3-methylaniline (14.87 g, 61.97 mmol), PyBrop (43.31 g, 92.95 mmol) and Et$_3$N (18.81 g, 185.91 mmol) in THF (300 mL) was stirred overnight at 80° C. The resulting mixture was purified by silica gel column chromatography (0-80% ethyl acetate in hexanes) to afford the title compound N-(4-([1,2,4]triazolo[1,5-a]pyridin-7-yloxy)-3-methylphenyl)-5-bromopyrrolo[2,1-f][1,2,4]triazin-4-amine, intermediate A (12 g, 27.33%). LCMS (ESI-MS) m/z=436.0 [M+H]$^+$.

In the synthetic examples below where pure stereoisomers were separated by chiral separation, all pure stereoisomers of these compounds were eluted into separate fractions as described herein. The $^1$H NMR and MS data for each eluted pure stereoisomer were obtained to verify that all pure stereoisomers of such compounds were separated. The absolute stereochemistry of each separated fraction was not determined.

In other synthetic examples, regular HPLC was used to separate endo-exo products or diastereomers to give fractions for each racemate. The $^1$H NMR and MS data for each eluted r endo-exo product, and diastereomer were obtained to verify that all endo-exo products or diastereomers of such compounds were separated. The absolute stereochemistry of each separated fraction was not determined.

All compounds in Table 1, were found to actively inhibit one or more of HER2-YVMA, HER2 WT and EGFR WT.

The following Example numbers correspond to the compound numbers in Table 1.

Example 1

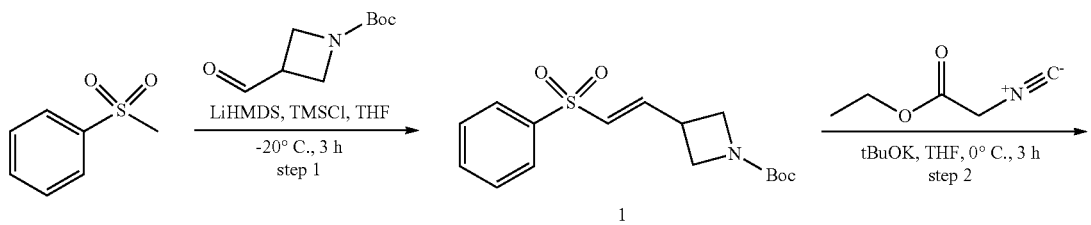

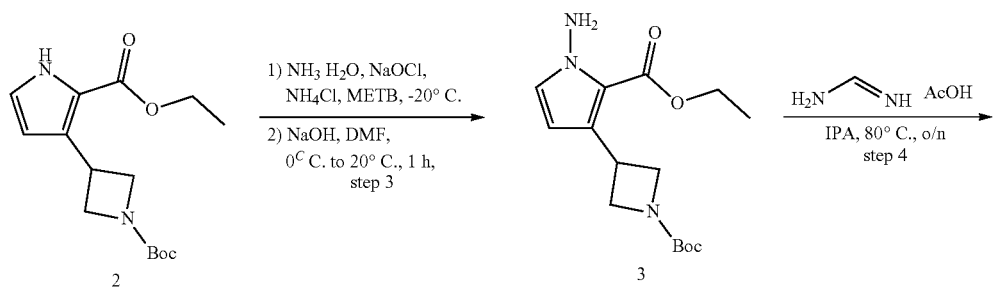

105 106

-continued

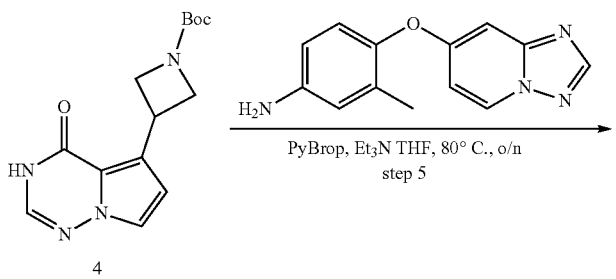

4

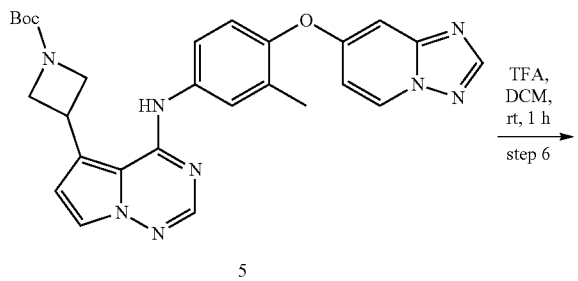

5

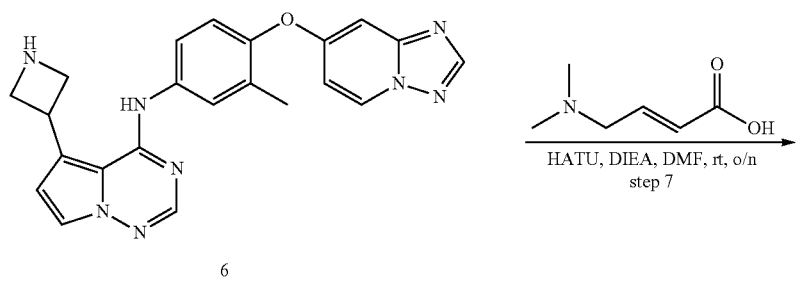

6

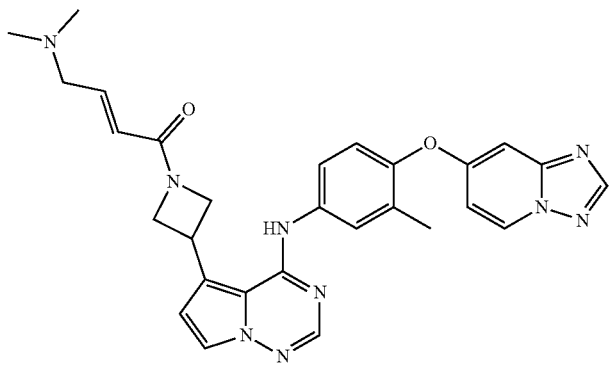

Example 1

Step 1. Tert-butyl (E)-3-(2-(phenylsulfonyl)vinyl)azetidine-1-carboxylate

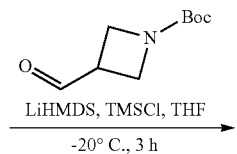

-continued

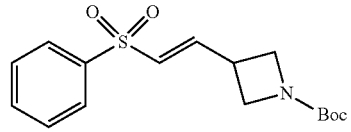

To a solution of methanesulfonylbenzene (16.7 g, 107 mmol) in anhydrous tetrahydrofuran (160 mL) at −20° C. under nitrogen atmosphere was added lithium bis(trimethylsilyl)amide (1M solution in THF, 189 mL, 189 mmol) dropwise and the reaction was allowed to stir for 30 minutes at −20° C. To the reaction mixture was added chlorotrimethylsilane (12.6 ml, 99.2 mmol) and slowed to stirred for a further 15 minutes. To the reaction mixture was added a solution of tert-butyl 3-formylazetidine-1-carboxylate (19.8 g, 106.9 mmol) in anhydrous tetrahydrofuran (200 mL) dropwise and allowed to stir at −20° C. for further 3 hours. The operation was repeated twice. The reaction mixture was quenched with saturated aqueous ammonium chloride (1 L) and extracted with ethyl acetate (2×1 L). The combined organics were dried over sodium sulfate filtered and concentrated under vacuum to afford the crude product. The crude product was purified by column chromatography (silica, petroleum ether/ethyl acetate, 15%) to give tert-butyl (E)-3-(2-(phenylsulfonyl)vinyl)azetidine-1-carboxylate (52 g, 47.6%). LCMS (ESI-MS) m/z=324.1 [M+H]$^+$.

Step 2. Ethyl 3-(1-(tert-butoxycarbonyl)azetidin-3-yl)-1H-pyrrole-2-carboxylate

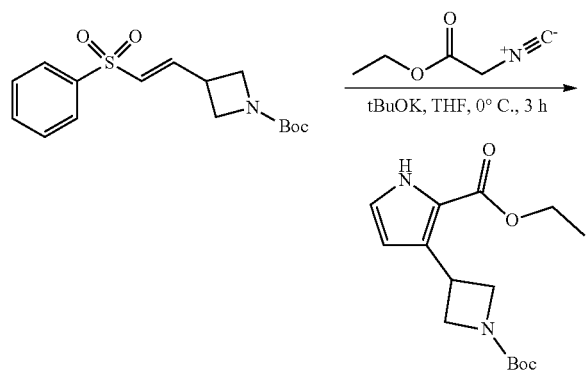

Potassium 2-methylpropan-2-olate (11.0 g, 98.2 mmol) was added to a mixture of ethyl 2-isocyanoacetate (8.4 g, 37.1 mmol) in tetrahydrofuran (100 mL) under nitrogen atmosphere at 0° C. and stirred for 10 minutes. Then tert-butyl (E)-3-(2-(phenylsulfonyl)vinyl)azetidine-1-carboxylate (20 g, 61.8 mmol) in THF (100 mL) was added to mixture and stirred at 25° C. over the time of one hour. The operation was repeated twice. The reaction was quenched by the addition of saturated aqueous ammonium chloride (500 mL) at 0° C. The resulting mixture was extracted with ethyl acetate (3×500 mL). The combined organic layers were washed with brine (3×500 mL), dried over anhydrous sodium sulfate. The filtrate was concentrated under reduced pressure. The residue was purified by silica gel column chromatography, eluted with petroleum ether/ethyl acetate (10%) to afford ethyl 3-(1-(tert-butoxycarbonyl)azetidin-3-yl)-1H-pyrrole-2-carboxylate (27 g, 42.2%). LCMS (ESI-MS) m/z=295.2 [M+H]$^+$.

Step 3. Ethyl 1-amino-3-(1-(tert-butoxycarbonyl)azetidin-3-yl)-1H-pyrrole-2-carboxylate

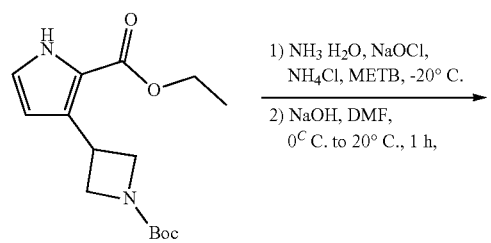

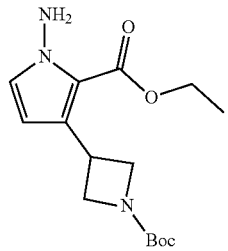

To a flask was added MTBE (1 L) and ammonium chloride (30 g, 0.565 mol). The reaction was cooled to −20° C. Then concentrated aq. ammonium hydroxide (80 mL) was added to the reaction followed by slow addition of commercial-grade sodium hypochlorite solution (750 mL). After addition, the reaction was stirred at −20° C. for additional 30 minutes. The MTBE layer was separated and washed with brine and dried over anhydrous sodium sulfate. In a separate flask under nitrogen was added ethyl 3-(1-(tert-butoxycarbonyl)azetidin-3-yl)-1H-pyrrole-2-carboxylate (27 g, 91.8 mmol) and dry DMF (300 mL). The reaction was cooled to 0° C. and sodium hydroxide (7.3 g, 183.6 mmol) was added portionwise to the reaction. The reaction was stirred at 0° C. for additional 1 hour before it was cooled to −20° C. At this time, the previously prepared MTBE solution of chloramine was added slowly to the reaction and the mixture was stirred at −20° C. for 1 hour. The reaction was quenched with saturated sodium thiosulfate solution. The organic layer of the reaction was separated and washed with water and brine, dried over sodium sulfate, filtered and concentrated to afford ethyl 1-amino-3-(1-(tert-butoxycarbonyl)azetidin-3-yl)-1H-pyrrole-2-carboxylate (21 g, 60.3%). LCMS (ESI-MS) m/z=310.2 [M+H].

Step 4. Tert-butyl 3-(4-oxo-3,4-dihydropyrrolo[2,1-f][1,2,4]triazin-5-yl)azetidine-1-carboxylate

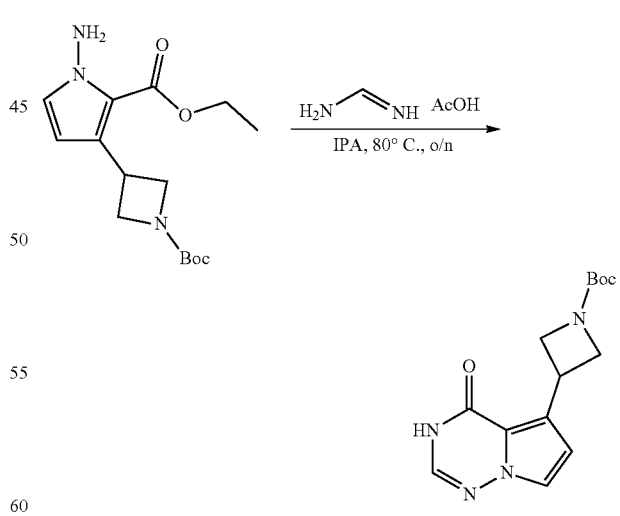

Acetic acid methanimidamide (7.06 g, 67.8 mmol) was added to a mixture of ethyl 1-amino-3-[1-(tert-butoxycarbonyl)azetidin-3-yl]pyrrole-2-carboxylate (4 g, 13.5 mmol) in iPrOH (15 mL). Then the reaction mixture was stirred at 80° C. for 12 hours. The reaction mixture was concentrated under vacuum and purified by silica gel column chromatography, eluted with PE/EA (37%) and concentrated to afford tert-butyl 3-(4-oxo-3,4-dihydropyrrolo[2,1-f][1,2,4]triazin-5-yl)azetidine-1-carboxylate (15 g, 76.1%). LCMS (ESI-MS) m/z=291.1 [M+H]⁺.

Step 5. Tert-butyl 3-(4-((4-([1,2,4]triazolo[1,5-a]pyridin-7-yloxy)-3-methylphenyl)amino)pyrrolo[2,1-f][1,2,4]triazin-5-yl)azetidine-1-carboxylate

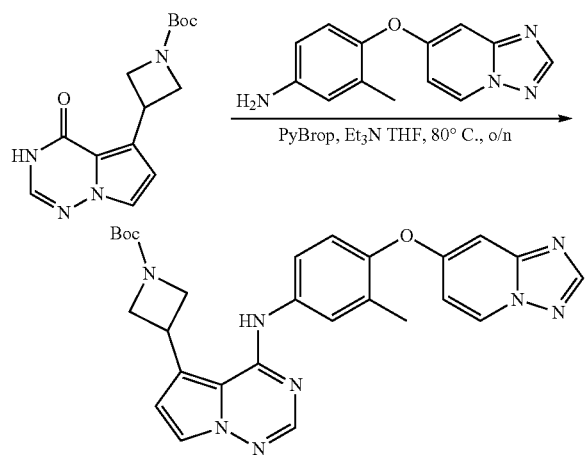

Bromotris(pyrrolidin-1-yl)phosphanium; hexafluoro-lambda5-phosphanuide (2.41 g, 5.16 mmol) was added to a mixture of tert-butyl 3-(4-oxo-3,4-dihydropyrrolo[2,1-f][1,2,4]triazin-5-yl)azetidine-1-carboxylate (1 g, 3.44 mmol), 4-([1,2,4]triazolo[1,5-a]pyridin-7-yloxy)-3-methylaniline (830 mg, 3.44 mmol) and triethylamine (1.1 g g, 10.33 mmol) in THF (30 mL). Then the reaction mixture was stirred at 80° C. for overnight. The resulting mixture was cooled down to room temperature, filtered, the filter cake was washed with dichloromethane (3×50 mL). The filtrate was concentrated under reduced pressure to afford the crude and then purified by silica gel column chromatography, eluted with petroleum ether/ethyl acetate (1:6) to afford the crude 1.2 g (contains 40% of SM). Then the crude material was re-purified by reversed-phase flash chromatography with the following conditions: column, C18 silica gel; mobile phase, ACN in Water (10 mmol/L NH₄HCO₃), 10% to 50% gradient in 10 min; detector, UV 254 nm and concentrated to give tert-butyl 3-(4-((4-([1,2,4]triazolo[1,5-a]pyridin-7-yloxy)-3-methylphenyl)amino)pyrrolo[2,1-f][1,2,4]triazin-5-yl)azetidine-1-carboxylate (553 mg, 31.25%). LCMS (ESI-MS) m/z=513.2 [M+H]⁺.

Step 6. N-(4-([1,2,4]triazolo[1,5-a]pyridin-7-yloxy)-3-methylphenyl)-5-(azetidin-3-yl)pyrrolo[2,1-f][1,2,4]triazin-4-amine

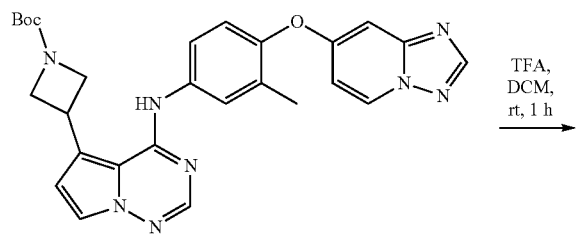

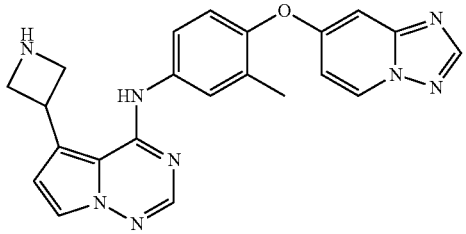

A solution of TFA (1 mL) and tert-butyl 3-(4-((4-([1,2,4]triazolo[1,5-a]pyridin-7-yloxy)-3-methylphenyl)amino)pyrrolo[2,1-f][1,2,4]triazin-5-yl)azetidine-1-carboxylate (300 mg, 0.58 mmol) in DCM (2 mL) was stirred for 1 hour at 25° C. The resulting mixture was concentrated under vacuum to afford the crude N-(4-([1,2,4]triazolo[1,5-a]pyridin-7-yloxy)-3-methylphenyl)-5-(azetidin-3-yl)pyrrolo [2,1-f][1,2,4]triazin-4-amine (250 mg). LCMS (ESI-MS) m/z=413.2 [M+H].

Step 7. (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(dimethylamino)but-2-en-1-one

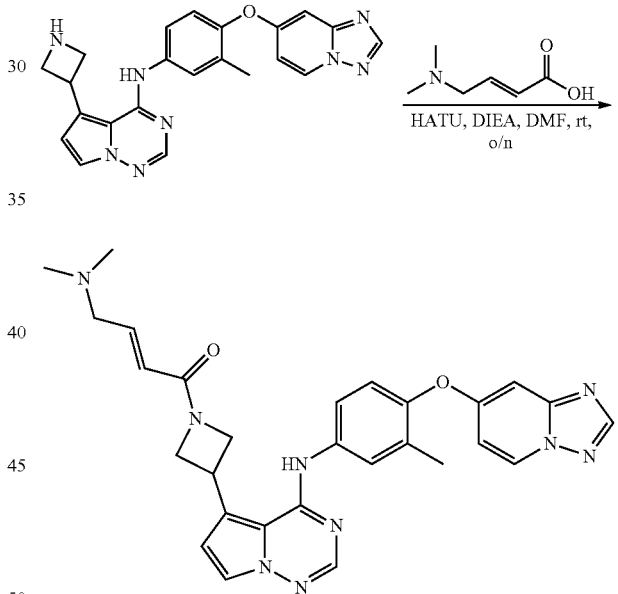

A solution of N-(4-([1,2,4]triazolo[1,5-a]pyridin-7-yloxy)-3-methylphenyl)-5-(azetidin-3-yl)pyrrolo[2,1-f][1,2,4]triazin-4-amine (250 mg, 0.61 mmol), (2E)-4-(dimethylamino)but-2-enoic acid (94 mg, 0.72 mmol), N,N,N,N-Tetramethyl-O-(7-azabenzotriazol-1-yl)uronium hexafluorophosphate (277 mg, 0.72 mmol) and N,N-Diisopropylethylamine (237 mg, 1.81 mmol) in DMF (5 mL) was stirred overnight at room temperature. The resulting mixture was purified by reverse phase flash with the following conditions (5 mmol/L NH₄HCO₃, Flow rate: 50 mL/min, 30%) to afford to afford (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(dimethylamino)but-2-en-1-one, Example 1 (138 mg, 42.9%). LCMS (ESI-MS) m/z=524.1 [M+H]⁺.

Example 3

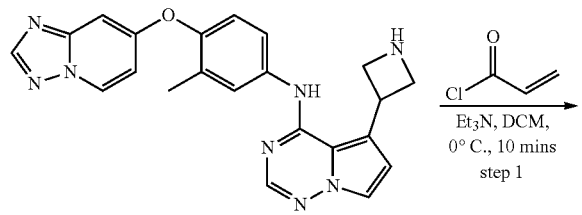

1-(3-(4-(((4-([1,2,4]triazolo[1,5-a]pyridin-7-yloxy)-3-methylphenyl)amino)pyrrolo[2,1-f][1,2,4] triazin-5-yl)azetidin-1-yl)prop-2-en-1-one A solution of acryloyl chloride (19.3 mg, 0.21 mmol) in DCM (1 mL) was added to a solution of N-(4-([1,2,4]triazolo[1,5-a]pyridin-7-yloxy)-3-methylphenyl)-5-(azetidin-3-yl)pyrrolo[2,1-f][1,2,4]triazin-4-amine (80 mg, 0.19 mmol) and Et$_3$N (98.1 mg, 0.97 mmol) in DCM (2 mL) dropwise at 0° C. The resulting mixture was stirred at 0° C. for 10 minutes, quenched by addition of water (10 mL) and extracted with ethyl acetate (3×10 mL). The combined organic layers were washed with brine (20 mL), dried over anhydrous Na$_2$SO$_4$ and concentrated under vacuum. The residue was purified by silica gel column chromatography, eluted with methanol in dichloromethane from 0% to 10% to afford the crude product. The crude product was re-purified by Prep-HPLC Mobile Phase A: Water (10 mmol/L NH$_4$HCO$_3$), Mobile Phase B: ACN; Gradient: 20% B to 50% B to afford the desired product 1-(3-(4-(((4-([1,2,4]triazolo[1,5-a]pyridin-7-yloxy)-3-methylphenyl)amino)pyrrolo[2,1-f][1,2,4] triazin-5-yl)azetidin-1-yl) prop-2-en-1-one, Example 3 (13.3 mg, 9.8% yield). LCMS (ESI-MS) m/z=467.3 [M+H]$^+$. $^1$H NMR (400 MHz, DMSO-d$_6$) δ (ppm) 8.94 (d, J=7.2 Hz, 1H), 8.53 (s, 1H), 8.39 (s, 1H), 7.68 (s, 1H), 7.29-7.17 (m, 2H), 7.12 (s, 1H), 7.09-7.02 (m, 1H), 6.99 (s, 2H), 6.81 (s, 1H), 6.47-6.32 (m, 1H), 6.13 (d, J=16.4 Hz, 1H), 5.77-5.63 (m, 1H), 4.70 (s, 2H), 4.42 (s, 1H), 4.29 (s, 1H), 4.10-3.99 (m, 1H), 2.18 (s, 3H).

Example 6

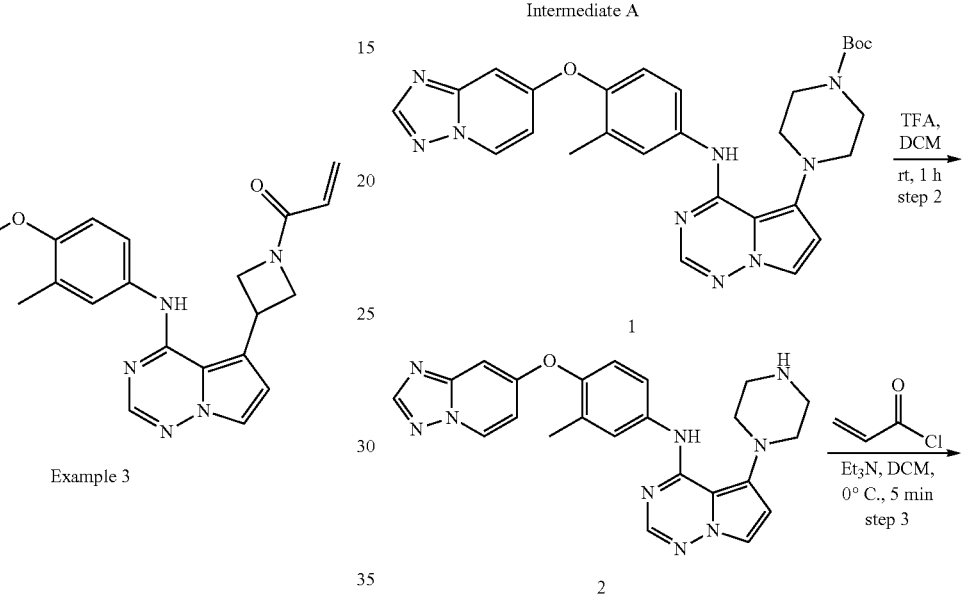

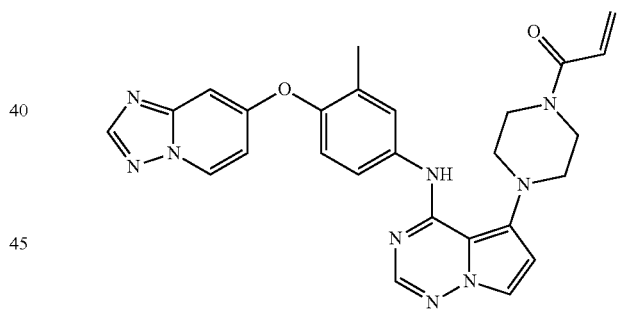

Step 1. Tert-butyl-4-(4-(((4-([1,2,4]triazolo[1,5-a]pyridin-7-yloxy)-3-methylphenyl)amino)pyrrolo[2,1-f][1,2,4]triazin-5-yl)piperazine-1-carboxylate

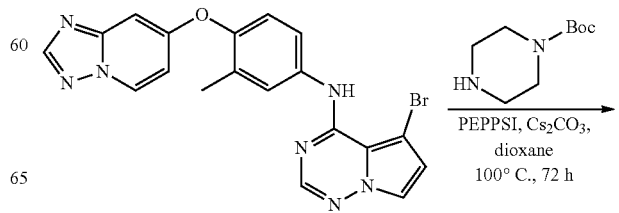

-continued

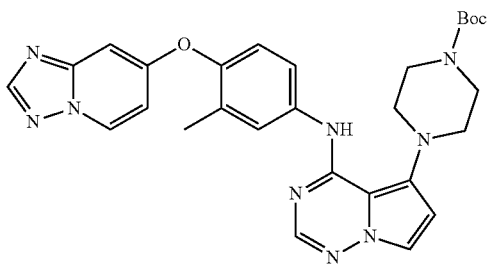

A mixture of N-(4-([1,2,4]triazolo[1,5-a]pyridin-7-yloxy)-3-methylphenyl)-5-bromopyrrolo[2,1-f][1,2,4]triazin-4-amine (200 mg, 0.45 mmol), tert-butyl piperazine-1-carboxylate (93.92 mg, 0.50 mmol), Pd$_2$(dba)$_3$ (41.98 mg, 0.05 mmol), BINAP (57.09 mg, 0.09 mmol) and t-BuONa (88.11 mg, 0.91 mmol) in dioxane (4 mL) was stirred for 72 hours at 100° C. under nitrogen atmosphere. The reaction mixture was filtered and the filtrate was concentrated to afford the crude product. The crude product was purified by column chromatography (silica gel, 25 g, eluted with ethyl acetate in petroleum ether from 0% to 80% with 20 mL/min flow rate), the desired fractions were combined and concentrated under vacuum to afford the desired product tert-butyl 4-(4-((4-([1,2,4]triazolo[1,5-a]pyridin-7-yloxy)-3-methylphenyl)amino)pyrrolo [2,1-f][1,2,4]triazin-5-yl)piperazine-1-carboxylate (200 mg, 69%). LCMS (ESI-MS) m/z=542.3 [M+H]$^+$.

Step 2. N-(4-([1,2,4]triazolo[1,5-a]pyridin-7-yloxy)-3-methylphenyl)-5-(piperazin-1-yl)pyrrolo[2,1-f][1,2,4]triazin-4-amine

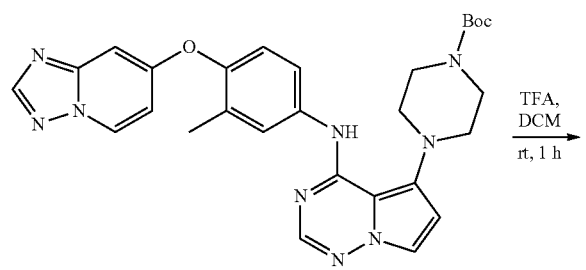

A mixture of tert-butyl 4-(4-((4-([1,2,4]triazolo[1,5-a]pyridin-7-yloxy)-3-methylphenyl)amino)pyrrolo[2,1-f][1,2,4]triazin-5-yl)piperazine-1-carboxylate (200 mg, 0.37 mmol) and TFA (3 mL, 39.99 mmol) in DCM (1 mL) was stirred for 1 hour at room temperature. The resulting mixture was concentrated under vacuum to afford the crude product. The crude product was purified by column chromatography (silica-gel, 25 g, eluted with methanol in dichloromethane from 0% to 10% with 20 mL/min flowrate), the desired fractions were combined and concentrated under vacuum to afford N-(4-([1,2,4]triazolo[1,5-a]pyridin-7-yloxy)-3-methylphenyl)-5-(piperazin-1-yl)pyrrolo[2,1-f][1,2,4]triazin-4-amine (210 mg crude). LCMS (ESI-MS) m/z=442.2 [M+H]$^+$.

Step 3. 1-(4-(4-((4-([1,2,4]triazolo[1,5-a]pyridin-7-yloxy)-3-methylphenyl)amino)pyrrolo[2,1-f][1,2,4]triazin-5-yl)piperazin-1-yl)prop-2-en-1-one

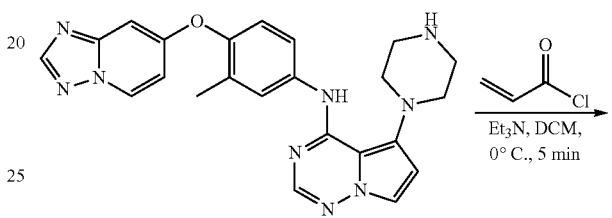

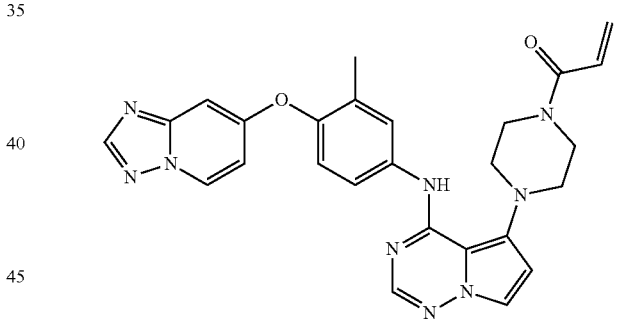

A mixture of N-(4-([1,2,4]triazolo[1,5-a]pyridin-7-yloxy)-3-methylphenyl)-5-(piperazin-1-yl)pyrrolo[2,1-f][1,2,4]triazin-4-amine (210 mg, 0.47 mmol), acryloyl chloride (43.05 mg, 0.47 mmol) and Et$_3$N (144.40 mg, 1.41 mmol) in DCM (2 mL) was stirred for 5 minutes at 0° C. The reaction mixture was purified by column chromatography (silica-gel, 25 g, eluted with ethyl acetate in petroleum ether from 0% to 80% with 20 mL/min). The fractions with desired mass signal were combined and concentrated under vacuum to afford the desired product 1-(4-(4-((4-([1,2,4]triazolo[1,5-a]pyridin-7-yloxy)-3-methylphenyl)amino)pyrrolo[2,1-f][1,2,4] triazin-5-yl)piperazin-1-yl)prop-2-en-1-one, Example 6 (27.5 mg, 11.62%). LCMS (ESI-MS) m/z=496.2 [M+H]$^+$.

Example 7
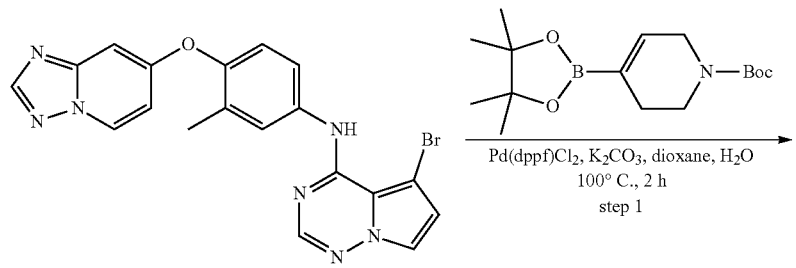
Intermediate A
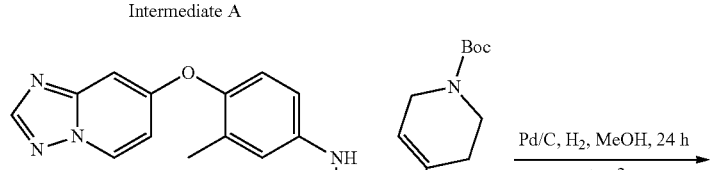
1
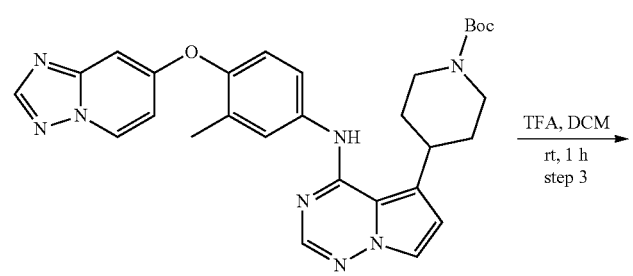
2
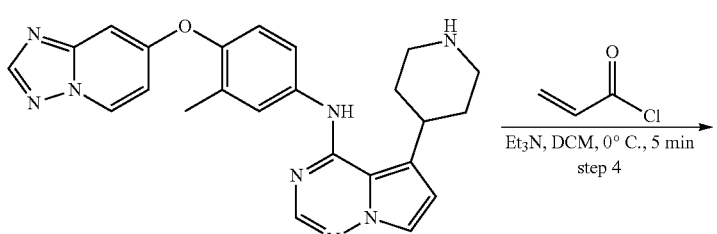
3
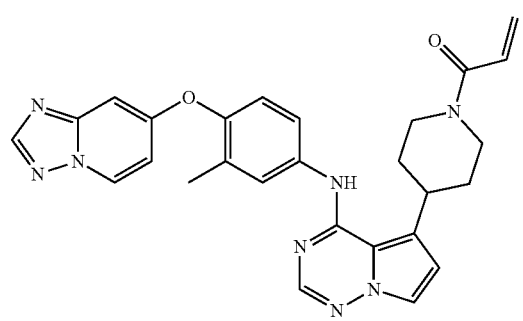
Example 7

Step 1. tert-butyl 4-(4-((4-([1,2,4]triazolo[1,5-a]pyridin-7-yloxy)-3-methylphenyl)amino)pyrrolo[2,1-f][1,2,4]triazin-5-yl)-3,6-dihydropyridine-1(2H)-carboxylate

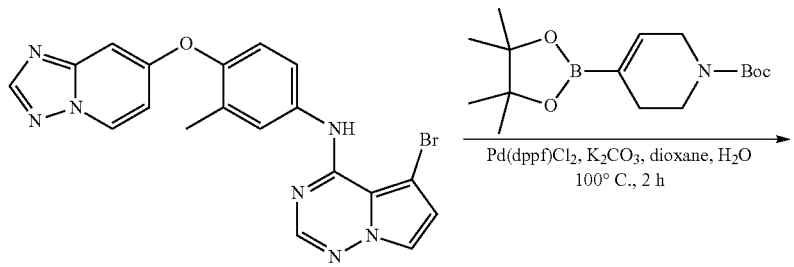

A solution of N-(4-([1,2,4]triazolo[1,5-a]pyridin-7-yloxy)-3-methylphenyl)-5-bromopyrrolo[2,1-f][1,2,4]triazin-4-amine (200 mg, 0.46 mmol), tert-butyl 4-(4,4,5,5-tetramethyl-1,3,2-dioxaborolan-2-yl)-3,6-dihydropyridine-1(2H)-carboxylate (141.75 mg, 0.46 mmol), Pd(dppf)Cl$_2$ (37.34 mg, 0.05 mmol) and K$_2$CO$_3$ (126.71 mg, 0.92 mmol) in dioxane (4 mL) and H$_2$O (1.2 mL) was stirred for 2 hours at 100° C. under nitrogen atmosphere. The resulting mixture was concentrated under vacuum to afford the crude product. The crude product was purified by Prep-TLC (petroleum ether/ethyl acetate 1:10) to afford tert-butyl tert-butyl 4-(4-((4-([1,2,4]triazolo[1,5-a]pyridin-7-yloxy)-3-methylphenyl)amino)pyrrolo[2,1-f][1,2,4]triazin-5-yl)-3,6-dihydropyridine-1(2H)-carboxylate (220 mg, purity=96.8%). LCMS (ESI-MS) m/z=539.2 [M+H]$^+$.

Step 2. Tert-butyl 4-(4-((4-([1,2,4]triazolo[1,5-a]pyridin-7-yloxy)-3-methylphenyl)amino)pyrrolo[2,1-f][1,2,4]triazin-5-yl)piperidine-1-carboxylate A solution of 4-(4-((4-([1,2,4]triazolo[1,5-a]pyridin-7-yloxy)-3-methylphenyl)amino)pyrrolo[2,1-f][1,2,4]triazin-5-yl)-3,6-dihydropyridine-1(2H)-carboxylate (200 mg, 0.37 mmol) and Pd/C (395.16 mg, 3.71 mmol) in MeOH was stirred overnight at room temperature under hydrogen atmosphere. The mixture was filtered off and the filtrate was concentrated under vacuum to afford crude product. The crude product was used in the next step directly without further purification. LCMS (ESI-MS) m/z=541.3 [M+H]$^+$.

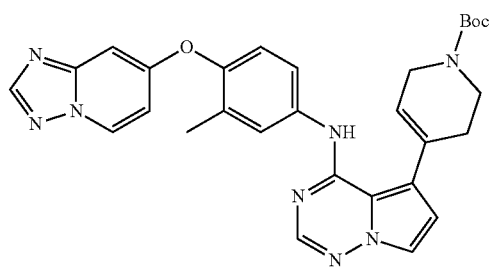

Step 3. N-(4-([1,2,4]triazolo[1,5-a]pyridin-7-yloxy)-3-methylphenyl)-5-(piperidin-4-yl)pyrrolo[2,1-f][1,2,4]triazin-4-amine

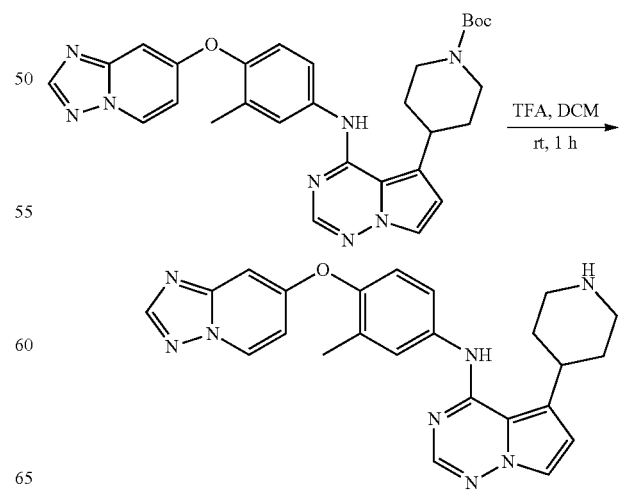

A solution of tert-butyl 4-(4-((4-([1,2,4]triazolo[1,5-a]pyridin-7-yloxy)-3-methylphenyl)amino)pyrrolo[2,1-f][1,2,4]triazin-5-yl)piperidine-1-carboxylate (140 mg, 0.26 mmol) in TFA (2 mL) was stirred for 1 hour at room temperature. The resulting mixture was concentrated under vacuum to afford the crude product. The crude product was used in the next step directly without further purification. LCMS (ESI-MS) m/z=441.2 [M+H]+.

Step 4. 1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)prop-2-en-1-one

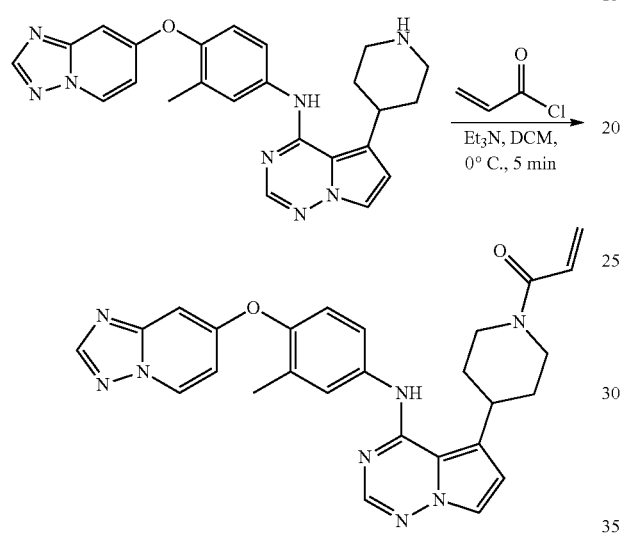

A solution of N-(4-([1,2,4]triazolo[1,5-a]pyridin-7-yloxy)-3-methylphenyl)-5-(piperidin-4-yl)pyrrolo[2,1-f][1,2,4]triazin-4-amine (70 mg, 0.16 mmol), acryloyl chloride (14.38 mg, 0.16 mmol) and Et₃N (32.16 mg, 0.32 mmol) in DCM (2 mL) was stirred for 5 minutes at 0° C. The resulting mixture was purified by Prep-TLC (ethyl acetate) to afford 1-(4-(4-((4-([1,2,4]triazolo[1,5-a]pyridin-7-yloxy)-3-methylphenyl) amino)pyrrolo[2,1-f][1,2,4]triazin-5-yl)piperidin-1-yl)prop-2-en-1-one, Example 7 (24.6 mg, 30.55%). LCMS (ESI-MS) m/z=495.2 [M+H]+.

Example 8

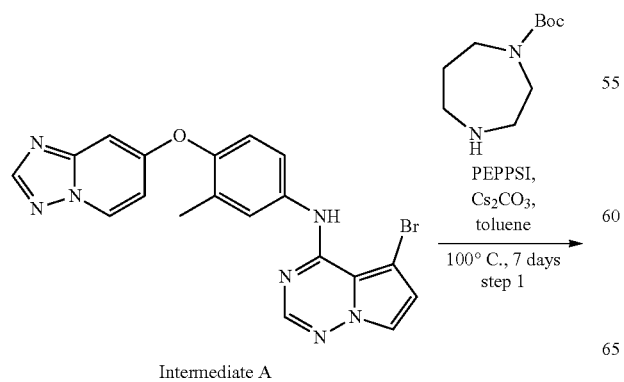

Intermediate A

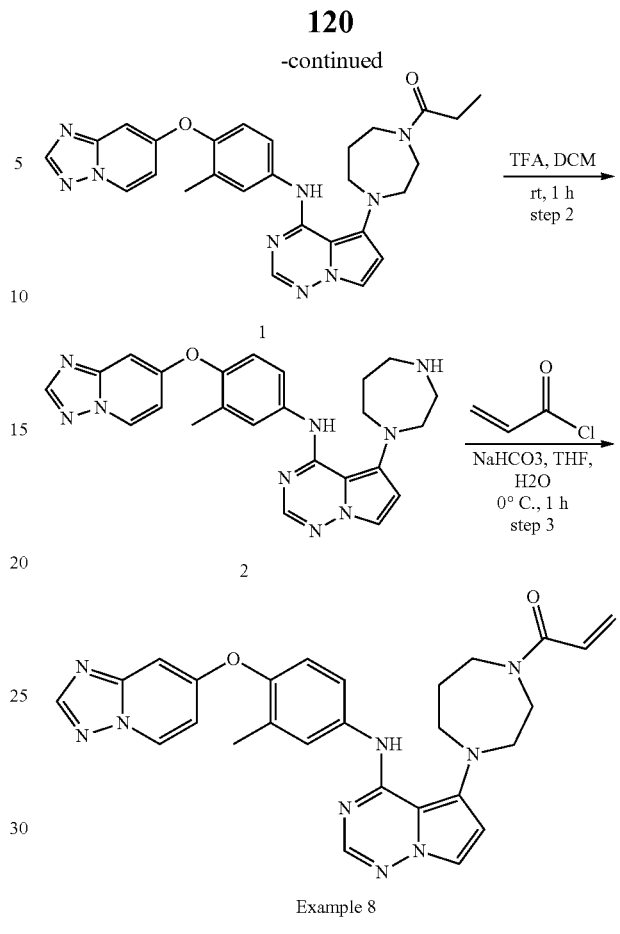

Example 8

Step 1. tert-butyl4-(4-((4-([1,2,4]triazolo[1,5-a]pyridin-7-yloxy)-3-methylphenyl)amino)pyrrolo[2,1-f][1,2,4]triazin-5-yl)-1,4-diazepane-1-carboxylate

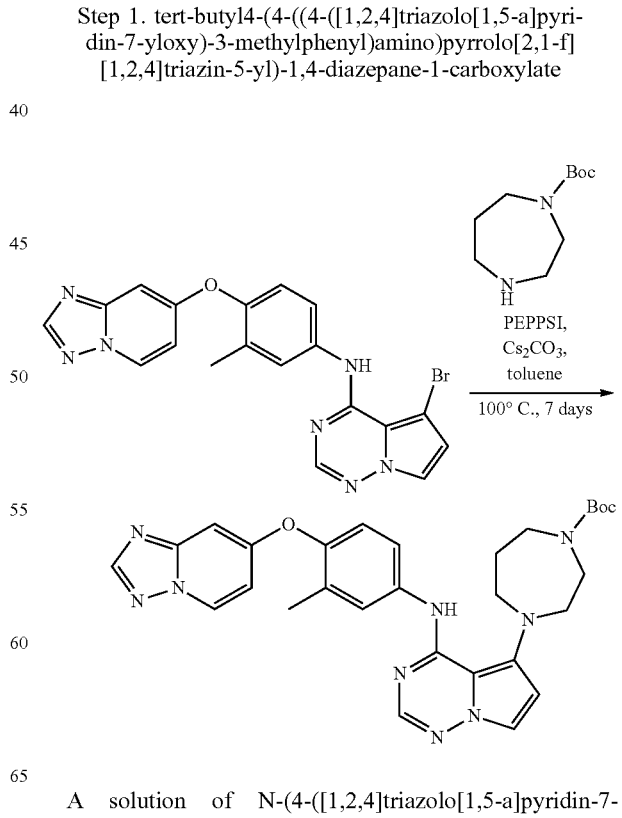

A solution of N-(4-([1,2,4]triazolo[1,5-a]pyridin-7-yloxy)-3-methylphenyl)-5-bromopyrrolo[2,1-f][1,2,4]triazin-4-amine (1 g, 2.29 mmol), tert-butyl 1,4-diazepane-1-carboxylate (918.15 mg, 4.58 mmol), PEPPSI (223.21 mg, 0.23 mmol) and Cs$_2$CO$_3$ (1493.65 mg, 4.58 mmol) in dioxane (10 mL) was stirred for 7 days at 100° C. under nitrogen atmosphere. The resulting mixture was concentrated under vacuum to afford a crude product.

The crude product was purified by Prep-TLC (petroleum ether/ethyl acetate 1:2) to afford tert-butyl4-(4-((4-([1,2,4]triazolo[1,5-a]pyridin-7-yloxy)-3-methylphenyl)amino)pyrrolo[2,1-f][1,2,4]triazin-5-yl)-1,4-diazepane-1-carboxylate (500 mg crude). LCMS (ESI-MS) m/z=556.3 [M+H]$^+$.

Step 2. N-(4-([1,2,4]triazolo[1,5-a]pyridin-7-yloxy)-3-methylphenyl)-5-(1-(2-aminoethyl)-1H-pyrazol-4-yl)pyrrolo[2,1-f][1,2,4]triazin-4-amine

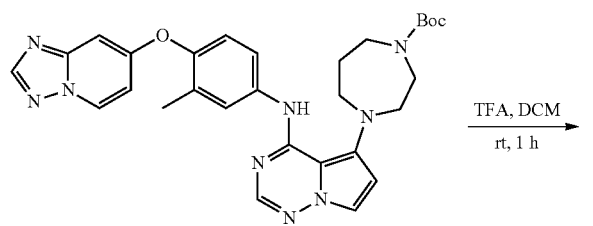

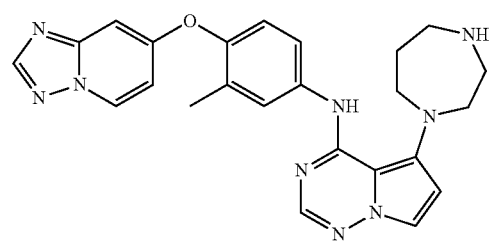

A solution of tert-butyl4-(4-((4-([1,2,4]triazolo[1,5-a]pyridin-7-yloxy)-3-methylphenyl)amino)pyrrolo[2,1-f][1,2,4]triazin-5-yl)-1,4-diazepane-1-carboxylate (500 mg, 0.90 mmol) and TFA (5 mL) in DCM (5 mL) was stirred for 1 hour at room temperature. The resulting mixture was concentrated under vacuum to afford a crude product. The crude product was purified by Prep-TLC (dichloromethane/methanol 10:1) to afford N-(4-([1,2,4]triazolo[1,5-a]pyridin-7-yloxy)-3-methylphenyl)-5-(1-(2-aminoethyl)-1H-pyrazol-4-yl)pyrrolo [2,1-f][1,2,4]triazin-4-amine. LCMS (ESI-MS) m/z=456.2 [M+H]$^+$.

Step 3. 1-(4-(4-((4-([1,2,4]triazolo[1,5-a]pyridin-7-yloxy)-3-methylphenyl)amino)pyrrolo[2,1-f][1,2,4]triazin-5-yl)-1,4-diazepan-1-yl)prop-2-en-1-one

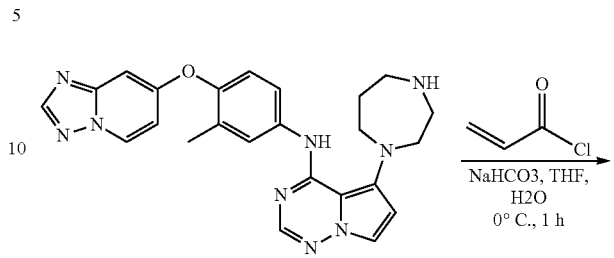

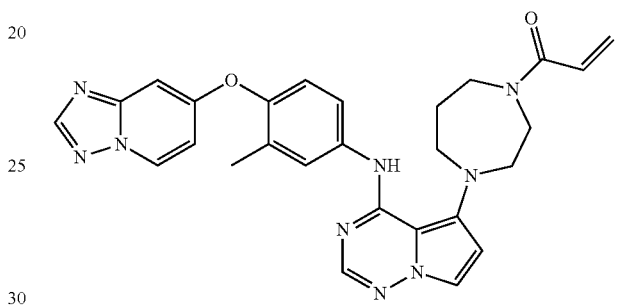

A solution of N-(4-([1,2,4]triazolo[1,5-a]pyridin-7-yloxy)-3-methylphenyl)-5-(1-(2-aminoethyl)-1H-pyrazol-4-yl)pyrrolo[2,1-f][1,2,4]triazin-4-amine (200 mg, 0.44 mmol), acryloyl chloride (40.44 mg, 0.45 mmol) and NaHCO$_3$ (110.65 mg, 1.32 mmol) in THF (1 mL) and H$_2$O (1 mL) was stirred for 1 hour at room temperature. The reaction mixture was diluted with water (5 mL) and extracted with EA (3×5 mL). The combined organic layers were washed with brine (5 mL), dried over anhydrous Na$_2$SO$_4$, filtered and concentrated under vacuum to afford the crude product. The crude product was purified by Prep-TLC (dichloromethane/methanol 10:1) to afford 1-(4-(4-((4-([1,2,4]triazolo[1,5-a]pyridin-7-yloxy)-3-methylphenyl)amino)pyrrolo[2,1-f][1,2,4] triazin-5-yl)-1,4-diazepan-1-yl)prop-2-en-1-one, Example 8 (31.5 mg, 13.85%). LCMS (ESI-MS) m/z=510.1[M+H]$^+$.

Example 9

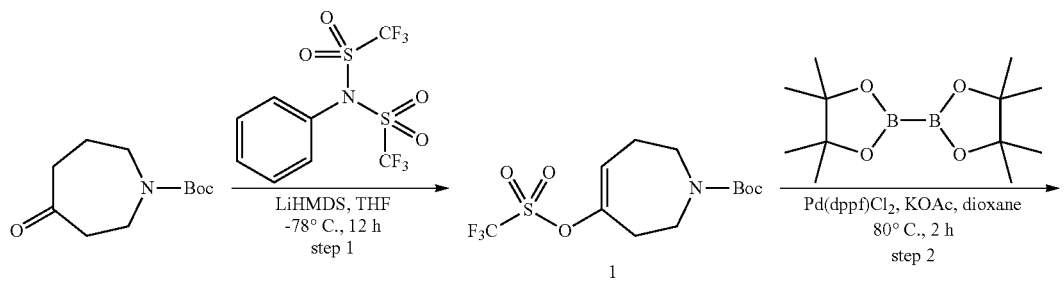

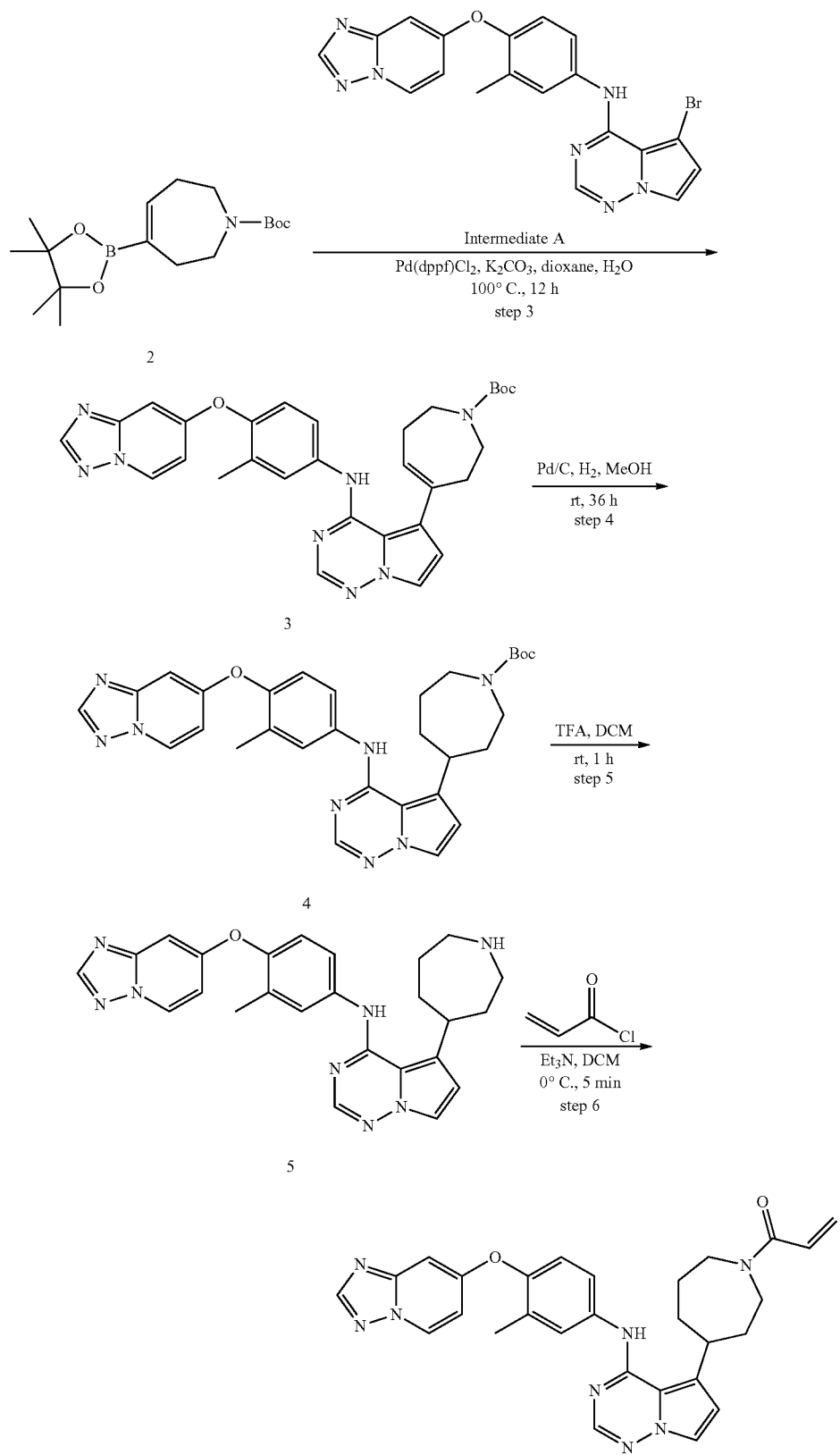

Step 1. Tert-butyl 4-(((trifluoromethyl)sulfonyl)oxy)-2,3,6,7-tetrahydro-1H-azepine-1-carboxylate

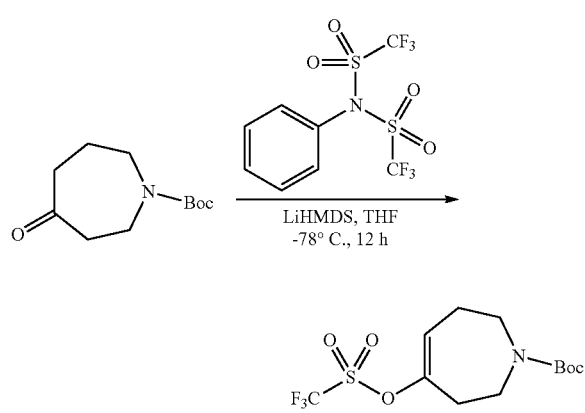

A solution of tert-butyl 4-oxoazepane-1-carboxylate (2 g, 9.37 mmol) in THF (20 mL) was treated with LiHMDS (10.3 mL, 10.31 mmol) for 1 hour at −78° C. under nitrogen atmosphere followed by the addition of 1,1,1-trifluoro-N-phenyl-N-trifluoromethanesulfonylmethanesulfonamide (3.69 g, 10.31 mmol) dropwise at −78° C. The resulting mixture was stirred overnight at room temperature under nitrogen atmosphere. The reaction mixture was quenched with water (100 mL) at 0° C. and extracted with EA (3×100 mL). The combined organic layers were dried over anhydrous Na$_2$SO$_4$, filtered and concentrated under vacuum to afford the crude product. The crude product was purified by silica gel column chromatography, eluted with PE/EA (9:1) to afford tert-butyl 4-(((trifluoromethyl)sulfonyl)oxy)-2,3,6,7-tetrahydro-1H-azepine-1-carboxylate (1.5 g, 46.32%). LCMS (ESI-MS) m/z=346.1 [M+H]$^+$.

Step 2. Tert-butyl 4-(4,4,5,5-tetramethyl-1,3,2-dioxaborolan-2-yl)-2,3,6,7-tetrahydro-1H-azepine-1-carboxylate

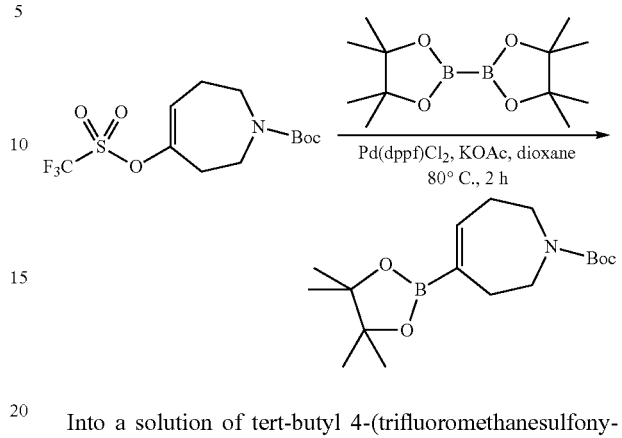

Into a solution of tert-butyl 4-(trifluoromethanesulfonyloxy)-2,3,6,7-tetrahydroazepine-1-carboxylate (1.4 g, 4.05 mmol) in dioxane (20 mL) was added 4,4,5,5-tetramethyl-2-(4,4,5-trimethyl-1,3,2-dioxaborolan-2-yl)-1,3,2-dioxaborolane (1.46 g, 6.08 mmol), KOAc (1.19 g, 12.16 mmol) and Pd(dppf)Cl$_2$ (0.30 g, 0.40 mmol). The resulting mixture was stirred for 2 hours at 100° C. under nitrogen atmosphere. The mixture was allowed to cool down to room temperature. The reaction mixture was filtered off and the filtrate was concentrated under vacuum to afford the crude product. The crude product was purified by silica gel column chromatography, eluted with PE/EA (9:1) to afford tert-butyl 4-(4,4,5,5-tetramethyl-1,3,2-dioxaborolan-2-yl)-2,3,6,7-tetrahydro-1H-azepine-1-carboxylate (1.1 g, 83.94%). LCMS (ESI-MS) m/z=324.2 [M+H]$^+$.

Step 3. Tert-butyl 4-(4-((4-([1,2,4]triazolo[1,5-a]pyridin-7-yloxy)-3-methylphenyl)amino)pyrrolo[2,1-f][1,2,4]triazin-5-yl)-2,3,6,7-tetrahydro-1H-azepine-1-carboxylate

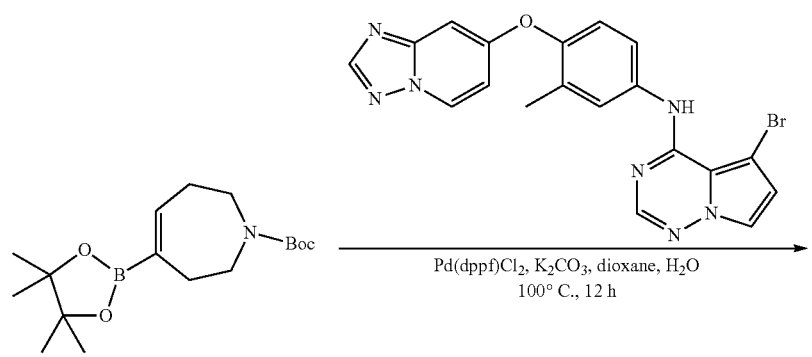

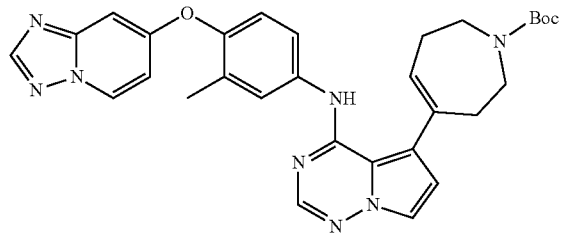

Into a solution of tert-butyl 4-(4,4,5,5-tetramethyl-1,3,2-dioxaborolan-2-yl)-2,3,6,7-tetrahydro-1H-azepine-1-carboxylate (200 mg, 0.61 mmol) in the mixture of dioxane (1 mL) and water (0.1 mL) was added 5-bromo-N-(4-([1,2,4]triazolo[1,5-a]pyridin-7-yloxy)-3-methylphenyl)-5-bromopyrrolo[2,1-f][1,2,4]triazin-4-amine (134.97 mg, 0.30 mmol), K₂CO₃ (86.14 mg, 0.61 mmol) and Pd(dppf)Cl₂ (22.64 mg, 0.03 mmol). The resulting mixture was stirred for 2 hours at 100° C. under nitrogen atmosphere. The resulting mixture was filtered off and the filtrate was concentrated under vacuum to afford a crude product. The crude product was purified by silica gel column chromatography, eluted with PE/EA (2:1) to afford tert-butyl 4-(4-((4-([1,2,4]triazolo[1,5-a]pyridin-7-yloxy)-3-methylphenyl)amino)pyrrolo[2,1-f][1,2,4]triazin-5-yl)-2,3,6,7-tetrahydro-1H-azepine-1-carboxylate (110 mg, 32.18%). LCMS (ESI-MS) m/z=553.3 [M+H]⁺.

Step 4. Tert-butyl4-(4-((4-([1,2,4]triazolo[1,5-a]pyridin-7-yloxy)-3-methylphenyl)amino)pyrrolo[2,1-f][1,2,4]triazin-5-yl)azepane-1-carboxylate

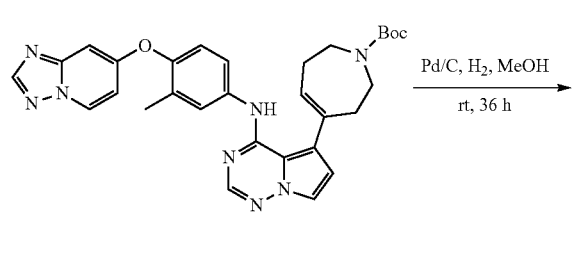

A mixture of tert-butyl 4-(4-((4-([1,2,4]triazolo[1,5-a]pyridin-7-yloxy)-3-methylphenyl)amino)pyrrolo[2,1-f][1,2,4]triazin-5-yl)-2,3,6,7-tetrahydro-1H-azepine-1-carboxylate (110 mg, 0.199 mmol) in MeOH (3 mL) was stirred for 24 hours at room temperature under hydrogen atmosphere. The resulting mixture was filtered, the filter cake was washed with MeOH (20 mL). The filtrate was concentrated under vacuum to afford the crude product. The crude product was purified by reversed-phase flash chromatography with the following conditions: column, C18 silica gel; mobile phase, MeCN in Water (10 mmol/L NH₄HCO₃), 10% to 100% gradient, and concentrated under reduced pressure to give tert-butyl 4-(4-((4-([1,2,4]triazolo[1,5-a]pyridin-7-yloxy)-3-methylphenyl)amino)pyrrolo[2,1-f][1,2,4]triazin-5-yl)azepane-1-carboxylate (80 mg, 72.46%). LCMS (ESI-MS) m/z=555.3 [M+H]⁺.

Step 5. N-(4-([1,2,4]triazolo[1,5-a]pyridin-7-yloxy)-3-methylphenyl)-5-(azepan-4-yl)pyrrolo[2,1-f][1,2,4]triazin-4-amine

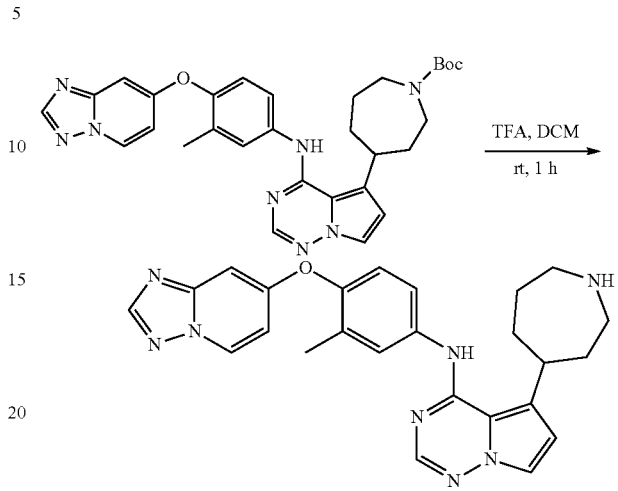

Into a solution of tert-butyl 4-(4-((4-([1,2,4]triazolo[1,5-a]pyridin-7-yloxy)-3-methylphenyl) amino) pyrrolo[2,1-f][1,2,4]triazin-5-yl)azepane-1-carboxylate (70 mg, 0.126 mmol) in methylene chloride (3 mL) was added TFA (1 mL) at room temperature under nitrogen atmosphere for 1 hour. The resulting mixture was concentrated under reduced pressure to N-(4-([1,2,4]triazolo[1,5-a]pyridin-7-yloxy)-3-methylphenyl)-5-(azepan-4-yl)pyrrolo[2,1-f][1,2,4]triazin-4-amine as a light yellow solid. LCMS (ESI-MS) m/z=455.2 [M+H]⁺.

Step 6. 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)prop-2-en-1-one

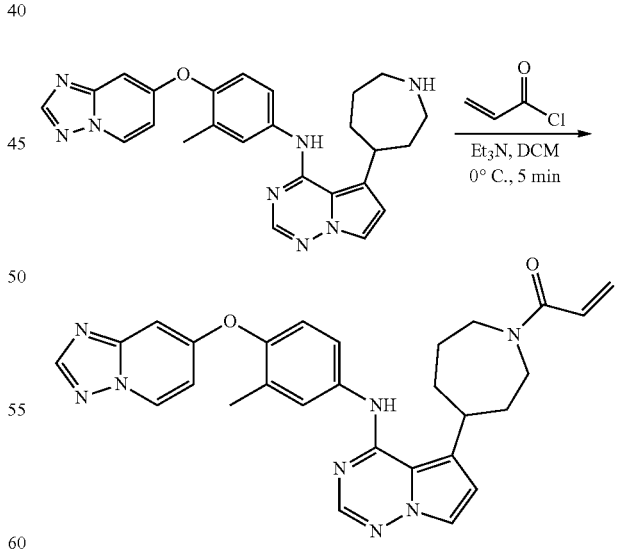

To a solution of N-(4-([1,2,4]triazolo[1,5-a]pyridin-7-yloxy)-3-methylphenyl)-5-(azepan-4-yl)pyrrolo[2,1-f][1,2,4]triazin-4-amine (60 mg, 0.13 mmol) and Et₃N (40.07 mg, 0.39 mmol) in DCM (2 mL) was added acryloyl chloride (11.95 mg, 0.13 mmol) at 0° C. The resulting mixture was stirred for 3 min at 0° C. The resulting mixture was concentrated and purified by Prep-TLC (CH₂Cl₂/MeOH 10:1) to afford the crude product, followed by purification by reverse phase flash with the following conditions (Column: XBridge Prep OBD C18 Column, 30*150 mm, 5 μm; Mobile Phase A: Water (10 mmol/L NH₄HCO₃+0.1% NH₃·H₂O), Mobile Phase B: ACN; Flow rate: 60 mL/min; Gradient: 30% B to 60% B in 7 min, 60% B) to afford 1-(4-(4-((4-([1,2,4]triazolo[1,5-a]pyridin-7-yloxy)-3-methylphenyl) amino)pyrrolo[2,1-f][1,2,4]triazin-5-yl)azepan-1-yl)prop-2-en-1-one (3.0 mg, 4.44%). LCMS (ESI-MS) m/z=510.2 [M+H]⁺.

Example 10

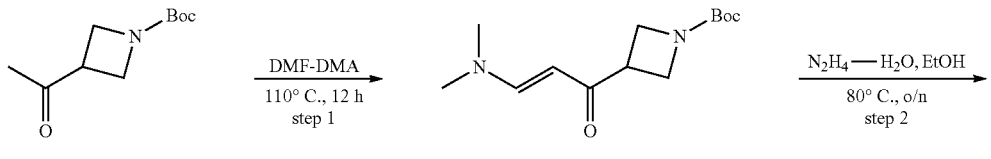

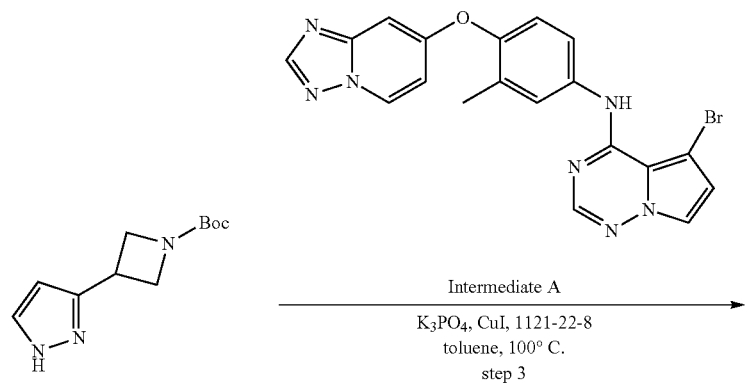

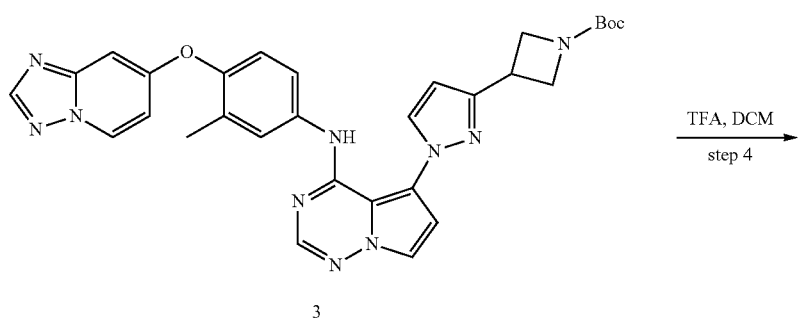

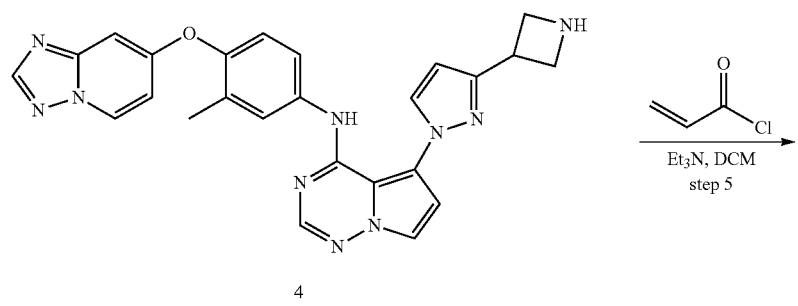

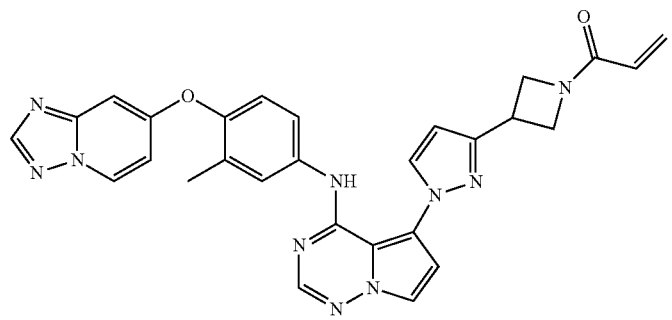

Example 10

Step 1. Tert-butyl (E)-3-(3-(dimethylamino)acryloyl)azetidine-1-carboxylate

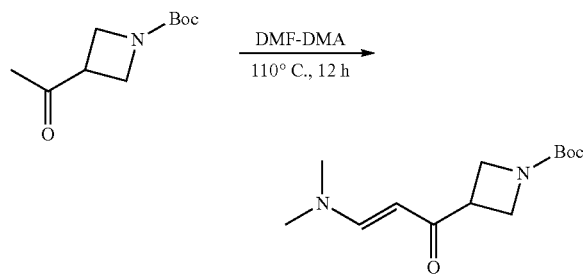

A solution of tert-butyl 3-acetylazetidine-1-carboxylate (2 g, 10.03 mmol) in DMF-DMA (15 mL) was stirred overnight at 110° C. The resulting mixture was concentrated under vacuum to afford tert-butyl 3-[(2E)-3-(dimethylamino)prop-2-enoyl]azetidine-1-carboxylate (2.3 g, crude). LCMS (ESI-MS) m/z=255.2 [M+H]$^+$ Step 2. Tert-butyl 3-(1H-pyrazol-3-yl)azetidine-1-carboxylate

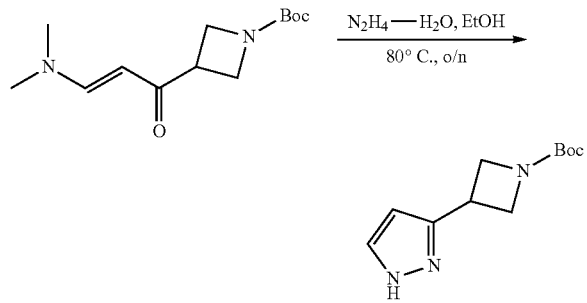

A solution of tert-butyl 3-[(2E)-3-(dimethylamino)prop-2-enoyl]azetidine-1-carboxylate (2.1 g, 8.25 mmol) in hydrazine hydrate (20 mL) was stirred overnight at 80° C. The resulting mixture was concentrated under vacuum. The residue was purified by silica column chromatography (0-40% ethyl acetate in hexanes) to provide the title compound tert-butyl 3-(1H-pyrazol-3-yl)azetidine-1-carboxylate (1.5 g, 66.92%). LCMS (ESI-MS) m/z=447.3 [2M+H]$^+$ Step 3. Tert-butyl 3-(1-(4-((4-([1,2,4]triazolo[1,5-a]pyridin-7-yloxy)-3-methylphenyl)amino)pyrrolo[2,1-f][1,2,4]triazin-5-yl)-1H-pyrazol-3-yl)azetidine-1-carboxylate

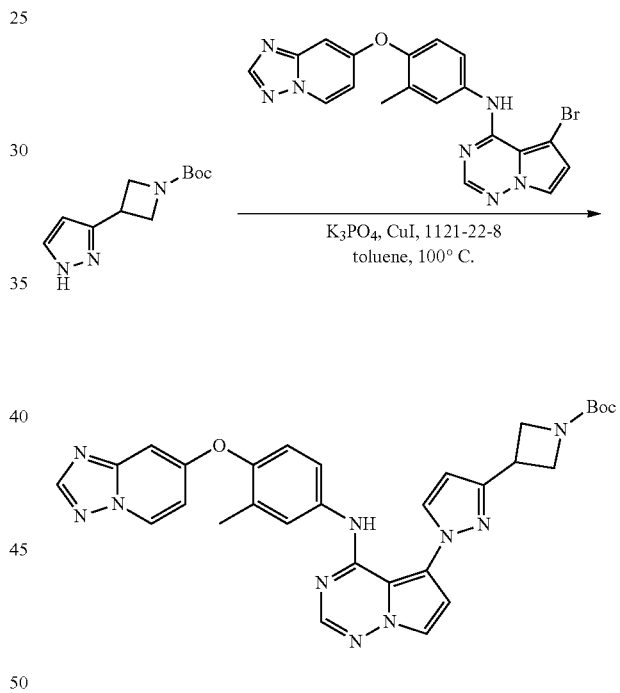

To a stirred mixture of tert-butyl 3-(1H-pyrazol-3-yl)azetidine-1-carboxylate (200 mg, 0.89 mmol) and N-(4-([1,2,4]triazolo[1,5-a]pyridin-7-yloxy)-3-methylphenyl)-5-bromopyrrolo[2,1-f][1,2,4]triazin-4-amine (781.59 mg, 0.89 mmol) in toluene (3 mL) was added (1R,2R)-cyclohexane-1,2-diamine (153.43 mg, 1.34 mmol) and potassium phosphate (380.27 mg, 1.79 mmol) and cuprous iodide (85.30 mg, 0.44 mmol) under nitrogen atmosphere. The resulting mixture was stirred at 100° C. and overnight. The reaction mixture was filtered off and the filtrate was concentrated. The residue was purified by silica column chromatography (0-40% ethyl acetate in hexanes) to provide the title compound tert-butyl 3-(1-(4-((4-([1,2,4]triazolo[1,5-a]pyridin-7-yloxy)-3-methylphenyl)amino)pyrrolo[2,1-f][1,2,4]triazin-5-yl)-1H-pyrazol-3-yl)azetidine-1-carboxylate (80 mg, 15.43%). LCMS (ESI-MS) m/z=579.3 [M+H]$^+$.

Step 4. N-(4-([1,2,4]triazolo[1,5-a]pyridin-7-yloxy)-3-methylphenyl)-5-(3-(azetidin-3-yl)-1H-pyrazol-1-yl)pyrrolo[2,1-f][1,2,4]triazin-4-amine

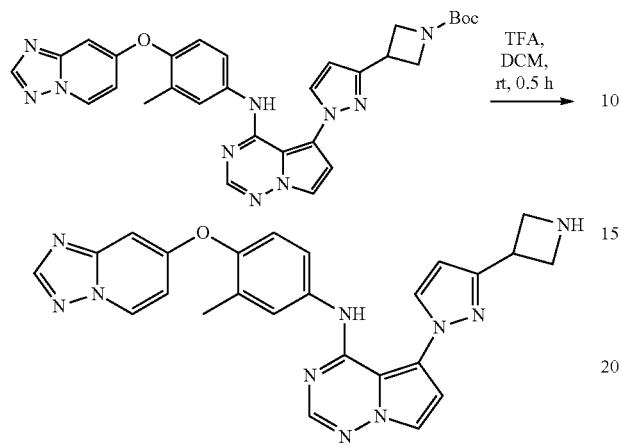

To a stirred solution of tert-butyl 3-(1-(4-((4-([1,2,4]triazolo[1,5-a]pyridin-7-yloxy)-3-methylphenyl)amino)pyrrolo[2,1-f][1,2,4]triazin-5-yl)-1H-pyrazol-3-yl)azetidine-1-carboxylate (80 mg, 0.13 mmol) in dichloromethane (10 mL) was added trifluoroacetic acid (1 mL). The resulting mixture was stirred at room temperature for 0.5 hour and concentrated under vacuum to afford N-(4-([1,2,4]triazolo[1,5-a]pyridin-7-yloxy)-3-methylphenyl)-5-(3-(azetidin-3-yl)-1H-pyrazol-1-yl)pyrrolo[2,1-f][1,2,4]triazin-4-amine (80 mg crude). LCMS (ESI-MS) m/z=479.2 [M+H]$^+$.

Step 5. 1-(3-(1-(4-((4-([1,2,4]triazolo[1,5-a]pyridin-7-yloxy)-3-methylphenyl)amino)pyrrolo[2,1-t][1,2,4]triazin-5-yl)-1H-pyrazol-3-yl)azetidin-1-yl)prop-2-en-1-one

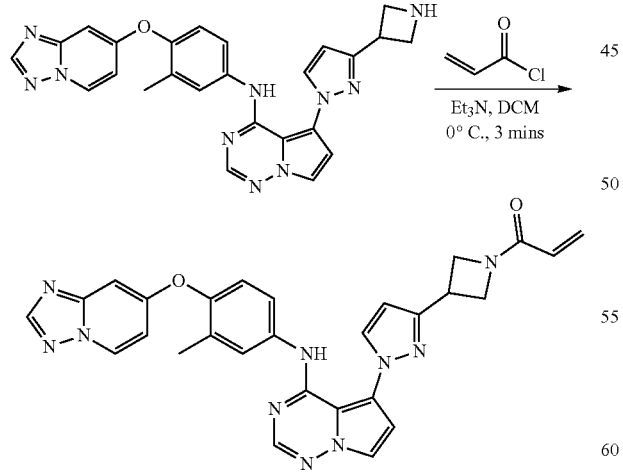

To a stirred mixture of N-(4-([1,2,4]triazolo[1,5-a]pyridin-7-yloxy)-3-methylphenyl)-5-(3-(azetidin-3-yl)-1H-pyrazol-1-yl)pyrrolo[2,1-f][1,2,4]triazin-4-amine (80 mg crude) and Et$_3$N (67.67 mg, 0.66 mmol) in dichloromethane (2 mL) was added acryloyl chloride (15.13 mg, 0.16 mmol) dropwise at 0° C. and stirred for 3 minutes. The reaction mixture was purified by Prep-TLC to afford the crude product. The crude product (60 mg) was purified by Prep-HPLC with the following conditions (Column: XBridge Shield RP18 OBD Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 28% B to 58% B in 7 min, 58% B) to afford 1-(3-(1-(4-((4-([1,2,4]triazolo[1,5-a]pyridin-7-yloxy)-3-methylphenyl)amino)pyrrolo[2,1-f][1,2,4]triazin-5-yl)-1H-pyrazol-3-yl)azetidin-1-yl)prop-2-en-1-one, Example 10 (11.2 mg, 12.57%). LCMS (ESI-MS) m/z=533.1 [M+H]$^+$.

Example 16

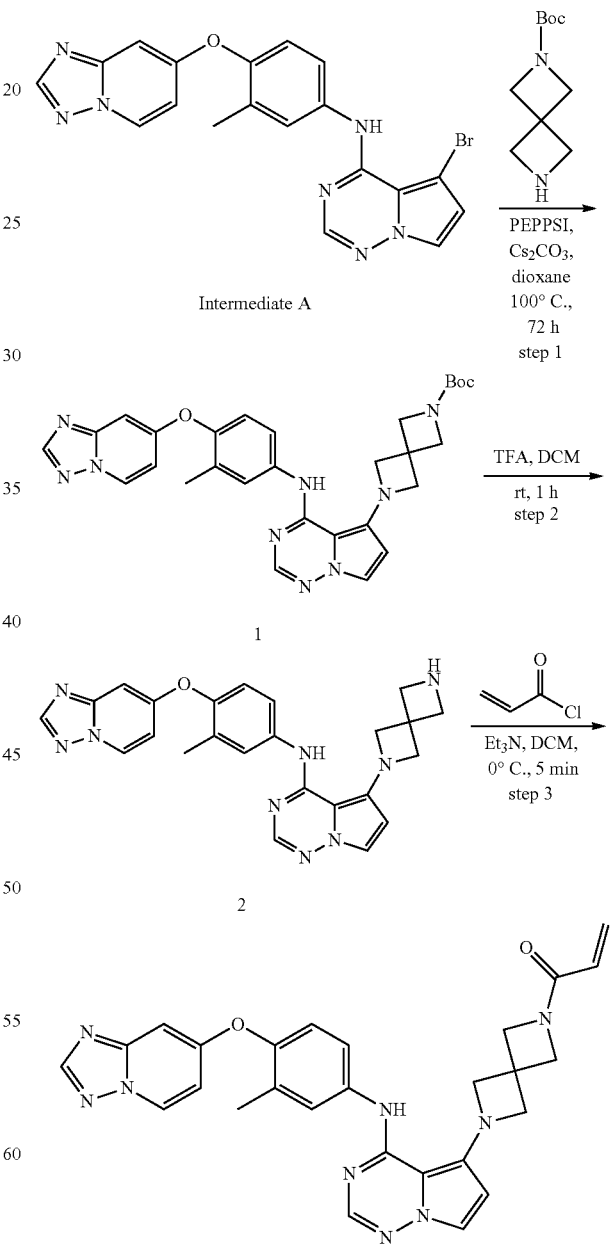

Example 16

135

Step 1. tert-butyl 6-(4-((4-([1,2,4]triazolo[1,5-a]pyridin-7-yloxy)-3-methylphenyl)amino)pyrrolo[2,1-f][1,2,4]triazin-5-yl)-2,6-diazaspiro[3.3]heptane-2-carboxylate

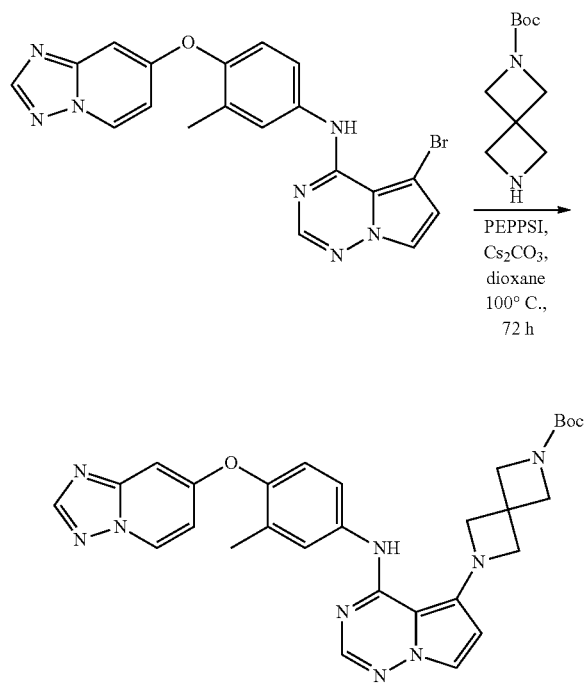

A mixture of Cs₂CO₃ (298.7 mg, 0.91 mmol) and N-(4-([1,2,4]triazolo[1,5-a]pyridin-7-yloxy)-3-methylphenyl)-5-bromopyrrolo[2,1-f][1,2,4]triazin-4-amine (200 mg, 0.45 mmol), tert-butyl 2,6-diazaspiro[3.3]heptane-2-carboxylate (100 mg, 0.50 mmol), PEPPSI (38.51 mg, 0.05 mmol) in dioxane (2 mL) was stirred for 72 hours at 100° C. under nitrogen atmosphere. The reaction mixture was filtered off and the filtrate was concentrated. The crude product was purified by column chromatography (silica-gel, 25 g, eluted with ethyl acetate in petroleum ether from 0% to 40% with 100 mL/min flow rate), the desired fractions were combined and concentrated under vacuum to afford tert-butyl 6-(4-((4-([1,2,4]triazolo[1,5-a]pyridin-7-yloxy)-3-methylphenyl)amino)pyrrolo[2,1-f][1,2,4]triazin-5-yl)-2,6-diazaspiro[3.3]heptane-2-carboxylate (150 mg, 41.73%). LCMS (ESI-MS) m/z=554.3 [M+H]⁺.

Step 2. N-(4-([1,2,4]triazolo[1,5-a]pyridin-7-yloxy)-3-methylphenyl)-5-(2,6-diazaspiro[3.3]heptan-2-yl)pyrrolo[2,1-f][1,2,4]triazin-4-amine

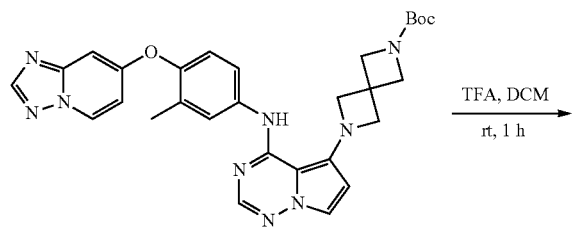

136

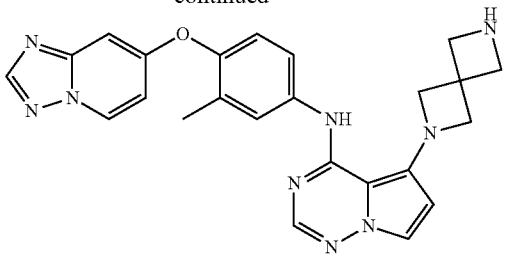

A mixture of tert-butyl 6-(4-((4-([1,2,4]triazolo[1,5-a]pyridin-7-yloxy)-3-methylphenyl)amino)pyrrolo[2,1-f][1,2,4]triazin-5-yl)-2,6-diazaspiro[3.3]heptane-2-carboxylate (150 mg, 0.27 mmol) and TFA (0.3 mL) in DCM (1 mL) was stirred for 1 hour at room temperature. The mixture was concentrated under vacuum to afford the crude product N-(4-([1,2,4]triazolo[1,5-a]pyridin-7-yloxy)-3-methylphenyl)-5-(2,6-diazaspiro[3.3]heptan-2-yl)pyrrolo[2,1-f][1,2,4]triazin-4-amine (100 mg crude). LCMS (ESI-MS) m/z=454.2 [M+H].

Step 3. 1-(6-(4-((4-([1,2,4]triazolo[1,5-a]pyridin-7-yloxy)-3-methylphenyl)amino)pyrrolo[2,1-f][1,2,4]triazin-5-yl)-2,6-diazaspiro[3.3]heptan-2-yl)prop-2-en-1-one

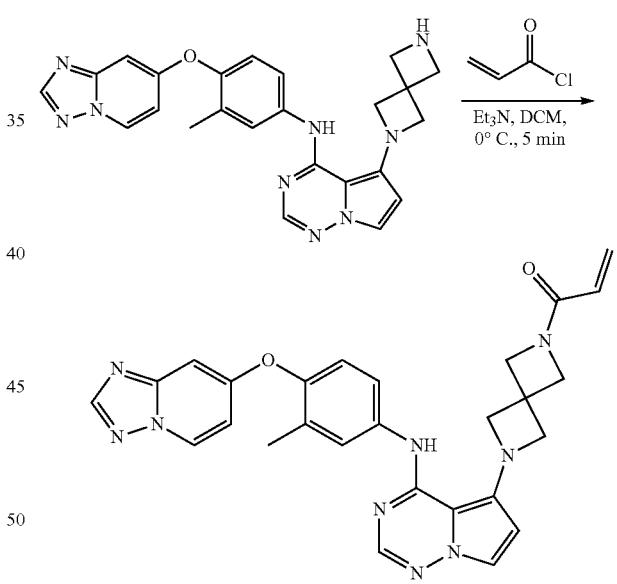

A mixture of N-(4-([1,2,4]triazolo[1,5-a]pyridin-7-yloxy)-3-methylphenyl)-5-(2,6-diazaspiro[3.3]heptan-2-yl)pyrrolo[2,1-t][1,2,4]triazin-4-amine (100 mg, 0.22 mmol,), acryloyl chloride (19.96 mg, 0.22 mmol) and Et₃N (66.94 mg, 0.65 mmol) in DCM (2 mL) was stirred for 5 minutes at 0° C. The resulting mixture was concentrated under vacuum. The residue was purified by Prep-TLC (ethyl acetate: petroleum ether=1:1), the fractions with desired mass signal was dissolved in dichloromethane/methanol (10:1, 50 mL) and filtered. The filter was concentrated under vacuum to afford the desired product 1-(6-(4-((4-([1,2,4]triazolo[1,5-a]pyridin-7-yloxy)-3-methylphenyl)amino)pyrrolo[2,1-f][1,2,4]triazin-5-yl)-2,6-diazaspiro[3.3]heptan-2- yl)prop-2-en-1-one, Example 16 (20.3 mg, 16.73%). LCMS (ESI-MS) m/z=508.2 [M+H]⁺.

Example 20

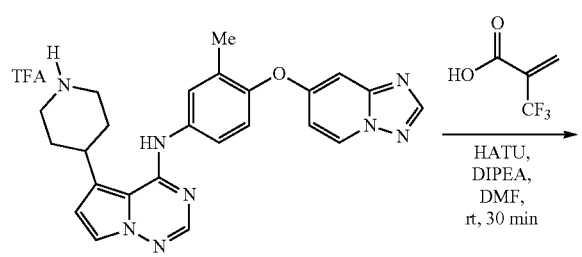

To a 1-dram vial with a Teflon-coated stir bar was added 2-(Trifluoromethyl)Acrylic Acid (18.9 mg, 1.5 Eq, 135 µmol) and HATU (51.4 mg, 1.5 Eq, 135 µmol). The vial was then capped and brought into a N₂ glovebox, and the vial was opened and DMF (1.4 mL) was added. The vial was recapped and brought out of the glovebox and DIPEA (81.6 mg, 110 µL, 7 Eq, 631 µmol) was added via syringe and the reaction mixture was stirred at rt. After 30 minutes, N-(4-([1,2,4]triazolo[1,5-a]pyridin-7-yloxy)-3-methylphenyl)-5-(piperidin-4-yl)pyrrolo[2,1-f][1,2,4]triazin-4-amine (TfOH salt, 50.0 mg, 1 Eq, 90.2 µmol in 1.0 mL DMF) was added via syringe and the reaction mixture was stirred at rt. After 30 minutes the reaction mixture was filtered then purified by preparative reverse phase HPLC (acetonitrile/water gradient with 0.1% TFA) to give Example 20 (3.99 mg, 6.78% yield). LCMS (ESI) [M+H]⁺=539.2.

Example 21

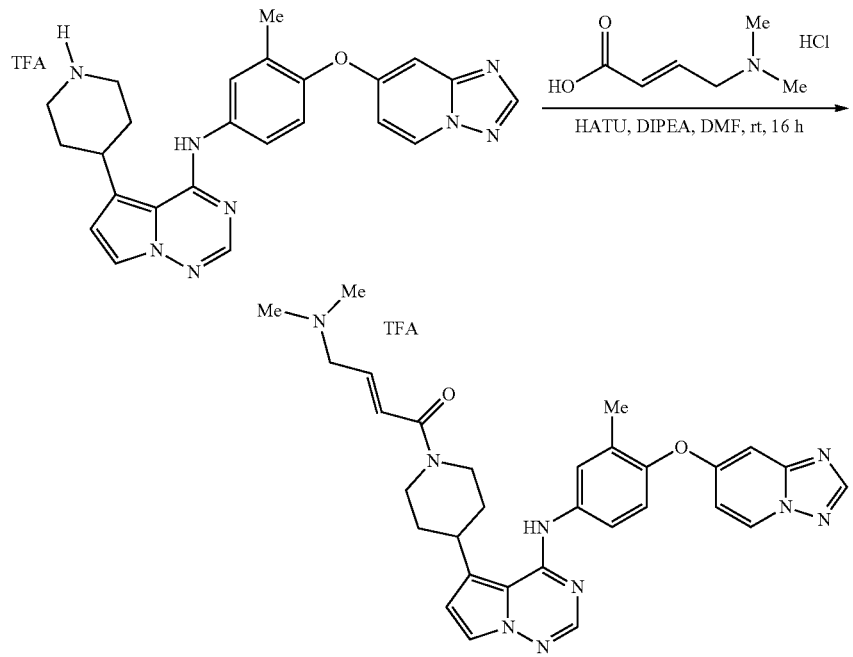

-continued

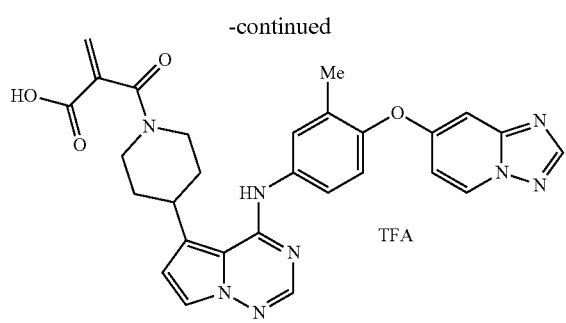

2-(4-(4-((4-([1,2,4]triazolo[1,5-a]pyridin-7-yloxy)-3-methylphenyl)amino)pyrrolo[2,1-f][1,2,4]triazin-5-yl)piperidine-1-carbonyl)acrylic acid (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(dimethylamino)but-2-en-1-one To a 20 mL scintillation vial with Teflon-coated stir bar was added N-(4-([1,2,4]triazolo[1,5-a]pyridin-7-yloxy)-3-methylphenyl)-5-(piperidin-4-yl)pyrrolo[2,1-f][1,2,4]triazin-4-amine (TFA salt, 50.0 mg, 1 Eq, 90.2 µmol), (E)-4-(dimethylamino)but-2-enoic acid hydrochloride (22.4 mg, 1.5 Eq, 135 µmol), and HATU (51.4 mg, 1.5 Eq, 135 µmol). The vial was then capped with a rubber septum and evacuated and refilled with N₂ (3×). Then DMF (3.0 mL) and Diisopropylethylamine (46.6 mg, 62.3 µL, 4 Eq, 361 µmol) were added via syringe and the reaction was stirred overnight at rt. The resulting mixture was filtered then purified by preparative reverse phase HPLC (acetonitrile/water gradient with 0.1% TFA) to give the title compound, Example 21 (2.0 mg, 3.3% yield. LCMS (ESI) [M+H]⁺=552.3.

Example 24

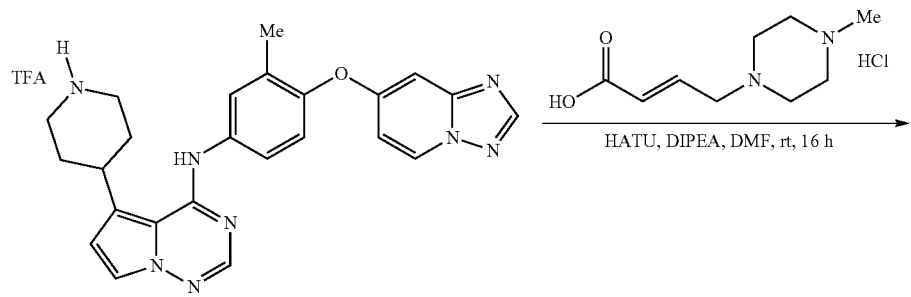

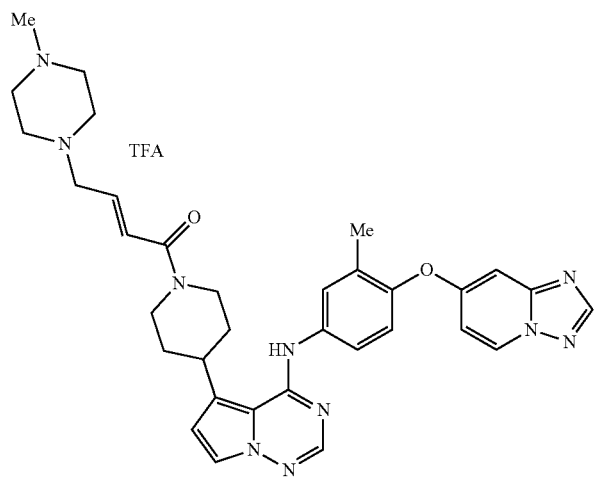

(E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(4-methylpiperazin-1-yl)but-2-en-1-one To a 20 mL scintillation vial with Teflon-coated stir bar was added N-(4-([1,2,4]triazolo[1,5-a]pyridin-7-yloxy)-3-methylphenyl)-5-(piperidin-4-yl)pyrrolo[2,1-f][1,2,4]triazin-4-amine (TFA salt, 50.0 mg, 1 Eq, 90.2 μmol), (E)-4-(4-methylpiperazin-1-yl)but-2-enoic acid hydrochloride (29.8 mg, 1.5 Eq, 135 μmol), and HATU (51.4 mg, 1.5 Eq, 135 μmol). The vial was then capped with a rubber septum and evacuated and refilled with N₂ (3×). Then DMF (3.0 mL) and diisopropylethylamine (46.6 mg, 62.3 μL, 4 Eq, 361 μmol) were added via syringe and the reaction was stirred overnight at rt. The resulting mixture was filtered then purified by preparative reverse phase HPLC (acetonitrile/water gradient with 0.1% TFA) to give Example 24 (1.8 mg, 2.8% yield). LCMS (ESI) [M+H]⁺=607.3.

Example 25

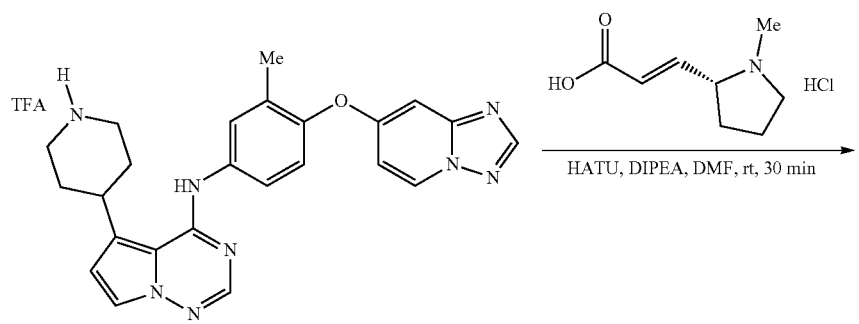

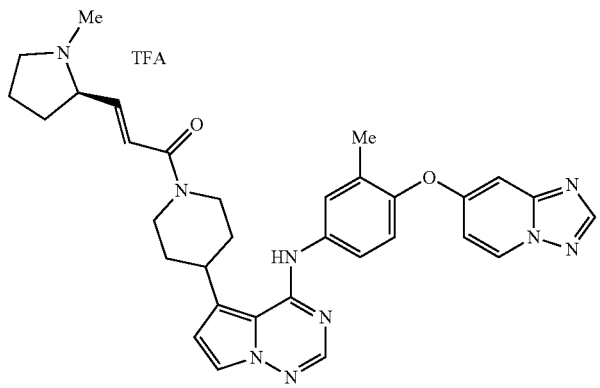

(R,E)-1-(4-(4-((4-([1,2,4]triazolo[1,5-a]pyridin-7-yloxy)-3-methylphenyl)amino)pyrrolo[2,1-A][1,2,4]triazin-5-yl)piperidin-1-yl)-3-(1-methylpyrrolidin-2-yl)prop-2-en-1-one To a 1-dram vial with a Teflon-coated stir bar was added (R,E)-3-(1-methylpyrrolidin-2-yl)acrylic acid hydrochloride (25.9 mg, 1.5 Eq, 135 μmol) and HATU (51.4 mg, 1.5 Eq, 135 μmol). The vial was then capped and brought into a N₂ glovebox and the vial was opened and DMF (1.4 mL) was added. The vial was recapped and brought out of the glovebox and DIPEA (81.6 mg, 110 μL, 7 Eq, 631 μmol) was added through the septum. The reaction mixture was stirred at rt for 30 minutes. N-(4-([1,2,4]triazolo[1,5-a]pyridin-7-yloxy)-3-methylphenyl)-5-(piperidin-4-yl)pyrrolo[2,1-f][1,2,4]triazin-4-amine (TFA salt, 50.0 mg, 1 Eq, 90.2 μmol in 1.0 mL DMF) was added via syringe. After 30 minutes the reaction mixture was filtered then purified by preparative reverse phase HPLC (acetonitrile/water gradient with 0.1% TFA) to give Example 25 (22.8 mg, 36.6% yield). LCMS (ESI) [M+H]⁺ 578.3.

Example 26

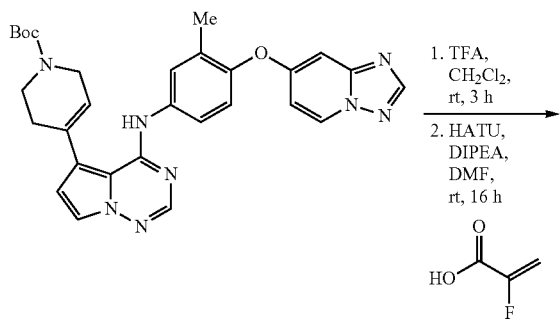

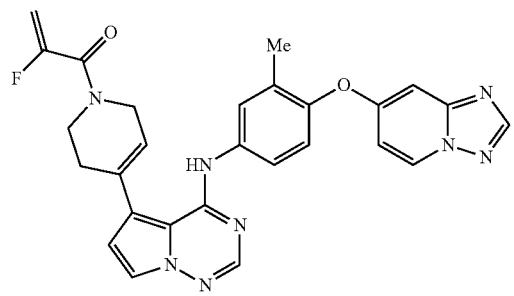

1-(4-(4-((4-([1,2,4]triazolo[1,5-a]pyridin-7-yloxy)-3-methylphenyl)amino)pyrrolo[2,1-f][1,2,4]triazin-5-yl)-3,6-dihydropyridin-1(2H)-yl)-2-fluoroprop-2-en-1-one To a 1-dram vial with stir bar was added tert-butyl 4-(4-((4-([1,2,4]triazolo[1,5-a]pyridin-7-yloxy)-3-methylphenyl)amino)pyrrolo[2,1-f][1,2,4]triazin-5-yl)-3,6-dihydropyridine-1(2H)-carboxylate (50.0 mg, 1 Eq, 92.8 μmol) and dichloromethane (0.5 mL). Then Trifluoroacetic acid (106 mg, 70.7 μL, 10 Eq, 928 μmol) was added slowly and the vial was capped and stirred at rt. After complete consumption of starting material via LCMS, the reaction was concentrated and used without further purification. The crude residue was reconstituted in dichloromethane (1.0 mL) and added to a premixed solution of HATU (52.9 mg, 1.5 Eq, 139 μmol), 2-fluoroacrylic acid (12.5 mg, 1.5 Eq, 139 μmol), and DIPEA (48.0 mg, 64.7 μL, 4 Eq, 371 μmol) in dichloromethane (1.5 mL) and stirred at rt. After 16 h, the reaction was filtered and concentrated under reduced pressure. The resulting residue was purified by silica column chromatography (0-10% methanol in dichloromethane) to provide Example 26 (4.2 mg, 8.9% yield). LCMS (ESI) [M+H]⁺=511.2.

Example 27

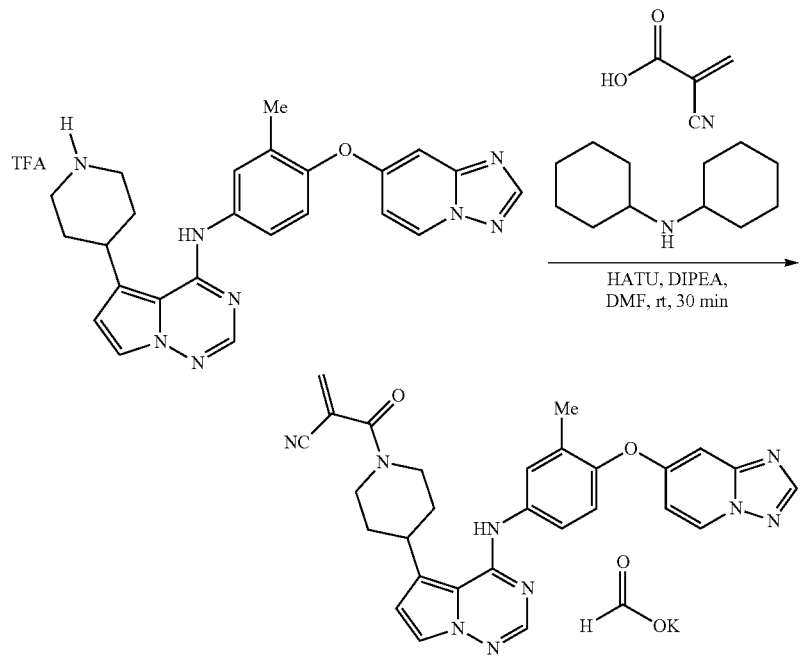

2-(4-(4-((4-([1,2,4]triazolo[1,5-a]pyridin-7-yloxy)-3-methylphenyl)amino)pyrrolo[2,1-f][1,2,4]triazin-5-yl)piperidine-1-carbonyl)acrylonitrile To a 1-dram vial with a Teflon-coated stir bar was added N-(4-([1,2,4]triazolo[1,5-a]pyridin-7-yloxy)-3-methylphenyl)-5-(piperidin-4-yl)pyrrolo[2,1-f][1,2,4]triazin-4-amine (TFA salt, 50.0 mg, 1 Eq, 90.2 µmol), Dicyclohexylamine 2-cyanoacrylate (75.3 mg, 3 Eq, 270 µmol) and HATU (171 mg, 5 Eq, 451 µmol). The vial was then capped and brought into a N₂ glovebox, and the vial was opened and DMF (1.4 mL) was added. The vial was recapped and brought out of the glovebox and DIPEA (117 mg, 157 µL, 10 Eq, 902 µmol) was added through the septum. After 30 minutes the reaction mixture was filtered then purified by preparative reverse phase HPLC (acetonitrile/water gradient with 0.1% TFA) to give Example 27 (10.0 mg, 18.4% yield). LCMS (ESI) [M+H]⁺=603.3.

Example 42

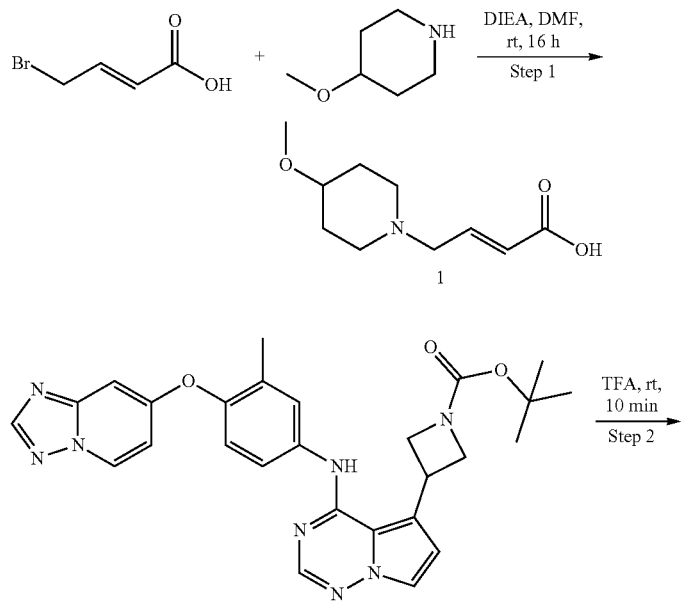

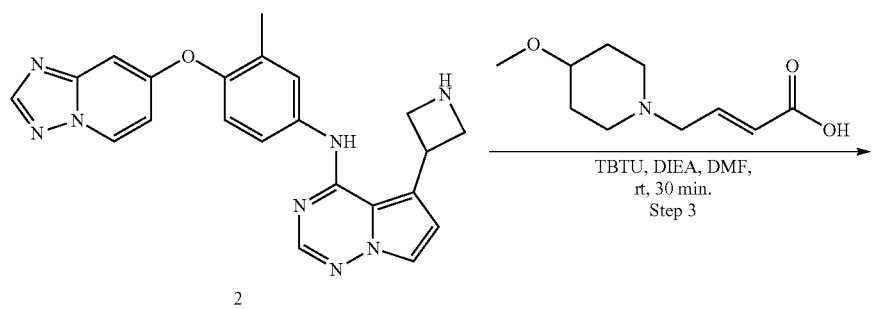

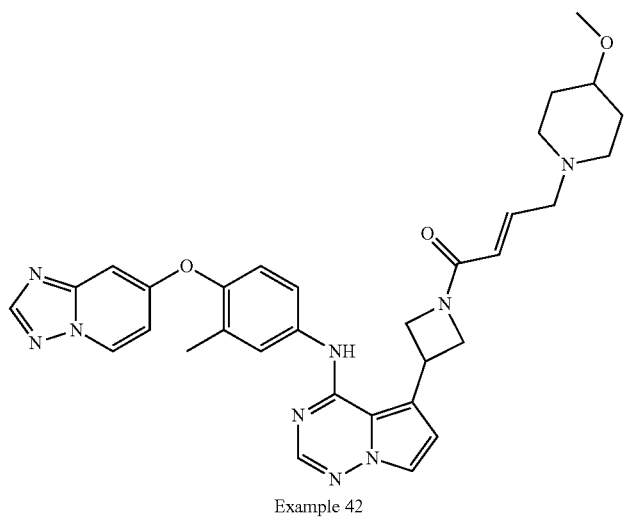

Example 42

Step 1. (E)-4-(4-methoxypiperidin-1-yl)but-2-enoic acid

Step 2. N-(4-([1,2,4]triazolo[1,5-a]pyridin-7-yloxy)-3-methylphenyl)-5-(azetidin-3-yl)pyrrolo[2,1-f][1,2,4]triazin-4-amine

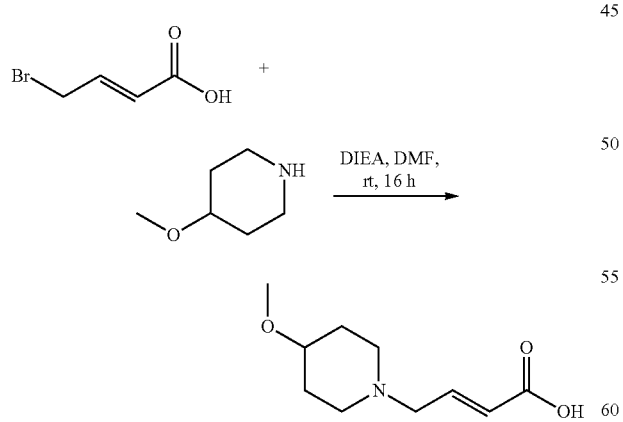

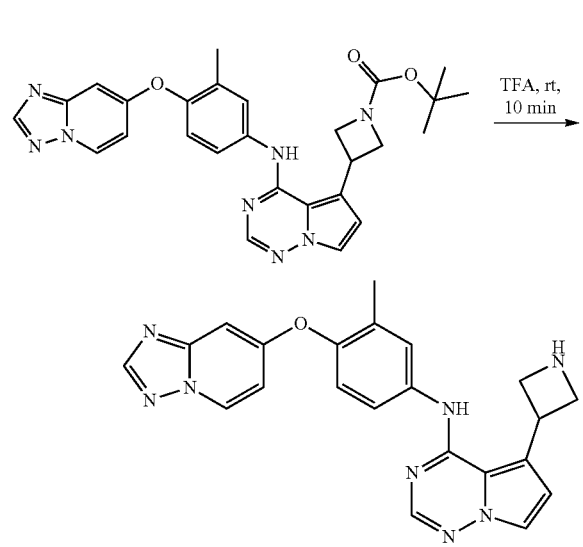

To a stirred mixture of (E)-4-bromobut-2-enoic acid (50 mg, 0.30 mmol) and 4-methoxypiperidine HCl (51 mg, 0.33 mmol) in DMF (1 mL), diisopropylethylamine (0.12 g, 0.91 mmol) was added, and the reaction stirred at RT overnight. The reaction mixture was used as is in the following step.

TFA (3 mL) was added to tert-butyl 3-(4-((4-([1,2,4]triazolo[1,5-a]pyridin-7-yloxy)-3-methylphenyl)amino)pyrrolo[2,1-f][1,2,4]triazin-5-yl)azetidine-1-carboxylate (438 mg, 855 mol) at RT and the mixture was stirred for 10 min. The resulting mixture was concentrated under vacuum to afford the crude product. The crude was diluted with ethyl acetate (2×20 mL) and washed with NaHCO₃ (20 mL). The organic layers were dried over MgSO₄, and was concentrated to provide N-(4-([1,2,4]triazolo[1,5-a]pyridin-7-yloxy)-3-methylphenyl)-5-(azetidin-3-yl)pyrrolo[2,1-f][1,2,4]triazin-4-amine that was used crude in the next step. LCMS (ESI-MS) m/z=413.2 [M+H]⁺.

Step 3. (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(4-methoxypiperidin-1-yl)but-2-en-1-one methoxypiperidin-1-yl)but-2-enoic acid (58 mg, 0.29 mmol) in DMF (1 mL) and diisopropylethylamine (from step 1). The reaction stirred at room temperature for 30 min. The reaction mixture was filtered and purified by prep HPLC, eluted with 10-40% ACN/water/0.1% TFA. Fractions were diluted with ethyl acetate (20 mL) and washed with saturated NaHCO₃(20 mL), the organic layer was filtered over MgSO₄, and the solvent was evaporated to provide (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(4-methoxypiperidin-1-yl)but-2-en-1-one, Example 42 (17.3 mg, 29%). ¹H NMR (499 MHz, CHLOROFORM-d) δ=8.50 (d, J=7.4 Hz, 1H), 8.23 (s, 1H), 8.00 (s, 1H), 7.63 (d, J=2.7 Hz, 1H), 7.60 (dd, J=2.6, 8.6 Hz, 1H), 7.57 (d, J=2.5 Hz, 1H), 7.10 (d, J=8.5 Hz, 2H), 6.94 (td, J=6.2, 15.3 Hz, 1H), 6.89 (dd, J=2.7, 7.4 Hz, 1H), 6.85 (d, J=2.5 Hz, 1H), 6.73 (d, J=2.7 Hz, 1H), 6.11 (br d, J=15.3 Hz, 1H),

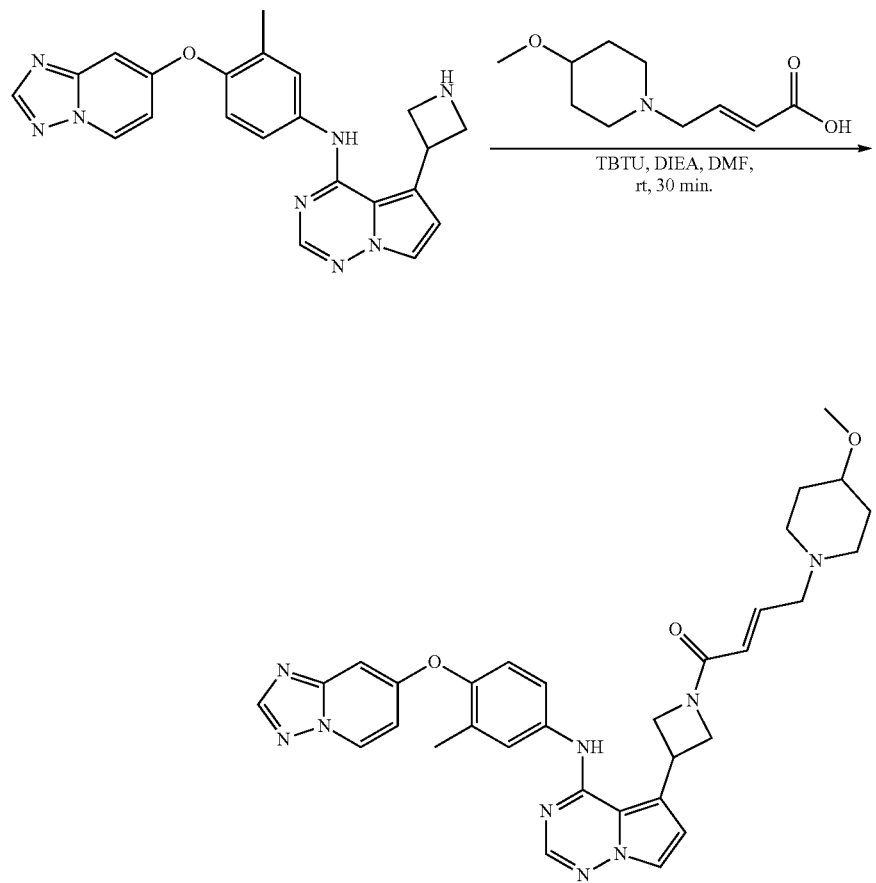

O-(Benzotriazol-1-yl)-N,N,N',N'-tetramethyluroniumTetrafluoroborate (TBTU) (93 mg, 0.29 mmol) and N-(4-([1,2,4]triazolo[1,5-a]pyridin-7-yloxy)-3-methylphenyl)-5-(azetidin-3-yl)pyrrolo[2,1-f][1,2,4]triazin-4-amine (40 mg, 97 μmol) were added to the crude mixture of (E)-4-(4-

4.83-4.72 (m, 1H), 4.65 (br t, J=8.5 Hz, 1H), 4.46-4.37 (m, 1H), 4.37-4.25 (m, 2H), 3.33 (s, 3H), 3.23 (br d, J=3.3 Hz, 1H), 3.21-3.14 (m, 2H), 2.74 (br s, 2H), 2.34-2.19 (m, 5H), 1.90 (br d, J=12.0 Hz, 2H), 1.63 (br d, J=8.8 Hz, 2H). LCMS (ESI-MS) m/z=594.3 [M+H]⁺.

Example 50
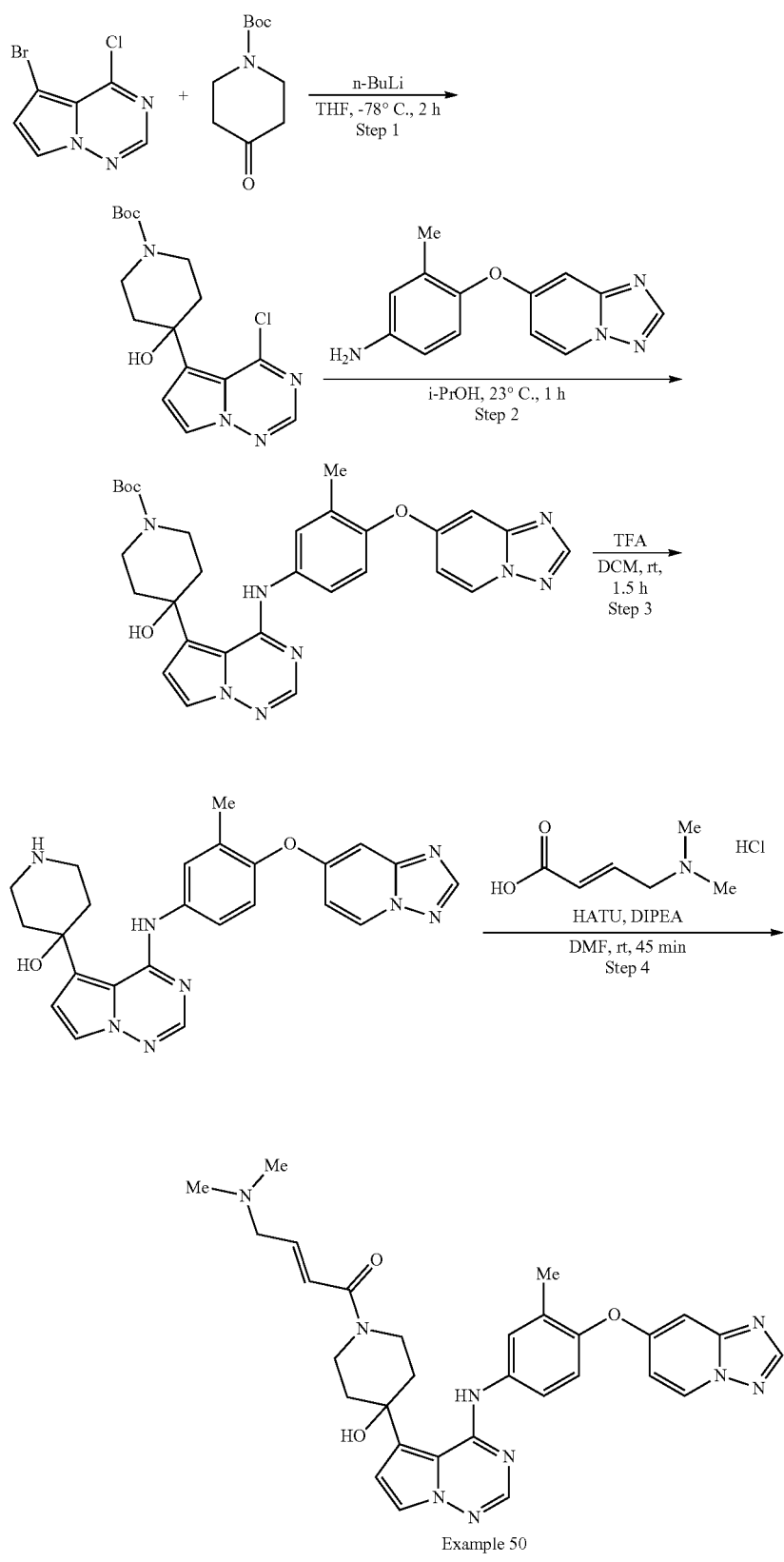

Step 1. tert-butyl 4-(4-chloropyrrolo[2,1-f][1,2,4]triazin-5-yl)-4-hydroxypiperidine-1-carboxylate

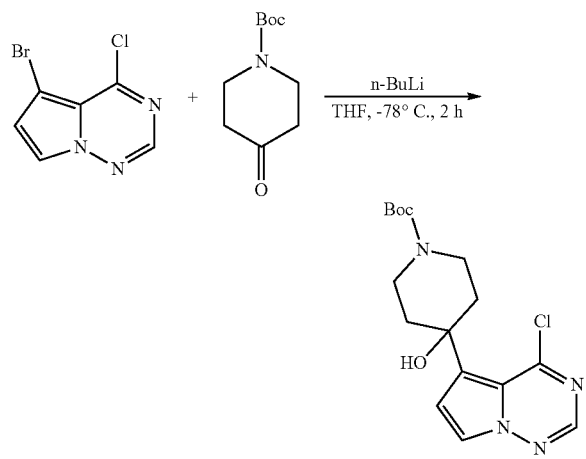

To a reaction tube with a stir bar was added 5-bromo-4-chloropyrrolo[2,1-f][1,2,4]triazine (100 mg, 430 μmol). The tube was capped and evacuated and refilled with N₂ (3×). Dry THF (4.0 mL) was added via syringe and the reaction mixture was cooled to −78° C. for 15 min. Then nBuLi (33.1 mg, 215 μL, 2.4 molar, 516 μmol) was added slowly via syringe and the reaction was stirred for 30 min. Then tert-butyl 4-oxopiperidine-1-carboxylate (103 mg, 516 μmol) in THF (1.0 mL) was added via syringe and the reaction mixture was stirred at −78° C. for 2 h. Then the reaction was quenched with sat NaHCO₃ and warmed to rt. Water was then added (10 mL) and the reaction mixture was extracted with DCM (3×10 mL). The combined organic layers were washed with brine, dried with MgSO₄, and concentrated. Purification via column chromatography (10-100% EtOAc in hexanes) provided tert-butyl 4-(4-chloropyrrolo[2,1-f][1,2,4]triazin-5-yl)-4-hydroxypiperidine-1-carboxylate (77 mg, 51%), used for the next step without further purification. LCMS (ESI) [M+H]⁺=352.1.

Step 2. tert-butyl 4-(4-((4-([1,2,4]triazolo[1,5-a]pyridin-7-yloxy)-3-methylphenyl)amino)pyrrolo[2,1-f][1,2,4]triazin-5-yl)-4-hydroxypiperidine-1-carboxylate

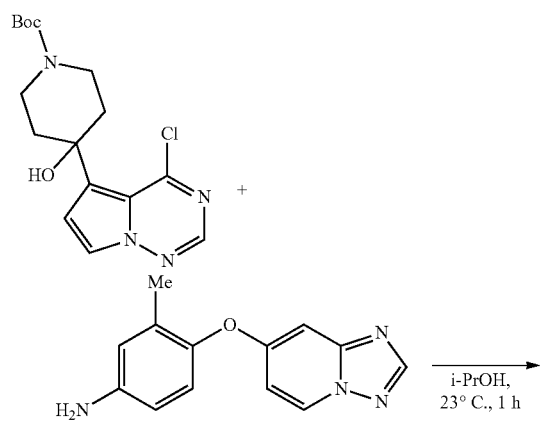

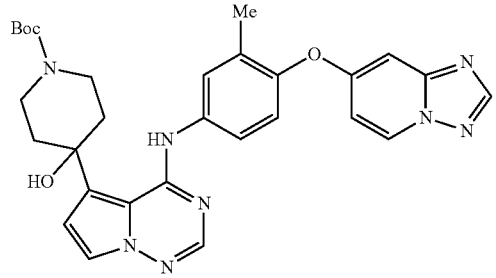

To a 40 mL scintillation vial with a stir bar was added tert-butyl 4-(4-chloropyrrolo[2,1-f][1,2,4]triazin-5-yl)-4-hydroxypiperidine-1-carboxylate (656 mg, 1.86 mmol) and 4-([1,2,4]triazolo[1,5-a]pyridin-7-yloxy)-3-methylaniline (447 mg, 1.86 mmol). The vial was capped and evacuated and refilled with N₂ (3×), then dry isopropanol (12.0 mL) was added via syringe and the reaction mixture stirred at rt. After 1 h the reaction mixture was washed with sat. NaHCO₃ (10 mL) and extracted with DCM (3×10 mL). Purification via column chromatography 10-100% EtOAc/EtOH (3:1 mixture) in hexanes provided tert-butyl 4-(4-((4-([1,2,4]triazolo[1,5-a]pyridin-7-yloxy)-3-methylphenyl)amino)pyrrolo[2,1-f][1,2,4]triazin-5-yl)-4-hydroxypiperidine-1-carboxylate (766 mg, 58%). LCMS (ESI) [M+H]⁺=557.3.

Step 3. 4-(4-((4-([1,2,4]triazolo[1,5-a]pyridin-7-yloxy)-3-methylphenyl)amino)pyrrolo[2,1-f][1,2,4]triazin-5-yl)piperidin-4-ol

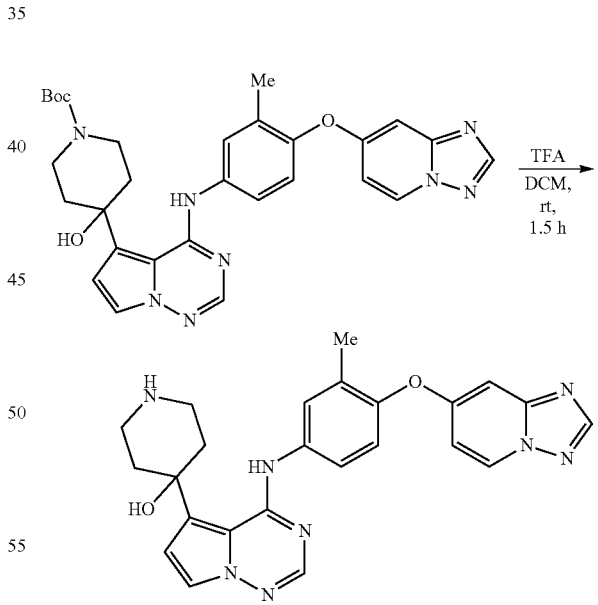

To a 1-dram vial with a stir bar was added tert-butyl 4-(4-((4-([1,2,4]triazolo[1,5-a]pyridin-7-yloxy)-3-methylphenyl)amino)pyrrolo[2,1-f][1,2,4]triazin-5-yl)-4-hydroxypiperidine-1-carboxylate (100 mg, 180 μmol) and TFA (246 mg, 166 μL, 2.16 mmol). The reaction mixture was stirred at rt for 1.5 h then concentrated in vacuo. The crude product was used in the next step without any further purification. LCMS (ESI) [M+H]⁺=456.2.

Step 4. (E)-1-(4-(4-((4-([1,2,4]triazolo[1,5-a]pyridin-7-yloxy)-3-methylphenyl)amino)pyrrolo[2,1-f][1,2,4]triazin-5-yl)-4-hydroxypiperidin-1-yl)-4-(dimethylamino)but-2-en-1-one

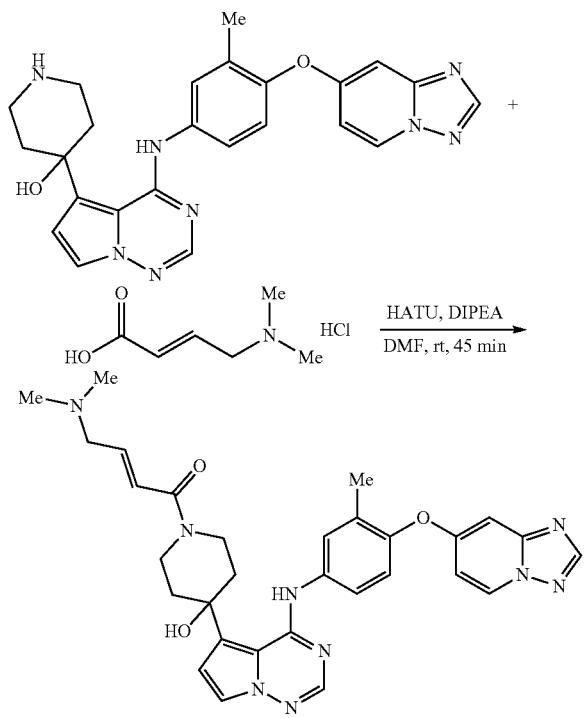

To a 2-dram vial with a stir bar added the crude product from the previous step, DMF (2.5 mL), diisopropylethylamine (139 mg, 188 μL, 1.08 mmol). (E)-4-(Dimethylamino)but-2-enoic acid hydrochloride (32.7 mg, 198 μmol), and HATU (102 mg, 269 μmol), then the reaction mixture was stirred at rt. After 45 min, the reaction mixture was purified directly via prepHPLC 10-50% ACN in 0.1% TFA water. The fractions containing the desired product mass were combined, neutralized with sat. aq. NaHCO₃ (10 mL) and extracted with DCM (4×15 mL). The combined organic layers were washed with brine, dried over MgSO₄, and concentrated to provide (E)-1-(4-(4-((4-([1,2,4]triazolo[1,5-a]pyridin-7-yloxy)-3-methylphenyl)amino)pyrrolo[2,1-f][1,2,4]triazin-5-yl)-4-hydroxypiperidin-1-yl)-4-(dimethylamino)but-2-en-1-one, Example 50 (59.13 mg, 57%). $^1$H NMR (499 MHz, CHLOROFORM-d) δ ppm 11.22 (s, 1H) 8.47 (d, J=7.4 Hz, 1H) 8.06 (s, 1H) 7.99 (s, 1H) 7.79 (d, J=2.5 Hz, 1H) 7.72 (dd, J=8.6, 2.6 Hz, 1H) 7.48 (d, J=2.7 Hz, 1H) 7.07 (d, J=8.8 Hz, 1H) 6.91 (dd, J=7.5, 2.6 Hz, 1H) 6.67-6.81 (m, 2H) 6.43-6.53 (m, 2H) 5.36 (br s, 1H) 4.57 (br d, J=11.8 Hz, 1H) 3.92 (br d, J=12.0 Hz, 1H) 3.67 (br t, J=12.5 Hz, 1H) 3.23 (br t, J=12.2 Hz, 1H) 3.10 (br d, J=6.0 Hz, 2H) 2.27 (s, 6H) 2.22 (s, 3H) 1.89-2.19 (m, 4H).

Example 51

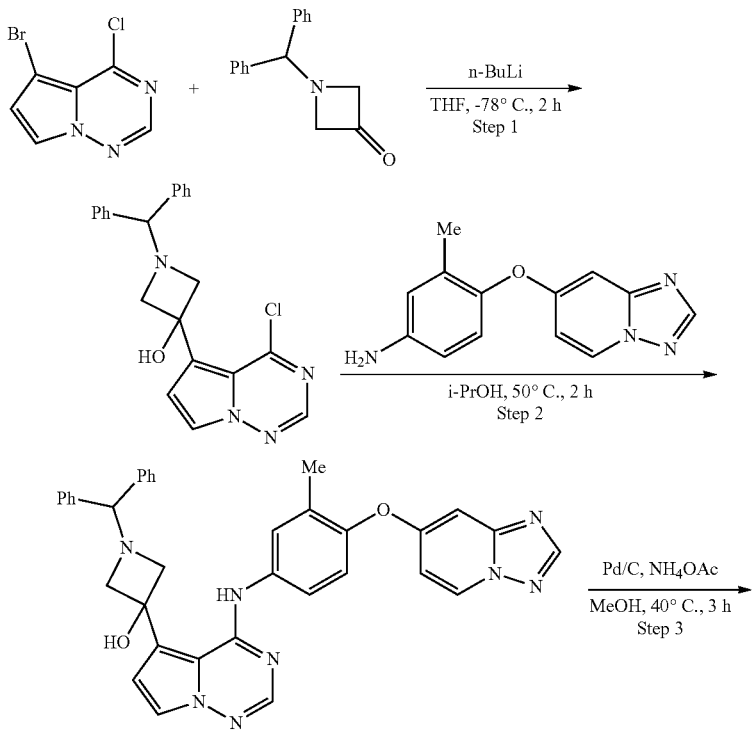

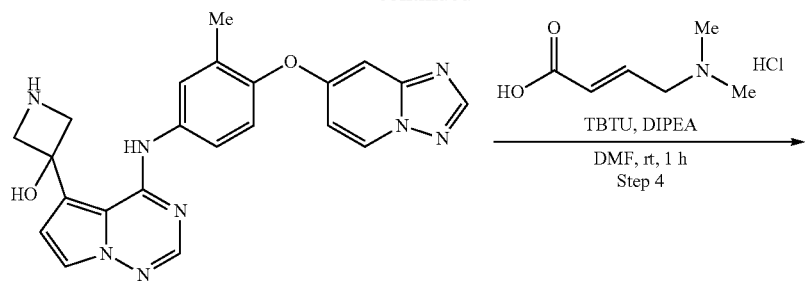

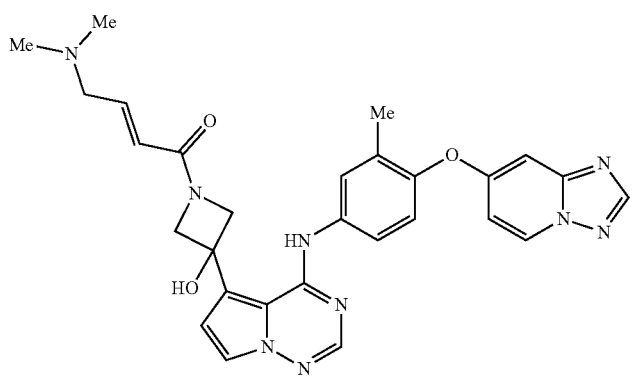

Example 51

Step 1. 1-benzhydryl-3-(4-chloropyrrolo[2,1-f][1,2,4]triazin-5-yl)azetidin-3-ol

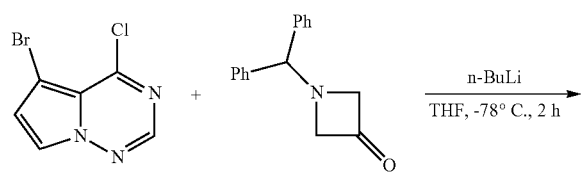

To a reaction tube with a stir bar was added 5-bromo-4-chloropyrrolo[2,1-f][1,2,4]triazine (865.0 mg, 3.721 mmol). The tube was capped and evacuated and refilled with $N_2$ (3×). Dry THF (18.0 mL) was added via syringe and the reaction mixture was cooled to −78° C. for 10 min. Then n-BuLi (309.9 mg, 2.015 mL, 2.4 molar, 4.837 mmol) was added slowly via syringe and the reaction was stirred for 30 min. Then 1-benzhydryl-azetidin-3-one (1.104 g, 4.651 mmol) in THF (6.0 mL) was added via syringe and the reaction mixture was stirred at −78° C. for 2 h. The reaction was quenched with sat $NaHCO_3$ and warmed to rt. The reaction mixture was diluted with water (20 mL) and extracted with DCM (3×30 mL). The combined organic layers were washed with brine and dried over $MgSO_4$, filtered, and concentrated. Purification via column chromatography (10-100% EtOAc in hexanes) provided 1-benzhydryl-3-(4-chloropyrrolo[2,1-f][1,2,4]triazin-5-yl)azetidin-3-ol (456 mg, 31.4%). $^1$H NMR (499 MHz, CHLOROFORM-d) δ 8.19 (s, 1H), 7.84 (d, J=2.5 Hz, 1H), 7.42 (br d, J=7.4 Hz, 6H), 7.27-7.30 (m, 4H), 7.17-7.24 (m, 3H), 7.01 (d, J=2.5 Hz, 2H), 4.46 (s, 1H), 3.79 (br d, J=7.9 Hz, 2H), 3.58 (br d, J=7.9 Hz, 2H). LCMS (ESI) [M+H]$^+$=391.1.

Step 2. 3-(4-((4-([1,2,4]triazolo[1,5-a]pyridin-7-yloxy)-3-methylphenyl)amino)pyrrolo[2,1-f][1,2,4]triazin-5-yl)-1-benzhydrylazetidin-3-ol

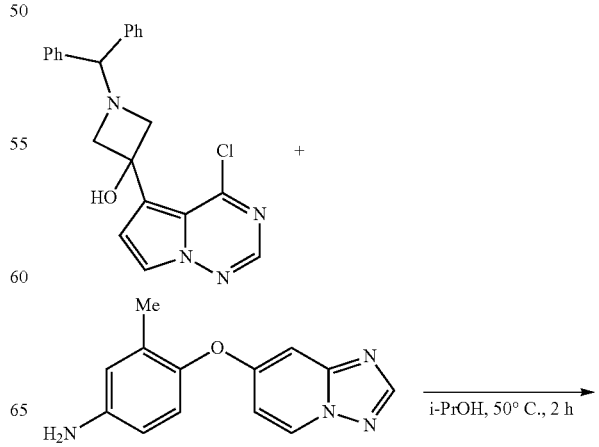

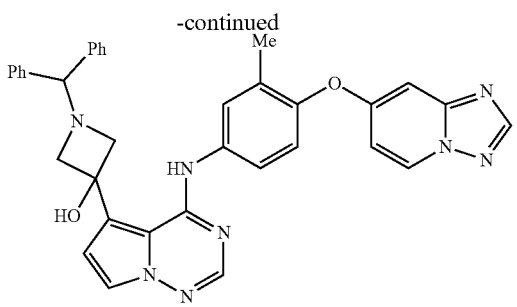

To a 2-dram vial with a stir bar was added 1-benzhydryl-3-(4-chloropyrrolo[2,1-f][1,2,4]triazin-5-yl)azetidin-3-ol (50.0 mg, 128 µmol) and 4-([1,2,4]triazolo[1,5-a]pyridin-7-yloxy)-3-methylaniline (32.3 mg, 134 µmol). The vial was capped and evacuated and refilled with N₂ (3×), then dry isopropanol (2.0 mL) was added via syringe and the reaction mixture was heated to 50° C. After 1 h the reaction was removed from the heat, diluted with sat. NaHCO₃(20 mL) and extracted with DCM (3×20 mL). Purification via column chromatography 10-100% EtOAc/EtOH (3:1 mixture) in hexanes provided 3-(4-((4-([1,2,4]triazolo[1,5-a]pyridin-7-yloxy)-3-methylphenyl)amino)pyrrolo[2,1-f][1,2,4]triazin-5-yl)-1-benzhydrylazetidin-3-ol, (69.9 mg, 91.9%). ¹H NMR (499 MHz, CHLOROFORM-d) δ 10.14 (br s, 1H), 8.46 (d, J=7.4 Hz, 1H), 8.20 (s, 1H), 8.00 (s, 1H), 7.60-7.69 (m, 3H), 7.55 (d, J=2.7 Hz, 1H), 7.39-7.51 (m, 5H), 7.29 (br t, J=7.4 Hz, 4H), 7.21 (br d, J=7.1 Hz, 3H), 6.96-7.10 (m, 2H), 6.85 (dd, J=7.4, 2.7 Hz, 2H), 6.80-6.83 (m, 1H), 6.68-6.80 (m, 2H), 4.49 (br s, 2H), 3.68 (br s, 3H), 3.48-3.61 (m, 3H), 2.19 (s, 4H), 1.96-2.14 (m, 2H). LCMS (ESI) [M+H]⁺=595.2.

Step 3. 3-(4-((4-([1,2,4]triazolo[1,5-a]pyridin-7-yloxy)-3-methylphenyl)amino)pyrrolo[2,1-f][1,2,4]triazin-5-yl)azetidin-3-ol

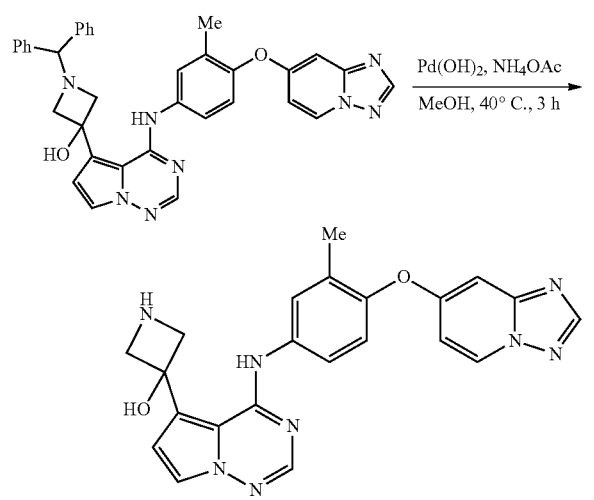

To a 1-dram vial with a stir bar was added 3-(5-((4-([1,2,4]triazolo[1,5-a]pyridin-7-yloxy)-3-methylphenyl)amino)pyrrolo[2,1-f][1,2,4]triazin-4-yl)-1-benzhydrylazetidin-3-ol (70 mg, 0.12 mmol), ammonium formate (0.22 g, 3.5 mmol), and palladium(II) hydroxide (83 mg, 20% Wt, 0.12 mmol). The vial was capped then evacuated and refilled with N₂ (3×). Anhydrous MeOH (5 mL) was then added through the septum and the reaction vial was then heated to 40° C. with stirring at 1600 rpm. After 3 h the reaction mixture was cooled to rt, neutralized with sat. aq. NaHCO₃ (20 mL) and extracted with DCM (3×15 mL). The organic layers were then washed with brine, dried with MgSO₄, and concentrated. The crude product was used immediately in the next step without further purification. LCMS (ESI) [M+H]⁺=429.2.

Step 4. (E)-1-(3-(4-((4-([1,2,4]triazolo[1,5-a]pyridin-7-yloxy)-3-methylphenyl)amino)pyrrolo[2,1-f][1,2,4]triazin-5-yl)-3-hydroxyazetidin-1-yl)-4-(dimethylamino)but-2-en-1-one

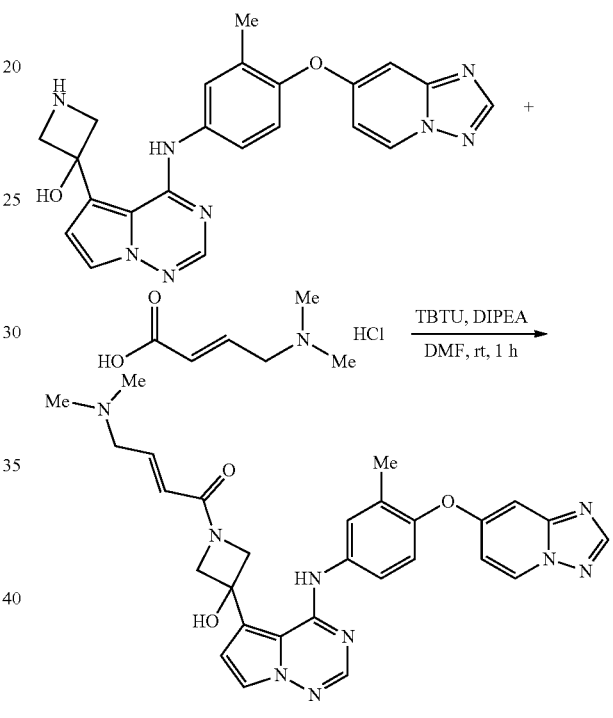

To the crude residue from the previous step (Step 3) was added O-(Benzotriazol-1-yl)-N,N,N',N'-tetramethyluronium tetrafluoroborate(TBTU) (57 mg, 0.18 mmol), (E)-4-(dimethylamino)but-2-enoic acid hydrochloride (29 mg, 0.18 mmol), DMF (2.0 mL), and diisopropylethylamine (61 mg, 0.47 mmol). The reaction mixture was then stirred at rt. After 1 h the reaction mixture was purified directly via prep HPLC 10-100% ACN in 0.1% TFA water. The collected fractions were combined, neutralized with sat. aq. NaHCO₃ (10 mL) and extracted with DCM (3×10 mL). The organic layers were then washed with brine, dried with MgSO₄, and concentrated to provide (E)-1-(3-(5-((4-([1,2,4]triazolo[1,5-a]pyridin-7-yloxy)-3-methylphenyl)amino)pyrrolo[2,1-f][1,2,4]triazin-4-yl)-3-hydroxyazetidin-1-yl)-4-(dimethylamino)but-2-en-1-one, Example 51 (1.89 mg, 2.7% yield over 2 steps). ¹H NMR (499 MHz, CHLOROFORM-d) δ ppm 10.63 (s, 1H) 8.48 (d, J=7.4 Hz, 1H) 8.13 (s, 1H) 8.02 (s, 1H) 7.78-7.82 (m, 1H) 7.70-7.74 (m, 1H) 7.52-7.57 (m, 1H) 7.08 (d, J=8.8 Hz, 1H) 6.83-6.92 (m, 2H) 6.75-6.80 (m, 1H) 6.67 (d, J=3.0 Hz, 1H) 6.19-6.27 (m, 1H) 4.52-4.66 (m, 3H) 4.40 (br d, J=11.0 Hz, 1H) 3.26 (br d, J=5.5 Hz, 2H) 3.08 (s, 1H) 2.29-2.38 (m, 6H) 2.19-2.25 (m, 3H).

Example 52
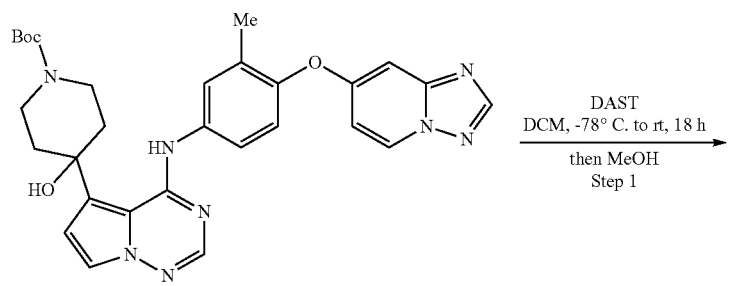
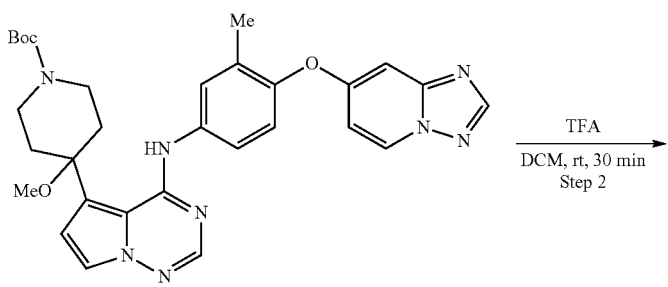
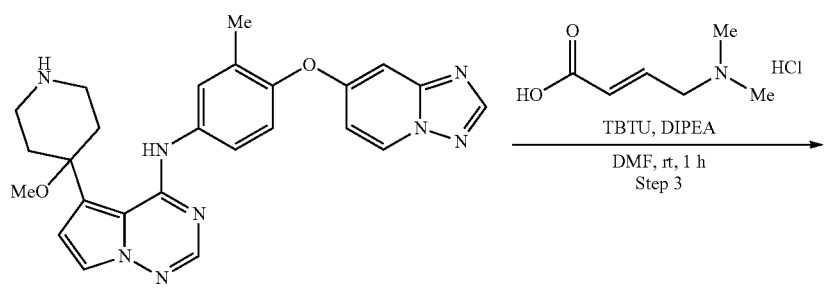
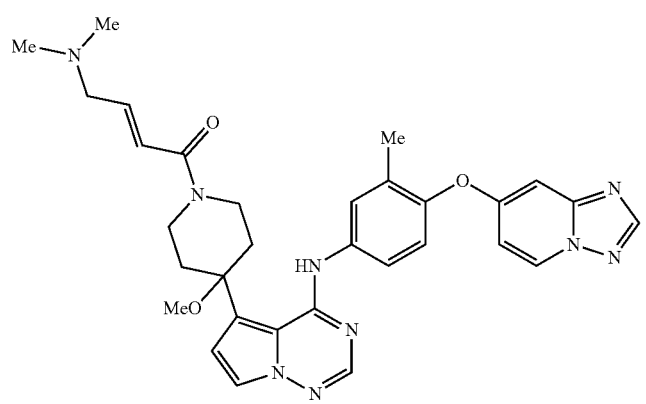
Example 52

Step 1. tert-butyl 4-(4-((4-([1,2,4]triazolo[1,5-a]pyridin-7-yloxy)-3-methylphenyl)amino)pyrrolo[2,1-f] [1,2,4]triazin-5-yl)-4-methoxypiperidine-1-carboxylate

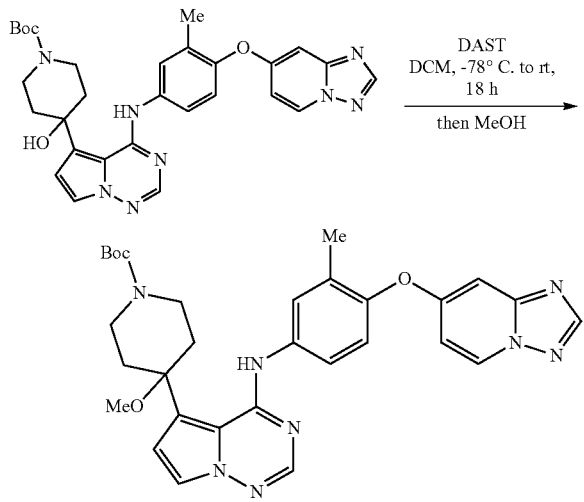

To a 1-dram vial with a stir bar was added tert-butyl 4-(4-((4-([1,2,4]triazolo[1,5-a]pyridin-7-yloxy)-3-methylphenyl)amino)pyrrolo[2,1-f][1,2,4]triazin-5-yl)-4-hydroxypiperidine-1-carboxylate (153 mg, 275 µmol) and DCM (1.0 mL). The vial was capped and cooled to −78° C., then DAST (266 mg, 218 µL. 1.65 mmol) was added slowly. The reaction mixture was stirred at −78° C. and allowed to warm slowly to rt overnight. The reaction was quenched with MeOH (1.0 mL) and stirred at rt for 1 h. Purification via column chromatography (0-15% MeOH in DCM) provided tert-butyl 4-(4-((4-([1,2,4]triazolo[1,5-a]pyridin-7-yloxy)-3-methylphenyl)amino)pyrrolo[2,1-f][1,2,4]triazin-5-yl)-4-methoxypiperidine-1-carboxylate (24 mg, 15%). $^1$H NMR (499 MHz, METHANOL-d4) δ 8.72 (d, J=7.4 Hz, 1H), 8.27 (s, 1H), 7.94 (s, 1H), 7.82 (d, J=2.5 Hz, 1H), 7.73 (dd, J=8.6, 2.6 Hz, 1H), 7.61 (d, J=2.7 Hz, 1H), 7.15 (d, J=8.8 Hz, 1H), 7.04 (dd, J=7.5, 2.6 Hz, 1H), 6.79 (d, J=2.5 Hz, 1H), 6.73 (d, J=2.7 Hz, 1H), 4.01 (br d, J=12.9 Hz, 2H), 3.17-3.40 (m, 5H), 2.30 (br d, J=13.7 Hz, 2H), 2.23 (s, 3H), 1.94-2.03 (m, 2H), 1.47 (s, 9H). LCMS (ESI) [M+H]$^+$=570.3.

Step 2. N-(4-([1,2,4]triazolo[1,5-a]pyridin-7-yloxy)-3-methylphenyl)-5-(4-methoxypiperidin-4-yl)pyrrolo[2,1-f][1,2,4]triazin-4-amine

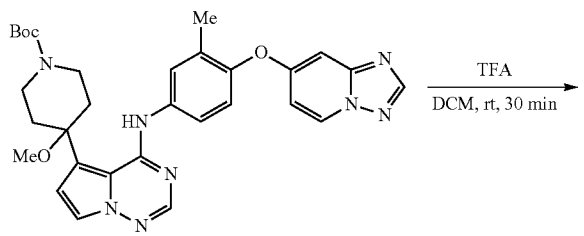

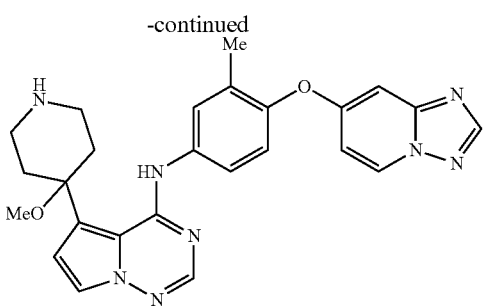

To a 1-dram vial with a stir bar was added tert-butyl 4-(4-((4-([1,2,4]triazolo[1,5-a]pyridin-7-yloxy)-3-methylphenyl)amino)pyrrolo[2,1-f][1,2,4]triazin-5-yl)-4-hydroxypiperidine-1-carboxylate (20 mg, 36 µmol) and TFA (41 mg, 28 µL, 0.36 mmol). The reaction mixture was stirred at rt for 20 min. The reaction mixture was then concentrated under vacuum and used directly in the next step without any further purification. LCMS (ESI) [M+H]$^+$=470.2.

Step 3. (E)-1-(4-(4-((4-([1,2,4]triazolo[1,5-a]pyridin-7-yloxy)-3-methylphenyl)amino)pyrrolo[2,1-f] [1,2,4]triazin-5-yl)-4-methoxypiperidin-1-yl)-4-(dimethylanilino)but-2-en-1-one

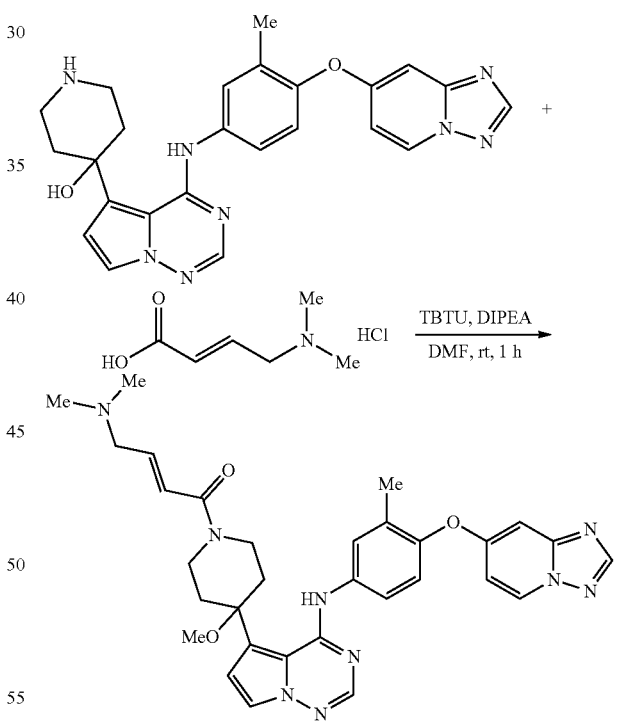

To a 1 dram vial with a stir bar was added N-(4-([1,2,4]triazolo[1,5-a]pyridin-7-yloxy)-3-methylphenyl)-5-(4-methoxypiperidin-4-yl)pyrrolo[2,1-f][1,2,4]triazin-4-amine (30.0 mg, 63.8 µmol), (E)-4-(dimethylamino)but-2-enoic acid hydrochloride (21.1 mg, 128 µmol), and O-(benzotriazol-1-yl)-N,N,N',N'-tetramethyluronium tetrafluoroborate (TBTU) (40.9 mg, 128 µmol). Then DMF (2 mL) was added, followed by diisopropylethylamine (33.0 mg, 44.4 µL, 255 µmol) then the reaction mixture was stirred at rt. After 1 h, the reaction mixture was directly purified via prepHPLC 10-100% ACN in water with 0.1% TFA. Fractions containing the desired product mass were combined and neutralized with sat. aq. NaHCO$_3$ (7 mL) and extracted with DCM (3×10 mL). The combined organic fractions were washed with brine, dried over anhydrous MgSO$_4$, and concentrated to provide (E)-1-(4-(4-((4-([1,2,4]triazolo[1,5-a]pyridin-7-yloxy)-3-methylphenyl)amino)pyrrolo[2,1-f][1,2,4]triazin-5-yl)-4-methoxypiperidin-1-yl)-4-(dimethylamino)but-2-en-1-one, Example 52 (4.27 mg, 11.0%). $^1$H NMR (499 MHz, CHLOROFORM-d) δ ppm 10.54 (s, 1H) 8.49 (d, J=7.4 Hz, 1H) 8.22 (s, 1H) 8.04 (s, 1H) 7.66-7.74 (m, 2H) 7.54-7.59 (m, 1H) 7.09 (d, J=8.8 Hz, 1H) 6.89 (dd, J=7.4, 2.7 Hz, 1H) 6.78-6.86 (m, 2H) 6.56 (d, J=2.7 Hz, 1H) 4.51-4.72 (m, 2H) 3.94-4.16 (m, 2H) 3.36-3.75 (m, 4H) 3.29 (s, 3H) 3.16-3.25 (m, 1H) 2.41-2.78 (m, 6H) 2.32-2.40 (m, 2H) 2.25 (s, 3H). LCMS (ESI) [M+H]$^+$=582.3.

Example 72

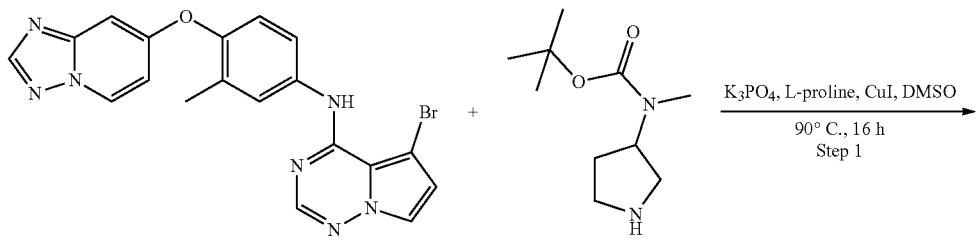

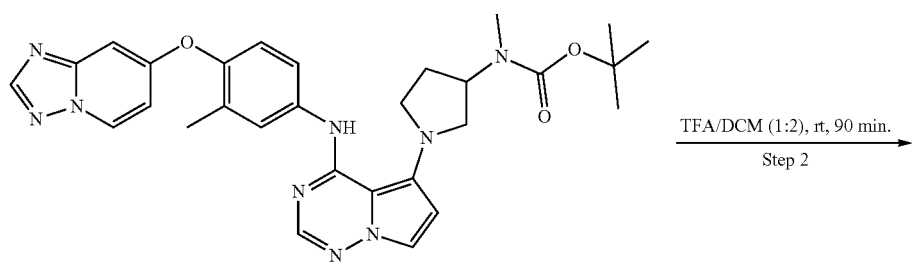

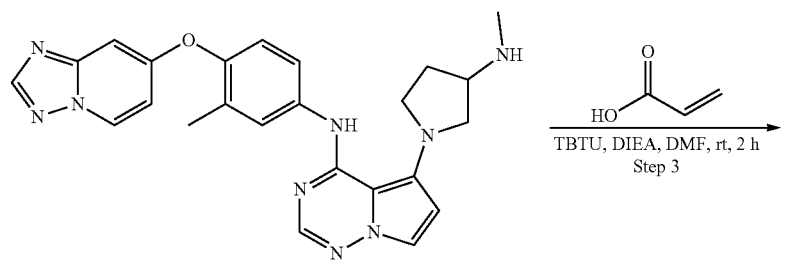

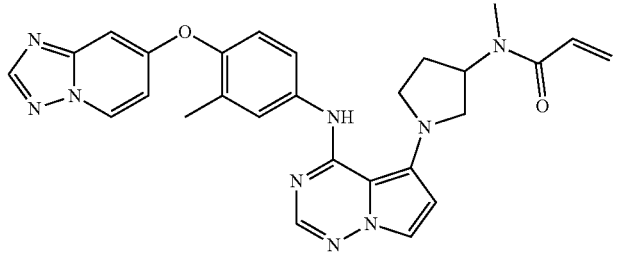

Example 72

Step 1. tert-butyl (1-(4-((4-([1,2,4]triazolo[1,5-a]pyridin-7-yloxy)-3-methylphenyl)amino)pyrrolo[2,1-f][1,2,4]triazin-5-yl)pyrrolidin-3-yl)(methyl)carbamate

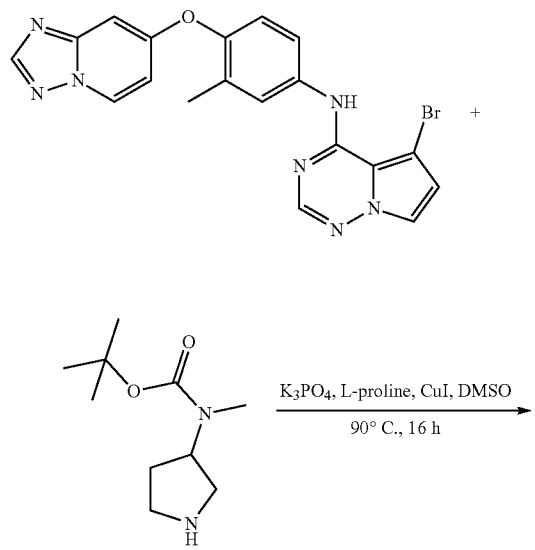

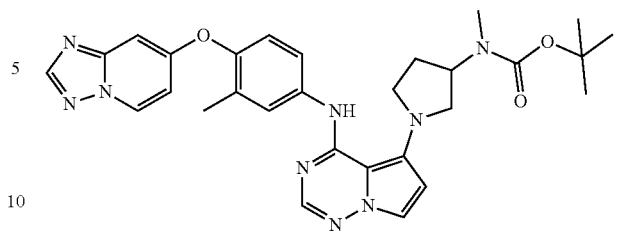

A solution of N-(4-([1,2,4]triazolo[1,5-a]pyridin-7-yloxy)-3-methylphenyl)-5-bromopyrrolo[2,1-f][1,2,4]triazin-4-amine (100 mg, 229 μmol), tert-butyl methyl(pyrrolidin-3-yl)carbamate (138 mg, 688 μmol), potassium phosphate (146 mg, 688 μmol), L-proline (10.6 mg, 91.7 μmol), and copper(I) iodide (8.73 mug, 45.8 μmol) in DMSO (2 mL) was stirred overnight at 90° C. The crude product was purified by reverse phase flash chromatography. Fractions were freeze-dried to afford tert-butyl (1-(4-((4-([1,2,4]triazolo[1,5-a]pyridin-7-yloxy)-3-methylphenyl)amino)pyrrolo[2,1-f][1,2,4]triazin-5-yl)pyrrolidin-3-yl)(methyl)carbamate (92 mg, 69%). LCMS (ESI-MS) m/z=556.3 [M+H]⁺.

Step 2. N-(4-([1,2,4]triazolo[1,5-a]pyridin-7-yloxy)-3-methylphenyl)-5-(3-(methylamino)pyrrolidin-1-yl)pyrrolo[2,1-f][1,2,4]triazin-4-amine

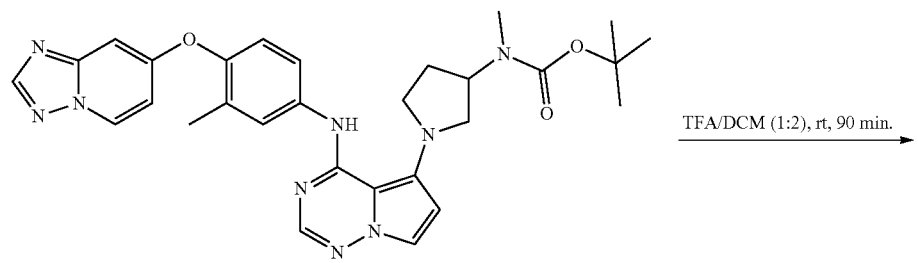

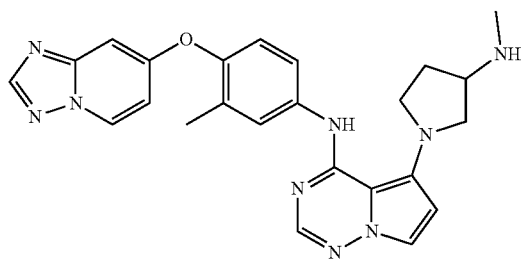

A mixture of tert-butyl (1-(4-((4-([1,2,4]triazolo[1,5-a]pyridin-7-yloxy)-3-methylphenyl)amino)pyrrolo[2,1-f][1,2,4]triazin-5-yl)pyrrolidin-3-yl)(methyl)carbamate (95 mg crude) in DCM (4 mL) and TFA (2 mL) was stirred at room temperature for 90 min and concentrated under vacuum. The crude was diluted with DCM (10 mL) and washed with NaHCO₃(5 mL). The mixture was filtered through a phase separator column, and the solvent was evaporated to afford the crude product N-(4-([1,2,4]triazolo[1,5-a]pyridin-7-yloxy)-3-methylphenyl)-5-(3-(methylamino)pyrrolidin-1-yl)pyrrolo[2,1-f][1,2,4]triazin-4-amine (50 mg, crude). The crude product was used for the next step without further purification. LCMS (ESI-MS) m/z=456.2 [M+H]⁺.

Step 3. N-(1-(4-((4-([1,2,4]triazolo[1,5-a]pyridin-7-yloxy)-3-methylphenyl)amino)pyrrolo[2,1-f][1,2,4]triazin-5-yl)pyrrolidin-3-yl)-N-methylacrylamide

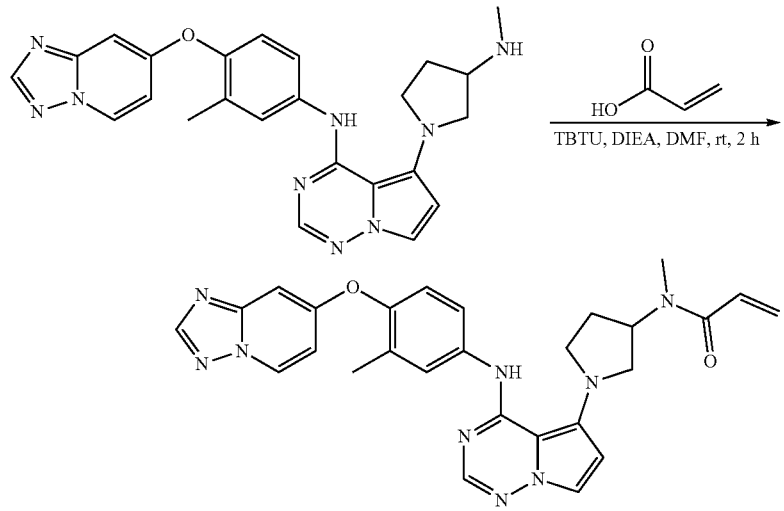

A solution of N-(4-([1,2,4]triazolo[1,5-a]pyridin-7-yloxy)-3-methylphenyl)-5-(3-(methylamino)pyrrolidin-1-yl)pyrrolo[2,1-f][1,2,4]triazin-4-amine (25 mg, 55 μmol), (acrylic acid (5.9 mg, 82 μmol)), and O-(benzotriazol-1-yl)-N,N,N',N'-tetramethyluronium tetrafluoroborate (TBTU) (26 rug, 82 μmol) and diisopropylethylamine (21 mg, 0.16 mmol) in DMF (1.5 mL) was stirred for two hours at room temperature. The crude product was purified by reverse phase flash chromatography. Fractions were combined, diluted with ethyl acetate (20 mL), and washed with saturated NaHCO₃(10 mL). The organic layer was dried over MgSO₄, and the solvent was evaporated to afford N-(1-(4-((4-([1,2,4]triazolo[1,5-a]pyridin-7-yloxy)-3-methylphenyl) amino)pyrrolo[2,1-f][1,2,4]triazin-5-yl)pyrrolidin-3-yl)-N-methylacrylamide, Example 72 (9 mg, 30%). ¹H NMR (499 MHz, DMSO-d₆) δ=9.67-9.57 (m, 11H), 8.93 (d, J=7.4 Hz, 1H), 8.40-8.35 (m, 1H), 7.99-7.95 (m, 1H), 7.82-7.74 (m, 2H), 7.67 (d, J=2.7 Hz, 1H), 7.26-7.20 (m, 1H), 7.04-6.99 (m, 1H), 6.87 (br s, 1H), 6.81-6.66 (m, 2H), 6.16-6.04 (m, 1H), 5.72-5.63 (m, 1H), 5.36-5.19 (m, 1H), 3.30-3.23 (m, 2H), 3.22-3.04 (m, 4H), 3.02-2.94 (m, 1H), 2.19 (s, 3H), 2.15-2.02 (m, 2H). LCMS (ESI-MS) m/z=510.3 [M+H]⁺.

Example 86

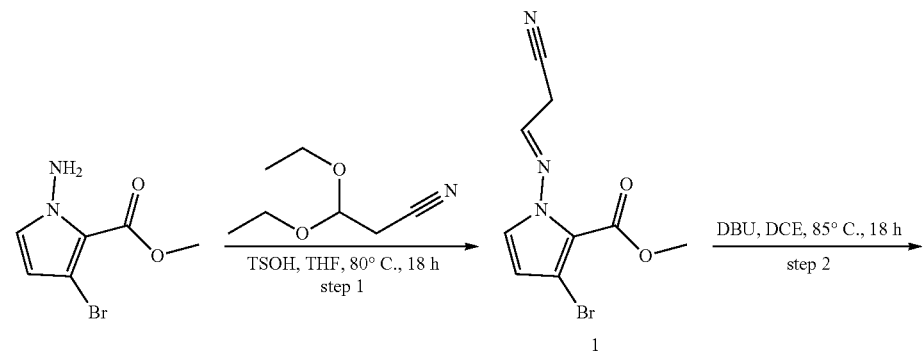

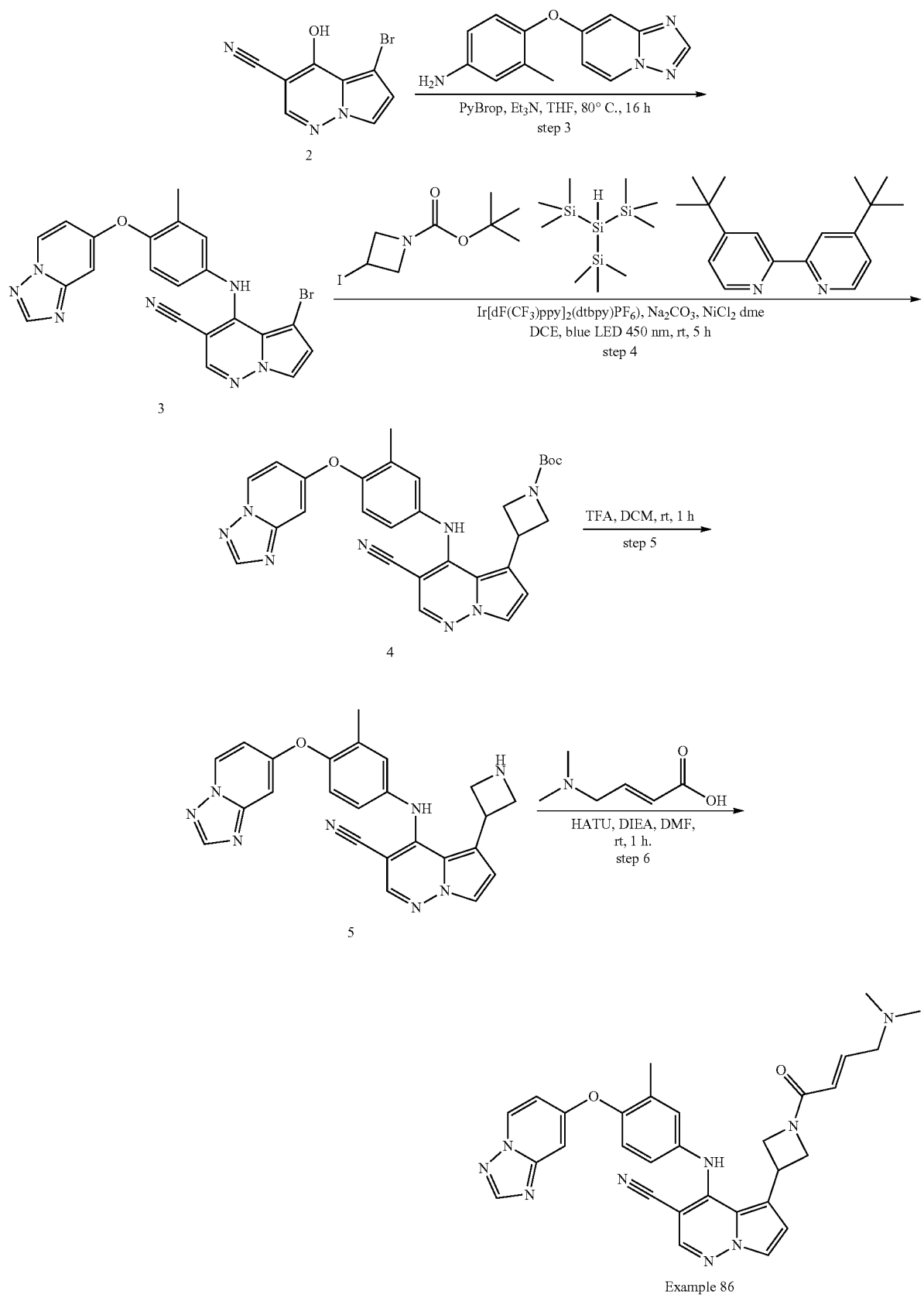

Step 1. Methyl (E)-3-bromo-1-((2-cyanoethylidene)amino)-1H-pyrrole-2-carboxylate

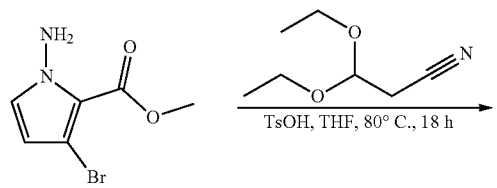

3,3-diethoxypropanenitrile (3.92 g, 27.39 mmol) and TsOH (1.18 g, 6.84 mmol) were added into a stirred solution of methyl 1-amino-3-bromopyrrole-2-carboxylate (3 g, 13.69 mmol) in THF (60 mL) at room temperature. The resulting mixture was stirred at 80° C. for 18 hours. After cooling to room temperature, the reaction mixture was concentrated under vacuum and purified with silica gel column with ethyl acetate/petroleum ether=1:1 to afford the desired product methyl (E)-3-bromo-1-((2-cyanoethylidene)amino)-1H-pyrrole-2-carboxylate (2 g, 32.1% yield). LCMS (ESI-MS) m/z=270.0 [M+H]$^+$.

Step 2. 5-bromo-4-hydroxypyrrolo[1,2-b]pyridazine-3-carbonitrile

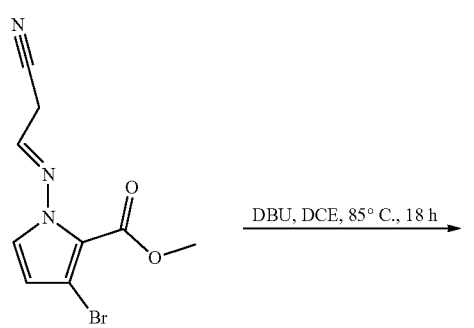

To a solution of methyl (E)-3-bromo-1-((2-cyanoethylidene)amino)-1H-pyrrole-2-carboxylate (2 g, 7.40 mmol) in DCE (20 mL) was added 1,8-diazabicycloundec-7-ene (1.13 g, 7.40 mmol). The resulting mixture was stirred at 85° C. for 18 hours and concentrated under vacuum to afford the crude product. The residue was purified by silica gel column with ethyl acetate/petroleum ether=2:1 to afford the desired product 5-bromo-4-hydroxypyrrolo[1,2-b]pyridazine-3-carbonitrile (1 g, 53.2% yield). LCMS (ESI-MS) m/z=238.0 [M+H]$^+$.

Step 3. 4-((4-([1,2,4]triazolo[1,5-a]pyridin-7-yloxy)-3-methylphenyl)amino)-5-bromopyrrolo[1,2-b]pyridazine-3-carbonitrile

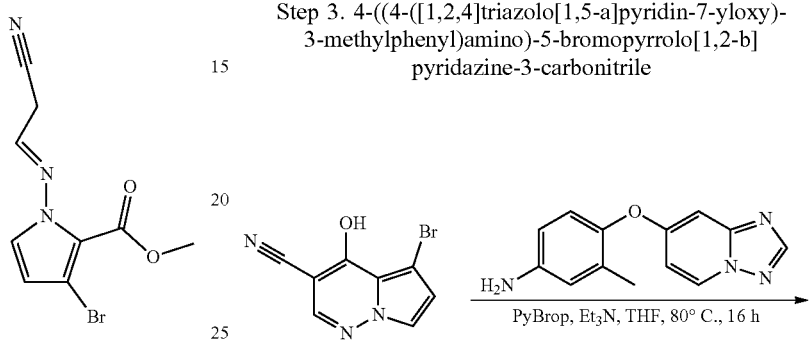

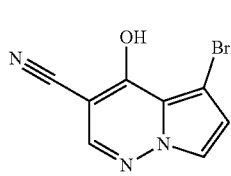

To a solution of 5-bromo-4-hydroxypyrrolo[1,2-b]pyridazine-3-carbonitrile (900 mg, 3.78 mmol) in THF (20 mL) was added 4-([1,2,4]triazolo[1,5-a]pyridin-7-yloxy)-3-methylaniline (908 mg, 3.78 mmol), Et$_3$N (1.47 g, 11.34 mmol) and PyBrop (2.64 g, 5.67 mmol). The resulting mixture was stirred at 80° C. for 16 hours and concentrated under vacuum to afford the crude product. The residue was purified by silica gel column with ethyl acetate/petroleum ether=2:1 to afford the desired product 4-((4-([1,2,4]triazolo[1,5-a]pyridin-7-yloxy)-3-methyl-phenyl)amino)-5-bromopyrrolo[1,2-b]pyridazine-3-carbonitrile (800 mg, 45.9% yield). LCMS (ESI-MS) m/z=460.0 [M+H]$^+$.

Step 4. tert-butyl 3-(4-((4-([1,2,4]triazolo[1,5-a]pyridin-7-yloxy)-3-methylphenyl)amino)-3-cyano-pyrrolo-[1,2-b]pyridazin-5-yl)azetidine-1-carboxylate

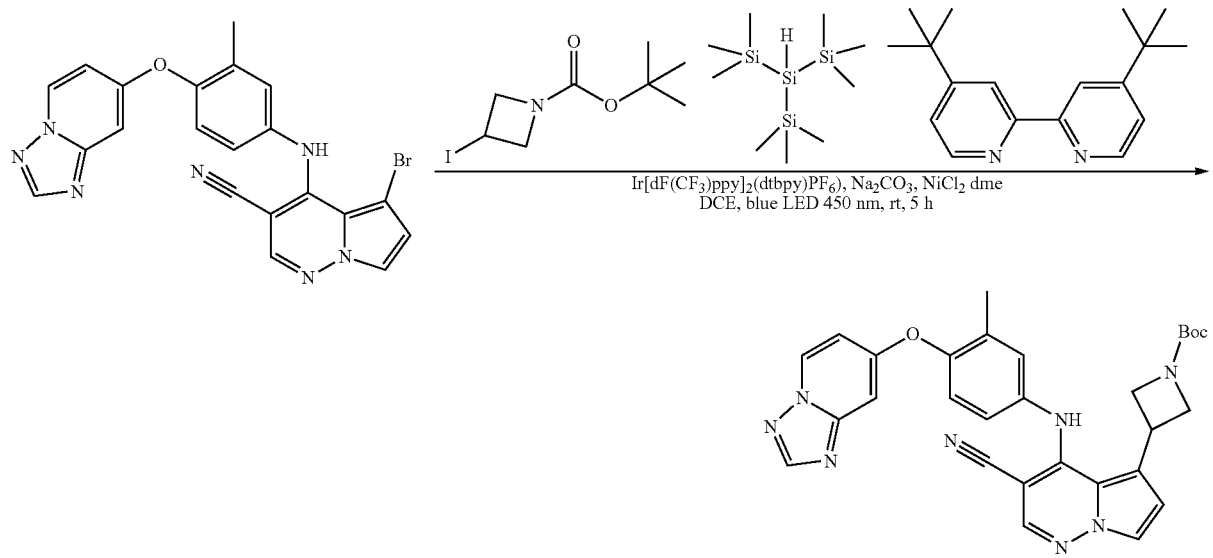

A mixture of 4,4'-di-tert-butyl-2,2'-bipyridine (29 mg, 0.11 mmol) and NiCl$_2$·dme (33 mg, 0.11 mmol) in DCE (1 mL) was heated to 60° C. for 10 minutes under nitrogen atmosphere. The solution was allowed to cool to room temperature (solution 1). Ir[dF(CF$_3$)ppy]$_2$(dtbpy)PF$_6$ (122 mg, 0.11 mmol) was added to a mixture of 4-((4-([1,2,4]-triazolo[1,5-a]pyridin-7-yloxy)-3-methylphenyl)amino)-5-bromopyrrolo[1,2-b]pyridazine-3-carbonitrile (616.6 mg, 2.0 mmol), 1,1,1,3,3,3-hexamethyl-2-(trimethylsilyl)trisilane (297 mg, 1.19 mmol) and Na$_2$CO$_3$ (230 mg, 2.17 mmol) in DCE (10 mL) under nitrogen atmosphere, followed by addition of the solution 1 via syringe. The resulting mixture was maintained under nitrogen, stirred at room temperature and irradiated by blue LED (450 nm) in Penn Photo reactor m2 for 5 hours. The reaction mixture was purified by Prep-TLC with DCM/MeOH=10:1 to afford tert-butyl 3-(4-((4-([1,2,4]triazolo[1,5-a]pyridin-7-yloxy)-3-methylphenyl)amino)-3-cyanopyrrolo[1,2-b]pyridazin-5-yl)azetidine-1-carboxylate (500 mg crude), the crude product was used for next step directly without further purification. LCMS (ESI-MS) m/z=537.2 [M+H]$^+$.

Step 5. 4-((4-([1,2,4]triazolo[1,5-a]pyridin-7-yloxy)-3-methylphenyl)amino)-5-(azetidin-3-yl)pyrrolo[1,2-b]pyridazine-3-carbonitrile -continued A mixture of tert-butyl 3-(4-((4-([1,2,4]triazolo[1,5-a]pyridin-7-yloxy)-3-methylphenyl)amino)-3-cyanopyrrolo[1,2-b]pyridazin-5-yl)azetidine-1-carboxylate (500 mg crude) and TFA (1.6 mL) in DCM (10 mL) was stirred at room temperature for 1 hour and concentrated under vacuum to afford the crude product 4-((4-([1,2,4]triazolo[1,5-a]pyridin-7-yloxy)-3-methylphenyl)amino)-5-(azetidin-3-yl)pyrrolo[1,2-b]pyridazine-3-carbonitrile (150 mg crude). LCMS (ESI-MS) m/z=437.2 [M+H]$^+$.

Step 6. (E)-4-((4-([1,2,4]triazolo[1,5-a]pyridin-7-yloxy)-3-methylphenyl)amino)-5-(1-(4-(dimethyl-amineo)-but-2-enoyl)azetidin-3-yl)pyrrolo[1,2-b]pyridazine-3-carbonitrile

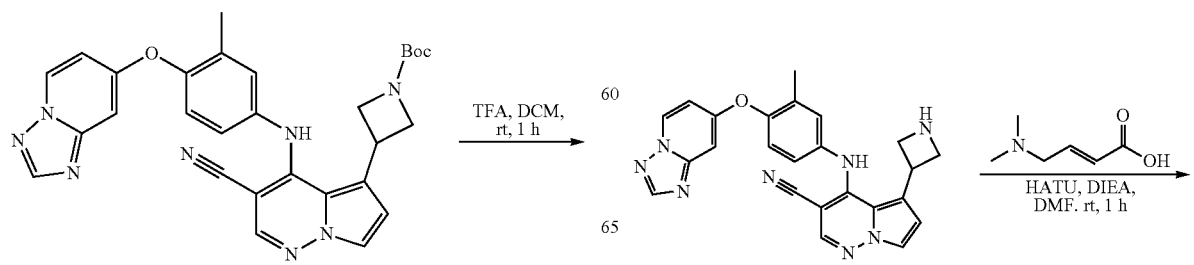

175

-continued

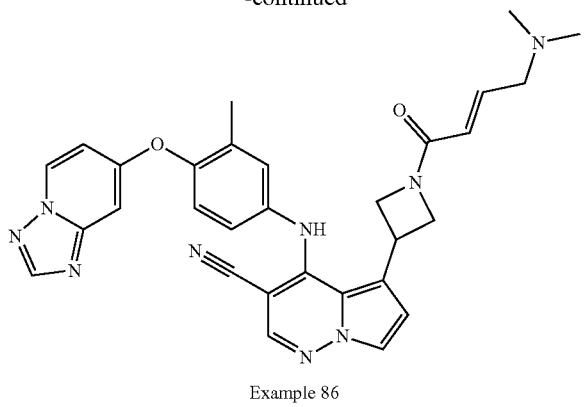

Example 86

Diisopropylethylamine (148.05 mg, 1.14 mmol) was added to a mixture of 3-(4-((4-([1,2,4]triazolo[1,5-a]pyridin-7-yloxy)-3-methylphenyl)amino)-3-cyanopyrrolo[1,2-b]pyridazin-5-yl)azetidine-1-carboxylate (100 mg, 0.22

176 mmol), (2E)-4-(dimethylamino)but-2-enoic acid (29.59 mg, 0.22 mmol) and HATU (130.67 mg, 0.34 mmol) in DMF (3 mL). The resulting mixture was stirred at 25° C. for 1 hour and concentrated under vacuum to afford the crude product. The residue was purified by preparative HPLC with the following conditions: column, C18 silica gel; mobile phase, ACN in Water (0.1% FA), 10% to 60% gradient in 10 min; to afford the crude desired product (E)-4-((4-([1,2,4]triazolo[1,5-a]pyridin-7-yloxy)-3-methylphenyl)amino)-5-(1-(4-(dimethylamino)-but-2-enoyl)azetidin-3-yl)pyrrolo[1,2-b]pyridazine-3-carbonitrile, Example 86 (11.8 mg, 9% yield). LCMS (ESI-MS) m/z=548.1 [M+H]$^+$. $^1$H NMR (400 MHz, Chloroform-d) δ 8.51 (d, J=7.5 Hz, 11H), 8.25 (s, 1H), 7.78 (s, 1H), 7.60-7.55 (m, 1H), 7.37 (d, J=2.6 Hz, 1H), 7.35-7.28 (m, 1H), 7.19 (d, J=8.4 Hz, 1H), 7.11 (d, J=2.6 Hz, 1H), 6.95-6.90 (m, 1H), 6.83-6.80 (m, 1H), 6.62 (d, J=2.6 Hz, 1H), 6.35 (s, 1H), 6.16 (d, J=15.5 Hz, 1H), 4.14-4.10 (m, 1H), 3.85-3.80 (m, 2H), 3.68-3.65 (m, 2H), 3.35 (d, J=6.3 Hz, 2H), 2.49 (s, 4H), 2.47-2.45 (m, 2H), 2.29 (s, 3H).

Example 87

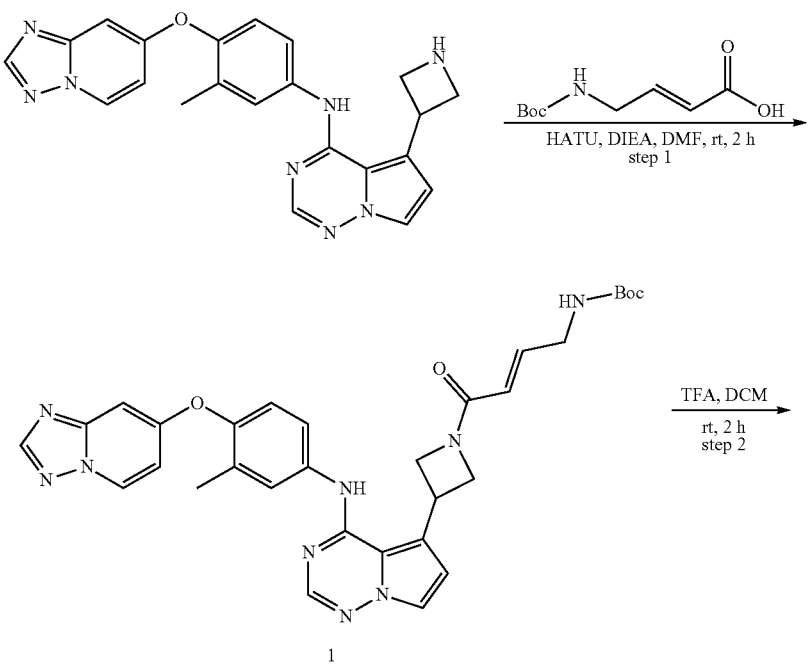

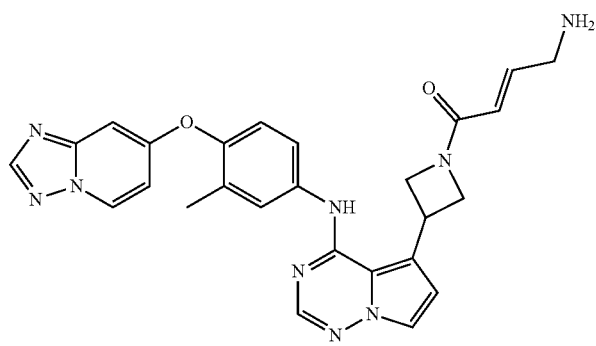

Example 87

Step 1. tert-butyl (E)-(4-(3-(4-((4-([1,2,4]triazolo[1,5-a]pyridin-7-yloxy)-3-methylphenyl)amino)pyrrolo-[2,1-f][1,2,4]triazin-5-yl)azetidin-1-yl)-4-oxobut-2-en-1-yl)carbamate

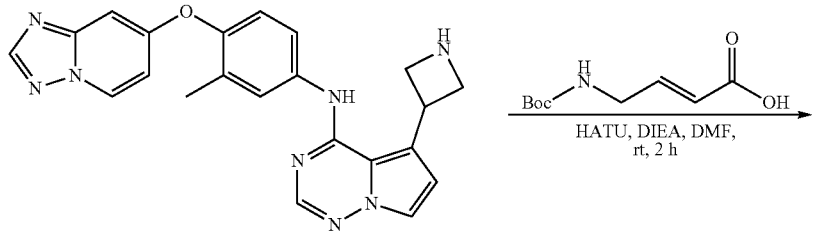

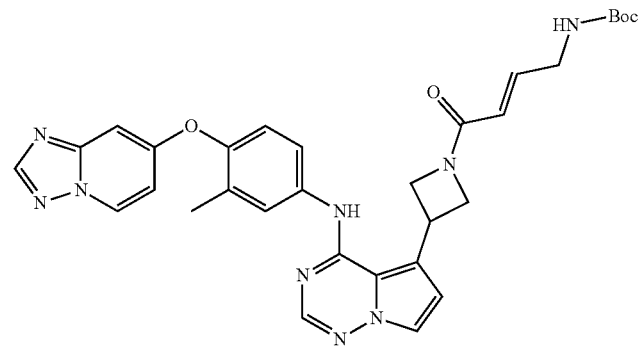

A mixture of N-(4-([1,2,4]triazolo[1,5-a]pyridin-7-yloxy)-3-methylphenyl)-5-(azetidin-3-yl)pyrrolo[2,1-f][1,2,4]triazin-4-amine (320 mg, 0.77 mmol), (E)-4-((tert-butoxycarbonyl)amino)but-2-enoic acid (186 mg, 0.92 mmol), HATU (350 mg, 0.92 mmol) and diisopropylethylamine (298 mg, 2.31 mmol) in DMF (30 mL) was stirred for 2 hours at room temperature. The reaction mixture was diluted with water (50 mL) and the resulting solution was extracted with ethyl acetate (3×50 mL). The combined organic layer was dried over anhydrous Na₂SO₄, filtered and concentrated under vacuum to afford the crude product. The crude product was purified by silica column chromatography (0-3% MeOH in DCM) to afford the desired product tert-butyl (E)-(4-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-oxobut-2-en-1-yl)carbamate (260 mg, 56.7% yield). LCMS (ESI-MS) m/z=596.3 [M+H]⁺

Step 2. (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-aminobut-2-en-1-one

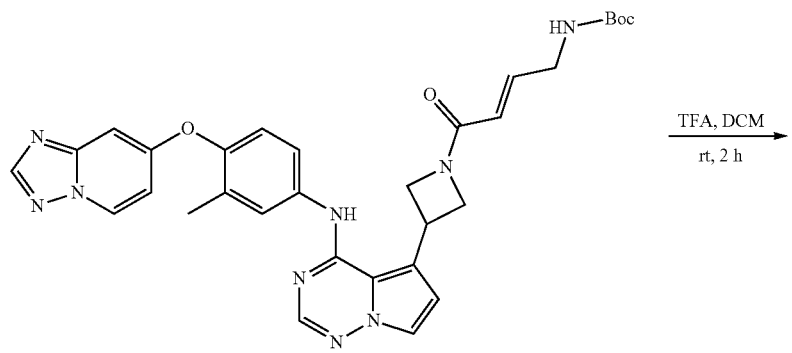

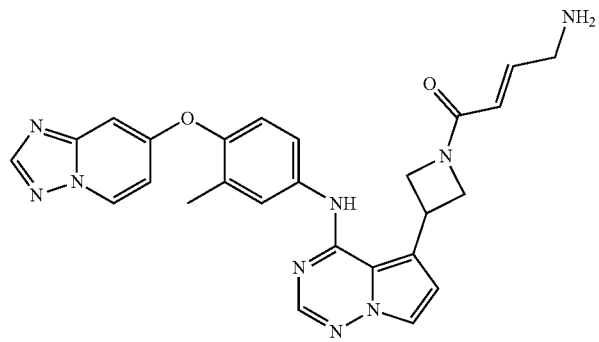

Example 87

To a stirred solution of tert-butyl (E)-(4-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-oxobut-2-en-1-yl)carbamate (260 mg, 0.44 mmol) in DCM (10 mL) was added TFA (5 mL). The resulting mixture was stirred for 2 hours at room temperature and concentrated to afford the crude product. The crude product was purified by Prep-HPLC Mobile Phase A: Water (10 mmol/L NH$_4$HCO$_3$+0.1% NH$_3$·H$_2$O), Mobile Phase B: MeOH to afford the desired product (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-aminobut-2-en-1-one, Example 87 (34.5 mg, 15.8% yield). LCMS (ESI-MS) m/z=496.2 [M+H]$^+$. $^1$H NMR (400 MHz, Chloroform-d) δ 8.51 (d, J=7.6 Hz, 1H), 8.24 (s, 1H), 8.01 (s, 1H), 7.70-7.52 (m, 3H), 7.15-6.99 (m, 3H), 6.95-6.79 (m, 2H), 6.73 (d, J=2.9 Hz, 1H), 6.13 (d, J=15.1 Hz, 1H), 4.85-4.62 (m, 2H), 4.48-4.27 (m, 3H), 3.54 (dd, J=4.9, 2.0 Hz, 2H), 2.25 (s, 31), 1.70-1.68 (m, 2H).

Example 88

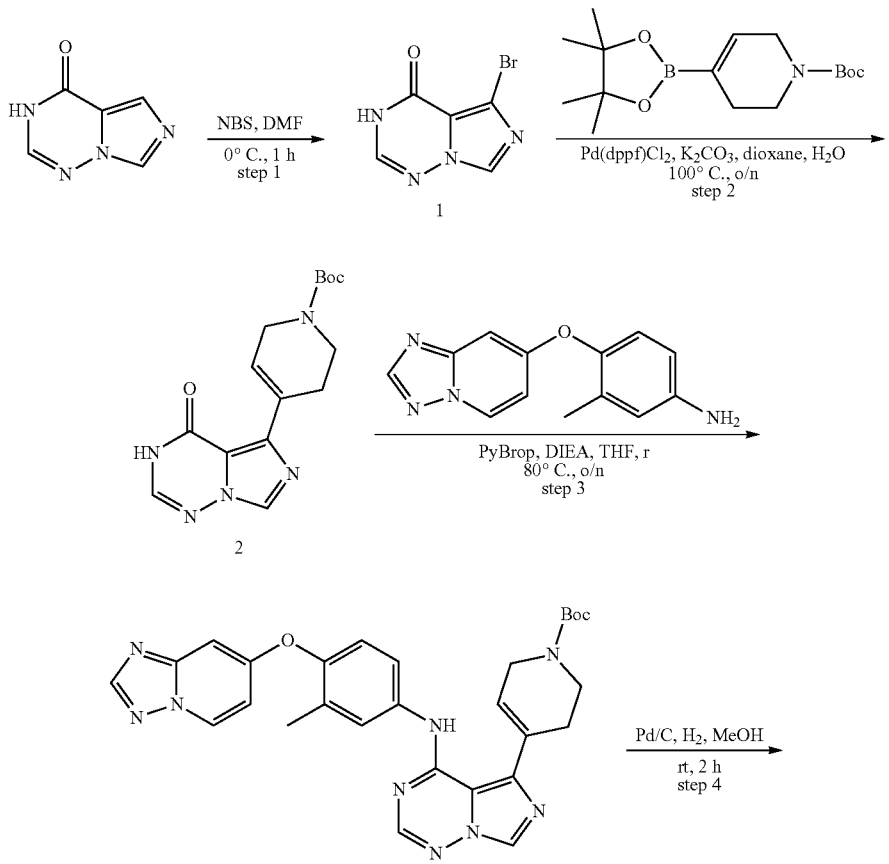

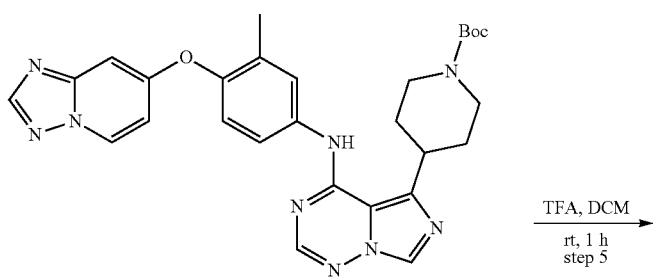

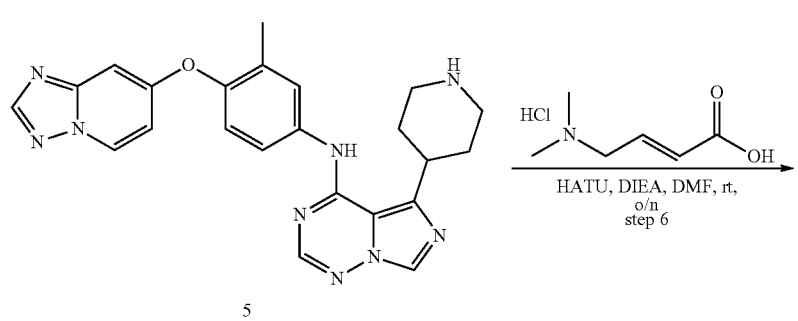

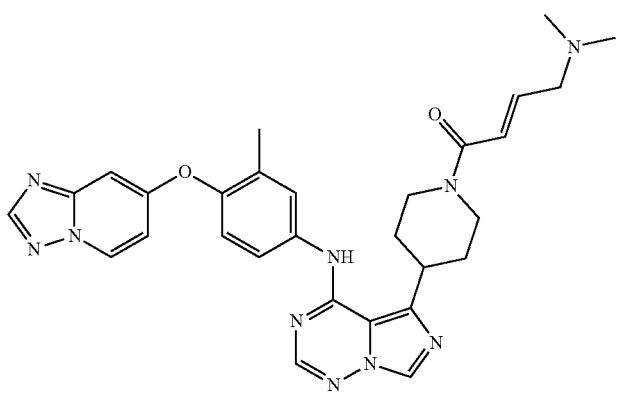

Example 88

Step 1. 5-bromoimidazo[5,1-f][1,2,4]triazin-4(3H)-one

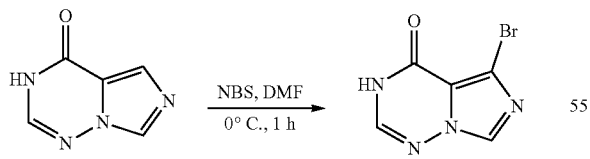

The mixture of imidazo[5,1-f][1,2,4]triazin-4(3H)-one (5 g, 36.73 mmol) and NBS (6.54 g, 36.73 mmol) in DMF (250 mL) was stirred for 1 hour at 0° C. The reaction was quenched by addition of saturated aqueous sodium bicarbonate (500 mL) at 0° C. The reaction mixture was diluted with water (2000 mL), the resulting solution was then extracted with ethyl acetate (3×1000 mL). The combined organic layers were washed with brine, dried over anhydrous Na$_2$SO$_4$, filtered and concentrated under vacuum to afford the crude product 5-bromoimidazo[5,1-f][1,2,4]triazin-4(3H)-one (3.5 g crude), the crude product was used in next step directly without further purification. LCMS (ESI-MS) m/z=215.0 [M+H]$^+$.

Step 2. tert-butyl 4-(4-oxo-3,4-dihydroimidazo[5,1-f][1,2,4]triazin-5-yl)-3,6-dihydropyridine-1(2H)-carboxylate

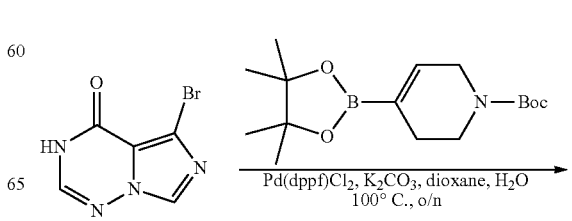

-continued

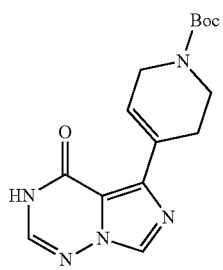

A mixture of 5-bromoimidazo[5,1-f][1,2,4]triazin-4(3H)-one (2 g, 9.30 mmol), tert-butyl 4-(4,4,5,5-tetramethyl-1,3,2-dioxaborolan-2-yl)-3,6-dihydropyridine-1(2H)-carboxylate (2.88 g, 9.30 mmol), K₂CO₃ (2.57 g, 18.60 mmol) and Pd(dppf)Cl₂ (754 mg, 0.93 mmol) in dioxane (20 mL) and water (6 mL) was stirred overnight at 100° C. under nitrogen atmosphere. The crude reaction mixture was diluted with water (50 mL) and extracted with ethyl acetate (3×100 mL). The combined organic layers were washed with brine, dried over anhydrous Na₂SO₄, filtered and concentrated under vacuum to afford the crude product. The crude product was purified by column chromatography, eluted with ethyl acetate in petroleum ether from 0% to 30% to afford the desired product tert-butyl 4-(4-oxo-3,4-dihydroimidazo[5,1-f][1,2,4]triazin-5-yl)-3,6-dihydropyridine-1(2H)-carboxylate (1.5 g, 50.6% yield). LCMS (ESI-MS) m/z=318.1 [M+H]⁺.

Step 3. tert-butyl 4-(4-((4-([1,2,4]triazolo[1,5-a]pyridin-7-yloxy)-3-methylphenyl)amino)imidazo[5,1-f][1,2,4] triazin-5-yl)-3,6-dihydropyridine-1(2H)-carboxylate

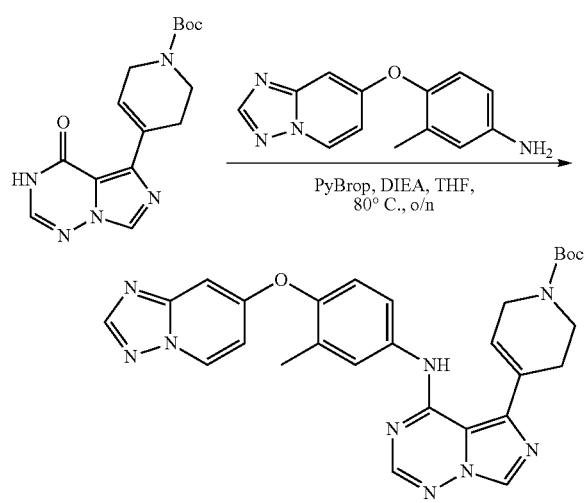

DIEA (1.43 g, 14.18 mmol) was added to a stirred mixture of tert-butyl 4-(4-oxo-3,4-dihydroimidazo[5,1-f][1,2,4]triazin-5-yl)-3,6-dihydropyridine-1(2H)-carboxylate (1.5 g, 4.72 mmol), 4-([1,2,4]triazolo[1,5-a]-pyridin-7-yloxy)-3-methylaniline (1.14 g, 4.72 mmol) and PyBrop (3.31 g, 7.09 mmol) in THF (30 mL). The resulting mixture was stirred overnight at 80° C., diluted with water (100 mL) and extracted with ethyl acetate (3×200 mL). The combined organic layers were washed with brine, dried over anhydrous Na₂SO₄, filtered and concentrated under vacuum to afford the crude product tert-butyl 4-(4-((4-([1,2,4]triazolo[1,5-a]pyridin-7-yloxy)-3-methylphenyl)amino)imidazo[5,1-f][1,2,4]triazin-5-yl)-3,6-dihydropyridine-1(2H)-carboxylate (2 g crude) the crude product was used for next step directly without further purification. LCMS (ESI-MS) m/z=540.2 [M+H]⁺.

Step 4. tert-butyl 4-(4-((4-([1,2,4]triazolo[1,5-a]pyridin-7-yloxy)-3-methylphenyl)amino)imidazo[5,1-f][1,2,4]triazin-5-yl)piperidine-1-carboxylate

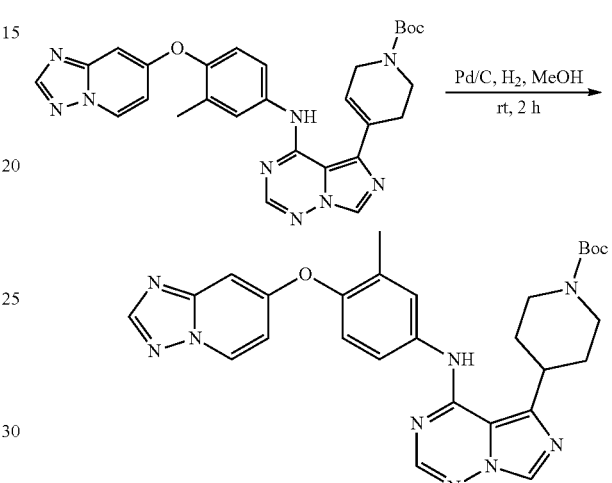

Pd/C (3.94 g, 37.06 mmol) was added to the solution of tert-butyl 4-(4-((4-([1,2,4]triazolo[1,5-a]pyridin-7-yloxy)-3-methylphenyl)amino)imidazo[5,1-f][1,2,4]triazin-5-yl)-3,6-dihydropyridine-1(2H)-carboxylate (2 g, 3.70 mmol) in MeOH (20 mL) under nitrogen atmosphere. The resulting mixture was degassed, then charged with an atmospheric pressure of hydrogen and stirred for 2 hours at room temperature. The reaction mixture was filtered, the filter cake was washed with MeOH (4×100 mL). The combined filtrate was concentrated under reduced pressure to afford crude product tert-butyl 4-(4-((4-([1,2,4]triazolo[1,5-a]pyridin-7-yloxy)-3-methylphenyl)amino)imidazo[5,1-f][1,2,4]triazin-5-yl)piperidine-1-carboxylate (300 mg crude), the crude product was used for next step directly without further purification. LCMS (ESI-MS) m/z=542.2 [M+H]⁺.

Step 5. N-(4-([1,2,4]triazolo[1,5-a]pyridin-7-yloxy)-3-methylphenyl)-5-(piperidin-4-yl)imidazo[5,1-f][1,2,4]triazin-4-amine

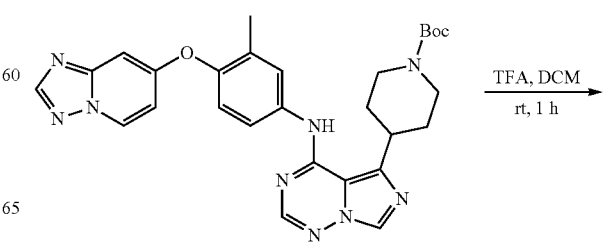

-continued

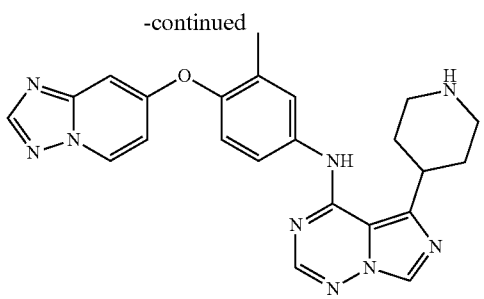

TFA (1 mL) was added to a stirred mixture of tert-butyl 4-(4-((4-(([1,2,4]triazolo[1,5-a]pyridin-7-yloxy)-3-methylphenyl)amino) imidazo[5,1-f][1,2,4]triazin-5-yl)piperidine-1-carboxylate (300 mg, 0.55 mmol) in DCM (3 mL). The resulting mixture was stirred for 1 hour at room temperature and concentrated under vacuum to afford the crude product. The residue was purified by column chromatography, eluted with MeOH in DCM from 0% to 10% to afford the desired product N-(4-([1,2,4]triazolo[1,5-a]pyridin-7-yloxy)-3-methylphenyl)-5-(piperidin-4-yl)imidazo[5,1-f][1,2,4]triazin-4-amine (150 mg, 61.3% yield). LCMS (ESI-MS) m/z=442.2 [M+H]$^+$.

Step 6. (E)-1-(4-(4-((4-([1,2,4]triazolo[1,5-a]pyridin-7-yloxy)-3-methylphenyl)amino)imidazo[5,1-f][1,2,4]triazin-5-yl)piperidin-1-yl)-4-(dimethylamino)but-2-en-1-one Diisopropylethylamine (131.74 mg, 1.02 mmol) was added to a stirred mixture of N-(4-([1,2,4]triazolo[1,5-a]pyridin-7-yloxy)-3-methylphenyl)-5-(piperidin-4-yl)imidazo[5,1-f][1,2,4]triazin-4-amine (150 mg, 0.34 mmol), (E)-4-(dimethylamino)but-2-enoic acid hydrochloride (65.82 mg, 0.51 mmol) and HATU (193.78 mg, 0.51 mmol) in DMF (3 mL). The resulting mixture was stirred overnight at room temperature, diluted with water (20 mL) and extracted with ethyl acetate (3×100 mL). The combined organic layers were washed with brine, dried over anhydrous Na$_2$SO$_4$, filtered and concentrated under vacuum to afford the crude product. The crude product was purified by column chromatography, eluted with MeOH in DCM from 0% to 10% to afford the desired product (E)-1-(4-(4-((4-(([1,2,4]triazolo[1,5-a]pyridin-7-yloxy)-3-methylphenyl)amino)imidazo[5,1-f][1,2,4]-triazin-5-yl)piperidin-1-yl)-4-(dimethylamino)but-2-en-1-one, Example 88 (6.6 mg, 3% yield). LCMS (ESI-MS) m/z=553.3 [M+H]$^+$. $^1$H NMR (400 MHz, DMSO-d$_6$) δ 9.03 (s, 1H), 8.96-8.91 (m, 1H), 8.51 (s, 1H), 8.42-8.35 (m, 1H), 8.16-7.99 (m, 1H), 7.65-7.57 (m, 1H), 7.57-7.46 (m, 1H), 7.28-7.21 (m, 1H), 7.18-7.06 (m, 1H), 7.01-6.99 (m, 1H), 6.87-6.77 (m, 1H), 6.69-6.57 (m, 2H), 4.58-4.43 (m, 1H), 4.20-4.06 (m, 1H), 3.49 (s, 1H), 3.09-3.03 (m, 2H), 2.24-2.16 (m, 9H), 1.95-1.83 (m, 2H), 1.81-1.65 (m, 2H), 1.06-0.97 (m, 1H).

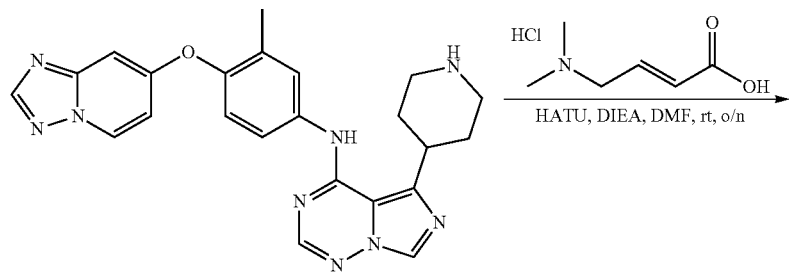

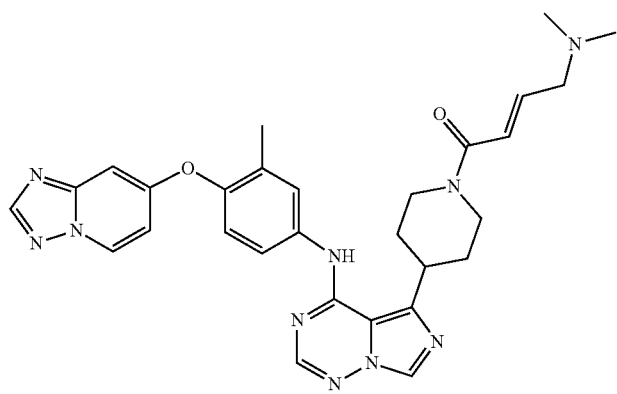

Example 88

Example 89

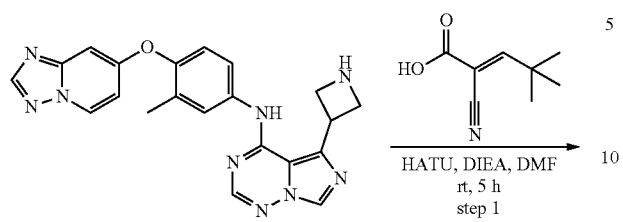

(E)-2-(3-(4-((4-([1,2,4]triazolo[1,5-a]pyridin-7-yloxy)-3-methylphenyl)amino)pyrrolo[2,1-f][1,2,4]triazin-5-yl)azetidine-1-carbonyl)-4,4-dimethylpent-2-enenitrile Diisopropylethylamine (321 mg, 2.48 mmol) was added to a solution of N-(4-([1,2,4]triazolo[1,5-a]pyridin-7-yloxy)-3-methylphenyl)-5-(azetidin-3-yl)pyrrolo[2,1-f][1,2,4]triazin-4-amine (256 mg, 0.62 mmol), (E)-2-cyano-4,4-dimethylpent-2-enoic acid (114 mg, 0.75 mmol) and HATU (472 mg, 1.24 mmol) in DMF (8 mL). The resulting mixture was stirred for 5 hours at room temperature, diluted with water (40 mL) and extracted with ethyl acetate (3×40 mL). The combined organic layers were washed with brine, dried over anhydrous $Na_2SO_4$, filtered and concentrated under vacuum. The residue was purified by silica gel column chromatography, eluted with MeOH in DCM from 0% to 10% to afford the desired product (E)-2-(3-(4-((4-([1,2,4]triazolo[1,5-a]pyridin-7-yloxy)-3-methylphenyl)amino)pyrrolo[2,1-f][1,2,4]triazin-5-yl)azetidine-1-carbonyl)-4,4-dimethylpent-2-enenitrile, Example 89 (45.3 mg, 13.3% yield). LCMS (ESI-MS) m/z=548.3 [M+H]$^+$. $^1$H NMR (400 MHz, Chloroform-d) δ (ppm) 8.55-8.48 (m, 1H), 8.24 (s, 1H), 7.97 (s, 1H), 7.67-7.50 (m, 4H), 7.14-7.07 (m, 1H), 6.94-6.84 (m, 3H), 6.79-6.74 (m, 1H), 5.14-5.05 (m, 1H), 4.77-4.64 (m, 2H), 4.45-4.33 (m, 2H), 2.25 (s, 3H), 1.32 (s, 9H).

Example 90

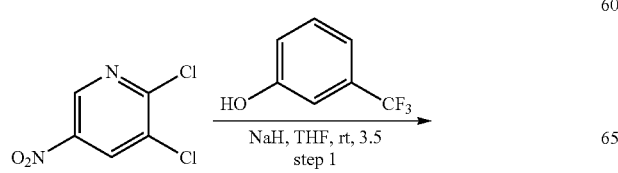

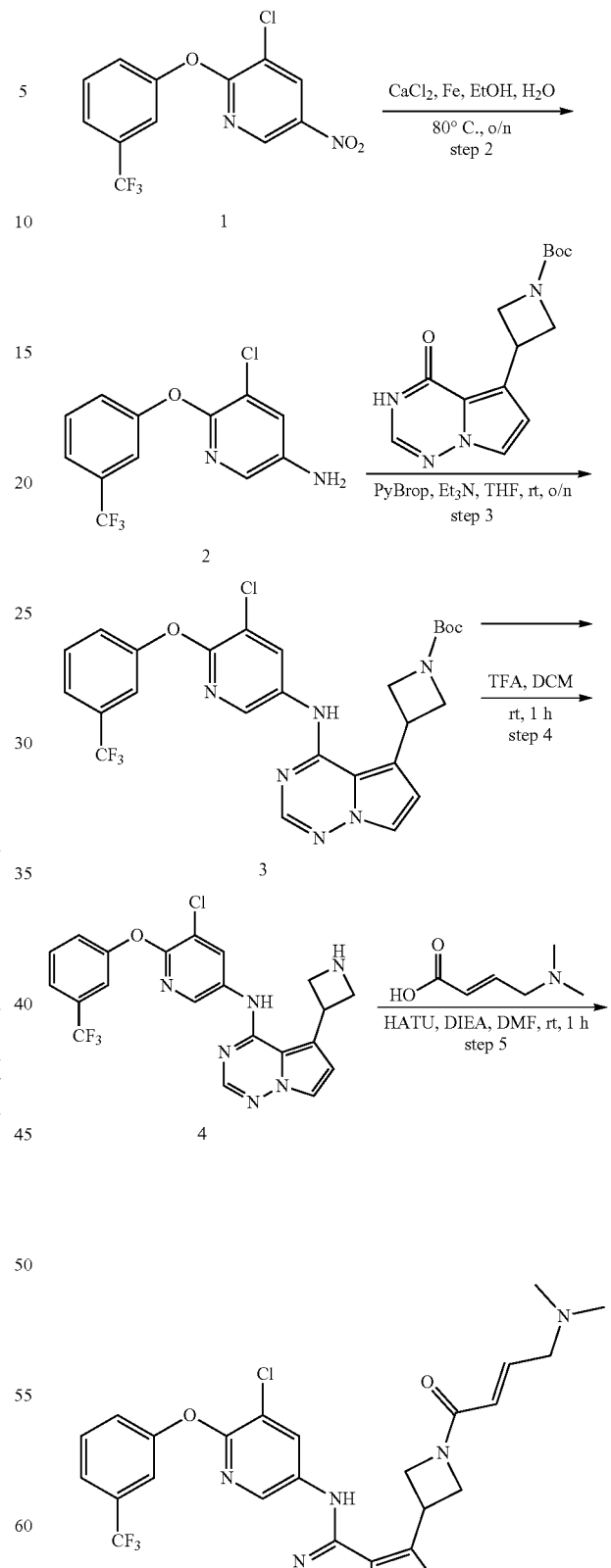

Step 1. 3-chloro-5-nitro-2-(3-(trifluoromethyl)phenoxy)pyridine

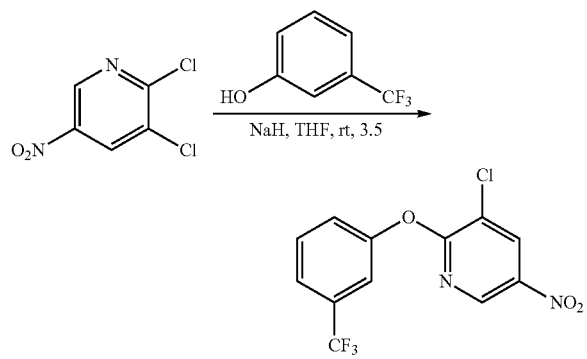

To a solution of 3-(trifluoromethyl)phenol (4.2 g, 25.91 mmol) in THF (80 mL) was added NaH (60% in mineral oil, 1.12 g, 46.6 mmol) and the resulting mixture was stirred for 1 hour at 0° C. under nitrogen atmosphere. Then 2,3-dichloro-5-nitropyridine (5 g, 25.9 mmol) was added to the mixture and then stirred for 2.5 hours at room temperature. The reaction mixture was quenched by addition of water (300 mL) and extracted with ethyl acetate (3×200 mL). The combined organic layers were washed with brine (100 mL), dried over anhydrous $Na_2SO_4$, filtered and the filtrate was concentrated under vacuum to afford the crude product. The residue was purified by silica gel column chromatography, eluted with petroleum ether/ethyl acetate=5:1 to afford 3-chloro-5-nitro-2-(3-(trifluoromethyl)-phenoxy)pyridine (7.91 g crude). LCMS (ESI-MS) m/z=319.0 [M+H]⁺.

Step 2. 5-chloro-6-(3-(trifluoromethyl)phenoxy)pyridin-3-amine

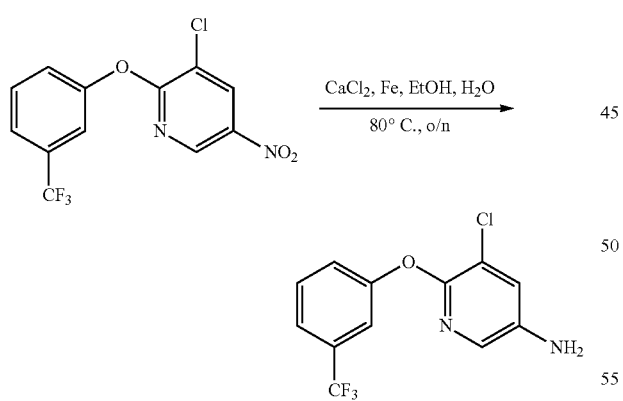

Iron powder (7.01 g, 125.53 mmol) was added to a mixture 3-chloro-5-nitro-2-(3-(trifluoromethyl)-phenoxy)pyridine (8 g, 25.11 mmol) and $CaCl_2$) (1.39 g, 12.53 mmol) in EtOH (223 mL) and water (40 mL) at room temperature. Then the resulting mixture was stirred overnight at 80° C., filtered and the filtrate was diluted with water (3×100 mL). The resulting mixture was extracted with ethyl acetate (3×500 mL). The combined organic layers were washed with brine (500 mL), dried over anhydrous $Na_2SO_4$, filtered and concentrated under vacuum to afford the crude product. The residue was purified by silica gel column chromatography, eluted with petroleum ether/ethyl acetate=1:1 to afford 5-chloro-6-(3-(trifluoromethyl)phenoxy)pyridin-3-amine (4.8 g, 52% yield). LCMS (ESI-MS) m/z=289.0 [M+H]⁺.

Step 3. tert-butyl 3-(4-((5-chloro-6-(3-(trifluoromethyl)phenoxy)pyridin-3-yl)amino)pyrrolo[2,1-f][1,2,4]-triazin-5-yl)azetidine-1-carboxylate

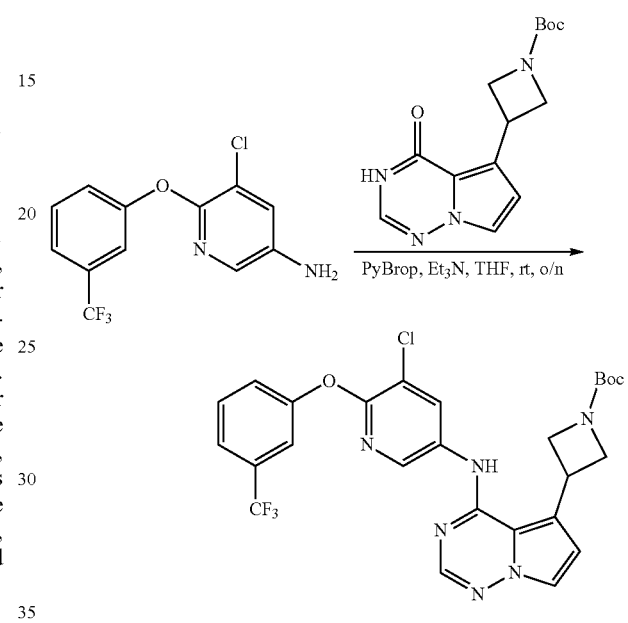

Et₃N (562.67 mg, 5.55 mmol) was added to a mixture of 5-chloro-6-(3-(trifluoromethyl)phenoxy)pyridin-3-amine (535 mg, 1.85 mmol), tert-butyl 3-(4-oxo-3,4-dihydropyrrolo[2,1-f][1,2,4]triazin-5-yl)azetidine-1-carboxylate (538.10 mg, 1.85 mmol) and PyBrop (1.30 g, 2.78 mmol) in THF (10 mL). The resulting mixture was stirred overnight at room temperature and concentrated under vacuum to afford the crude product. The residue was purified by preparative HPLC, ACN in water (10 mmol/L NH₄HCO₃), 10% to 50% to afford tert-butyl 3-(4-((5-chloro-6-(3-(trifluoromethyl)phenoxy)pyridin-3-yl)amino)pyrrolo[2,1-f][1,2,4]-triazin-5-yl)azetidine-1-carboxylate (550 mg, 20% yield). LCMS (ESI-MS) m/z=561.2[M+H]⁺.

Step 4. 5-(azetidin-3-yl)-N-(5-chloro-6-(3-(trifluoromethyl)phenoxy)pyridin-3-yl)pyrrolo[2,1-f][1,2,4]triazin-4-amine

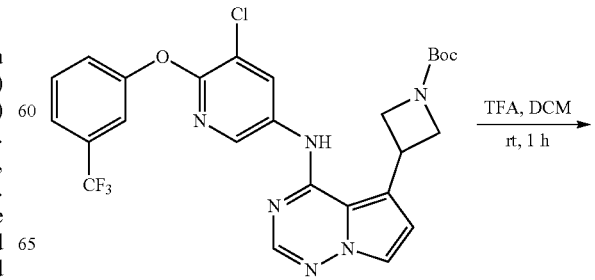

191

-continued

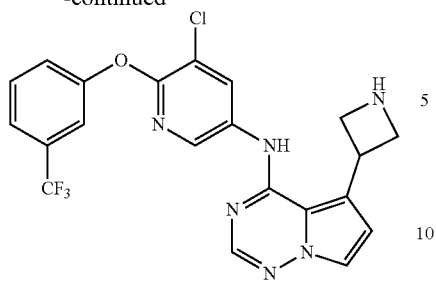

TFA (2 mL) was added to a solution of tert-butyl 3-(4-((5-chloro-6-(3-(trifluoromethyl)phenoxy)pyridin-3-yl)amino)pyrrolo[2,1-f][1,2,4]triazin-5-yl)azetidine-1-carboxylate (550 mg, 0.98 mmol) in DCM (6 mL). The resulting mixture was stirred for 1 hour at room temperature and concentrated under vacuum to afford the crude product. The residue was purified by Prep-TLC with petroleum ether/ethyl acetate=1:1 to afford the desired product 5-(azetidin-3-yl)-N-(5-chloro-6-(3-(trifluoromethyl)phenoxy)pyridin-3-yl)pyrrolo[2,1-t][1,2,4]triazin-4-amine (278 mg, 61.5% yield). LCMS (ESI-MS) m/z=461.1 [M+H]$^+$.

Step 5. (E)-1-(3-(4-((5-chloro-6-(3-(trifluoromethyl)phenoxy)pyridin-3-yl)amino)pyrrolo[2,1-f][1,2,4]triazin-5-yl)azetidin-1-yl)-4-(dimethylamino)but-2-en-1-one

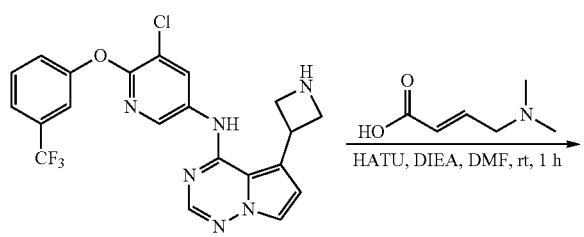

192

-continued

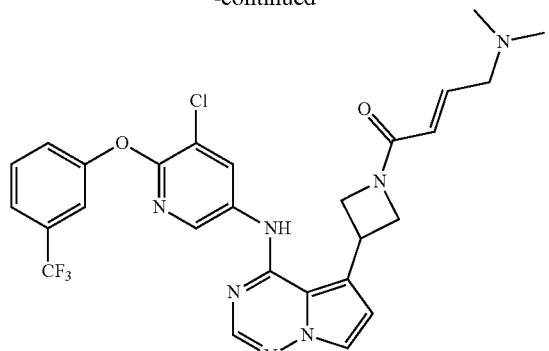

Example 90

Diisopropylethylamine (389.8 mg, 3.01 mmol) was added to a mixture of 5-(azetidine-3-yl)-N-(5-chloro-6-(3-(trifluoromethyl)phenoxy)azetidin-3-yl)pyrrolo[2,1-t][1,2,4]triazin-4-amine (278 mg, 0.60 mmol), (2E)-4-(dimethylamino)but-2-enoic acid (93.50 mg, 0.72 mmol) and HATU (344.06 mg, 0.90 mmol) in DMF (0.5 mL). The resulting mixture was stirred for 1 hour at room temperature and concentrated under vacuum to afford the crude product. The residue was purified by preparative-HPLC, Mobile Phase A: Water (0.1% FA), Mobile Phase B: ACN to afford (E)-1-(3-(4-((5-chloro-6-(3-(trifluoromethyl)phenoxy)pyridin-3-yl)amino)-pyrrolo[2,1-f][1,2,4]triazin-5-yl)azetidin-1-yl)-4-(dimethylamino)but-2-en-1-one, Example 90 (14.9 mg, 4.31% yield). LCMS (ESI-MS) m/z=572.3 [M+H]$^+$. $^1$H NMR (400 MHz, DMSO-$d_6$) δ 9.56 (s, 1H), 8.51-8.50 (m, 1H), 8.36 (d, J=2.4 Hz, 1H), 8.27 (d, J=2.4 Hz, 1H), 7.93 (s, 11H), 7.76-7.68 (m, 2H), 7.68-7.62 (m, 2H), 7.56 (d, J=7.9 Hz, 1H), 6.63 (d, J=2.5 Hz, 1H), 6.58-6.55 (m, 1H), 6.26 (d, J=15.4 Hz, 1H), 4.20 (dd, J=12.4, 4.9 Hz, 1H), 3.89 (dd, J=12.6, 5.2 Hz, 3H), 3.61-3.45 (m, 2H), 2.76 (d, J=4.1 Hz, 6H).

Example 91

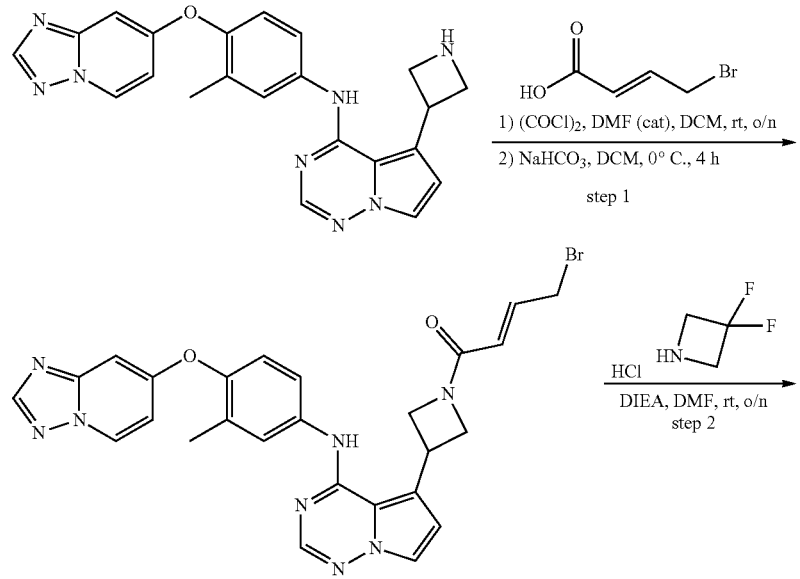

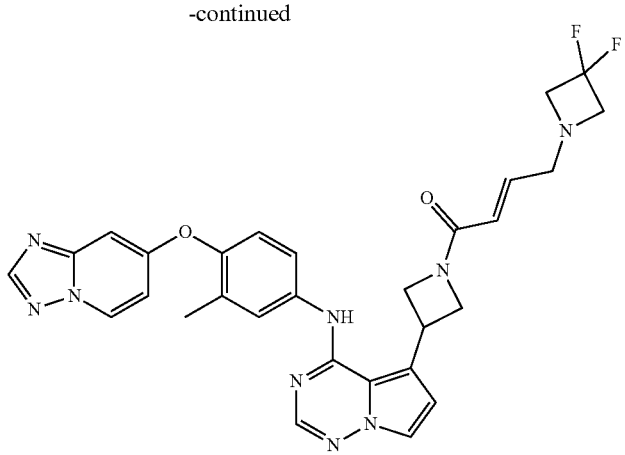
Example 91
(E)-1-(3-(4-((4-([1,2,4]triazolo[1,5-a]pyridin-7-yloxy)-3-methylphenyl)amino)pyrrolo[2,1-f][1,2,4]-triazin-5-yl)azetidin-1-yl)-4-(3,3-difluoroazetidin-1-yl)but-2-en-1-one
Example 91 was prepared using similar procedure as in preparation of Example 94.
Example 92
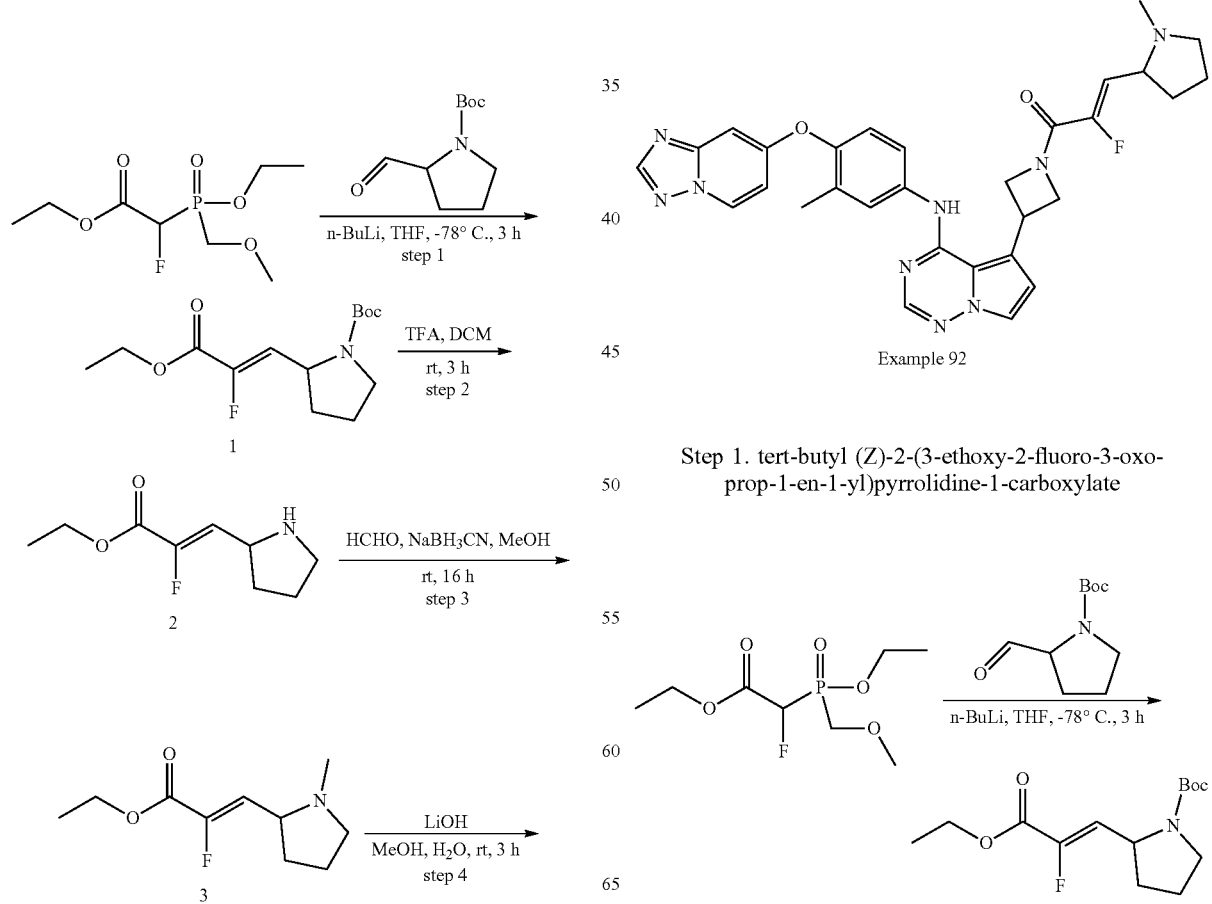
Step 1. tert-butyl (Z)-2-(3-ethoxy-2-fluoro-3-oxo-prop-1-en-1-yl)pyrrolidine-1-carboxylate To a cold solution (−78° C.) of ethyl 2-(diethoxyphosphoryl)-2-fluoroacetate (5 g, 20.6 mmol) in THF (50 mL) was added n-BuLi (2.5 M in hexane, 9.91 mL, 24.7 mmol) dropwise. The resulting mixture was stirred for 30 min at −78° C., followed by addition of tert-butyl 2-formylpyrrolidine-1-carboxylate (4.11 g, 20.6 mmol). The resulting solution was stirred at −78° C. for another 3 h. The reaction mixture was quenched with sat. aqueous NH₄Cl at −78° C. and extracted with ethyl acetate (50 mL×2). The combined organic layers were washed with brine (100 mL), dried over anhydrous Na₂SO₄ and concentrated to afford crude product tert-butyl (Z)-2-(3-ethoxy-2-fluoro-3-oxoprop-1-en-1-yl)pyrrolidine-1-carboxylate (5 g, crude). The crude product was used for next step without further purification. LCMS (ESI-MS) m/z=288.1 [M+H]⁺

Step 2. ethyl (Z)-2-fluoro-3-(pyrrolidin-2-yl)acrylate

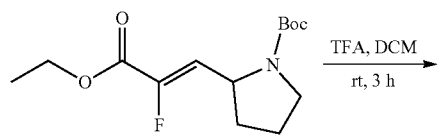

To a solution of tert-butyl tert-butyl (Z)-2-(3-ethoxy-2-fluoro-3-oxoprop-1-en-1-yl)pyrrolidine-1-carboxylate (5 g, 17.4 mmol) in DCM (50 mL) was added TFA (10 mL). The resulting solution was stirred at room temperature for 3 h and concentrated under vacuum to afford the crude product ethyl (Z)-2-fluoro-3-(pyrrolidin-2-yl)acrylate (4 g). The crude product was used for next step without further purification. LCMS (ESI-MS) m/z=188.2 [M+H]⁺

Step 3. ethyl (Z)-2-fluoro-3-(1-methylpyrrolidin-2-yl)acrylate

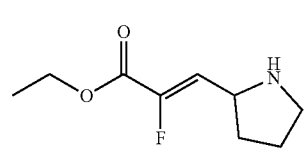

To a solution of ethyl (Z)-2-fluoro-3-(pyrrolidin-2-yl)acrylate (2 g, 10.7 mmol) in methanol (40 mL) was added formaldehyde (1.28 g, 42.7 mmol) and NaBH₃CN (1.01 g, 16.0 mmol). The resulting mixture was stirred at room temperature for 16 h, quenched by addition of sat. aqueous NH₄CL (50 mL) and extracted with ethyl acetate (50 mL×3). The combined organic phase were washed with brine (100 mL), dried with anhydrous Na₂SO₄, filtered and concentrated to afford ethyl (Z)-2-fluoro-3-(1-methylpyrrolidin-2-yl)acrylate (1 g, 27.7% yield). LCMS (ESI-MS) m/z=201.9 [M+H]⁺.

Step 4. (Z)-2-fluoro-3-(1-methylpyrrolidin-2-yl)acrylic acid

Lithium hydroxide (335.6 mg, 14.0 mmol) was added to a stirred mixture of ethyl (2Z)-2-fluoro-3-(1-methylpyrrolidin-2-yl)prop-2-enoate (940 mg, 4.67 mmol) in methanol (10 mL) and water (3 mL). The resulting mixture was stirred at room temperature for 3 h and concentrated to afford (2Z)-2-fluoro-3-(1-methylpyrrolidin-2-yl)prop-2-enoic acid (crude) without neutralization. LCMS (ESI-MS) m/z=174.1 [M+H]⁺.

Step 5. (Z)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-2-fluoro-3-(1-methylpyrrolidin-2-yl)prop-2-en-1-one

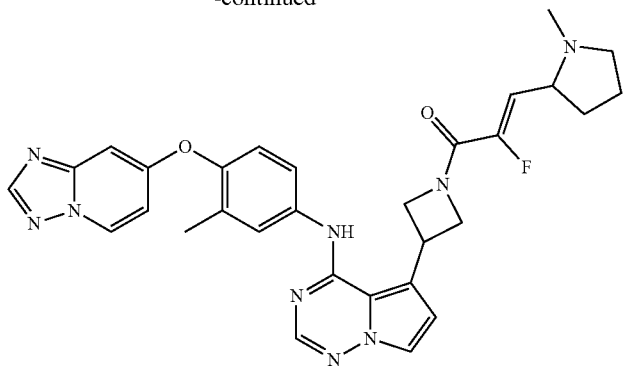

Example 92

A mixture of (2Z)-2-fluoro-3-(1-methylpyrrolidin-2-yl)prop-2-enoic acid (200 mg, crude, 1.16 mmol), N-(4-([1,2,4]triazolo[1,5-a]pyridin-7-yloxy)-3-methylphenyl)-5-(azetidin-3-yl)pyrrolo[2,1-f][1,2,4]triazin-4-amine (476.3 mg, 1.16 mmol), EDCl (198.5 mg, 1.39 mmol), HOBT (187.3 mg, 1.39 mmol) and Et$_3$N (233.7 mg, 2.31 mmol) in DMF (5 mL) was stirred at room temperature for 16 h. The reaction mixture was purified by Prep-HPLC, Mobile Phase A: Water (0.1% FA), Mobile Phase B: ACN; Gradient: 11% B to 31% B to afford (Z)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-2-fluoro-3-(1-methylpyrrolidin-2-yl)prop-2-en-1-one, Example 92 (11.5 mg, 2% yield). LCMS (ESI-MS) m/z=568.4 [M+H]$^+$. $^1$H NMR (400 MHz, DMSO-d$_6$) δ (ppm) 8.95 (s, 1H), 8.54 (s, 1H), 8.38 (s, 1H), 8.18 (s, 1H), 7.95 (s, 1H), 7.82 (s, 1H), 7.67-7.33 (m, 2H), 7.22-7.12 (m, 1H), 7.10-6.79 (m, 2H), 6.78-6.56 (m, 1H), 5.70-5.58 (m, 1H), 4.80-4.63 (m, 2H), 4.51-4.37 (m, 2H), 4.08-4.04 (m, 1H), 3.70-3.58 (m, 1H), 3.03-2.95 (m, 1H), 2.19-2.13 (m, 6H), 2.04-1.81 (m, 2H), 1.71 (s, 1H), 1.47 (s, 11H).

Example 93

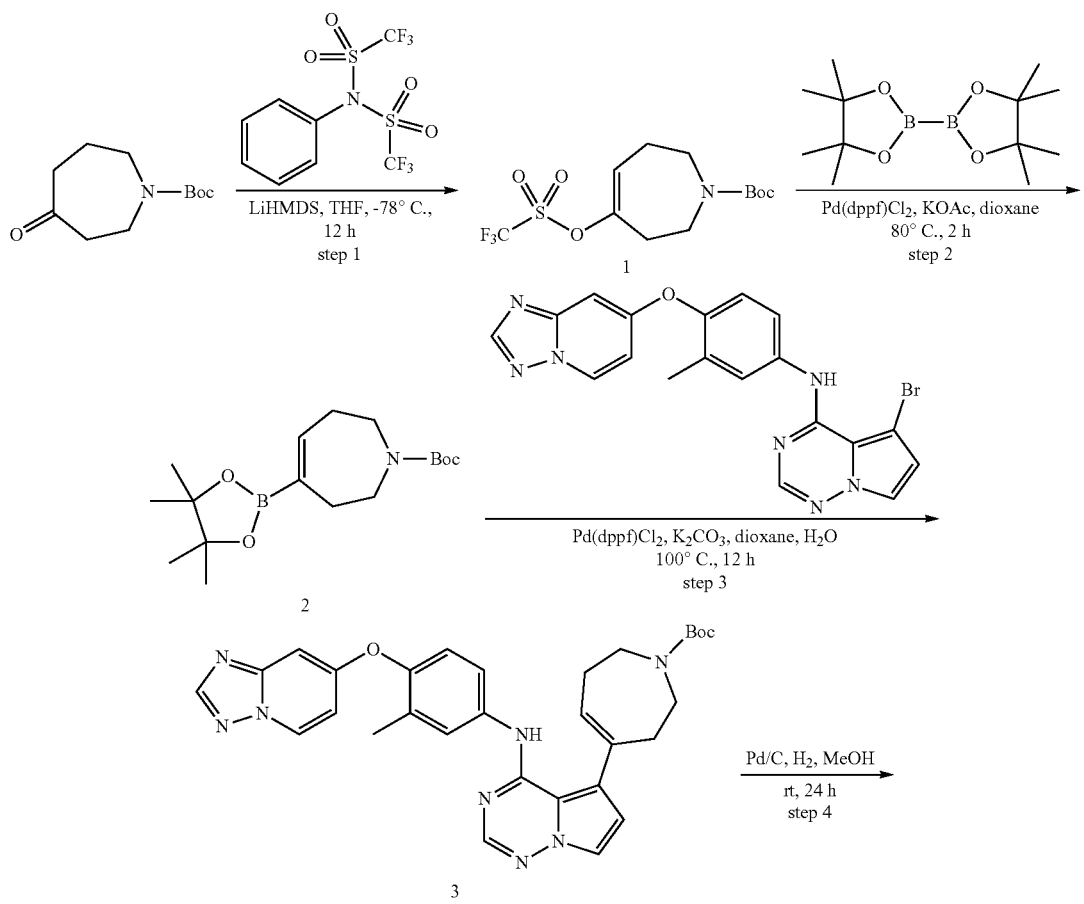

-continued

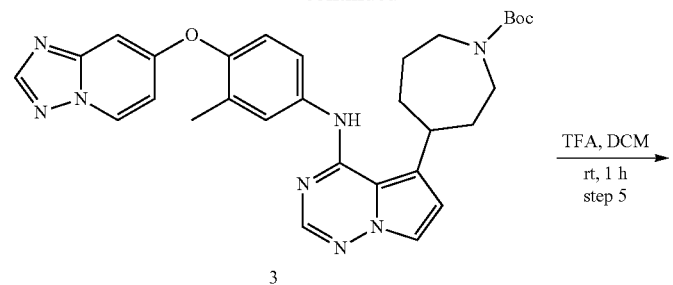

3

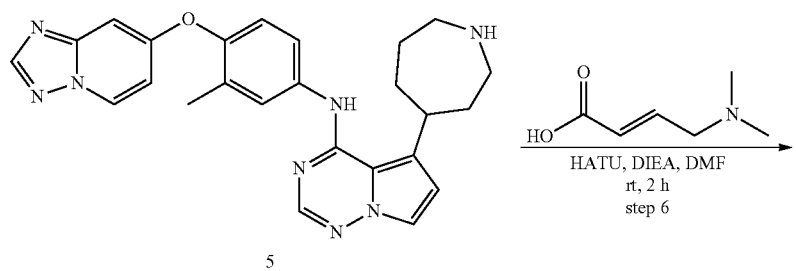

5

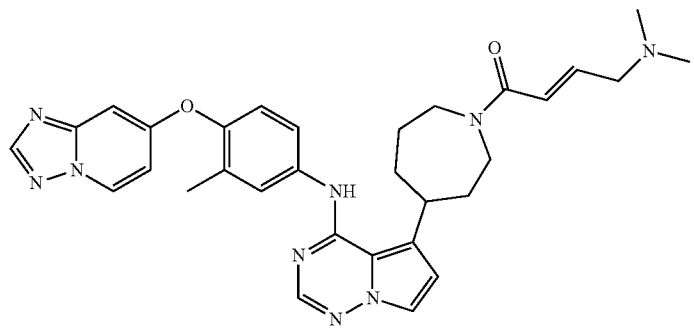

Example 93

Step 1. tert-butyl 4-(((trifluoromethyl)sulfonyl)oxy)-2,3,6,7-tetrahydro-1H-azepine-1-carboxylate

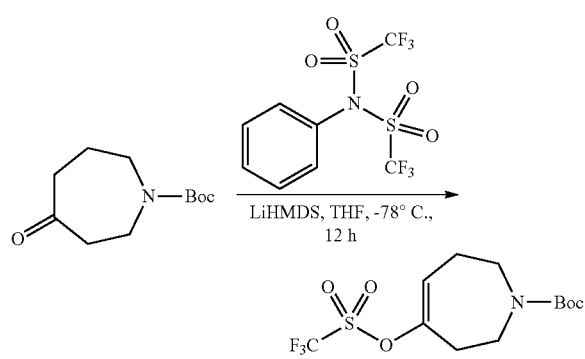

A solution of tert-butyl 4-oxoazepane-1-carboxylate (5 g, 23.47 mmol) in THF (100 mL) was treated with a solution of LiHMDS (1 M in THF, 25.8 mL, 25.78 mmol) for 1 hour at −78° C. under nitrogen atmosphere. A solution of 1,1,1-trifluoro-N-phenyl-N-(((trifluoromethyl)sulfonyl)methane-sulfonamide (9.21 g, 25.82 mmol) in THF (150 mL) was then added dropwise at −78° C. over a period of 0.5 hour.

The resulting mixture was stirred for 3 hours at −78° C. and overnight at room temperature under nitrogen atmosphere. The reaction mixture was quenched with water (1000 mL) at 0° C. and extracted with ethyl acetate (3×1000 mL). The combined organic layers were dried over anhydrous $Na_2SO_4$, filtered and concentrated under vacuum to afford the crude product. The crude product was purified by silica gel column chromatography, eluted with petroleum ether/ethyl acetate=9:1 to afford the crude product tert-butyl 4-(((trifluoromethyl)sulfonyl)oxy)-2,3,6,7-tetrahydro-1H-azepine-1-carboxylate (6.8 g crude). LCMS (ESI-MS) m/z=346.0 $[M+H]^+$.

Step 2. tert-butyl 4-(4,4,5,5-tetramethyl-1,3,2-dioxaborolan-2-yl)-2,3,6,7-tetrahydro-1H-azepine-1-carboxylate

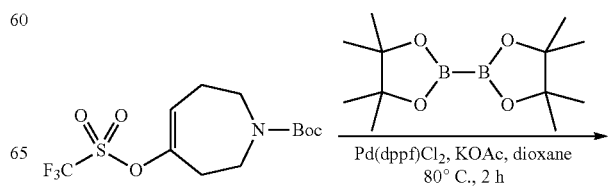

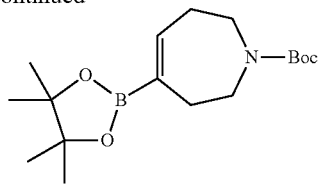

A mixture of tert-butyl 4-(((trifluoromethyl)sulfonyl)oxy)-2,3,6,7-tetrahydro-1H-azepine-1-carboxylate (6.7 g, 19.40 mmol), 4,4,4',4',5,5,5',5'-octamethyl-2,2'-bi(1,3,2-dioxaborolane) (9.85 g, 38.80 mmol), KOAc (3.81 g, 38.80 mmol) and Pd(dppf)Cl$_2$ (1.42 g, 1.94 mmol) in dioxane (200 mL) was stirred for 2 hours at 80° C. under nitrogen atmosphere. The reaction mixture was allowed to cool down to room temperature, filtered and the filtrate was concentrated under vacuum to afford the crude product. The crude product was purified by silica gel column chromatography, eluted with petroleum ether/ethyl acetate=2:1 to afford tert-butyl 4-(4,4,5,5-tetramethyl-1,3,2-dioxaborolan-2-yl)-2,3,6,7-tetrahydro-1H-azepine-1-carboxylate (1.8 g, 23.7% yield). LCMS (ESI-MS) m/z=324.1 [M+H]$^+$ Step 3. tert-butyl 4-(4-((4-([1,2,4]triazolo[1,5-a]pyridin-7-yloxy)-3-methylphenyl)amino)pyrrolo[2,1-f][1,2,4]triazin-5-yl)-2,3,6,7-tetrahydro-1H-azepine-1-carboxylate

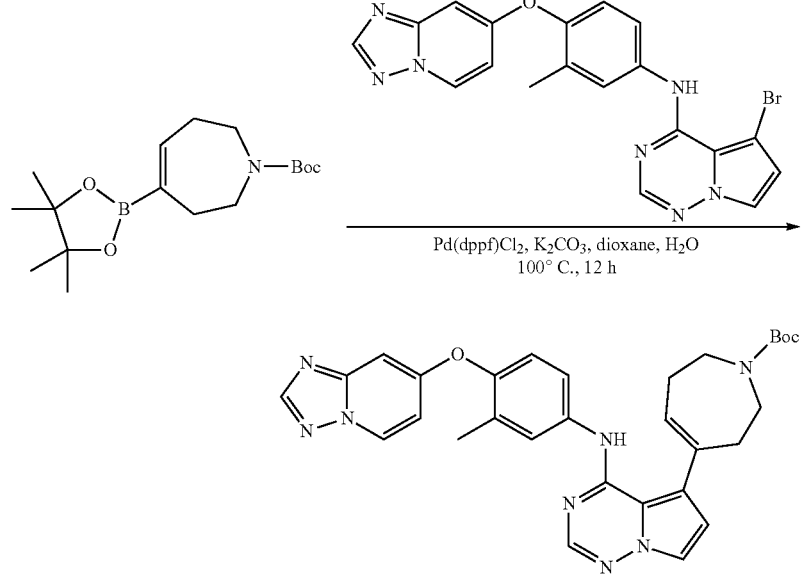

A mixture of tert-butyl 4-(4,4,5,5-tetramethyl-1,3,2-dioxaborolan-2-yl)-2,3,6,7-tetrahydro-1H-azepine-1-carboxylate (1.7 g, 5.25 mmol), 5-bromo-N-(4-([1,2,4]triazolo[1,5-a]pyridin-7-yloxy)-3-methylphenyl)-5-bromopyrrolo[2,1-f][1,2,4]triazin-4-amine (2.29 g, 5.25 mmol), K$_2$CO$_3$ (1.45 g, 10.51 mmol) and Pd(dppf)Cl$_2$ (0.38 g, 0.52 mmol) in 1,4-dioxane (24 mL) and water (6 mL) was stirred for 12 hours at 100° C. under nitrogen atmosphere. The resulting mixture was filtered and the filtrate was concentrated under vacuum to afford the crude product. The crude product was purified by silica gel column chromatography, eluted with petroleum ether/ethyl acetate=2:1 to afford tert-butyl 4-(4-((4-([1,2,4]triazolo[1,5-a]pyridin-7-yloxy)-3-methylphenyl)amino)pyrrolo[2,1-f][1,2,4]triazin-5-yl)-2,3,6,7-tetrahydro-1H-azepine-1-carboxylate (1.3 g, 42.2% yield). LCMS (ESI-MS) m/z=553.2 [M+H]$^+$ Step 4. tert-butyl 4-(4-((4-([1,2,4]triazolo[1,5-a]pyridin-7-yloxy)-3-methylphenyl)amino)pyrrolo[2,1-t][1,2,4]triazin-5-yl)azepane-1-carboxylate

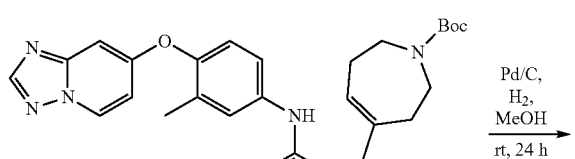

-continued

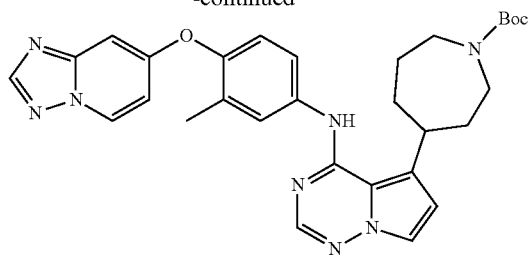

A mixture of tert-butyl 4-(4-((4-([1,2,4]triazolo[1,5-a]pyridin-7-yloxy)-3-methylphenyl)amino)pyrrolo[2,1-f][1,2,4]triazin-5-yl)-2,3,6,7-tetrahydro-1H-azepine-1-carboxylate (1.3 g, 2.35 mmol) and Pd/C (2.5 g, 23.52 mmol) in MeOH (20 mL) was degassed under vacuum and charged with an atmospheric pressure of hydrogen. The resulting mixture was stirred for 24 hours at room temperature. The solids were filtered off and the filtrate was concentrated under vacuum to afford the crude product tert-butyl 4-(4-((4-([1,2,4]triazolo[1,5-a]pyridin-7-yloxy)-3-methylphenyl)amino)pyrrolo[2,1-f][1,2,4]triazin-5-yl)azepane-1-carboxylate (700 mg crude). The crude product was used in the next step directly without further purification. LCMS (ESI-MS) m/z=555.4 [M+H]+.

Step 5. N-(4-([1,2,4]triazolo[1,5-a]pyridin-7-yloxy)-3-methylphenyl)-5-(azepan-4-yl)pyrrolo[2,1-f][1,2,4]triazin-4-amine

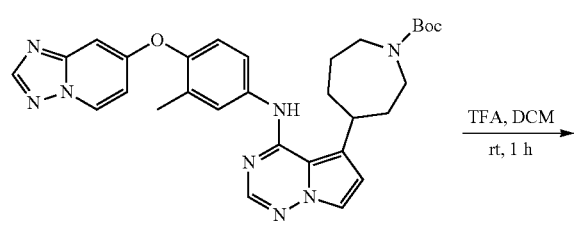

TFA, DCM
rt, 1 h

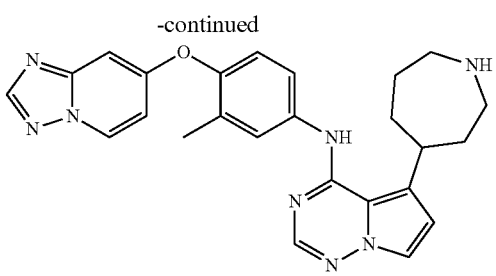

A mixture of tert-butyl 4-(4-((4-([1,2,4]triazolo[1,5-a]pyridin-7-yloxy)-3-methylphenyl)amino)pyrrolo[2,1-f][1,2,4]triazin-5-yl)azepane-1-carboxylate (300 mg, 0.54 mmol) and TFA (1 mL, 13.46 mmol) in DCM (10 mL) was stirred for 1 hour at room temperature and then concentrated under vacuum to afford the crude product N-(4-([1,2,4]triazolo[1,5-a]pyridin-7-yloxy)-3-methylphenyl)-5-(azepan-4-yl)pyrrolo[2,1-f][1,2,4]triazin-4-amine (360 mg crude). The crude product was used in the next step without further purification. LCMS (ESI-MS) m/z=455.3 [M+H]+

Step 6. (E)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-4-(dimethylamino)but-2-en-1-one

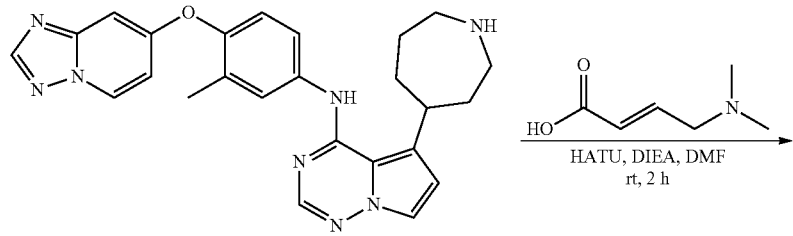

HATU, DIEA, DMF
rt, 2 h

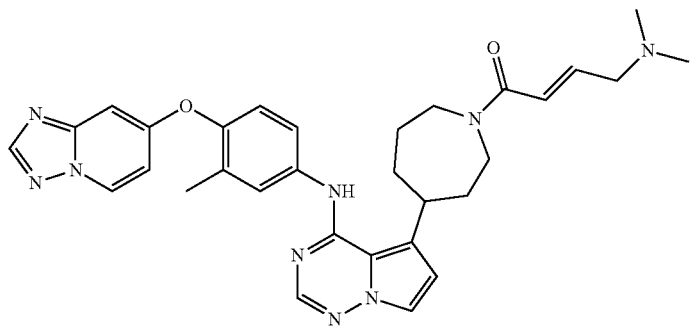

Example 93

A mixture of N-(4-([1,2,4]triazolo[1,5-a]pyridin-7-yloxy)-3-methylphenyl)-5-(azepan-4-yl)pyrrolo[2,1-f][1,2,4]triazin-4-amine (360 mg, 0.79 mmol), (E)-4-(dimethylamino)but-2-enoic acid (133 mg, 1.03 mmol), diisopropylethylamine (204.73 mg, 1.58 mmol) and HATU (451.73 mg, 1.18 mmol) in DMF (4 mL) was stirred at room temperature for 2 hours. The reaction mixture was filtered and the filtrate was purified by Prep-HPLC, Mobile Phase A: Water (0.1% FA), Mobile Phase B: ACN; Gradient: 15% B to 30% B to afford the desired product (E)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-4-(dimethylamino)but-2-en-1-one, Example 93 (6.7 mg, 2% yield). LCMS (ESI-MS) m/z=566.4 [M+H]+. 1H NMR (400 MHz, methanol-d4) δ (ppm) 8.74 (s, 1H), 8.32 (s, 2H), 7.72 (s, 1H), 7.62 (s, 1H), 7.56-7.41 (m, 2H), 7.19-7.17 (m, 1H), 7.10-7.06 (m, 11H), 6.95-6.88 (m, 1H), 6.84 (s, 1H), 6.77-6.70 (m, 1H), 6.64-6.62 (m, 1H), 3.96-3.61 (m, 6H), 3.55-3.39 (m, 1H), 2.82-2.73 (m, 6H), 2.35-2.30 (m, 1H), 2.24 (s, 5H), 1.98-1.73 (m, 3H).

Example 94

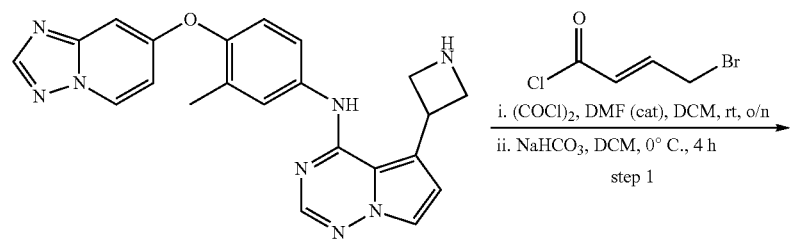

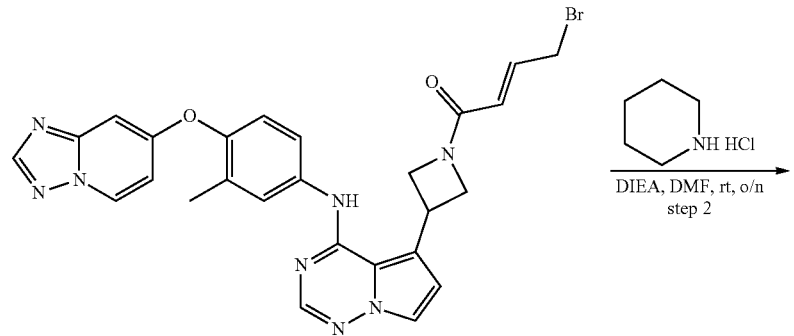

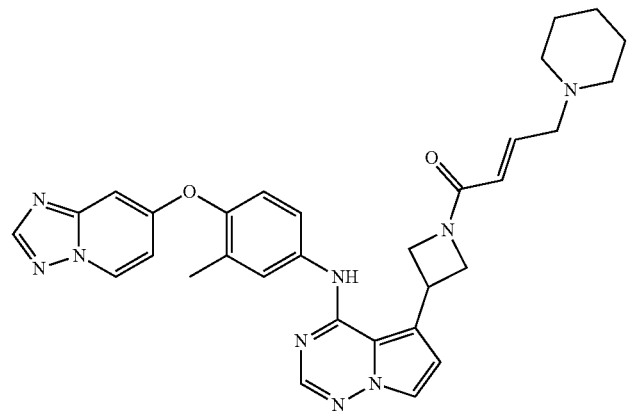

Example 94

Step 1. (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-bromobut-2-en-1-one

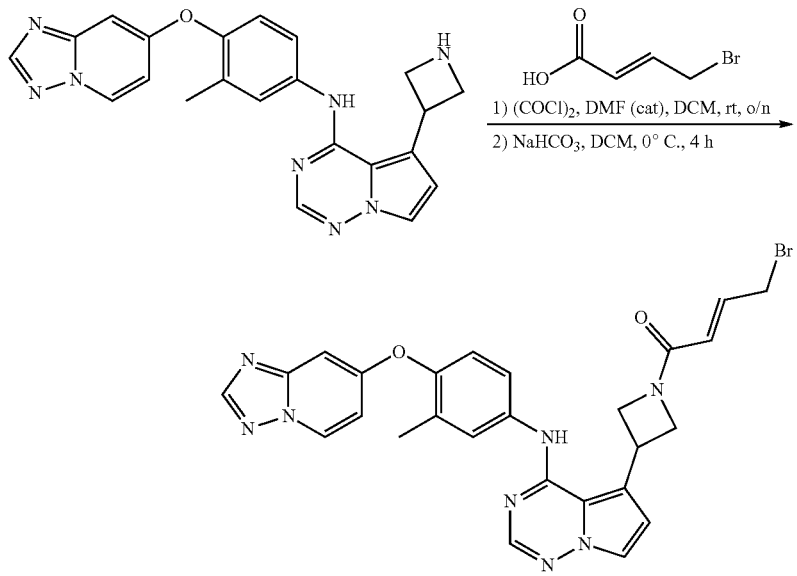 [SMILES: Cc1cc(Nc2ncnn3ccc(C4CNC4)c23)ccc1Oc1ccn2ncnc2c1 ; O=C(O)/C=C/CBr ; Cc1cc(Nc2ncnn3ccc(C4CN(C(=O)/C=C/CBr)C4)c23)ccc1Oc1ccn2ncnc2c1]

To a stirred mixture of (E)-4-bromobut-2-enoic acid (0.40 g, 2.42 mmol) an DMF (0.05 mL) in DCM (30 mL) was added oxalyl chloride (0.62 g, 4.92 mmol) dropwise at 0° C. The resulting mixture was stirred overnight at room temperature. The reaction mixture was concentrated under vacuum. The residue was dissolved in DCM (15 mL). The solution was added to a stirred mixture of N-(4-([1,2,4]triazolo[1,5-a]pyridin-7-yloxy)-3-methylphenyl)-5-(azetidin-3-yl)pyrrolo[2,1-f][1,2,4]triazin-4-amine (1 g, 2.42 mmol) and NaHCO$_3$ (0.75 g, 8.92 mmol) in THF (30 mL). The reaction mixture was stirred for 4 hours at room temperature and concentrated under vacuum to afford the residue. The residue was purified by silica gel column chromatography, eluted with petroleum ether/ethyl acetate (1:4). The fractions with desired mass signal were combined and concentrated under vacuum to afford (E)-1-(3-(4-((4-([1,2,4]triazolo[1,5-a]pyridin-7-yloxy)-3-methyl-phenyl)amino) pyrrolo[2,1-f][1,2,4]triazin-5-yl)azetidin-1-yl)-4-bromobut-2-en-1-one (1.2 g, 70.8% yield). LCMS (ESI-MS) m/z=559.1 [M+H]$^+$ Step 2. (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(piperidin-1-yl)but-2-en-1-one

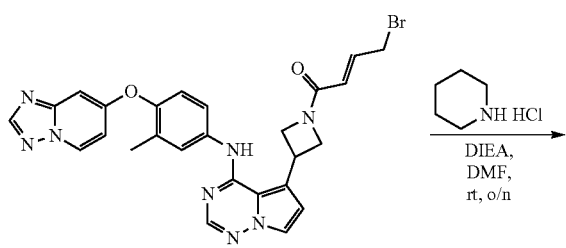

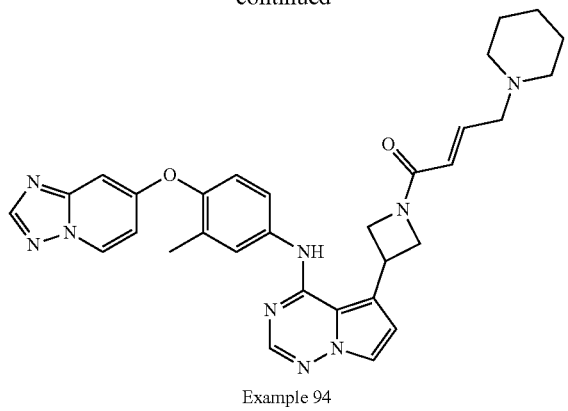

Example 94

Diisopropylethylamine (69 mg, 0.53 mmol) was added to a mixture of piperidine hydrochloride (15 mg, 0.17 mmol) and (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-bromobut-2-en-1-one (100 mg, 0.17 mmol) in DMF (2 mL). The resulting mixture was stirred overnight at room temperature. The mixture was quenched by addition of water (5 mL) and extracted with ethyl acetate (3×5 mL). The combined organic layers were washed with brine (15 mL), dried over anhydrous Na$_2$SO$_4$, filtered and the filtrate was concentrated under reduced pressure to afford the crude product. The residue was purified by Prep-TLC (DCM/MeOH 10:1). The fractions with desired mass signal were combined and concentrated under vacuum to afford the product (E)-1-(3-(4-((4-([1,2,4]triazolo[1,5-a]pyridin-7-yloxy)-3-methylphenyl)-amino)pyrrolo[2,1-f][1,2,4]triazin-5-yl)azetidin-1-yl)-4-(piperidin-1-yl)but-2-en-1-one, Example 94. (12 mg, 11.7% yield). LCMS (ESI-MS)

m/z=564.2 [M+H]⁺. $^1$H NMR (400 MHz, Chloroform-d) δ (ppm) 8.56-8.49 (m, 1H), 8.28-8.21 (m, 1H), 8.06-7.98 (m, 1H), 7.65-7.67 (m, 1H), 7.62 (s, 2H), 7.60 (d, J=2.5 Hz, 1H), 7.32-7.24 (m, 1H), 7.12 (d, J=10.7 Hz, 2H), 6.99 (s, 1H), 6.90-7.00 (m, 2H), 6.75-6.82 (m, 1H), 6.12-6.14 (m, 1H), 4.79 (s, 1H), 4.68 (s, 1H), 4.44 (s, 1H), 4.33 (s, 3H), 3.16 (s, 2H), 2.43 (s, 1H), 2.29-2.22 (m, 3H), 2.04 (s, 1H), 1.45 (s, 2H), 1.27-1.25 (m, 3H).
Example 95
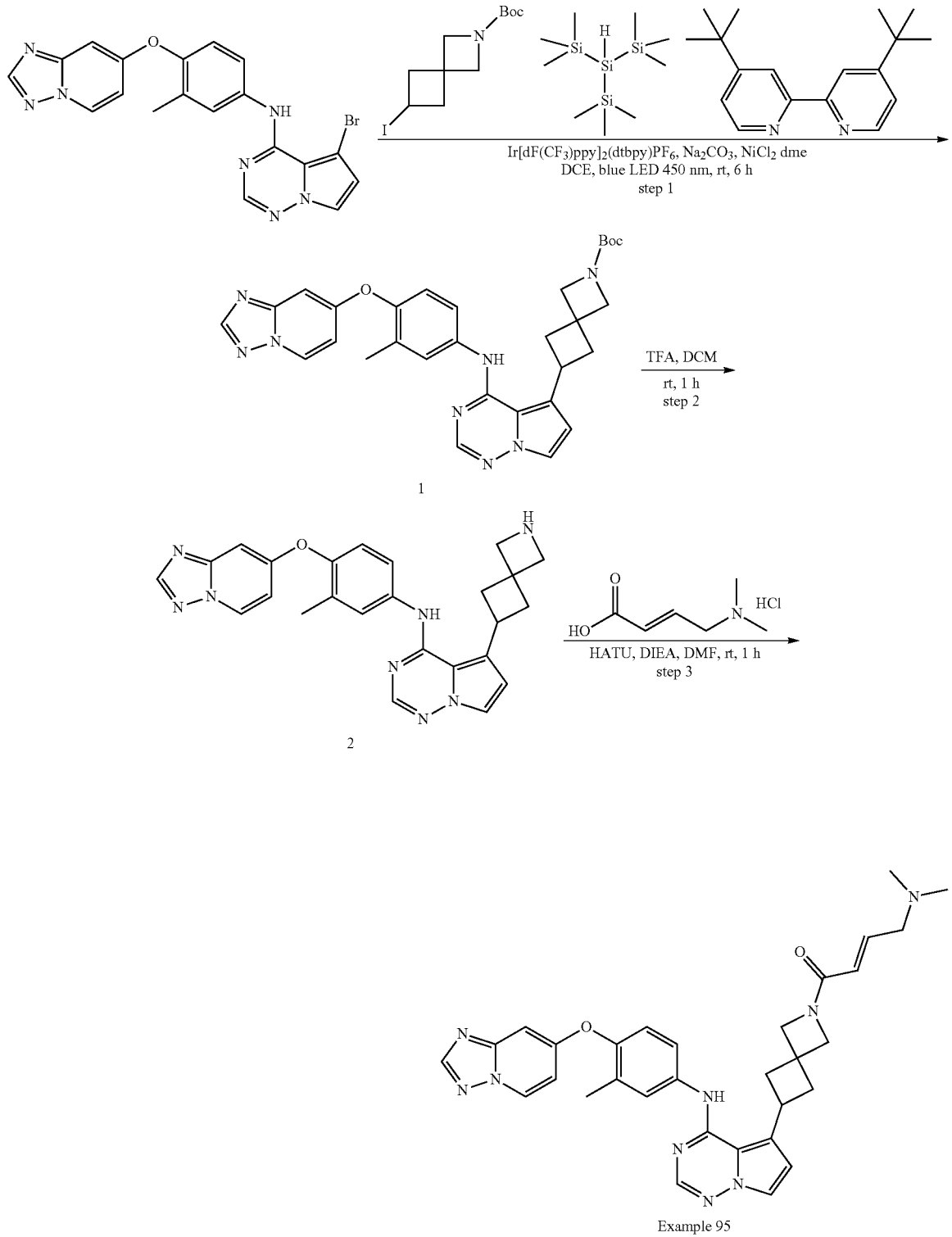
Example 95

Step 1. tert-butyl 6-(4-((4-([1,2,4]triazolo[1,5-a]pyridin-7-yloxy)-3-methylphenyl)amino)pyrrolo[2,1-f][1,2,4]triazin-5-yl)-2-azaspiro[3.3]heptane-2-carboxylate

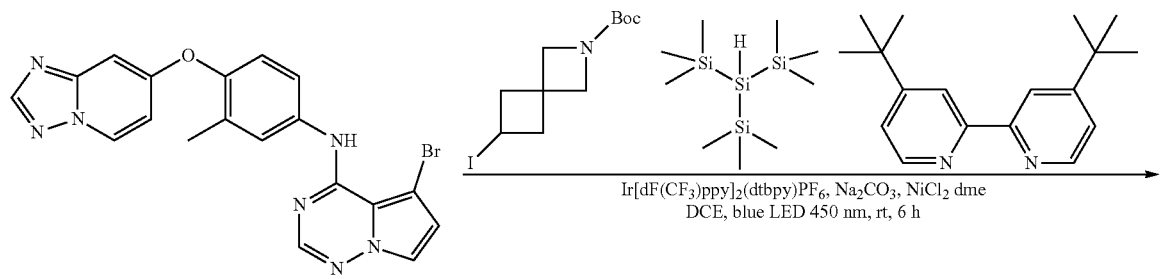

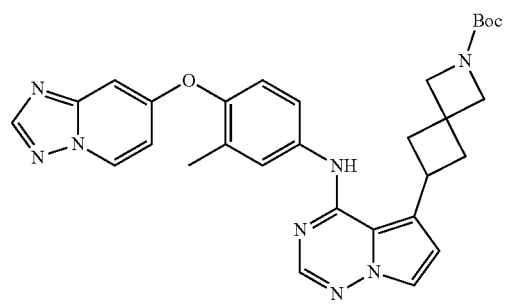

A mixture of 4,4'-di-tert-butyl-2,2'-bipyridine (30.76 mg, 0.11 mmol) and NiCl₂·dme (25.18 mg, 0.11 mmol) in DCE (1 mL) was heated to 60° C. for 10 minutes under nitrogen atmosphere. The solution was allowed to cool to room temperature to produce solution 1. Ir[dF(CF₃)ppy]₂(dtbpy)PF₆ (128.58 mg, 0.11 mmol) was added to a mixture of of N-(4-([1,2,4]triazolo[1,5-a]pyridin-7-yloxy)-3-methylphenyl)-5-bromopyrrolo[2,1-f][1,2,4]triazin-4-amine (500 mg, 1.14 mmol), tert-butyl 6-iodo-2-azaspiro[3.3]heptane-2-carboxylate (740.76 mg, 2.29 mmol), 1,1,1,3,3,3-hexamethyl-2-(trimethylsilyl)trisilane (313.48 mg, 1.26 mmol) and Na₂CO₃ (364.41 mg, 3.43 mmol) in DCE (10 mL) under nitrogen atmosphere, followed by addition of the solution 1 via syringe. The resulting mixture was maintained under nitrogen, stirred at room temperature and irradiated by blue LED (450 nm) in Penn Photoreactor m2 for 6 hours. The reaction mixture was diluted with water (20 mL) and extracted with ethyl acetate (3×100 mL). The combined organic layers were washed with brine, dried over anhydrous Na₂SO₄, filtered and concentrated under vacuum to afford the crude product. The crude product was purified by column chromatography, eluted with ethyl acetate in petroleum ether from 0% to 30% to afford the desired product tert-butyl 6-(4-((4-([1,2,4]triazolo[1,5-a]pyridin-7-yloxy)-3-methylphenyl)amino)-pyrrolo[2,1-f][1,2,4]triazin-5-yl)-2-azaspiro[3.3]heptane-2-carboxylate (200 mg crude), the crude product was used for next step directly without further purification. LCMS (ESI-MS) m/z=553.2 [M+H]⁺.

Step 2. N-(4-([1,2,4]triazolo[1,5-a]pyridin-7-yloxy)-3-methylphenyl)-5-(2-azaspiro[3.3]heptan-6-yl)pyrrolo[2,1-f][1,2,4]triazin-4-amine

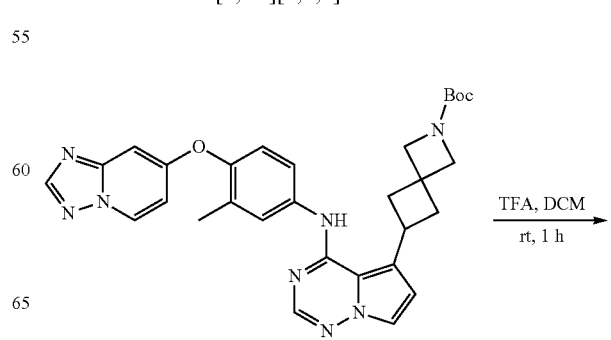

-continued

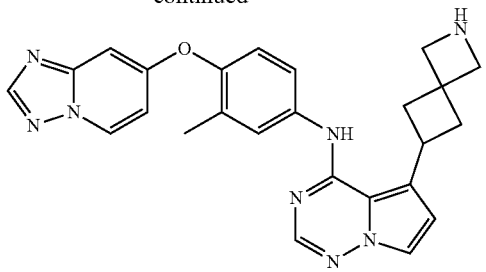

TFA (6 mL) was added to a stirred mixture of tert-butyl 6-(4-((4-([1,2,4]triazolo[1,5-a]pyridin-7-yloxy)-3-methylphenyl)amino)pyrrolo[2,1-f][1,2,4]triazin-5-yl)-2-azaspiro[3.3]heptane-2-carboxylate (200 mg, 0.36 mmol) in DCM (2 mL). The resulting mixture was stirred for 1 hour at room temperature and concentrated under vacuum to afford the crude product. The crude product was purified by column chromatography, eluted with MeOH in DCM from 0% to 10% to afford the desired product N-(4-([1,2,4]triazolo[1,5-a]pyridin-7-yloxy)-3-methylphenyl)-5-(2-azaspiro[3.3]heptan-6-yl)pyrrolo[2,1-f][1,2,4]triazin-4-amine (60 mg crude), the crude product was used for next step directly without further purification. LCMS (ESI-MS) m/z=453.2 [M+H]$^+$.

Step 3. (E)-1-(6-(4-((4-([1,2,4]triazolo[1,5-a]pyridin-7-yloxy)-3-methylphenyl)amino)pyrrolo[2,1-f][1,2,4]triazin-5-yl)-2-azaspiro[3.3]heptan-2-yl)-4-(dimethylamino)but-2-en-1-one

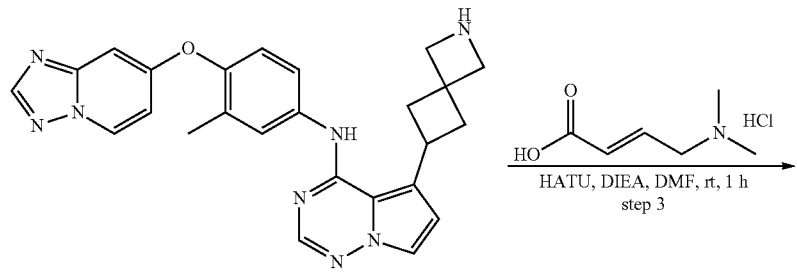

Diisopropylethylamine (51.4 mg, 0.39 mmol) was added to a stirred mixture of N-(4-([1,2,4]triazolo[1,5-a]pyridin-7-yloxy)-3-methylphenyl)-5-(2-azaspiro[3.3]heptan-6-yl)pyrrolo[2,1-f][1,2,4]triazin-4-amine (60 mg, 0.13 mmol), (E)-4-(dimethylamino)but-2-enoic acid hydrochloride (33 mg, 0.20 mmol) and HATU (75.6 mg, 0.20 mmol) in DMF (1 mL). The resulting mixture was stirred for 1 hour at room temperature and purified by Prep-HPLC, Mobile Phase A: Water (10 mmol/L NH$_4$HCO$_3$), Mobile Phase B: ACN; Gradient: 17% B to 47% B to afford the desired product (E)-1-(6-(4-((4-([1,2,4]triazolo[1,5-a]pyridin-7-yloxy)-3-methylphenyl)amino)pyrrolo[2,1-f][1,2,4]triazin-5-yl)-2-azaspiro-[3.3]heptan-2-yl)-4-(dimethylamino)but-2-en-1-one, Example 95 (16.7 mg, 22.1% yield). LCMS (ESI-MS) m/z=564.4 [M+H]$^+$. 1H NMR (400 MHz, DMSO-d$_6$) δ 8.57-8.37 (m, 1H), 8.32-8.13 (m, 1H), 8.05-7.88 (m, 1H), 7.71-7.47 (m, 3H), 7.16-7.03 (m, 1H), 7.01-6.78 (m, 4H), 6.68-6.53 (m, 1H), 6.17-5.96 (m, 1H), 4.51-4.36 (m, 1H), 4.31-4.13 (m, 2H), 4.11-4.00 (m, 1H), 3.94-3.79 (m, 1H), 3.18-3.01 (m, 2H), 2.91-2.73 (m, 2H), 2.70-2.52 (m, 2H), 2.41-2.15 (m, 9H).

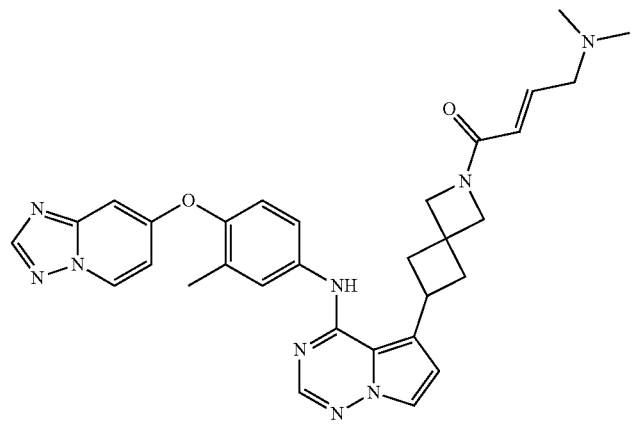

Example 96
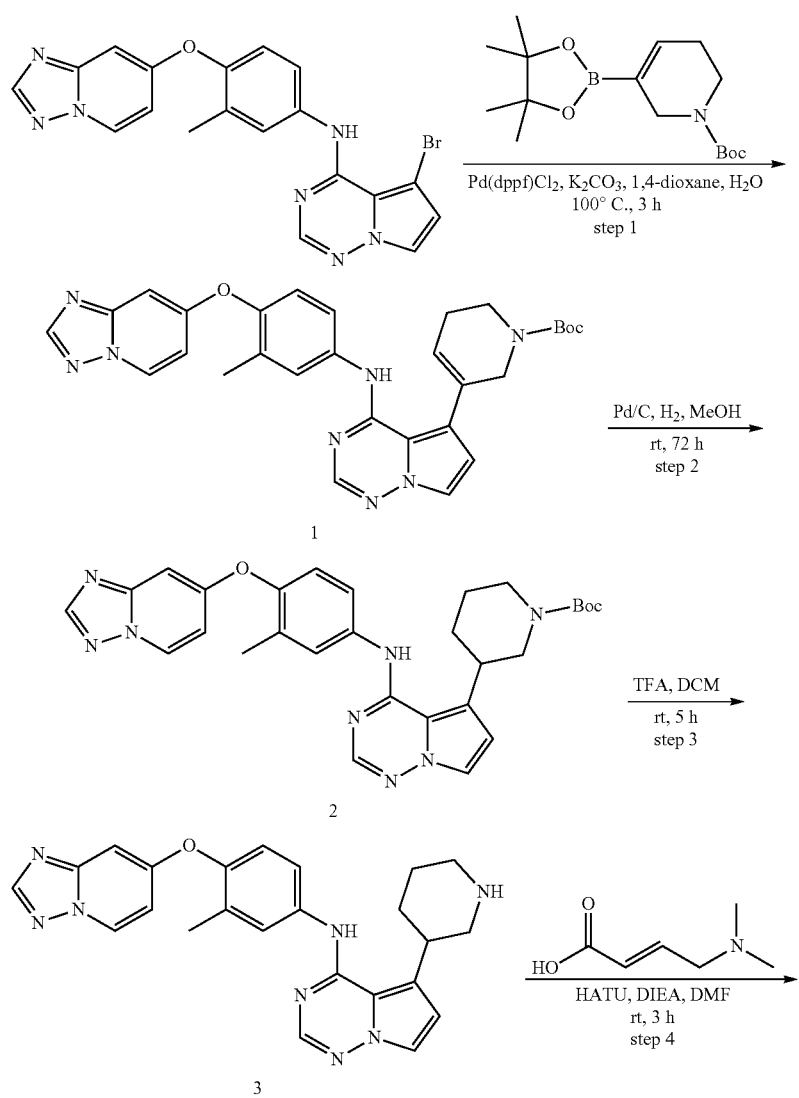
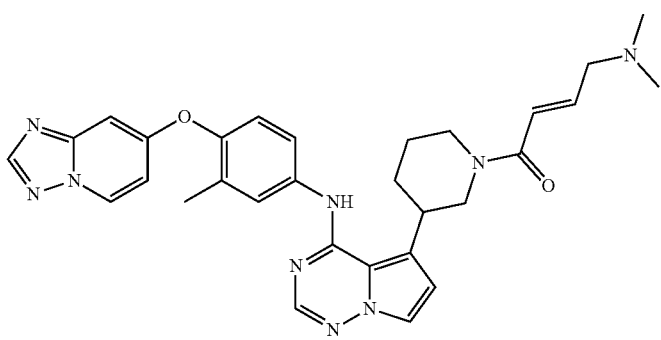
Example 96

217

(E)-1-(3-(4-((4-(([1,2,4]triazolo[1,5-a]pyridin-7-yloxy)-3-methylphenyl)amino)-pyrrolo-[2,1-f] [1,2,4]-triazin-5-yl)piperidin-1-yl)-4-(dimethylamino)but-2-en-1-one Example 96 was prepared using similar procedure as Steps 3-6 in preparation of Example 93.

Example 97

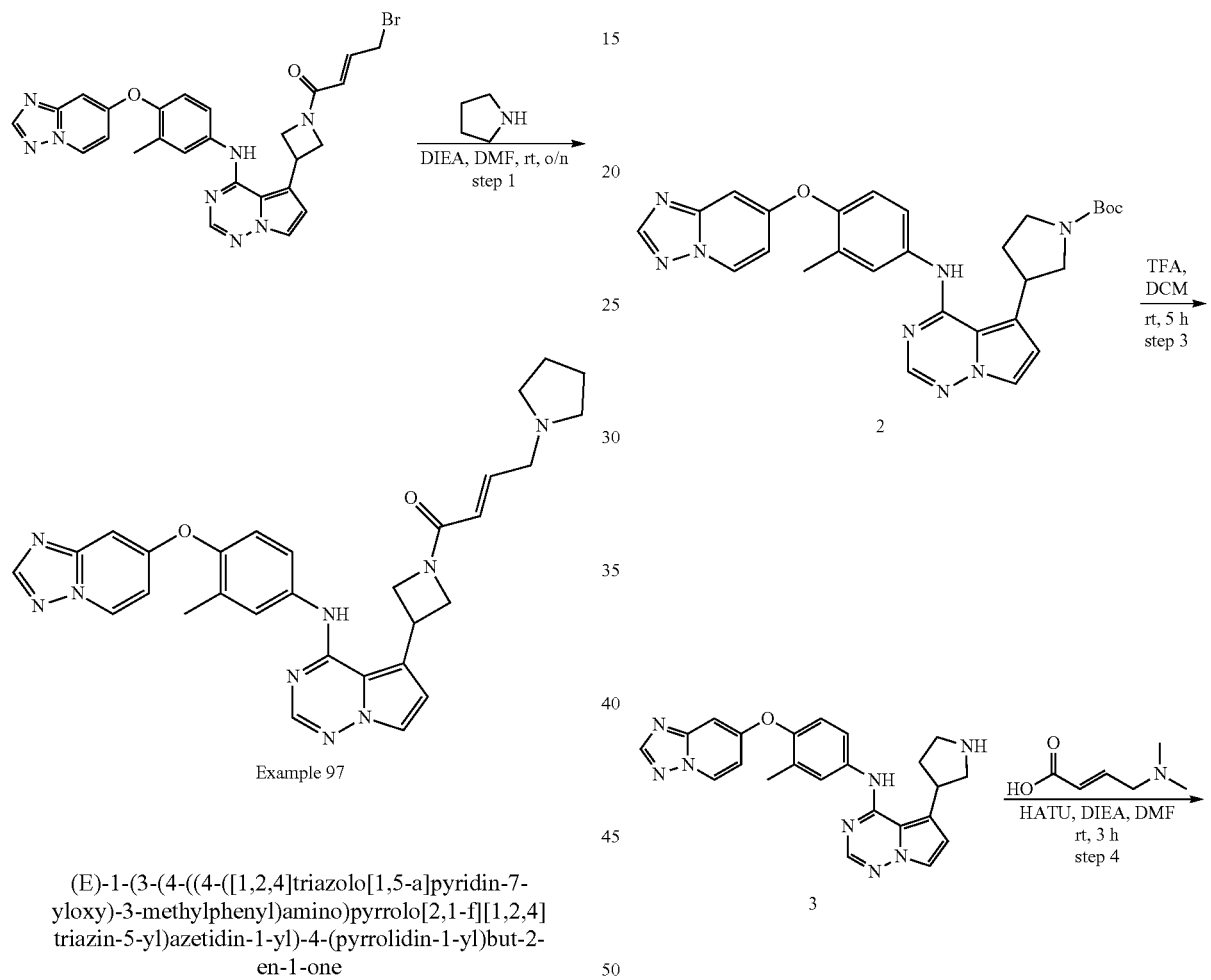

(E)-1-(3-(4-((4-(([1,2,4]triazolo[1,5-a]pyridin-7-yloxy)-3-methylphenyl)amino)pyrrolo[2,1-f][1,2,4]triazin-5-yl)azetidin-1-yl)-4-(pyrrolidin-1-yl)but-2-en-1-one Example 97 was prepared using similar procedure as in preparation of Example 94.

Example 98

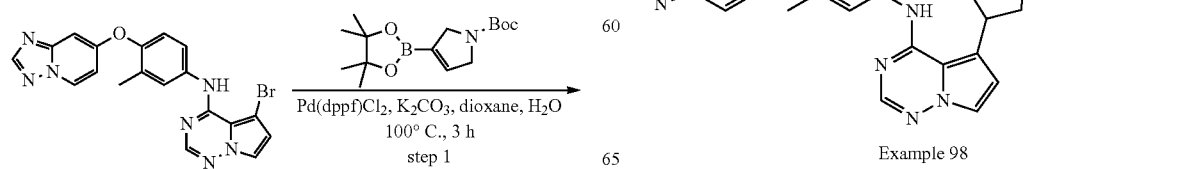

(E)-1-(3-(4-((4-([1,2,4]triazolo[1,5-a]pyridin-7-yloxy)-3-methylphenyl)amino)-pyrrolo-[2,1-f][1,2,4]triazin-5-yl)pyrrolidin-1-yl)-4-(dimethylamino)but-2-en-1-one Example 98 was prepared using similar procedure as Steps 3-6 in preparation of Example 93.

Examples 99 and 100

4]triazin-5-yl)pyrrolidin-1-yl)-4-(dimethylamino)but-1-one (50 mg, 0.09 mmol) was separated by Prep-Chiral-HPLC using the following conditions: Column: CHIRALPAK IF-3, 4.6*50 mm, 3 μm; Mobile Phase A: MtBE(0.1% DEA): EtOH=50:50; Flow rate: 1 mL/min; Gradient: 0% B to 0% B; Injection Volume: 5 ul mL. The desired fractions were combined and lyophilized to afford the two desired separated isomers Examples 99 and 100:

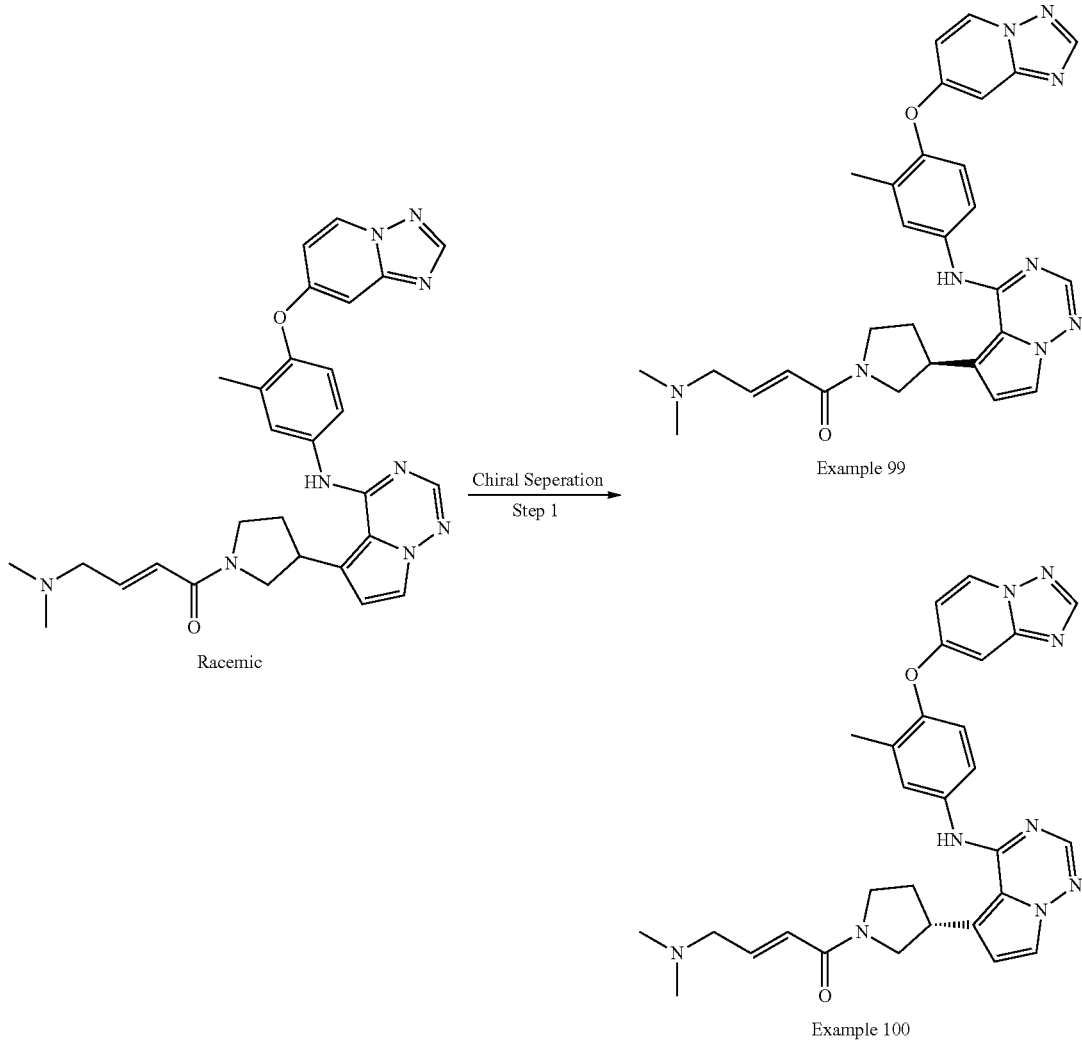 [SMILES: Cc1cc(Nc2ncnn3ccc(C4CCN(C(=O)/C=C/CN(C)C)C4)c23)ccc1Oc1ccn2ncnc2c1 ; Cc1cc(Nc2ncnn3ccc([C@@H]4CCN(C(=O)/C=C/CN(C)C)C4)c23)ccc1Oc1ccn2ncnc2c1 ; Cc1cc(Nc2ncnn3ccc([C@H]4CCN(C(=O)/C=C/CN(C)C)C4)c23)ccc1Oc1ccn2ncnc2c1]

(S,E)-1-(3-(4-((4-([1,2,4]triazolo[1,5-a]pyridin-7-yloxy)-3-methylphenyl)amino)pyrrolo[2,1-f][1,2,4]triazin-5-yl)pyrrolidin-1-yl)-4-(dimethylamino)but-2-en-1-one (Example 99) & (R,E)-1-(3-(4-((4-([1,2,4]triazolo[1,5-a]pyridin-7-yloxy)-3-methylphenyl)amino)-pyrrolo[2,1-f][1,2,4]-triazin-5-yl)pyrrolidin-1-yl)-4-(dimethylamino)but-2-en-1-one

Example 100

The racemate of (E)-1-(3-(4-((4-([1,2,4]triazolo[1,5-a]pyridin-7-yloxy)-3-methylphenyl)amino)pyrrolo[2,1-f][1,2, First eluting isomer of (E)-1-(3-(4-((4-([1,2,4]triazolo[1,5-a]pyridin-7-yloxy)-3-methylphenyl)amino)pyrrolo[2,1-f][1,2,4]triazin-5-yl)pyrrolidin-1-yl)-4-(dimethylamino)but-2-en-1-one (14.1 mg, 100% ee, 27.6% yield). LCMS (ESI-MS) m/z=538.2 [M+H]$^+$, 100% ee. $^1$H NMR (400 MHz, DMSO-d$_6$) δ (ppm) 8.98-8.91 (m, 1H), 8.66-8.59 (m, 1H), 8.41-8.36 (s, 1H), 7.94-7.90 (s, 1H), 7.80-7.74 (m, 1H), 7.66-7.55 (m, 2H), 7.25-7.19 (m, 1H), 7.07-7.01 (m, 1H), 6.85-6.75 (m, 2H), 6.70-6.58 (m, 1H), 6.48-6.37 (m, 1H), 4.29-4.04 (m, 2H), 4.01-3.90 (m, 1H), 3.82-3.58 (m, 11H), 3.55-3.41 (m, 1H), 3.08-2.98 (m, 2H), 2.22-2.00 (m, 11H).

Cell growth inhibition activity of first eluting isomer based on assays described for Table 3:

| HER2—YVMA IC$_{50}$ (nM) | HER2 WT IC$_{50}$ (nM) | EGFR WT IC$_{50}$ (nM) |
|---|---|---|
| ++++ | ++++ | + |

Second eluting isomer of (E)-1-(3-(4-((4-([1,2,4]triazolo[1,5-a]pyridin-7-yloxy)-3-methylphenyl)amino)pyrrolo[2,1-f][1,2,4]triazin-5-yl)pyrrolidin-1-yl)-4-(dimethylamino)but-2-en-1-one (12.9 mg, 99.5% ee, 25.6% yield). LCMS (ESI-MS) m/z=538.2 [M+H]$^+$. $^1$H NMR (400 MHz, DMSO-d$_6$) δ (ppm) 8.98-8.91 (m, 1H), 8.66-8.59 (m, 1H), 8.41-8.36 (s, 1H), 7.94-7.90 (s, 1H), 7.80-7.74 (m, 1H), 7.66-7.55 (m, 2H), 7.25-7.19 (m, 1H), 7.07-7.01 (m, 1H), 6.85-6.75 (m, 2H), 6.70-6.58 (m, 1H), 6.48-6.37 (m, 1H), 4.29-4.04 (m, 2H), 4.01-3.90 (m, 1H), 3.82-3.58 (m, 1H), 3.55-3.41 (m, 1H), 3.08-2.98 (m, 2H), 2.22-2.00 (m, 11H).

Cell growth inhibition activity of second eluting isomer based on assays described for Table 3:

| HER2—YVMA IC$_{50}$ (nM) | HER2 WT IC$_{50}$ (nM) | EGFR WT IC$_{50}$ (nM) |
|---|---|---|
| ++ | ++++ | + |

Example 101

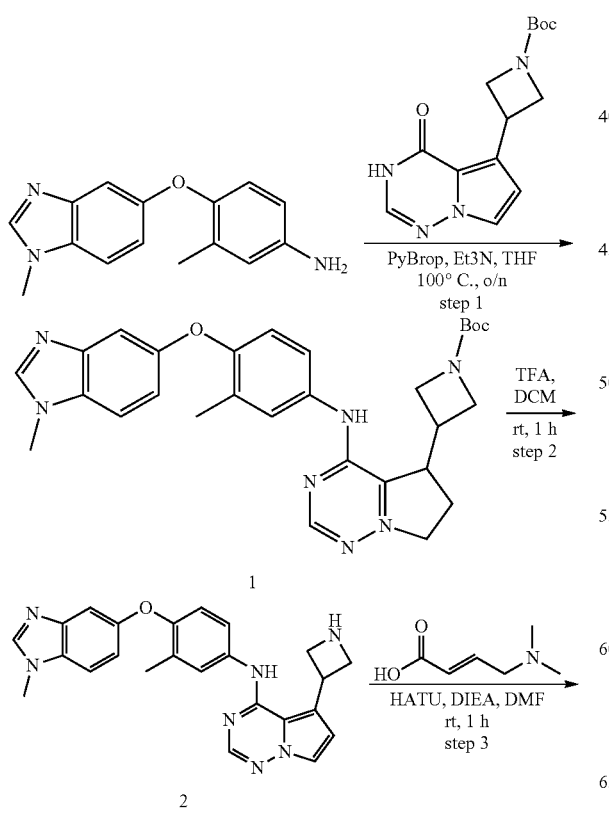

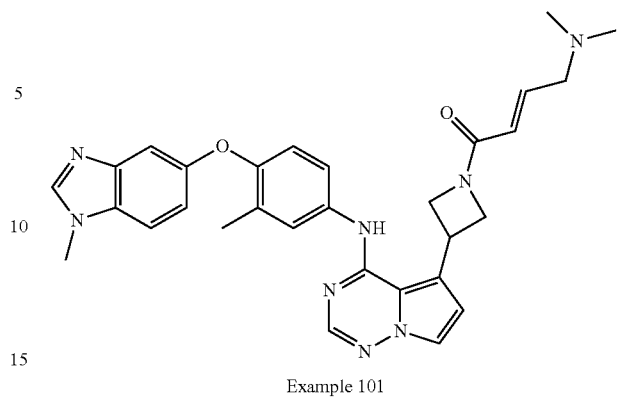

Example 101

Step 1. tert-butyl 3-(4-((3-methyl-4-((1-methyl-1H-benzo[d]imidazol-5-yl)oxy)phenyl)amino)pyrrolo[2,1-f][1,2,4]triazin-5-yl)azetidine-1-carboxylate

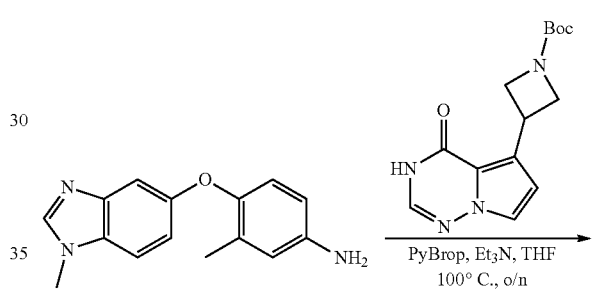

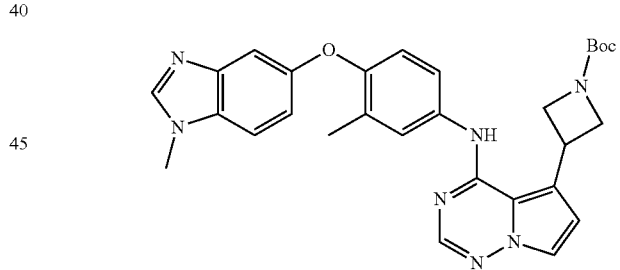

Et$_3$N (1.80 g, 17.8 mmol) was added to a mixture of 3-methyl-4-((1-methyl-1H-benzo[d]imidazol-5-yl)oxy)aniline (1.5 g, 5.92 mmol), tert-butyl 3-(4-oxo-3,4-dihydropyrrolo[2,1-f][1,2,4]triazin-5-yl)azetidine-1-carboxylate (1.72 g, 5.92 mmol), PyBrop (4.14 g, 8.88 mmol) in THF (30 mL). The resulting mixture was stirred overnight at 100° C. and concentrated under vacuum to afford the crude product. The residue was purified by silica column chromatography eluting with petroleum ether/ethyl acetate=1:8 to afford the desired product tert-butyl 3-(4-((3-methyl-4-((1-methyl-1H-benzo[d]imidazol-5-yl)oxy)phenyl)-amino)-pyrrolo-[2,1-f][1,2,4]triazin-5-yl)azetidine-1-carboxylate (120 mg, 4% yield).

LCMS (ESI-MS) m/z=526.2 [M+H]$^+$.

Step 2. 5-(azetidin-3-yl)-N-(3-methyl-4-((1-methyl-1H-benzo[d]imidazol-5-yl)oxy)phenyl)pyrrolo[2,1-f][1,2,4]triazin-4-amine

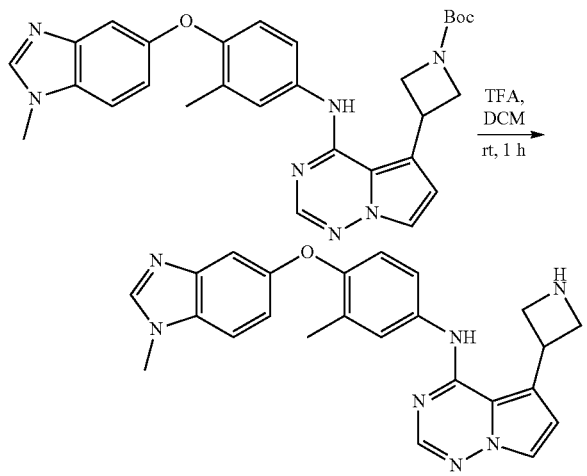

TFA (3 mL) was added to a solution of tert-butyl 3-(4-((3-methyl-4-((1-methyl-1H-benzo[d]imidazol-5-yl)oxy)phenyl)-amino)pyrrolo[2,1-f][1,2,4]triazin-5-yl)azetidine-1-carboxylate (120 mg, 0.23 mmol) in DCM (1 mL). The resulting mixture was stirred for 1 hour at room temperature and concentrated under vacuum to afford the crude product. The residue was purified by silica column chromatography eluting with DCM/MeOH=10:1 to afford the desired product 5-(azetidin-3-yl)-N-(3-methyl-4-((1-methyl-1H-benzo[d]-imidazol-5-yl)oxy)phenyl)pyrrolo[2,1-f]-[1,2,4]-triazin-4-amine (120 mg, crude). LCMS (ESI-MS) m/z=426.2 [M+H]$^+$.

Step 3. (E)-4-(dimethylamino)-1-(3-(4-((3-methyl-4-((1-methyl-1H-benzo[d]imidazol-5-yl)oxy)phenyl)-amino)pyrrolo[2,1-f][1,2,4]triazin-5-yl)azetidin-1-yl)but-2-en-1-one

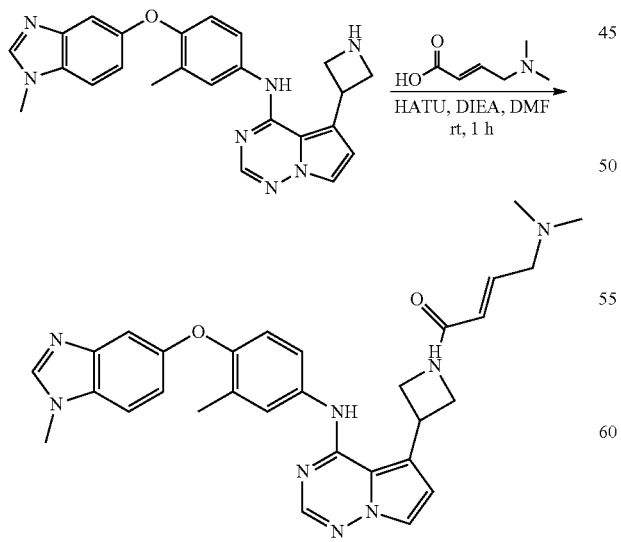

Diisopropylethylamine (87.5 mg, 0.68 mmol) was added to a mixture of 5-(azetidin-3-yl)-N-(3-methyl-4-((1-methyl-1H-benzo[d]imidazol-5-yl)oxy)-phenyl)-pyrrolo-[2,1-f][1,2,4]triazin-4-amine (120 mg, 0.23 mmol), (E)-4-(dimethylamino)but-2-enoic acid (35.0 mg, 0.27 mmol) and HATU (128.7 mg, 0.34 mmol) in DMF (2 mL). The resulting mixture was stirred for 1 hour at room temperature and concentrated under vacuum to afford the crude product. The residue was purified by Prep-HPLC Mobile Phase A: Water (10 mmol/L NH$_4$HCO$_3$+0.1% NH$_3$·H$_2$O), Mobile Phase B: MeOH, Gradient: 60% B to 90% B to afford the title compound (E)-4-(dimethylamino)-1-(3-(4-((3-methyl-4-((1-methyl-1H-benzo[d]imidazol-5-yl)oxy)phenyl)amino)pyrrolo[2,1-f][1,2,4]triazin-5-yl)azetidin-1-yl)but-2-en-1-one, Example 101 (26.5 mg, 22% yield). LCMS (ESI-MS) m/z=537.4 [M+H]$^+$. $^1$H NMR (400 MHz, DMSO-d$_6$) δ (ppm) 8.42 (s, 1H), 8.18 (s, 1H), 7.91 (s, 1H), 7.78 (d, J=2.7 Hz, 1H), 7.61-7.52 (m, 2H), 7.47 (dd, J=8.6, 2.6 Hz, 1H), 7.10 (d, J=2.2 Hz, 1H), 7.00 (dd, J=8.7, 2.4 Hz, 1H), 6.95 (d, J=2.8 Hz, 1H), 6.86 (d, J=8.6 Hz, 1H), 6.75-6.71 (m, 1H), 6.61 (dt, J=15.4, 6.3 Hz, 1H), 4.69 (d, J=5.4 Hz, 2H), 4.41 (t, J=8.7 Hz, 1H), 4.27 (s, 1H), 4.03 (dd, J=9.6, 5.0 Hz, 1H), 3.84 (s, 3H), 3.20 (s, 2H), 2.26 (d, J=10.3 Hz, 9H).

Example 102

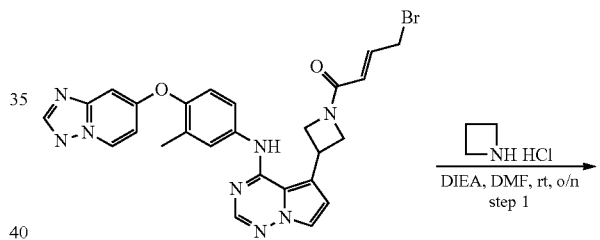

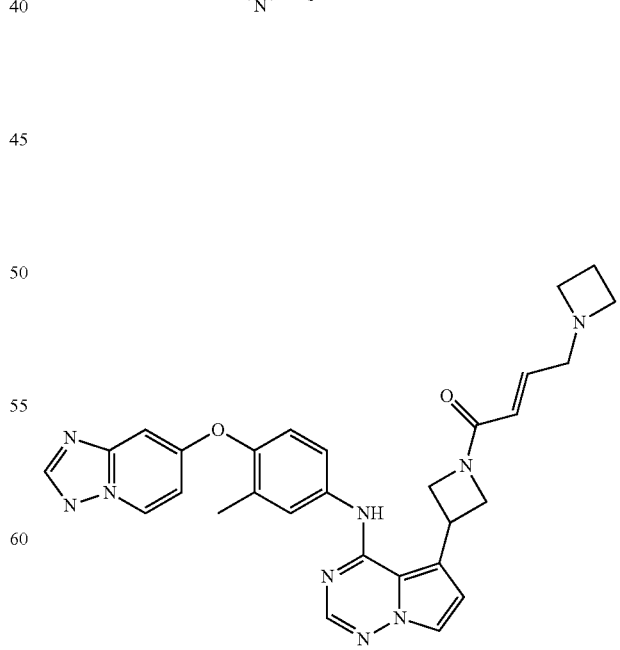

Example 102

(E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(azetidin-1-yl)but-2-en-1-one
Example 102 was prepared using similar procedure as in preparation of Example 94.
Example 103
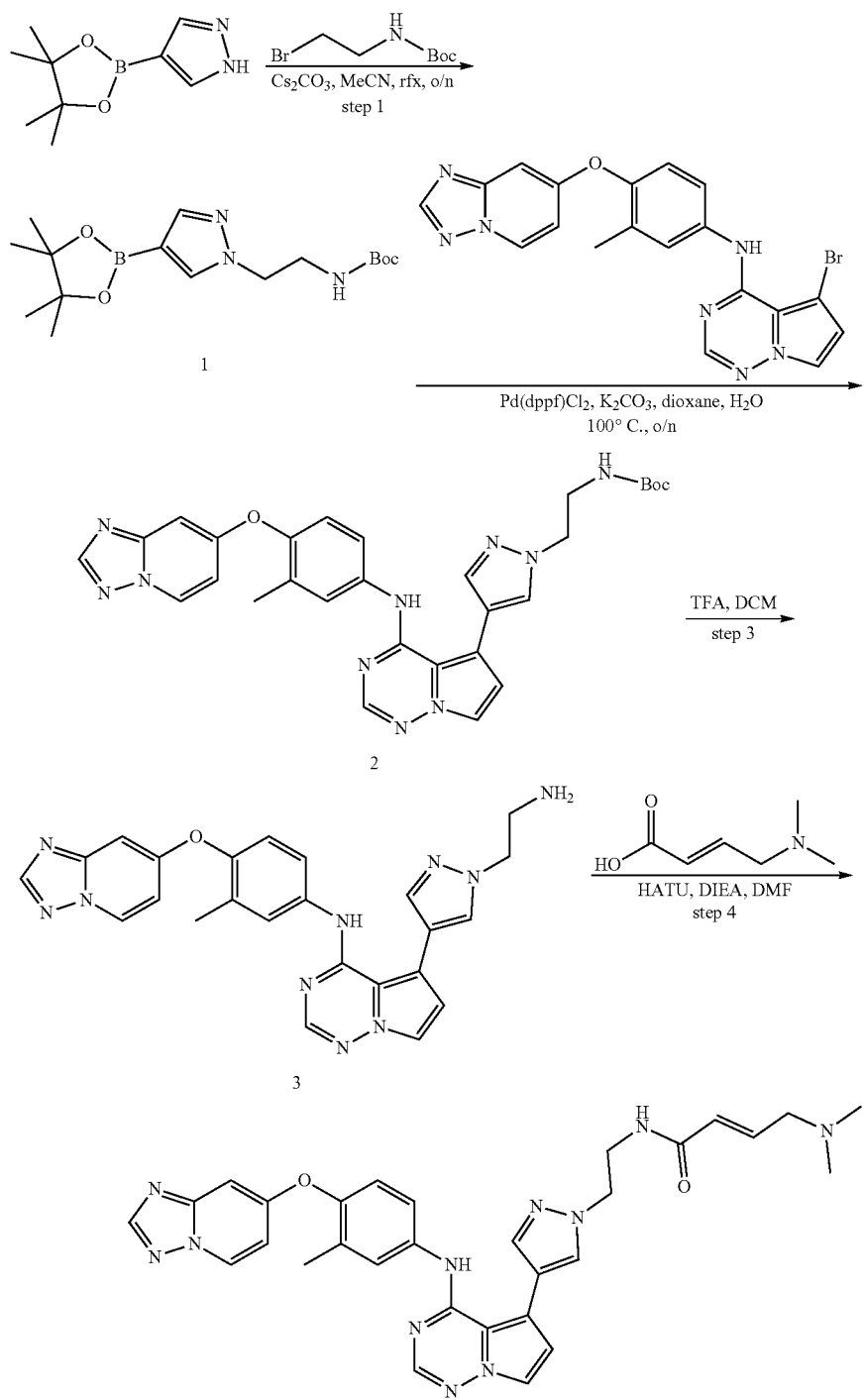

Step 1. tert-butyl (2-(4-(4,4,5,5-tetramethyl-1,3,2-dioxaborolan-2-yl)-1H-pyrazol-1-yl)ethyl)carbamate

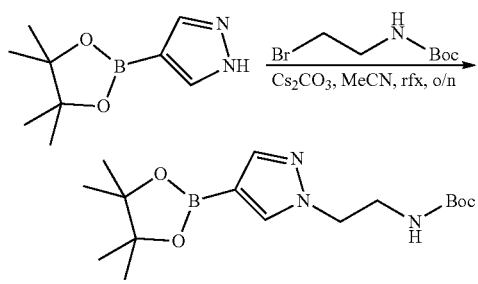

A mixture of 4-(4,4,5,5-tetramethyl-1,3,2-dioxaborolan-2-yl)-1H-pyrazole (1.00 g, 5.15 mmol), tert-butyl (2-bromoethyl)carbamate (1.15 g, 5.15 mmol) and $Cs_2CO_3$ (3.36 g, 10.30 mmol) in MeCN (10 mL) was stirred with reflux overnight. The reaction mixture was diluted with water (20 mL), the resulting solution was then extracted with ethyl acetate (3×10 mL). The combined organic layers were washed with brine, dried over anhydrous $Na_2SO_4$, filtered and concentrated under vacuum to afford the crude product. The crude product was purified by column chromatography (eluted with ethyl acetate in petroleum ether from 0% to 30%), the desired fractions were combined and concentrated under vacuum to afford the desired product tert-butyl (2-(4-(4,4,5,5-tetramethyl-1,3,2-dioxaborolan-2-yl)-1H-pyrazol-1-yl)ethyl)carbamate (1.25 g, 72% yield). LCMS (ESI-MS) m/z=338.2 [M+H]$^+$.

Step 2. tert-butyl(2-(4-(4-((4-([1,2,4]triazolo[1,5-a]pyridin-7-yloxy)-3-methylphenyl)amino)pyrrolo[2,1-f][1,2,4]triazin-5-yl)-1H-pyrazol-1-yl)ethyl)carbamate A mixture of tert-butyl (2-(4-(4,4,5,5-tetramethyl-1,3,2-dioxaborolan-2-yl)-1H-pyrazol-1-yl)ethyl)carbamate (400 mg, 1.18 mmol), N-(4-([1,2,4]triazolo[1,5-a]pyridin-7-yloxy)-3-methylphenyl)-5-bromopyrrolo[2,1-f][1,2,4]triazin-4-amine (517.48 mg, 1.18 mmol), Pd(dppf)Cl$_2$ (86.79 mg, 0.11 mmol), $K_2CO_3$ (327.86 mg, 2.37 mmol) in dioxane (4 mL) was stirred overnight at 100° C. under nitrogen atmosphere. The reaction mixture was diluted with water (15 mL), the resulting solution was extracted with ethyl acetate (3×5 mL). The combined organic layers were washed with brine, dried over anhydrous $Na_2SO_4$, filtered and concentrated under vacuum to afford the crude product. The crude product was purified by column chromatography (silica gel, 25 g, eluted with ethyl acetate in petroleum ether from 0% to 30%), the desired fractions were combined and concentrated under vacuum to afford the desired product tert-butyl (2-(4-(4-((4-([1,2,4]triazolo[1,5-a]pyridin-7-yloxy)-3-methylphenyl)amino)pyrrolo[2,1-f][1,2,4]triazin-5-yl)-1H-pyrazol-1-yl)ethyl)carbamate (480 mg, 71% yield). LCMS (ESI-MS) m/z=567.2 [M+H]$^+$.

Step 3. N-(4-([1,2,4]triazolo[1,5-a]pyridin-7-yloxy)-3-methylphenyl)-5-(1-(2-aminoethyl)-1H-pyrazol-4-yl)pyrrolo[2,1-f][1,2,4]triazin-4-amine

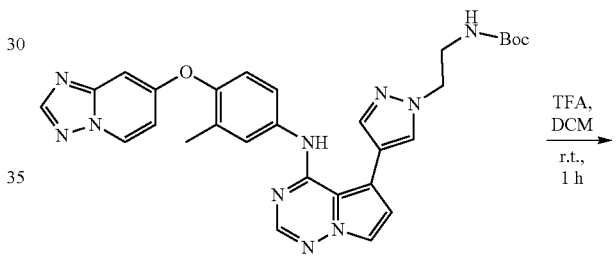

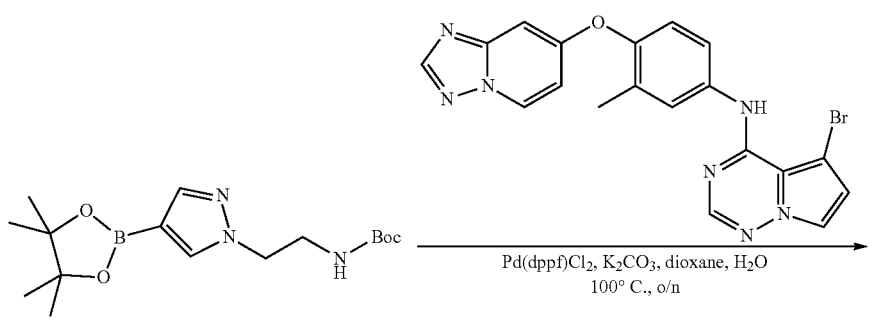

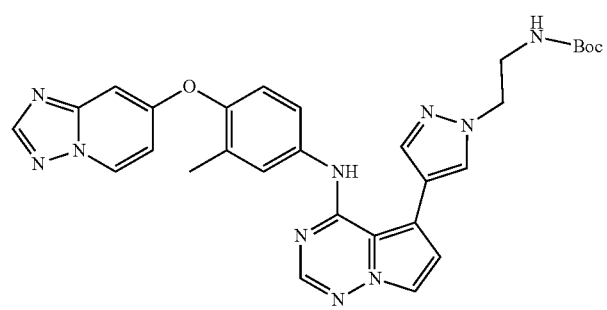

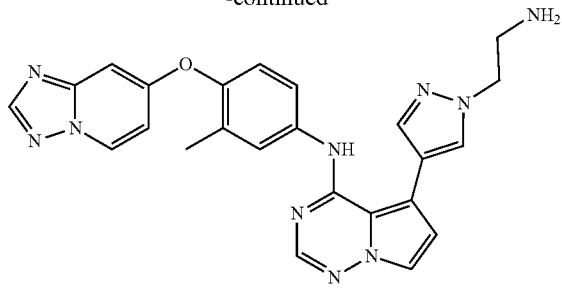

A mixture of tert-butyl (2-(4-(4-((4-([1,2,4]triazolo[1,5-a]pyridin-7-yloxy)-3-methylphenyl)amino)pyrrolo[2,1-f][1,2,4]triazin-5-yl)-1H-pyrazol-1-yl)ethyl)carbamate (480 mg, 0.84 mmol) and TFA (1 mL, 13.46 mmol) in DCM (3 mL) was stirred for 1 hour at room temperature. The resulting mixture was concentrated under vacuum to afford the crude product N-(4-([1,2,4]triazolo[1,5-a]pyridin-7-yloxy)-3-methylphenyl)-5-(1-(2-aminoethyl)-1H-pyrazol-4-yl)pyrrolo[2,1-f][1,2,4]triazin-4-amine (480 mg), the crude product was used in next step directly without further purification. LCMS (ESI-MS) m/z=467.2 [M+H]⁺.

Step 4. (E)-N-(2-(4-(4-((4-([1,2,4]triazolo[1,5-a]pyridin-7-yloxy)-3-methylphenyl)amino)pyrrolo[2,1-f][1,2,4]triazin-5-yl)-1H-pyrazol-1-yl)ethyl)-4-(dimethylamino)but-2-enamide

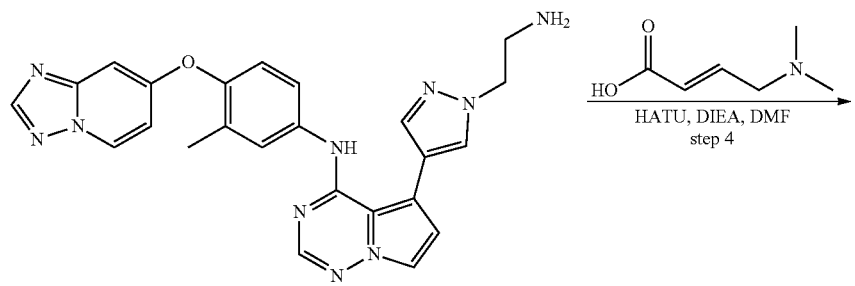

A solution of N-(4-([1,2,4]triazolo[1,5-a]pyridin-7-yloxy)-3-methylphenyl)-5-(1-(2-aminoethyl)-1H-pyrazol-4-yl)pyrrolo[2,1-f][1,2,4]triazin-4-amine (50 mg, 0.10 mmol), (E)-4-(dimethylamino)but-2-enoic acid (16.61 mg, 0.12 mmol), HATU (81.51 mg, 0.21 mmol) and diisopropylethylamine (41.56 mg, 0.32 mmol) in DMF (2 mL) was stirred for 2 hours at room temperature. The reaction mixture was diluted with water (20 mL), the resulting solution was extracted with ethyl acetate (3×20 mL), and the organic layers were concentrated under vacuum. The crude product was purified by Prep-HPLC, Mobile Phase A: Water (0.05% TFA), Mobile Phase B: ACN; Gradient: 14% B to 44% B to afford (E)-N-(2-(4-(4-((4-([1,2,4]triazolo[1,5-a]pyridin-7-yloxy)-3-methylphenyl)amino)pyrrolo[2,1-f][1,2,4]triazin-5-yl)-1H-pyrazol-1-yl)ethyl)-4-(dimethylamino)but-2-enamide, Example 103 (47.2 mg, 76% yield). LCMS (ESI-MS) m/z=578.2 [M+H]⁺. ¹H NMR (400 MHz, DMSO-d₆) δ 9.63 (s, 1H), 8.97 (d, J=7.3 Hz, 1H), 8.45 (d, J=10.9 Hz, 2H), 8.10 (s, 1H), 8.05 (s, 1H), 7.85 (s, 1H), 7.79 (s, 1H), 7.65 (s, 1H), 7.60 (s, 1H), 7.21 (d, J¹⁼⁸·⁷ Hz, 1H), 7.06 (dd, J=7.5, 2.6 Hz, 1H), 6.81 (d, J=2.6 Hz, 1H), 6.76 (d, J=2.7 Hz, 1H), 6.53 (m, J=14.7, 7.2 Hz, 1H), 6.21 (m, J=15.4, 1.3 Hz, 1H), 4.30 (t, J=6.1 Hz, 2H), 3.83 (t, J=5.8 Hz, 2H), 3.64 (q, J=6.0 Hz, 2H), 2.72 (d, J=4.3 Hz, 6H), 2.17 (s, 3H).

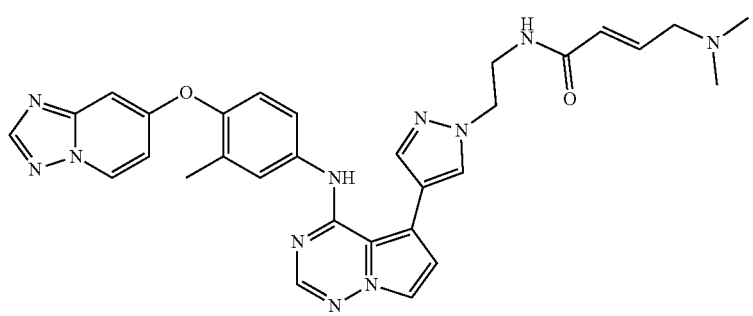

Example 103

Example 104
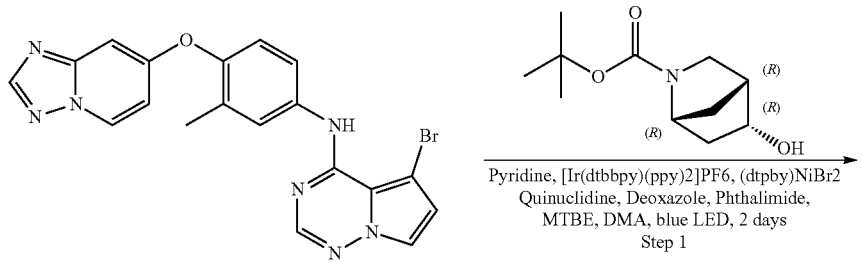
Pyridine, [Ir(dtbbpy)(ppy)2]PF6, (dtpby)NiBr2
Quinuclidine, Deoxazole, Phthalimide,
MTBE, DMA, blue LED, 2 days
Step 1
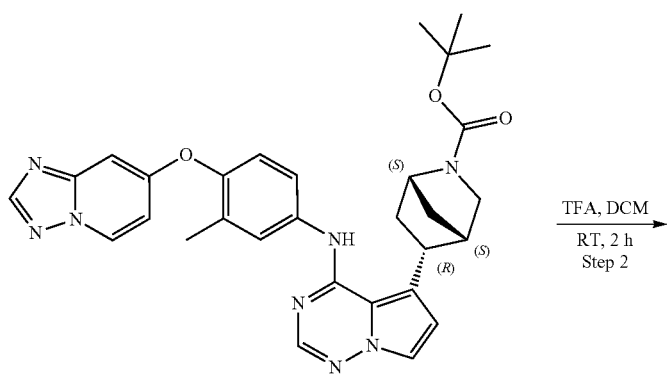
TFA, DCM
RT, 2 h
Step 2
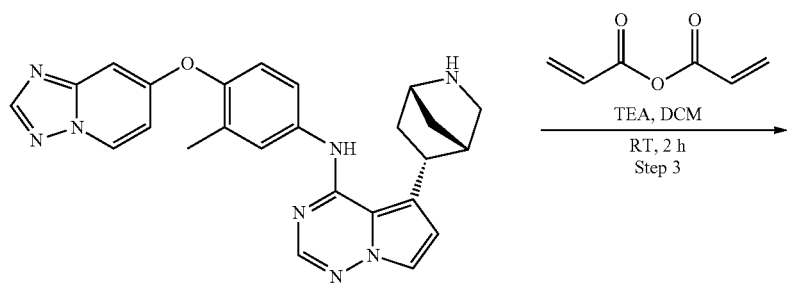
TEA, DCM
RT, 2 h
Step 3
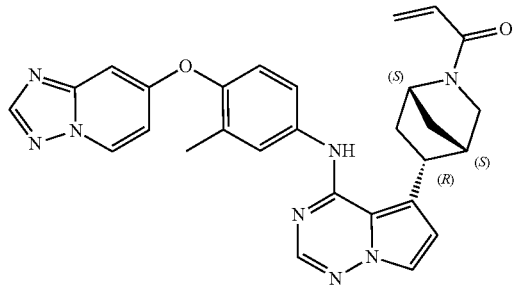
Example 104

Rel-1-[(1S,4S,5R)-5-{4-[(3-methyl-4-{[1,2,4]triazolo[1,5-a]pyridin-7-yloxy}phenyl)amino]pyrrolo[2,1-f][1,2,4]triazin-5-yl}-2-azabicyclo[2.2.1]heptan-2-yl]prop-2-en-1-one
Example 104, was synthesized using similar procedure as in preparation of Example 141 employing rel-(1R,4R,5R)-tert-butyl 5-hydroxy-2-azabicyclo[2.2.1]heptane-2-carboxylate in Step 1.
Example 105
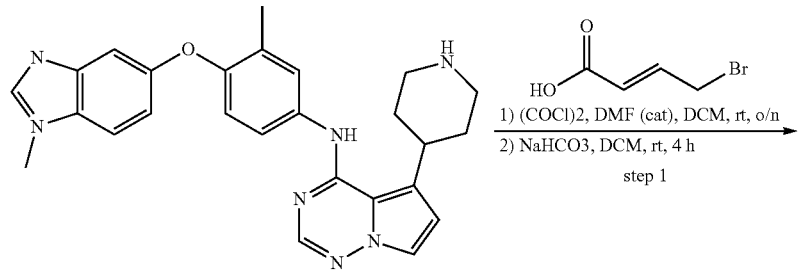
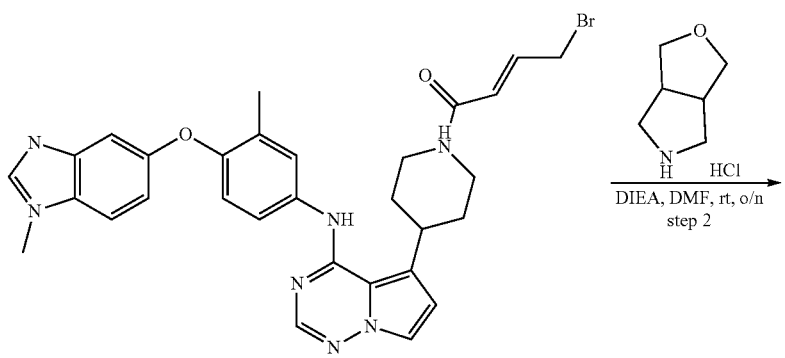
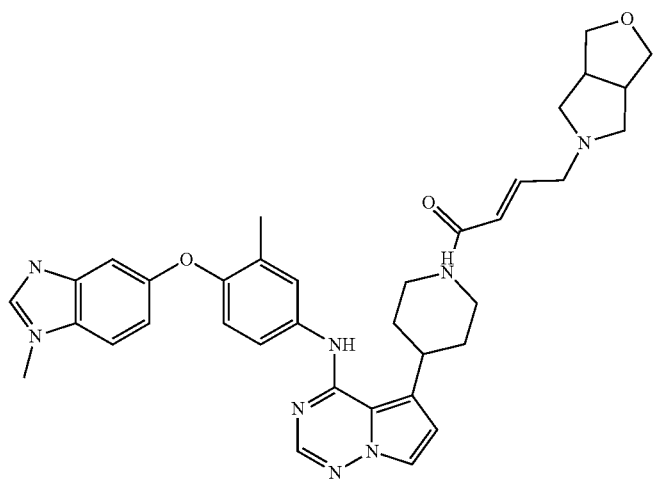
Example 105

Step 1. (E)-4-bromo-1-(4-(4-((3-methyl-4-((1-methyl-1H-benzo[d]imidazol-5-yl)oxy)phenyl)amino)-pyrrolo[2,1-f][1,2,4]triazin-5-yl)piperidin-1-yl)but-2-en-1-one

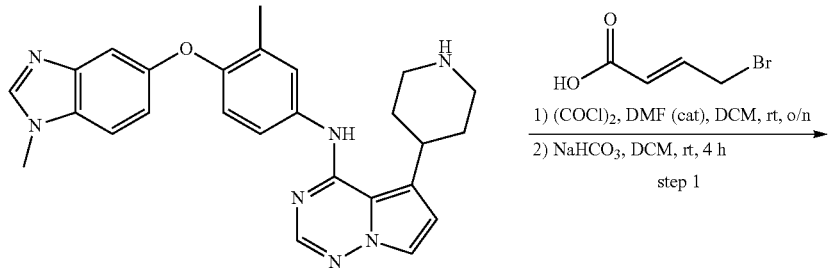

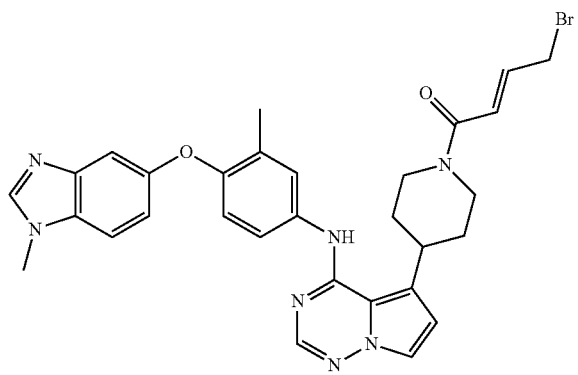

To a cold (0° C.) solution of (E)-4-bromobut-2-enoic acid (0.73 g, 4.41 mmol) in DMF (0.05 mL) and DCM (10 mL) was added oxalyl chloride (1.12 g, 8.82 mmol) dropwise. The reaction mixture was stirred overnight at room temperature. The resulting crude mixture was concentrated under vacuum. The residue was dissolved in DCM (15 mL). The solution was added to a stirred mixture of N-(3-methyl-4-((1-methyl-1H-benzo[d]imidazol-5-yl)oxy)phenyl)-5-(piperidin-4-yl)pyrrolo[2,1-f][1,2,4]triazin-4-amine (2 g, 4.41 mmol) and NaHCO₃ (0.75 g, 8.92 mmol) in DCM (20 mL). The resulting mixture was stirred for 4 hours at room temperature and concentrated under vacuum to afford the crude product. The crude product was purified by silica gel column chromatography, eluted with petroleum ether/ethyl acetate=1:4 to afford the desired product (E)-4-bromo-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one (800 mg, 27.2% yield). LCMS (ESI-MS) m/z=600.2 [M+H]⁺

Step 2. (E)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)-4-(tetrahydro-1H-furo[3,4-c]pyrrol-5(3H)-yl)but-2-en-1-one

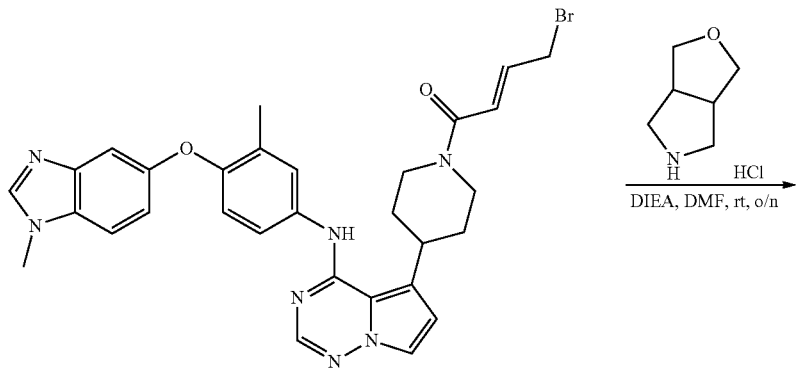

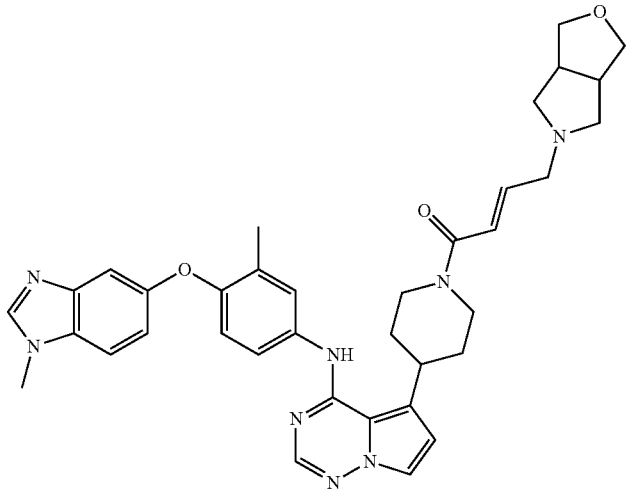

Diisopropylethylamine (161 mg, 1.25 mmol) was added to a mixture of (E)-4-bromo-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one (150 mg, 0.25 mmol), hexahydro-1H-furo[3,4-c]pyrrole hydrochloride (25 mg, 0.22 mmol) in DMF (2 mL). The resulting mixture was stirred overnight at room temperature. The reaction mixture was purified by Prep-HPLC, Mobile Phase A: Water (0.1% FA), Mobile Phase B: ACN; Gradient: 2% B to 25% B to afford the desired product (E)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)-4-(tetrahydro-1H-furo[3,4-c]pyrrol-5(3H)-yl)but-2-en-1-one, Example 105 (15.5 mg, 10% yield). LCMS (ESI-MS) m/z=633.5 [M+H]⁺. ¹H NMR (400 MHz, DMSO-d₅) δ (ppm) 8.43 (s, 1H), 8.17 (s, 2H), 7.85 (s, 1H), 7.68 (d, J=2.7 Hz, 1H), 7.57 (d, J=8.7 Hz, 1H), 7.52 (d, J=2.6 Hz, 1H), 7.40-7.35 (m, 1H), 7.10 (d, J=2.3 Hz, 11H), 7.00-6.98 (m, 1H), 6.87 (d, J=8.6 Hz, 1H), 6.70-6.60 (m, 3H), 4.57 (d, J=12.6 Hz, 1H), 4.12 (s, 11H), 3.71 (s, 1H), 3.39-3.35 (m, 2H), 3.31 (d, J=14.0 Hz, 1H), 2.84 (s, 1H), 2.70 (s, 2H), 2.53 (s, 2H), 2.47 (s, 4H), 2.33-2.35 (m, 2H), 2.30 (s, 1H), 2.25 (s, 3H), 1.96 (s, 2H), 1.55 (s, 3H).

Example 106

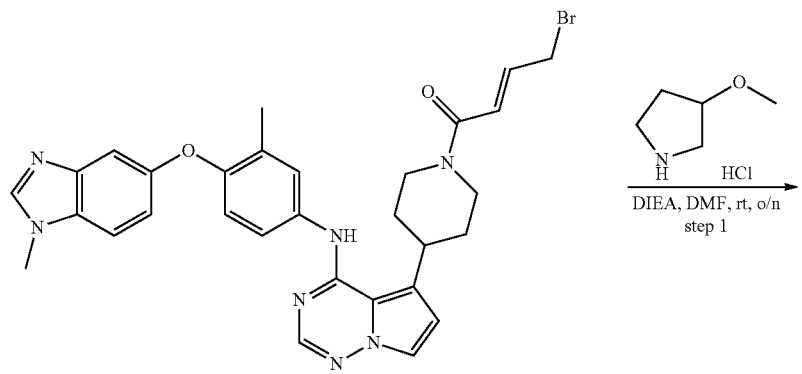

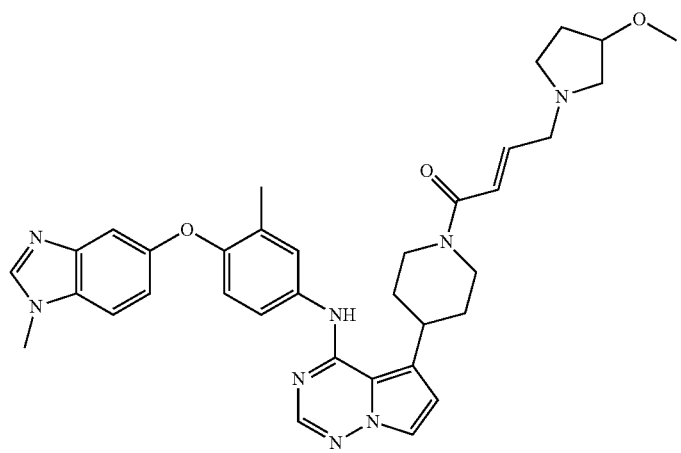
Example 106
(E)-4-(3-methoxypyrrolidin-1-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one
Example 106 was prepared using similar procedure as in preparation of Example 105, Step 2.
Examples 107 and 108
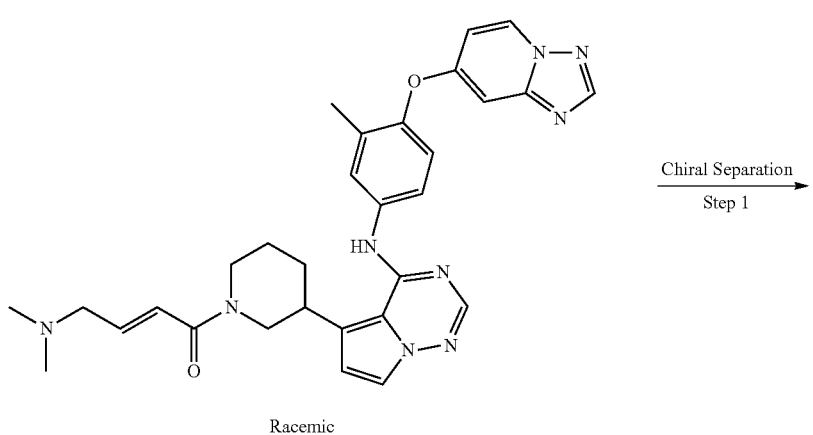

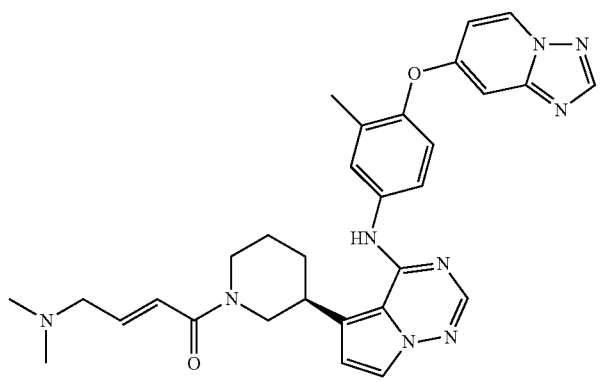

Example 107

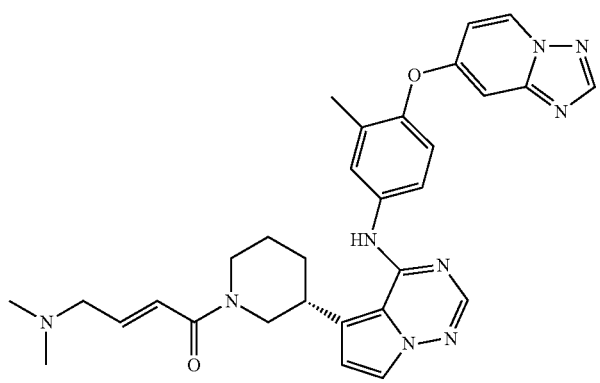

Example 108

(S,E)-1-(3-(4-((4-([1,2,4]triazolo[1,5-a]pyridin-7-yloxy)-3-methylphenyl)amino)-pyrrolo[2,1-f][1,2,4]triazin-5-yl)piperidin-1-yl)-4-(dimethylamino)but-2-en-1-one (Example 107) &

(R,E)-1-(3-(4-((4-([1,2,4]triazolo[1,5-a]pyridin-7-yloxy)-3-methylphenyl)amino)-pyrrolo[2,1-f][1,2,4]-triazin-5-yl)piperidin-1-yl)-4-(dimethylamino)but-2-en-1-one Example 108

The racemate of (E)-1-(3-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(dimethylamino)but-2-en-1-one (130 mg, 0.23 mmol) was separated by Prep-Chiral-HPLC using the following conditions: Column: CHIRALPAK IF-3, 4.6*50 mm, 3 μm; Mobile Phase A: MTBE (0.1% DEA): EtOH=50:50; Flow rate: 1 mL/min; Gradient: 0% B to 0% B; Injection Volume: 5 ul mL. The desired fractions were combined and lyophilized to afford the two desired separated isomers Example 107 and Example 108:

First eluting isomer of (E)-1-(3-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(dimethylamino)but-2-en-1-one (30.7 mg, 100% ee, 23% yield). LCMS (ESI-MS) m/z=552.3 [M+H]$^+$. $^1$H NMR (400 MHz, methanol-d4) δ (ppm) 8.76-8.70 (m, 1H), 8.33-8.28 (m, 1H), 7.86-7.72 (m, 2H), 7.67-7.54 (m, 2H), 7.21-7.04 (m, 2H), 6.93-6.78 (m, 2H), 6.77-6.64 (m, 2H), 4.75-4.57 (m, 1H), 4.25-4.15 (m, 1H), 3.64-3.46 (m, 1H), 3.20-3.12 (m, 2H), 2.83-2.68 (m, 2H), 2.31-2.17 (m, 8H), 2.16-2.02 (m, 4H), 2.00-1.89 (m, 11H).

Cell growth inhibition activity of first eluting isomer based on assays described for Table 3:

| HER2—YVMA IC$_{50}$ (nM) | HER2 WT IC$_{50}$ (nM) | EGFR WT IC$_{50}$ (nM) |
|---|---|---|
| ++ | ++++ | + |

Second eluting isomer of (E)-1-(3-(4-((4-([1,2,4]triazolo[1,5-a]pyridin-7-yloxy)-3-methylphenyl)amino)pyrrolo[2,1-f] [1,2,4]triazin-5-yl)piperidin-1-yl)-4-(dimethylamino)but-2-en-1-one (38.2 mg, 99.7% ee, 30% yield). LCMS (ESI-MS) m/z=552.3 [M+H]$^+$. $^1$H NMR (400 MHz, methanol-d4) δ (ppm) 8.76-8.70 (m, 1H), 8.33-8.28 (m, 1H), 7.86-7.72 (m, 2H), 7.67-7.54 (m, 2H), 7.22-7.13 (m, 1H), 7.11-7.05 (m, 1H), 6.93-6.64 (m, 4H), 4.75-4.57 (m, 1H), 4.25-4.15 (m, 1H), 3.64-3.46 (m, 1H), 3.20-3.12 (m, 2H), 2.83-2.68 (m, 2H), 2.31-2.17 (m, 8H), 2.16-2.02 (m, 4H), 2.00-1.89 (m, 1H)

Cell growth inhibition activity of second eluting isomer based on assays described for Table 3:

| HER2—YVMA IC$_{50}$ (nM) | HER2 WT IC$_{50}$ (nM) | EGFR WT IC$_{50}$ (nM) |
|---|---|---|
| + | ++ | + |

Examples 109 and 110

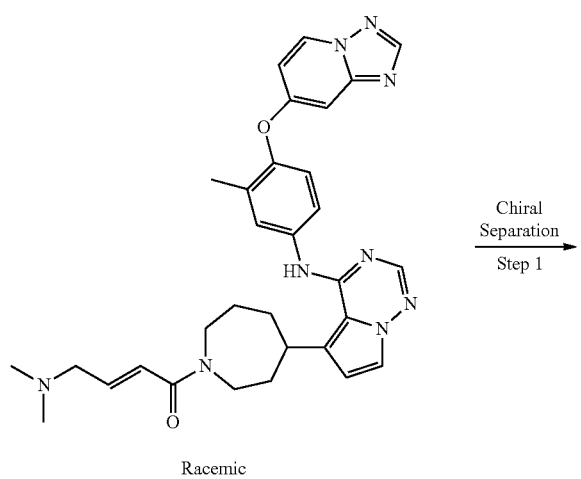

Racemic

Chiral Separation Step 1

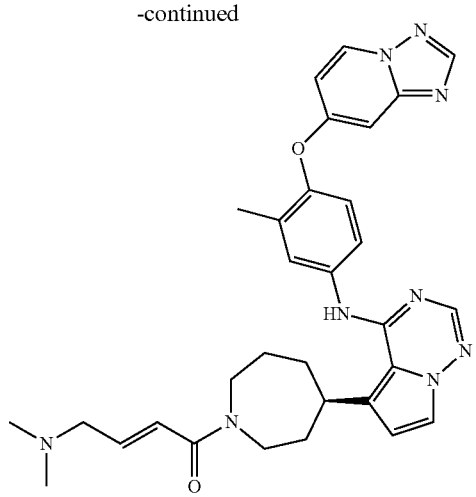

Example 109

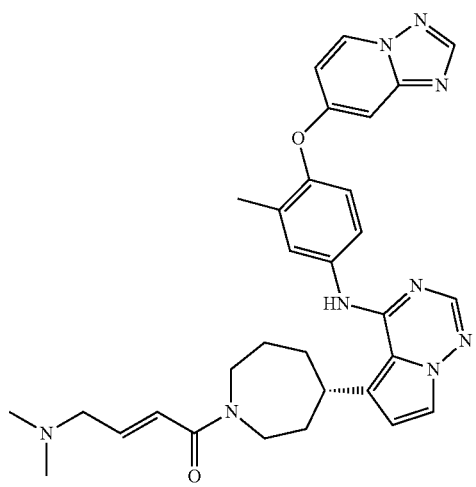

Example 110

(R,E)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-4-(dimethylamino)but-2-en-1-one (Example 109) &

(S,E)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-4-(dimethylamino)but-2-en-1-one (Example 110)

The racemate of (E)-1-(4-(4-((4-([1,2,4]triazolo[1,5-a]pyridin-7-yloxy)-3-methylphenyl)amino)pyrrolo[2,1-f][1,2,4]-triazin-5-yl)azepan-1-yl)-4-(dimethylamino)but-2-en-1-one (100 mg, 0.17 mmol) was separated by Prep-Chiral-HPLC using the following conditions: Column: CHIRAL ART Cellulose-SB, 2*25 cm, 5 μm; Mobile Phase A: Hex (0.5% 2M NH$_3$-MeOH)-HPLC, Mobile Phase B: EtOH-HPLC; Flow rate: 20 mL/min; Gradient: 40% B to 40% B in 19 min; Wave Length: 220/254 nm; RT1(min): 13.493; RT2(min): 16.888; Sample Solvent: EtOH-HPLC; Injection Volume: 0.5 mL; Number Of Runs: 12. The desired fractions were combined and lyophilized to afford the two desired separated isomers Example 109 and 110:

First eluting isomer of (E)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-4-(dimethylamino)but-2-en-1-one (45.7 mg, 100% ee, 46% yield). LCMS (ESI-MS) m/z=566.4 [M+H]$^+$. $^1$H NMR (400 MHz, DMSO-d$_6$) δ 8.96-8.92 (m, 1H), 8.42 (s, 1H), 8.23 (s, 1H), 7.91-7.56 (m, 3H), 7.41-6.49 (m, 7H), 3.85-3.70 (m, 2H), 3.62-3.49 (m, 3H), 3.10-2.99 (m, 1H), 2.99 (s, 1H), 2.20 (s, 3H), 2.13 (s, 7H), 2.07-1.80 (m, 3H), 1.79-1.60 (m, 2H).

Cell growth inhibition activity of first eluting isomer based on assays described for Table 3:

| HER2—YVMA IC$_{50}$ (nM) | HER2 WT IC$_{50}$ (nM) | EGFR WT IC$_{50}$ (nM) |
|---|---|---|
| ++++ | ++++ | + |

Second eluting isomer of (E)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-4-(dimethylamino)but-2-en-1-one (44.2 mg, 99.5% ee, 44% yield). LCMS (ESI-MS) m/z=566.4 [M+H]$^+$.

$^1$H NMR (400 MHz, DMSO-d$_6$) δ 8.96-8.92 (m, 1H), 8.48-8.25 (m, 2H), 7.92-7.54 (m, 3H), 7.41-6.44 (m, 7H), 3.87-3.67 (m, 2H), 3.65-3.40 (m, 31H), 3.05-2.89 (m, 1H), 2.99-2.89 (m, 1H), 2.20 (s, 3H), 2.14-2.05 (m, 7H), 2.06-1.82 (m, 3H), 1.80-1.60 (m, 2H).

Cell growth inhibition activity of second eluting isomer based on assays described for Table 3:

| HER2—YVMA IC$_{50}$ (nM) | HER2 WT IC$_{50}$ (nM) | EGFR WT IC$_{50}$ (nM) |
|---|---|---|
| ++++ | ++++ | + |

Examples 111 and 112

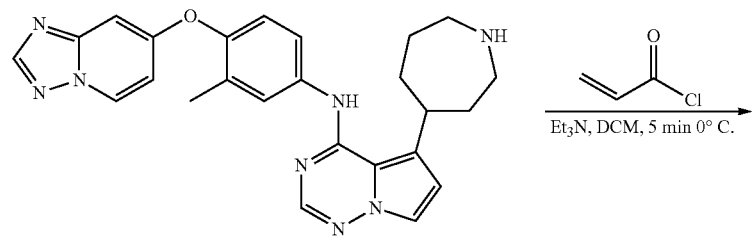

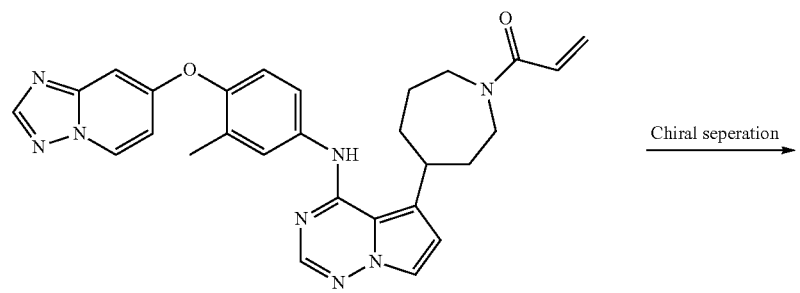

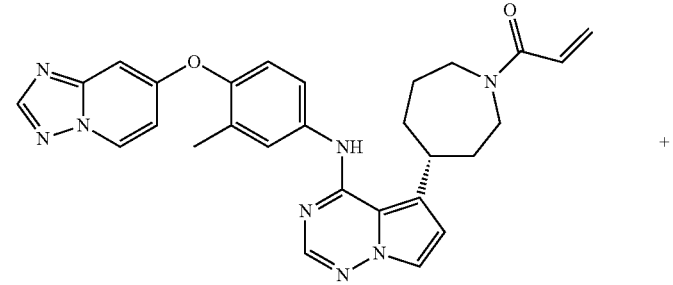

Example 111

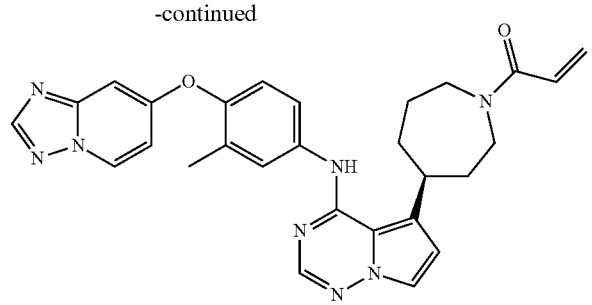

Example 112

Step 1. 1-(4-(4-((4-([1,2,4]triazolo[1,5-a]pyridin-7-yloxy)-3-methylphenyl)amino)pyrrolo[2,1-f][1,2,4]-triazin-5-yl)azepan-1-yl)prop-2-en-1-one

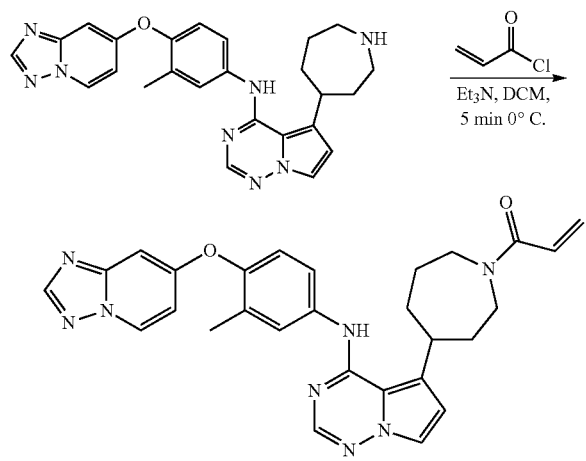

To a cold mixture (0° C.) of N-(4-([1,2,4]triazolo[1,5-a]pyridin-7-yloxy)-3-methylphenyl)-5-(azepan-4-yl)pyrrolo[2,1-f][1,2,4]triazin-4-amine (300 mg, 0.66 mmol) and Et$_3$N (267.46 mg, 2.64 mmol) in DCM (1 mL) was added a solution of acryloyl chloride (65.41 mg, 0.72 mmol) in DCM (1 mL) dropwise. The resulting mixture was stirred at 0° C. for 5 minutes and concentrated under vacuum to afford the crude product. The crude product was purified by Prep-HPLC, Mobile Phase A: Water (0.1% FA), Mobile Phase B: ACN; Gradient: 40% B to 55% to afford 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)prop-2-en-1-one (40 mg, 11.9% yield). LCMS (ESI-MS) n/z=509.1 [M+H]$^+$.

Step 2. (R)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)prop-2-en-1-one (Example 111) & (S)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)prop-2-en-1-one

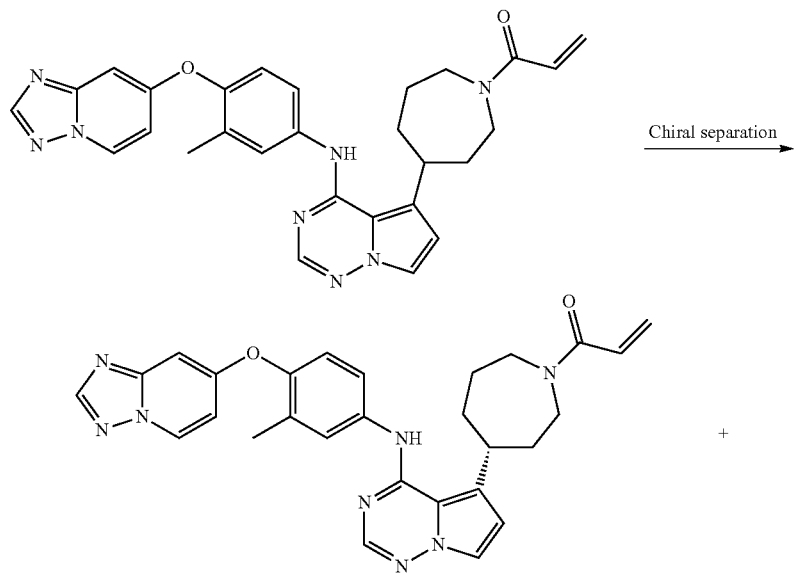

Example 111

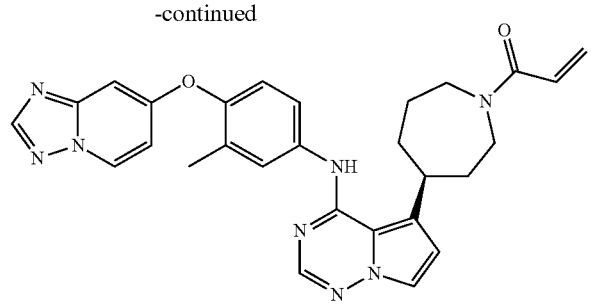

Example 112

The racemate of 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)prop-2-en-1-one (40 mg, 0.07 mmol) was separated by Prep-Chiral-HPLC using the following conditions: Column: CHIRAL ART Cellulose-SB, 2*25 cm, 5 μm; Mobile Phase A: Hex:DCM=3:1(0.5% 2M NH₃-MeOH)-HPLC, Mobile Phase B: EtOH-HPLC; Flow rate: 20 mL/min; Gradient: 30% B to 30% B in 7.5 min; Wave Length: 220/254 nm; RT1(min): 5.352; RT2(min): 6.493; Sample Solvent: EtOH, Injection Volume: 0.5 mL; Number of Runs: 7. The desired fractions were combined and lyophilized to afford the two desired separated isomers Examples 111 and 112:

First eluting isomer of 1-(4-(4-((4-([1,2,4]triazolo[1,5-a]pyridin-7-yloxy)-3-methylphenyl)amino)pyrrolo-[2,1-f][1,2,4]triazin-5-yl)azepan-1-yl)prop-2-en-1-one (11.8 mg, 100% ee, 29.5% yield). LCMS (ESI-MS) m/z=509.1 [M+H]⁺, 99.2%. ¹H NMR (400 MHz, DMSO-d₆) δ 9.06-8.80 (m, 1H), 8.58-8.26 (m, 2H), 7.95-7.52 (m, 3H), 7.43-6.25 (m, 6H), 6.20-6.00 (m, 1H), 5.80-5.45 (m, 1H), 4.00-3.69 (m, 2H), 3.67-3.40 (m, 3H), 2.30-2.10 (m, 4H), 2.09-1.82 (m, 3H), 1.80-1.55 (m, 2H).

Cell growth inhibition activity of first eluting isomer based on assays described for Table 3:

| HER2 - YVMA IC₅₀ (nM) | HER2 WT IC₅₀ (nM) | EGFR WT IC₅₀ (nM) |
|---|---|---|
| ++++ | ++++ | + |

Second eluting isomer of 1-(4-(4-((4-([1,2,4]triazolo[1,5-a]pyridin-7-yloxy)-3-methylphenyl)amino)pyrrolo-[2,1-f][1,2,4]triazin-5-yl)azepan-1-yl)prop-2-en-1-one (12.8 mg, 99.7% ee, 32% yield). LCMS (ESI-MS) m/z=509.1 [M+H]⁺. ¹H NMR (400 MHz, DMSO-d₆) δ 9.08-8.82 (m, 1H), 8.60-8.20 (m, 2H), 7.95-7.60 (m, 3H), 7.45-6.28 (m, 6H), 6.27-6.00 (m, 1H), 5.83-5.50 (m, 1H), 3.98-3.71 (m, 2H), 3.70-3.40 (m, 3H), 2.28-2.11 (m, 4H), 2.10-1.82 (m, 3H), 1.80-1.55 (m, 2H).

Cell growth inhibition activity of second eluting isomer based on assays described for Table 3:

| HER2 - YVMA IC₅₀ (nM) | HER2 WT IC₅₀ (nM) | EGFR WT IC₅₀ (nM) |
|---|---|---|
| ++++ | ++++ | + |

Example 113

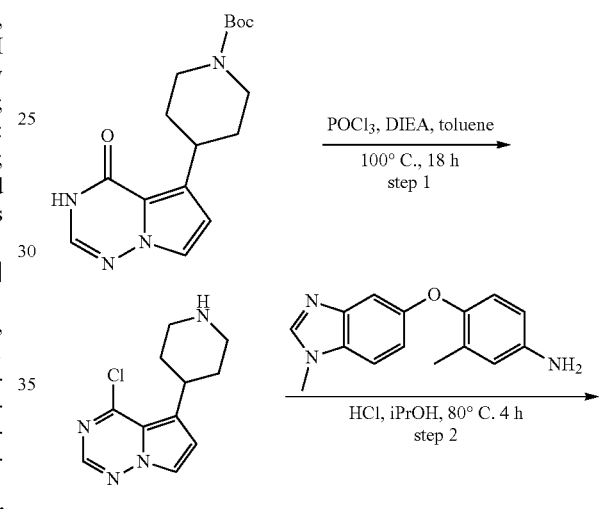

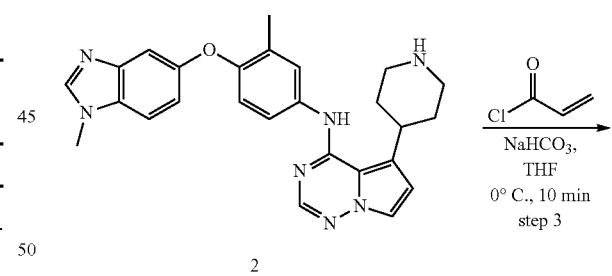

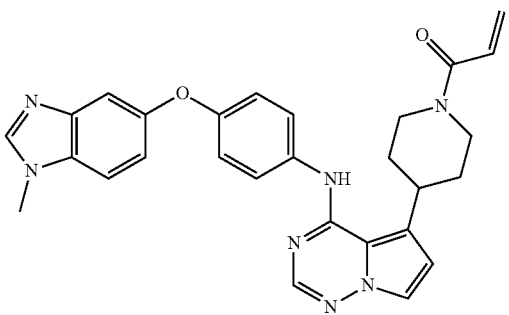

Example 113

Step 1. 4-chloro-5-(piperidin-4-yl)pyrrolo[2,1-f][1,2,4]triazine

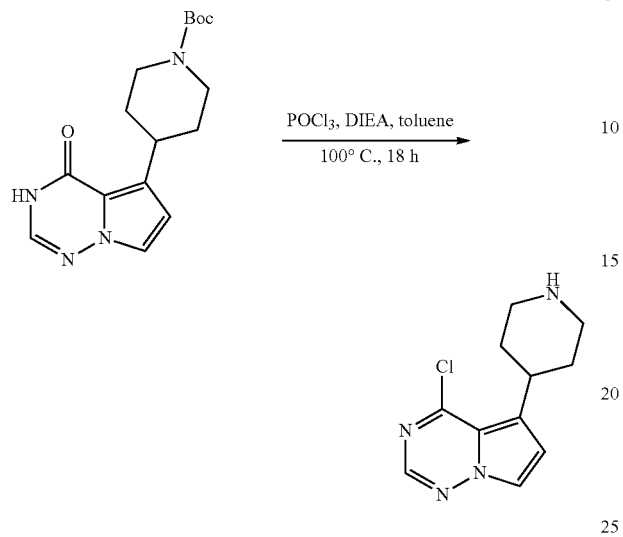

To a solution of tert-butyl 4-(4-oxo-3,4-dihydropyrrolo[2,1-f][1,2,4]triazin-5-yl)piperidine-1-carboxylate (6 g, 18.8 mmol) in toluene (60 mL) was added POCl₃ (5.27 mL, 56.54 mmol) followed by addition of diisopropylethylamine (16.41 mL, 56.54 mmol) at room temperature. The resulting mixture was heated to 100° C. and stirred for 18 hours. After cooling to room temperature, the reaction was concentrated under reduced pressure to afford the crude product 4-chloro-5-(piperidin-4-yl)pyrrolo[2,1-f][1,2,4]triazine (6.8 g crude), the crude product was used in next step directly without further purification. LCMS (ESI-MS) m/z=237.1 [M+H]⁺.

Step 2. N-(3-methyl-4-((1-methyl-1H-benzo[d]imidazol-5-yl)oxy)phenyl)-5-(piperidin-4-yl)pyrrolo[2,1-f][1,2,4]triazin-4-amine

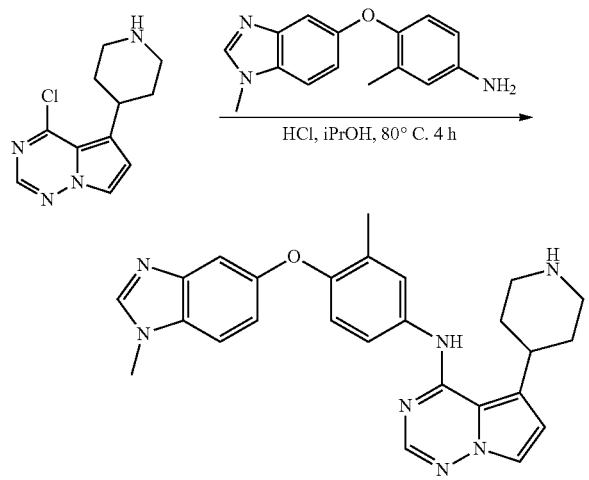

Catalytic amount of aq. HCl (10M, 0.05 mL) was added to a stirred solution of 4-chloro-5-(piperidin-4-yl)pyrrolo[2,1-f][1,2,4]triazine (6.8 g crude) and 3-methyl-4-((1-methyl-1H-benzo[d]imidazol-5-yl)oxy)aniline (2.31 g, 9.13 mmol) in iPrOH (50 mL) at room temperature. The resulting mixture was stirred for 4 hours at 80° C. and concentrated under vacuum to afford the crude product. The crude product was purified by Prep-HPLC, Mobile Phase A: MeOH, Mobile Phase B: ACN; Gradient: 40% B to 70% B to afford N-(3-methyl-4-((1-methyl-1H-benzo[d]imidazol-5-yl)oxy)phenyl)-5-(piperidin-4-yl)pyrrolo[2,1-f][1,2,4]triazin-4-amine (5 g, 58.4% yield for two steps). LCMS (ESI-MS) m/z=454.2 [M+H].

Step 3. 1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)prop-2-en-1-one

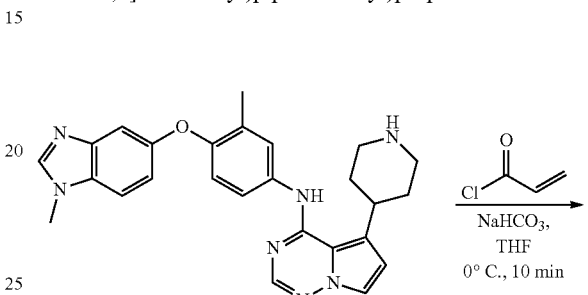

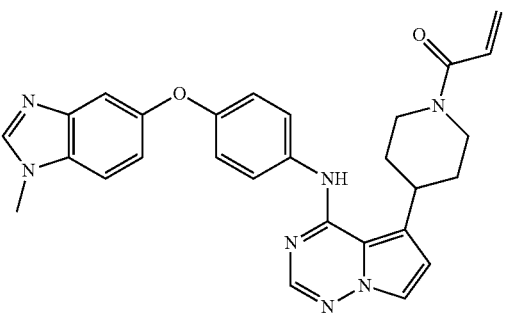

Example 113

Acryloyl chloride (15.96 mg, 0.18 mmol) was added dropwise to a stirred mixture of N-(3-methyl-4-((1-methyl-1H-benzo[d]imidazol-5-yl)oxy)phenyl)-5-(piperidin-4-yl)pyrrolo[2,1-f][1,2,4]triazin-4-amine (100 mg, 0.22 mmol) and NaHCO₃ (55.57 mg, 0.66 mmol) in THF (1 mL). The resulting mixture was stirred for 10 minutes at 0° C., diluted with water (10 mL) and extracted with ethyl acetate (3×10 mL). The combined organic layers were dried over anhydrous Na₂SO₄ and concentrated under vacuum to afford the crude product. The residue was purified by Prep-HPLC, Mobile Phase A: Water (10 mmol/L NH₄HCO₃+0.1% NH₃·H₂O), Mobile Phase B: ACN; Gradient: 29% B to 59% B to afford 1-(4-(4-((3-methyl-4-((1-methyl-1H-benzo[d]imidazol-5-yl)oxy)phenyl)amino)pyrrolo [2,1-f][1,2,4]triazin-5-yl)piperidin-1-yl)prop-2-en-1-one, Example 113 (8.8 mg, 8% yield). LCMS (ESI-MS) m/z=508.3 [M+H]⁺.

¹H NMR (400 MHz, DMSO-d₆) δ (ppm) 8.45 (s, 1H), 8.17 (s, 1H), 7.84 (s, 1H), 7.68 (s, 1H), 7.57 (d, J=8.8 Hz, 1H), 7.51 (s, 1H), 7.40 (d, J=12.9 Hz, 1H), 7.10 (d, J=2.3 Hz, 1H), 7.00 (dd, J=8.7, 2.3 Hz, 1H), 6.91-6.79 (m, 2H), 6.67 (s, 1H), 6.11 (dd, J=16.7, 2.5 Hz, 1H), 5.67 (dd, J=10.4, 2.5 Hz, 1H), 4.57 (d, J=12.9 Hz, 1H), 4.16 (d, J=13.6 Hz, 1H), 3.84 (s, 3H), 3.66 (s, 1H), 3.31 (s, 1H), 2.85 (s, 1H), 2.24 (s, 3H), 1.96 (d, J=12.6 Hz, 2H), 1.56 (s, 2H).

Example 114
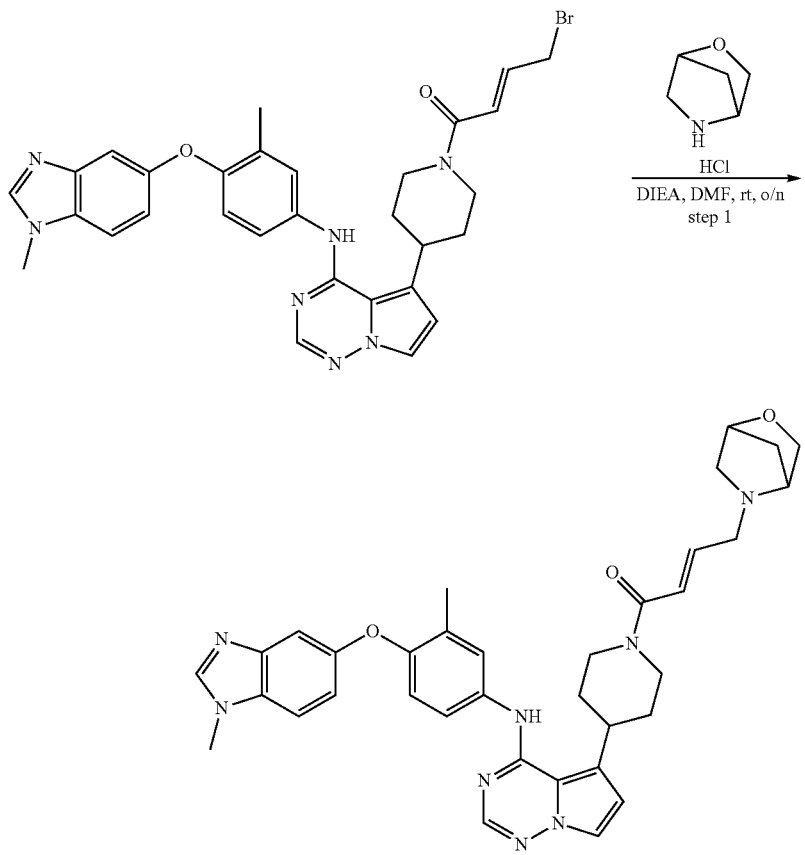
Example 114
(E)-4-(2-oxa-5-azabicyclo[2.2.1]heptan-5-yl)-1-(4-
(4-((3-methyl-4-((1-methyl-1H-benzo[d]imidazol-5-
yl)oxy)phenyl)amino)pyrrolo[2,1-f][1,2,4]triazin-5-
yl)piperidin-1-yl)but-2-en-1-one
Example 114 was prepared using similar procedure as in preparation of Example 105, Step 2.
Example 115
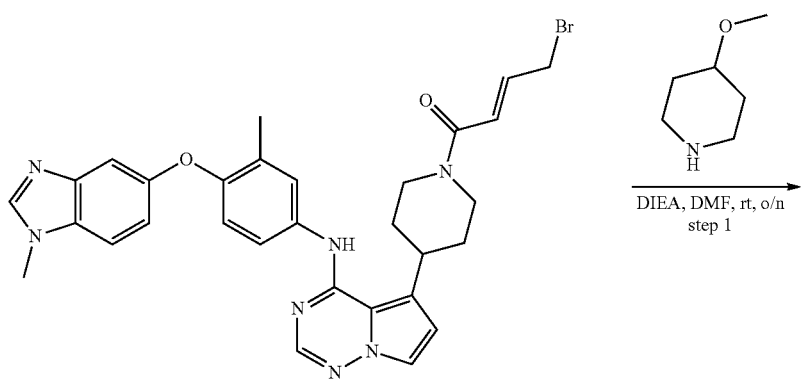

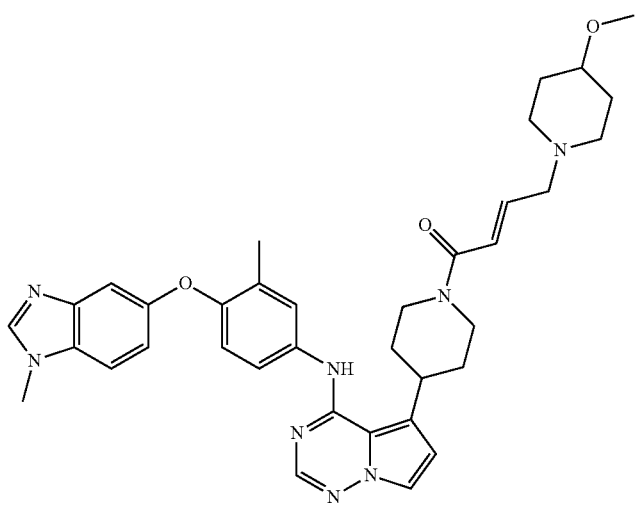

Example 115

(E)-4-(4-methoxypiperidin-1-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one Example 115 was prepared using similar procedure as in preparation of Example 105, Step 2.

Example 117

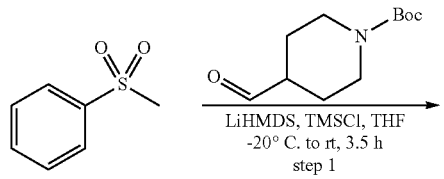

LiHMDS, TMSCl, THF
-20° C. to rt, 3.5 h
step 1

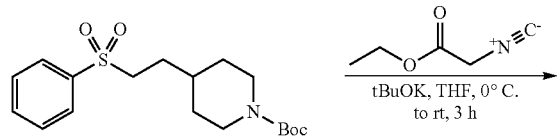

tBuOK, THF, 0° C.
to rt, 3 h
step 2

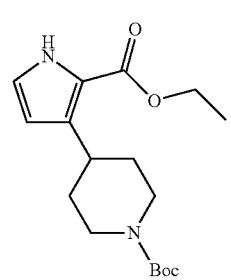

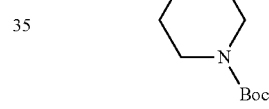

DMF, NaH, THF, rt, 8 h
step 3

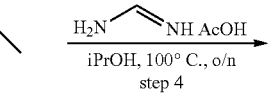

H₂N—⟨⟩—NH AcOH
iPrOH, 100° C., o/n
step 4

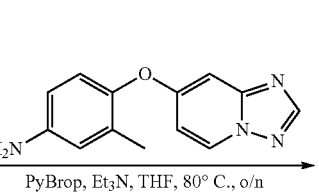

PyBrop, Et₃N, THF, 80° C., o/n
step 5

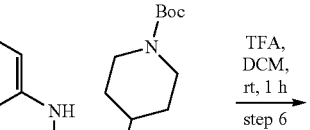

TFA, DCM, rt, 1 h
step 6

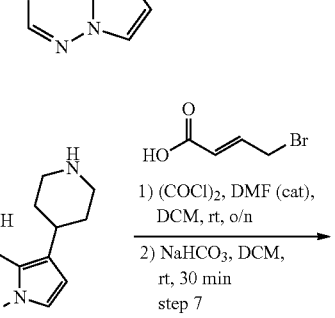

1) (COCl)₂, DMF (cat), DCM, rt, o/n
2) NaHCO₃, DCM, rt, 30 min
step 7

-continued

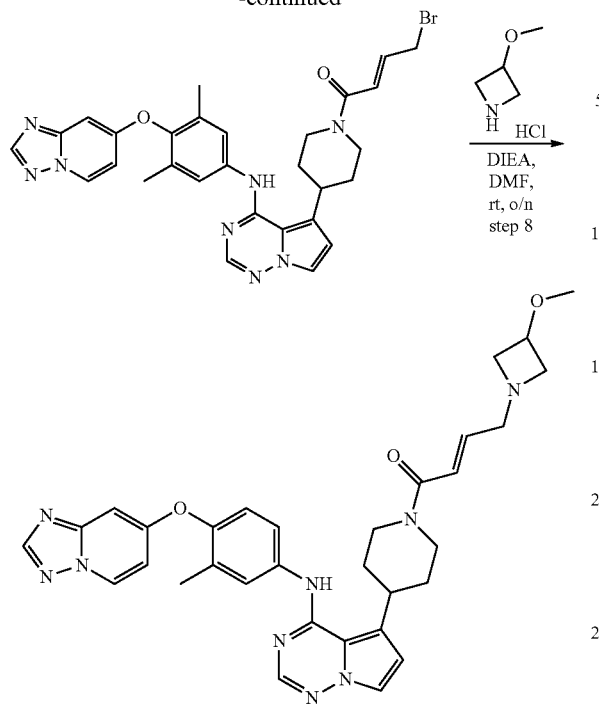

Example 117

Step 1. tert-butyl (E)-4-(2-(phenylsulfonyl)vinyl)piperidine-1-carboxylate

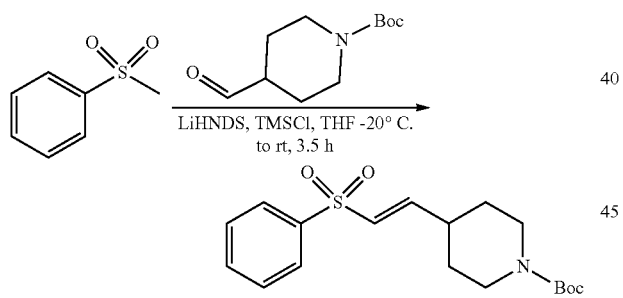

A solution of LiHMDS (1 M solution in THF, 384.6 mL, 384.6 mmol) was added dropwise to a solution of (methylsulfonyl)benzene (50 g, 320.5 mmol) in anhydrous THF (2.5 L) at −20° C. under nitrogen atmosphere. The reaction mixture was allowed to stir for 30 minutes at −20° C. followed by addition of TMSCl (48.8 ml, 99.2 mmol). The resulting mixture was slowly allowed to warm up to room temperature and stirred for another 3 hours. The reaction mixture was quenched by addition of saturated aqueous NH$_4$Cl (1 L) and extracted with EA (2×1 L). The combined organic layers were washed with brine (2 L), dried over anhydrous Na$_2$SO$_4$ and concentrated under vacuum to afford the product. The residue was purified by silica gel column chromatography, eluted with ethyl acetate in petroleum ether from 0% to 20% to afford the desired product tert-butyl (E)-4-(2-(phenylsulfonyl)vinyl)piperidine-1-carboxylate (32.0 g, 44.9% yield). LCMS (ESI-MS) m/z=352.1 [M+H]$^+$.

Step 2. tert-butyl 4-(2-(ethoxycarbonyl)-1H-pyrrol-3-yl)piperidine-1-carboxylate

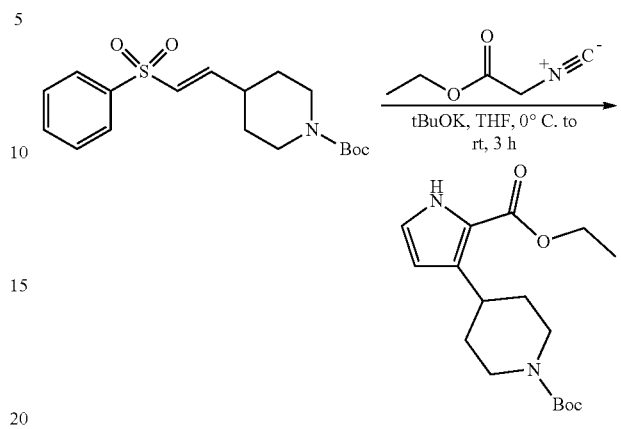

tBuOK (18.8 g, 168 mmol) was added to a solution of ethyl 2-isocyanoacetate (14.5 g, 128.18 mmol) in THF (320 mL) under nitrogen atmosphere. The resulting mixture was stirred at 0° C. for 30 minutes. Then a solution of tert-butyl 4-(2-(ethoxycarbonyl)-1H-pyrrol-3-yl)piperidine-1-carboxylate (32 g, 91.0 mmol) in THF (320 mL) was added to the mixture above. The resulting mixture was warmed to room temperature, stirred for 3 hours and quenched by the addition of saturated aqueous NH$_4$Cl (100 mL) at 0° C. The resulting mixture was extracted with ethyl acetate (3×250 mL). The combined organic layers were washed with brine (400 mL), dried over anhydrous Na$_2$SO$_4$ and concentrated under vacuum to afford the crude product. The residue was purified by silica gel column chromatography, eluted with ethyl acetate in petroleum ether from 0% to 20% to afford the desired product tert-butyl 4-(2-(ethoxycarbonyl)-1H-pyrrol-3-yl)piperidine-1-carboxylate (11.2 g, 38.1% yield). LCMS (ESI-MS) m/z=323.1 [M+H]$^+$.

Step 3. tert-butyl 4-(1-amino-2-(ethoxycarbonyl)-1H-pyrrol-3-yl)piperidine-1-carboxylate

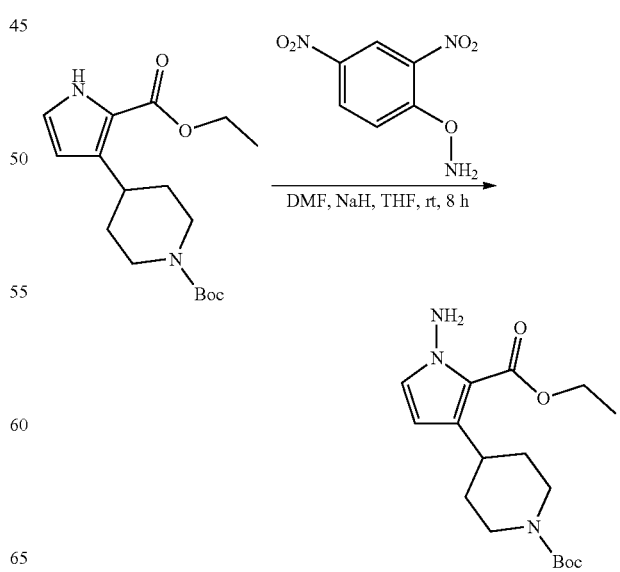

NaH (60% in mineral oil, 5.09 g, 127.17 mmol) in DMF (180 mL) was added to a solution of tert-butyl 4-(2-(ethoxycarbonyl)-1H-pyrrol-3-yl)piperidine-1-carboxylate (20 g, 62.03 mmol) in THF (900 mL) at 0° C. The resulting mixture was stirred for 1 hour at room temperature, followed by addition of O-(2,4-dinitrophenyl)hydroxylamine (23.47 g, 117.86 mmol) portionwise. The resulting mixture was stirred at room temperature for 8 hours, quenched by the addition of saturated aqueous NH$_4$Cl (300 mL) at 0° C. and extracted with ethyl acetate (3×500 mL). The combined organic layers were washed with brine (100 mL), dried over anhydrous Na$_2$SO$_4$ and concentrated under vacuum. The residue was purified by silica gel column chromatography, eluted with ethyl acetate in petroleum ether from 0% to 20% to afford the desired product tert-butyl 4-(1-amino-2-(ethoxycarbonyl)-1H-pyrrol-3-yl)piperidine-1-carboxylate (14 g, 66.8% yield). LCMS (ESI-MS) m/z=338.2 [M+H]$^+$.

Step 4. tert-butyl 4-(4-oxo-3,4-dihydropyrrolo[2,1-f][1,2,4]triazin-5-yl)piperidine-1-carboxylate

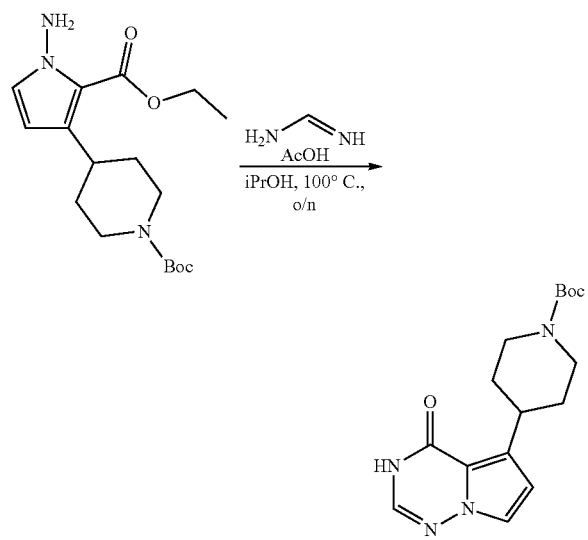

Formamidine acetate (14.62 g, 332 mmol) was added to a solution of tert-butyl 4-(1-amino-2-(ethoxycarbonyl)-1H-pyrrol-3-yl)piperidine-1-carboxylate (14 g, 41.49 mmol) in iPrOH (14 mL) at 25° C. The resulting mixture was stirred overnight at 100° C. After cooled to room temperature, the reaction mixture was quenched by the addition of water (100 mL) and extracted with ethyl acetate (3×100 mL). The combined organic layers were washed with brine (200 mL), dried over anhydrous Na$_2$SO$_4$ and concentrated under reduced pressure to afford the crude product. The residue was purified by silica gel column chromatography, eluted with ethyl acetate in petroleum ether from 0% to 50% to afford the desired product tert-butyl 4-(4-oxo-3,4-dihydropyrrolo[2,1-f][1,2,4] triazin-5-yl)piperidine-1-carboxylate (10.4 g, 92.0% yield). LCMS (ESI-MS) m/z=319.2 [M+H]$^+$. $^1$H NMR (400 MHz, DMSO-d$_6$) δ 11.47 (d, J=4.0 Hz, 1H), 7.72 (d, J=4.0 Hz, 1H), 7.46 (d, J=2.8 Hz, 1H), 6.45 (d, J=2.7 Hz, 1H), 4.05 (s, 2H), 3.33-3.34 (m, 1H), 2.79 (s, 2H), 1.83-1.74 (m, 2H), 1.51-1.25 (m, 2H), 1.41 (s, 9H).

Step 5. tert-butyl 4-(4-((4-([1,2,4]triazolo[1,5-a]pyridin-7-yloxy)-3-methylphenyl)amino)pyrrolo[2,1-f][1,2,4]triazin-5-yl)piperidine-1-carboxylate

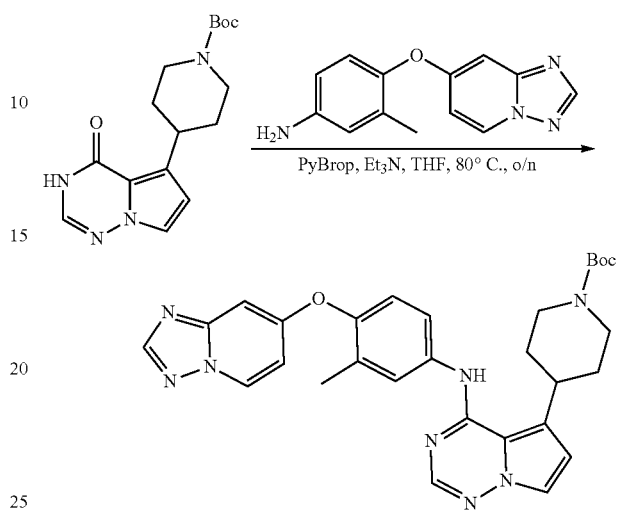

Et$_3$N (3.2 g, 31.5 mmol) was added to a mixture of tert-butyl 4-(4-oxo-3,4-dihydropyrrolo[2,1-f][1,2,4]triazin-5-yl)piperidine-1-carboxylate (3.2 g, 10.5 mmol), 4-([1,2,4]triazolo[1,5-a]pyridin-7-yloxy)-3-methylaniline (4.1 g, 10.5 mmol) and PyBrop (12 g, 25.8 mmol) in THF (50 mL). The resulting mixture was stirred at 80° C. overnight then cooled to room temperature. The reaction mixture was filtered, the filter cake was washed with DCM (300 mL). The filtrate was concentrated under vacuum to afford the crude product. The residue was purified by silica gel column chromatography, eluted with ethyl acetate in petroleum ether from 0% to 100% to afford the desired product tert-butyl 4-(4-((4-([1,2,4]triazolo[1,5-a]pyridin-7-yloxy)-3-methylphenyl)amino)pyrrolo[2,1-f][1,2,4]triazin-5-yl)piperidine-1-carboxylate (1.7 g, 31.1% yield). LCMS (ESI-MS) m/z=541.3 [M+H]$^+$. $^1$H NMR (400 MHz, DMSO-d$_6$) δ 8.94-8.92 (m, 1H), 8.47 (s, 1H), 8.38 (d, J=4.4 Hz, 1H), 7.90 (s, 1H), 7.72 (d, J=2.7 Hz, 1H), 7.66 (d, J=2.5 Hz, 1H), 7.61-7.60 (m, 1H), 7.22 (d, J=8.6 Hz, 1H), 7.16-6.99 (m, 1H), 6.79 (d, J=2.7 Hz, 1H), 4.12-4.03 (m, 4H), 3.56-3.55 (m, 1H), 3.17 (d, J=3.9 Hz, 1H), 2.19 (s, 3H), 2.12-2.01 (m, 2H), 1.95-1.87 (m, 2H), 1.41 (s, 9H).

Step 6. N-(4-([1,2,4]triazolo[1,5-a]pyridin-7-yloxy)-3-methylphenyl)-5-(piperidin-4-yl)pyrrolo[2,1-f][1,2,4]triazin-4-amine

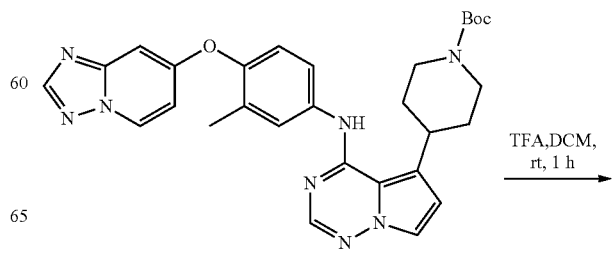

-continued

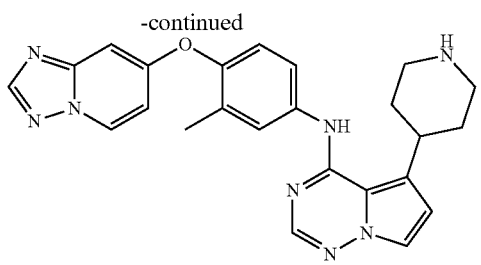

A solution of tert-butyl 4-(4-((4-([1,2,4]triazolo[1,5-a]pyridin-7-yloxy)-3-methylphenyl)amino)pyrrolo[2,1-f][1,2,4]triazin-5-yl)piperidine-1-carboxylate (1 g, 1.85 mmol) and TFA (5 mL) in DCM (5 mL) was stirred for 1 hour at room temperature. The resulting mixture was concentrated under vacuum to afford the crude product N-(4-([1,2,4]triazolo[1,5-a]pyridin-7-yloxy)-3-methylphenyl)-5-(piperidin-4-yl)pyrrolo[2,1-f][1,2,4]triazin-4-amine (1 g crude). LCMS (ESI-MS) m/z=441.2 [M+H]+.

Step 7. (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-bromobut-2-en-1-one

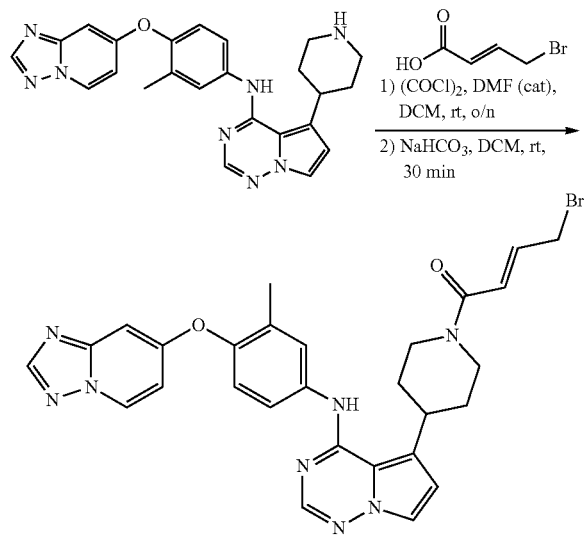

To a cold mixture (0° C.) of (E)-4-bromobut-2-enoic acid (1.46 g, 8.82 mmol) in DMF (0.1 mL) and DCM (15 mL) was added oxalyl chloride (2.42 g, 17.6 mmol) dropwise. The reaction mixture was stirred overnight at room temperature and concentrated under vacuum. The residue was dissolved in DCM (15 mL). The solution was added to a stirred mixture of N-(4-([1,2,4]triazolo[1,5-a]pyridin-7-yloxy)-3-methylphenyl)-5-(piperidin-4-yl)pyrrolo[2,1-f][1,2,4]triazin-4-amine (1 g, 2.27 mmol) and NaHCO3 (1.14 g, 13.5 mmol) in THF (20 mL). The resulting mixture was stirred for 30 minutes at room temperature and concentrated under vacuum to afford the crude product. The crude product was purified by silica gel column chromatography, eluted with DCM/MeOH (10:1 volume ratio) to afford the desired product (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-bromobut-2-en-1-one (800 mg, 73.6% yield for two steps). LCMS (ESI-MS) m/z=587.1 [M+H]+.

Step 8. (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-bromobut-2-en-1-one

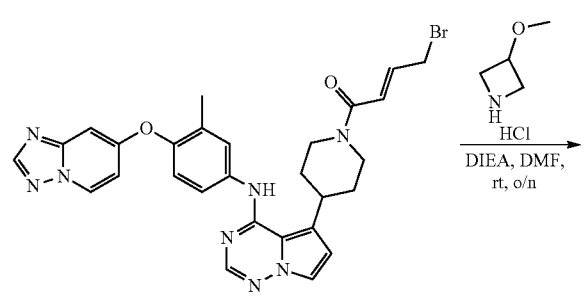

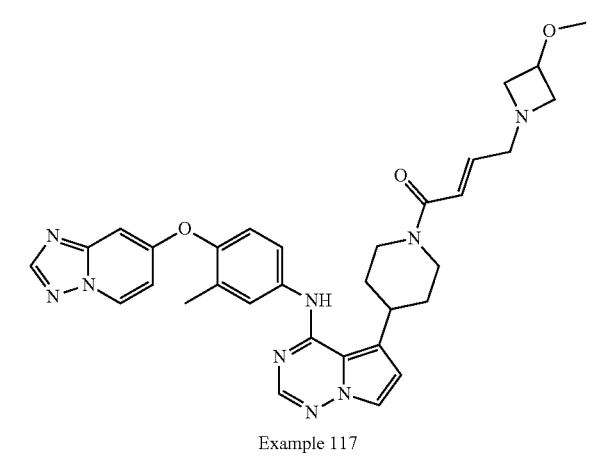

Example 117

Diisopropylethylamine (66 mg, 0.51 mmol) was added to a mixture of (E)-1-(4-(4-((4-([1,2,4]triazolo[1,5-a]-207-imidazol-7-yloxy)-3-methylphenyl)amino)pyrrolo[2,1-f][1,2,4]triazin-5-yl)piperidin-1-yl)-4-bromobut-2-en-1-one (100 mg, 0.17 mmol) and 3-methoxyazetidine hydrochloride (19 mg, 0.15 mmol) in DMF (1 mL). The resulting mixture was stirred overnight at room temperature. The reaction mixture was purified by Prep-HPLC; Mobile Phase A: Water (10 mmol/L NH4HCO3+0.05% NH3H2O), Mobile Phase B: ACN; Gradient: 24% B to 54% to afford the desired product (E)-1-(4-(4-((4-([1,2,4]triazolo[1,5-a]-207-midazol-7-yloxy)-3-methylphenyl)amino)pyrrolo[2,1-f][1,2,4]triazin-5-yl)piperidin-1-yl)-4-(3-methoxyazetidin-1-yl)but-2-en-1-one, Example 117 (14.4 mg, 13.6% yield). LCMS (ESI-MS) m/z=594.3 [M+H]+. 1H NMR (400 MHz, Chloroform-d) δ (ppm) 8.50-8.45 (m, 1H), 8.23 (s, 1H), 7.97 (s, 1H), 7.59-7.50 (m, 3H), 7.12 (d, J=8.6 Hz, 1H), 7.04 (s, 1H), 6.93-6.83 (m, 2H), 6.82-6.74 (m, 1H), 6.57 (d, J=2.8 Hz, 1H), 4.89 (s, 1H), 4.33 (s, 1H), 4.15 (s, 1H), 3.90 (s, 1H), 3.45 (d, J=7.1 Hz, 1H), 3.29 (s, 3H), 3.15 (s, 3H), 2.85 (s, 1H), 2.26 (s, 3H), 2.17-2.10 (m, 3H), 1.84-1.80 (m, 3H), 1.25 (s, 2H).

Example 118

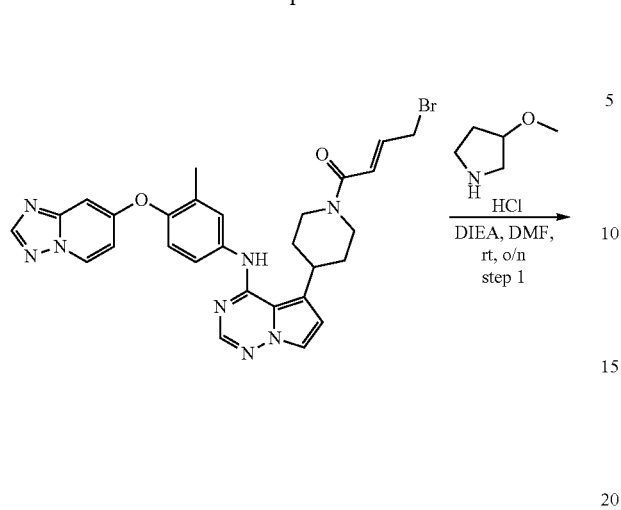

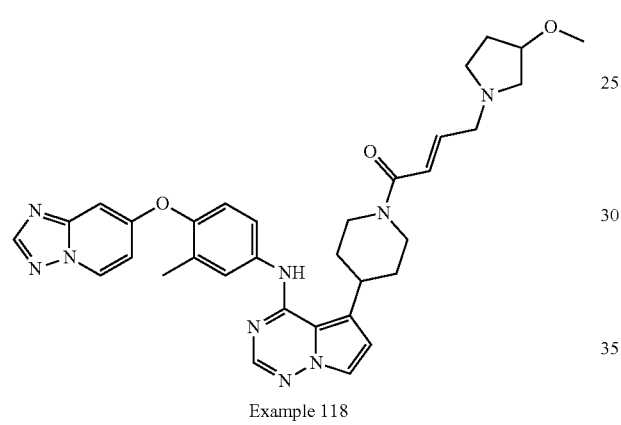

Example 118

E-1-(4-(4-((4-([1,2,4]triazolo[1,5-a]-207-midazol-7-yloxy)-3-methylphenyl)amino)pyrrolo[2,1-f][1,2,4]triazin-5-yl)piperidin-1-yl)-4-(3-methoxypyrrolidin-1-yl)but-2-en-1-one Example 118 was prepared using similar procedure as in preparation of Example 117, Step 8.

Example 119

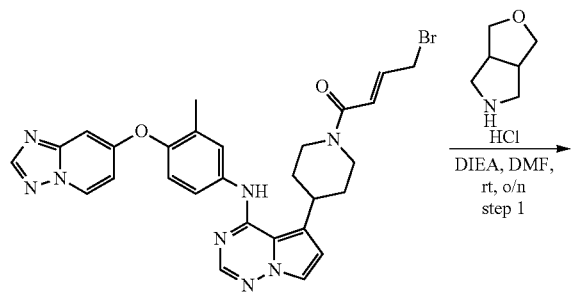

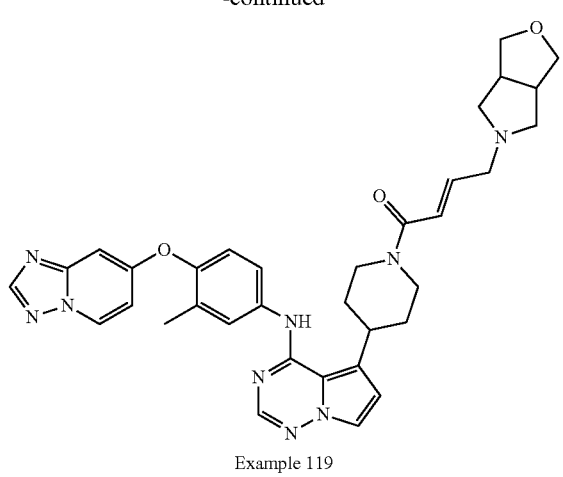

Example 119

E-1-(4-(4-((4-([1,2,4]triazolo[1,5-a]-208-midazol-7-yloxy)-3-methylphenyl)amino)pyrrolo[2,1-f][1,2,4]triazin-5-yl)piperidin-1-yl)-4-(tetrahydro-1H-furo[3,4-c]pyrrol-5(3H)-yl)but-2-en-1-one Example 119 was prepared using similar procedure as in preparation of example 117, Step 8.

Example 120

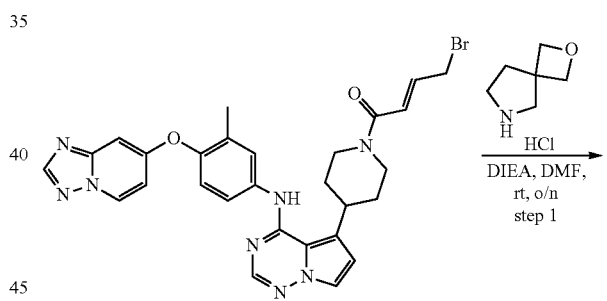

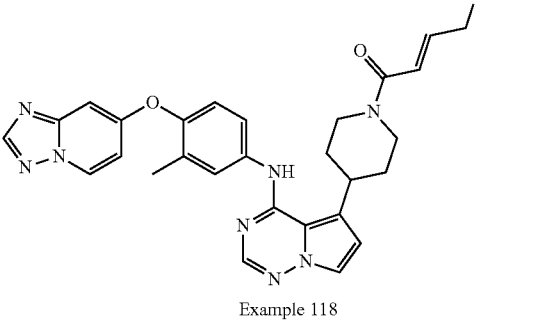

Example 118

E-1-(4-(4-((4-([1,2,4]triazolo[1,5-a]-208-midazol-7-yloxy)-3-methylphenyl)amino)pyrrolo[2,1-f][1,2,4]triazin-5-yl)piperidin-1-yl)-4-(2-oxa-6-azaspiro[3.4]octan-6-yl)but-2-en-1-one Example 120 was prepared using similar procedure as in preparation of Example 117, Step 8.

Example 121

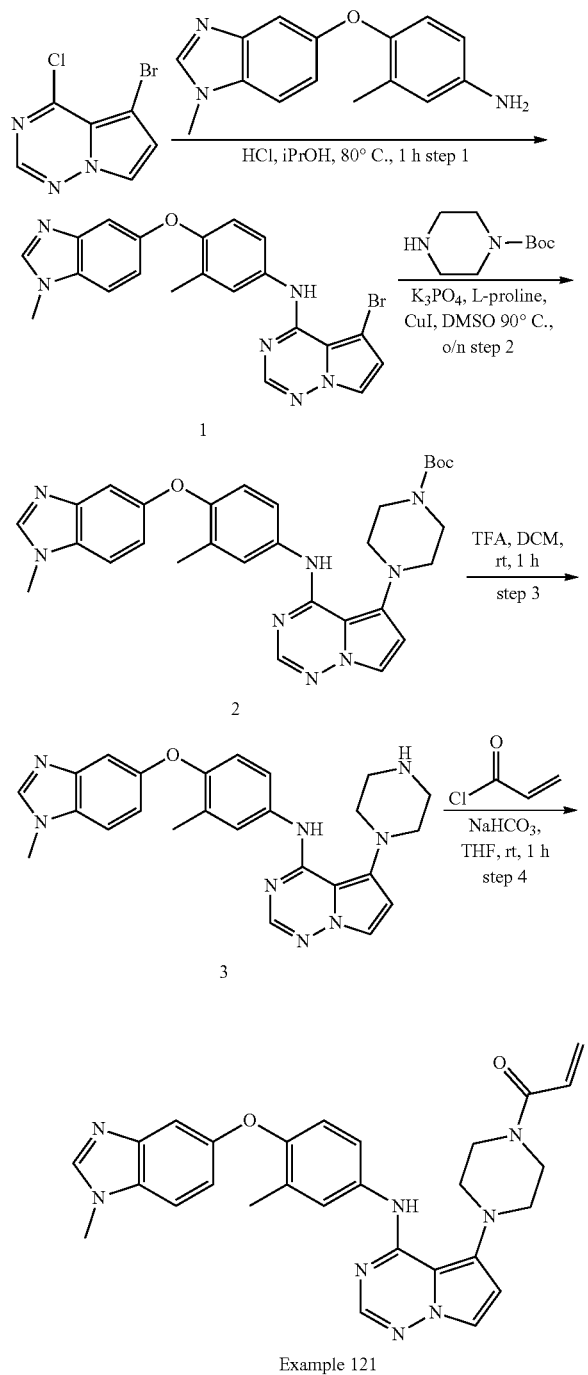

Example 121

Step 1. 5-bromo-N-(3-methyl-4-((1-methyl-1H-benzo[d]-209-midazole-5-yl)oxy)phenyl)pyrrolo[2,1-f][1,2,4]triazin-4-amine

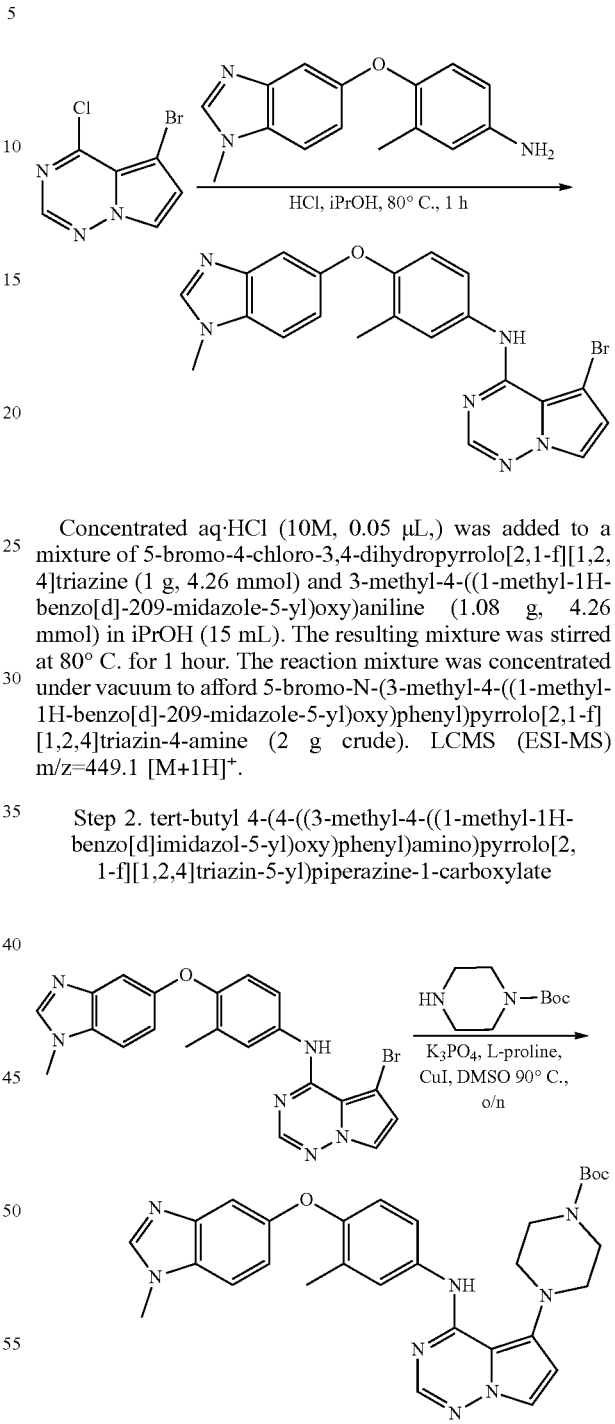

Concentrated aq·HCl (10M, 0.05 μL,) was added to a mixture of 5-bromo-4-chloro-3,4-dihydropyrrolo[2,1-f][1,2,4]triazine (1 g, 4.26 mmol) and 3-methyl-4-((1-methyl-1H-benzo[d]-209-midazole-5-yl)oxy)aniline (1.08 g, 4.26 mmol) in iPrOH (15 mL). The resulting mixture was stirred at 80° C. for 1 hour. The reaction mixture was concentrated under vacuum to afford 5-bromo-N-(3-methyl-1H-benzo[d]-209-midazole-5-yl)oxy)phenyl)pyrrolo[2,1-f][1,2,4]triazin-4-amine (2 g crude). LCMS (ESI-MS) m/z=449.1 [M+1H]⁺.

Step 2. tert-butyl 4-(4-((3-methyl-4-((1-methyl-1H-benzo[d]imidazol-5-yl)oxy)phenyl)amino)pyrrolo[2,1-f][1,2,4]triazin-5-yl)piperazine-1-carboxylate CuI (1.27 g, 6.67 mmol) was added to a mixture of 5-bromo-N-(3-methyl-4-((1-methyl-1H-benzo[d]imidazol-5-yl)oxy)phenyl)pyrrolo[2,1-f][1,2,4]triazin-4-amine (2.0 g, 4.45 mmol), tert-butyl piperazine-1-carboxylate (0.83 g, 4.45 mmol), K₃PO₄ (2.83 g, 13.35 mmol) and L-proline (0.61 g, 5.34 mmol) in DMSO (15 mL) under nitrogen atmosphere. The resulting mixture was stirred overnight at 90° C. The reaction mixture was purified by silica gel column chromatography, eluted with DCM/MeOH (10:1) to afford tert-butyl 4-(4-((3-methyl-4-((1-methyl-1H-benzo[d]imidazol-5-yl)oxy)phenyl)amino)pyrrolo[2,1-f][1,2,4]triazin-5-yl)piperazine-1-carboxylate (500 mg, 21.1% yield for two steps). LCMS (ESI-MS) m/z=555.3 [M+H]⁺.

Step 3. N-(3-methyl-4-((1-methyl-1H-benzo[d]imidazol-5-yl)oxy)phenyl)-5-(piperazin-1-yl)pyrrolo[2,1-f][1,2,4]triazin-4-amine

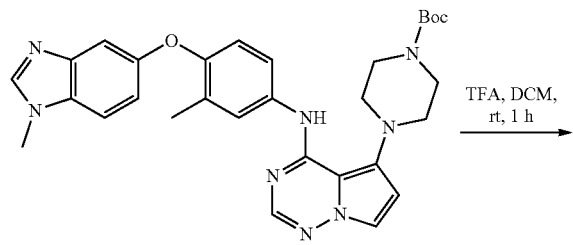

TFA (5 mL) was added to a solution of tert-butyl 4-(4-((3-methyl-4-((1-methyl-1H-benzo[d]imidazol-5-yl)oxy)phenyl) amino)pyrrolo[2,1-f][1,2,4]triazin-5-yl)piperazine-1-carboxylate (500 mg, 0.90 mmol) in DCM (5 mL). The resulting mixture was stirred at room temperature for 1 hour. The resulting mixture was concentrated under reduced pressure to afford N-(3-methyl-4-((1-methyl-1H-benzo[d]imidazol-5-yl)oxy)phenyl)-5-(piperazin-1-yl)pyrrolo[2,1-f][1,2,4]triazin-4-amine (480 mg crude). LCMS (ESI-MS) m/z=455.2 [M+H]⁺.

Step 4. 1-(4-(4-((3-methyl-4-((1-methyl-1H-benzo[d]imidazol-5-yl)oxy)phenyl)amino)pyrrolo[2,1-f][1,2,4]triazin-5-yl)piperazin-1-yl)prop-2-en-1-one

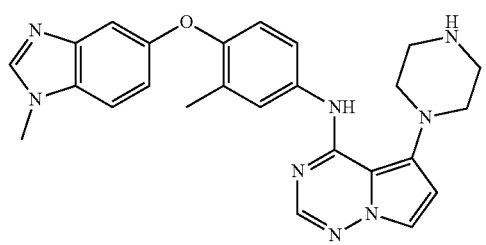

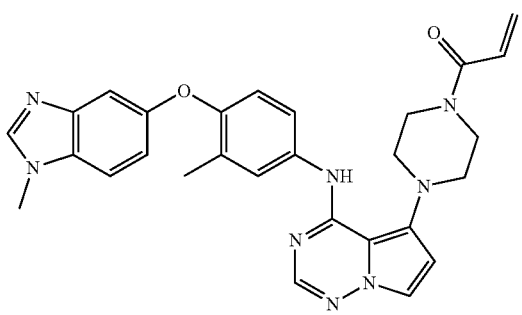

Acryloyl chloride (20 mg, 0.22 mmol) was added to a mixture of N-(3-methyl-4-((1-methyl-1H-benzo[d]imidazol-5-yl)oxy)phenyl)-5-(piperazin-1-yl)pyrrolo[2,1-t][1,2,4]triazin-4-amine (100 mg, 0.22 mmol) and NaHCO₃ (55 mg, 0.44 mg) in THF (1 mL). The resulting mixture was stirred at room temperature for 1 hour. The reaction mixture was purified by Prep-HPLC, Mobile Phase A: Water (10 mmol/L NH₄HCO₃), Mobile Phase B: ACN; Gradient: 20% B to 50% B to afford the desired product 1-(4-(4-((3-methyl-4-((1-methyl-1H-benzo[d]imidazol-5-yl)oxy)phenyl)amino)pyrrolo[2,1-f][1,2,4]triazin-5-yl)piperazin-1-yl)prop-2-en-1-one, Example 121 (8.5 mg, 7.5% yield). LCMS (ESI-MS) m/z=509.2 [M+H]⁺. ¹H NMR (400 MHz, Chloroform-d) δ (ppm) 9.63 (s, 1H), 8.22 (s, 1H), 7.97 (s, 1H), 7.70 (s, 1H), 7.54 (d, J=8.6 Hz, 1H), 7.45 (d, J=2.8 Hz, 1H), 7.41 (s, 1H), 7.15 (d, J=8.7 Hz, 1H), 6.96 (d, J=8.7 Hz, 1H), 6.65 (dd, J=16.8, 10.5 Hz, 1H), 6.59 (d, J=2.8 Hz, 1H), 6.43-6.34 (m, 1H), 5.79 (dd, J=10.6, 1.9 Hz, 1H), 4.86 (s, 2H), 4.15 (s, 1H), 3.94 (s, 3H), 3.51 (s, 2H), 3.23 (s, 2H), 2.98 (s, 2H), 2.32 (s, 3H).

Examples 122 and 123

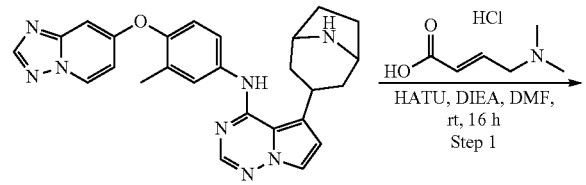

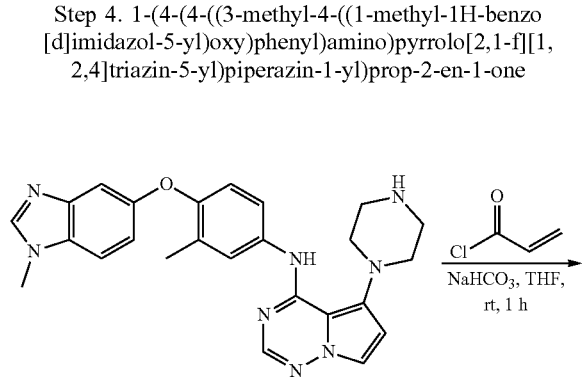

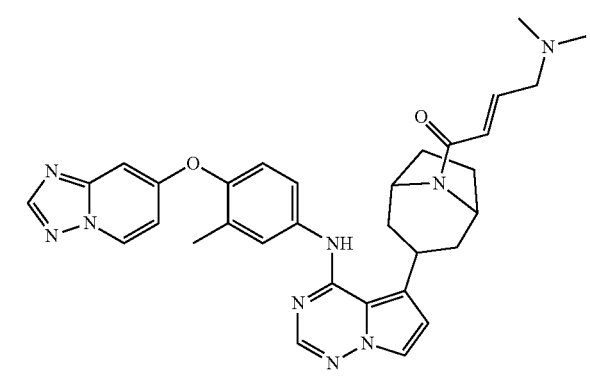

-continued

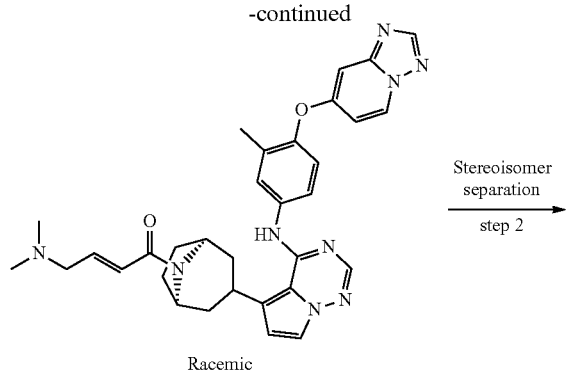

Racemic

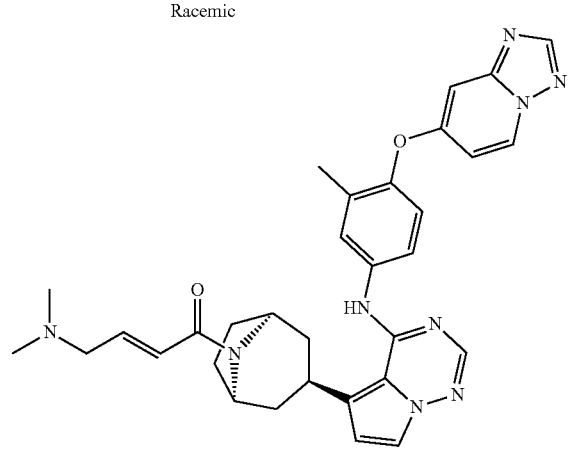

Example 122

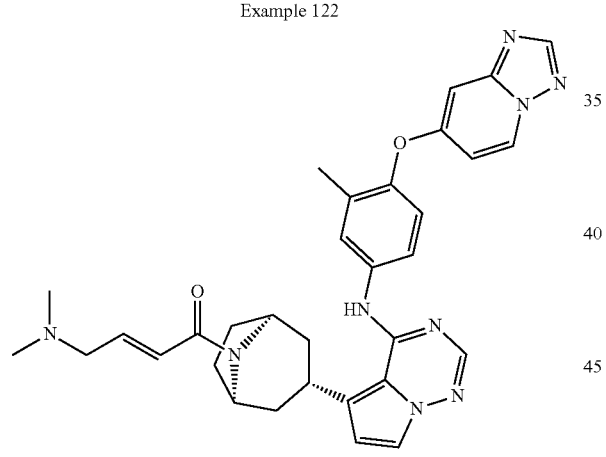

Example 123

Step 1. (E)-1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-4-(dimethylamino)but-2-en-1-one

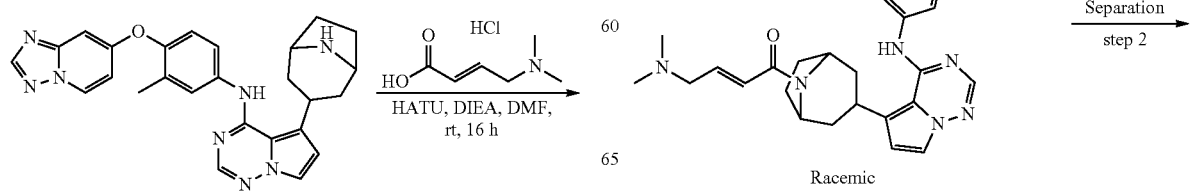

-continued

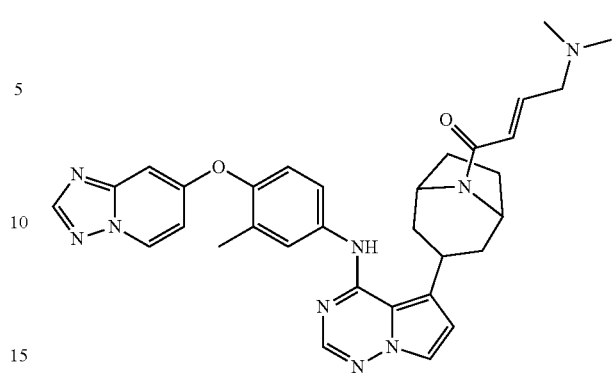

To a solution of N-(4-([1,2,4]triazolo[1,5-a]pyridin-7-yloxy)-3-methylphenyl)-5-(8-azabicyclo[3.2.1]octan-3-yl)pyrrolo[2,1-f][1,2,4]triazin-4-amine (800 mg, 1.72 mmol) in DMF (5 mL) was added (2E)-4-(dimethylamino)but-2-enoic acid hydrochloride (221.47 mg, 1.72 mmol), HATU (978 mg, 2.58 mmol) and diisopropylethylamine (665 mg, 5.15 mmol). The resulting solution was stirred at room temperature for 16 hours. The residue was purified by reversed-phase flash chromatography, mobile phase, MeCN in Water (10 mmol/L $NH_4HCO_3$), 10% to 50% gradient to give (E)-1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-4-(dimethylamino)but-2-en-1-one (160 mg, 15.8% yield). LCMS (ESI-MS) m/z=578.3 $[M+H]^+$.

Step 2. (E)-1-((1R,3r,5S)-3-(4-((4-([1,2,4]triazolo[1,5-a]pyridin-7-yloxy)-3-methylphenyl)amino)pyrrolo-[2,1-f][1,2,4]triazin-5-yl)-8-azabicyclo[3.2.1]octan-8-yl)-4-(dimethylamino)but-2-en-1-one (Example 122) & (E)-1-((1R,3s,5S)-3-(4-((4-([1,2,4]triazolo[1,5-a]pyridin-7-yloxy)-3-methylphenyl)amino)pyrrolo-[2,1-f][1,2,4]triazin-5-yl)-8-azabicyclo[3.2.1]octan-8-yl)-4-(dimethylamino)but-2-en-1-one Example 123

-continued

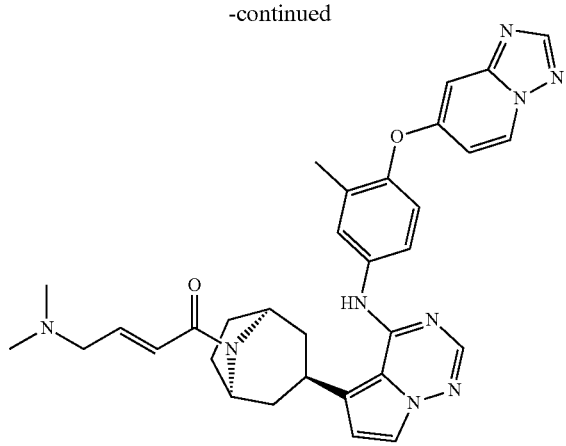

Example 122

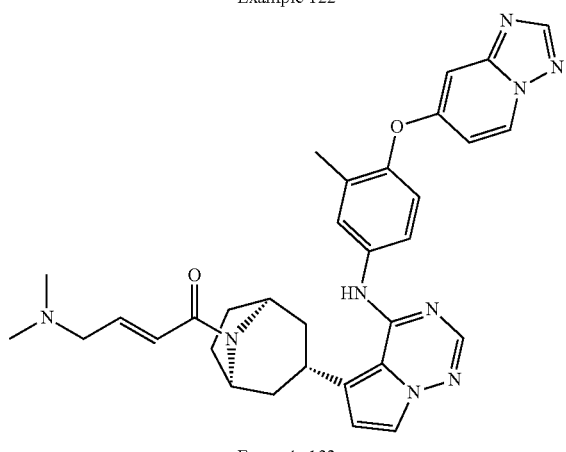

Example 123

(E)-1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-4-(dimethylamino)but-2-en-1-one (160 mg, 0.277 mmol) was purified with Prep-HPLC using the following conditions: Column: XBridge Prep OBD C18 Column, 30*150 mm, 5 μm; Mobile Phase A: Water (10 mmol/L NH4HCO3), Mobile Phase B: ACN; Flow rate: 60 mL/min mL/min; Gradient: 25% B to 55% B in 7 min; Wave Length: 254 nm/220 nm nm; RT1 (min): 6.3. The desired fractions were combined and lyophilized to afford the two desired separated isomers Examples 122 and 123:
First eluting isomer of (E)-1-(-3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-4-(dimethylamino)but-2-en-1-one
(31.5 mg, 39.4% yield). LCMS (ESI-MS) m/z=578.3 [M+H]+. 1H NMR (400 MHz, DMSO-d6) δ (ppm) 8.95-8.92 (m, 1H), 8.68 (s, 1H), 8.39 (s, 1H), 7.96 (s, 1H), 7.78-7.64 (m, 2H), 7.42-6.68 (m, 4H), 6.64-6.29 (m, 3H), 4.62-4.52 (m, 2H), 4.21-3.91 (m, 1H), 3.06 (s, 2H), 2.19-2.13 (m, 9H), 2.06-1.97 (m, 4H), 1.90-1.79 (m, 3H), 1.63-1.54 (in, 1H).

Cell growth inhibition activity of first eluting isomer based on assays described for Table 3:

|  | HER2 | EGFR |
|---|---|---|
| HER2 - YVMA IC50 (nM) | WT IC50 (nM) | WT IC50 (nM) |
| ++++ | ++++ | ++ |

Second eluting isomer of (E)-1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-4-(dimethylamino)but-2-en-1-one (21.1 mg, 26.4% yield). LCMS (ESI-MS) m/z=578.3 [M+H]+. 1H NMR (400 MHz, DMSO-d6) δ (ppm) 8.95-8.92 (m, 1H), 8.39 (s, 1H), 8.10 (s, 1H), 7.94 (s, 1H), 7.76-7.73 (m, 2H), 7.41-6.87 (m, 3H), 6.84-6.52 (m, 4H), 4.61-4.33 (m, 2H), 3.36 (s, 1H), 2.98-2.80 (m, 2H), 2.56-2.54 (m, 1H), 2.46-2.42 (m, 1H), 2.18-2.12 (m, 31H), 2.08-1.99 (m, 6H), 1.97-1.87 (m, 1H), 1.85-1.81 (m, 1H), 1.77-1.69 (m, 4H).

Cell growth inhibition activity of second eluting isomer based on assays described for Table 3:

|  | HER2 | EGFR |
|---|---|---|
| HER2 - YVMA IC50 (nM) | WT IC50 (nM) | WT IC50 (nM) |
| +++ | ++++ | + |

Examples 124 and 125

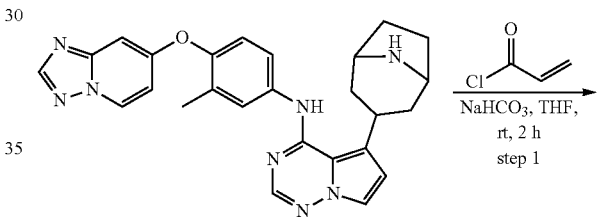

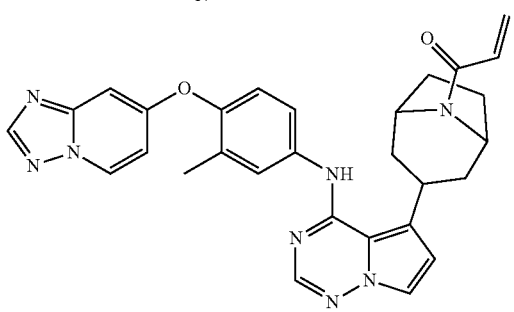

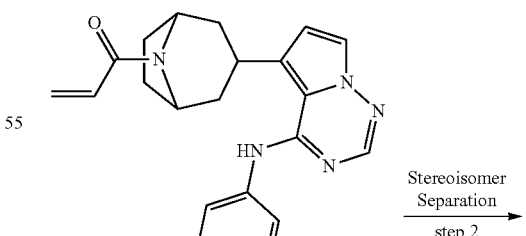

Racemic

-continued

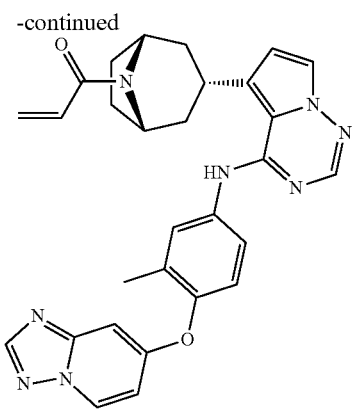

Example 124

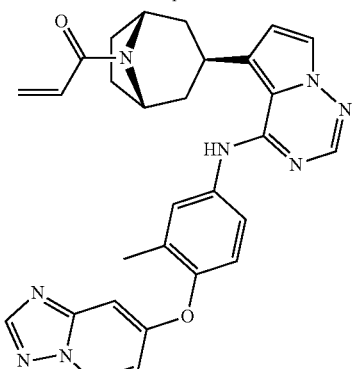

Example 125

Step 1. 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)prop-2-en-1-one

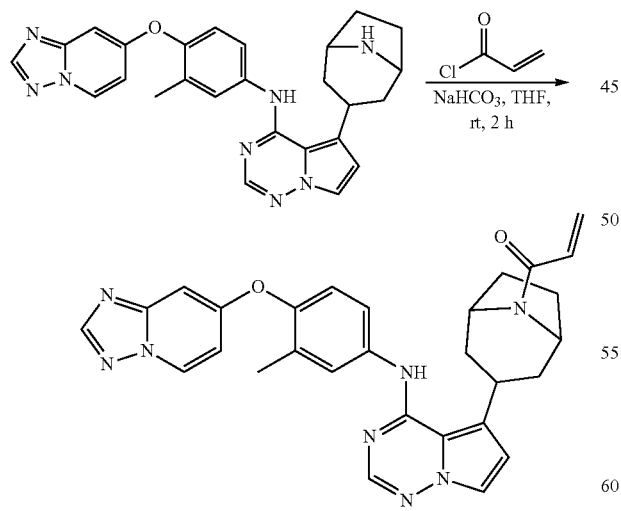

To a solution of N-(4-([1,2,4]triazolo[1,5-a]pyridin-7-yloxy)-3-methylphenyl)-5-(8-azabicyclo[3.2.1]octan-3-yl)pyrrolo[2,1-f][1,2,4]triazin-4-amine (600 mg, 1.29 mmol) in water (3 mL) and THF (3 mL) was added acryloyl chloride (116 mg, 1.29 mmol) and sodium bicarbonate (324 mg, 3.86 mmol). The resulting solution was stirred at room temperature for 2 hours. The mixture was evaporated and purified with silica gel column (ethyl acetate/petroleum ether=1:1) to give 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)prop-2-en-1-one (400 mg, 38.2% yield). LCMS (ESI-MS) m/z=521.5 [M+H]$^+$.

Step 2. 1-((1R,3r,5S)-3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)prop-2-en-1-one (Example 124) & 1-((1R,3s,5S)-3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)prop-2-en-1-one (Example 125)

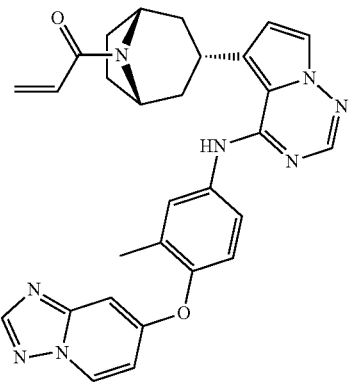

Racemic

Chiral Separation
step 2

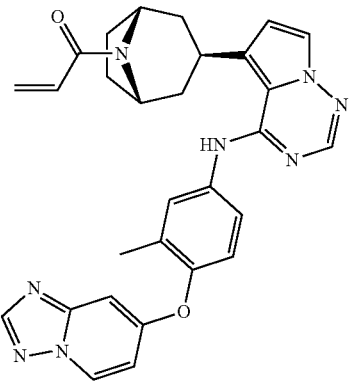

Example 124

Example 125

The racemate 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)prop-2-en-1-one (400 mg, 0.768 mmol) was purified by Prep-HPLC using the following conditions: Column: XselectCSH Prep OBD C18 Column, 30*150 mm, 5 μm; Mobile Phase A: Water (0.1% FA), Mobile Phase B: ACN; Flow rate: 60 mL/min mL/min; Gradient: 38% B to 53% B in 8 min; Wave Length: 254 nm/220 nm nm; RT1(min): 6.05; 7.03. The desired fractions were combined and lyophilized to afford the two desired separated isomers Examples 124 and 125:

First eluting isomer of 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)prop-2-en-1-one (52.9 mg, 13.03% yield). LCMS (ESI-MS) m/z=521.2 [M+H]$^+$. $^1$H NMR (400 MHz, DMSO-d$_6$) δ (ppm) 8.95-8.93 (m, 1H), 8.69 (s, 1H), 8.39 (s, 1H), 7.96-7.65 (m, 3H), 7.26-6.64 (m, 6H), 6.39-6.16 (m, 1H), 5.69-5.67 (m, 1H), 4.62-4.56 (m, 2H), 4.22-3.90 (m, 1H), 2.19 (s, 3H), 2.14-1.79 (m, 7H), 1.70-1.55 (m, 1H).

Second eluting isomer of 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)prop-2-en-1-one (44.1 mg, 10.91% yield). LCMS (ESI-MS) m/z=521.2 [M+H]$^+$. $^1$H NMR (400 MHz, DMSO-d$_6$) δ (ppm) 8.95-8.93 (m, 1H), 8.38 (s, 1H), 8.11 (s, 1H), 7.95-7.69 (m, 3H), 7.41-6.39 (m, 6H), 6.29-6.04 (m, 1H), 5.71-5.51 (m, 1H), 4.61-4.40 (m, 2H), 3.40-3.35 (m, 1H), 2.53-2.51 (m, 1H), 2.48-2.31 (m, 1H), 2.19-2.03 (m, 3H), 2.02-1.97 (m, 1H), 1.91-1.71 (m, 5H).

Cell growth inhibition activity of first eluting isomer based on assays described for Table 3:

| HER2 - YVMA IC$_{50}$ (nM) | HER2 WT IC$_{50}$ (nM) | EGFR WT IC$_{50}$ (nM) |
|---|---|---|
| ++++ | ++++ | ++++ |

Examples 126 and 127

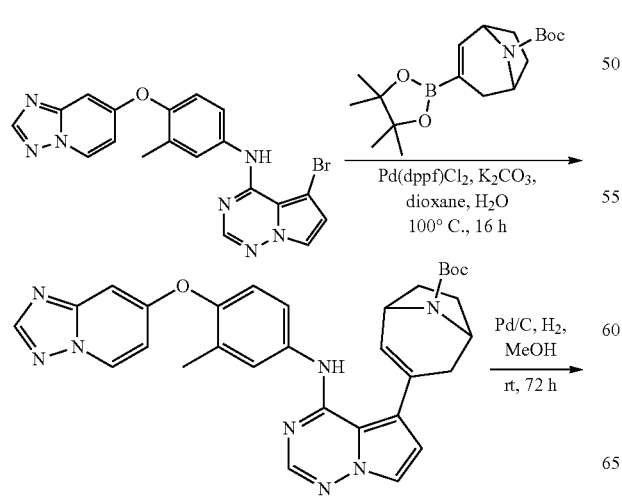

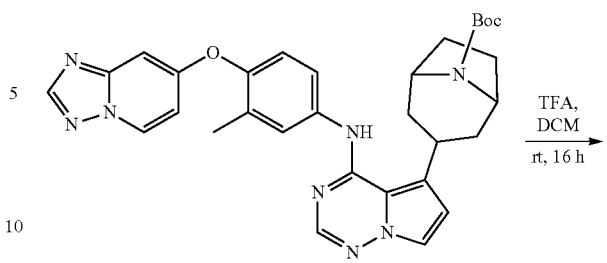

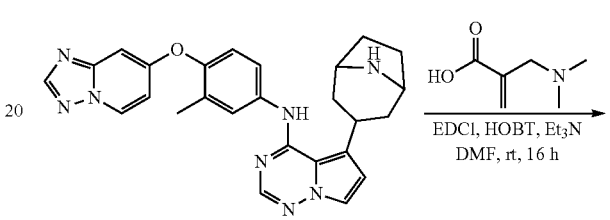

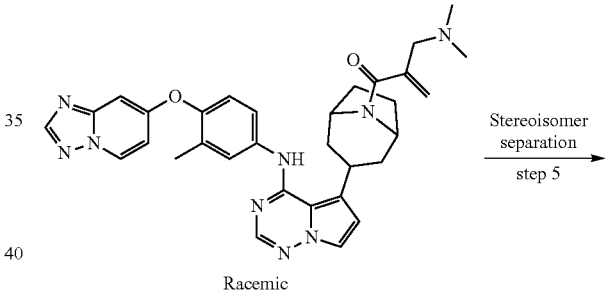

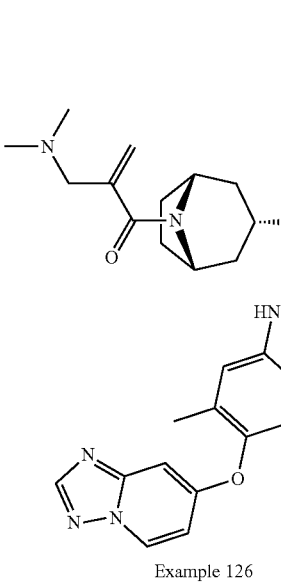

Example 126

277
-continued

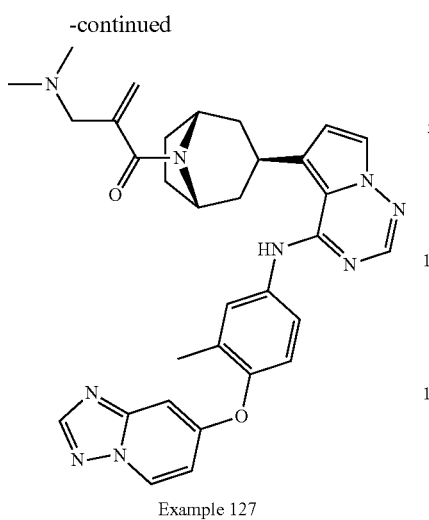

Example 127

Step 1. tert-butyl 3-(4-((4-([1,2,4]triazolo[1,5-a]
pyridin-7-yloxy)-3-methylphenyl)amino)pyrrolo[2,
1-f][1,2,4]triazin-5-yl)-8-azabicyclo[3.2.1]oct-2-ene-
8-carboxylate

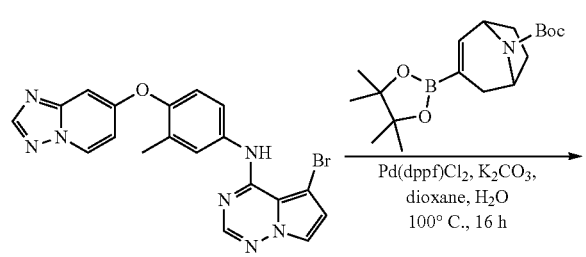

To a solution of N-(4-([1,2,4]triazolo[1,5-a]pyridin-7-yloxy)-3-methylphenyl)-5-bromopyrrolo[2,1-f][1,2,4]triazin-4-amine (5.0 g, 11.5 mmol) in 1,4-dioxane (50 mL, 573.1 mmol) and water (15 mL, 172 mmol) was added tert-butyl 3-(4,4,5,5-tetramethyl-1,3,2-dioxaborolan-2-yl)-8-azabicyclo[3.2.1]oct-2-ene-8-carboxylate (4.23 g, 12.6 mmol), potassium carbonate (4.75 g, 34.4 mmol) and Pd(dppf)Cl₂ (0.93 g, 1.15 mmol). The resulting solution was stirred at 100° C. for 16 hours. The residue was evaporated and purified by silica gel column (ethyl acetate/petroleum ether 1:1) to give tert-butyl 3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]oct-2-ene-8-carboxylate (4.5 g, 67.5% yield). LCMS (ESI-MS) m/z=565.5 [M+H]⁺.

278

Step 2. tert-butyl 3-(4-((4-([1,2,4]triazolo[1,5-a]
pyridin-7-yloxy)-3-methylphenyl)amino)pyrrolo[2,
1-f][1,2,4]triazin-5-yl)-8-azabicyclo[3.2.1]octane-8-
carboxylate

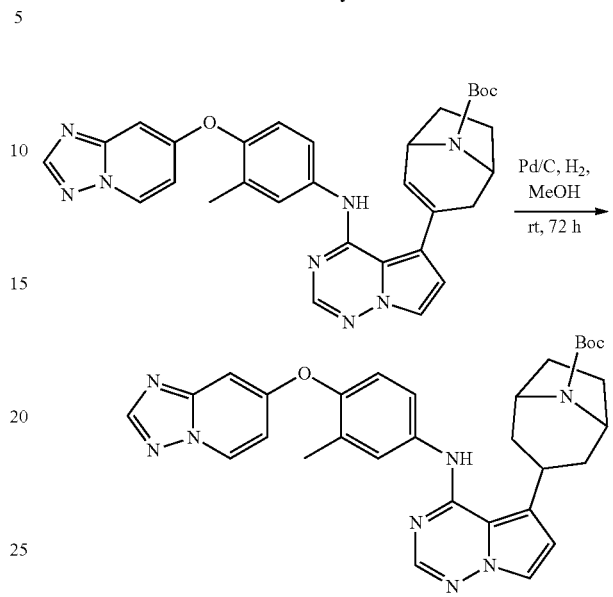

To a solution of tert-butyl 3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]oct-2-ene-8-carboxylate (4.2 g, 7.44 mmol) in methanol (80 mL) was added Pd/C (10% on carbon, 400 mg). The mixture was degassed under vacuum and charged with hydrogen at 3.5 atm and stirred at room temperature for 72 hours. The resulting solution was filtered. The filtrate was evaporated to give tert-butyl 3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octane-8-carboxylate (3 g, 64.2% yield). LCMS (ESI-MS) m/z=567.6 [M+H]⁺.

Step 3. N-(4-([1,2,4]triazolo[1,5-a]pyridin-7-yloxy)-
3-methylphenyl)-5-(8-azabicyclo[3.2.1]octan-3-yl)
pyrrolo[2,1-f][1,2,4]triazin-4-amine

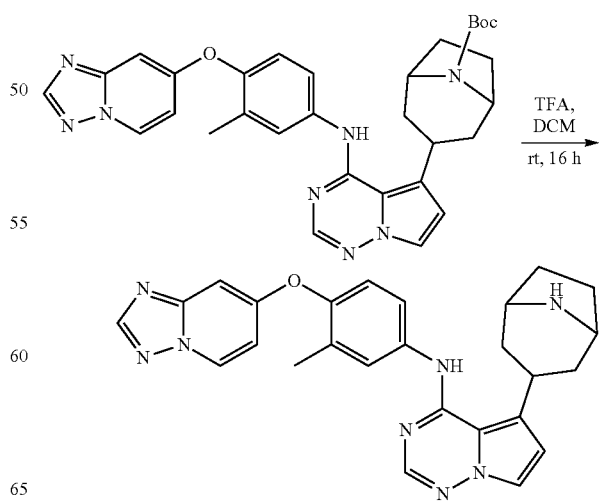

To a solution of tert-butyl 3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octane-8-carboxylate (3 g, 5.29 mmol) in DCM (30 mL) was added TFA (3.02 g, 26.5 mmol). The resulting solution was stirred at room temperature for 16 hours. The residue was evaporated to give N-(4-([1,2,4]triazolo[1,5-a]pyridin-7-yloxy)-3-methylphenyl)-5-(8-azabicyclo[3.2.1]octan-3-yl)pyrrolo[2,1-f][1,2,4]triazin-4-amine (1.9 g crude). LCMS (ESI-MS) m/z=467.2 [M+H]$^+$.

Step 4. 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-2-((dimethylamino)methyl)prop-2-en-1-one

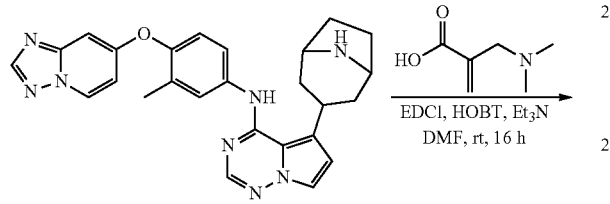

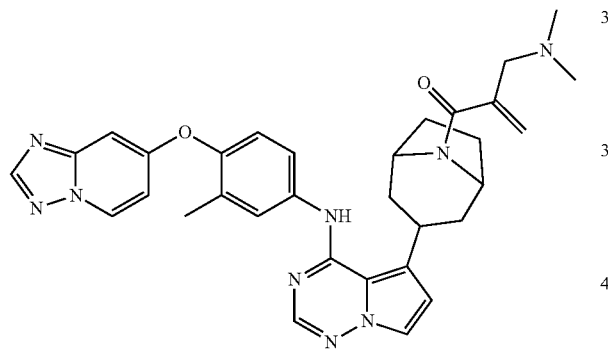

To a solution of N-(4-([1,2,4]triazolo[1,5-a]pyridin-7-yloxy)-3-methylphenyl)-5-(8-azabicyclo[3.2.1]octan-3-yl)pyrrolo[2,1-f][1,2,4]triazin-4-amine (700 mg, 1.5 mmol) in DMF (5 mL) was added 2-[(dimethylamino)methyl]prop-2-enoic acid (213 mg, 1.65 mmol), EDCl (345 mg, 1.8 mmol), HOBT (243 mg, 1.8 mmol) and TEA (455 mg, 4.5 mmol). The resulting solution was stirred at room temperature for 16 hours. The residue was purified by reversed-phase flash chromatography; mobile phase: MeCN in Water (10 mmol/L NH$_4$HCO$_3$), 10% to 50% gradient to give 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-2-((dimethylamino)methyl)prop-2-en-1-one (160 mg, 18% yield). LCMS (ESI-MS) m/z=578.6 [M+H]$^+$. Step 5. 1-((1R,3r,5S)-3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-2-((dimethylamino)methyl)prop-2-en-1-one (Example 126) & 1-((1R,3s,5S)-3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-2-((dimethylamino)methyl)prop-2-en-1-one (Example 127)

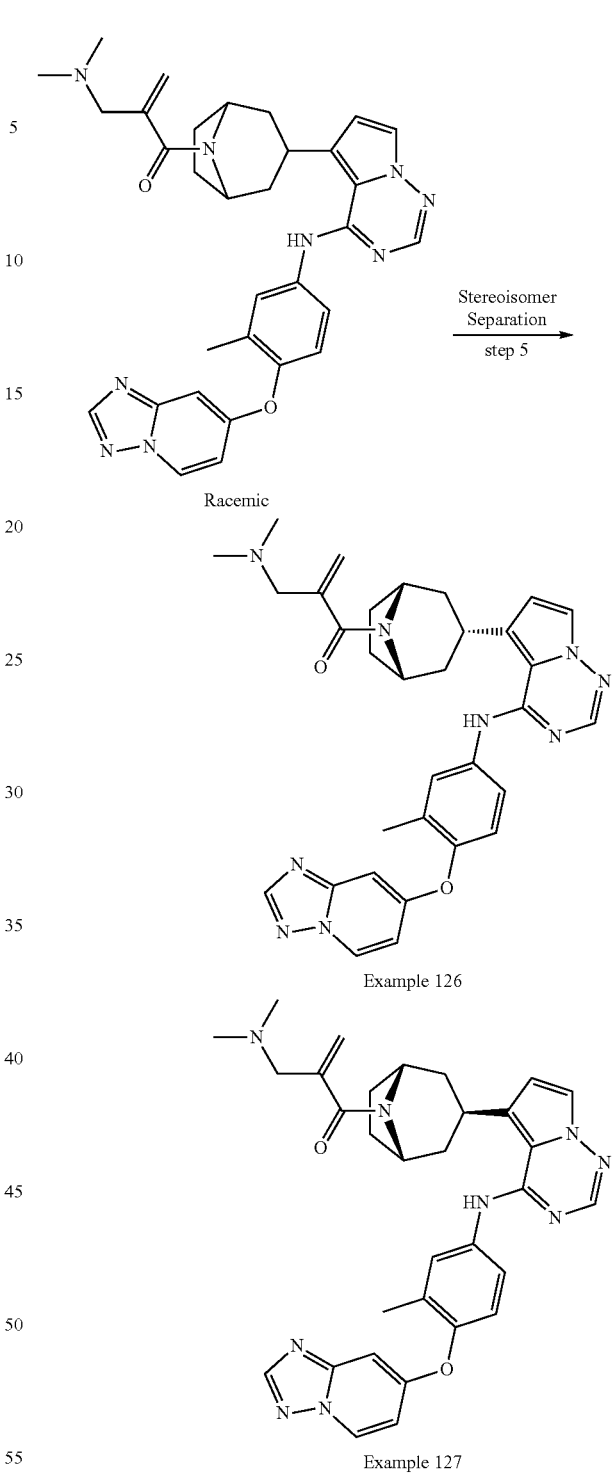

The racemate 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-2-((dimethylamino)methyl)prop-2-en-1-one (160 mg, 0.277 mmol) was purified with prep-HPLC using the following conditions: Column: XBridge Prep OBD C18 Column, 19*250 mm, 5 μm; Mobile Phase A: Water (10 mmol/L NH$_4$HCO$_3$+0.05% NH$_3$·H$_2$O), Mobile Phase B: ACN; Flow rate: 25 mL/min mL/min; Gradient: 24% B to 54% B in 18 min; Wave Length: 254 nm/220 nm nm; RT1(min): 17.3. The desired fractions were combined and lyophilized to afford the two desired separated isomers Examples 126 and 127:

First eluting isomer of 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-2-((dimethylamino)methyl)prop-2-en-1-one (11.0 mg, 6.3% yield). LCMS (ESI-MS) m/z=578.3 [M+H]⁺. ¹H NMR (400 MHz, DMSO-d₆) δ (ppm) 8.95-8.93 (m, 1H), 8.54 (s, 1H), 8.39 (s, 1H), 7.95 (s, 1H), 7.79-7.67 (m, 3H), 7.25-6.69 (m, 5H), 5.37 (s, 1H), 5.07 (s, 1H), 3.64-3.58 (m, 1H), 3.25-3.21 (m, 2H), 3.10 (s, 1H), 3.00 (s, 3H), 2.86 (s, 3H), 2.19-2.07 (m, 3H), 2.06-1.96 (m, 2H), 1.87-1.71 (m, 6H).

Cell growth inhibition activity of first eluting isomer based on assays described for Table 3:

| HER2 - YVMA IC₅₀ (nM) | HER2 WT IC₅₀ (nM) | EGFR WT IC₅₀ (nM) |
|---|---|---|
| +++ | ++++ | + |

Second eluting isomer of 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-2-((dimethylamino)methyl)prop-2-en-1-one (10.9 mg, 6.8% yield). LCMS (ESI-MS) m/z=578.3 [M+H]⁺. ¹H NMR (400 MHz, DMSO-d₆) δ (ppm) 8.95-8.93 (m, 1H), 8.39 (s, 1H), 8.24 (s, 1H), 7.91 (s, 1H), 7.70-7.68 (m, 2H), 7.37-6.77 (m, 5H), 5.42-5.19 (m, 1H), 5.17-4.95 (m, 1H), 3.73-3.68 (m, 1H), 3.30-3.11 (m, 2H), 3.05-2.67 (m, 7H), 2.63 (s, 1H), 2.49-2.35 (m, 2H), 2.19-2.12 (m, 3H), 2.07-1.92 (m, 2H), 1.57-1.23 (m, 4H).

Cell growth inhibition activity of second eluting isomer based on assays described for Table 3:

| HER2 - YVMA IC₅₀ (nM) | HER2 WT IC₅₀ (nM) | EGFR WT IC₅₀ (nM) |
|---|---|---|
| ++ | ++++ | + |

Example 128

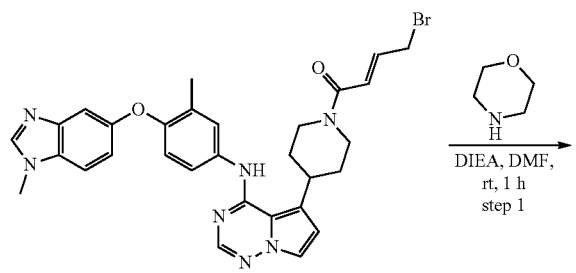

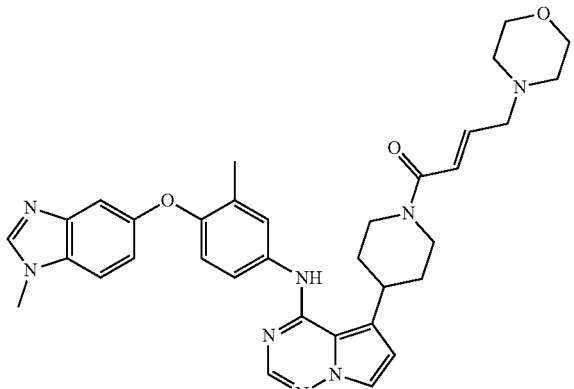

Example 128

(E)-1-(4-(4-(4-((3-methyl-4-((1-methyl-1H-benzo[d]imidazol-5-yl)oxy)phenyl)amino)-pyrrolo[2,1-f][1,2,4]triazin-5-yl)piperidin-1-yl)-4-morpholinobut-2-en-1-one Example 128 was prepared using similar procedure as in preparation of Example 105, Step 2.

Example 129

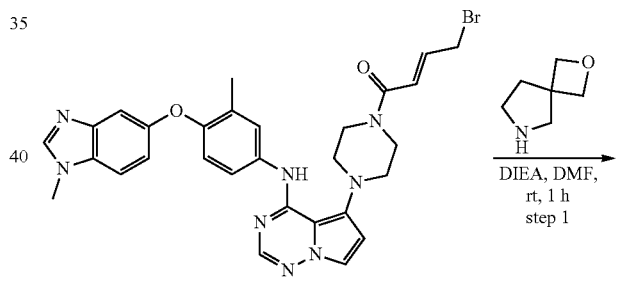

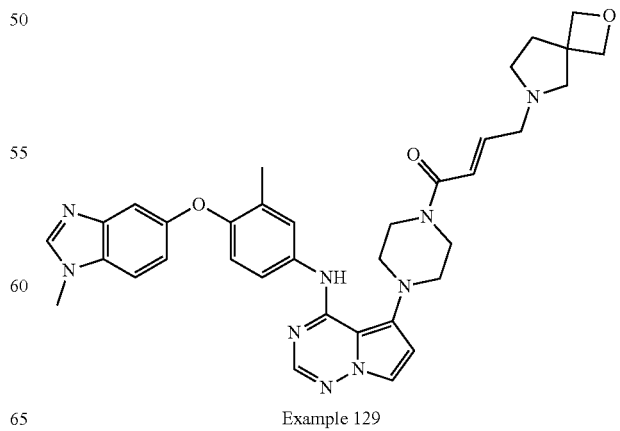

Example 129

(E)-1-(4-(4-((3-methyl-4-((1-methyl-1H-benzo[d]
imidazol-5-yl)-oxy)phenyl)amino)-pyrrolo[2,1-f][1,
2,4]triazin-5-yl)piperidin-1-yl)-4-(2-oxa-6-azaspiro
[3.4]octan-6-yl)but-2-en-1-one Example 129 was prepared using similar procedure as in preparation of Example 105, Step 2.

Example 130

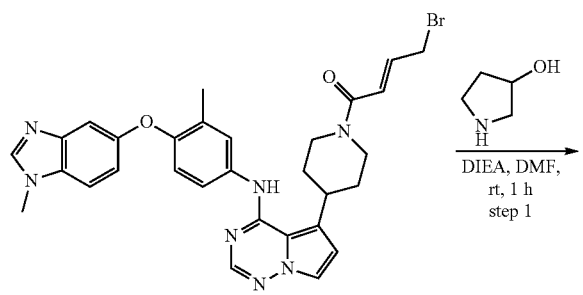

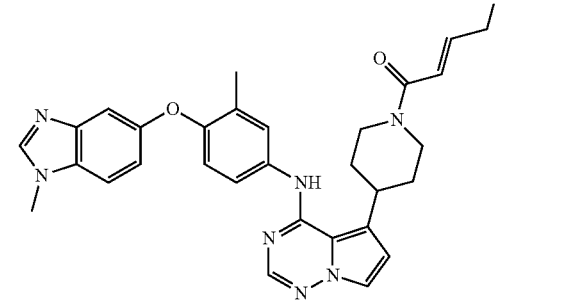

Example 130

(E)-4-(3-hydroxypyrrolidin-1-yl)-1-(4-(4-((3-methyl-
4-((1-methyl-1H-benzo[d]imidazol-5-yl)oxy)phenyl)
amino)pyrrolo[2,1-f][1,2,4]-triazin-5-yl)piperidin-1-
yl)but-2-en-1-one Example 130 was prepared using similar procedure as in preparation of Example 105, Step 2.

Example 131

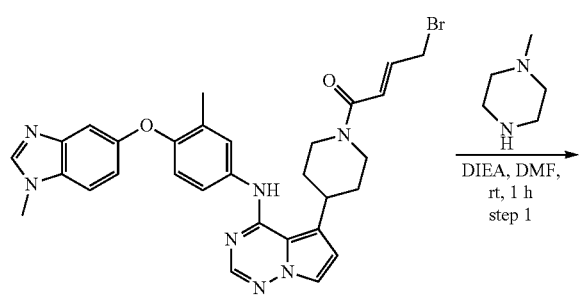

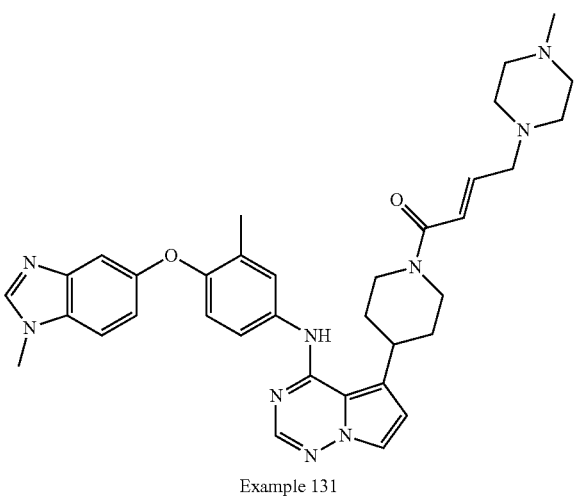

Example 131

(E)-1-(4-(4-((3-methyl-4-((1-methyl-1H-benzo[d]
imidazol-5-yl)oxy)phenyl)-amino)pyrrolo[2,1-f][1,2,
4]triazin-5-yl)piperidin-1-yl)-4-(4-methylpiperazin-
1-yl)but-2-en-1-one Example 131 was prepared using similar procedure as in preparation of Example 105, Step 2.

Example 132

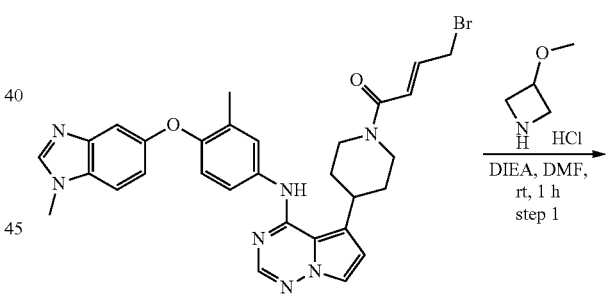

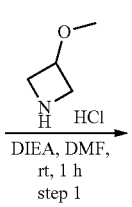

Example 132

(E)-4-(3-methoxyazetidin-1-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one Example 132 was prepared using similar procedure as in preparation of Example 105, Step 2.

Example 133

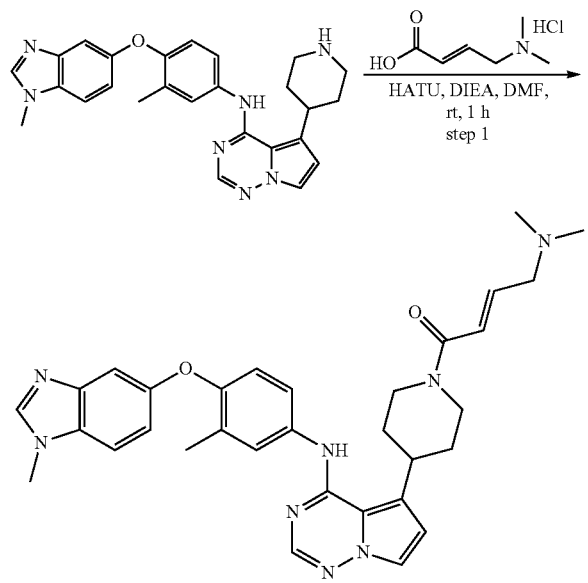

(E)-4-(dimethylamino)-1-(4-(4-((3-methyl-4-((1-methyl-1H-benzo[d]-224-midazole-5-yl)oxy)phenyl)amino)pyrrolo[2,1-f][1,2,4]triazin-5-yl)piperidin-1-yl)but-2-en-1-one To a solution of N-(3-methyl-4-((1-methyl-1H-benzo[d]imidazole-5-yl)oxy)phenyl)-5-(piperidin-4-yl)pyrrolo[2,1-f][1,2,4]triazin-4-amine (150 mg, 0.33 mmol) in DMF (2 mL) was added HATU (188.63 mg, 0.49 mmol), DIEA (128.24 mg, 0.99 mmol) and E-4-(dimethylamino)but-2-enoic acid hydrochloride (65.73 mg, 0.39 mmol), the mixture was stirred for 1 hour. The reaction mixture was purified by reversed-phase flash chromatography Mobile Phase A: Water (0.1% FA), Mobile Phase B: ACN; Gradient: 17% B to 33% B to afford E-4-(dimethylamino)-1-(4-(4-((3-methyl-4-((1-methyl-1H-benzo[d]-224-midazole-5-yl)oxy)phenyl)amino)pyrrolo[2,1-f][1,2,4]triazin-5-yl)piperidin-1-yl)but-2-en-1-one, Example 133 (58.2 mg, 30.63% yield). LCMS (ESI-MS) m/z=565.3 [M+H]$^+$. $^1$H NMR (400 MHz, DMSO-d6) δ (ppm) 8.45 (s, 1H), 8.20-8.14 (m, 2H), 7.85 (s, 1H), 7.71-7.68 (m, 1H) 7.61-7.56 (m, 2H), 7.52-7.49 (m, 1H), 7.43-7.37 (m, 1H), 7.12-7.09 (m, 1H), 7.03-6.99 (m, 1H), 6.90-6.84 (m, 1H), 6.76-6.64 (m, 1H), 4.19-4.09 (m, 2H), 3.84 (s, 3H), 3.72-3.64 (m, 1H), 3.35-3.19 (m, 3H), 2.84 (s, 1H), 2.31 (s, 6H), 2.25 (s, 3H), 2.04-1.93 (m, 2H), 1.55 (s, 2H).

Example 134

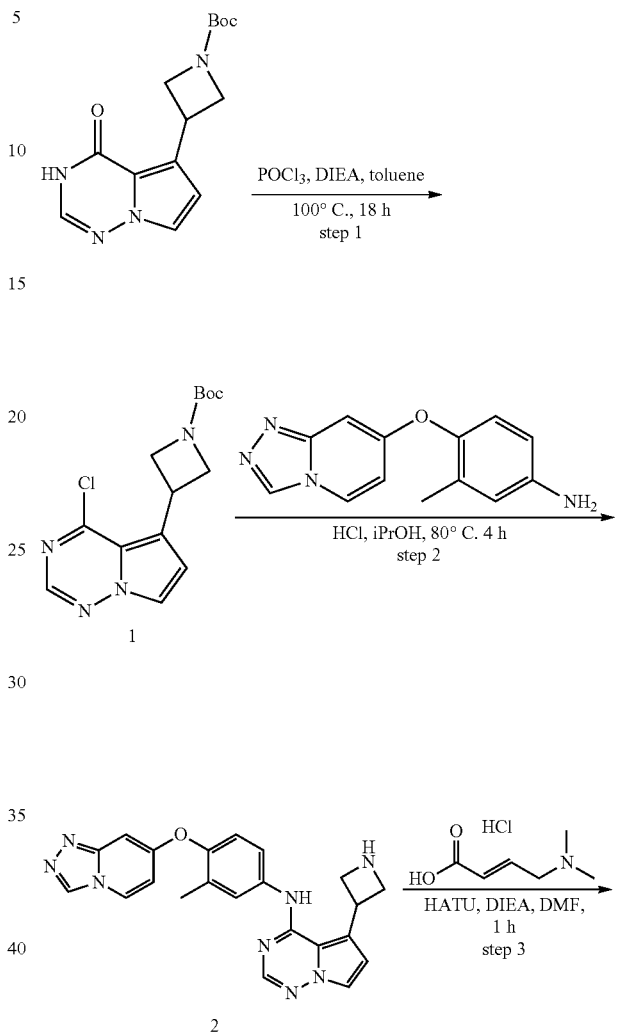

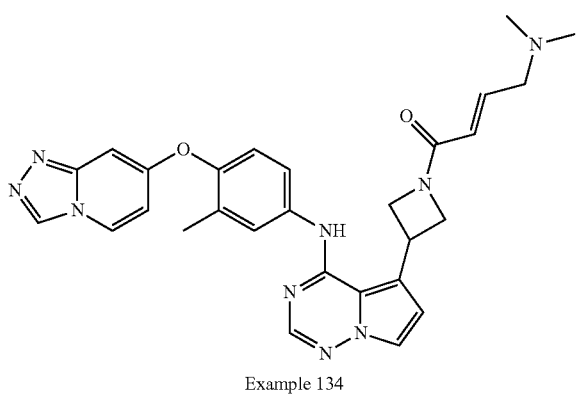

Example 134

Step 1. tert-butyl 3-(4-chloropyrrolo[2,1-f][1,2,4]triazin-5-yl)azetidine-1-carboxylate

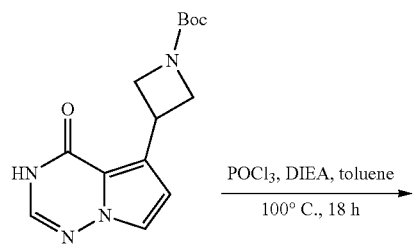

To a solution of tert-butyl 3-(4-oxo-3,4-dihydropyrrolo[2,1-f][1,2,4]triazin-5-yl)azetidine-1-carboxylate (300 mg, 1.04 mmol) in toluene (6 mL) at 25° C. was added POCl$_3$ (957 mg, 6.24 mmol) followed by diisopropylethylamine (1345 mg, 10.41 mmol). The mixture was stirred for 18 hours at 100° C. After cooling to room temperate, the reaction was concentrated under reduced pressure to afford tert-butyl 3-(4-chloropyrrolo[2,1-f][1,2,4]triazin-5-yl)azetidine-1-carboxylate (360 mg crude), the crude product was used for next step directly without further purification. LCMS (ESI-MS) m/z=309.1 [M+H]$^+$.

Step 2. N-(4-([1,2,4]triazolo[4,3-a]pyridin-7-yloxy)-3-methylphenyl)-5-(azetidin-3-yl)pyrrolo[2,1-f][1,2,4]triazin-4-amine

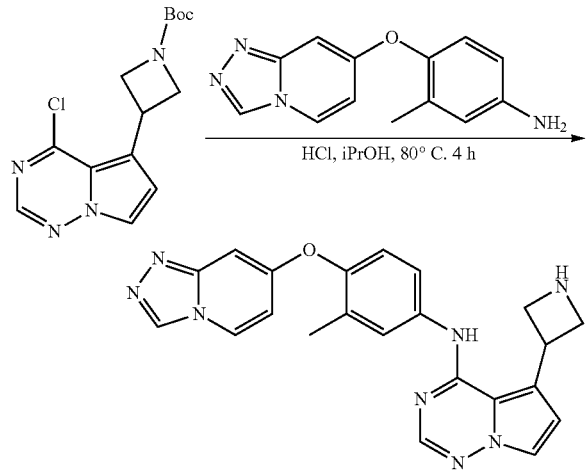

To a solution of tert-butyl 3-(4-chloropyrrolo[2,1-f][1,2,4]triazin-5-yl)azetidine-1-carboxylate (360 mg crude) in iPrOH (6 mL) was added 4-([1,2,4]triazolo[4,3-a]pyridin-7-yloxy)-3-methylaniline (125 mg, 0.52 mmol) at room temperature. Catalytic amount of aq. HCl (10M, 50p) was added, the reaction mixture was stirred for 4 hours at 80° C. Then the reaction mixture was concentrated under reduced pressure and purified by Prep-HPLC Mobile Phase A: MeOH, Mobile Phase B: ACN; Gradient: 40% B to 70% B to afford to afford N-(4-([1,2,4]triazolo[4,3-a]pyridin-7-yloxy)-3-methylphenyl)-5-(azetidin-3-yl)pyrrolo[2,1-f][1,2,4]triazin-4-amine (220 mg, 25.8% over two steps). LCMS (ESI-MS) m/z=454.2 [M+H].

Step 3. (E)-1-(3-(4-((4-([1,2,4]triazolo[4,3-a]pyridin-7-yloxy)-3-methylphenyl)amino)pyrrolo[2,1-f][1,2,4]triazin-5-yl)azetidin-1-yl)-4-(dimethylamino)but-2-en-1-one

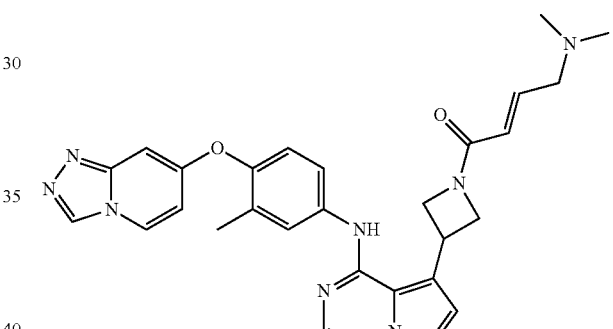

Example 134

To a solution of N-(4-([1,2,4]triazolo[4,3-a]pyridin-7-yloxy)-3-methylphenyl)-5-(azetidin-3-yl)pyrrolo[2,1-f][1,2,4]triazin-4-amine (220 mg, 0.53 mmol) in DMF (3 mL) was added HATU (380.24 mg, 0.55 mmol), diisopropylethylamine (70.51 mg, 0.55 mmol) and (E)-4-(dimethylamino)but-2-enoic acid hydrochloride (72.28 mg, 0.44 mmol), the mixture was allowed to stirred for 1 hour. The reaction mixture was purified by reversed-phase flash chromatography; Mobile Phase A: Water (0.1% formic acid), Mobile Phase B: ACN; Gradient: 2% B to 25% B to afford (E)-1-(3-(4-((4-([1,2,4]triazolo[4,3-a]pyridin-7-yloxy)-3-methylphenyl)amino)pyrrolo[2,1-f][1,2,4]triazin-5-yl)azetidin-1-yl)-4-(dimethylamino)but-2-en-1-one, Example 134 (15.7 mg, 7.51% yield). LCMS (ESI-MS) m/z=524.2 [M+H]$^+$. $^1$H NMR (400 MHz, DMSO-d$_6$) δ (ppm) 8.97 (d, J=7.4 Hz, 1H), 8.53 (s, 1H), 8.41 (s, 1H), 7.91 (s, 1H), 7.68 (d, J=2.5 Hz, 1H), 7.56 (d, J=2.7 Hz, 1H), 7.46 (dd, J=8.7, 2.7 Hz, 1H), 7.26 (d, J=8.7 Hz, 1H), 7.05 (dd, J=7.5, 2.7 Hz, 1H), 6.82 (d, J=2.7 Hz, 1H), 6.67-6.58 (m, 2H), 6.22 (d, J=15.5 Hz, 1H), 4.34-4.19 (m, 2H), 3.98-3.90 (m, 1H), 3.64-3.56 (m, 1H), 3.59-3.45 (m, 3H), 3.41-3.29 (m, 2H), 2.48 (s, 4H), 2.21 (s, 3H).

Examples 135 and 136
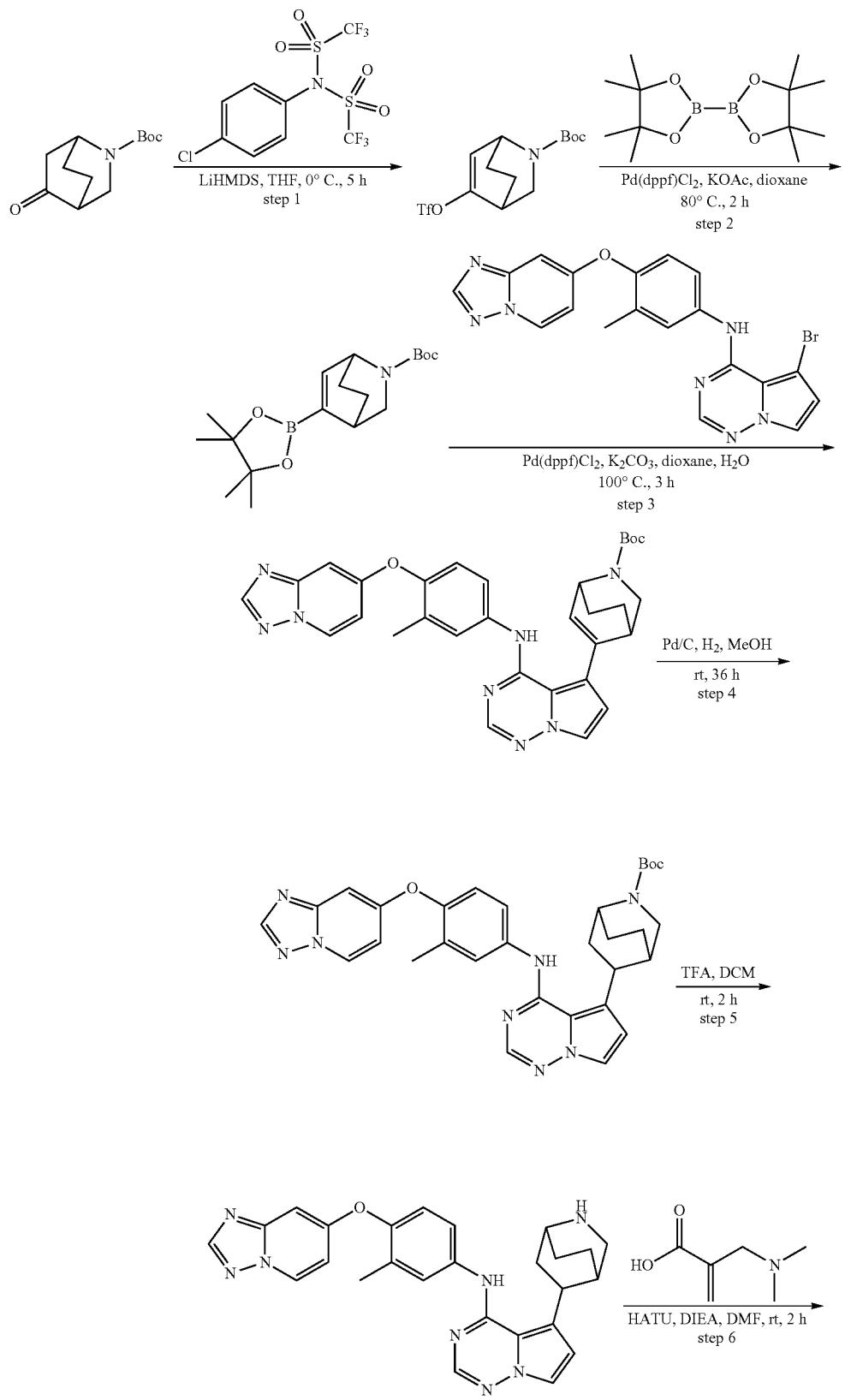

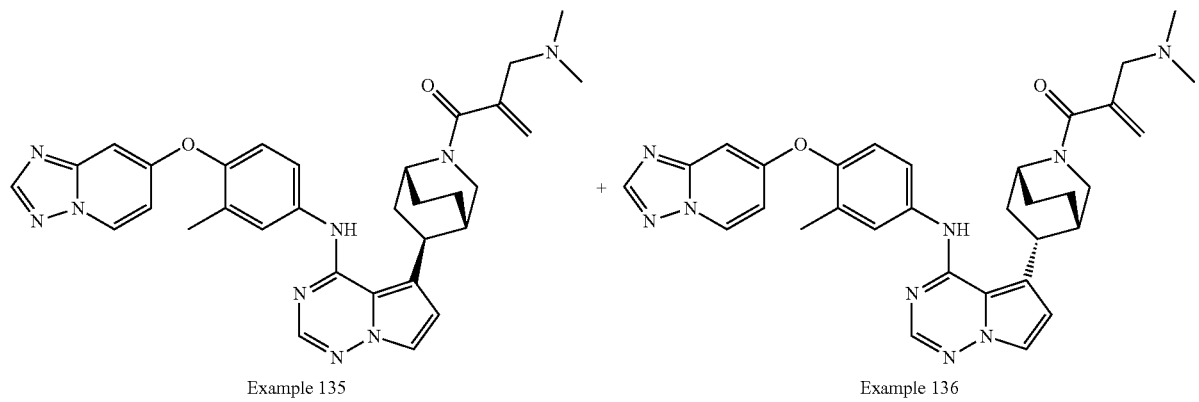 [SMILES: C=C(CN(C)C)C(=O)N1C[C@H]2CC[C@@H]1C[C@@H]2c1ccn2ncnc(Nc3ccc(Oc4ccn5ncnc5c4)c(C)c3)c12 ; C=C(CN(C)C)C(=O)N1C[C@H]2CC[C@@H]1C[C@H]2c1ccn2ncnc(Nc3ccc(Oc4ccn5ncnc5c4)c(C)c3)c12]

Example 135      Example 136

Step 1. tert-butyl 5-(((trifluoromethyl)sulfonyl)oxy)-2-azabicyclo[2.2.2]oct-5-ene-2-carboxylate Step 2. tert-butyl 5-(4,4,5,5-tetramethyl-1,3,2-dioxaborolan-2-yl)-2-azabicyclo[2.2.2]oct-5-ene-2-carboxylate

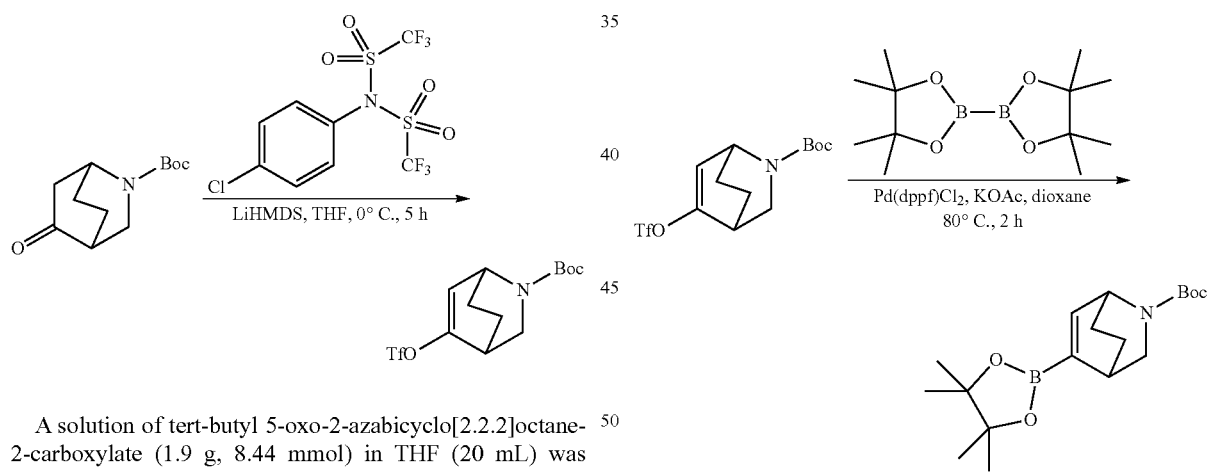

A solution of tert-butyl 5-oxo-2-azabicyclo[2.2.2]octane-2-carboxylate (1.9 g, 8.44 mmol) in THF (20 mL) was treated with LiHMDS (1M in THF, 15.2 mL, 15.19 mmol) for 1 h at 0° C. under nitrogen atmosphere. A solution of N-(4-chlorophenyl)-1,1,1-trifluoro-N-((trifluoromethyl)sulfonyl)methanesulfonamide (4.95 g, 12.66 mmol) in THF (10 mL) was added dropwise at 0° C. and the mixture was stirred for 5 hours at 0° C. The reaction was quenched with water (500 mL) at 0° C., extracted with ethyl acetate (3×500 ml). The combined organic layers were dried over anhydrous sodium sulfate and concentrated under reduced pressure to afford a crude product. The residue was purified by silica gel column chromatography, eluted with petroleum ether/ethyl acetate (9:1) to afford tert-butyl 5-(((trifluoromethyl)sulfonyl)oxy)-2-azabicyclo[2.2.2]oct-5-ene-2-carboxylate (1.47 g, 48.7% yield). LCMS (ESI-MS) m/z=343.1 [M+H]+.

A mixture of tert-butyl 5-(((trifluoromethyl)sulfonyl)oxy)-2-azabicyclo[2.2.2]oct-5-ene-2-carboxylate (1.47 g, 4.11 mmol), 4,4,4',4',5,5,5',5'-octamethyl-2,2'-bi(1,3,2-dioxaborolane) (2.09 g, 8.22 mmol), Pd(dppf)Cl$_2$ (335.11 mg, 0.41 mmol) and KOAc (807.46 mg, 8.22 mmol) in 1,4-dioxane (20 mL) was stirred at 80° C. for 2 hours under nitrogen atmosphere. The reaction mixture was filtered and the filtrate was concentrated to afford the crude product. The residue was purified by silica gel column chromatography, eluted with petroleum ether/ethyl acetate (5:1) to afford tert-butyl 5-(4,4,5,5-tetramethyl-1,3,2-dioxaborolan-2-yl)-2-azabicyclo[2.2.2]oct-5-ene-2-carboxylate (650 mg, 47.1% yield). LCMS (ESI-MS) m/z=321.2 [M+H]+.

Step 3. tert-butyl 5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]oct-5-ene-2-carboxylate

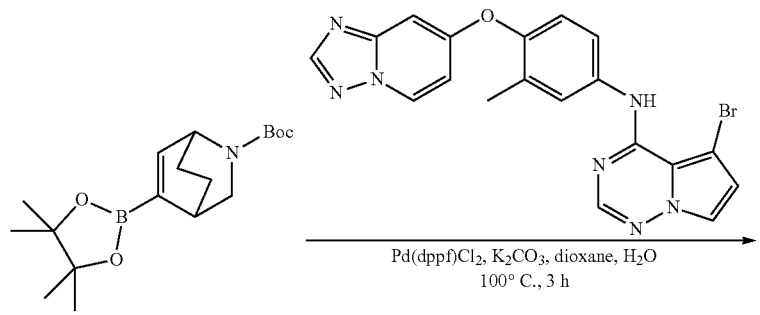

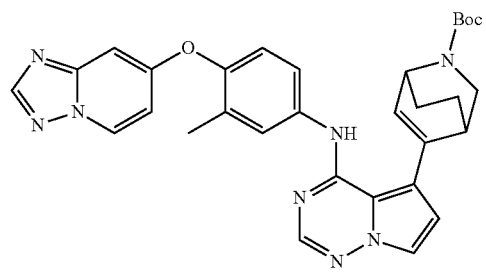

To a solution of tert-butyl 5-(4,4,5,5-tetramethyl-1,3,2-dioxaborolan-2-yl)-2-azabicyclo[2.2.2]oct-5-ene-2-carboxylate (650 mg, 1.93 mmol) and N-(4-([1,2,4]triazolo[1,5-a]pyridin-7-yloxy)-3-methylphenyl)-5-bromopyrrolo[2,1-f][1,2,4]triazin-4-amine (1.35 g, 3.10 mmol) in 1,4-dioxane (9 mL) and water (3 mL) were added Pd(dppf)Cl$_2$ (141.87 mg, 0.19 mmol) and K$_2$CO$_3$ (535.92 mg, 3.87 mmol) portionwise at room temperature under nitrogen atmosphere. The mixture was then stirred for 3 hours at 100° C. The reaction mixture was filtered and the filtrate was concentrated to afford the crude product. The crude product was purified by silica gel column chromatography, eluted with petroleum ether/ethyl acetate (1:1) to afford tert-butyl 5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]oct-5-ene-2-carboxylate (640 mg, 58.4% yield). LCMS (ESI-MS) m/z=565.2 [M+H]$^+$.

Step 4. tert-butyl 5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octane-2-carboxylate

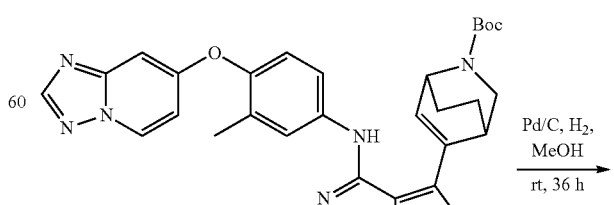

-continued

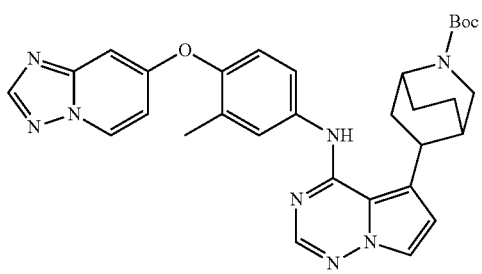

To a solution of tert-butyl 5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]oct-5-ene-2-carboxylate (640 mg, 1.13 mmol) in MeOH (10 mL) was added Pd/C (10% on carbon, 1.21 g) under nitrogen atmosphere and the mixture was stirred for 36 hours at room temperature under hydrogen atmosphere. The reaction mixture was filtered and the filtrate was concentrated to afford the crude product tert-butyl 5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octane-2-carboxylate (580 mg crude). LCMS (ESI-MS) m/z=567.5 [M+H]⁺.

Step 5. N-(4-([1,2,4]triazolo[1,5-a]pyridin-7-yloxy)-3-methylphenyl)-5-(2-azabicyclo[2.2.2]octan-5-yl)pyrrolo[2,1-f][1,2,4]triazin-4-amine

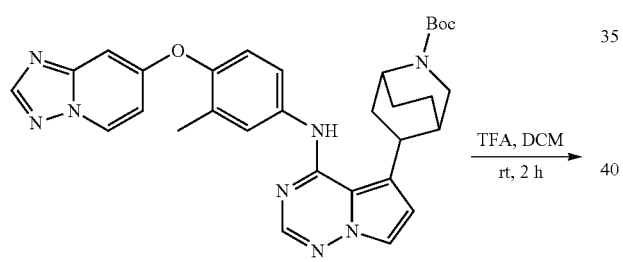

A solution of tert-butyl 5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octane-2-carboxylate (160 mg, 0.28 mmol) and TFA (2 mL, 26.92 mmol) in DCM (6 mL) was stirred for 2 hours at room temperature. The resulting mixture was concentrated under reduced pressure to afford the crude product N-(4-([1,2,4]triazolo[1,5-a]pyridin-7-yloxy)-3-methylphenyl)-5-(2-azabicyclo[2.2.2]octan-5-yl)pyrrolo[2,1-f][1,2,4]triazin-4-amine (200 mg crude). The crude product was used in the next step without further purification. LCMS (ESI-MS) m/z=467.1 [M+H]⁺.

Step 6. 1-((1R,4S,5S)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)-2-((dimethylamino)methyl)prop-2-en-1-one (Example 135) & 1-((1R,4S,5R)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)-2-((dimethylamino)methyl)prop-2-en-1-one (Example 136)

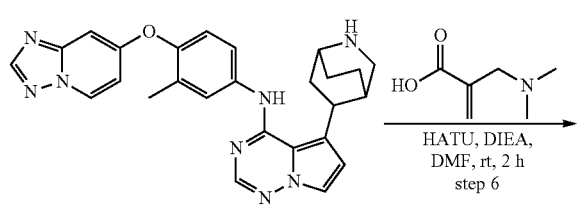

Example 135

Example 136

A solution of N-(4-([1,2,4]triazolo[1,5-a]pyridin-7-yloxy)-3-methylphenyl)-5-(2-azabicyclo[2.2.2]octan-5-yl)pyrrolo[2,1-f][1,2,4]triazin-4-amine (200 mg, 0.42 mmol), 2-((dimethylamino)methyl)acrylic acid (55.37 mg, 0.42 mmol), HATU (244.50 mg, 0.64 mmol) and diisopropylethylamine (110.81 mg, 0.85 mmol) in DMF (2 mL) was stirred at room temperature for 2 hours. The reaction mixture was filtered and the filtrate was concentrated to afford the crude product. The crude product was purified by Prep-HPLC using the following conditions: Column: XBridge Prep OBD C18 Column, 30*150 mm, m; Mobile Phase A: Water (10 mmol/L NH$_4$HCO$_3$), Mobile Phase B: ACN; Flow rate: 60 mL/min mL/min; Gradient: 27% B to 57% B in 7 min; Wave Length: 254 nm/220 nm nm; RT1(min): 6.1. The desired fractions were combined and lyophilized to afford the two desired separated isomers Examples 135 and 136:

First eluting isomer of 1-(5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)-2-((dimethylamino)methyl)prop-2-en-1-one (11.6 mg, 7.1% yield) LCMS (ESI-MS) m/z=578.3 [M+H]$^+$. $^1$H NMR (400 MHz, Chloroform-d) δ (ppm) 8.50 (d, J=7.4 Hz, 1H), 8.23 (s, 1H), 7.94 (s, 1H), 7.75-7.30 (m, 3H), 7.10 (d, J=8.6 Hz, 1H), 6.96 (s, 1H), 6.90 (dd, J=7.5, 2.3 Hz, 1H), 6.84 (s, 1H), 5.87 (s, 1H), 5.42 (s, 1H), 4.35 (s, 2H), 3.79 (d, J=14.0 Hz, 1H), 3.69 (d, J=13.9 Hz, 1H), 3.51 (s, 1H), 3.30 (s, 1H), 3.10 (s, 2H), 3.02 (s, 4H), 2.91 (s, 1H), 2.69-2.59 (m, 1H), 2.39-2.27 (m, 1H), 2.28-1.97 (m, 5H), 1.96-1.87 (m, 11H), 1.85-1.60 (m, 1H).

Cell growth inhibition activity of first eluting isomer based on assays described for Table 3:

| HER2 - YVMA IC$_{50}$ (nM) | HER2 WT IC$_{50}$ (nM) | EGFR WT IC$_{50}$ (nM) |
|---|---|---|
| ++++ | ++++ | + |

Second eluting isomer of 1-(5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)-2-((dimethylamino)methyl)prop-2-en-1-one (1.1 mg, 0.7% yield). LCMS (ESI-MS) m/z=578.3 [M+H]$^+$. $^1$H NMR (400 MHz, Chloroform-d) δ (ppm) 8.50 (d, J=7.4 Hz, 1H), 8.23 (s, 1H), 7.94 (s, 1H), 7.75-7.30 (m, 3H), 7.10 (d, J=8.6 Hz, 1H), 6.96 (s, 1H), 6.90 (dd, J=7.5, 2.3 Hz, 1H), 6.84 (s, 1H), 5.87 (s, 1H), 5.42 (s, 1H), 4.35 (s, 2H), 3.79 (d, J=14.0 Hz, 1H), 3.69 (d, J=13.9 Hz, 1H), 3.51 (s, 1H), 3.30 (s, 1H), 3.10 (s, 2H), 3.02 (s, 4H), 2.91 (s, 1H), 2.69-2.59 (m, 1H), 2.39-2.27 (m, 1H), 2.28-1.97 (m, 5H), 1.96-1.87 (m, 1H), 1.85-1.60 (m, 1H).

Cell growth inhibition activity of second eluting isomer based on assays described for Table 3:

| HER2 - YVMA IC$_{50}$ (nM) | HER2 WT IC$_{50}$ (nM) | EGFR WT IC$_{50}$ (nM) |
|---|---|---|
| +++ | ++++ | ++++ |

Examples 137 and 138

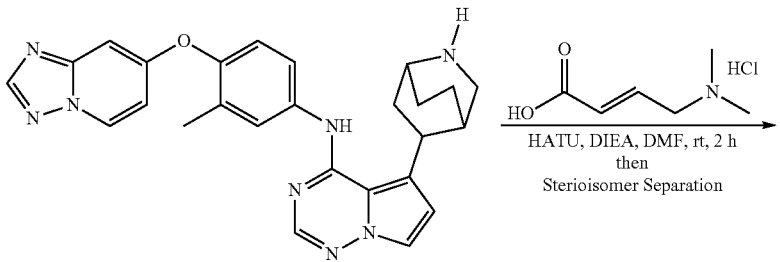

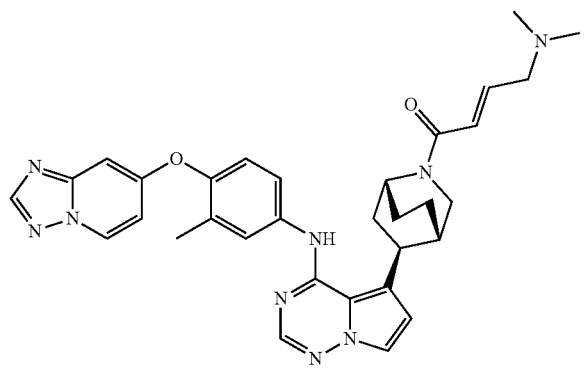

Example 137

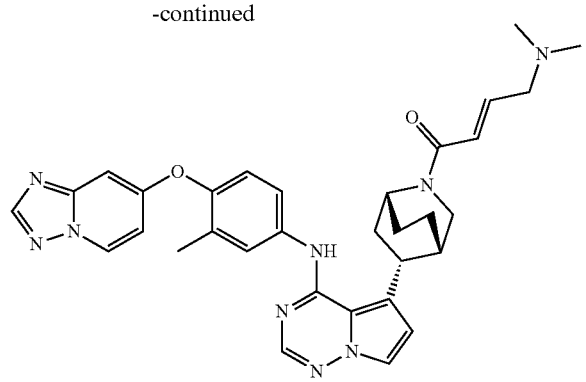

Example 138

€-1-((1R,4S,5S)-5-(4-((4-([1,2,4]triazolo[1,5-233-yridinedin-7-yloxy)-3-methylphenyl)amino)pyrrolo[2,1-f][1,2,4]triazin-5-yl)-2-azabicyclo[2.2.2]octan-2-yl)-4-(dimethylamino)but-2-en-1-one (Example 137) & (E)-1-((1R,4S,5R)-5-(4-((4-([1,2,4]triazolo[1,5-233-yridinedin-7-yloxy)-3-methylphenyl)amino)pyrrolo[2,1-f][1,2,4]triazin-5-yl)-2-azabicyclo[2.2.2]octan-2-yl)-4-(dimethylamino)but-2-en-1-one Example 138

A solution of N-(4-([1,2,4]triazolo[1,5-233-yridinedin-7-yloxy)-3-methylphenyl)-5-(2-azabicyclo[2.2.2]octan-5-yl)pyrrolo[2,1-f][1,2,4]triazin-4-amine (220 mg, 0.47 mmol), (E)-4-(dimethylamino)but-2-enoic acid hydrochloride (60.90 mg, 0.47 mmol), HATU (268.95 mg, 0.70 mmol) and diisopropylethylamine (121.89 mg, 0.94 mmol) in DMF (3 mL) was stirred at room temperature for 2 hours. The reaction mixture was filtered and the filtrate was concentrated to afford the crude product. The crude product (100 mg) was purified by Prep-HPLC using the following conditions: Column: XBridge Prep OBD C18 Column, 30*150 mm, 5 μm; Mobile Phase A: Water (10 mmol/L NH₄HCO₃), Mobile Phase €ACN; Flow rate: 60 mL/min mL/min; Gradient: 25% B to 55% B in 7 min; Wave Length: 254 nm/220 nm nm; RT1 (min): 6.5. The desired fractions were combined and lyophilized to afford the two desired separated isomers Examples 137 and 138:

First eluting isom€of (E)-1-(5-(4-((4-([1,2,4]triazo-233-yridinea]pyridin-7-yloxy)-3-methylphenyl)amino)pyrrolo[2,1-f][1,2,4]triazin-5-yl)-2-azabicyclo[2.2.2]octan-2-yl)-4-(dimethylamino)but-2-en-1-one (21.6 mg, 13.2% yield). LCMS (ESI-MS) m/z=578.3 [M+H]. ¹H NMR (400 MHz, DMSO-d₆) δ (ppm) 9.00-8.80 (m, 1H), 8.52-8.40 (m, 1H), 8.39-8.25 (m, 1H), 8.03-7.60 (m, 3H), 7.48-6.86 (m, 3H), 6.84-6.25 (m, 4H), 4.62-4.12 (m, 1H), 4.11-3.85 (m, 1H), 3.60-3.35 (m, 1H), 3.30-3.10 (m, 1H), 3.09-2.89 (m, 2H), 2.30-1.95 (m, 13H), 1.93-1.60 (n, 3H).

Cell growth inhibition activity of first eluting isomer based on assays described for Table 3:

| HER2 - YVMA IC₅₀ (nM) | HER2 WT IC₅₀ (nM) | EGFR WT IC₅₀ (nM) |
|---|---|---|
| +++ | ++++ | + |

Second eluting isomer of (E)-1-(5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)-4-(dimethylamino)but-2-en-1-one (3.0 mg, 1.8% yield). LCMS (ESI-MS) m/z=578.3 [M+H]⁺. ¹H NMR (400 MHz, DMSO-d₆) δ (ppm) 9.00-8.87 (m, 1H), 8.52-8.40 (m, 1H), 8.39-8.28 (m, 1H), 8.03-7.57 (m, 3H), 7.48-6.96 (m, 3H), 6.95-6.31 (m, 4H), 4.62-4.15 (m, 1H), 4.14-4.02 (m, 1H), 4.00-3.72 (m, 1H), 3.70-3.50 (m, 1H), 3.30-3.25 (m, 1H), 3.09-2.96 (m, 2H), 2.32-1.95 (m, 12H), 1.93-1.80 (m, 1H), 1.79-1.35 (m, 2H).

Cell growth inhibition activity of second eluting isomer based on assays described for Table 3:

| HER2 - YVMA IC₅₀ (nM) | HER2 WT IC₅₀ (nM) | EGFR WT IC₅₀ (nM) |
|---|---|---|
| + | ++ | + |

Examples 139 and 140

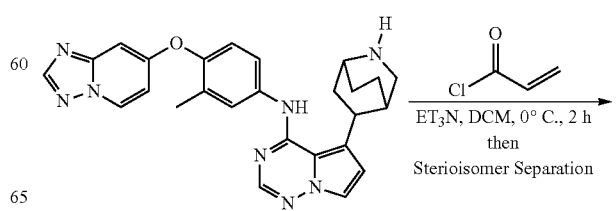

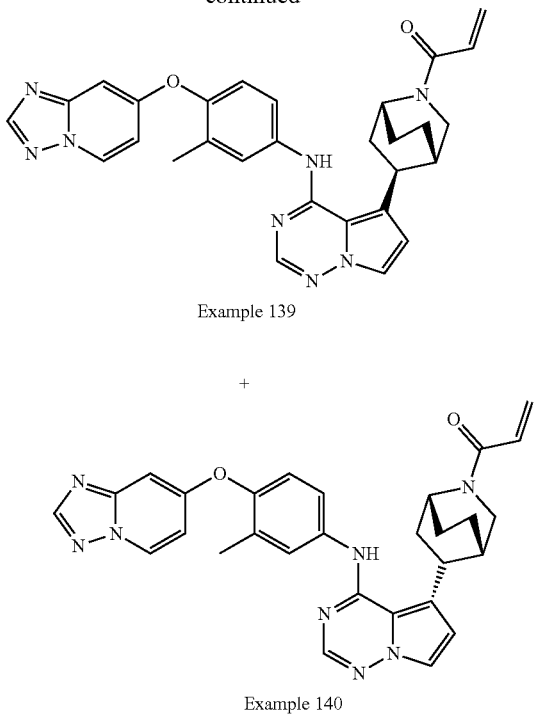

Example 139

+

Example 140

1-((1R,4S,5S)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)prop-2-en-1-one (Example 139) & 1-((1R,4S,5R)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)prop-2-en-1-one (Example 140)

A solution of N-(4-([1,2,4]triazolo[1,5-a]pyridin-7-yloxy)-3-methylphenyl)-5-(2-azabicyclo[2.2.2]octan-5-yl)pyrrolo[2,1-f][1,2,4]triazin-4-amine (330 mg, 0.70 mmol) and Et$_3$N (286.30 mg, 2.82 mmol) in DCM (4 mL) was added acryloyl chloride (64.02 mg, 0.70 mmol) in DCM (1 mL) dropwise at 0° C. The mixture was stirred at 0° C. for 10 minutes and concentrated under vacuum to afford the crude product. The crude product was purified by Prep-HPLC using the following conditions: Column: YMC-AC-TUS Triart C18 ExRS30*150 mm. 8 m; Mobile Phase A: Water (10 nmol/LNH$_4$HCO$_3$+0.05% NH$_3$·H$_2$O), Mobile Phase B: ACN; Flow rate: 60 mL/min mL/min; Gradient: 30% B to30% B in 10 min; Wave Length: 254 nm/220 nm nm; RT1(min): 8.5. The desired fractions were combined and lyophilized to afford the two desired separated isomers Examples 139 and 140:

First eluting isomer of 1-(5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)prop-2-en-1-one (57.4 mg, 24.0% yield). LCMS (ESI-MS) m/z=521.2 [M+H]$^+$. $^1$H NMR (400 MHz, DMSO-d$_6$) δ (ppm) 9.10-8.80 (m, 1H), 8.55-8.40 (m, 1H), 8.39-8.28 (m, 1H), 8.06-7.86 (m, 1H), 7.83-7.30 (m, 3H), 7.29-7.12 (m, 1H), 7.11-6.95 (m, 1H), 6.94-6.75 (m, 2H), 6.73-6.43 (m, 11H), 6.35-6.05 (m, 1H), 5.80-5.50 (m, 1H), 4.68-4.20 (m, 1H), 4.19-3.90 (m, 1H), 3.60-3.39 (m, 1H), 3.30-3.10 (m, 1H), 2.32-2.11 (m, 5H), 2.10-1.95 (m, 2H), 1.93-1.55 (m, 3H).

Cell growth inhibition activity of first eluting isomer based on assays described for Table 3:

| HER2 - YVMA IC$_{50}$ (nM) | HER2 WT IC$_{50}$ (nM) | EGFR WT IC$_{50}$ (nM) |
|---|---|---|
| ++++ | ++++ | + |

Second eluting isomer of 1-(5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)prop-2-en-1-one (10.7 mg, 4.4% yield). LCMS (ESI-MS) m/z=521.2 [M+H]$^+$. $^1$H NMR (400 MHz, DMSO-d$_6$) δ (ppm) 9.10-8.80 (m, 1H), 8.52-8.42 (m, 1H), 8.41-8.30 (m, 1H), 8.01-7.84 (m, 1H), 7.83-7.75 (m, 1H), 7.74-7.31 (m, 2H), 7.29-7.11 (m, 1H), 7.10-7.00 (m, 1H), 6.99-6.88 (m, 1H), 6.87-6.65 (m, 2H), 6.35-6.00 (m, 1H), 5.88-5.50 (m, 1H), 4.68-4.20 (m, 1H), 4.19-3.93 (m, 1H), 3.89-3.60 (m, 1H), 3.40-3.27 (m, 1H), 2.35-1.99 (m, 6H), 1.97-1.65 (m, 2H), 1.64-1.50 (m, 1H), 1.49-1.33 (m, 1H).

Cell growth inhibition activity of second eluting isomer based on assays described for Table 3:

| HER2 - YVMA IC$_{50}$ (nM) | HER2 WT IC$_{50}$ (nM) | EGFR WT IC$_{50}$ (nM) |
|---|---|---|
| + | ++ | + |

Example 141

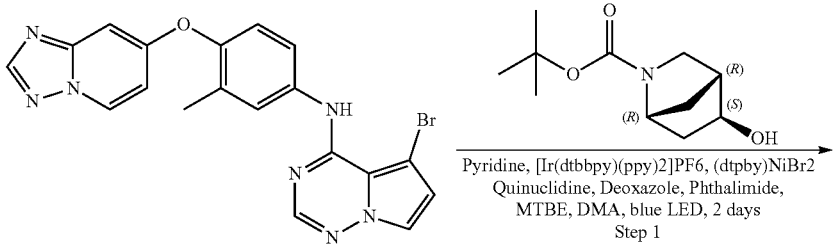

Pyridine, [Ir(dtbbpy)(ppy)2]PF6, (dtpby)NiBr2
Quinuclidine, Deoxazole, Phthalimide,
MTBE, DMA, blue LED, 2 days
Step 1

-continued
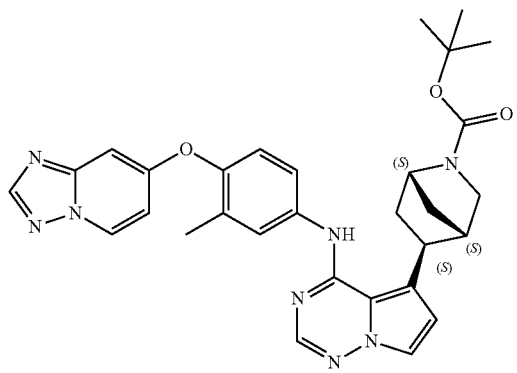
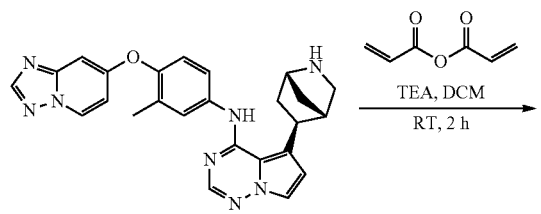
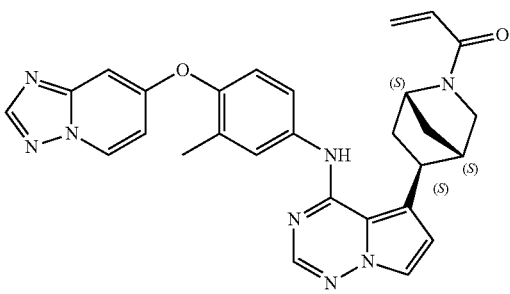
Example 141
Step 1: tert-butyl (1R,4R,5S)-5-{4-[(3-methyl-4-{[1,2,4]triazolo[1,5-a]pyridin-7-yloxy}phenyl)amino]pyrrolo[2,1-f][1,2,4]triazin-5-yl}-2-azabicyclo[2.2.1]heptane-2-carboxylate
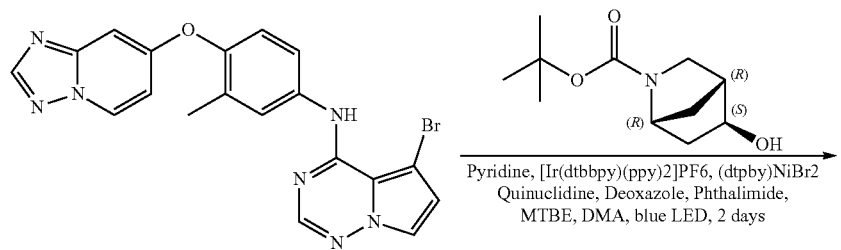

-continued

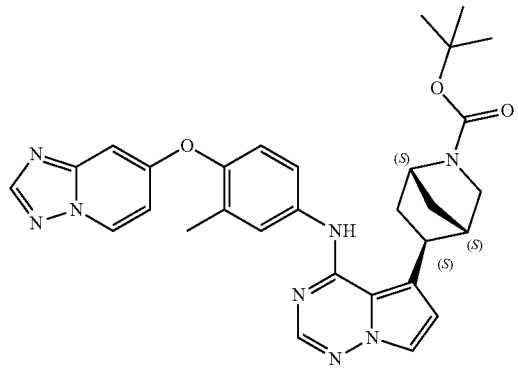

A sealed tube was charged with deoxazole (0.331 g, 0.836 mmol, 1.6 eq) and tert-butyl (1R,4R,5S) 5-hydroxy-2-azabicyclo[2.2.1]heptane-2-carboxylate (0.195 g, 0.915 mmol, 1.75 eq). The mixture was degasses under vacuum and charged with argon. This process was repeated two times. Then dry MTBE (5.23 ml, 0.1 M) was added via syringe to the tube and the mixture was stirred for 5 min at room temperature. A solution of dry pyridine (0.068 ml, 0.836 mmol, 1.6 eq) in dry MTBE (0.99 ml, 15.0 vol) was then added dropwise over 2 min and the resulting solution was stirred for 10 minutes. In a 7 mL vial, 5-bromo-N-(3-methyl-4-{[1,2,4]triazolo[1,5-a]pyridin-7-yloxy}phenyl)pyrrolo[2,1-f][1,2,4]triazin-4-amine (0.24 g, 0.523 mmol, 1.0 eq), [Ir(dtbbpy)(ppy)$_2$]PF$_6$(0.007 g, 0.008 mmol, 0.015 eq), [4,4'-bis(tert-butyl)-2,2'-bipyridine]nickel dibromide (0.019 g, 0.039 mmol, 0.075 eq), phthalimide (0.017 g, 0.118 mmol, 0.225 eq) and quinuclidine (0.102 g, 0.915 mmol, 1.75 eq) were added and the mixture was suspended in dry dimethylacetamide (4.8 ml, 20.0 vol) under argon. MTBE solution was transferred to a syringe and filtered prior to addition. The reaction mixture was purged with argon for 15 minutes and sealed with parafilm. The vial was placed in a PennPhD Photoreactor stirring at 1500 rpm under 450 nm LED irradiation at 100% intensity with a fan speed of 2800 rpm. Stirring was carried out for 2 days. Reaction mixture was filtered through celite pad and washed with ethyl acetate. Solvents were evaporated and purification was performed. Purification via flash chromatography (DCM/MeOH 100:0→95:5) was performed to give a crude product. Additional re-purification was performed via preparative TLC (plate was developed 3 times; DCM/MeOH 100:0→96:4). Tert-butyl (1S,4S,5S)-5-{4-[(3-methyl-4-{[1,2,4]triazolo[1,5-a]pyridin-7-yloxy}phenyl)amino]pyrrolo[2,1-f][1,2,4]triazin-5-yl}-2-azabicyclo[2.2.1]heptane-2-carboxylate (0.03 g, 8%) was isolated. $^1$H NMR (300 MHz, DMSO-d6) δ 8.94 (dd, J=7.5, 3.1 Hz, 1H), 8.43 (s, 1H), 8.39 (s, 1H), 7.92 (s, 1H), 7.73-7.65 (m, 2H), 7.22 (d, J=8.4 Hz, 1H), 7.03 (dd, J=7.5, 2.6 Hz, 1H), 6.81 (d, J=2.0 Hz, 1H), 6.71 (d, J=2.7 Hz, 1H), 4.19 (d, J=15.1 Hz, 1H), 3.90 (dd, J=9.4, 4.1 Hz, 1H), 3.30 (s, 1H), 2.70 (dd, J=4.9, 2.1 Hz, 1H), 2.19 (s, 4H), 1.88-1.78 (m, 1H), 1.66 (d, J=10.8 Hz, 1H), 1.62-1.54 (m, 1H), 1.42 (s, 9H), 1.24 (s, 2H). UPLC (ESI) [M+H]$^+$=553.10

Step 2: 5-[(1S,4S,5S)-2-azabicyclo[2.2.1]heptan-5-yl]-N-(3-methyl-4-{[1,2,4]triazolo[1,5-a]pyridin-7-yloxy}phenyl)pyrrolo[2,1-f][1,2,4]triazin-4-amine

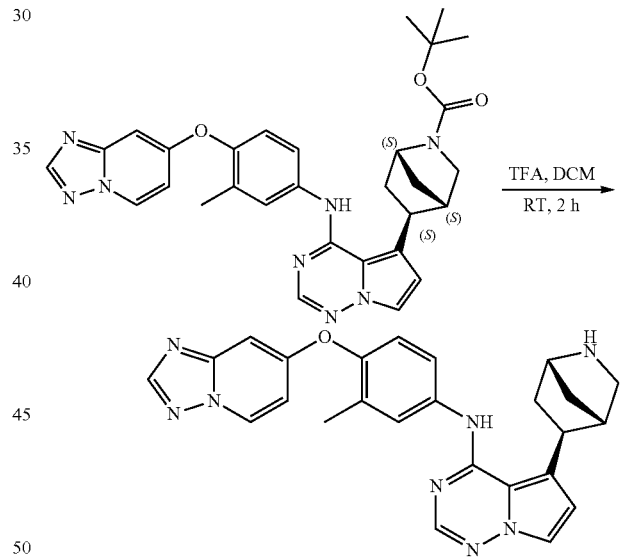

To a stirring solution of tert-butyl (1S,4S,5S)-5-{4-[(3-methyl-4-{[1,2,4]triazolo[1,5-a]pyridin-7-yloxy}phenyl)amino]pyrrolo[2,1-f][1,2,4]triazin-5-yl}-2-azabicyclo[2.2.1]heptane-2-carboxylate (0.03 g, 0.044 mmol, 1.0 eq) in DCM (0.6 ml, 20.0 vol) was added TFA (0.3 ml, 10.0 vol). The reaction was stirred at RT for 2 hours. Solvents were evaporated and the crude was used in the next step without further purification. 5-[(1S,4S,5S)-2-azabicyclo[2.2.1]heptan-5-yl]-N-(3-methyl-4-{[1,2,4]triazolo[1,5-a]pyridin-7-yloxy}phenyl)pyrrolo[2,1-f][1,2,4]triazin-4-amine (0.045 g, crude) was isolated in the form of trifluoroacetic acid salt. $^1$H NMR (300 MHz, Methanol-d4) δ 8.82 (d, J=7.5 Hz, 1H), 8.42 (s, 1H), 7.77 (s, 1H), 7.67 (d, J=2.8 Hz, 1H), 7.56-7.52 (m, 1H), 7.47 (dd, J=8.8, 2.8 Hz, 1H), 7.27 (d, J=8.5 Hz, 1H), 7.17 (dd, J=7.6, 2.6 Hz, 1H), 6.89 (d, J=2.5 Hz, 1H), 6.79 (d, J=2.8 Hz, 1H), 4.25 (s, 1H), 3.91 (dd, J=8.4, 4.8 Hz, 1H), 3.37 (d, J=7.8 Hz, 1H), 3.03 (s, 1H), 2.47 (ddd, J=14.4, 8.9, 2.4 Hz, 1H), 2.30 (s, 1H), 2.27 (s, 3H), 2.18-2.11 (m, 2H), 1.87-1.78 (m, 1H). UPLC (ESI) [M+H]⁺=492.95

Step 3: 1-[(1S,4S,5S)-5-{4-[(3-methyl-4-{[1,2,4]triazolo[1,5-a]pyridin-7-yloxy}phenyl)amino]pyrrolo[2,1-f][1,2,4]triazin-5-yl}-2-azabicyclo[2.2.1]heptan-2-yl]prop-2-en-1-one

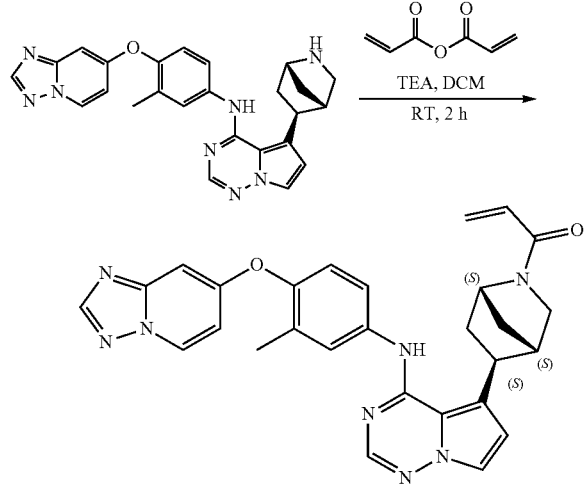

To a stirring solution of 5-[(1S,4S,5S)-2-azabicyclo[2.2.1]heptan-5-yl]-N-(3-methyl-4-{[1,2,4]triazolo[1,5-a]pyridin-7-yloxy}phenyl)pyrrolo[2,1-f][1,2,4]triazin-4-amine (0.045 g, 0.086 mmol, 1.0 eq) in dry DCM (0.9 ml, 20.0 vol) was added triethylamine (0.072 ml, 0.513 mmol, 6.0 eq) and acrylic anhydride (0.008 g, 0.064 mmol, 0.75 eq) at room temperature. The reaction was stirred at room temperature for 2 h. The solvent was evaporated, followed by purification using preparative TLC (plate was developed 4 times at DCM/MeOH 100:0→98:2→96:4→95:5). 1-[(1S,4S,5S)-5-{4-[(3-methyl-4-{[1,2,4]triazolo[1,5-a]pyridin-7-yloxy}phenyl)amino]pyrrolo[2,1-f][1,2,4]triazin-5-yl}-2-azabicyclo[2.2.1]heptan-2-yl]prop-2-en-1-one, Example 141 (0.011 g, 25%) was isolated. LCMS (ESI) [M+H]⁺=507.33. ¹H NMR (300 MHz, DMSO-d6) δ 8.95 (d, J=7.4 Hz, 11H), 8.41 (d, J=12.2 Hz, 2H), 7.91 (s, 1H), 7.75-7.65 (m, 2H), 7.58 (dt, J=8.5, 2.1 Hz, 1H), 7.22 (d, J=8.6 Hz, 1H), 7.03 (dd, J=7.4, 2.4 Hz, 1H), 6.81 (d, J=2.4 Hz, 1H), 6.75 (dd, J=5.7, 2.3 Hz, 1H), 6.16 (ddd, J=16.7, 5.7, 2.4 Hz, 1H), 5.67 (td, J=9.7, 2.4 Hz, 1H), 4.60 (d, J=9.0 Hz, 1H), 3.88 (dd, J=8.5, 5.2 Hz, 1H), 3.58 (s, 1H), 3.46 (d, J=11.0 Hz, 11H), 2.79 (d, J=8.1 Hz, 1H), 2.25-2.21 (m, 1H), 2.19 (s, 3H), 1.91-1.74 (m, 2H), 1.74-1.55 (m, 2H).

Example 142

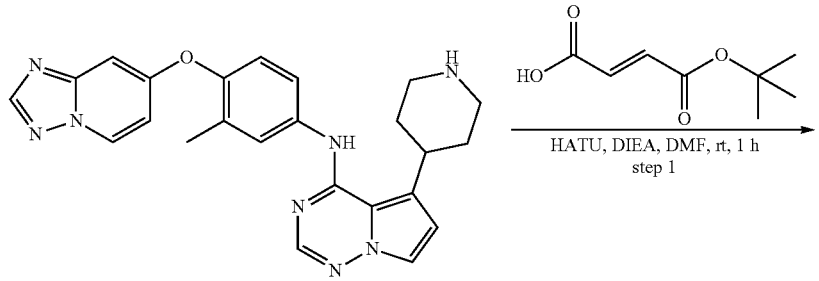

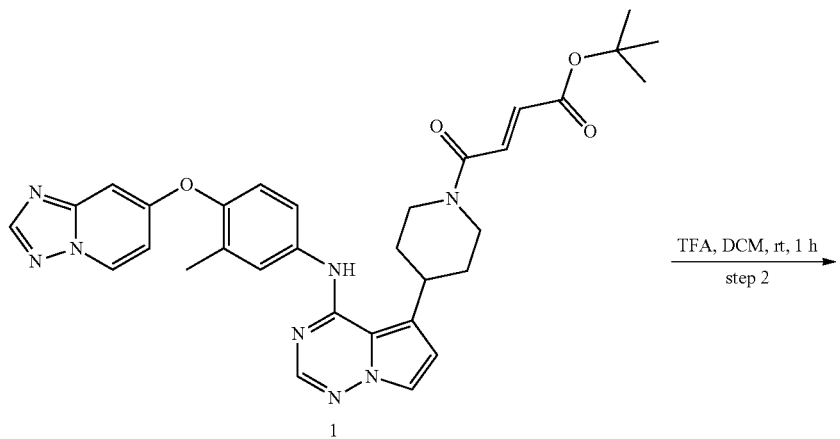

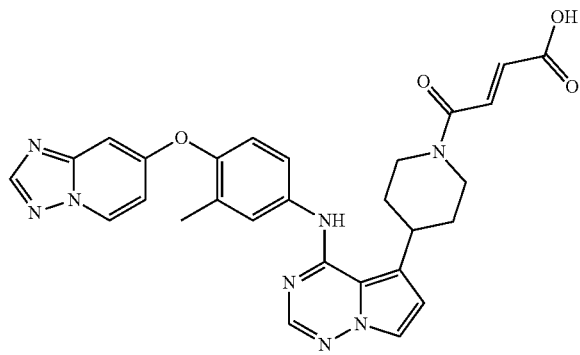

Example 142

Step 1. tert-butyl (E)-4-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-oxobut-2-enoate

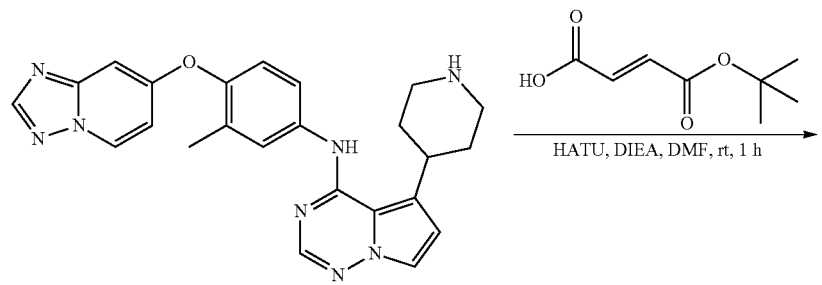

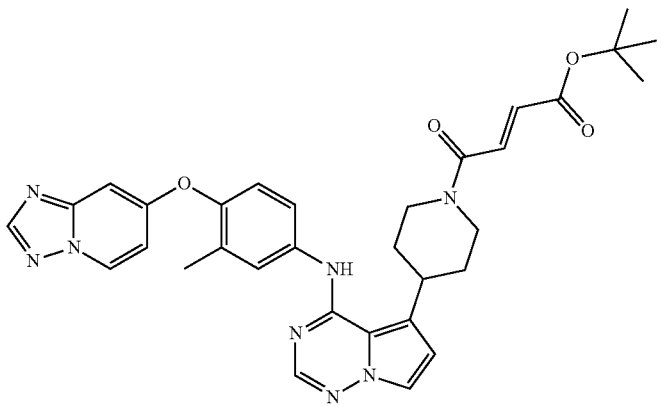

Diisopropylethylamine (176 mg, 1.36 mmol) was added to a mixture of N-(4-([1,2,4]triazolo[1,5-a]pyridin-7-yloxy)-3-methylphenyl)-5-(piperidin-4-yl)pyrrolo[2,1-f][1,2,4]triazin-4-amine (200 mg, 0.45 mmol), (E)-4-(tert-butoxy)-4-oxobut-2-enoic acid (117 mg, 0.68 mmol) and HATU (259 mg, 0.68 mmol) in DMF (4 mL). The resulting mixture was stirred for 1 hour at room temperature, then diluted with water (40 mL) and extracted with ethyl acetate (3×40 mL). The combined organic layers were washed with brine, dried over anhydrous $Na_2SO_4$ and concentrated under vacuum. The residue was purified by Prep-TLC (petroleum ether/ethyl acetate=1:2) to afford the desired product tert-butyl (E)-4-(4-(4-((4-([1,2,4]triazolo[1,5-a]pyridin-7-yloxy)-3-methylphenyl)amino)pyrrolo[2,1-f][1,2,4] triazin-5-yl)piperidin-1-yl)-4-oxobut-2-enoate (150 mg, 55.5% yield). LCMS (ESI-MS) m/z=595.2 [M+H]$^+$.

Step 2. (E)-4-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-oxobut-2-enoic acid

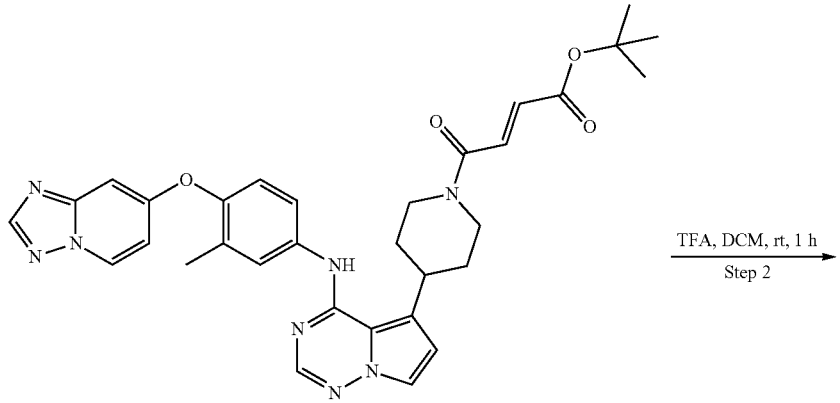

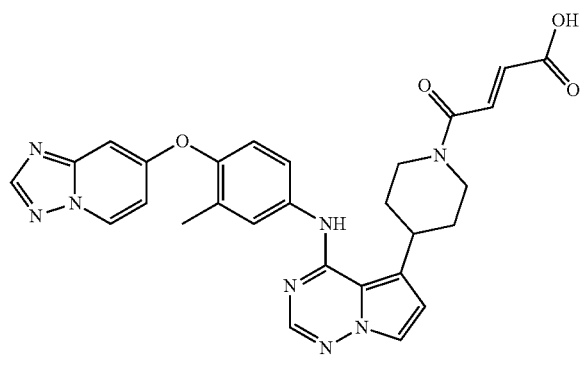

Example 142

TFA (633 mg, 5.55 mmol) was added to a mixture of tert-butyl (E)-4-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-oxobut-2-enoate (150 mg, 0.25 mmol) in DCM (6 mL). The resulting mixture was stirred for 1 hour at room temperature and concentrated under vacuum. The residue was purified by Prep-HPLC; Mobile Phase A: Water (0.1% FA), Mobile Phase B: ACN; Gradient: 26% B to 42% B to afford the desired product (E)-4-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-oxobut-2-enoic acid, Example 142 (9.7 mg, 7.2% yield). LCMS (ESI-MS) m/z=539.2 [M+H]$^+$. $^1$H NMR (400 MHz, DMSO-d$_6$) δ (ppm) 12.97 (s, 1H), 8.95 (d, J=7.5 Hz, 1H), 8.53 (s, 1H), 8.39 (s, 1H), 7.90 (s, 11H), 7.72 (d, J=2.8 Hz, 1H), 7.68-7.57 (m, 2H), 7.44 (d, J=15.4 Hz, 1H), 7.23 (d, J=8.6 Hz, 1H), 7.17-7.00 (m, 1H), 6.80 (d, J=2.6 Hz, 1H), 6.72 (d, J=2.8 Hz, 1H), 6.52 (d, J=15.4 Hz, 1H), 4.58 (d, J=12.9 Hz, 1H), 4.09 (d, J=13.5 Hz, 1H), 3.75-3.65 (m, 1H), 3.45-3.29 (m, 1H), 2.96-2.84 (m, 1H), 2.20 (s, 3H), 2.04-1.91 (m, 2H), 1.74-1.45 (m, 2H).

Example 143 and 144

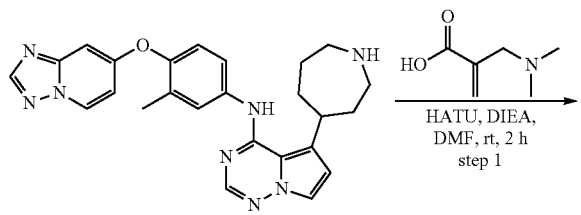

-continued
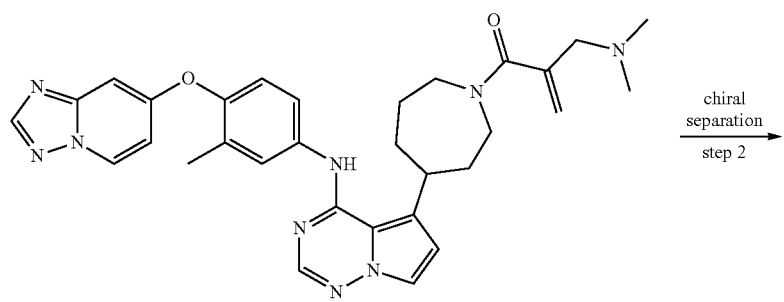
chiral separation step 2
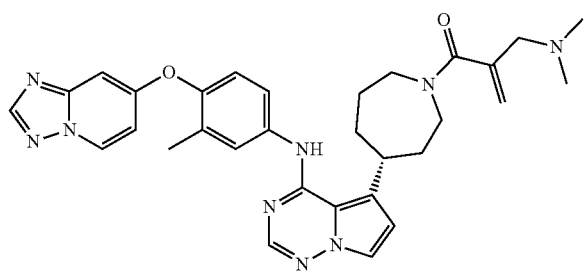
Example 143
+
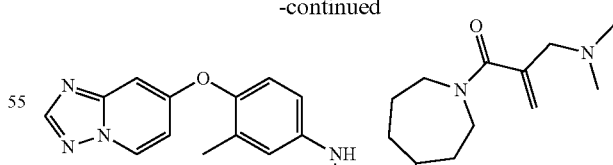
Example 144
Step 1. 1-(4-(4-(4-([1,2,4]triazolo[1,5-a]pyridin-7-yloxy)-3-methylphenyl)amino)pyrrolo[2,1-f][1,2,4]triazin-5-yl)azepan-1-yl)-2-((dimethylamino)methyl)prop-2-en-1-one
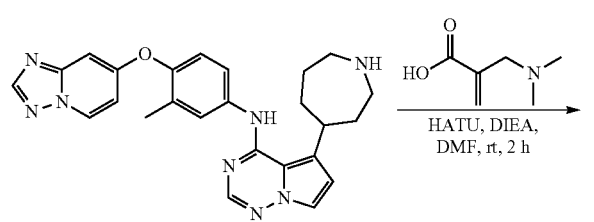
-continued
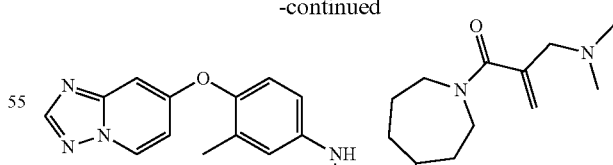
A mixture of N-(4-([1,2,4]triazolo[1,5-a]pyridin-7-yloxy)-3-methylphenyl)-5-(azepan-4-yl)pyrrolo[2,1-t][1,2,4]triazin-4-amine (100 mg, 0.22 mmol), 2-((dimethylamino)methyl)acrylic acid (34.10 mg, 0.26 mmol), diisopropylethylamine (85.35 mg, 0.66 mmol) and HATU (125.47 mg, 0.33 mmol) in DMF (1 mL) was stirred at room temperature for 2 hours. The reaction mixture was filtered and the filtrate was purified by Prep-HPLC using the following conditions: Column: XBridge Prep OBD C18 Column, 30*150 mm, 5 μm; Mobile Phase A: Water (10 mmol/L NH₄HCO₃), Mobile Phase B: 20 mm NaOH+10% ACN; Flow rate: 60 mL/min mL/min; Gradient: 28% B to 58% B in 7 min; Wave Length: 254 nm/220 nm nm; RT1(min): 5.9 to afford the desired product 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-((dimethylamino)methyl)prop-2-en-1-one (40 mg). LCMS (ESI-MS) m/z=566.2 [M+H]⁺.

Step 2. (S)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-((dimethylamino)methyl)prop-2-en-1-one Example 143 & (R)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-((dimethylamino)methyl)prop-2-en-1-one (Example 144)

The racemate of 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-((dimethylamino)methyl)prop-2-en-1-one (40 mg, 0.07 mmol) was separated by Prep-Chiral-HPLC with the condition: Column: CHIRAL ART Amylose-SA, 2*25 cm, 5 m; Mobile Phase A: MtBE(0.5% 2M NH3-MeOH)-HPLC, Mobile Phase B: EtOH-HPLC; Flow rate: 20 ML/MIN mL/min; Gradient: isocratic 20; Wave Length: 254/220 nm nm; RT1(min): 7.451; RT2(min): 10.262; Sample Solvent: EtOH-HPLC; Injection Volume: 0.9 mL; Number Of Runs: 6. The desired fractions were combined and lyophilized to afford the two desired separated isomers Examples 143 and 144:

First eluting isomer of 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-((dimethylamino)methyl)prop-2-en-1-one (1.6 mg, 100% ee, 3.94% yield). LCMS (ESI-MS) m/z=566.3 [M+H]⁺. ¹H NMR (400 MHz, DMSO-d₆) δ (ppm) 8.94 (d, J=7.4 Hz, 1H), 8.37 (d, J=7.8 Hz, 2H), 7.90 (s, 1H), 7.69 (d, J=12.8 Hz, 2H), 7.22 (d, J=8.5 Hz, 1H), 7.03 (d, J=6.2 Hz, 1H), 6.78 (s, 1H), 6.62 (s, 1H), 5.33 (s, 1H), 5.27 (s, 1H), 3.84 (s, 1H), 3.57 (s, 3H), 3.12-2.95 (m, 2H), 2.18 (d, J=10.6 Hz, 11H), 1.93 (s, 3H), 1.78 (d, J=12.5 Hz, 2H), 1.24 (s, 1H).

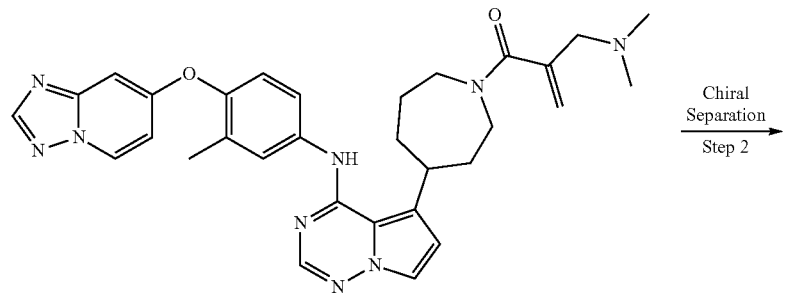

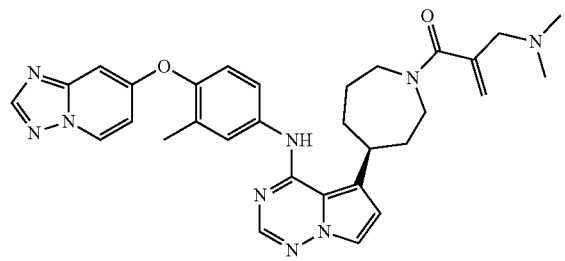

Example 143

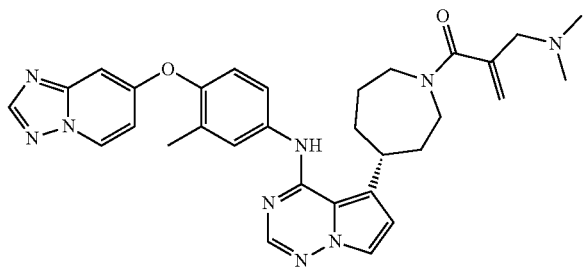

Example 144

Cell growth inhibition activity of first eluting isomer based on assays described for Table 3:

| HER2 - YVMA IC$_{50}$ (nM) | HER2 WT IC$_{50}$ (nM) | EGFR WT IC50 (nM) |
|---|---|---|
| ++ | ++++ | + |

Second eluting isomer of 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-((dimethylamino)methyl)prop-2-en-1-one (2.7 mg, 100% ee, 6.69% yield). LCMS (ESI-MS) m/z=566.3 [M+H]$^+$. $^1$H NMR (400 MHz, DMSO-d$_6$) δ (ppm) 8.95 (d, J=7.4 Hz, 1H), 8.42 (s, 1H), 8.37 (d, J=8.5 Hz, 1H), 7.90 (s, 1H), 7.74-7.65 (m, 2H), 7.29-7.18 (m, 1H), 7.03 (dd, J=7.5, 2.6 Hz, 1H), 6.79 (d, J=3.0 Hz, 1H), 6.62 (d, J=2.7 Hz, 1H), 5.33 (s, 1H), 5.18 (d, J=10.4 Hz, 1H), 3.84 (s, 1H), 3.55 (s, 3H), 3.00 (d, J=12.2 Hz, 1H), 2.97-2.87 (m, 1H), 2.21-2.06 (m, 11H), 2.03-1.95 (m, 3H), 1.78 (d, J=11.2 Hz, 1H), 1.74 (s, 1H), 1.24 (s, 1H).

Cell growth inhibition activity of second eluting isomer based on assays described for Table 3:

| HER2 - YVMA IC$_{50}$ (nM) | HER2 WT IC$_{50}$ (nM) | EGFR WT IC$_{50}$ (nM) |
|---|---|---|
| ++++ | ++++ | + |

Examples 145, 146, 147, 148

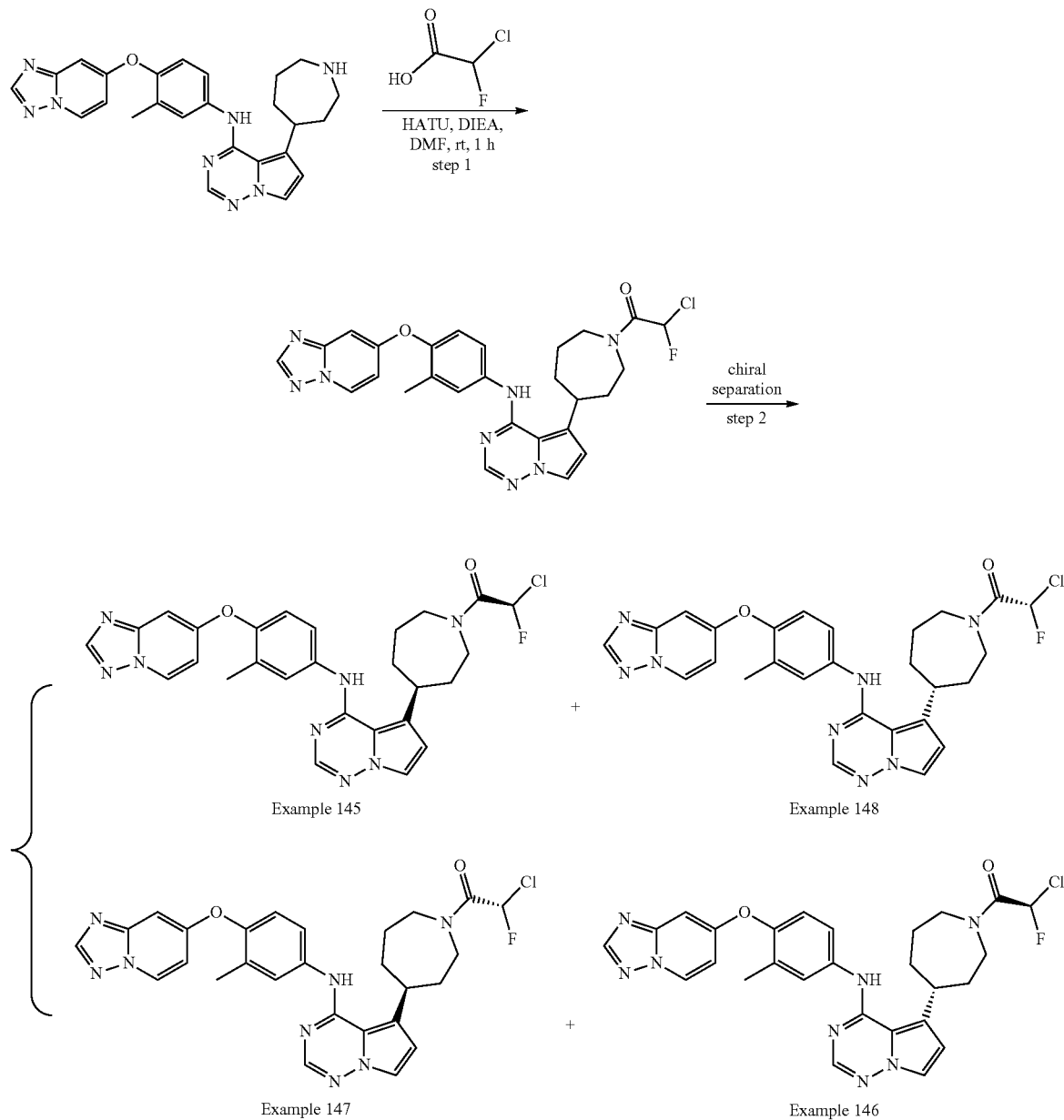

Step 1. 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one

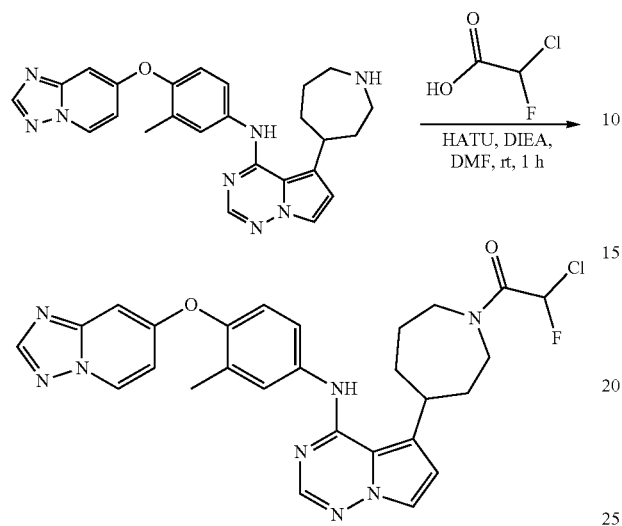

Diisopropylethylamine (710 mg, 1.32 mmol) was added to a mixture of N-(4-([1,2,4]triazolo[1,5-a]pyridin-7-yloxy)-3-methylphenyl)-5-(azepan-4-yl)pyrrolo[2,1-f][1,2,4]triazin-4-amine (200 mg, 0.44 mmol), 2-chloro-2-fluoroacetic acid (59.40 mg, 0.53 mmol) and HATU (250 mg, 0.66 mmol) in DMF (2 mL). The resulting mixture was stirred for 1 hour at room temperature. The residue was concentrated under vacuum and purified by Prep-TLC with ethyl acetate to afford the desired product 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (80 mg, 33.1% yield). LCMS (ESI-MS) m/z=549.2 [M+H]$^+$.

Step 2. (R)-1-((S)-4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (Example 145), (R)-1-((R)-4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (Example 146), (S)-1-((S)-4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (Example 147), & (S)-1-((R)-4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (Example 148)

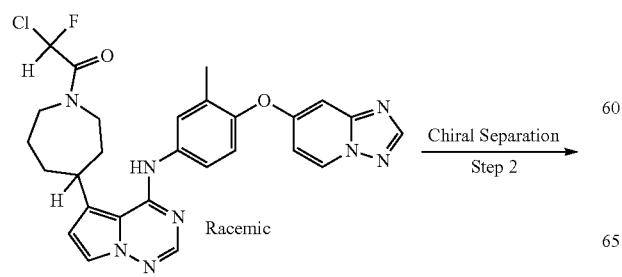

Racemic

Chiral Separation
Step 2

-continued

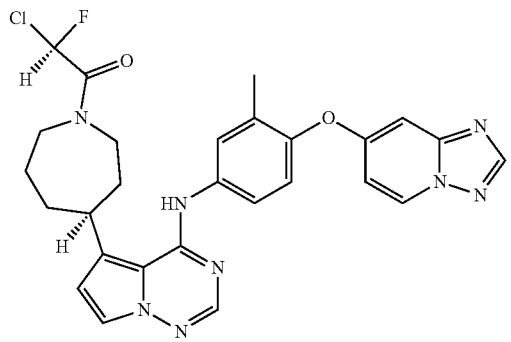

Example 145

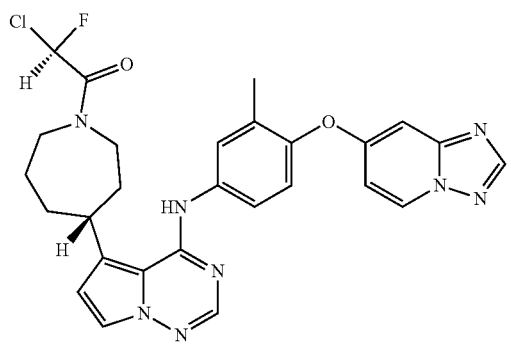

Example 146

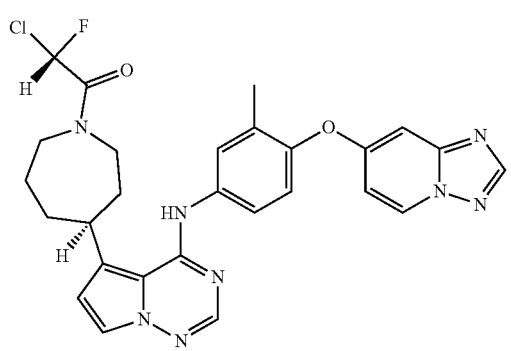

Example 147

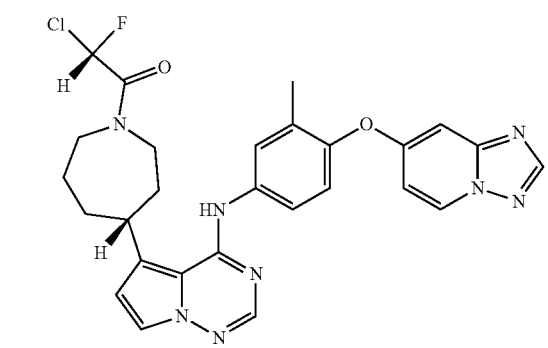

Example 148

The racemate of 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (80 mg, 0.14 mmol) was separated by Prep-Chiral-HPLC with the condition: Column: Column: CHIRAL ART Cellulose-SB, 2*25 cm, 5 μm; Mobile Phase A: Hex:DCM=3:1(0.5% 2M $NH_3$-MeOH)-HPLC, Mobile Phase B: IPA-HPLC; Flow rate: 20 ML/MIN mL/min; Gradient: isocratic 40; Wave Length: 254/220 nm nm; RT1(min): 8.17; RT2(min): 11.11; Sample Solvent: EtOH-HPLC; Injection Volume: 0.6 mL; Number Of Runs: 11. The desired fractions were combined and lyophilized to afford the four desired separated isomers Examples 145, 146, 147 and 148:

First eluting isomer of 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (8.4 mg, % ee, 10.4% yield). LCMS (ESI-MS) m/z=549.2 $[M+H]^+$. $^1$H NMR (400 MHz, Chloroform-d) δ (ppm) 8.52 (d, J=7.2 Hz, 1H), 8.25 (s, 1H), 7.97_(s, 1H), 7.70 (d, J=12.1 Hz, 1H), 7.61-7.56 (m, 2H), 7.12 (d, J=8.5 Hz, 1H), 7.08 (s, 1H), 6.95-6.85 (m, 2H), 6.68-6.58 (m, 1H), 6.52 (d, J=12.4 Hz, 1H), 3.99 (d, J=17.2 Hz, 1H), 3.86-3.79 (m, 2H), 3.61 (s, 1H), 3.11 (s, 1H), 2.48 (s, 1H), 2.27 (d, J=3.1 Hz, 4H), 2.20 (s, 1H), 2.04-1.81 (in, 3H).

Cell growth inhibition activity of first eluting isomer based on assays described for Table 3:

| HER2-YVMA $IC_{50}$ (nM) | HER2 WT $IC_{50}$ (nM) | EGFR WT $IC_{50}$ (nM) |
| --- | --- | --- |
| +++ | ++++ | + |

Second eluting isomer of 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (7.0 mg, 100% ee, 8.6% yield). LCMS (ESI-MS) m/z=549.2 $[M+H]^+$. $^1$H NMR (400 MHz, Chloroform-d) δ (ppm) 8.52 (d, J=7.4 Hz, 1H), 8.25 (s, 1H), 7.97 (s, 1H), 7.69 (s, 1H), 7.59 (d, J=3.0 Hz, 2H), 7.12 (d, J=8.5, 2.6 Hz, 2H), 6.95-6.87 (in, 2H), 6.62 (d, J=12.9 Hz, 11H), 6.51 (d, J=4.7 Hz, 1H), 4.07 (d, J=16.8 Hz, 11H), 3.89-3.79 (m, 1H), 3.75 (s, 1H), 3.58 (s, 1H), 3.13 (s, 1H), 2.47 (d, J=15.1 Hz, 1H), 2.32 (s, 2H), 2.21 (s, 1H), 2.17 (s, 1H), 2.00 (s, 2H), 1.89 (s, 2H).

Cell growth inhibition activity of second eluting isomer based on assays described for Table 3:

| HER2-YVMA $IC_{50}$ (nM) | HER2 WT $IC_{50}$ (nM) | EGFR WT $IC_{50}$ (nM) |
| --- | --- | --- |
| ++++ | ++++ | ++ |

Third eluting isomer of 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (9.9 mg, 100% ee, 12.3% yield). LCMS (ESI-MS) m/z=549.2 $[M+H]^+$. $^1$H NMR (400 MHz, Chloroform-d) δ (ppm) 8.53 (d, J=7.3 Hz, 1H), 8.29 (s, 1H), 7.98 (s, 1H), 7.68 (s, 1H), 7.60 (s, 2H), 7.14 (d, J=8.4 Hz, 2H), 6.91 (s, 2H), 6.64 (d, J=10.9 Hz, 1H), 6.52 (s, 1H), 4.05 (d, J=15.9 Hz, 11H), 3.86 (s, 1H), 3.75 (s, 1H), 3.58 (s, 1H), 3.16 (s, 1H), 2.49 (s, 1H), 2.27 (s, 1H), 2.18 (s, 3H), 2.01 (s, 4H).

Cell growth inhibition activity of third eluting isomer based on assays described for Table 3:

| HER2-YVMA $IC_{50}$ (nM) | HER2 WT $IC_{50}$ (nM) | EGFR WT $IC_{50}$ (nM) |
| --- | --- | --- |
| ++ | +++ | + |

Fourth eluting isomer of (R)-1-((R)-4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one (10.0 mg, 98.4% ee, 12.4% yield). LCMS (ESI-MS) m/z=549.2 $[M+H]^+$. $^1$H NMR (400 MHz, Chloroform-d) δ (ppm) 8.52 (d, J=7.2 Hz, 1H), 8.25 (s, 1H), 7.98 (s, 1H), 7.69 (s, 1H), 7.59 (s, 2H), 7.13 (d, J=8.6 Hz, 1H), 6.96-6.87 (m, 1H), 6.64 (d, J=21.6 Hz, 2H), 6.52 (d, J=11.7 Hz, 2H), 3.99 (d, J=17.1 Hz, 1H), 3.83 (d, J=10.3 Hz, 1H), 3.76 (s, 1H), 3.61 (s, 1H), 3.12 (s, 1H), 2.48 (s, 1H), 2.31 (s, 1H), 2.19 (s, 3H), 2.01 (d, J=12.3 Hz, 3H), 1.92-1.81 (m, 1H).

Cell growth inhibition activity of fourth eluting isomer based on assays described for Table 3:

| HER2-YVMA $IC_{50}$ (nM) | HER2 WT $IC_{50}$ (nM) | EGFR WT $IC_{50}$ (nM) |
| --- | --- | --- |
| ++ | +++ | + |

Example 149

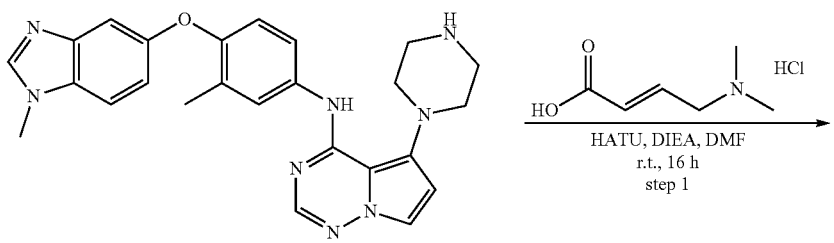

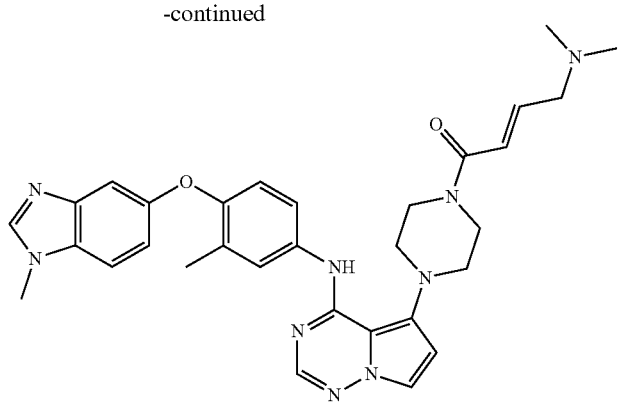

Example 149

(2E)-4-(dimethylamino)-1-{4-[4-({3-methyl-4-[(1-methyl-1,3-benzodiazol-5-yl)oxy]phenyl}amino)pyrrolo[2,1-f][1,2,4]triazin-5-yl]piperazin-1-yl}but-2-en-1-one (E)-4-(dimethylamino)but-2-enoic acid hydrochloride (65.59 mg, 0.39 mmol), HATU (188.22 mg, 0.49 mmol) and diisopropylethylamine (127.96 mg, 0.99 mmol) were added to a stirred solution of N-(3-methyl-4-((1-methyl-1H-benzo[d]imidazol-5-yl)oxy)phenyl)-5-(piperazin-1-yl)pyrrolo[2,1-f][1,2,4]triazin-4-amine (150.10 mg, 0.33 mmol) in DMF (2 mL) at room temperature. The resulting mixture was stirred at room temperature for 16 hours. The reaction mixture was then filtered and the filtrate was purified by Prep-HPLC, Mobile Phase A: Water (0.1% FA), Mobile Phase B, Gradient: 2% B to 30% to afford (E)-4-(dimethylamino)-1-(4-(4-((3-methyl-4-((1-methyl-1H-benzo[d]imidazol-5-yl)oxy)phenyl)-amino)pyrrolo[2,1-f][1,2,4]triazin-5-yl)piperazin-1-yl)but-2-en-1-one, Example 149 (21.5 mg, 11% yield). LCMS (ESI-MS) m/z=566.3 [M+H]$^+$. 1H NMR (400 MHz, Chloroform-d) δ (ppm) 9.60 (s, 1H), 7.97 (s, 1H), 7.87 (s, 1H), 7.68 (s, 1H), 7.52 (d, J=8.9 Hz, 1H), 7.44 (d, J=2.9 Hz, 1H), 7.29 (d, J=5.4 Hz, 1H), 7.11-7.04 (m, 1H), 6.92 (dd, J=11.9, 7.4 Hz, 2H), 6.58 (dd, J=9.2, 6.3 Hz, 2H), 3.87 (s, 3H), 3.22 (d, J=6.2 Hz, 4H), 2.97 (s, 3H), 2.36 (d, J=8.7 Hz, 9H), 2.09 (s, 3H).

Example 150

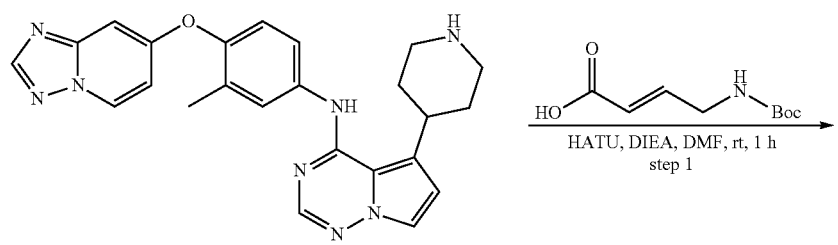

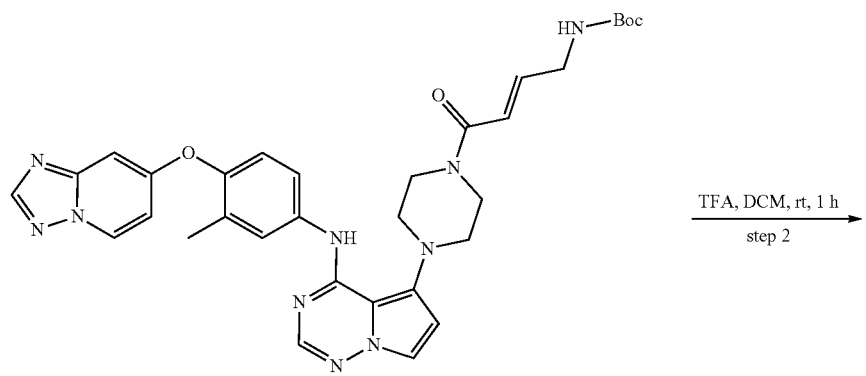

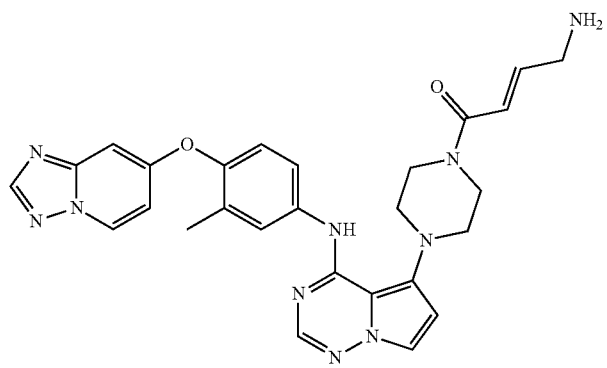

Example 150

Step 1. tert-butyl (E)-(4-(4-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-oxobut-2-en-1-yl)carbamate

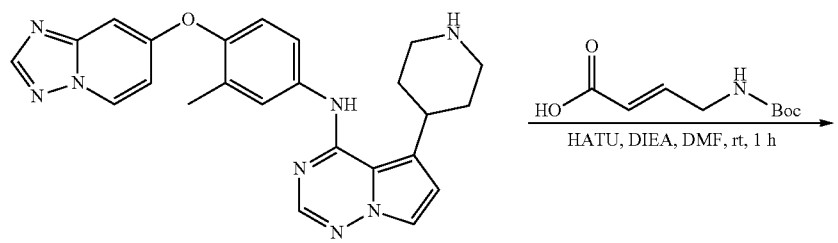

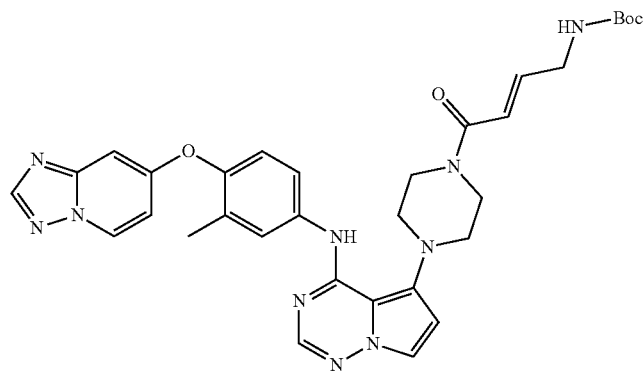

Diisopropylethylamine (88 mg, 0.68 mmol) was added to a mixture of N-(4-([1,2,4]triazolo[1,5-a]pyridin-7-yloxy)-3-methylphenyl)-5-(piperidin-4-yl)pyrrolo[2,1-f][1,2,4]triazin-4-amine (100 mg, 0.23 mmol), (E)-4-((tert-butoxycarbonyl)amino)but-2-enoic acid (45 mg, 0.23 mmol) and HATU (129 mg, 0.34 mmol) in DMF (1 mL). The resulting mixture was stirred for 1 hour at room temperature and concentrated under vacuum. The residue was purified by Prep-TLC (DCM/MeOH 10:1) to afford the desired product tert-butyl (E)-(4-(4-(4-((4-([1,2,4]triazolo[1,5-a]pyridin-7-yloxy)-3-methylphenyl)amino)pyrrolo[2,1-f][1,2,4]triazin-5-yl)piperidin-yl)-4-oxobut-2-en-1-yl)carbamate (60 mg, 36% yield). LCMS (ESI-MS) m/z=625.2 [M+H]$^+$ Step 2. (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-aminobut-2-en-1-one

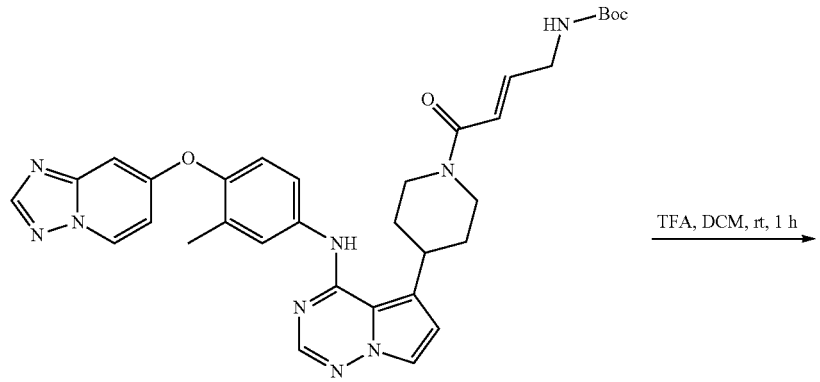

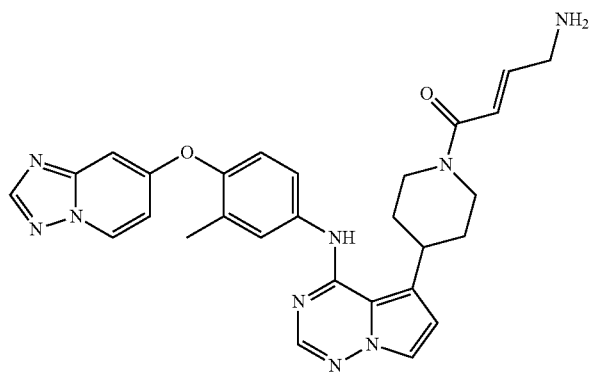

Example 150

TFA (1 mL) was added to a solution of tert-butyl (E)-(4-(4-(4-((4-([1,2,4]triazolo[1,5-a]pyridin-7-yloxy)-3-methylphenyl)amino) pyrrolo[2,1-f][1,2,4]triazin-5-yl)piperidin-1-yl)-4-oxobut-2-en-1-yl)carbamate (60 mg, 0.096 mmol) in DCM (2 mL). The resulting mixture was stirred for 1 hour at room temperature and concentrated under vacuum. The residue was purified by Prep-HPLC, Mobile Phase A: Water (10 mmol $NH_4HCO_3$+0.1% $NH_3 \cdot H_2O$), Mobile Phase B:ACN; Gradient: 47% B to 67% B in 7 min; to afford the desired product (E)-1-(4-(4-(4-((4-([1,2,4]triazolo[1,5-a]pyridin-7-yloxy)-3-methylphenyl)amino)pyrrolo[2,1-f][1,2,4] triazin-5-yl)piperidin-1-yl)-4-aminobut-2-en-1-one, Example 150 (7.4 mg, 14.1% yield). LCMS (ESI-MS) m/z=524.2 [M+H]+. 1H NMR (400 MHz, Methanol-d4) δ 8.76 (d, J=7.5 Hz, 1H), 8.31 (s, 1H), 7.82 (s, 1H), 7.64 (d, J=15.9 Hz, 2H), 7.20 (d, J=8.7 Hz, 1H), 7.10 (d, J=7.4 Hz, 1H), 6.94-6.81 (m, 2H), 6.68-6.67 (m, 2H), 4.77-4.55 (m, 2H), 4.32-4.30 (m, 1H), 3.40-3.24 (m, 1H), 3.22-3.12 (m, 1H) 2.15 (s, 3H), 1.76-1.73 (m, 3H), 1.29-1.10 (m, 4H).

Example 151

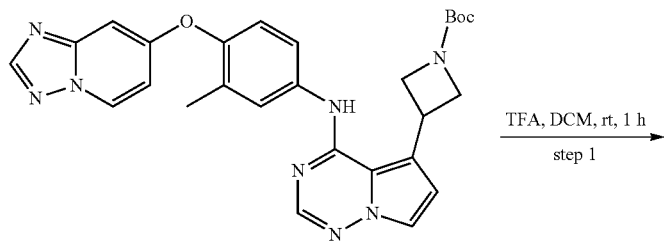

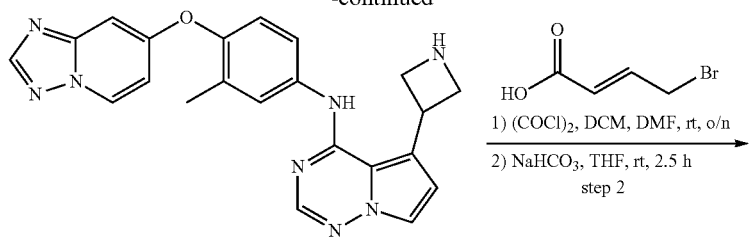

1) (COCl)₂, DCM, DMF, rt, o/n
2) NaHCO₃, THF, rt, 2.5 h
step 2

1

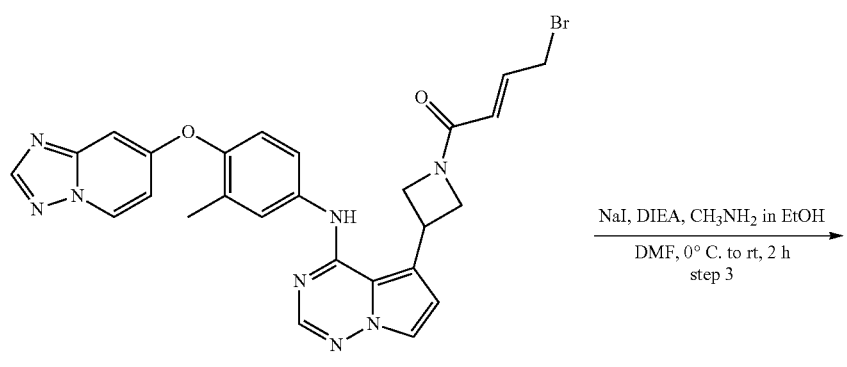

NaI, DIEA, CH₃NH₂ in EtOH
DMF, 0° C. to rt, 2 h
step 3

2

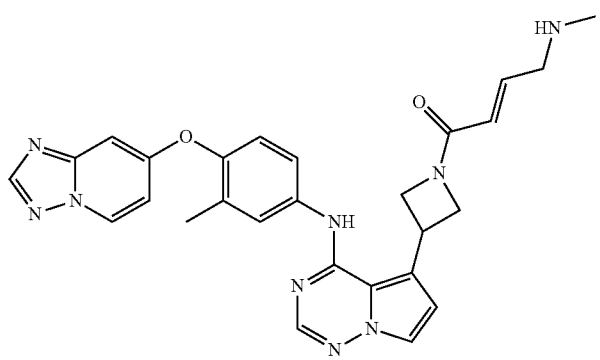

Example 151

Step 1. N-(4-([1,2,4]triazolo[1,5-a]pyridin-7-yloxy)-3-methylphenyl)-5-(azetidin-3-yl)pyrrolo[2,1-f][1,2,4]triazin-4-amine

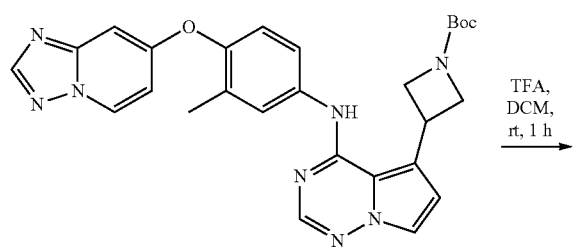

TFA, DCM, rt, 1 h

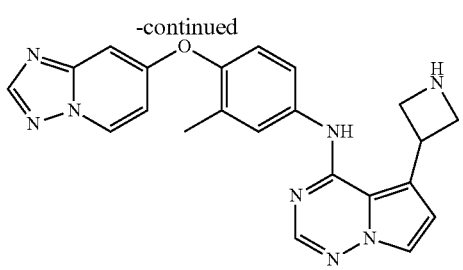

TFA (2 mL) was added into a stirred mixture of tert-butyl 3-(4-((4-([1,2,4]triazolo[1,5-a]pyridin-7-yloxy)-3-methylphenyl)amino)pyrrolo[2,1-f][1,2,4]triazin-5-yl)azetidine-1-carboxylate (300 mg, 0.58 mmol) in DCM (5 mL). The resulting mixture was stirred for 1 hour at room temperature and then concentrated under high vacuum to afford the crude product N-(4-([1,2,4]triazolo[1,5-a]pyridin-7-yloxy)-3-methylphenyl)-5-(azetidin-3-yl)pyrrolo[2,1-f][1,2,4]triazin-4-amine (200 mg crude). The crude product was used in the next step immediately without further purification. LCMS (ESI-MS) m/z=413.2 [M+H]$^+$.

Step 2. (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-bromobut-2-en-1-one

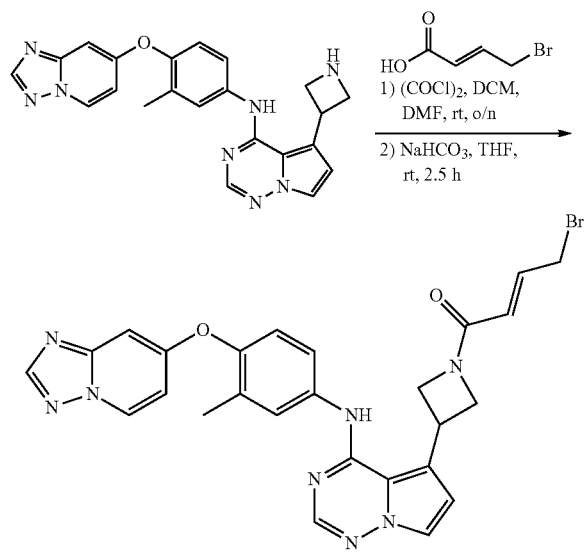

Oxalyl chloride (462 mg, 3.63 mmol) was added to a mixture of (E)-4-bromobut-2-enoic acid (240 mg, 1.45 mmol) in DCM (3 mL) at 0° C., followed by addition of catalytic amount of DMF (0.01 mL). The resulting mixture was stirred overnight at room temperature and concentrated under vacuum to afford the crude (E)-4-bromobut-2-enoyl chloride. A mixture of N-(4-([1,2,4]triazolo[1,5-a]pyridin-7-yloxy)-3-methylphenyl)-5-(azetidin-3-yl)pyrrolo[2,1-f][1,2,4]triazin-4-amine (200 mg, 0.48 mmol) and NaHCO$_3$ (407 mg, 4.85 mmol) in THF (3 mL) was stirred for 1.5 hours at room temperature. Then a solution of (E)-4-bromobut-2-enoyl chloride in 3 mL THF was added to the reaction mixture dropwise and stirred for another hour. The resulting mixture was quenched by addition of water (50 mL) and extracted with ethyl acetate (3×50 mL). The combined organic layers were washed with brine, dried over anhydrous Na$_2$SO$_4$ and concentrated under vacuum to afford the crude product. The residue was purified by Prep-TLC (DCM/MeOH10:1) to afford the desired product (E)-1-(3-(4-((4-([1,2,4]triazolo[1,5-a]pyridin-7-yloxy)-3-methylphenyl)amino)-pyrrolo[2,1-f][1,2,4]triazin-5-yl)azetidin-1-yl)-4-bromobut-2-en-1-one (150 mg, 46.5% yield for two steps). LCMS (ESI-MS) m/z=559.2 [M+H]$^+$.

Step 3. (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(methylamino)but-2-en-1-one

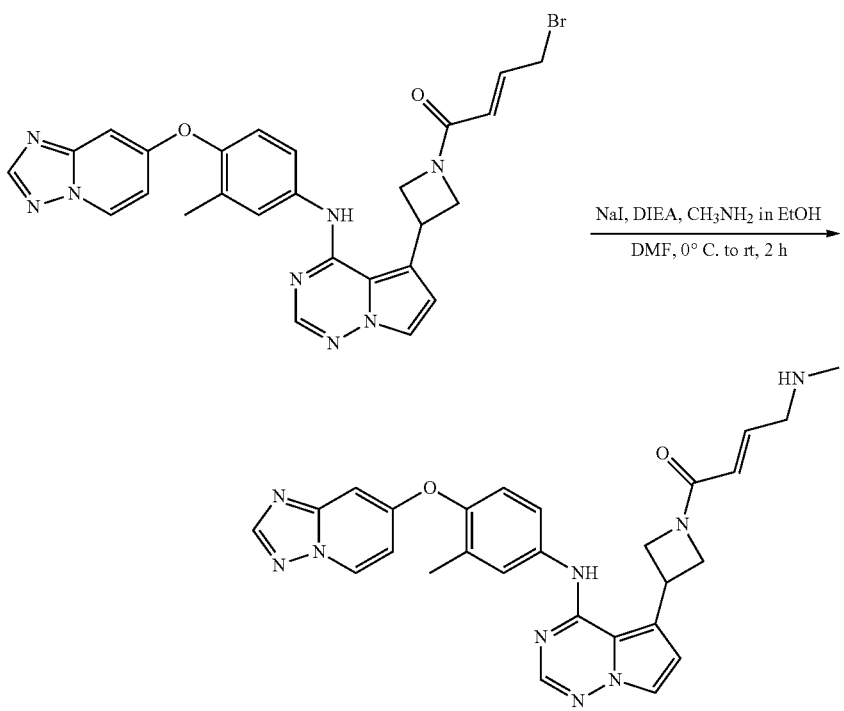

Example 151

A solution of methylamine in EtOH (33% wt, 100 mg, 1.06 mmol) was added to a mixture of (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-bromobut-2-en-1-one (150 mg, 0.27 mmol) and diisopropylethylamine (104 mg, 0.8 mmol) in DMF (2 mL) at 0° C. The resulting mixture was stirred for 2 hours at room temperature and concentrated under vacuum to afford the crude product. The residue was purified by reverse phase flash chromatography; Mobile Phase A: Water (0.1% FA), Mobile Phase B: ACN; Gradient: 4% B to 31% B to afford the desired product (E)-1-(3-(4-((4-([1,2,4]triazolo[1,5-a]pyridin-7-yloxy)-3-methylphenyl)amino)pyrrolo[2,1-f][1,2,4] triazin-5-yl)azetidin-1-yl)-4-(methylamino)but-2-en-1-one, Example 151 (9.5 mg, 6.9% yield). LCMS (ESI-MS) m/z=510.2 [M+H]. $^1$H NMR (400 MHz, DMSO-$d_6$) δ (ppm) 8.94 (d, J=7.4 Hz, 1H), 8.56 (s, 1H), 8.38 (s, 1H), 7.95 (s, 1H), 7.81 (s, 1H), 7.68 (s, 2H), 7.20 (d, J=8.5 Hz, 1H), 7.05-7.04 (m, 1H), 6.95 (s, 1H), 6.80 (s, 1H), 6.69-6.54 (m, 1H), 6.34 (d, J=15.3 Hz, 1H), 4.70 (s, 3H), 4.42 (s, 1H), 4.26 (s, 1H), 4.05 (s, 1H), 3.61 (d, J=5.9 Hz, 2H), 2.47 (s, 3H), 2.24-2.13 (s, 3H).

Example 152

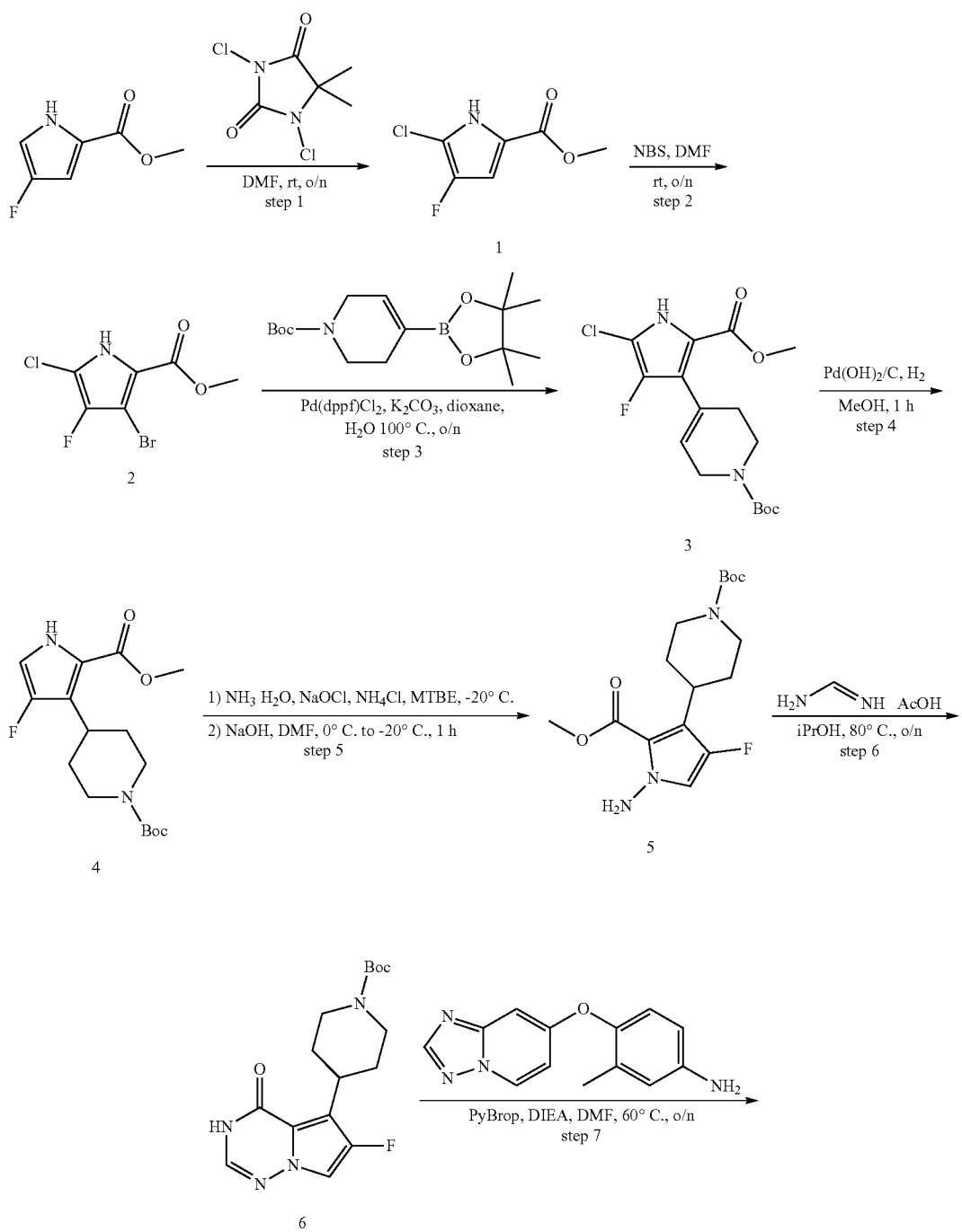

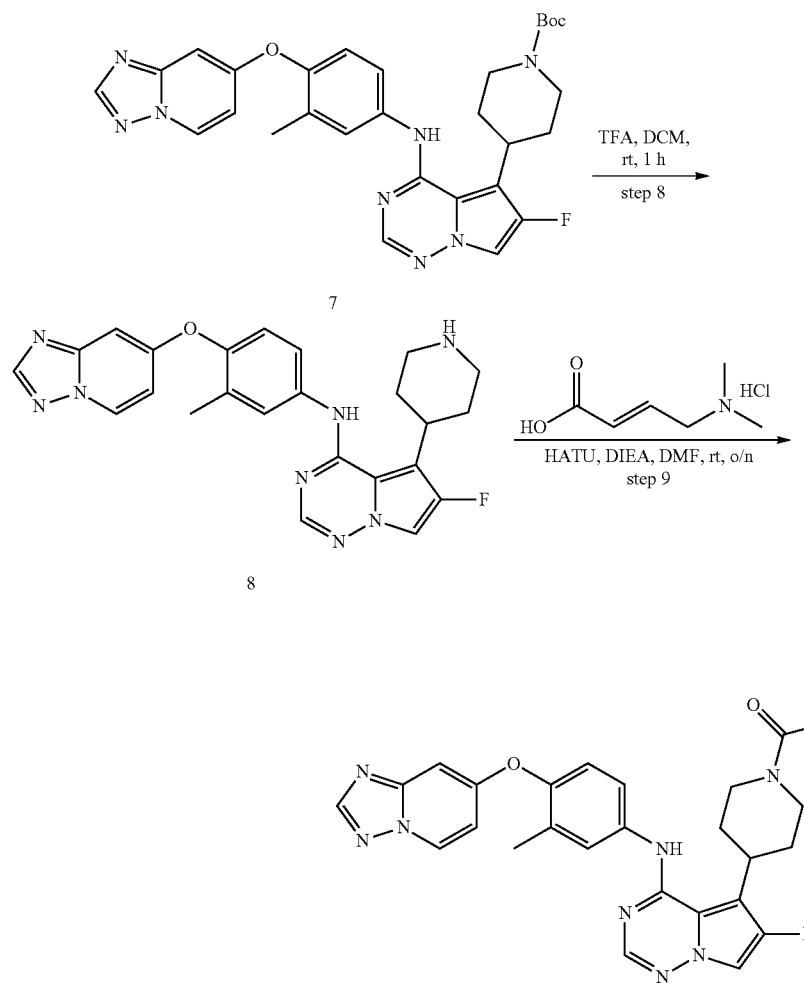

Example 152

Step 1. Methyl 5-chloro-4-fluoro-1H-pyrrole-2-carboxylate

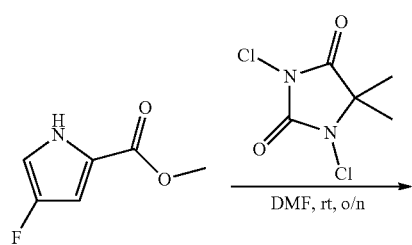

A mixture of 1,3-dichloro-5,5-dimethylimidazolidine-2,4-dione (345 mg, 1.74 mmol) and methyl 4-fluoro-1H-pyrrole-2-carboxylate (500 mg, 3.49 mmol) in DMF (5 mL) was stirred overnight at room temperature, then quenched by addition of water (100 mL) and extracted with ethyl acetate (3×100 mL). The combined organic layers were washed with brine, dried over anhydrous $Na_2SO_4$, filtered and concentrated under vacuum to afford the crude product. The residue was purified by Prep-TLC (petroleum ether/ethyl acetate 5:1) to afford the desired product methyl 5-chloro-4-fluoro-1H-pyrrole-2-carboxylate (450 mg, 72.5% yield). LCMS (ESI-MS) m/z=178.0 [M+H]⁺.

Step 2. Methyl 3-bromo-5-chloro-4-fluoro-1H-pyrrole-2-carboxylate

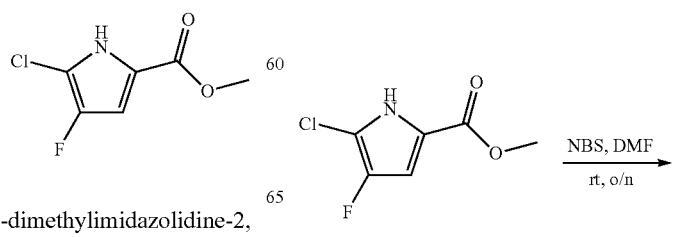

-continued

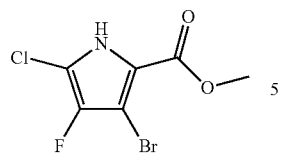

NBS (361 mg, 2.02 mmol) was added to a mixture of methyl 5-chloro-4-fluoro-1H-pyrrole-2-carboxylate (450 mg, 2.53 mmol) in DMF (5 mL). The resulting mixture was stirred overnight at room temperature, quenched by addition of water (50 mL) and extracted with ethyl acetate (3×50 mL). The combined organic layers were washed with brine, dried over anhydrous $Na_2SO_4$, filtered and concentrated under vacuum to afford the crude product. The residue was purified by Prep-TLC (petroleum ether/ethyl acetate=5:1) to afford the desired product methyl 3-bromo-5-chloro-4-fluoro-1H-pyrrole-2-carboxylate (500 mg, 77.1% yield). LCMS (ESI-MS) m/z=255.9 [M+H]+.

Step 3. tert-butyl 4-(5-chloro-4-fluoro-2-(methoxycarbonyl)-1H-pyrrol-3-yl)-3,6-dihydropyridine-1(2H)-carboxylate

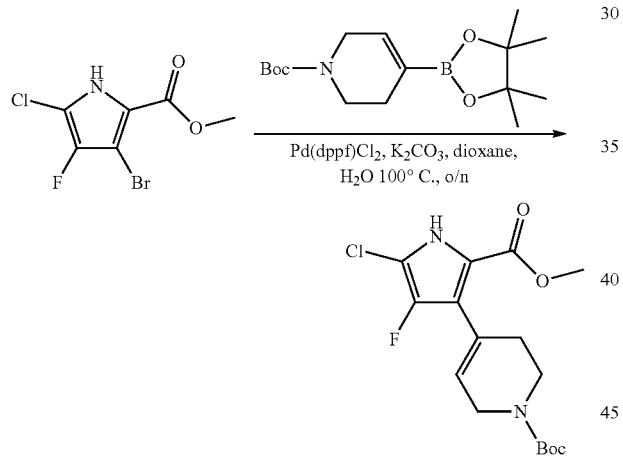

Pd(dppf)Cl$_2$—CH$_2$Cl$_2$ (159 mg, 0.19 mmol) was added to a mixture of methyl 3-bromo-5-chloro-4-fluoro-1H-pyrrole-2-carboxylate (500 mg, 1.95 mmol), tert-butyl 4-(4,4,5,5-tetramethyl-1,3,2-dioxaborolan-2-yl)-3,6-dihydropyridine-1(2H)-carboxylate (603 mg, 1.95 mmol) and K$_2$CO$_3$ (808 mg, 5.85 mmol) in dioxane (10 mL) and H$_2$O (3 mL) under nitrogen atmosphere. The resulting mixture was stirred overnight at 100° C. under nitrogen atmosphere. After cooling to room temperature, the reaction mixture was diluted with H$_2$O (50 mL) and extracted with ethyl acetate (3×50 mL). The combined organic layers were washed with brine, dried over anhydrous Na$_2$SO$_4$ and concentrated under vacuum to afford the crude product. The residue was purified by Prep-TLC (petroleum ether/ethyl acetate=1:1) to afford the desired product tert-butyl 4-(5-chloro-4-fluoro-2-(methoxycarbonyl)-1H-pyrrol-3-yl)-3,6-dihydropyridine-1(2H)-carboxylate (250 mg, 35.4% yield). LCMS (ESI-MS) m/z=359.1 [M+H]+.

Step 4. tert-butyl 4-(4-fluoro-2-(methoxycarbonyl)-1H-pyrrol-3-yl)piperidine-1-carboxylate

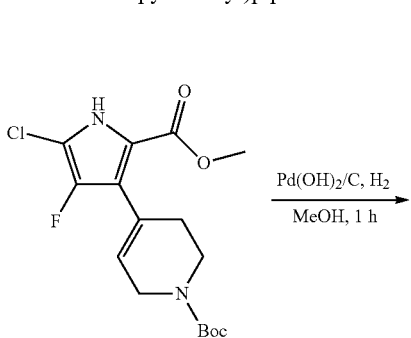

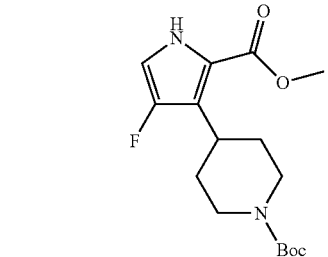

Pd(OH)$_2$/C (20% on carbon, nominally 50% water, 742 mg) was added to a mixture of tert-butyl 4-(5-chloro-4-fluoro-2-(methoxycarbonyl)-1H-pyrrol-3-yl)-3,6-dihydropyridine-1(2H)-carboxylate (250 mg, 0.69 mmol) in MeOH (10 mL) under nitrogen atmosphere. The resulting mixture was degassed under vacuum and charged with an atmospheric pressure of hydrogen. The resulting mixture was stirred for 1 hour, purged with nitrogen and filtered. The filter cake was washed with DCM (3×100 mL). The filtrate was concentrated under vacuum to afford the crude product tert-butyl 4-(4-fluoro-2-(methoxycarbonyl)-1H-pyrrol-3-yl)piperidine-1-carboxylate (250 mg crude). The crude product was used in the next step directly without further purification. LCMS (ESI-MS) m/z=327.2 [M+H]+.

Step 5. tert-butyl 4-(1-amino-4-fluoro-2-(methoxycarbonyl)-1H-pyrrol-3-yl)piperidine-1-carboxylate

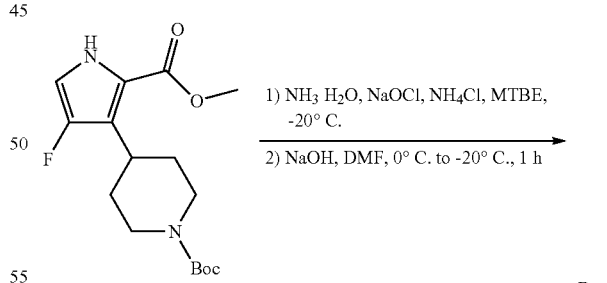

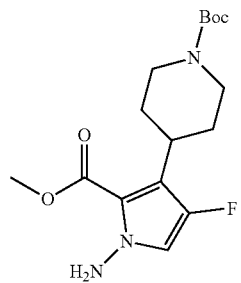

To a flask was added MTBE (100 mL) and NH₄Cl (246 mg, 4.59 mmol). The reaction mixture was cooled to −20° C. Then saturated NH₃·H₂O (3 mL, 77 mmol) was added followed by slow addition of NaOCl (7.5 mL, 111 mmol). After addition, the reaction was stirred at −20° C. for an additional 30 minutes. The MTBE layer was separated and washed with brine and dried over anhydrous sodium sulfate. In a separate flask under nitrogen was added tert-butyl 4-(4-fluoro-2-(methoxycarbonyl)-1H-pyrrol-3-yl)piperidine-1-carboxylate (250 mg, 0.76 mmol) and dry DMF (5 mL). The reaction was cooled to 0° C. whereupon NaOH (61 mg, 1.53 mmol) was added portion wise to the reaction. The reaction was stirred at 0° C. for additional 1 hour before it was cooled to −20° C. At this time, the previously prepared MTBE solution of chloramine was added slowly to the reaction and the reaction mixture was stirred at −20° C. for 1 hour. The reaction was quenched with saturated sodium thiosulfate solution. The organic layer of the reaction was separated and washed with water and brine, dried over sodium sulfate, filtered and concentrated to afford tert-butyl 4-(1-amino-4-fluoro-2-(methoxycarbonyl)-1H-pyrrol-3-yl)piperidine-1-carboxylate (100 mg, 42% yield for two steps). LCMS (ESI-MS) m/z=342.2 [M+H]⁺.

Step 6. tert-butyl 4-(6-fluoro-4-oxo-3,4-dihydropyrrolo[2,1-f][1,2,4]triazin-5-yl)piperidine-1-carboxylate

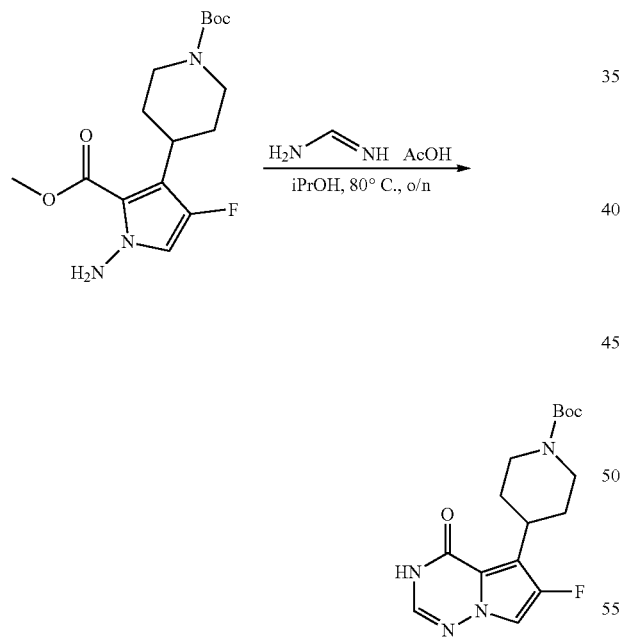

A mixture of tert-butyl 4-(1-amino-4-fluoro-2-(methoxycarbonyl)-1H-pyrrol-3-yl)piperidine-1-carboxylate (100 mg, 0.29 mmol) and formamidine acetate (305 mg, 2.93 mmol) in isopropyl alcohol (2 mL) was stirred overnight at 80° C. and concentrated under vacuum to afford the crude product tert-butyl 4-(6-fluoro-4-oxo-3,4-dihydropyrrolo[2,1-t][1,2,4]triazin-5-yl)piperidine-1-carboxylate (100 mg crude). The crude product was used in the next step without further purification. LCMS (ESI-MS) m/z=337.2 [M+H]⁺.

Step 7. tert-butyl 4-(4-((4-([1,2,4]triazolo[1,5-a]pyridin-7-yloxy)-3-methylphenyl)amino)-6-fluoropyrrolo[2,1-f][1,2,4]triazin-5-yl)piperidine-1-carboxylate

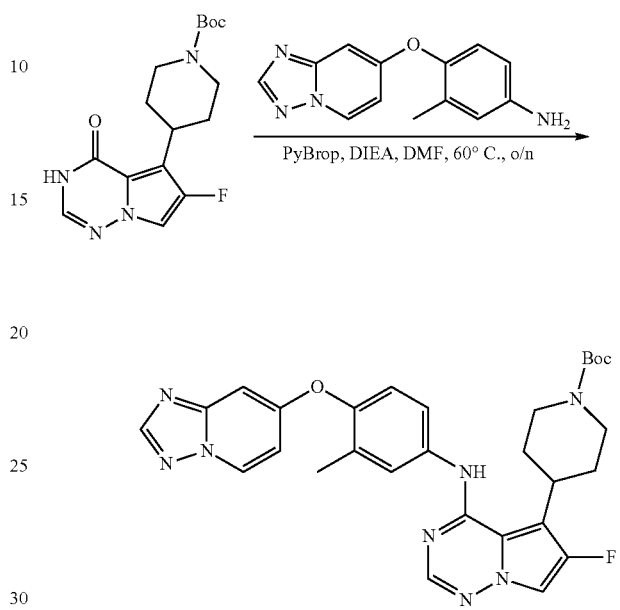

Diisopropylethylamine (231 mg, 1.78 mmol) was added to a mixture of tert-butyl 4-(6-fluoro-4-oxo-3,4-dihydropyrrolo[2,1-f][1,2,4]triazin-5-yl)piperidine-1-carboxylate (100 mg, 0.29 mmol), 4-([1,2,4]triazolo[1,5-a]pyridin-7-yloxy)-3-methylaniline (143 mg, 0.59 mmol) and PyBrOP (416 mg, 0.89 mmol) in DMF (2 mL). The resulting mixture was stirred overnight at 60° C., quenched by addition of water (50 mL) and extracted with ethyl acetate (3×50 mL). The combined organic layers were washed with brine (50 mL), dried over anhydrous Na₂SO₄ and concentrated under vacuum to afford the crude product. The residue was purified by Prep-TLC (petroleum ether/ethyl acetate=1:2) to afford the desired product tert-butyl 4-(4-((4-([1,2,4]triazolo[1,5-a]pyridin-7-yloxy)-3-methylphenyl)amino)-6-fluoropyrrolo[2,1-f][1,2,4]triazin-5-yl)piperidine-1-carboxylate (50 mg, 30.9% yield for two steps). LCMS (ESI-MS) m/z=559.2 [M+H]⁺.

Step 8. N-(4-([1,2,4]triazolo[1,5-a]pyridin-7-yloxy)-3-methylphenyl)-6-fluoro-5-(piperidin-4-yl)pyrrolo[2,1-f][1,2,4]triazin-4-amine

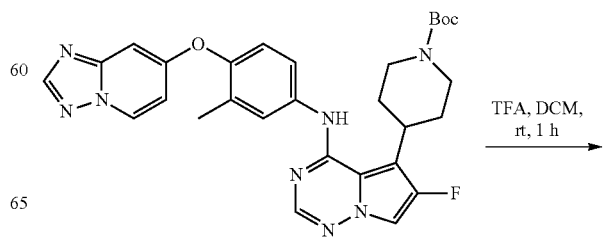

-continued

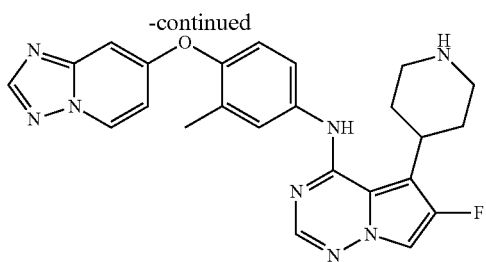

TFA (1 mL) was added to a mixture of tert-butyl 4-(4-((4-([1,2,4]triazolo[1,5-a]pyridin-7-yloxy)-3-methylphenyl)amino)-6-fluoropyrrolo[2,1-f][1,2,4]triazin-5-yl)piperidine-1-carboxylate (50 mg, 0.09 mmol) in DCM (3 mL). The resulting mixture was stirred for 1 hour at room temperature and concentrated under vacuum to afford the crude product N-(4-([1,2,4]triazolo[1,5-a]pyridin-7-yloxy)-3-methylphenyl)-6-fluoro-5-(piperidin-4-yl)pyrrolo[2,1-f][1,2,4]triazin-4-amine (50 mg crude). The crude product was used in the next step directly without further purification. LCMS (ESI-MS) m/z=459.2 [M+H].

Step 9. (E)-1-(4-(4-((4-([1,2,4]triazolo[1,5-a]pyridin-7-yloxy)-3-methylphenyl)amino)-6-fluoropyrrolo[2,1-f][1,2,4]triazin-5-yl)piperidin-1-yl)-4-(dimethylamino)but-2-en-1-one

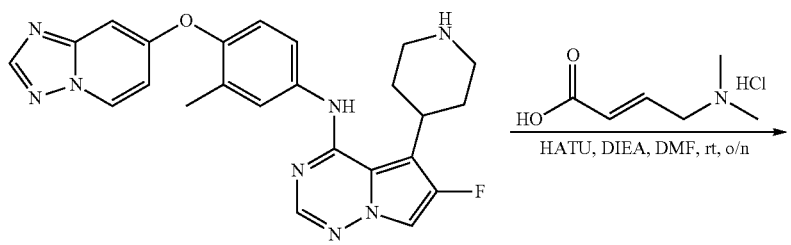

Diisopropylethylamine (42.3 mg, 0.32 mmol) was added to a mixture of N-(4-([1,2,4]triazolo[1,5-a]pyridin-7-yloxy)-3-methylphenyl)-6-fluoro-5-(piperidin-4-yl)pyrrolo[2,1-f][1,2,4]triazin-4-amine (50 mg, 0.11 mmol), (E)-4-(dimethylamino)but-2-enoic acid hydrochloride (27.1 mg, 0.16 mmol) and HATU (62.2 mg, 0.16 mmol) in DMF (2 mL). The resulting mixture was stirred overnight at room temperature, diluted with water (10 mL) and extracted with ethyl acetate (3×10 mL). The combined organic layers were washed with brine, dried over anhydrous $Na_2SO_4$, filtered and concentrated under vacuum to afford the crude product. The crude product was purified by Prep-TLC (petroleum ether/ethyl acetate 1:2) to afford (E)-1-(4-(4-((4-([1,2,4]triazolo[1,5-a]pyridin-7-yloxy)-3-methylphenyl)amino)-6-fluoropyrrolo[2,1-f][1,2,4]triazin-5-yl)piperidin-1-yl)-4-(dimethylamino)but-2-en-1-one, Example 152 (19.7 mg, 38.4% yield for two steps). LCMS (ESI-MS) m/z=570.3 [M+H]$^+$. $^1$H NMR (400 MHz, DMSO-$d_6$) δ (ppm) 8.95 (d, J=7.6 Hz, 1H), 8.67 (s, 1H), 8.39 (s, 1H), 7.99 (s, 1H), 7.89 (s, 1H), 7.61 (s, 1H), 7.56 (d, J=8.7 Hz, 1H), 7.23 (d, J=8.7 Hz, 1H), 7.04 (d, J=7.5 Hz, 1H), 6.79 (s, 1H), 6.65 (s, 1H), 6.60 (s, 1H), 4.57 (s, 1H), 4.17 (s, 1H), 3.62 (s, 1H), 3.04 (s, 2H), 2.18 (d, J=16.2 Hz, 111H), 1.97 (s, 2H), 1.78 (s, 2H).

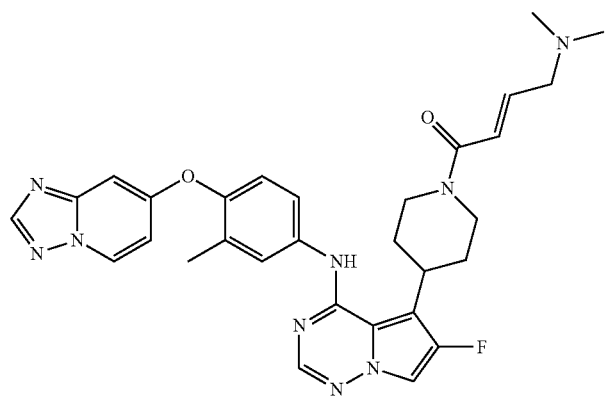

Example 152

Example 154

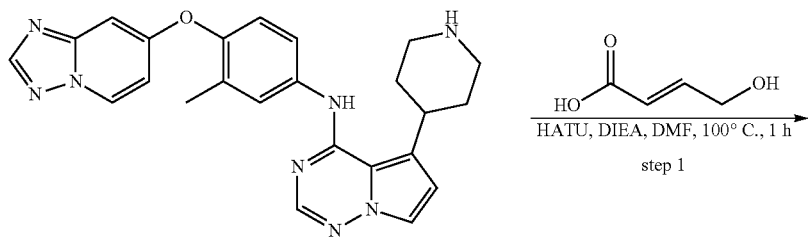

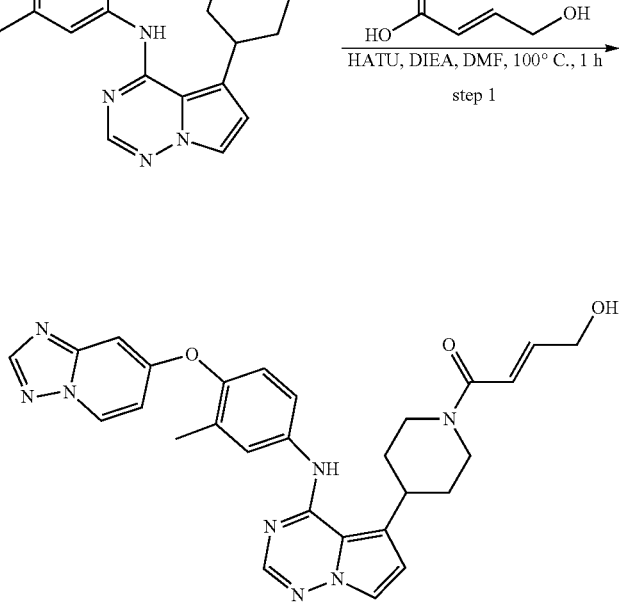

Example 154

Step 1. (E)-1-(4-(4-((4-([1,2,4]triazolo[1,5-a]pyridin-7-yloxy)-3-methylphenyl)amino)pyrrolo[2,1-f][1,2,4] triazin-5-yl)piperidin-1-yl)-4-hydroxybut-2-en-1-one Diisopropylethylamine (88 mg, 0.68 mmol) was added to a solution of N-(4-([1,2,4]triazolo[1,5-a]pyridin-7-yloxy)-3-methylphenyl)-5-(piperidin-4-yl)pyrrolo[2,1-f][1,2,4]triazin-4-amine (100 mg, 0.22 mmol), (E)-4-hydroxybut-2-enoic acid (23.2 mg, 0.22 mmol) and HATU (129 mg, 0.34 mmol) in DMF (2 mL). The resulting mixture was stirred at 100° C. for 1 hour. After cooling the reaction mixture to room temperature, the residue was purified by Prep-HPLC; Mobile Phase A: Water (0.1% FA), Mobile Phase B: ACN; Gradient: 15% B to 45% B to afford the desired product (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-hydroxybut-2-en-1-one, Example 154 (58.0 mg, 50.2% yield). LCMS (ESI-MS) m/z=525.4 [M+H]$^+$. $^1$H NMR (400 MHz, DMSO-d$_6$) δ (ppm) 8.99 (d, J=7.2 Hz, 1H), 8.47 (s, 1H), 8.05-7.72 (m, 2H), 7.69-7.40 (m, 2H), 7.39-7.02 (m, 2H), 6.89 (s, 1H), 6.77-6.73 (m, 2H), 6.64-6.60 (m, 1H), 6.52-4.80 (m, 2H), 4.58 (s, 1H), 4.14 (s, 3H), 3.80-3.51 (m, 1H), 3.43-3.11 (m, 1H), 2.95-2.73 (m, 1H), 2.20 (s, 3H), 1.98 (s, 2H), 1.57 (s, 2H).

Example 157

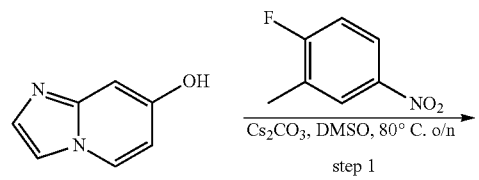

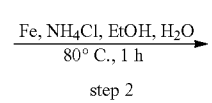

-continued

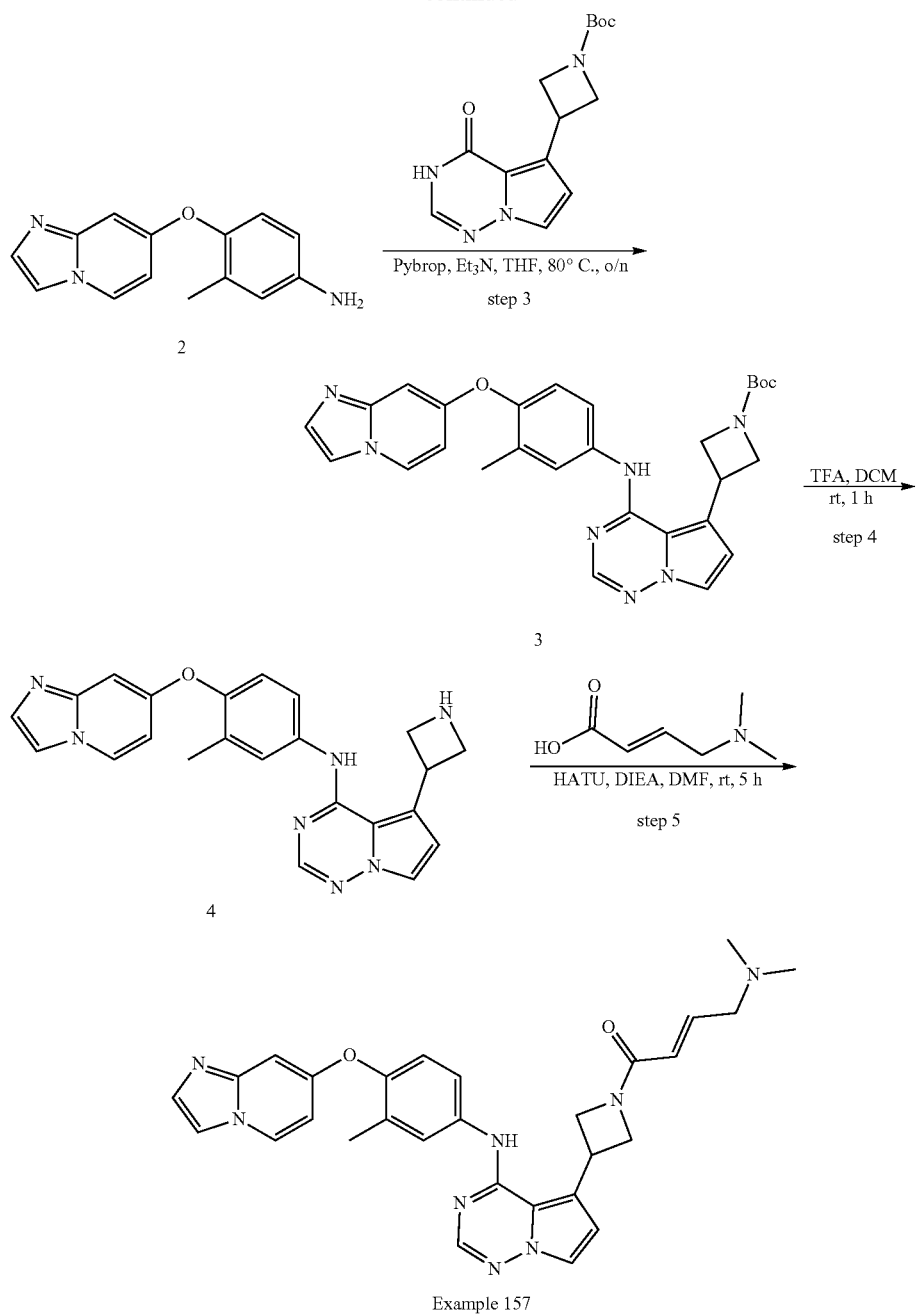

Example 157

Step 1. 7-(2-methyl-4-nitrophenoxy)imidazo[1,2-a]pyridine

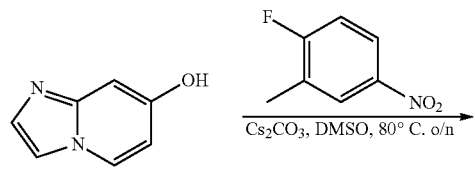 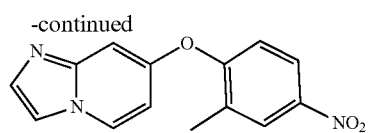

A mixture of imidazo[1,2-a]pyridin-7-ol (1.00 g, 7.45 mmol), 1-fluoro-2-methyl-4-nitrobenzene (1.16 g, 7.45 mmol) and $Cs_2CO_3$ (4.86 g, 14.9 mmol) in DMSO (10 mL) was stirred overnight at 80° C. After cooling to room temperature, the reaction mixture was diluted with water (100 mL) and extracted with ethyl acetate (3×100 mL). The combined organic layers were washed with brine, dried over anhydrous $Na_2SO_4$, filtered and concentrated under vacuum to afford the crude product 7-(2-methyl-4-nitrophenoxy) imidazo[1,2-a]pyridine (1.85 g crude). The crude product was used in the next step directly without further purification. LCMS (ESI-MS) m/z=270.1 [M+H]+.

Step 2. 4-(imidazo[1,2-a]pyridin-7-yloxy)-3-methylaniline

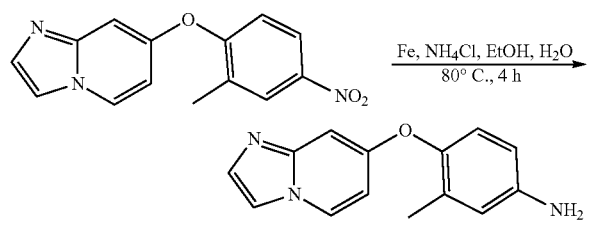

NH4Cl (1.1 g, 20.62 mmol) and iron (3.84 g, 68.7 mmol) were added to a solution of 7-(2-methyl-4-nitrophenoxy) imidazo[1,2-a]pyridine (1.85 g, 6.87 mmol) in EtOH (15 mL) and H2O (5 mL). The resulting mixture was stirred for 4 hours at 80° C. After cooling to room temperature, the resulting mixture was filtered. The filter cake was washed with EtOH (4×50 mL) and the filtrate was concentrated under vacuum to afford the crude product. The residue was purified by silica gel column chromatography, eluted with ethyl acetate in petroleum ether from 0% to 50% to afford the desired product 4-(imidazo[1,2-a]pyridin-7-yloxy)-3-methylaniline (1.45 g, 81.3% yield for two steps). LCMS (ESI-MS) m/z=240.1 [M+H]+.

Step 3. tert-butyl 3-(4-((4-(imidazo[1,2-a]pyridin-7-yloxy)-3-methylphenyl)amino)pyrrolo[2,1-f][1,2,4]triazin-5-yl)azetidine-1-carboxylate

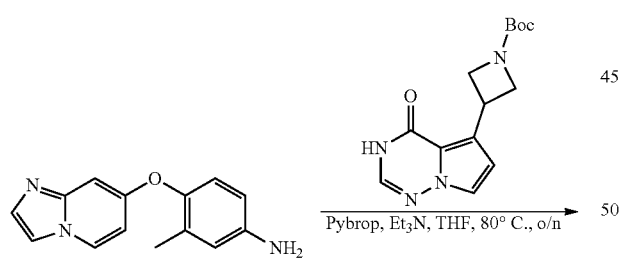

Et3N (1.81 g, 17.8 mmol) was added to a mixture of 4-(imidazo[1,2-a]pyridin-7-yloxy)-3-methylaniline (1.42 g, 5.95 mmol), tert-butyl 3-(4-oxo-3,4-dihydropyrrolo[2,1-f][1,2,4]triazin-5-yl)azetidine-1-carboxylate (1.73 g, 5.95 mmol) and PyBrOP (3.33 g, 7.14 mmol) in THF (10 mL). The resulting mixture was stirred at 80° C. overnight and concentrated under vacuum. The residue was purified by reversed-phase flash chromatography using the following conditions: column, C18 silica gel; mobile phase, MeCN in Water (0.1% NH3·H2O), 10% to 50% gradient in 10 min; detector, UV 254 nm and the desired fractions were combined and concentrated under vacuum to afford the desired product tert-butyl 3-(4-((4-(imidazo[1,2-a]pyridin-7-yloxy)-3-methylphenyl)amino)pyrrolo[2,1-f][1,2,4]triazin-5-yl)azetidine-1-carboxylate (1.4 g, 46% yield). LCMS (ESI-MS) m/z=512.2 [M+H]+.

Step 4. 5-(azetidin-3-yl)-N-(4-(imidazo[1,2-a]pyridin-7-yloxy)-3-methylphenyl)pyrrolo[2,1-f][1,2,4]triazin-4-amine

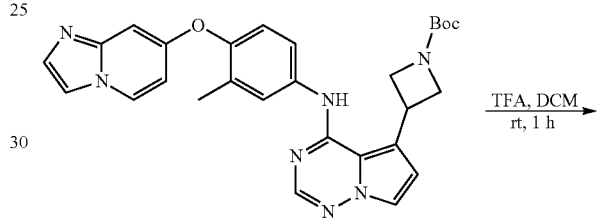

TFA (1.4 mL) was added to a mixture of tert-butyl 3-(4-((4-(imidazo[1,2-a]pyridin-7-yloxy)-3-methylphenyl)amino)pyrrolo[2,1-f][1,2,4]triazin-5-yl)azetidine-1-carboxylate (1.4 g, 2.73 mmol) in DCM (14 mL). The resulting mixture was stirred for 1 hour at room temperature and then concentrated under vacuum to afford the crude product 5-(azetidin-3-yl)-N-(4-(imidazo[1,2-a]pyridin-7-yloxy)-3-methylphenyl)pyrrolo[2,1-f][1,2,4]triazin-4-amine (1.21 g crude). The crude product was used in the next step directly without further purification. LCMS (ESI-MS) m/z=412.2 [M+H]+.

Step 5. (E)-4-(dimethylamino)-1-(3-(4-((4-(imidazo[1,2-a]pyridin-7-yloxy)-3-methylphenyl)amino)pyrrolo [2,1-f][1,2,4]triazin-5-yl)azetidin-1-yl)but-2-en-1-one

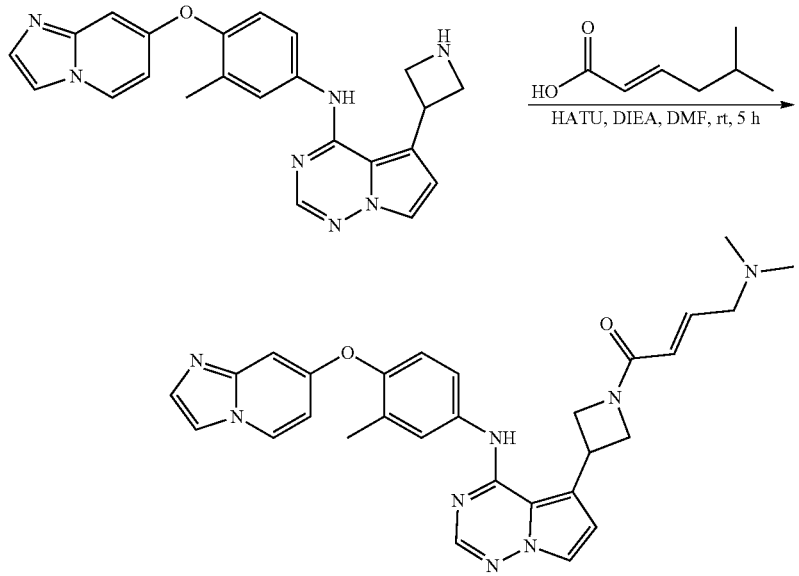

Example 157

Diisopropylethylamine (47.1 mg, 0.36 mmol) was added to a mixture of 5-(azetidin-3-yl)-N-(4-(imidazo[1,2-a]pyridin-7-yloxy)-3-methylphenyl)pyrrolo[2,1-f][1,2,4] triazin-4-amine (50 mg, 0.12 mmol), (2E)-4-(dimethylamino)but-2-enoic acid (18.8 mg, 0.14 mmol) and HATU (69.3 mg, 0.18 mmol) in DMF (0.5 mL). The resulting mixture was stirred for 5 hours at room temperature and concentrated under vacuum to afford the crude product. The residue was purified by reversed-phase flash chromatography; Mobile Phase A: Water (10 mmol/L $NH_4HCO_3$+0.05% $NH_3H_2O$), Mobile Phase B: ACN; Gradient: 23% B to 53% B to afford the desired product (E)-4-(dimethylamino)-1-(3-(4-((4-(imidazo[1,2-a]pyridin-7-yloxy)-3-methylphenyl)amino)pyrrolo-[2,1-f][1,2,4]triazin-5-yl)azetidin-1-yl)but-2-en-1-one, Example 157 (9.0 mg, 14.4% yield). LCMS (ESI-MS) m/z=523.3 [M+H]$^+$. $^1$H NMR (400 MHz, DMSO-$d_6$) δ (ppm) 8.55 (d, J=7.4 Hz, 1H), 8.48 (s, 1H), 7.94 (s, 1H), 7.87-7.78 (m, 2H), 7.68-7.59 (m, 2H), 7.44 (d, J=1.3 Hz, 1H), 7.14 (d, J=8.5 Hz, 1H), 6.97 (d, J=2.8 Hz, 1H), 6.81 (dd, J=7.4, 2.5 Hz, 1H), 6.61 (dt, J=15.4, 6.2 Hz, 1H), 6.54 (d, J=2.5 Hz, 1H), 6.17 (dt, J=15.5, 1.7 Hz, 1H), 4.69 (t, J=7.1 Hz, 2H), 4.41 (t, J=8.7 Hz, 1H), 4.26 (d, J=13.1 Hz, 1H), 4.02 (dd, J=10.0, 5.0 Hz, 1H), 3.02 (dd, J=6.2, 1.6 Hz, 2H), 2.20 (s, 3H), 2.14 (d, J=4.1 Hz, 6H).

Example 158

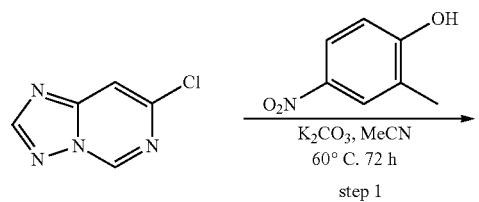

step 1

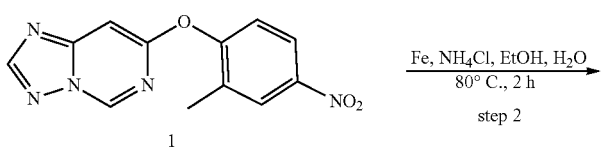

step 2

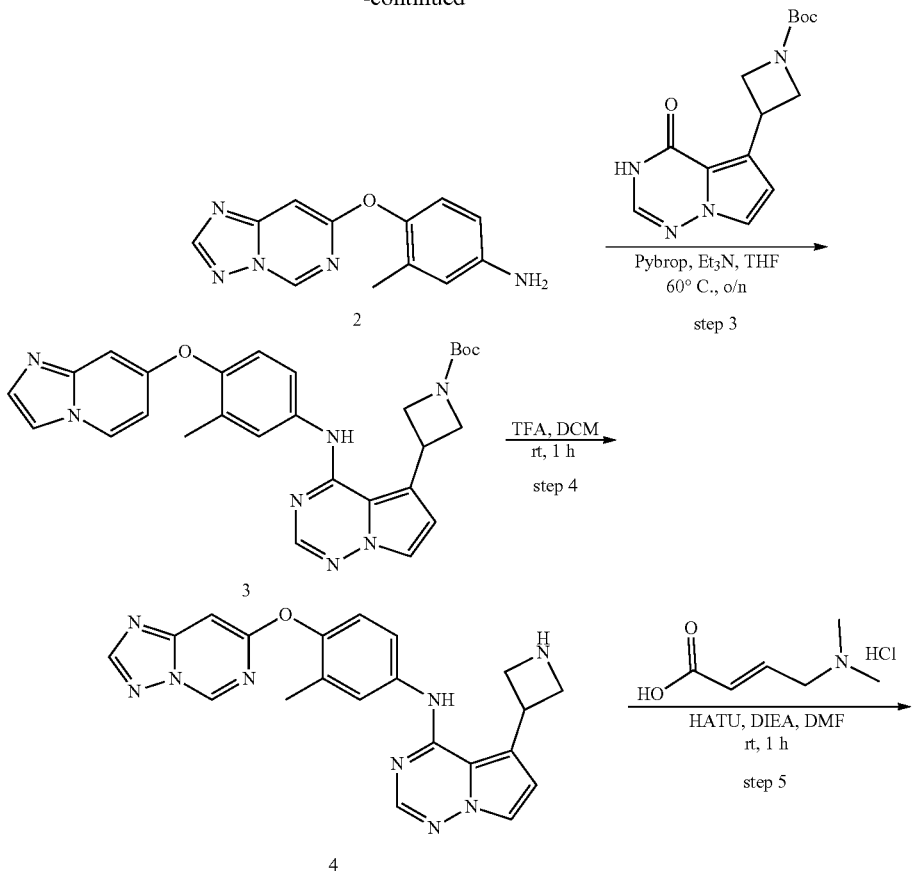
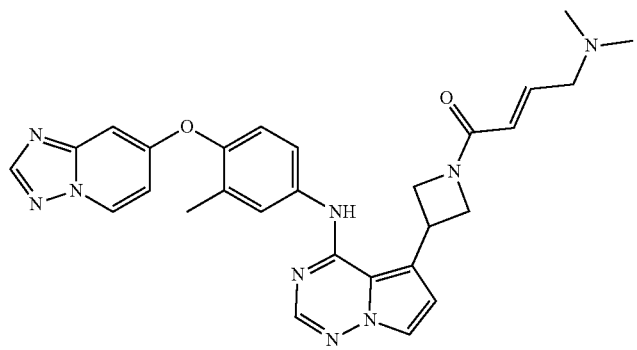
Example 158
Step 1. 7-(2-methyl-4-nitrophenoxy)-[1,2,4]triazolo[1,5-c]pyrimidine
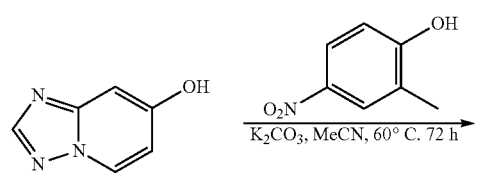
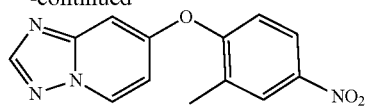
K$_2$CO$_3$ (8.05 g, 58.2 mmol) was added to a solution of 7-chloro-[1,2,4]triazolo[1,5-c]pyrimidine (3.0 g, 19.4 mmol) and 2-methyl-4-nitrophenol (2.97 g, 19.4 mmol) in MeCN (15 mL). The reaction mixture was stirred for 72 hours at 60° C. and concentrated under vacuum. The residue was diluted with water (60 mL) and extracted with ethyl acetate (3×60 mL). The combined organic layers were washed with brine, dried over anhydrous Na₂SO₄, filtered and concentrated under vacuum to afford the crude product. The residue was purified by silica gel column chromatography, eluted with ethyl acetate in petroleum ether from 0% to 70% to afford the desired product 7-(2-methyl-4-nitrophenoxy)-[1,2,4]triazolo[1,5-c]pyrimidine (1.8 g, 34.2% yield). LCMS (ESI-MS) m/z=272.2 [M+H]⁺.

Step 2. 4-([1,2,4]triazolo[1,5-c]pyrimidin-7-yloxy)-3-methylaniline

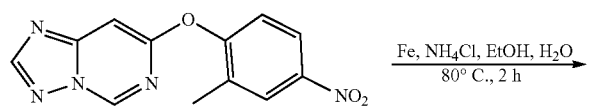

To a solution of 7-(2-methyl-4-nitrophenoxy)-[1,2,4]triazolo[1,5-c]pyrimidine (1.8 g, 6.63 mmol) in EtOH (30 mL) and H₂O (10 mL) was added iron (1.85 g, 33.2 mmol) and NH₄Cl (1.42 g, 26.5 mmol). Then the reaction mixture was stirred for 2 hours at 80° C. and concentrated under vacuum. The residue was diluted with water (20 mL) and extracted with ethyl acetate (3×20 mL). The combined organic layers were washed with brine, dried over anhydrous Na₂SO₄, filtered and concentrated under vacuum to afford the crude product 4-([1,2,4]triazolo[1,5-c]pyrimidin-7-yloxy)-3-methylaniline (1.2 g crude). The crude product was used for next step directly without any further purification. LCMS (ESI-MS) m/z=242.1 [M+H]⁺.

Step 3. tert-butyl 3-(4-((4-([1,2,4]triazolo[1,5-c]pyrimidin-7-yloxy)-3-methylphenyl)amino)pyrrolo[2,1-f][1,2,4]triazin-5-yl)azetidine-1-carboxylate

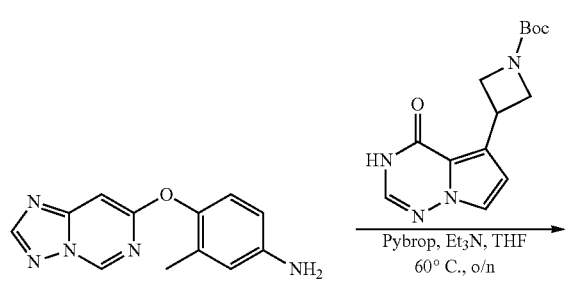

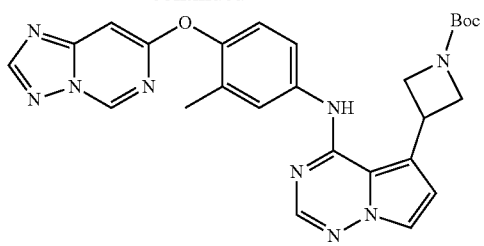

Et₃N (1.38 mL) was added to a mixture of 4-([1,2,4]triazolo[1,5-c]pyrimidin-7-yloxy)-3-methylaniline (800 mg, 3.31 mmol), tert-butyl 3-(4-oxo-3,4-dihydropyrrolo[2,1-f][1,2,4]triazin-5-yl)azetidine-1-carboxylate (481 mg, 1.65 mmol) and PyBrOP (2.32 g, 4.97 mmol) in THF (12 mL). The resulting mixture was stirred overnight at 60° C. After cooling to room temperature, the reaction mixture was filtered, and the filtrate was concentrated under vacuum to afford the crude product. The residue was purified by silica gel column chromatography, eluted with ethyl acetate in petroleum ether from 0% to 100% to afford the desired product tert-butyl 3-(4-((4-([1,2,4]triazolo[1,5-c]pyrimidin-7-yloxy)-3-methylphenyl)amino)pyrrolo[2,1-f][1,2,4]triazin-5-yl)azetidine-1-carboxylate (360 mg, 15.8% yield for two steps). LCMS (ESI-MS) m/z=514.2 [M+H]⁺.

Step 4. N-(4-([1,2,4]triazolo[1,5-c]pyrimidin-7-yloxy)-3-methylphenyl)-5-(azetidin-3-yl)pyrrolo[2,1-f][1,2,4]triazin-4-amine

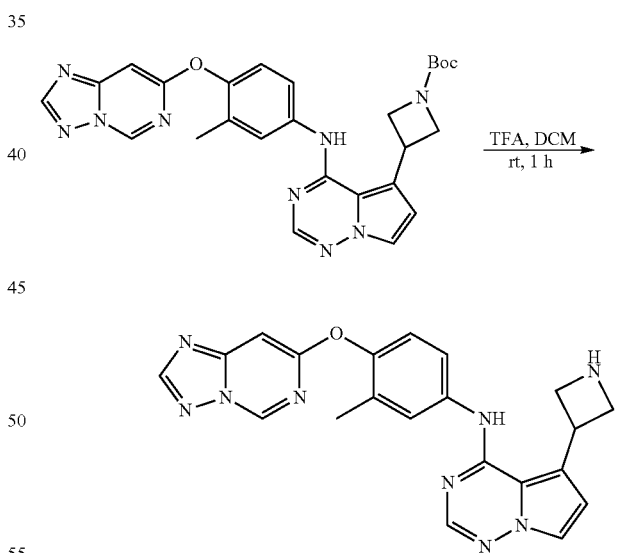

TFA (2 mL) was added to a solution of tert-butyl 3-(4-((4-([1,2,4]triazolo[1,5-c]pyrimidin-7-yloxy)-3-methylphenyl)amino)pyrrolo[2,1-f][1,2,4]triazin-5-yl)azetidine-1-carboxylate (360 mg, 0.7 mmol) in DCM (6 mL). The reaction mixture was stirred for 1 hour at room temperate and concentrated to afford crude product N-(4-([1,2,4]triazolo[1,5-c]pyrimidin-7-yloxy)-3-methylphenyl)-5-(azetidin-3-yl)pyrrolo[2,1-f][1,2,4]triazin-4-amine (300 mg crude). The crude product was used in next step directly without any further purification. LCMS (ESI-MS) m/z=414.2 [M+H]⁺.

Step 5. (E)-1-(3-(4-((4-([1,2,4]triazolo[1,5-c]pyrimidin-7-yloxy)-3-methylphenyl)amino)pyrrolo[2,1-f][1,2,4]triazin-5-yl)azetidin-1-yl)-4-(dimethylamino)but-2-en-1-one

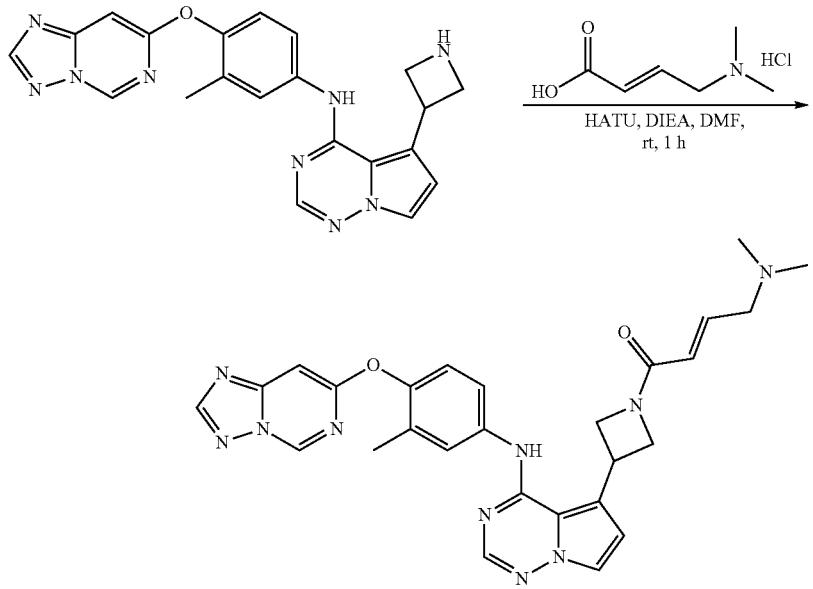

Example 158

Diisopropylethylamine (1.8 g, 13.9 mmol) was added to a mixture of N-(4-([1,2,4]triazolo[1,5-c]pyrimidin-7-yloxy)-3-methylphenyl)-5-(azetidin-3-yl)pyrrolo[2,1-f][1,2,4]triazin-4-amine (960 mg, 2.32 mmol), (E)-4-(dimethylamino)but-2-enoic acid hydrochloride (300 mg, 2.32 mmol) and HATU (1.32 g, 3.48 mmol) in DMF (5 mL). The reaction mixture was then stirred at room temperature for 1 hour and concentrated under high vacuum. The residue was purified by Prep-HPLC, Mobile Phase A: Water (10 mmol/L $NH_4HCO_3$+0.05% $NH_3H_2O$), Mobile Phase B: ACN; Gradient: 23% B to 53% B to afford the desired product (E)-1-(3-(4-((4-([1,2,4]triazolo[1,5-c]pyrimidin-7-yloxy)-3-methylphenyl)amino)pyrrolo[2,1-f][1,2,4]triazin-5-yl)azetidin-1-yl)-4-(dimethylamino)but-2-en-1-one, Example 158 (129.4 mg, 2% yield for two steps). LCMS (ESI-MS) m/z=525.2 [M+H]$^+$. $^1$H NMR (400 MHz, Chloroform-d) δ (ppm) 9.21 (d, J=1.3 Hz, 1H), 8.35 (s, 1H), 8.01 (s, 1H), 7.68-7.61 (m, 2H), 7.59 (d, J=2.7 Hz, 1H), 7.14 (d, J=8.6 Hz, 1H), 7.09 (s, 1H), 7.01-6.90 (m, 2H), 6.74 (d, J=2.8 Hz, 1H), 6.13 (dt, J=15.4, 1.7 Hz, 1H), 4.77 (t, J=8.1 Hz, 2H), 4.67 (s, 1H), 4.43 (s, 2H), 3.11 (dd, J=6.0, 1.7 Hz, 2H), 2.27 (d, J=3.0 Hz, 9H).

Example 159

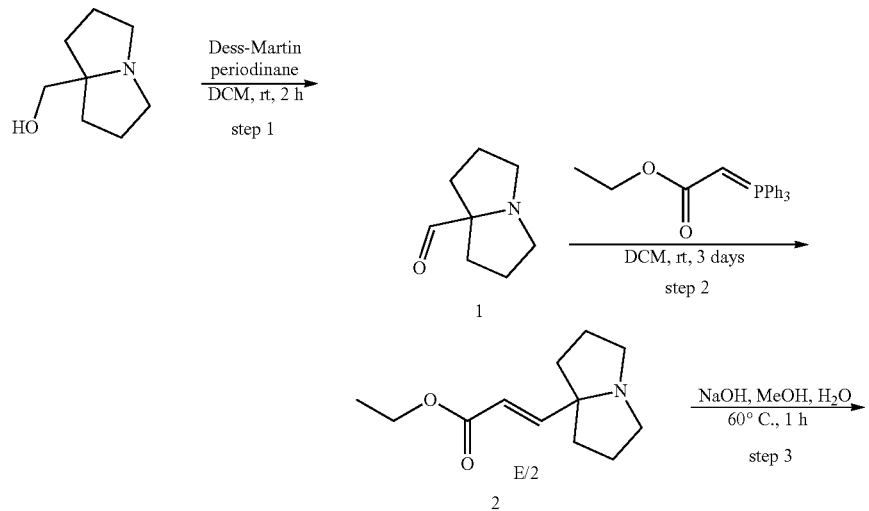

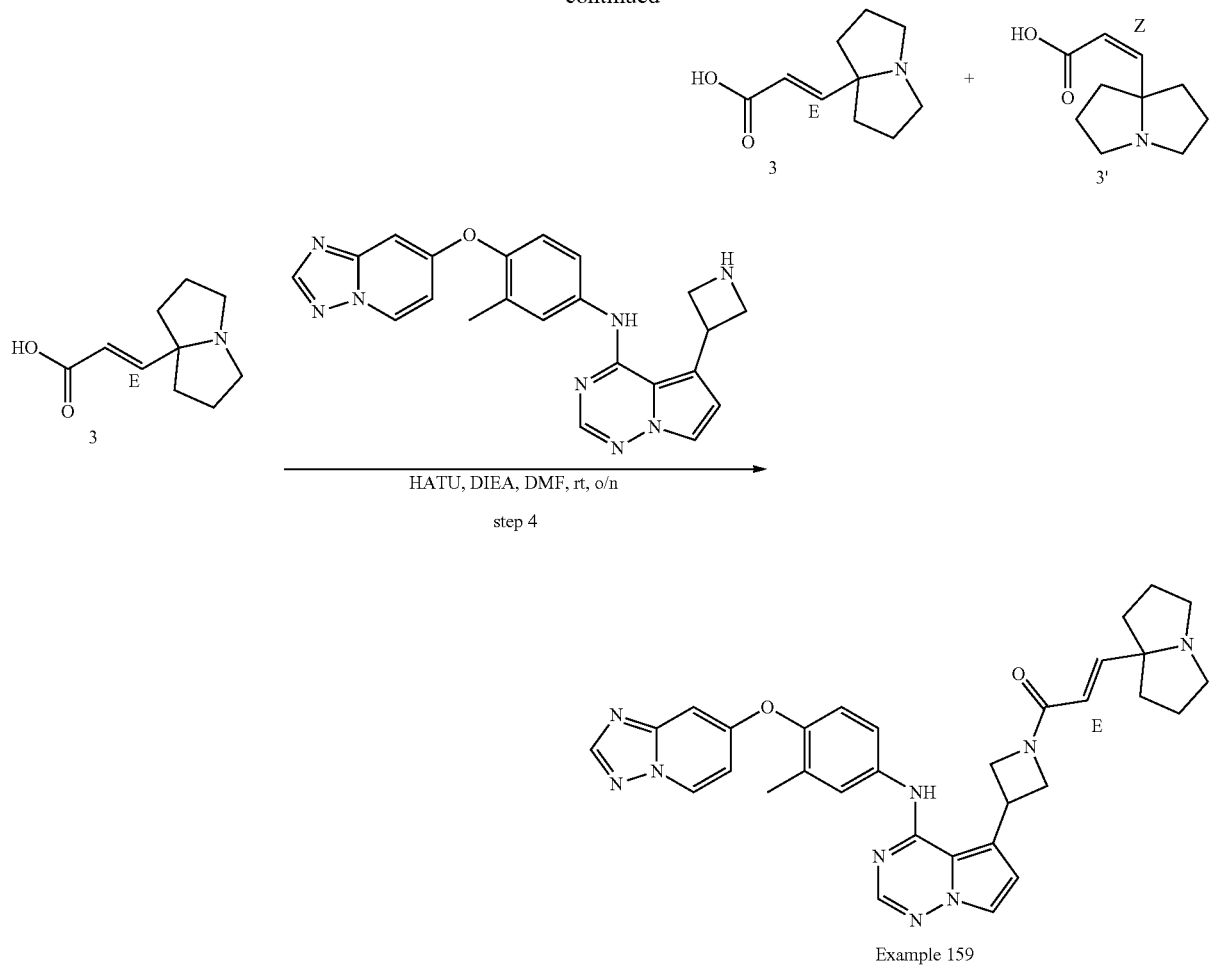

Example 159

Step 1.
tetrahydro-1H-pyrrolizine-7a(5H)-carbaldehyde

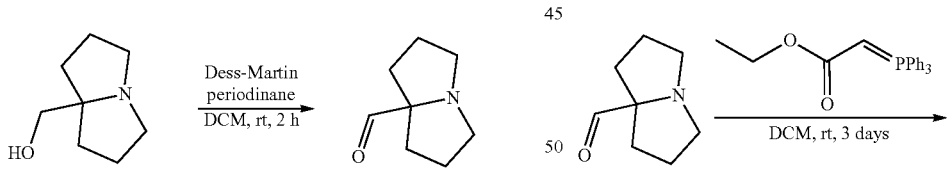

Dess-Martin periodinane (22.5 g, 53.1 mmol) was added to a solution of (tetrahydro-1H-pyrrolizin-7a(5H)-yl)methanol (3 g, 21.2 mmol) in DCM (100 mL) under nitrogen atmosphere. The resulting mixture was stirred at room temperature for 2 hours, quenched by the addition of saturated aqueous $Na_2S_2O_3$ (100 mL) at 0° C. and extracted with DCM (3×100 mL). The combined organic layers were washed with brine, dried over anhydrous $Na_2SO_4$, filtered and concentrated under vacuum to afford the crude product. The residue was purified by silica gel column chromatography, eluted with ethyl acetate in petroleum ether from 0% to 10% to afford the desired product tetrahydro-1H-pyrrolizine-7a(5H)-carbaldehyde (1.5 g, 50.8% yield) as colorless oil. LCMS (ESI-MS) m/z=140.1 $[M+H]^+$.

Step 2. ethyl 3-(tetrahydro-1H-pyrrolizin-7a(5H)-yl)acrylate

Ethyl 2-(triphenyl-15-phosphaneylidene)acetate (3 g, 8.62 mmol) was added to a solution of tetrahydro-1H-pyrrolizine-7a(5H)-carbaldehyde (1.5 g, 10.8 mmol) in DCM (30 mL). The reaction mixture was stirred at room temperature for 3 days and then concentrated under vacuum to afford the crude product. The residue was purified by silica gel column chromatography, eluted with ethyl acetate in petroleum ether from 0% to 10% to afford the desired product ethyl 3-(tetrahydro-1H-pyrrolizin-7a(5H)-yl)acrylate (800 mg, 35.4% yield). LCMS (ESI-MS) m/z=210.1 [M+H]+.

Step 3. (E)-3-(tetrahydro-1H-pyrrolizin-7a(5H)-yl) acrylic acid & (Z)-3-(tetrahydro-1H-pyrrolizin-7a (5H)-yl)acrylic acid

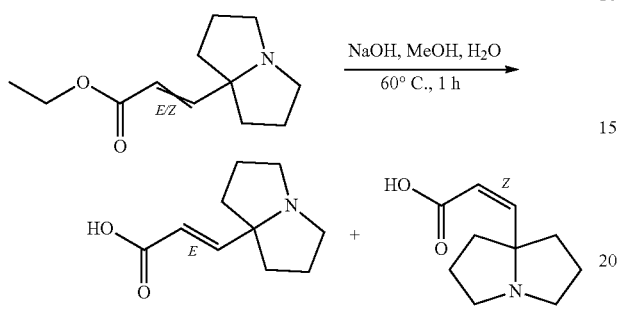

NaOH (305 mg, 7.64 mmol) was added to a mixture of ethyl 3-(tetrahydro-1H-pyrrolizin-7a(5H)-yl)acrylate (800 mg, 3.82 mmol) in MeOH (10 mL) and H$_2$O (3 mL). The resulting mixture was stirred at 60° C. for 1 hour. The reaction mixture was concentrated under vacuum to remove MeOH, the remained aqueous phase was adjusted to pH=6 by addition of aqueous HCl (1 N) and then concentrated under high vacuum to afford the crude acid. The residue was purified by Prep-HPLC Mobile Phase A: Water (10 MMOL/L NH$_4$HCO$_3$+0.1% NH$_3$·H$_2$O), Mobile Phase B: ACN; Gradient: 3 to 20% B to afford two isomers: €-3-(tetrahydro-1H-pyrrolizin-7a(5H)-yl)acrylic acid (90 mg, 13.0% yield) and (Z)-3-(tetrahydro-1H-pyrrolizin-7a(5H)-yl)acrylic acid (20 mg, 2.9% yield). The E-isomer and Z-isomer were identified by $^1$HNMR.

E-isomer: (E)-3-(tetrahydro-1H-pyrrolizin-7a(5H)-yl) acrylic acid. LCMS (ESI-MS) m/z=182.1 [M+H]+. $^1$H NMR (400 MHz, Chloroform-d) δ (ppm) 6.87 (d, J=15.6 Hz, 1H), 6.04 (d, J=15.6 Hz, 1H), 3.95-3.85 (m, 2H), 2.86-2.75 (m, 2H), 2.33-2.24 (m, 2H), 2.22-2.10 (m, 2H), 2.10-1.99 (m, 2H), 1.95-1.86 (m, 2H).

Z-isomer: (Z)-3-(tetrahydro-1H-pyrrolizin-7a(5H)-yl) acrylic acid. LCMS (ESI-MS) m/z=182.1 [M+H]+. $^1$H NMR (400 MHz, Chloroform-d) δ (ppm) 5.94 (d, J=13.2 Hz, 1H), 5.84 (d, J=13.2 Hz, 1H), 3.53-3.43 (m, 2H), 2.95-2.85 (m, 2H), 2.50-2.12 (m, 1H), 2.12-1.87 (m, 8H).

Step 4. (E)-1-(3-(4-((4-([1,2,4]triazolo[1,5-a]pyridin-7-yloxy)-3-methylphenyl)amino)pyrrolo[2,1-f] [1,2,4] triazin-5-yl)azetidin-1-yl)-3-(tetrahydro-1H-pyrrolizin-7a(5H)-yl)prop-2-en-1-one

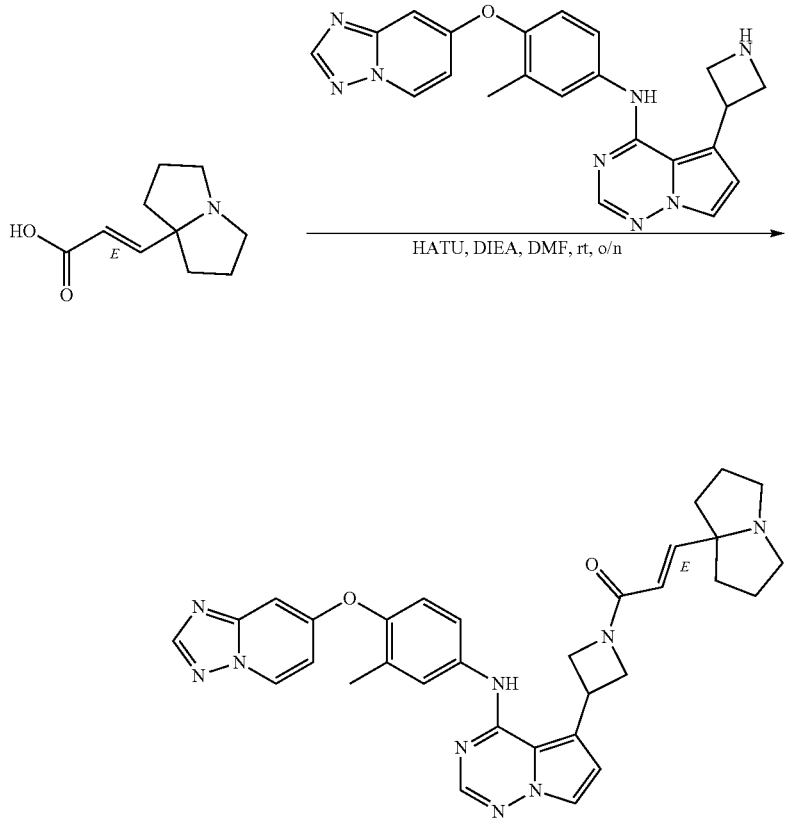

Diisopropylethylamine (192 mg, 1.49 mmol) was added to a mixture of (E)-3-(tetrahydro-1H-pyrrolizin-7a(5H)-yl) acrylic acid (90 mg, 0.49 mmol), N-(4-([1,2,4] triazolo[1, 5-a]pyridin-7-yloxy)-3-methylphenyl)-5-(azetidin-3-yl) pyrrolo[2,1-f][1,2,4]triazin-4-amine (204 mg, 0.49 mmol) and HATU (283 mg, 0.74 mmol) in DMF (2 mL). The resulting mixture was stirred overnight at room temperature and concentrated under vacuum to afford the crude product. The residue was purified by Prep-HPLC with the following conditions: Column: X-Bridge Prep OBD C18 Column, 30*150 mm, 5 m; Mobile Phase A: Water (10 mmol/L $NH_4HCO_3$+0.05% $NH_3H_2O$), Mobile Phase B: ACN; Flow rate: 60 mL/min mL/min; Gradient: 28% B to 58% B in 8 min; Wave Length: 254 nm/220 nm nm; RT1(min): 6.98 to afford the desired product (E)-1-(3-(4-((4-([1,2,4]triazolo[1,5-a]pyridin-7-yloxy)-3-methylphenyl)-amino)pyrrolo[2,1-f][1,2,4]triazin-5-yl)azetidin-1-yl)-3-(tetrahydro-1H-pyrrolizin-7a(5H)-yl)prop-2-en-1-one, Example 159 (33.7 mg, 11.9% yield). LCMS (ESI-MS) m/z=576.3 [M+H]$^+$. $^1$H NMR (400 MHz, Chloroform-d) δ 8.48 (ppm) (dd, J=7.4, 0.7 Hz, 1H), 8.20 (s, 1H), 7.97 (s, 1H), 7.73-7.64 (m, 2H), 7.61 (d, J=2.8 Hz, 1H), 7.11-7.01 (m, 3H), 6.87 (dd, J=7.5, 2.6 Hz, 1H), 6.82 (d, J=2.5 Hz, 1H), 6.77 (d, J=2.8 Hz, 1H), 6.28 (d, J=15.6 Hz, 1H), 4.96 (t, J=8.3 Hz, 1H), 4.60 (t, J=9.2 Hz, 1H), 4.53-4.45 (m, 1H), 4.45-4.37 (m, 1H), 4.27-4.19 (m, 1H), 3.96-3.81 (m, 2H), 3.11-3.14 (m, 2H), 2.33-2.43 (m, 2H), 2.20 (s, 3H), 2.08 (s, 1H), 2.14-2.01 (m, 1H), 1.25 (s, 3H), 0.86 (s, 1H).

Example 160

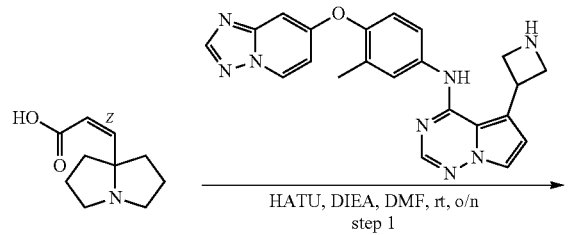

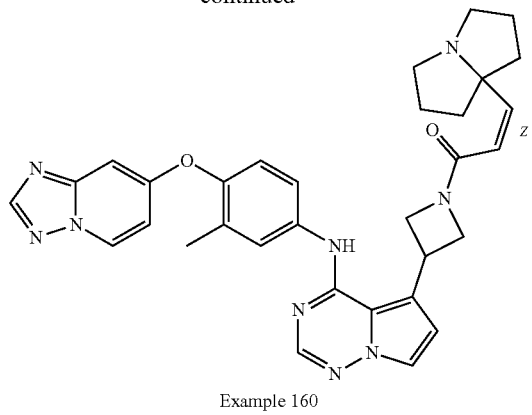

Example 160

(Z)-1-(3-(4-((4-([1,2,4]triazolo[1,5-a]pyridin-7-yloxy)-3-methylphenyl)amino)pyrrolo[2,1-f] [1,2,4]triazin-5-yl)azetidin-1-yl)-3-(tetrahydro-1H-pyrrolizin-7a(5H)-yl)prop-2-en-1-one Diisopropylethylamine (21 mg, 0.16 mmol) was added to a mixture of (Z)-3-(tetrahydro-1H-pyrrolizin-7a(5H)-yl) acrylic acid (20 mg, 0.11 mmol), N-(4-([1,2,4]triazolo[1,5-a]pyridin-7-yloxy)-3-methylphenyl)-5-(azetidin-3-yl)pyrrolo [2,1-f][1,2,4]triazin-4-amine (45 mg, 0.11 mmol) and HATU (62 mg, 0.16 mmol) in DMF (2 mL). The mixture was stirred overnight at room temperature and concentrated under vacuum to afford the crude product. The residue was purified by Prep-HPLC; Mobile Phase A: Water (10 mmol/L $NH_4HCO_3$+0.05% $NH_3H_2O$), Mobile Phase B: ACN; Gradient: 25% B to 55% B to afford the desired product (Z)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(tetrahydro-1H-pyrrolizin-7a(5H)-yl) prop-2-en-1-one, Example 160 (8.8 mg, 13.9% yield). LCMS (ESI-MS) m/z=576.3 [M+H]$^+$. $^1$H NMR (400 MHz, Chloroform-d) δ (ppm) 8.54-8.48 (m, 1H), 8.25 (s, 1H), 8.01 (s, 1H), 7.68-7.59 (m, 3H), 7.11-6.98 (m, 2H), 6.98 (d, J=15.0 Hz, 1H), 6.92-6.85 (m, 2H), 6.75 (d, J=2.8 Hz, 1H), 6.50-6.20 (m, 2H), 4.90 (s, 1H), 4.66 (s, 1H), 4.49 (s, 1H), 4.31 (s, 2H), 3.19 (s, 2H), 2.69 (s, 2H), 2.26 (s, 3H), 1.88 (s, 7H).

Examples 171 and 172

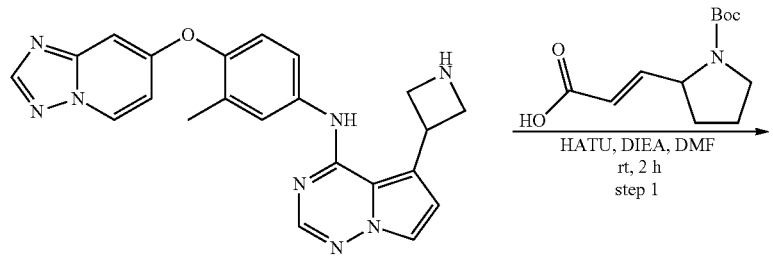

-continued
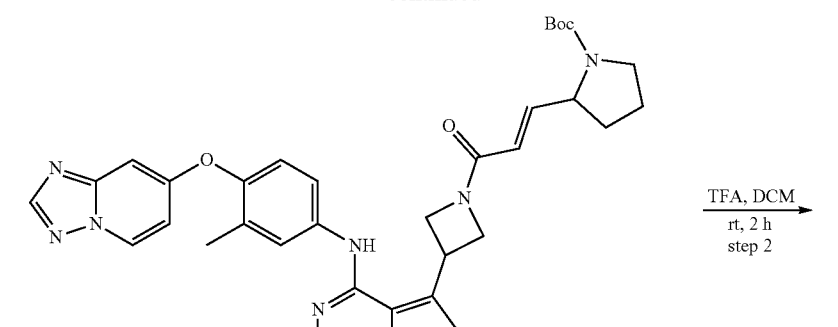
TFA, DCM
rt, 2 h
step 2
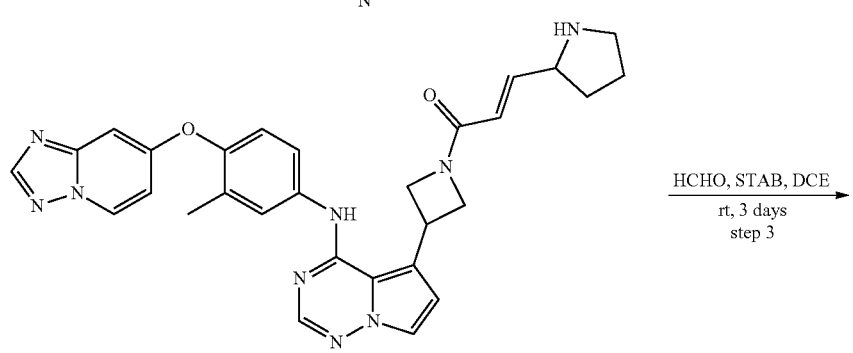
HCHO, STAB, DCE
rt, 3 days
step 3
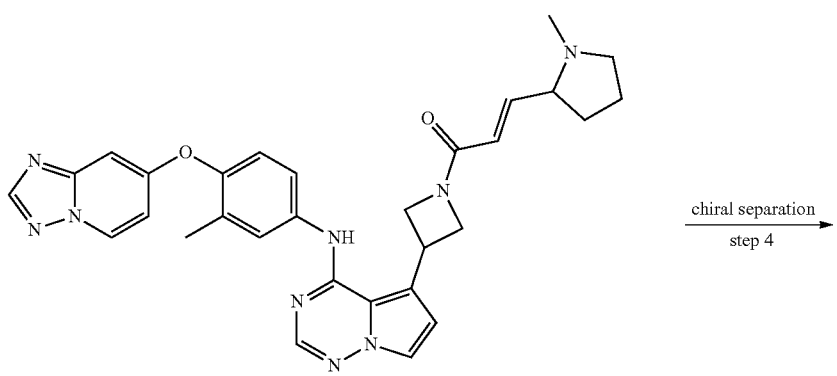
chiral separation
step 4
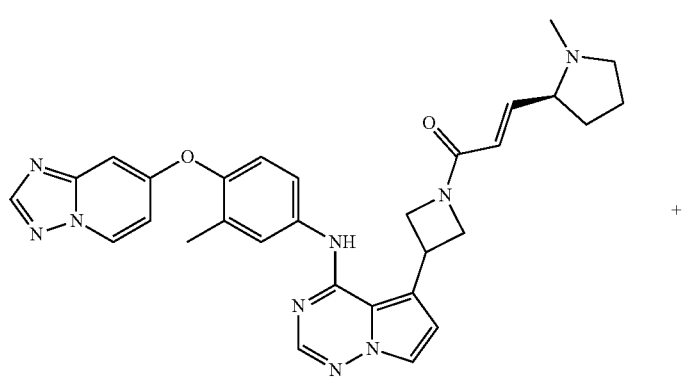
Example 171
+

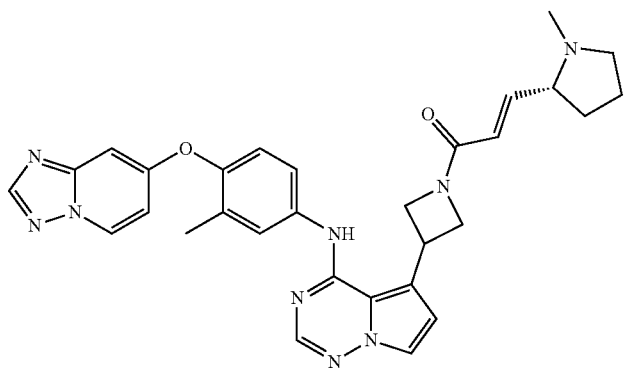

Example 172

Step 1. tert-butyl (E)-2-(3-(3-(4-((4-([1,2,4]triazolo [1,5-a]pyridin-7-yloxy)-3-methylphenyl)amino)pyrrolo [2,1-f][1,2,4]triazin-5-yl)azetidin-1-yl)-3-oxoprop-1-en-1-yl)pyrrolidine-1-carboxylate

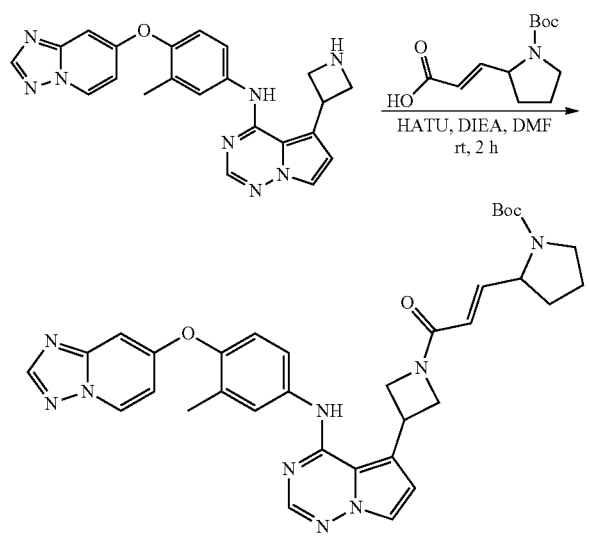

Diisopropylethylamine (1.13 g, 8.73 mmol) was added to a mixture of N-(4-([1,2,4]triazolo[1,5-a]pyridin-7-yloxy)-3-methylphenyl)-5-(azetidin-3-yl)pyrrolo[2,1-f][1,2,4]triazin-4-amine (600 mg, 1.45 mmol), (E)-3-(1-(tert-butoxycarbonyl)pyrrolidin-2-yl)acrylic acid (351 mg, 1.45 mmol) and HATU (830 mg, 2.18 mmol) in DMF (8 mL). The resulting mixture was stirred at room temperature for 2 hours, diluted with water (100 mL) and extracted with ethyl acetate (3×100 mL). The combined organic layers were washed with brine, dried over anhydrous Na$_2$SO$_4$ and concentrated under vacuum to afford the crude product. The residue was purified by silica gel column chromatography, eluted with methanol in dichloromethane from 0% to 10% to afford the desired product tert-butyl (E)-2-(3-(3-(4-((4-([1,2,4]triazolo[1,5-a] pyridin-7-yloxy)-3-methyl-phenyl)amino)pyrrolo [2,1-f][1,2,4]triazin-5-yl)azetidin-1-yl)-3-oxoprop-1-en-1-yl)pyrrolidine-1-carboxylate (800 mg, 99.1% yield). LCMS (ESI-MS) m/z=636.5 [M+H]$^+$.

Step 2. (E)-1-(3-(4-((4-([1,2,4]triazolo[1,5-a]pyridin-7-yloxy)-3-methylphenyl)amino)pyrrolo[2,1-f] [1,2,4] triazin-5-yl)azetidin-1-yl)-3-(pyrrolidin-2-yl)prop-2-en-1-one

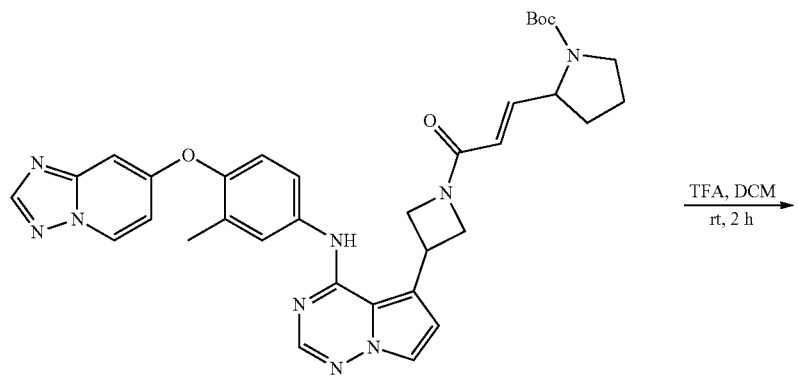

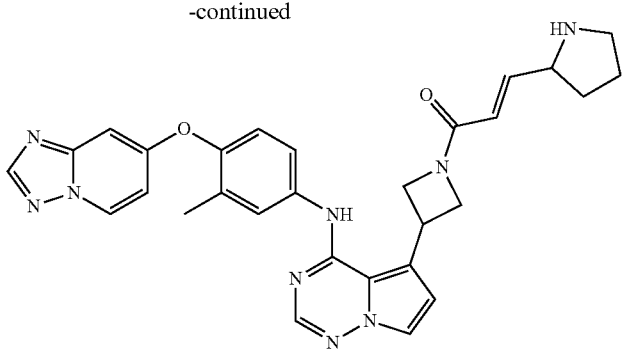

TFA (2 mL) was added to a solution of tert-butyl (E)-2-(3-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-oxoprop-1-en-1-yl)pyrrolidine-1-carboxylate (700 mg, 1.10 mmol) in DCM (10 mL). The mixture was stirred at room temperature for 2 hours and then concentrated under vacuum to afford the crude product (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(pyrrolidin-2-yl)prop-2-en-1-one (450 mg crude). The crude product was used in the next step directly without further purification. LCMS (ESI-MS) m/z=536.4 [M+H]⁺.

Step 3. (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(1-methylpyrrolidin-2-yl)prop-2-en-1-one STAB (267 mg, 1.26 mmol) was added to a mixture of (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(pyrrolidin-2-yl)prop-2-en-1-one (450 mg, 0.84 mmol), paraformaldehyde (303 mg, 3.36 mmol) in DCE (15 mL). The resulting mixture was stirred at room temperature for 3 days and concentrated under vacuum. The residue was purified by silica gel column chromatography, eluted with methanol in dichloromethane from 0% to 20% to afford the crude product. The crude product was further purified by Prep-HPLC; Mobile Phase A: Water (10 mmol/L NH₄HCO₃+0.05% NH₃·H₂O), Mobile Phase B: ACN; Gradient: 20% B to 50% B to afford the desired product (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(1-methylpyrrolidin-2-yl)prop-2-en-1-one (60 mg, 9.9% yield for two steps). LCMS (ESI-MS) m/z=550.3 [M+H]⁺.

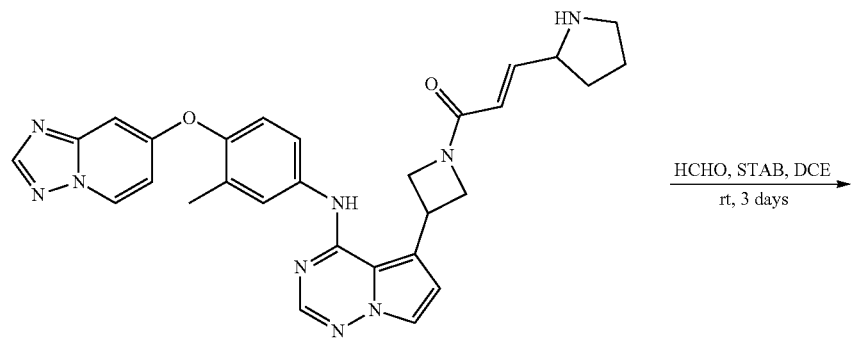

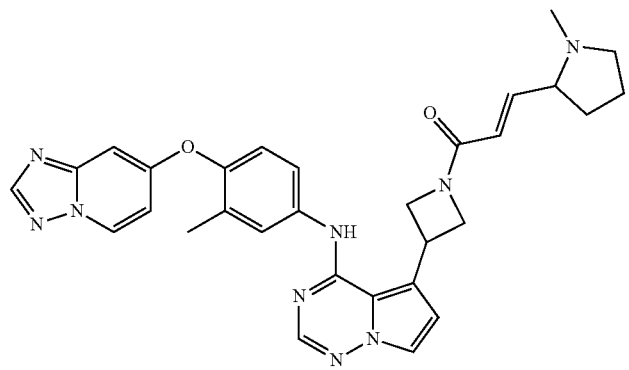

Step 4. (S,E)-1-(3-(4-((4-([1,2,4]triazolo[1,5-a]pyridin-7-yloxy)-3-methylphenyl)amino)pyrrolo[2,1-f][1,2,4] triazin-5-yl)azetidin-1-yl)-3-(1-methylpyrrolidin-2-yl)prop-2-en-1-one (Example 171) and (R,E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(1-methylpyrrolidin-2-yl)prop-2-en-1-one (Example 172)

First eluting isomer of (E)-1-(3-(4-((4-([1,2,4]triazolo[1,5-a]pyridin-7-yloxy)-3-methylphenyl)amino) pyrrolo[2,1-f][1,2,4]triazin-5-yl)azetidin-1-yl)-3-(1-methylpyrrolidin-2-yl)prop-2-en-1-one (21.4 mg, 100% ee, 35.6% yield). LCMS (ESI-MS) m/z=550.3 [M+H]+. $^1$H NMR (400 MHz, DMSO-$d_6$) δ (ppm) 8.93 (d, J=4.4 Hz, 1H), 8.51 (s, 1H), 8.42-8.34 (m, 1H), 7.95 (s, 1H), 7.84-7.78 (m, 1H), 7.72-7.66 (m, 2H), 7.28-7.19 (m, 1H), 7.18-7.00 (m, 1H), 6.99-6.94 (m, 1H), 6.88-6.78 (m, 1H), 6.50-6.66 (m, 11H),

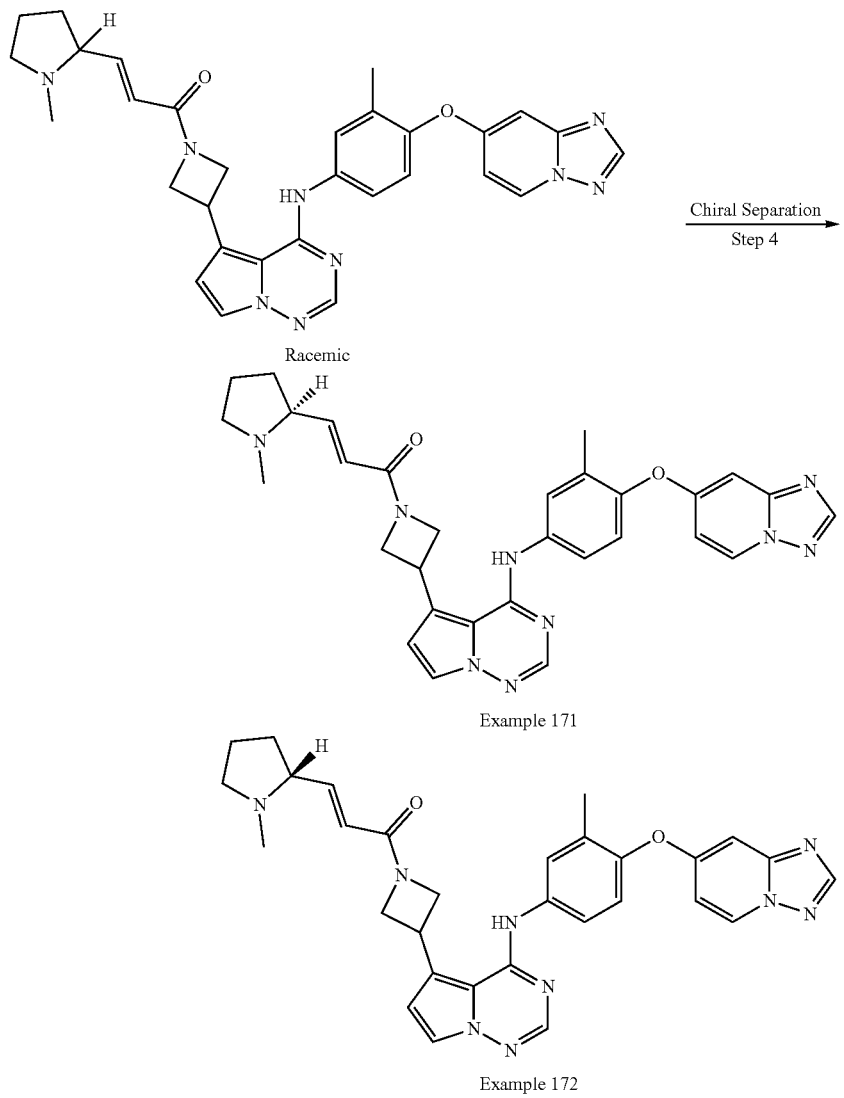

The racemic mixture of (E)-1-(3-(4-((4-([1,2,4]triazolo[1,5-a]pyridin-7-yloxy)-3-methylphenyl)amino) pyrrolo[2,1-f][1,2,4]triazin-5-yl)azetidin-1-yl)-3-(1-methylpyrrolidin-2-yl)prop-2-en-1-one (60 mg, 0.10 mmol) was separated by Prep-Chiral-HPLC using the following conditions: Column: CHIRAL ART Cellulose-SB, 2*25 cm, 5 m; Mobile Phase A: MtBE(0.5% 2M NH$_3$-MeOH)-HPLC, Mobile Phase B: IPA-HPLC; Flow rate: 20 ML/MIN mL/min; Gradient: isocratic 50; Wave Length: 254/220 nm nm; RT1(min): 12.658; RT2(min): 16.163; Sample Solvent: EtOH-HPLC; Injection Volume: 0.5 mL; Number Of Runs: 9. The desired fractions were combined and lyophilized to afford the two desired separated isomers Examples 171 and 172:

6.18-6.08 (m, 1H), 4.69 (s, 2H), 4.50-4.45 (m, 1H), 4.44-4.20 (m, 1H), 4.10-3.96 (m, 1H), 3.06-2.98 (m, 1H), 2.80-2.76 (m, 11H), 2.28-2.06 (m, 7H), 1.94 (s, 1H), 1.70 (s, 2H), 1.60-1.48 (m, 1H).

Cell growth inhibition activity of first eluting isomer based on assays described for Table 3:

| HER2-YVMA IC$_{50}$ (nM) | HER2 WT IC$_{50}$ (nM) | EGFR WT IC$_{50}$ (nM) |
| --- | --- | --- |

Second eluting isomer of (E)-1-(3-(4-((4-([1,2,4]triazolo[1,5-a]pyridin-7-yloxy)-3-methylphenyl)amino) pyrrolo[2,1-f][1,2,4]triazin-5-yl)azetidin-1-yl)-3-(1-methylpyrrolidin-2-yl)prop-2-en-1-one (19.0 mg, 99.4% ee, 31.6% yield). LCMS (ESI-MS) m/z=550.3 [M+H]$^+$. $^1$H NMR (400 MHz, DMSO-d$_6$) δ (ppm) 8.94 (d, J=8.0 Hz, 11H), 8.51 (s, 1H), 8.38 (s, 1H), 7.95 (s, 1H), 7.83-7.75 (m, 1H), 7.72-7.64 (m, 2H), 7.21 (d, J=8.4 Hz, 1H), 7.07-7.00 (m, 1H), 6.99-6.95 (m, 1H), 6.81-6.75 (m, 11H), 6.53-6.47 (m, 1H), 6.20-6.06 (m, 1H), 4.80-4.60 (m, 2H), 4.50-4.36 (m, 1H), 4.35-4.19 (m, 1H), 4.10-3.90 (m, 1H), 3.10-2.90 (m, 1H), 2.80-2.61 (m, 1H), 2.29-2.08 (m, 7H), 2.02-1.88 (m, 1H), 1.87-1.60 (m, 2H), 1.59-1.43 (m, 1H).

Cell growth inhibition activity of second eluting isomer based on assays described for Table 3:

| HER2-YVMA IC$_{50}$ (nM) | HER2 WT IC$_{50}$ (nM) | EGFR WT IC$_{50}$ (nM) |
|---|---|---|
| ++++ | ++++ | + |

Examples 173 and 174

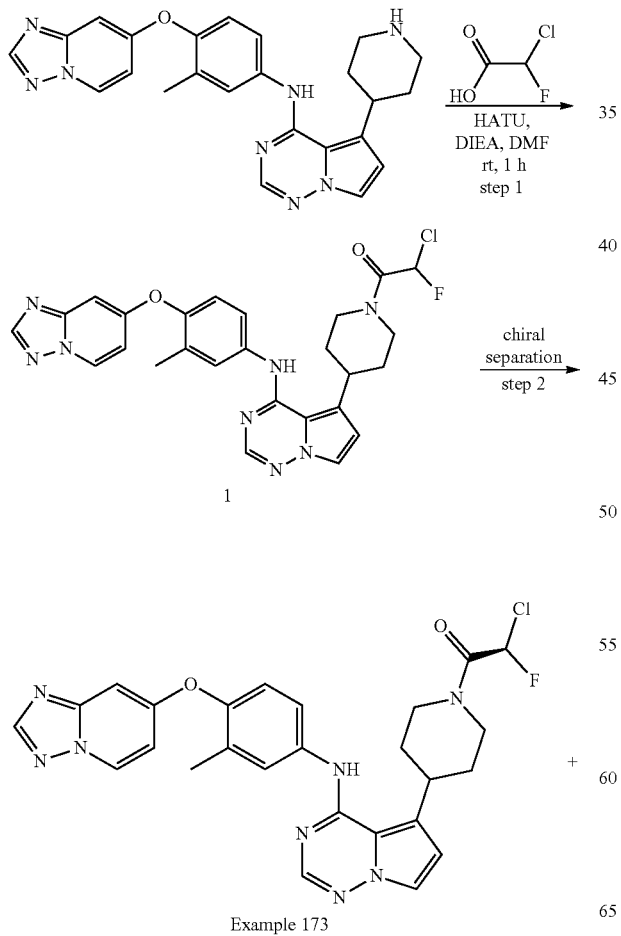

Example 173

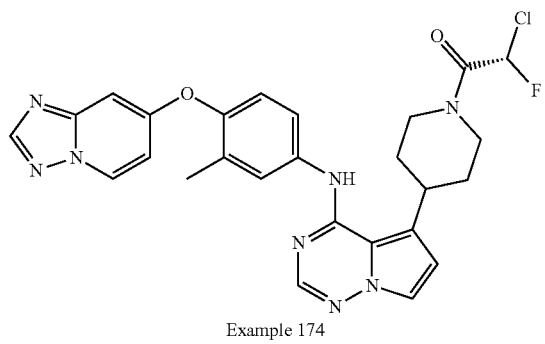

Example 174

Step 1. 1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-2-chloro-2-fluoroethan-1-one

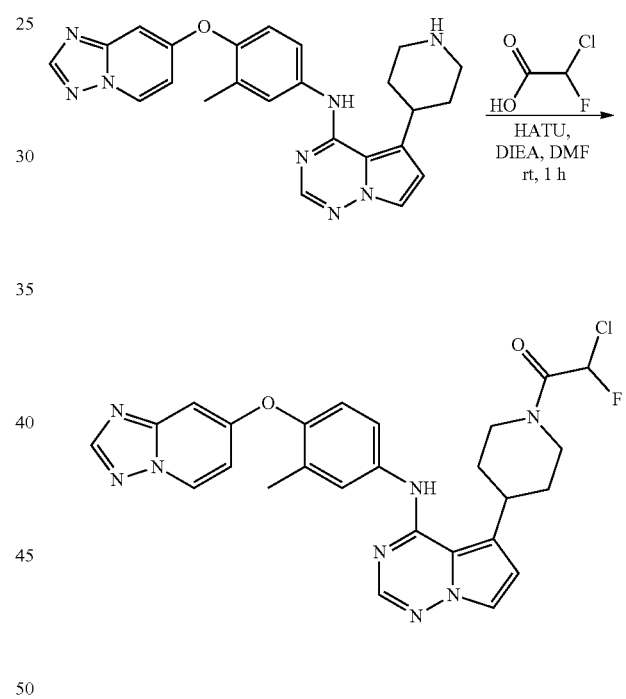

Diisopropylethylamine (88 mg, 0.68 mmol) was added to a mixture of N-(4-([1,2,4]triazolo[1,5-a]pyridin-7-yloxy)-3-methylphenyl)-5-(piperidin-4-yl)pyrrolo[2,1-f][1,2,4]triazin-4-amine (100 mg, 0.22 mmol), 2-chloro-2-fluoroacetic acid (25 mg, 0.22 mmol) and HATU (129 mg, 0.34 mmol) in DMF (2 mL). The resulting mixture was stirred for 1 hour at room temperature, diluted with water (5 mL) and extracted with DCM (3×5 mL). The combined organic layers were washed with brine, dried over anhydrous Na$_2$SO$_4$ and concentrated under vacuum to afford the crude product. The residue was purified by Prep-TLC using ethyl acetate to afford the desired product 1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-2-chloro-2-fluoroethan-1-one (100 mg, 69.2% yield). LCMS (ESI-MS) m/z=535.2 [M+H]$^+$.

Step 2. (R)-1-(4-(4-((4-([1,2,4]triazolo[1,5-a]pyridin-7-yloxy)-3-methylphenyl)amino)pyrrolo[2,1-f][1,2,4] triazin-5-yl)piperidin-1-yl)-2-chloro-2-fluoroethan-1-one (Example 173) & (S)-1-(4-(4-((4-([1,2,4]triazolo[1,5-a]pyridin-7-yloxy)-3-methylphenyl)amino)pyrrolo[2,1-f][1,2,4] triazin-5-yl)piperidin-1-yl)-2-chloro-2-fluoroethan-1-one (Example 174)

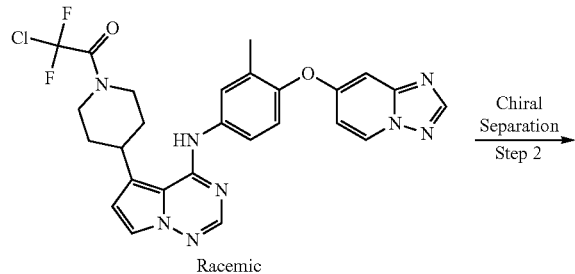

Racemic

Chiral Separation Step 2

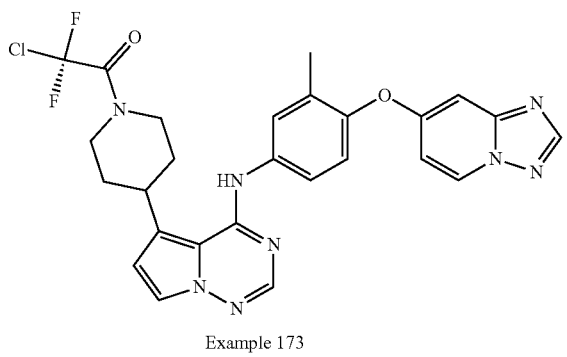

Example 173

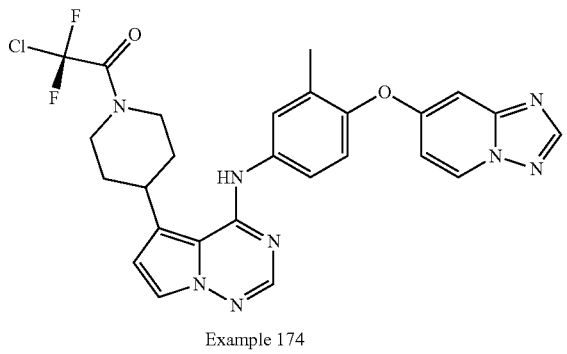

Example 174

The racemic mixture of 1-(4-(4-((4-([1,2,4]triazolo[1,5-a]pyridin-7-yloxy)-3-methylphenyl)amino) pyrrolo[2,1-f][1,2,4]triazin-5-yl)piperidin-1-yl)-2-chloro-2-fluoroethan-1-one (100 mg, 0.18 mmol) was separated by Prep-Chiral-HPLC using the following conditions:Column: CHIRAL ART Anylose-C NEO 3*25 cm, 5 um; Mobile Phase A: $CO_2$, Mobile Phase B: EtOH: Hex=1:1(1%-2M-$NH_3$-MeOH); Flow rate: 85 mL/min; Gradient: isocratic 60% B; Column Temperature(° C.): 35; Back Pressure (bar): 100; Wave Length: 220 nm; RT1(min): 18.15; RT2 (min): 22.3; Sample Solvent: EtOH; Injection Volume: 2 mL). The desired fractions were combined and lyophilized to afford the two desired separated isomers products Examples 173 and 174:

First eluting isomer of (R)-1-(4-(4-((4-([1,2,4]triazolo[1,5-a]pyridin-7-yloxy)-3-methylphenyl)amino) pyrrolo[2,1-f][1,2,4]triazin-5-yl)piperidin-1-yl)-2-chloro-2-fluoroethan-1-one (19.7 mg, 100% ee, 19.7% yield). LCMS (ESI-MS) m/z=535.2 [M+H]$^+$. $^1$H NMR (400 MHz, Chloroform-d) δ (ppm) 8.54 (d, J=7.5 Hz, 1H), 8.26 (s, 1H), 7.97 (s, 1H), 7.61-7.56 (m, 3H), 7.28 (s, 1H), 7.13 (d, J=8.5 Hz, 1H), 6.95 (d, J=7.5 Hz, 1H), 6.87 (s, 1H), 6.62 (s, 1H), 4.77 (d, J=13.6 Hz, 1H), 4.37 (t, J=15.6 Hz, 1H), 3.43-3.19 (m, 2H), 2.96 (t, J=13.1 Hz, 1H), 2.32-2.12 (m, 5H), 2.02-1.81 (m, 2H), 1.27 (s, 1H).

Cell growth inhibition activity of first eluting isomer based on assays described for Table 3:

| HER2-YVMA $IC_{50}$ (nM) | HER2 WT $IC_{50}$ (nM) | EGFR WT $IC_{50}$ (nM) |
| --- | --- | --- |
| + | +++ | + |

Second eluting isomer of (S)-1-(4-(4-((4-([1,2,4]triazolo[1,5-a]pyridin-7-yloxy)-3-methylphenyl)amino) pyrrolo[2,1-f][1,2,4]triazin-5-yl)piperidin-1-yl)-2-chloro-2-fluoroethan-1-one (39.1 mg, 95.5% ee, 39.1% yield). LCMS (ESI-MS) m/z=535.2 [M+H]$^+$.

$^1$H NMR (400 MHz, Chloroform-d) δ (ppm) 8.52 (d, J=7.4 Hz, 1H), 8.24 (s, 11H), 8.00 (s, 1H), 7.65-7.51 (m, 3H), 7.14 (d, J=8.6 Hz, 1H), 6.95-6.90 (m, 1H), 6.85 (d, J=2.6 Hz, 1H), 6.62-6.50 (m, 2H), 4.78 (d, J=13.4 Hz, 1H), 4.45-4.36 (m, 1H), 3.37 (q, J=12.1, 11.6 Hz, 1H), 3.22 (s, 1H), 2.97 (t, J=13.1 Hz, 1H), 2.30-2.18 (m, 5H), 2.05-1.82 (s, 2H), 1.27 (s, 1H).

Cell growth inhibition activity of second eluting isomer based on assays described for Table 3:

| HER2-YVMA $IC_{50}$ (nM) | HER2 WT $IC_{50}$ (nM) | EGFR WT $IC_{50}$ (nM) |
| --- | --- | --- |
| ++++ | ++++ | + |

Example 175

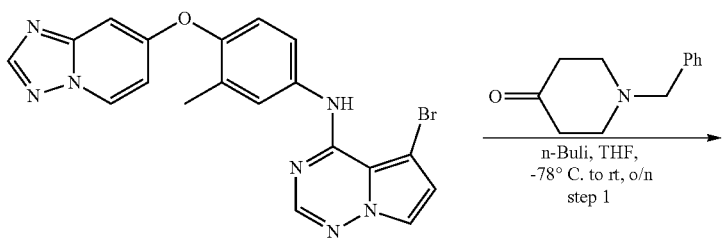

-continued
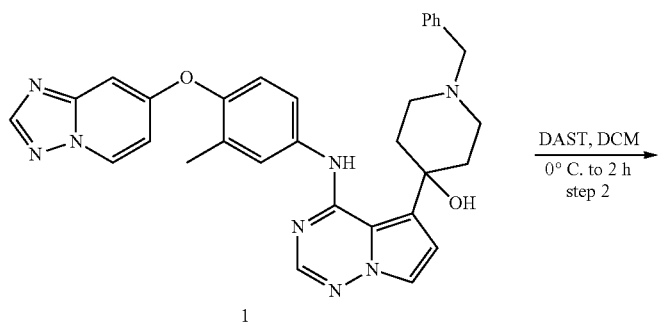
1
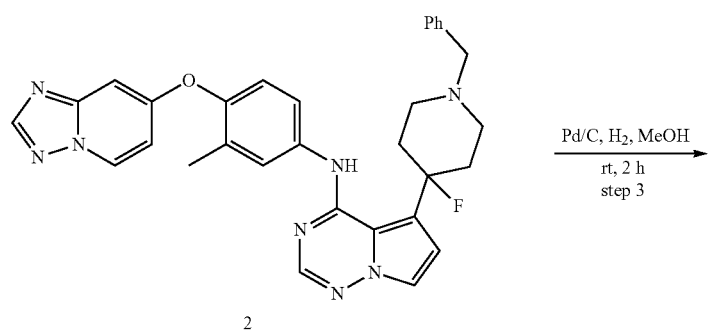
2
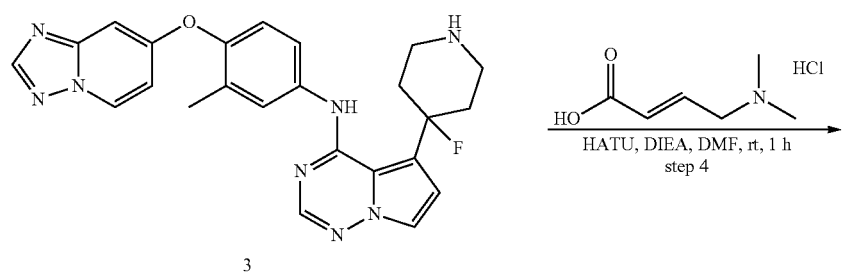
3
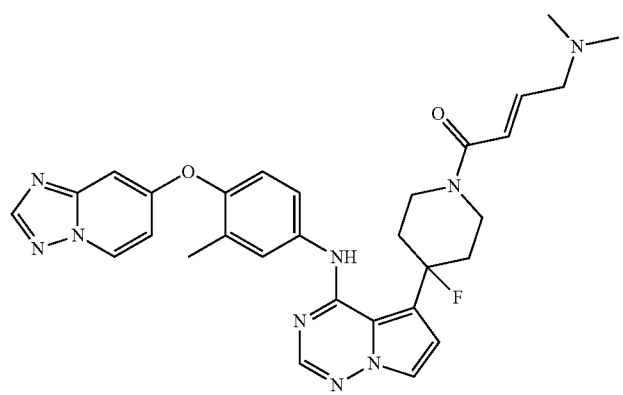
Example 175

377

Step 1. 4-(4-((4-([1,2,4]triazolo[1,5-a]pyridin-7-yloxy)-3-methylphenyl)amino)pyrrolo[2,1-f][1,2,4]triazin-5-yl)-1-benzylpiperidin-4-ol

378

Step 2. N-(4-([1,2,4]triazolo[1,5-a]pyridin-7-yloxy)-3-methylphenyl)-5-(1-benzyl-4-fluoropiperidin-4-yl)pyrrolo[2,1-f][1,2,4]triazin-4-amine

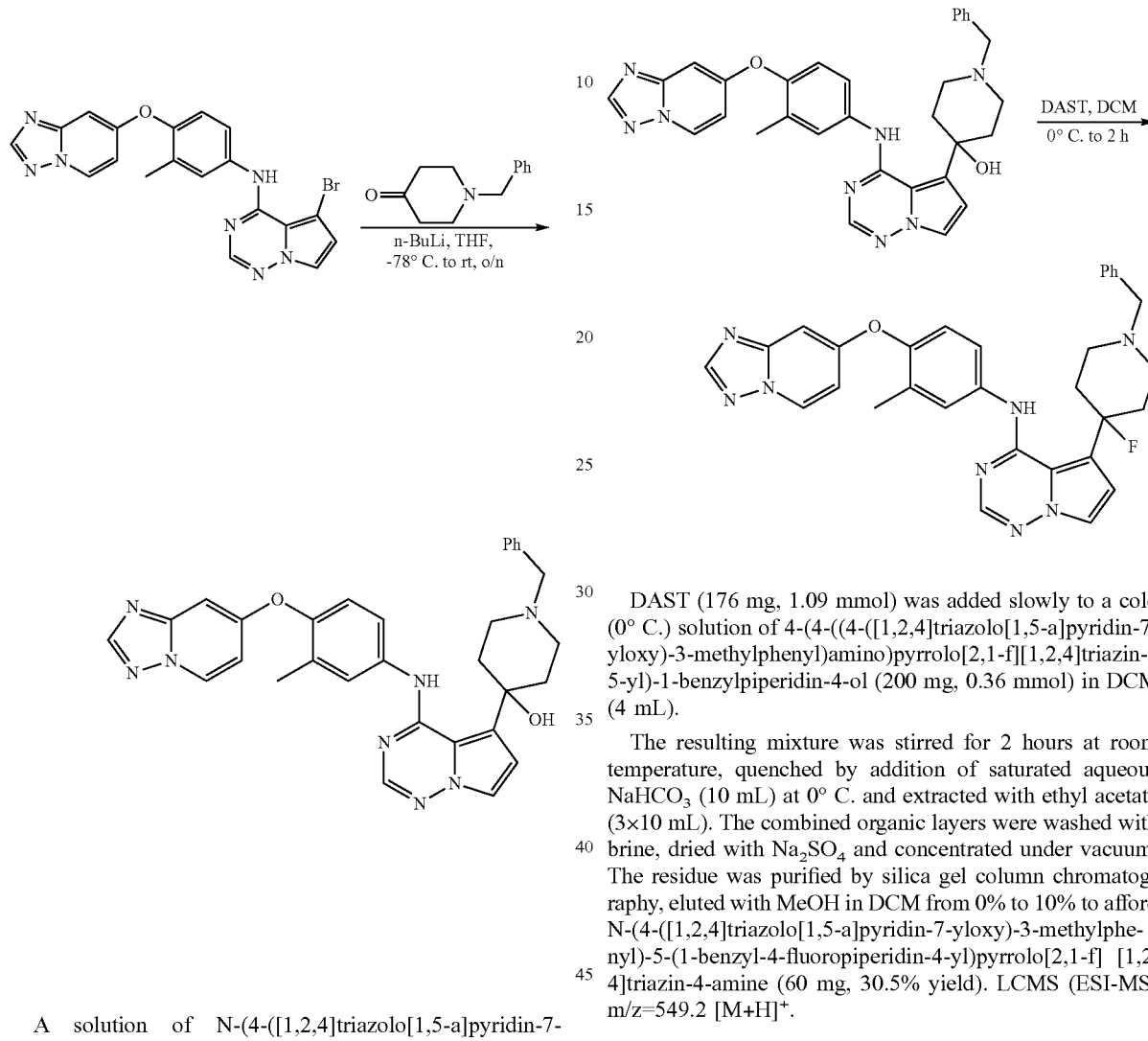

A solution of N-(4-([1,2,4]triazolo[1,5-a]pyridin-7-yloxy)-3-methylphenyl)-5-bromopyrrolo[2,1-f][1,2,4]triazin-4-amine (2 g, 4.58 mmol) in THF (40 mL) was cooled to −78° C., followed by addition of n-BuLi (2.5 M, 9.2 mL, 23 mmol) dropwise under nitrogen atmosphere. After the addition was complete, the reaction mixture was stirred for 2 hours at −78° C. under nitrogen atmosphere, followed by the addition of a solution of 1-benzylpiperidin-4-one (2.6 g, 13.7 mmol) in 10 mL THF. The reaction mixture was allowed to warm to room temperature and stirred overnight. The reaction mixture was quenched by addition of saturated aqueous NH₄Cl (40 mL) and extracted with ethyl acetate (3×60 mL). The combined organic layers were washed with brine, dried with Na₂SO₄ and concentrated under vacuum. The residue was purified by silica gel column chromatography, eluted with ethyl acetate in petroleum ether from 0% to 100% to afford the desired product 4-(4-((4-([1,2,4]triazolo[1,5-a]pyridin-7-yloxy)-3-methylphenyl)amino)pyrrolo[2,1-f][1,2,4]triazin-5-yl)-1-benzyl-piperidin-4-ol (220 mg, 8.8% yield). LCMS (ESI-MS) m/z=547.2 [M+H]⁺.

DAST (176 mg, 1.09 mmol) was added slowly to a cold (0° C.) solution of 4-(4-((4-([1,2,4]triazolo[1,5-a]pyridin-7-yloxy)-3-methylphenyl)amino)pyrrolo[2,1-f][1,2,4]triazin-5-yl)-1-benzylpiperidin-4-ol (200 mg, 0.36 mmol) in DCM (4 mL).

The resulting mixture was stirred for 2 hours at room temperature, quenched by addition of saturated aqueous NaHCO₃ (10 mL) at 0° C. and extracted with ethyl acetate (3×10 mL). The combined organic layers were washed with brine, dried with Na₂SO₄ and concentrated under vacuum. The residue was purified by silica gel column chromatography, eluted with MeOH in DCM from 0% to 10% to afford N-(4-([1,2,4]triazolo[1,5-a]pyridin-7-yloxy)-3-methylphenyl)-5-(1-benzyl-4-fluoropiperidin-4-yl)pyrrolo[2,1-f][1,2,4]triazin-4-amine (60 mg, 30.5% yield). LCMS (ESI-MS) m/z=549.2 [M+H]⁺.

Step 3. N-(4-([1,2,4]triazolo[1,5-a]pyridin-7-yloxy)-3-methylphenyl)-5-(4-fluoropiperidin-4-yl)pyrrolo[2,1-f][1,2,4]triazin-4-amine

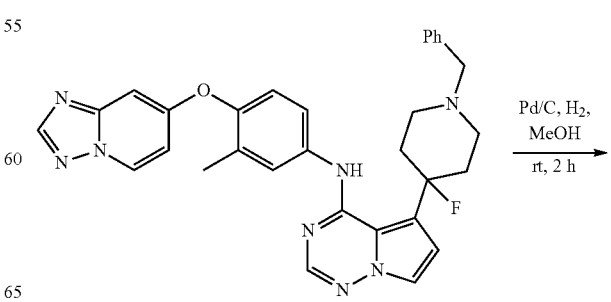

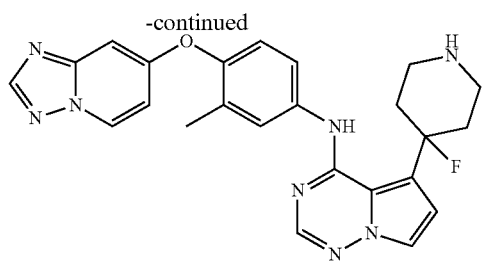

Pd/C (10% on carbon, 7.76 mg, 0.01 mmol) was added to a solution of N-(4-([1,2,4]triazolo[1,5-a]pyridin-7-yloxy)-3-methylphenyl)-5-(1-benzyl-4-fluoropiperidin-4-yl)pyrrolo[2,1-f][1,2,4]triazin-4-amine (60 mg, 0.11 mmol) in MeOH (2 mL) under nitrogen atmosphere. The resulting mixture was degassed under vacuum and charged with an atmospheric pressure of hydrogen. The resulting mixture was stirred for 2 hours at room temperature. The reaction mixture was filtered and the filtrate was concentrated under vacuum to afford crude product N-(4-([1,2,4]triazolo[1,5-a]pyridin-7-yloxy)-3-methylphenyl)-5-(4-fluoropiperidin-4-yl)pyrrolo[2,1-f][1,2,4]triazin-4-amine (50 mg crude). The crude product was used in next step directly without further purification. LCMS (ESI-MS) m/z=459 [M+H]$^+$.

Step 4. (E)-1-(4-(4-((4-([1,2,4]triazolo[1,5-a]pyridin-7-yloxy)-3-methylphenyl)amino)pyrrolo[2,1-f][1,2,4]triazin-5-yl)-4-fluoropiperidin-1-yl)-4-(dimethylamino)but-2-en-1-one Diisopropylethylamine (42.3 mg, 0.32 mmol) was added to a solution of N-(4-([1,2,4]triazolo[1,5-a]pyridin-7-yloxy)-3-methylphenyl)-5-(4-fluoropiperidin-4-yl)pyrrolo[2,1-f][1,2,4]triazin-4-amine (50 mg, 0.11 mmol), (E)-4-(dimethylamino)but-2-enoic acid hydrochloride (21.6 mg, 0.13 mmol) and HATU (62.2 mg, 0.16 mmol) in DMF (1 mL). The resulting mixture was stirred for 1 hour at room temperature. Then the resulting mixture was purified by Prep-HPLC; Mobile Phase A: Water (0.1% FA), Mobile Phase B: ACN; Gradient: 9% B to 39% B to afford (E)-1-(4-(4-((4-([1,2,4]triazolo[1,5-a]pyridin-7-yloxy)-3-methylphenyl)amino)pyrrolo[2,1-f][1,2,4]triazin-5-yl)-4-fluoropiperidin-1-yl)-4-(dimethylamino)but-2-en-1-one, Example 175 (1.6 mg, 2.5% yield for two steps). LCMS (ESI-MS) m/z=570.3 [M+H]$^+$. $^1$H NMR (400 MHz, Chloroform-d) δ (ppm) 8.28-8.19 (m, 2H), 8.07 (s, 1H), 7.66 (s, 3H), 7.12 (s, 2H), 6.87 (s, 2H), 6.81 (s, 1H), 6.75 (s, 1H), 6.67 (s, 1H), 4.80 (s, 1H), 4.17 (s, 1H), 3.63 (s, 1H), 3.49 (s, 2H), 3.17 (s, 3H), 2.62-2.53 (m, 6H), 2.30-2.23 (m, 3H), 2.01 (s, 2H).

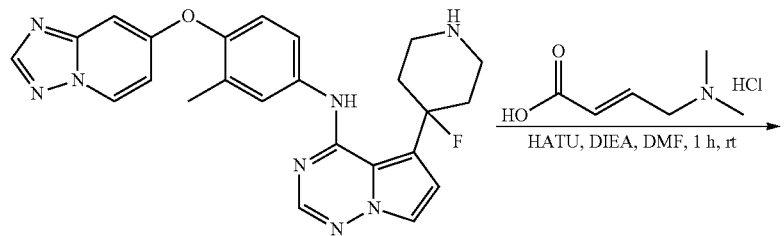

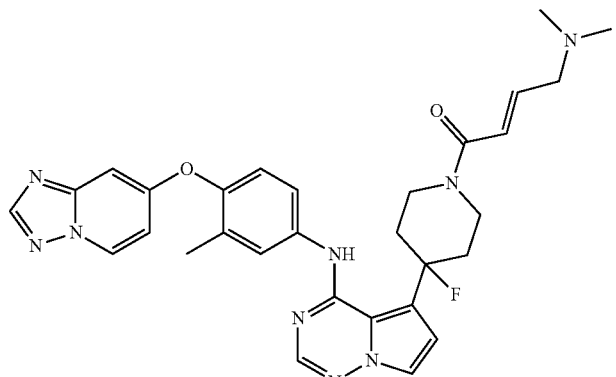

Example 175

Example 176

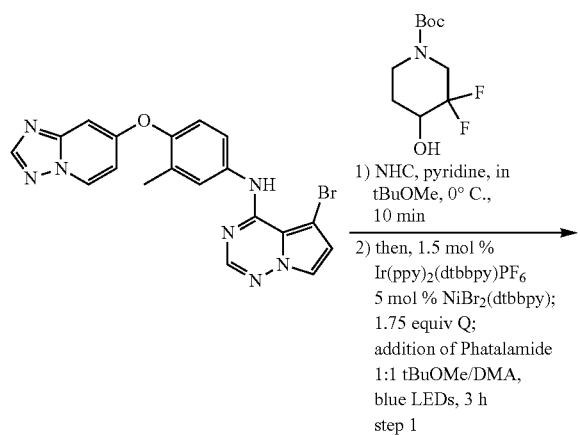

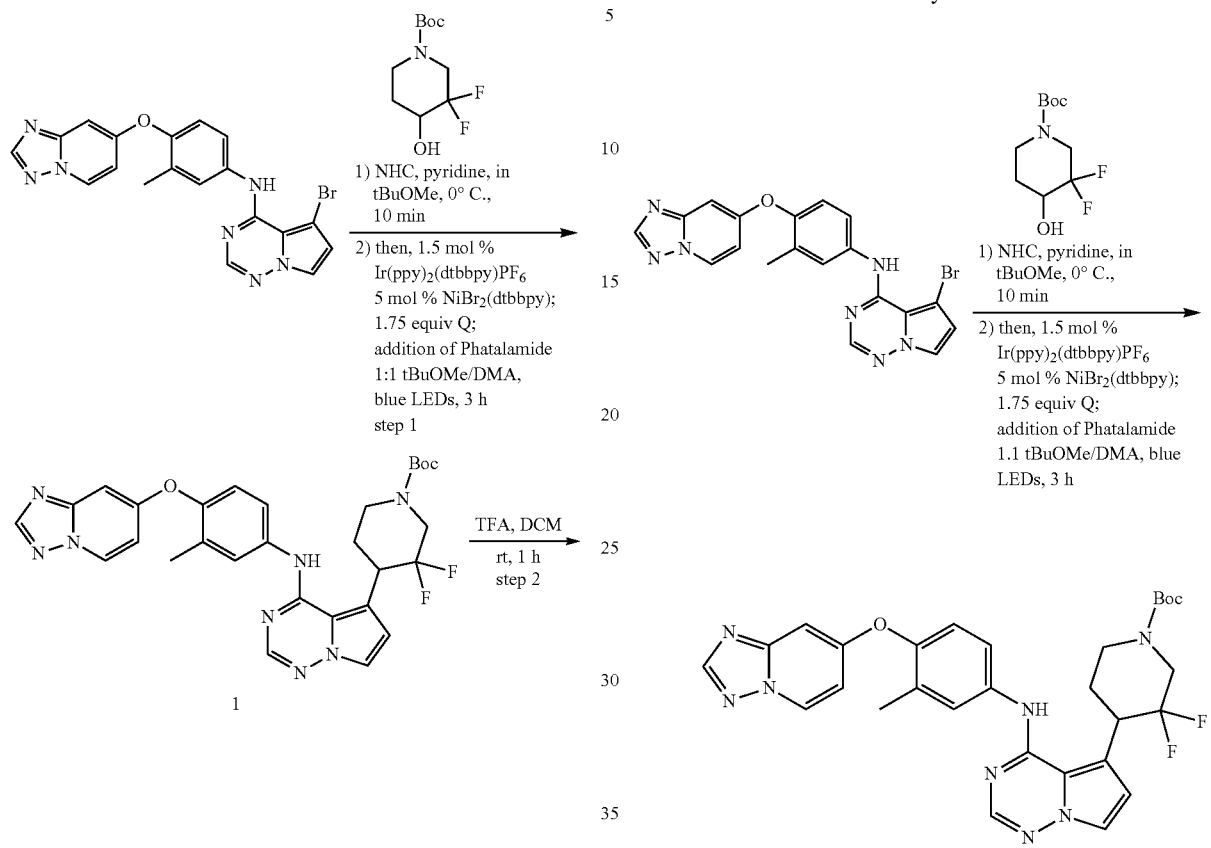

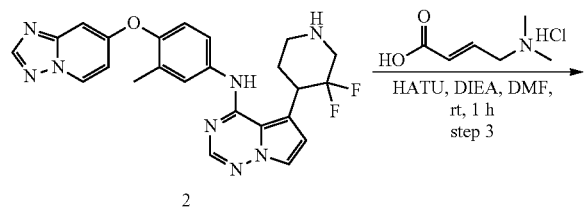

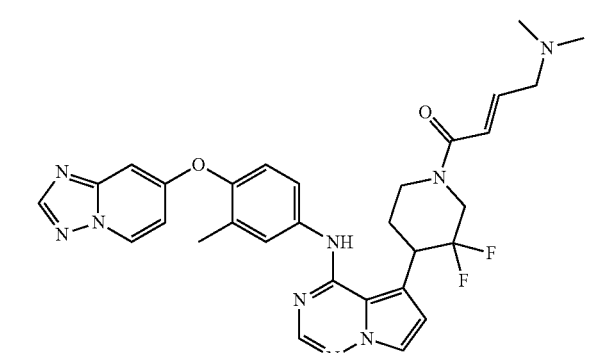

Example 176

Step 1. tert-butyl 4-(4-((4-([1,2,4]triazolo[1,5-a]pyridin-7-yloxy)-3-methylphenyl)amino)pyrrolo[2,1-f] [1,2,4]triazin-5-yl)-3,3-difluoropiperidine-1-carboxylate An oven-dried 20 mL vial was charged with tert-butyl 3,3-difluoro-4-hydroxypiperidine-1-carboxylate (191 mg, 0.80 mmol) and benzoxazolium, 5,7-bis(1,1-dimethylethyl)-3-phenyl-, tetrafluoroborate(1-) (1:1) (AC1) (290 mg, 0.73 nmol). After the vial was degassed under vacuum and charged with nitrogen atmosphere, tert-butyl methyl ether (4 mL) was added to the reaction and stirred at room temperature for 5 minutes. A mixture of pyridine (58.0 mg, 0.73 mmol) in tert-butyl methyl ether (1 mL) was added to the above mixture stirred at room temperature for 10 minutes. Another oven-dried 40 mL vial was charged with N-(4-([1,2,4]triazolo[1,5-a]pyridin-7-yloxy)-3-methylphenyl)-5-bromopyrrolo[2,1-f][1,2,4]triazin-4-amine (200 mg, 0.46 mmol), NiBr$_2$(dtbbpy) (17 mg, 0.03 mmol), Ir(ppy)$_2$(dtbbpy)PF$_6$ (6.3 mg, 0.006 mmol), phthalamide (15.2 mg, 0.1 mmol) and 1-azabicyclo[2.2.2]octane (89.3 mg, 0.81 mmol) in DMA (5 mL) under nitrogen atmosphere. The mixture was stirred at 800 rpm stir rate and irradiated under 450 nm LED modules at 100% light intensity with maxed fan speed of 800 rpm for 3 hours. The residue was dissolved in water (20 mL). The aqueous layer was extracted with ethyl acetate (3×20 mL). The resulting mixture was concentrated under vacuum and purified by Prep-TLC (petroleum ether/ethyl acetate=1:2) to afford tert-butyl 4-(4-((4-([1,2,4]triazolo[1,5-a]pyridin-7-yloxy)-3-methylphenyl)amino)pyrrolo[2,1-f][1,2,4]triazin-5-yl)-3,3-difluoropiperidine-1-carboxylate (50 mg crude). LCMS (ESI-MS) m/z=577.2 [M+H]$^+$.

383

Step 2. N-(4-([1,2,4]triazolo[1,5-a]pyridin-7-yloxy)-3-methylphenyl)-5-(3,3-difluoropiperidin-4-yl)pyrrolo [2,1-f][1,2,4]triazin-4-amine

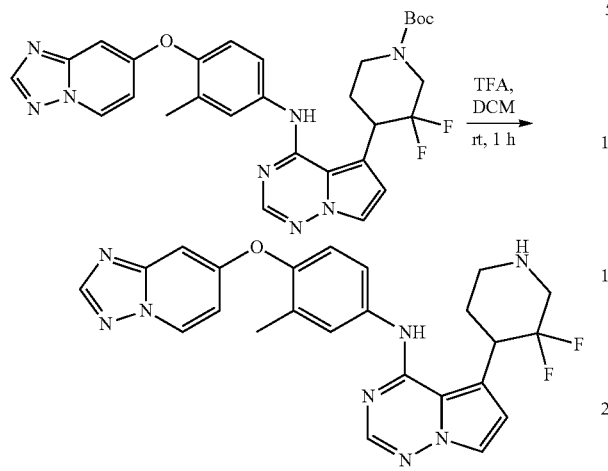

384

TFA (1 mL) was added into a mixture of tert-butyl 4-(4-((4-([1,2,4]triazolo[1,5-a]pyridin-7-yloxy)-3-methylphenyl)amino)pyrrolo[2,1-f][1,2,4]triazin-5-yl)-3,3-difluoropiperidine-1-carboxylate (50 mg, 0.08 mmol) in DCM (2 mL). The resulting mixture was stirred for 1 hour at room temperature and concentrated under vacuum. The residue was purified by silica gel column chromatography, eluted with eluted with MeOH in DCM from 0% to 10% to afford N-(4-([1,2,4]triazolo[1,5-a]pyridin-7-yloxy)-3-methylphenyl)-5-(3,3-difluoropiperidin-4-yl)pyrrolo[2,1-f][1,2,4]triazin-4-amine (40 mg, 18.2% yield for two steps). LCMS (ESI-MS) m/z=477.2 [M+H]$^+$.

Step 3. (E)-1-(4-(4-((4-([1,2,4]triazolo[1,5-a]pyridin-7-yloxy)-3-methylphenyl)amino)pyrrolo[2,1-f][1,2,4]triazin-5-yl)-3,3-difluoropiperidin-1-yl)-4-(dimethylamino)but-2-en-1-one

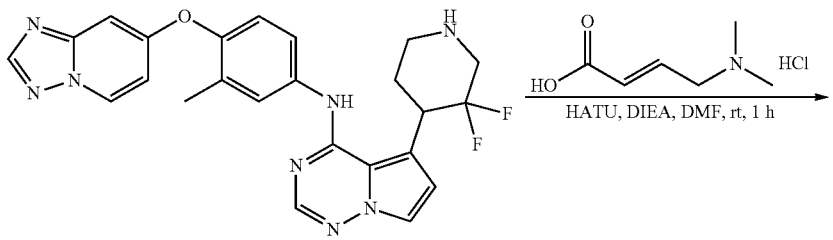

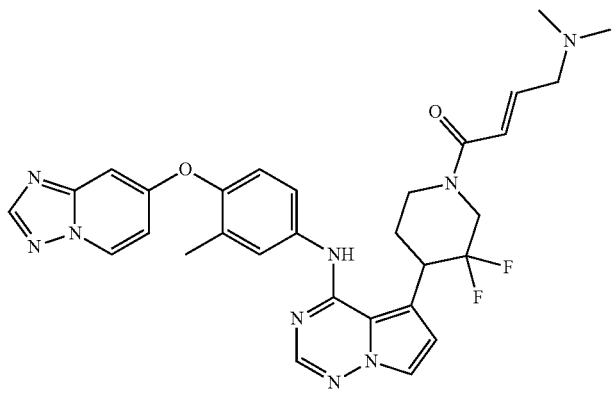

Example 176

Diisopropylethylamine (32.6 mg, 0.25 mmol) was added into a mixture of N-(4-([1,2,4]triazolo[1,5-a]pyridin-7-yloxy)-3-methylphenyl)-5-(3,3-difluoropiperidin-4-yl)pyrrolo[2,1-f][1,2,4]triazin-4-amine (40 mg, 0.08 mmol), (E)-4-(dimethylamino)but-2-enoic acid hydrochloride (14.6 mg, 0.088 mmol) and HATU (47.9 mg, 0.12 mmol) in DMF (1 mL). The resulting mixture was stirred overnight at room temperature then diluted with water (10 mL) and extracted with ethyl acetate (3×10 mL). The combined organic layers were washed with brine (30 mL), dried over anhydrous $Na_2SO_4$, filtered and concentrated under vacuum to afford the crude product. The residue was purified by Prep-TLC (DCM/MeOH=10:1) to afford (E)-1-(4-(4-((4-([1,2,4]triazolo[1,5-a]pyridin-7-yloxy)-3-methylphenyl)amino)pyrrolo[2,1-f][1,2,4]triazin-5-yl)-3,3-difluoropiperidin-1-yl)-4-(dimethylamino)but-2-en-1-one, Example 176 (4 mg, 8.5% yield). LCMS (ESI-MS) m/z=588.3 [M+H]$^+$. $^1$H NMR (400 MHz, $CD_3OD$) δ (ppm) 8.75 (d, J=7.6 Hz, 1H), 8.30 (s, 1H), 7.85 (s, 1H), 7.68 (s, 1H), 7.59 (s, 1H), 7.53 (s, 1H), 7.20 (d, J=8.7 Hz, 1H), 7.12-7.05 (m, 1H), 6.96-6.75 (m, 4H), 5.05-4.91 (m, 1H), 4.56-4.11 (m, 3H), 3.72-3.41 (m, 4H), 2.60 (d, J=8.3 Hz, 6H), 2.25 (s, 3H), 2.22-2.11 (m, 2H).

Example 177

(E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(methylamino)but-2-en-1-one Diisopropylethylamine (66.0 mg, 0.51 mmol) was added to a mixture of (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-bromobut-2-en-1-one (100 mg, 0.17 mmol), $CH_3NH_2$ (33 wt % in EtOH 64 mg, 0.68 mmol,), NaI (38.3 mg, 0.25 mmol) in DMF (1 mL). The resulting mixture was stirred at room temperature for 2 hours. The reaction mixture was purified by Prep-HPLC; Mobile Phase A: Water (10 nmol/$NH_4HCO_3$+0.05% $NH_3 \cdot H_2O$); Mobile Phase B: Gradient: 18% B to 48% B to afford the desired product (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(methylamino)but-2-en-1-one, Example 177 (5.1 mg, 5.6% yield). LCMS (ESI-MS) m/z=538.2 [M+H]$^+$. $^1$H NMR (400 MHz, Chloroform-d) δ (ppm) 8.52 (d, J=7.4 Hz, 1H), 8.24 (s, 1H), 7.99 (s, 1H), 7.67-7.54 (m, 3H), 7.16-7.07 (m, 2H), 6.95-6.87 (m, 2H), 6.86-6.74 (m, 2H), 6.59 (d, J=2.8 Hz, 1H), 4.94-4.80 (m, 1H), 4.36-4.33 (m, 1H), 3.61 (s, 2H), 3.40-3.24 (m, 1H), 3.22-3.12 (m, 1H), 2.96-2.81 (m, 1H), 2.64 (s, 3H), 2.27 (s, 3H), 2.22-2.12 (m, 2H), 1.92-1.77 (m, 2H), 1.39-1.30 (m, 1H).

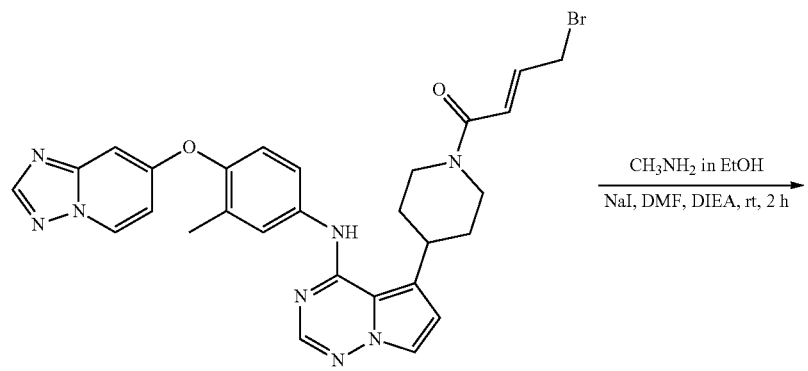

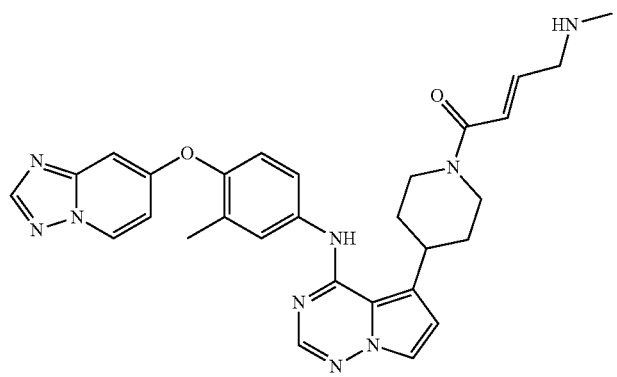

Example 177

387

Example 178

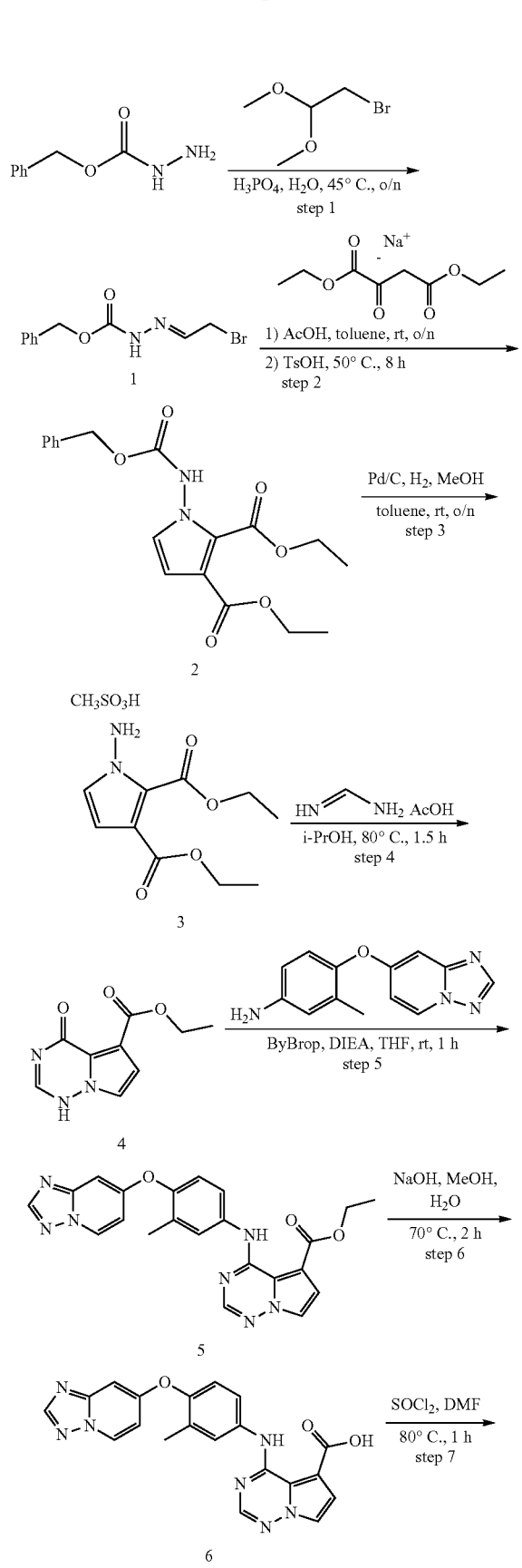

388

-continued

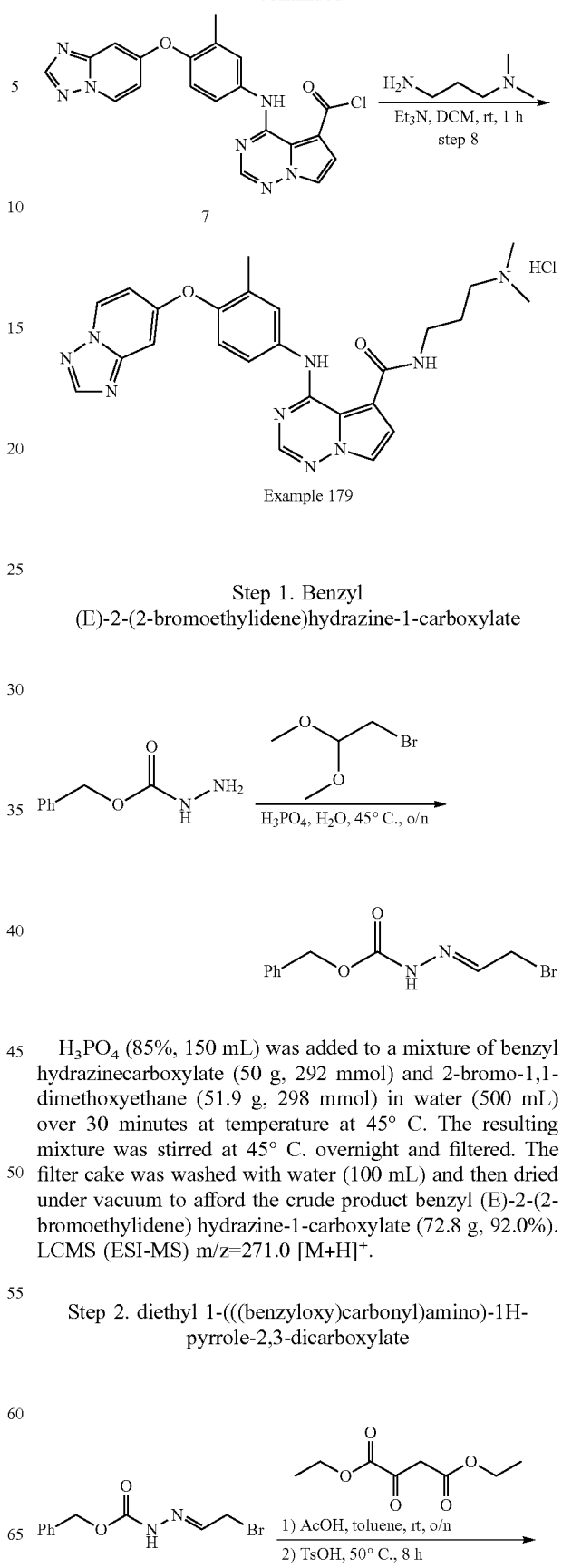

Example 179

Step 1. Benzyl (E)-2-(2-bromoethylidene)hydrazine-1-carboxylate

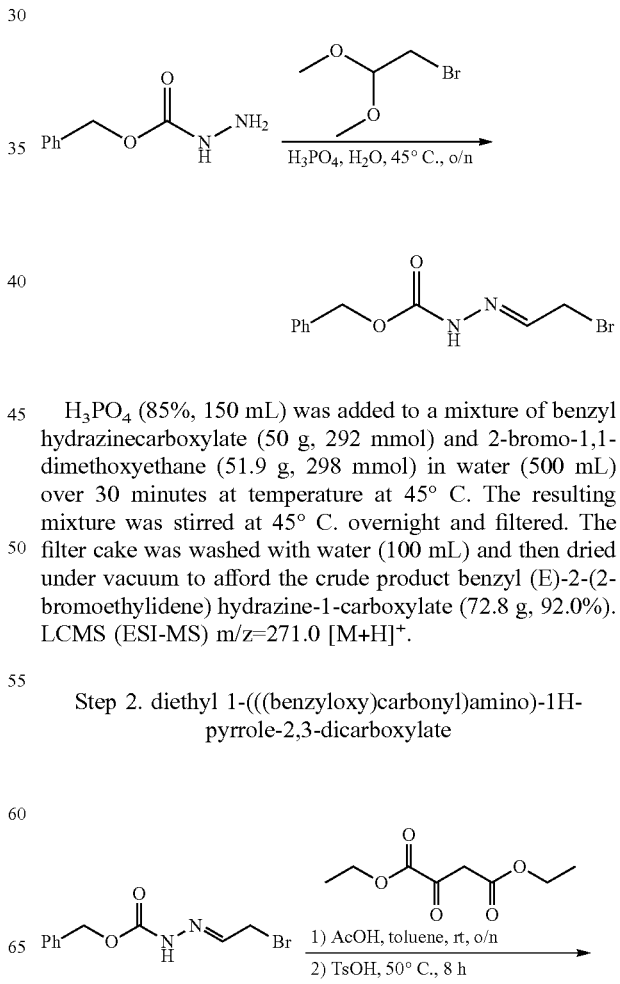

H$_3$PO$_4$ (85%, 150 mL) was added to a mixture of benzyl hydrazinecarboxylate (50 g, 292 mmol) and 2-bromo-1,1-dimethoxyethane (51.9 g, 298 mmol) in water (500 mL) over 30 minutes at temperature at 45° C. The resulting mixture was stirred at 45° C. overnight and filtered. The filter cake was washed with water (100 mL) and then dried under vacuum to afford the crude product benzyl (E)-2-(2-bromoethylidene) hydrazine-1-carboxylate (72.8 g, 92.0%). LCMS (ESI-MS) m/z=271.0 [M+H]$^+$.

Step 2. diethyl 1-(((benzyloxy)carbonyl)amino)-1H-pyrrole-2,3-dicarboxylate

389
-continued

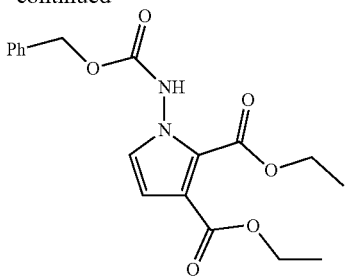

AcOH (0.40 g, 6.6 mmol) was added to a mixture of benzyl (E)-2-(2-bromoethylidene)hydrazine-1-carboxylate (30 g, 110.6 mmol) in toluene (400 mL). The resulting mixture was stirred for 30 minutes, then diethyl oxalacetate sodium salt (23.3 g, 110.65 mmol) was added into the mixture, the mixture was stirred for 12 hours at room temperature. TsOH·H$_2$O (6.31 g, 33.19 mmol) was added, the mixture was stirred for 8 hours at 50° C. The mixture was washed with 5% KH$_2$PO$_4$ aq. (150 mL), washed with water (200 mL), the organic layer was dried, the solution (400 mL) was used for next step directly. LCMS (ESI-MS) m/z=361.1 [M+H]$^+$.

Step 3. Diethyl 1-amino-1H-pyrrole-2,3-dicarboxylate methanesulfonate

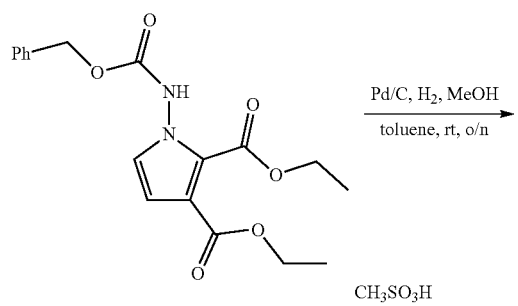

Pd/C (8.27 g, 7.77 mmol, 10%) was added to the solution of step 2 (40 g, 110.99 mmol) in MeOH (50 mL) and toluene (100 mL). The resulting mixture was stirred for 16 hours at 25° C. under hydrogen atmosphere. The mixture was filtered and concentrated under vacuum to afford the crude product. The crude product was dissolved in toluene (50 mL) and i-PrOH (30 mL), added MeOH (5.5 mL) to the mixture above. The resulting mixture was stirred for 2 hours at room temperature and solids appeared. The resulting mixture was filtered and the solids were collected and dried to afford diethyl 1-amino-1H-pyrrole-2,3-dicarboxylate methanesulfonate (20 g, 56.0%). LCMS (ESI-MS) m/z=227.1 [M-CH$_3$SO$_3$H+H]$^+$

390

Step 4. ethyl 4-oxo-1,4-dihydropyrrolo[2,1-f][1,2,4]triazine-5-carboxylate

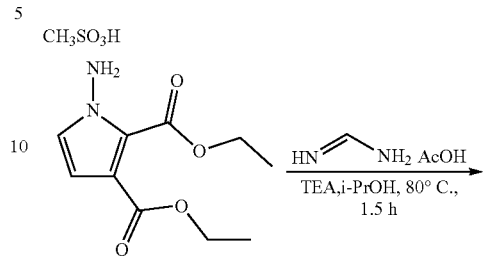

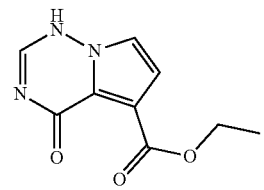

To a slurry of diethyl 1-amino-1H-pyrrole-2,3-dicarboxylate methanesulfonate (15 g, 467 mmol) in isopropanol (38 mL) was charged formamidine acetate (8.59 g, 817 mmol) and TEA (4.55 mL, 327 mmol). The resulting slurry became a clear solution upon heating to 83° C., and the solution remained clear for ~1.5 h before the product started to precipitate. The reaction progress was monitored by HPLC until the starting material was consumed. Water (75 mL) was then added to the reaction slurry, resulting in a decrease of the reaction temperature from 83° C. to 60° C. The slurry was further cooled to 21° C. over 1 hour and then was held for 16 hours and filtered. The solids were washed with water (3×30 mL) and dried under vacuum at 40-50° C. to afford ethyl 4-oxo-1,4-dihydropyrrolo[2,1-f][1,2,4]triazine-5-carboxylate (5 g,). LCMS (ESI-MS) m/z=208.1 [M+H]$^+$.

Step 5. ethyl 4-((4-([1,2,4]triazolo[1,5-a]pyridin-7-yloxy)-3-methylphenyl)amino)pyrrolo[2,1-f][1,2,4]-triazine-5-carboxylate

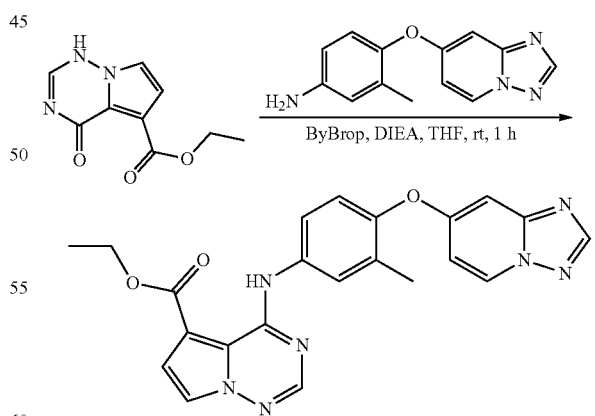

Et$_3$N (1.90 g, 18.82 mmol) was added to a mixture of ethyl 4-oxo-1H-pyrrolo[2,1-f][1,2,4]triazine-5-carboxylate (1.3 g, 6.27 mmol), 4-([1,2,4]triazolo[1,5-a]pyridin-7-yloxy)-3-methylaniline (1.66 g, 6.90 mmol) and PyBrOP (4.39 g, 9.41 mmol) in THF (60 mL), the resulting mixture was stirred for 1 hour at room temperature. The reaction mixture was dilute with THF (50 mL). The resulting mixture was filtered off and the filtrate was concentrated under vacuum to afford the crude product. The crude product was purified by column chromatography (100% EA) to afford ethyl 4-((4-([1,2,4]triazolo[1,5-a]pyridin-7-yloxy)-3-methylphenyl)amino)pyrrolo[2,1-f][1,2,4]triazine-5-carboxylate (1.7 g, 63.09%). LCMS (ESI-MS) m/z=430.2 [M+H]⁺.

Step 6. ethyl 4-((4-([1,2,4]triazolo[1,5-a]pyridin-7-yloxy)-3-methylphenyl)amino)pyrrolo[2,1-f][1,2,4]-triazine-5-carboxylate

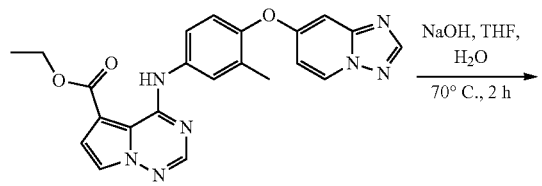

NaOH (1.85 g, 46.45 mmol) was added to a mixture of ethyl 4-((4-([1,2,4]triazolo[1,5-a]pyridin-7-yloxy)-3-methylphenyl)amino)pyrrolo[2,1-f][1,2,4]triazine-5-carboxylate (4 g, 9.29 mmol) in THF (60 mL) and water (20 mL), the resulting mixture was stirred for 2 hours at 70° C. The reaction mixture was concentrated under vacuum. The pH value of the resulting solution was adjusted to 6-7, then the resulting mixture was extracted with THF (with 10% EA) (3×90 mL), dried over anhydrous Na₂SO₄, filtered and concentrated under vacuum to afford ethyl 4-((4-([1,2,4]triazolo[1,5-a] pyridine-7-yloxy)-3-methylphenyl)amino)pyrrolo[2,1-f][1,2,4] triazine-5-carboxylate (2.75 g, 73.7%). LCMS (ESI-MS) m/z=402.1 [M+H]⁺.

Step 7. 4-((4-([1,2,4]triazolo[1,5-a]pyridin-7-yloxy)-3-methylphenyl)amino)pyrrolo[2,1-f][1,2,4]triazine-5-carbonyl chloride

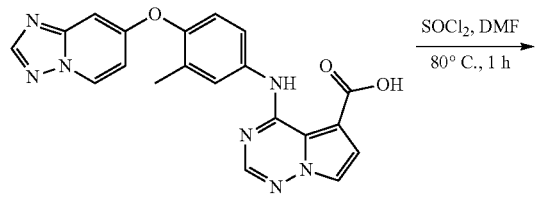

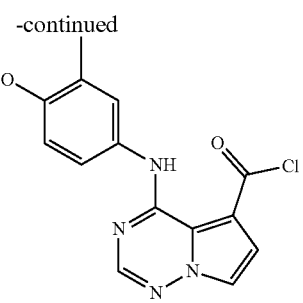

DMF (0.05 g, 0.68 mmol) was added to a mixture of 4-((4-([1,2,4]triazolo[1,5-a]pyridin-7-yloxy)-3-methylphenyl)amino)pyrrolo[2,1-f][1,2,4]-triazine-5-carboxylate (2.75 g, 6.85 mmol) in sulfoaroyl dichloride (0.82 g, 6.85 mmol) at 25° C. Then the reaction mixture was stirred at 80° C. for 1 hour. The resulting mixture was concentrated under reduced pressure to afford the crude product. The crude product was used for next step directly.

Step 8. 4-((4-([1,2,4]triazolo[1,5-a]pyridin-7-yloxy)-3-methylphenyl)amino)-N-(3-(dimethylamino)-propyl)pyrrolo[2,1-f][1,2,4]triazine-5-carboxamide hydrochloride

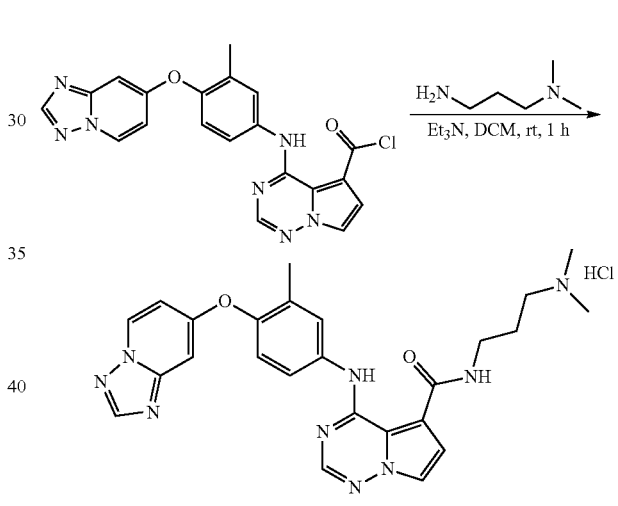

(3-aminopropyl)dimethylamine (3.50 g, 34.25 mmol) was added to the reaction mixture of 4-((4-([1,2,4]triazolo[1,5-a]pyridin-7-yloxy)-3-methylphenyl)amino)pyrrolo[2,1-f][1,2,4]triazine-5-carbonyl chloride in DCM (50 mL) and stirred at 25° C. for 1 hour. Then the resulting mixture was concentrated under reduced pressure. The residue was purified by reversed-phase flash chromatography with the following conditions: column, C18 silica gel; mobile phase, ACN in Water (10 mmol/L NH₄HCO₃), 10% to 50% gradient in 10 min; detector, UV 254 nm. The fractions with desired mass signals were combined to afford the desired product (900 mg) as a yellow solid. Then 1M HCl in EA (1.8 mL) was added to the desired product in EA (5 ml) and the resulting mixture was concentrated under reduced pressure and lyophilized to afford the product 4-((4-([1,2,4]triazolo [1,5-a]pyridin-7-yloxy)-3-methylphenyl)amino)-N-(3-(dimethylamino)-propyl)pyrrolo [2,1-f][1,2,4]triazine-5-carboxamide hydrochloride (919.2 mg, 25.06%). LCMS (ESI-MS) m/z=486.2 [M−HCl+H]⁺. All compounds in Table 1 listed below can be made according to the synthetic examples described in this disclosure, and by making any necessary substitutions of starting materials that the skilled artisan would be able to obtain either commercially or otherwise.

TABLE 1

| E # | Structure | Mass Spec. M + H/1 | Name |
|---|---|---|---|
| 1 | 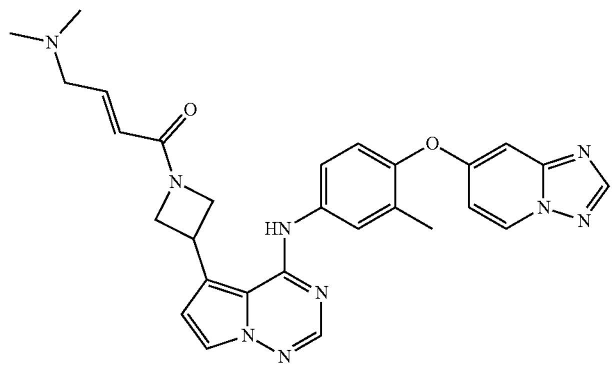 [SMILES: Cc1cc(Nc2ncnn3ccc(C4CN(C(=O)/C=C/CN(C)C)C4)c23)ccc1Oc1ccn2ncnc2c1] | 524.2 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(dimethylamino)but-2-en-1-one |
| 2 | 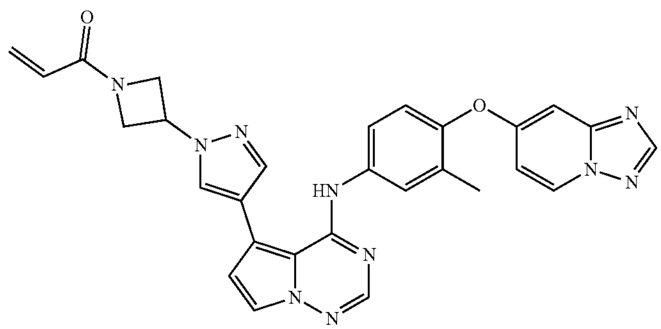 [SMILES: C=CC(=O)N1CC(n2cc(-c3ccn4ncnc(Nc5ccc(Oc6ccn7ncnc7c6)c(C)c5)c34)cn2)C1] | 533.2 | 1-(3-(4-(4-((4-([1,2,4]triazolo[1,5-a]pyridin-7-yloxy)-3-methylphenyl)amino)pyrrolo[2,1-f][1,2,4]triazin-5-yl)-1H-pyrazol-1-yl)azetidin-1-yl)prop-2-en-1-one |
| 3 | 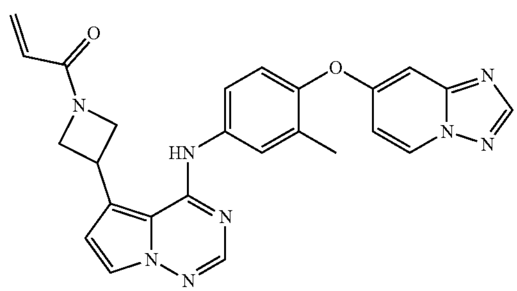 [SMILES: C=CC(=O)N1CC(c2ccn3ncnc(Nc4ccc(Oc5ccn6ncnc6c5)c(C)c4)c23)C1] | 467.2 | 1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)prop-2-en-1-one |
| 4 | 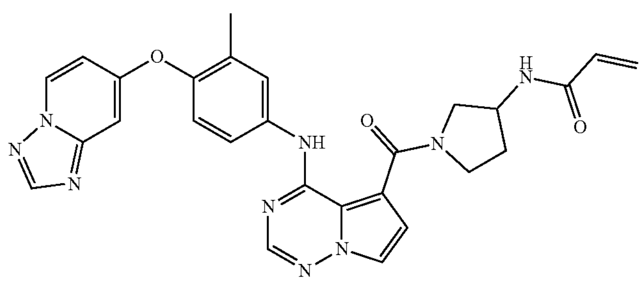 [SMILES: C=CC(=O)NC1CCN(C(=O)c2ccn3ncnc(Nc4ccc(Oc5ccn6ncnc6c5)c(C)c4)c23)C1] | 542.2 | N-(1-(4-((4-([1,2,4]triazolo[1,5-a]pyridin-7-yloxy)-3-methylphenyl)amino)pyrrolo[2,1-f][1,2,4]triazine-5-carbonyl)pyrrolidin-3-yl)acrylamide |
| 5 | 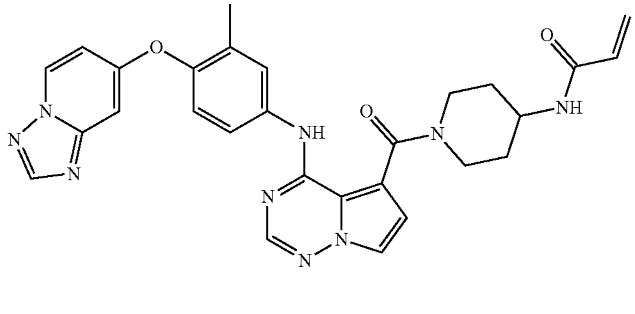 [SMILES: C=CC(=O)NC1CCN(C(=O)c2ccn3ncnc(Nc4ccc(Oc5ccn6ncnc6c5)c(C)c4)c23)CC1] | 538.2 | N-(1-(4-((4-([1,2,4]triazolo[1,5-a]pyridin-7-yloxy)-3-methylphenyl)amino)pyrrolo[2,1-f][1,2,4]triazine-5-carbonyl)piperidin-4-yl)acrylamide |

TABLE 1-continued

| E # | Structure | Mass Spec. M + H/1 | Name |
|---|---|---|---|
| 6 | 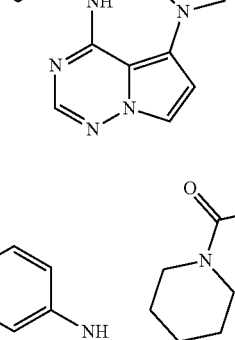 | 496.2 | 1-(4-(4-((4-([1,2,4]triazolo[1,5-a]pyridin-7-yloxy)-3-methylphenyl)amino)pyrrolo[2,1-f][1,2,4]triazin-5-yl)piperazin-1-yl)prop-2-en-1-one |
| 7 | 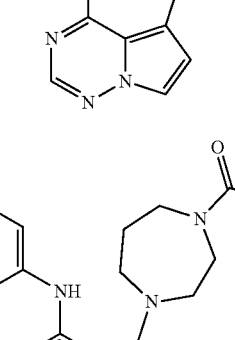 | 495.2 | 1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)prop-2-en-1-one |
| 8 | 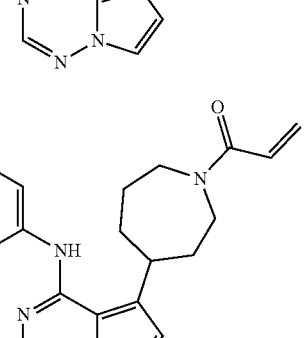 | 510.2 | 1-(4-(4-((4-([1,2,4]triazolo[1,5-a]pyridin-7-yloxy)-3-methylphenyl)amino)pyrrolo[2,1-f][1,2,4]triazin-5-yl)-1,4-diazepan-1-yl)prop-2-en-1-one |
| 9 | 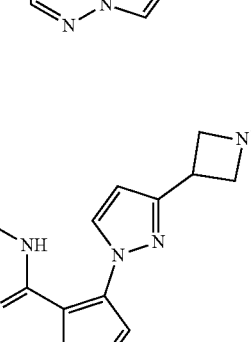 | 509.2 | 1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)prop-2-en-1-one |
| 10 | 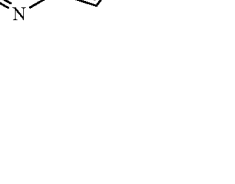 | 533.2 | 1-(3-(1-(4-((4-([1,2,4]triazolo[1,5-a]pyridin-7-yloxy)-3-methylphenyl)amino)pyrrolo[2,1-f][1,2,4]triazin-5-yl)-1H-pyrazol-3-yl)azetidin-1-yl)prop-2-en-1-one |

TABLE 1-continued

| E # | Structure | Mass Spec. M + H/1 | Name |
|---|---|---|---|
| 11 | 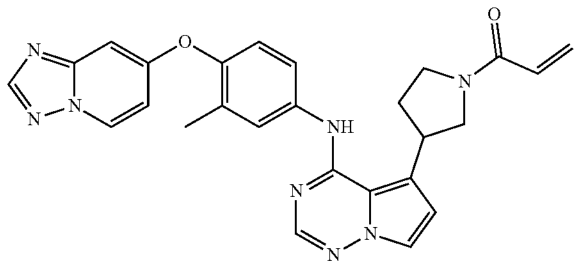 [SMILES: C=CC(=O)N1CCC(c2ccn3ncnc(Nc4ccc(Oc5ccn6ncnc6c5)c(C)c4)c23)C1] | 481.2 | 1-(3-(4-((4-([1,2,4]triazolo[1,5-a]pyridin-7-yloxy)-3-methylphenyl)amino)pyrrolo[2,1-f][1,2,4]triazin-5-yl)pyrrolidin-1-yl)prop-2-en-1-one |
| 12 | 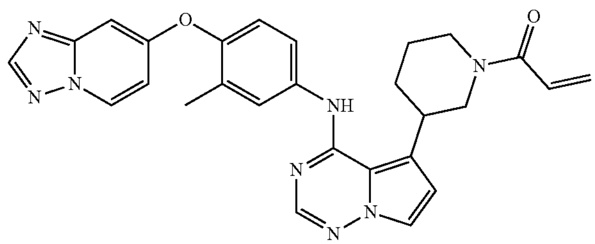 [SMILES: C=CC(=O)N1CCCC(c2ccn3ncnc(Nc4ccc(Oc5ccn6ncnc6c5)c(C)c4)c23)C1] | 495.1 | 1-(3-(4-((4-([1,2,4]triazolo[1,5-a]pyridin-7-yloxy)-3-methylphenyl)amino)pyrrolo[2,1-f][1,2,4]triazin-5-yl)piperidin-1-yl)prop-2-en-1-one |
| 13 | 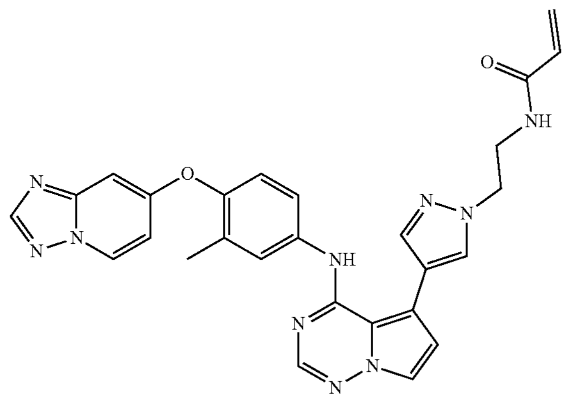 [SMILES: C=CC(=O)NCCn1cc(-c2ccn3ncnc(Nc4ccc(Oc5ccn6ncnc6c5)c(C)c4)c23)cn1] | 521.2 | N-(2-(4-(4-((4-([1,2,4]triazolo[1,5-a]pyridin-7-yloxy)-3-methylphenyl)amino)pyrrolo[2,1-f][1,2,4]triazin-5-yl)-1H-pyrazol-1-yl)ethyl)acrylamide |
| 14 | 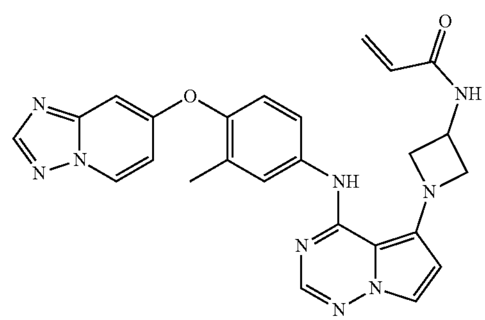 [SMILES: C=CC(=O)NC1CN(c2ccn3ncnc(Nc4ccc(Oc5ccn6ncnc6c5)c(C)c4)c23)C1] | 482.2 | N-(1-(4-((4-([1,2,4]triazolo[1,5-a]pyridin-7-yloxy)-3-methylphenyl)amino)pyrrolo[2,1-f][1,2,4]triazin-5-yl)azetidin-3-yl)acrylamide |
| 15 | 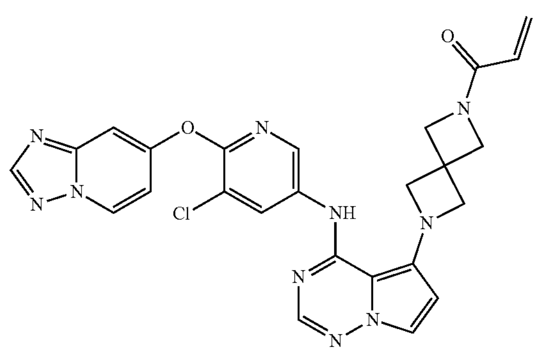 [SMILES: C=CC(=O)N1CC2(C1)CN(c1ccn3ncnc(Nc4cnc(Oc5ccn6ncnc6c5)c(Cl)c4)c13)C2] | 529.1 | 1-(6-(4-((6-([1,2,4]triazolo[1,5-a]pyridin-7-yloxy)-5-chloropyridin-3-yl)amino)pyrrolo[2,1-f][1,2,4]triazin-5-yl)-2,6-diazaspiro[3.3]heptan-2-yl)prop-2-en-1-one |

TABLE 1-continued

| E # | Structure | Mass Spec. M + H/1 | Name |
|---|---|---|---|
| 16 | 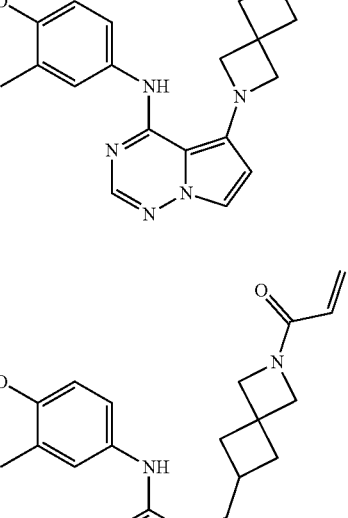 | 508.2 | 1-(6-(4-((4-([1,2,4]triazolo[1,5-a]pyridin-7-yloxy)-3-methylphenyl)amino)pyrrolo[2,1-f][1,2,4]triazin-5-yl)-2,6-diazaspiro[3.3]heptan-2-yl)prop-2-en-1-one |
| 17 | 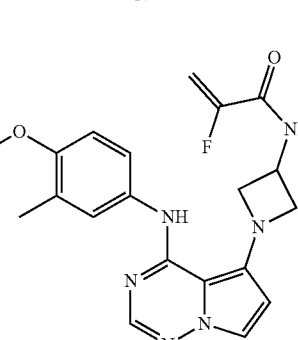 | 507.2 | 1-(6-(4-((4-([1,2,4]triazolo[1,5-a]pyridin-7-yloxy)-3-methylphenyl)amino)pyrrolo[2,1-f][1,2,4]triazin-5-yl)-2-azaspiro[3.3]heptan-2-yl)prop-2-en-1-one |
| 18 | 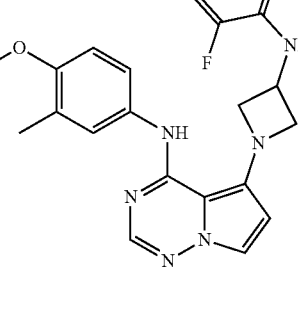 | 500.2 | N-(1-(4-((4-([1,2,4]triazolo[1,5-a]pyridin-7-yloxy)-3-methylphenyl)amino)pyrrolo[2,1-f][1,2,4]triazin-5-yl)azetidin-3-yl)-2-fluoroacrylamide |
| 19 | 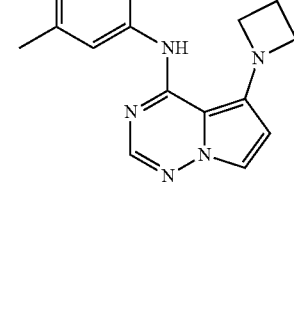 | 551.2 | 1-(3-(4-(4-((4-([1,2,4]triazolo[1,5-a]pyridin-7-yloxy)-3-methylphenyl)amino)pyrrolo[2,1-f][1,2,4]triazin-5-yl)-1H-pyrazol-1-yl)azetidin-1-yl)-2-fluoroprop-2-en-1-one |

TABLE 1-continued

| E # | Structure | Mass Spec. M + H/1 | Name |
|---|---|---|---|
| 20 | 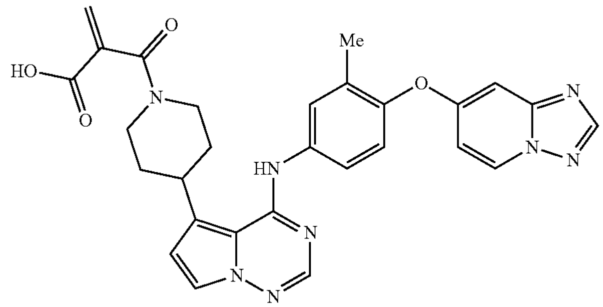 [SMILES: C=C(C(=O)O)C(=O)N1CCC(c2ccn3ncnc(Nc4ccc(Oc5ccn6ncnc6c5)c(C)c4)c23)CC1] | 539.2 | 2-(4-(4-((4-([1,2,4]triazolo[1,5-a]pyridin-7-yloxy)-3-methylphenyl)amino)pyrrolo[2,1-f][1,2,4]triazin-5-yl)piperidine-1-carbonyl)acrylic acid |
| 21 | 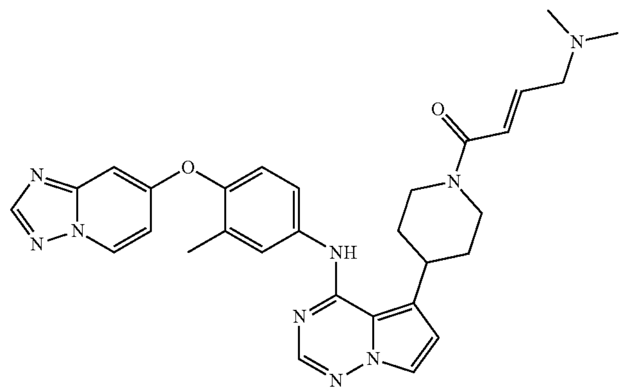 [SMILES: Cc1cc(Nc2ncnn3ccc(C4CCN(C(=O)/C=C/CN(C)C)CC4)c23)ccc1Oc1ccn2ncnc2c1] | 552.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(dimethylamino)but-2-en-1-one |
| 22 | 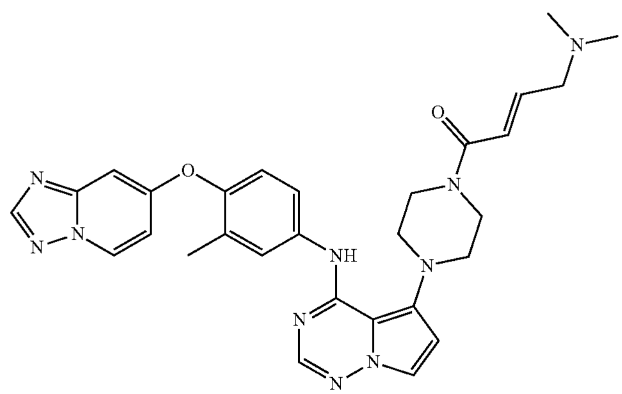 [SMILES: Cc1cc(Nc2ncnn3ccc(N4CCN(C(=O)/C=C/CN(C)C)CC4)c23)ccc1Oc1ccn2ncnc2c1] | 553.2 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperazin-1-yl)-4-(dimethylamino)but-2-en-1-one |
| 23 | 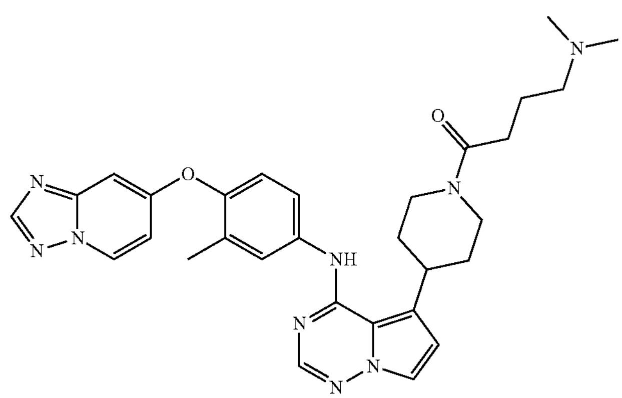 [SMILES: Cc1cc(Nc2ncnn3ccc(C4CCN(C(=O)CCCN(C)C)CC4)c23)ccc1Oc1ccn2ncnc2c1] | 554.3 | 1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(dimethylamino)butan-1-one |

TABLE 1-continued

| E # | Structure | Mass Spec. M + H/1 | Name |
|---|---|---|---|
| 24 | 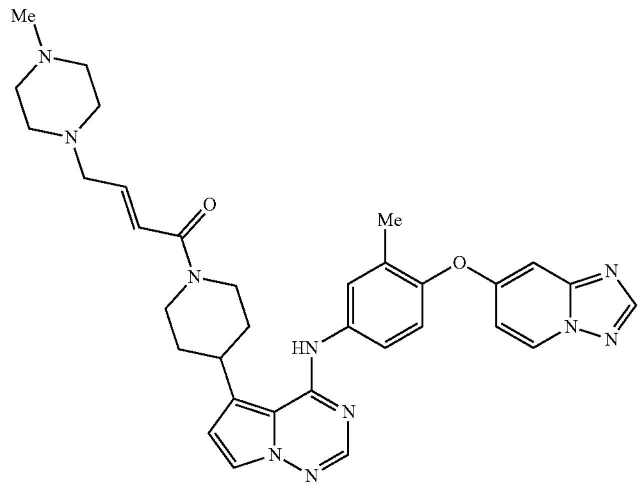 [SMILES: Cc1cc(Nc2ncnn3ccc(C4CCN(C(=O)/C=C/CN5CCN(C)CC5)CC4)c23)ccc1Oc1ccn2ncnc2c1] | 607.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(4-methylpiperazin-1-yl)but-2-en-1-one |
| 25 | 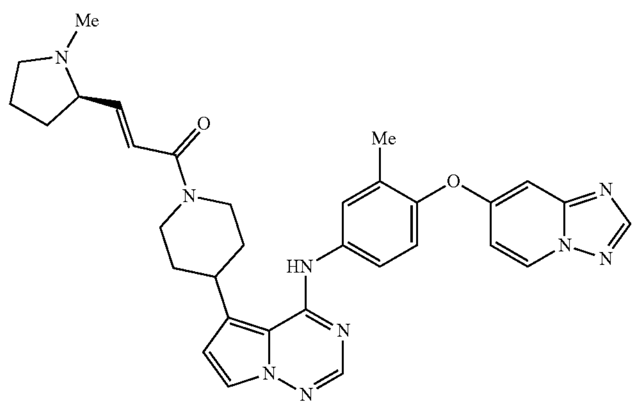 [SMILES: Cc1cc(Nc2ncnn3ccc(C4CCN(C(=O)/C=C/[C@H]5CCCN5C)CC4)c23)ccc1Oc1ccn2ncnc2c1] | 578.3 | (R,E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-3-(1-methylpyrrolidin-2-yl)prop-2-en-1-one |
| 26 | 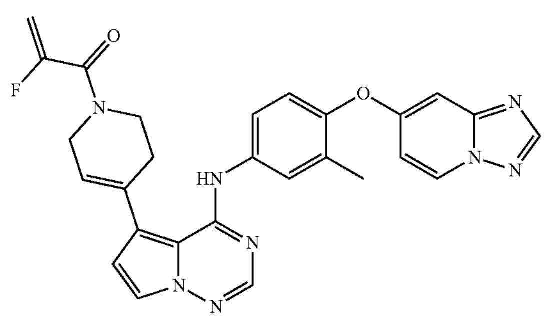 [SMILES: C=C(F)C(=O)N1CC=C(c2ccn3ncnc(Nc4ccc(Oc5ccn6ncnc6c5)c(C)c4)c23)CC1] | 511.2 | 1-(4-(4-((4-([1,2,4]triazolo[1,5-a]pyridin-7-yloxy)-3-methylphenyl)amino)pyrrolo[2,1-f][1,2,4]triazin-5-yl)-3,6-dihydropyridin-1(2H)-yl)-2-fluoroprop-2-en-1-one |
| 27 | 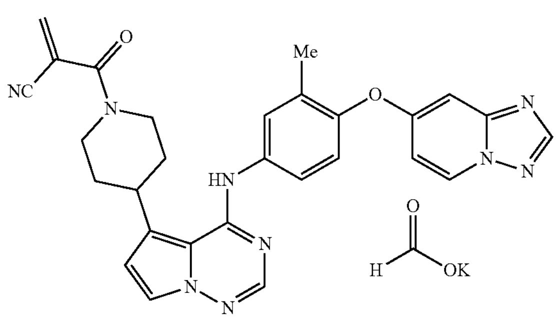 | 603.3 | 2-(4-(4-((4-([1,2,4]triazolo[1,5-a]pyridin-7-yloxy)-3-methylphenyl)amino)pyrrolo[2,1-f][1,2,4]triazin-5-yl)piperidine-1-carbonyl)acrylonitrile (potassium formate adduct) |

TABLE 1-continued

| E # | Structure | Mass Spec. M + H/1 | Name |
|---|---|---|---|
| 28 | 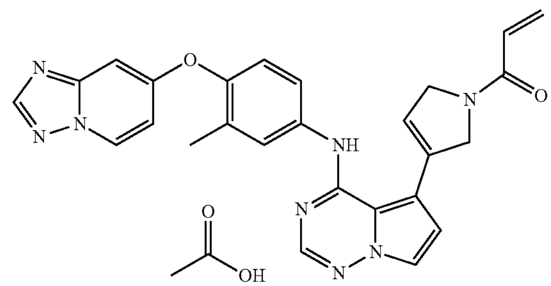 | 479.2 | 1-(3-(4-((4-([1,2,4]triazolo[1,5-a]pyridin-7-yloxy)-3-methylphenyl)amino)pyrrolo[2,1-f][1,2,4]triazin-5-yl)-2,5-dihydro-1H-pyrrol-1-yl)prop-2-en-1-one acetate |
| 29 | 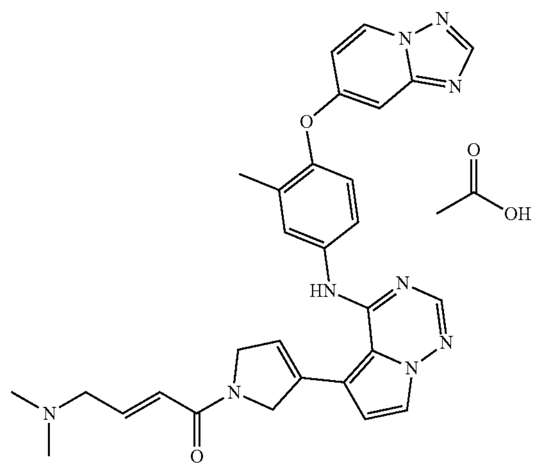 | 536.2 | (E)-1-(3-(4-((4-([1,2,4]triazolo[1,5-a]pyridin-7-yloxy)-3-methylphenyl)amino)pyrrolo[2,1-f][1,2,4]triazin-5-yl)-2,5-dihydro-1H-pyrrol-1-yl)-4-(dimethylamino)but-2-en-1-one acetate |
| 30 | 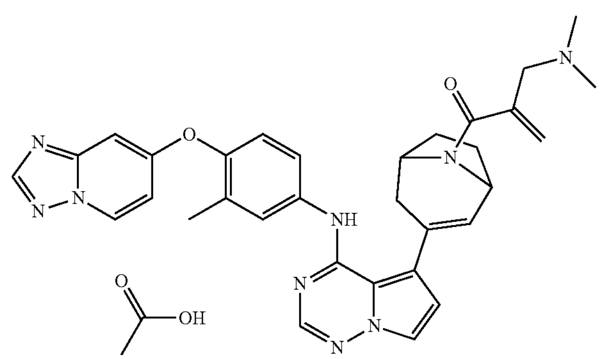 | 576.3 | 1-(3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]oct-2-en-8-yl)-2-((dimethylamino)methyl)prop-2-en-1-one acetate |
| 32 | 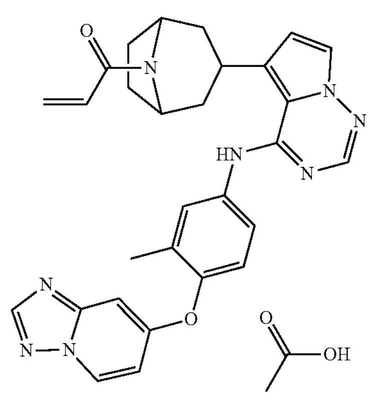 | 543.3 | 1-(3-(5-((4-([1,2,4]triazolo[4,3-a]pyridin-7-yloxy)-3-methylphenyl)amino)pyrrolo[2,1-f][1,2,4]triazin-4-yl)-8-azabicyclo[3.2.1]octan-8-yl)prop-2-en-1-one acetate |

TABLE 1-continued

| E # | Structure | Mass Spec. M + H/1 | Name |
|---|---|---|---|
| 33 | 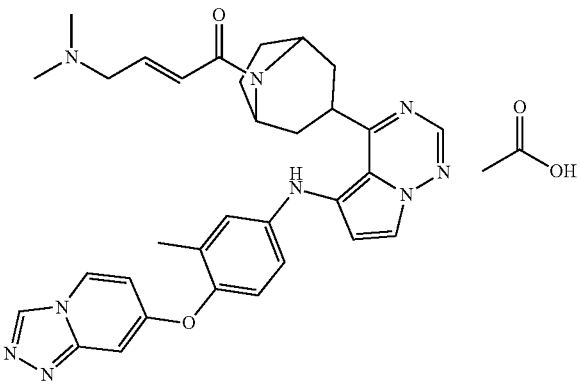 | 578.3 | (E)-1-(3-(5-((4-([1,2,4]triazolo[4,3-a]pyridin-7-yloxy)-3-methylphenyl)amino)pyrrolo[2,1-f][1,2,4]triazin-4-yl)-8-azabicyclo[3.2.1]octan-8-yl)-4-(dimethylamino)but-2-en-1-one acetate |
| 34 | 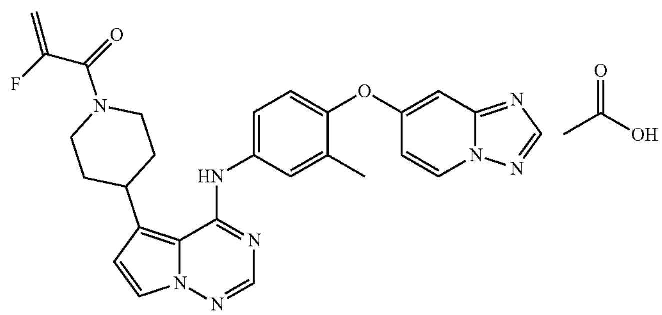 | 513.3 | 1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-2-fluoroprop-2-en-1-one acetate |
| 35 | 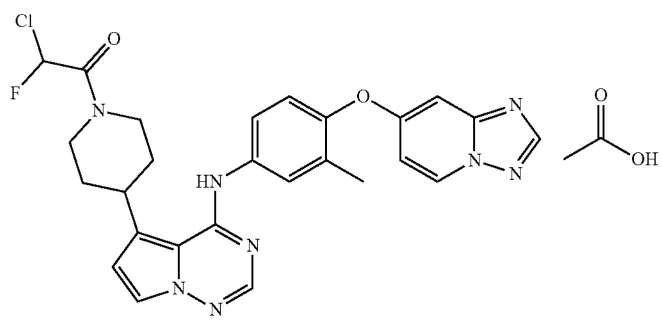 | 535.2 | 1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-2-chloro-2-fluoroethan-1-one acetate |
| 36 | 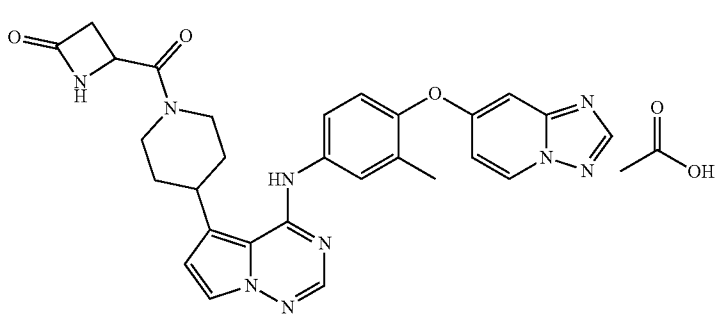 | 538.4 | 4-(4-(4-((4-([1,2,4]triazolo[1,5-a]pyridin-7-yloxy)-3-methylphenyl)amino)pyrrolo[2,1-f][1,2,4]triazin-5-yl)piperidine-1-carbonyl)azetidin-2-one acetate |

TABLE 1-continued

| E # | Structure | Mass Spec. M + H/1 | Name |
|---|---|---|---|
| 37 | 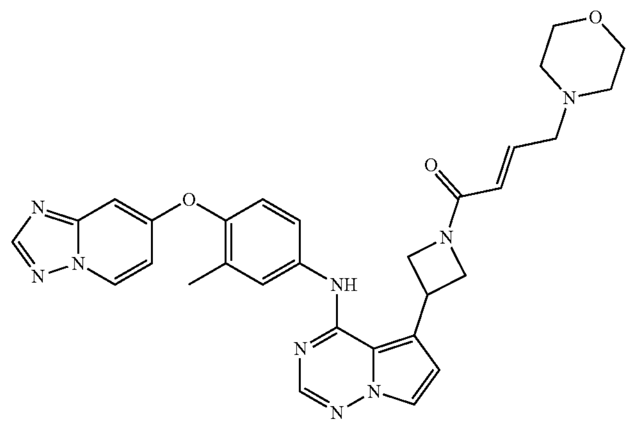 [SMILES: Cc1cc(Nc2ncnn3ccc(C4CN(C(=O)/C=C/CN5CCOCC5)C4)c23)ccc1Oc1ccn2ncnc2c1] | 566.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-morpholinobut-2-en-1-one |
| 38 | 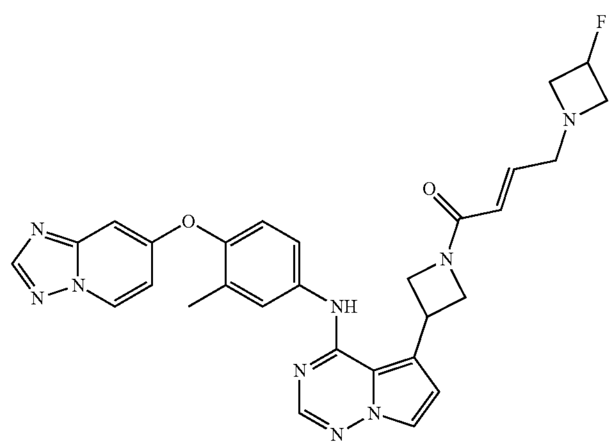 [SMILES: Cc1cc(Nc2ncnn3ccc(C4CN(C(=O)/C=C/CN5CC(F)C5)C4)c23)ccc1Oc1ccn2ncnc2c1] | 554.2 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(3-fluoroazetidin-1-yl)but-2-en-1-one |
| 39 | 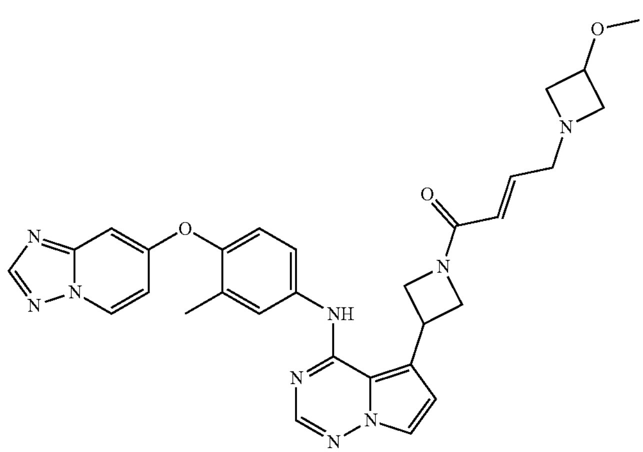 [SMILES: COC1CN(C/C=C/C(=O)N2CC(c3ccn4ncnc(Nc5ccc(Oc6ccn7ncnc7c6)c(C)c5)c34)C2)C1] | 566.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(3-methoxyazetidin-1-yl)but-2-en-1-one |

TABLE 1-continued

| E # | Structure | Mass Spec. M + H/1 | Name |
|---|---|---|---|
| 40 | 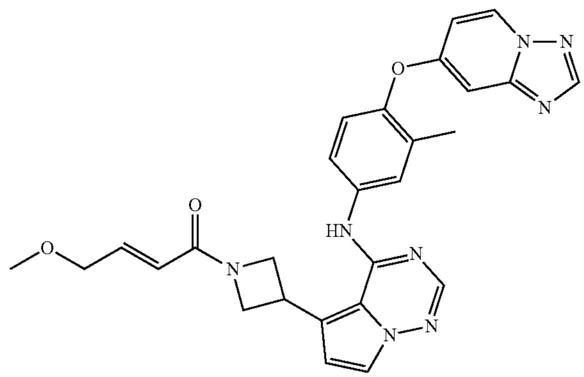 [SMILES: COC/C=C/C(=O)N1CC(c2ccn3ncnc(Nc4ccc(Oc5ccn6ncnc6c5)c(C)c4)c23)C1] | 511.2 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-methoxybut-2-en-1-one |
| 41 | 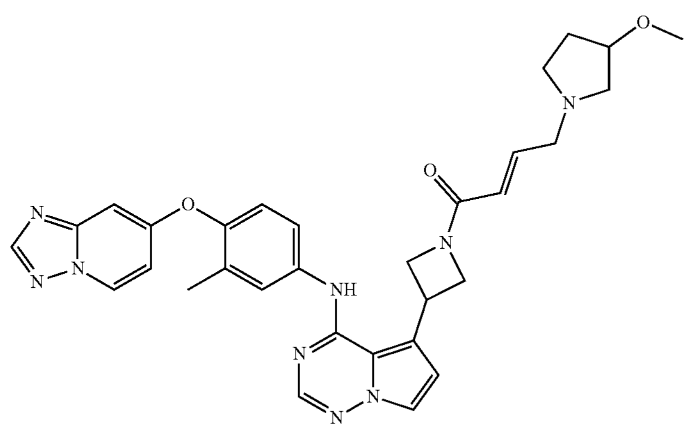 [SMILES: COC1CCN(C/C=C/C(=O)N2CC(c3ccn4ncnc(Nc5ccc(Oc6ccn7ncnc7c6)c(C)c5)c34)C2)C1] | 580.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(3-methoxypyrrolidin-1-yl)but-2-en-1-one |
| 42 | 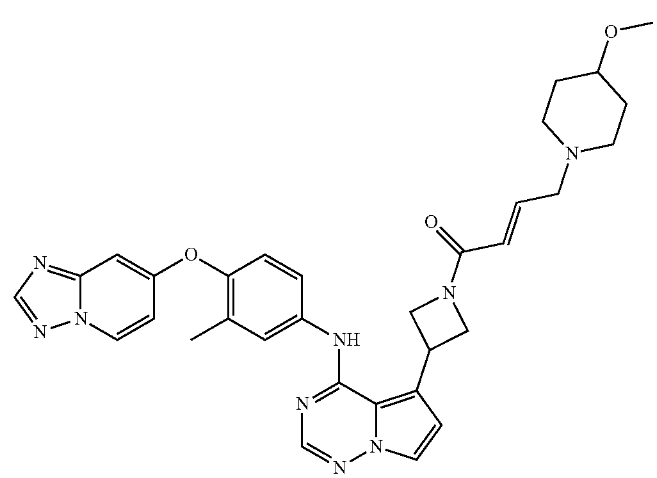 [SMILES: COC1CCN(C/C=C/C(=O)N2CC(c3ccn4ncnc(Nc5ccc(Oc6ccn7ncnc7c6)c(C)c5)c34)C2)CC1] | 594.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(4-methoxypiperidin-1-yl)but-2-en-1-one |

TABLE 1-continued

| E # | Structure | Mass Spec. M + H/1 | Name |
|---|---|---|---|
| 43 | 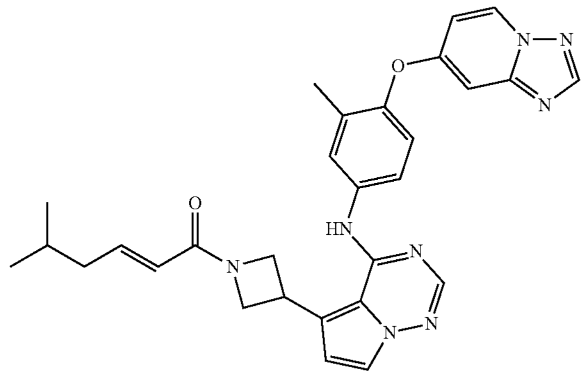 [SMILES: Cc1cc(Nc2ncnn3ccc(C4CN(C(=O)/C=C/CC(C)C)C4)c23)ccc1Oc1ccn2ncnc2c1] | 523.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-5-methylhex-2-en-1-one |
| 44 | 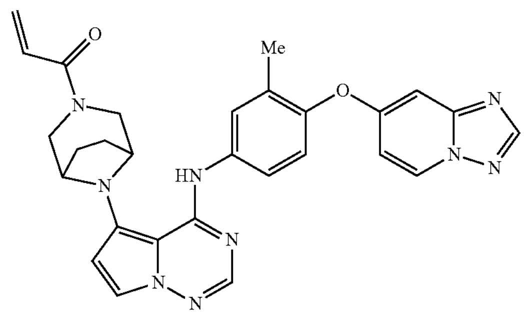 [SMILES: C=CC(=O)N1CC2CCC(C1)N2c1ccn2ncnc(Nc3ccc(Oc4ccn5ncnc5c4)c(C)c3)c12] | 522.2 | 1-(8-(4-((4-([1,2,4]triazolo[1,5-a]pyridin-7-yloxy)-3-methylphenyl)amino)pyrrolo[2,1-f][1,2,4]triazin-5-yl)-3,8-diazabicyclo[3.2.1]octan-3-yl)prop-2-en-1-one |
| 45 | 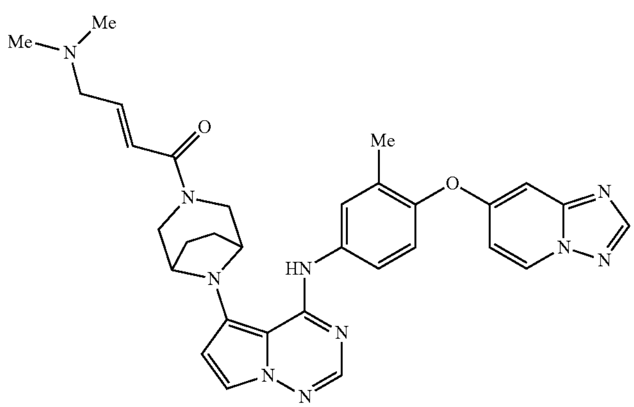 [SMILES: Cc1cc(Nc2ncnn3ccc(N4C5CCC4CN(C(=O)/C=C/CN(C)C)C5)c23)ccc1Oc1ccn2ncnc2c1] | 579.3 | (E)-1-(8-(4-((4-([1,2,4]triazolo[1,5-a]pyridin-7-yloxy)-3-methylphenyl)amino)pyrrolo[2,1-f][1,2,4]triazin-5-yl)-3,8-diazabicyclo[3.2.1]octan-3-yl)-4-(dimethylamino)but-2-en-1-one |
| 46 | 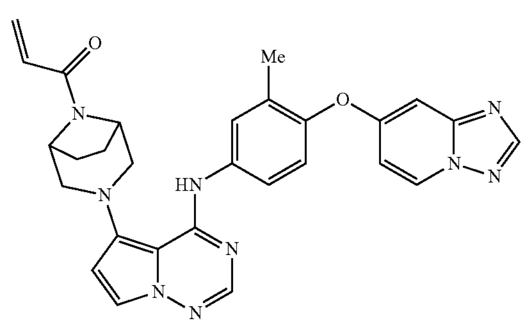 [SMILES: C=CC(=O)N1C2CCC1CN(c1ccn3ncnc(Nc4ccc(Oc5ccn6ncnc6c5)c(C)c4)c13)C2] | 522.2 | 1-(3-(4-((4-([1,2,4]triazolo[1,5-a]pyridin-7-yloxy)-3-methylphenyl)amino)pyrrolo[2,1-f][1,2,4]triazin-5-yl)-3,8-diazabicyclo[3.2.1]octan-8-yl)prop-2-en-1-one |

TABLE 1-continued

| E # | Structure | Mass Spec. M + H/1 | Name |
|---|---|---|---|
| 47 | 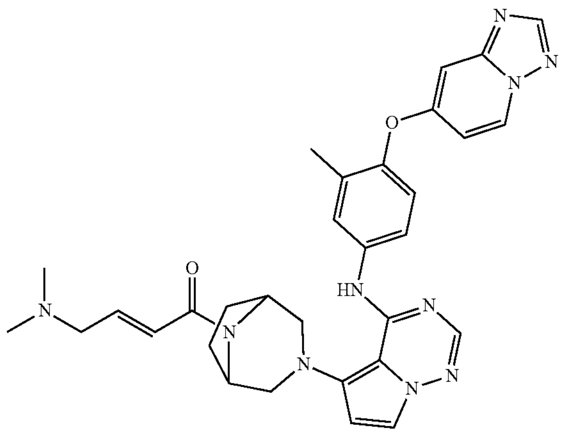 [SMILES: Cc1cc(Nc2ncnn3ccc(N4CC5CCC(C4)N5C(=O)/C=C/CN(C)C)c23)ccc1Oc1ccn2ncnc2c1] | 579.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)-3,8-diazabicyclo[3.2.1]octan-8-yl)-4-(dimethylamino)but-2-en-1-one |
| 48 | 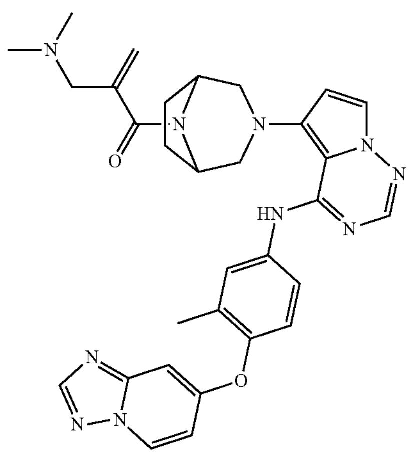 [SMILES: C=C(CN(C)C)C(=O)N1C2CCC1CN(c1ccn3ncnc(Nc4ccc(Oc5ccn6ncnc6c5)c(C)c4)c13)C2] | 579.3 | 1-(3-(4-((4-([1,2,4]triazolo[1,5-a]pyridin-7-yloxy)-3-methylphenyl)amino)pyrrolo[2,1-f][1,2,4]triazin-5-yl)-3,8-diazabicyclo[3.2.1]octan-8-yl)-2-((dimethylamino)methyl)prop-2-en-1-one |
| 49 | 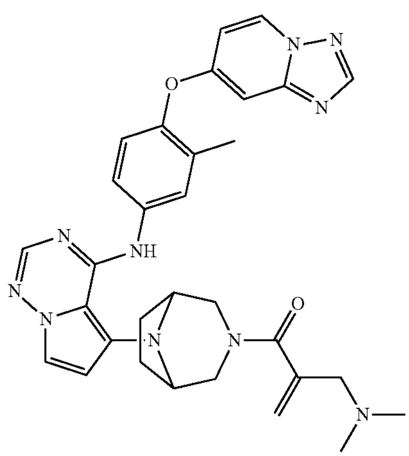 [SMILES: C=C(CN(C)C)C(=O)N1CC2CCC(C1)N2c1ccn2ncnc(Nc3ccc(Oc4ccn5ncnc5c4)c(C)c3)c12] | 579.3 | 1-(8-(4-((4-([1,2,4]triazolo[1,5-a]pyridin-7-yloxy)-3-methylphenyl)amino)pyrrolo[2,1-f][1,2,4]triazin-5-yl)-3,8-diazabicyclo[3.2.1]octan-3-yl)-2-((dimethylamino)methyl)prop-2-en-1-one acetate |

TABLE 1-continued

| E # | Structure | Mass Spec. M + H/1 | Name |
|---|---|---|---|
| 50 | 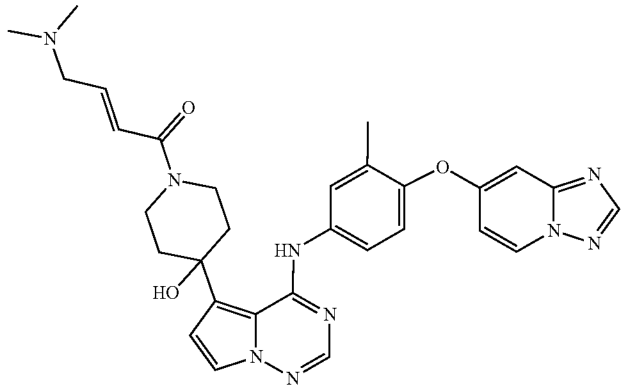 [SMILES: Cc1cc(Nc2ncnn3ccc(C4(O)CCN(C(=O)/C=C/CN(C)C)CC4)c23)ccc1Oc1ccn2ncnc2c1] | 568.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)-4-hydroxypiperidin-1-yl)-4-(dimethylamino)but-2-en-1-one |
| 51 | 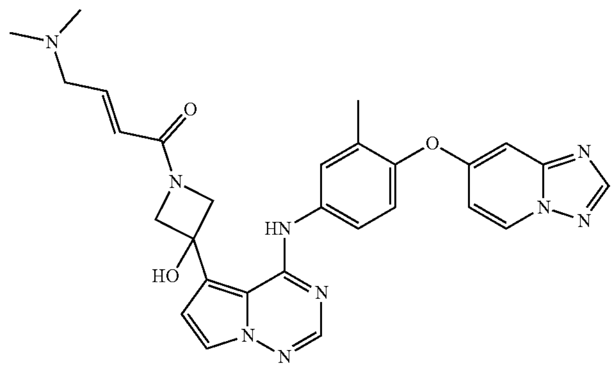 [SMILES: Cc1cc(Nc2ncnn3ccc(C4(O)CN(C(=O)/C=C/CN(C)C)C4)c23)ccc1Oc1ccn2ncnc2c1] | 540.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)-3-hydroxyazetidin-1-yl)-4-(dimethylamino)but-2-en-1-one |
| 52 | 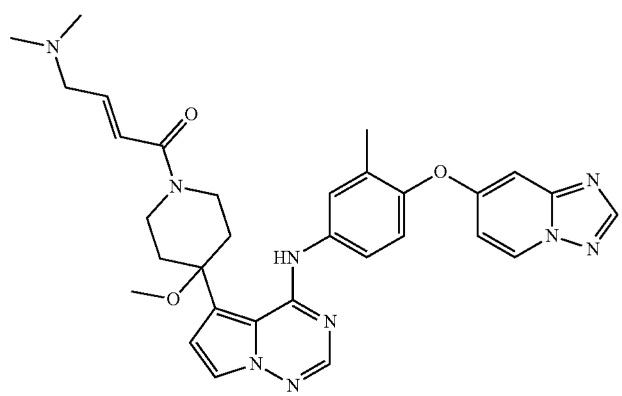 [SMILES: COC1(c2ccn3ncnc(Nc4ccc(Oc5ccn6ncnc6c5)c(C)c4)c23)CCN(C(=O)/C=C/CN(C)C)CC1] | 582.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)-4-methoxypiperidin-1-yl)-4-(dimethylamino)but-2-en-1-one |
| 53 | 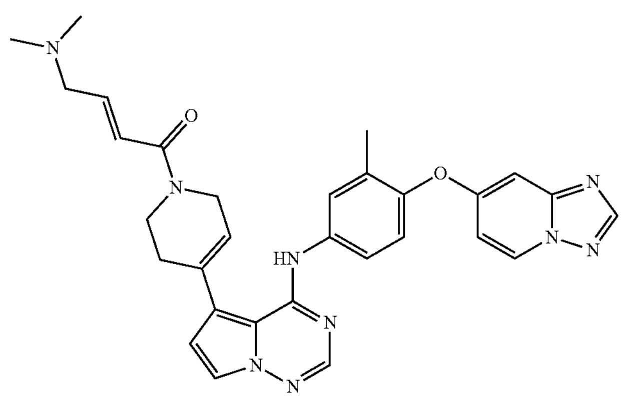 [SMILES: Cc1cc(Nc2ncnn3ccc(C4=CCN(C(=O)/C=C/CN(C)C)CC4)c23)ccc1Oc1ccn2ncnc2c1] | 550.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)-3,6-dihydropyridin-1(2H)-yl)-4-(dimethylamino)but-2-en-1-one |

TABLE 1-continued

| E # | Structure | Mass Spec. M + H/1 | Name |
|---|---|---|---|
| 54 | 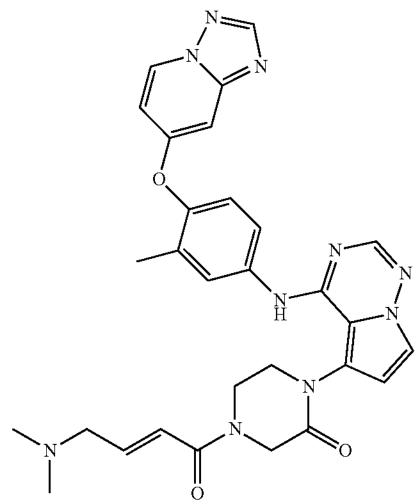 [SMILES: Cc1cc(Nc2ncnn3ccc(N4CCN(C(=O)/C=C/CN(C)C)CC4=O)c23)ccc1Oc1ccn2ncnc2c1] | 567.7 | (E)-1-(4-((4-([1,2,4]triazolo[1,5-a]pyridin-7-yloxy)-3-methylphenyl)amino)pyrrolo[2,1-f][1,2,4]triazin-5-yl)-4-(4-(dimethylamino)but-2-enoyl)piperazin-2-one |
| 55 | 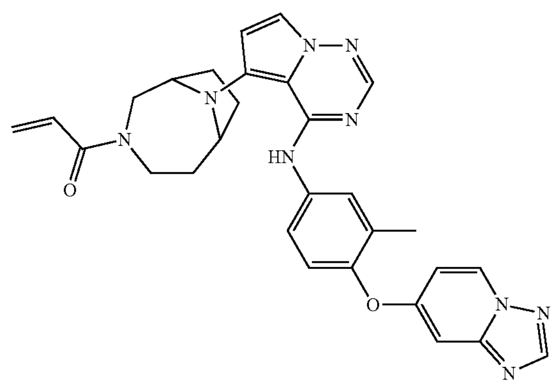 [SMILES: C=CC(=O)N1CCC2CCC(C1)N2c1ccn2ncnc(Nc3ccc(Oc4ccn5ncnc5c4)c(C)c3)c12] | 536.6 | 1-(9-(4-((4-([1,2,4]triazolo[1,5-a]pyridin-7-yloxy)-3-methylphenyl)amino)pyrrolo[2,1-f][1,2,4]triazin-5-yl)-3,9-diazabicyclo[4.2.1]nonan-3-yl)prop-2-en-1-one |
| 56 | 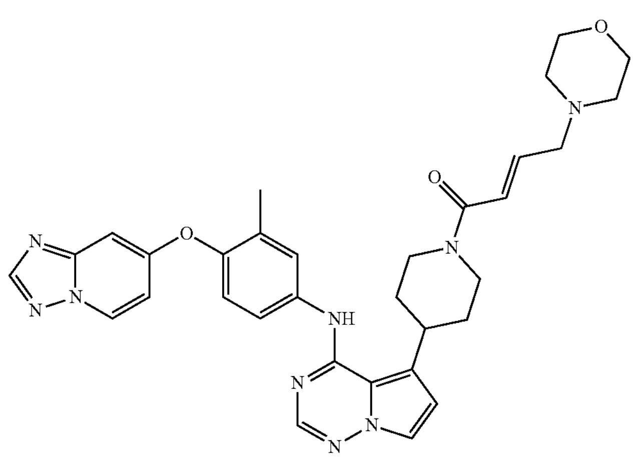 [SMILES: Cc1cc(Nc2ncnn3ccc(C4CCN(C(=O)/C=C/CN5CCOCC5)CC4)c23)ccc1Oc1ccn2ncnc2c1] | 594.7 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-morpholinobut-2-en-1-one |

TABLE 1-continued

| E # | Structure | Mass Spec. M + H/1 | Name |
|---|---|---|---|
| 57 | 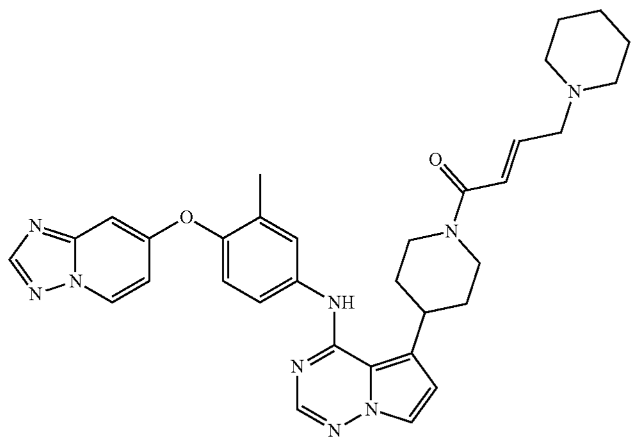 [SMILES: Cc1cc(Nc2ncnn3ccc(C4CCN(C(=O)/C=C/CN5CCCCC5)CC4)c23)ccc1Oc1ccn2ncnc2c1] | 592.8 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(piperidin-1-yl)but-2-en-1-one |
| 58 | 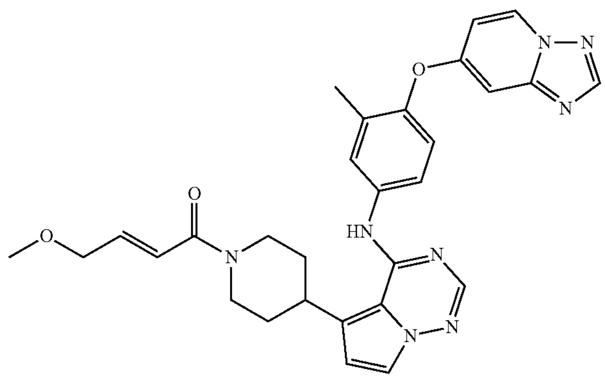 [SMILES: COC/C=C/C(=O)N1CCC(c2ccn3ncnc(Nc4ccc(Oc5ccn6ncnc6c5)c(C)c4)c23)CC1] | 539.6 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-methoxybut-2-en-1-one |
| 59 | 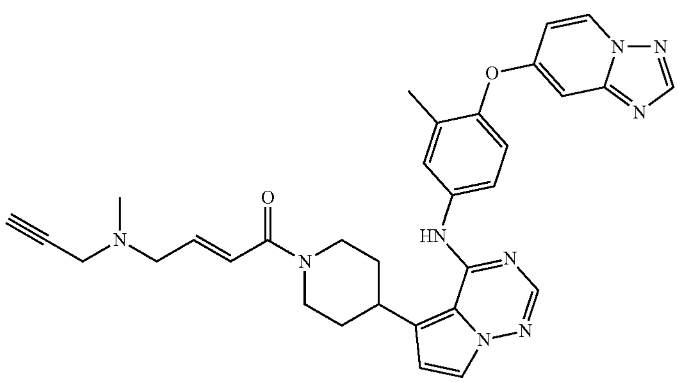 [SMILES: C#CCN(C)C/C=C/C(=O)N1CCC(c2ccn3ncnc(Nc4ccc(Oc5ccn6ncnc6c5)c(C)c4)c23)CC1] | 576.6 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(methyl(prop-2-yn-1-yl)amino)but-2-en-1-one |
| 60 | 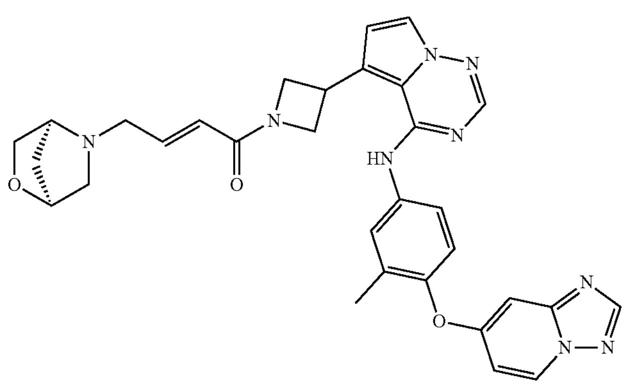 [SMILES: Cc1cc(Nc2ncnn3ccc(C4CN(C(=O)/C=C/CN5C[C@@H]6C[C@H]5CO6)C4)c23)ccc1Oc1ccn2ncnc2c1] | 578.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-((1S,4S)-2-oxa-5-azabicyclo[2.2.1]heptan-5-yl)but-2-en-1-one |

TABLE 1-continued

| E # | Structure | Mass Spec. M + H/1 | Name |
|---|---|---|---|
| 61 | 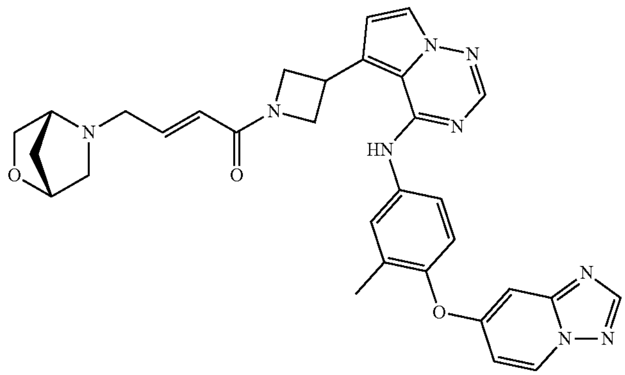 [SMILES: Cc1cc(Nc2ncnn3ccc(C4CN(C(=O)/C=C/CN5C[C@H]6C[C@@H]5CO6)C4)c23)ccc1Oc1ccn2ncnc2c1] | 578.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-((1R,4R)-2-oxa-5-azabicyclo[2.2.1]heptan-5-yl)but-2-en-1-one |
| 62 | 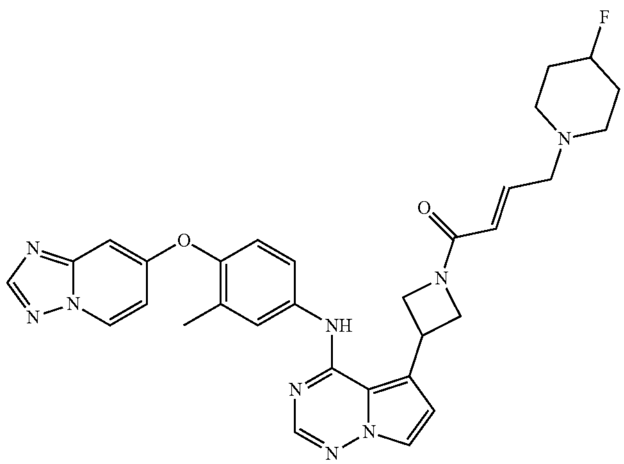 [SMILES: Cc1cc(Nc2ncnn3ccc(C4CN(C(=O)/C=C/CN5CCC(F)CC5)C4)c23)ccc1Oc1ccn2ncnc2c1] | 582.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(4-fluoropiperidin-1-yl)but-2-en-1-one |
| 63 | 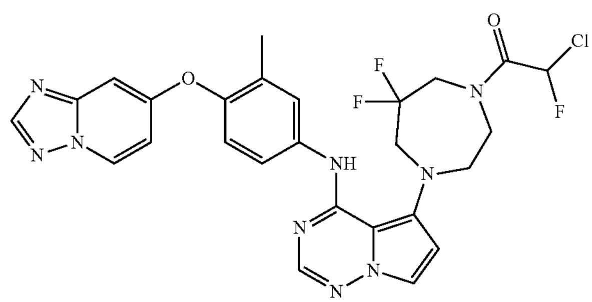 [SMILES: Cc1cc(Nc2ncnn3ccc(N4CCN(C(=O)C(F)Cl)CC(F)(F)C4)c23)ccc1Oc1ccn2ncnc2c1] | 586.2 | 1-(4-(4-((4-([1,2,4]triazolo[1,5-a]pyridin-7-yloxy)-3-methylphenyl)amino)pyrrolo[2,1-f][1,2,4]triazin-5-yl)-6,6-difluoro-1,4-diazepan-1-yl)-2-chloro-2-fluoroethan-1-one |
| 64 | 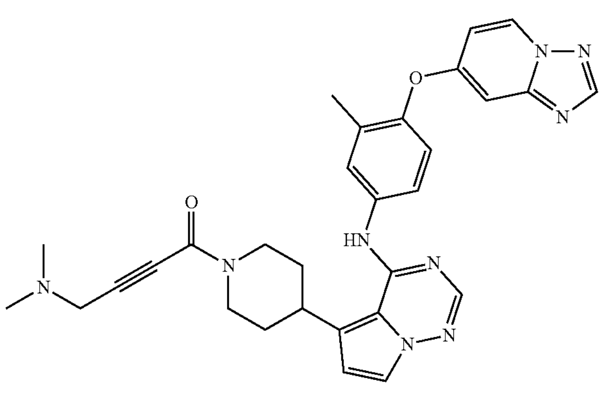 [SMILES: Cc1cc(Nc2ncnn3ccc(C4CCN(C(=O)C#CCN(C)C)CC4)c23)ccc1Oc1ccn2ncnc2c1] | 550.3 | 1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(dimethylamino)but-2-yn-1-one |

TABLE 1-continued

| E # | Structure | Mass Spec. M + H/1 | Name |
|---|---|---|---|
| 65 | 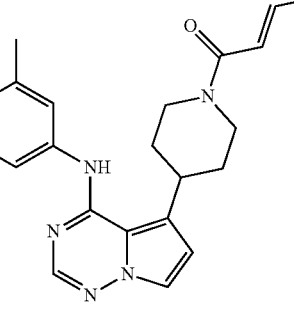 | 578.4 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-3-(1-methylpyrrolidin-2-yl)prop-2-en-1-one |
| 66 | 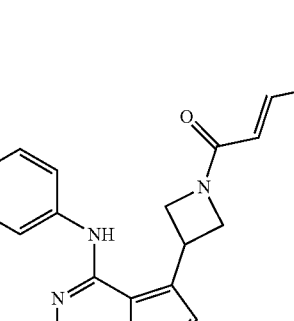 | 550.4 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(1-methylpyrrolidin-2-yl)prop-2-en-1-one |
| 67 | 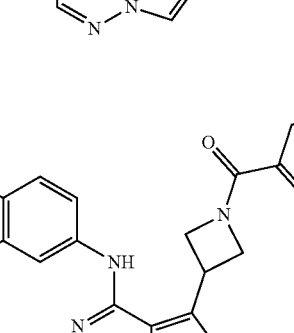 | 537.3 | 2-((dimethylamino)methyl)-1-(3-(4-((3-methyl-4-((1-methyl-1H-benzo[d]imidazol-5-yl)oxy)phenyl)amino)pyrrolo[2,1-f][1,2,4]triazin-5-yl)azetidin-1-yl)prop-2-en-1-one |
| 68 | 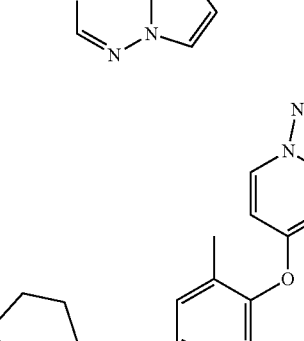 | 581.3 | (E)-N-(1-(4-((4-([1,2,4]triazolo[1,5-a]pyridin-7-yloxy)-3-methylphenyl)amino)pyrrolo[2,1-f][1,2,4]triazin-5-yl)piperidin-3-yl)-4-(dimethylamino)-N-methylbut-2-enamide |

TABLE 1-continued

| E # | Structure | Mass Spec. M + H/1 | Name |
|---|---|---|---|
| 69 | 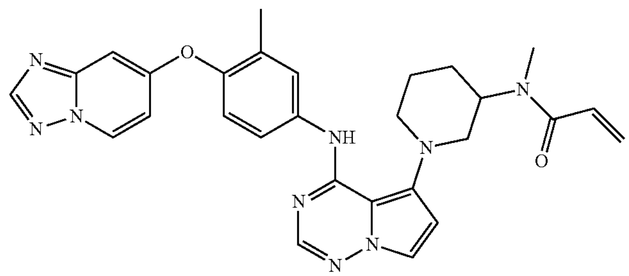 [SMILES: C=CC(=O)N(C)C1CCCN(c2ccn3ncnc(Nc4ccc(Oc5ccn6ncnc6c5)c(C)c4)c23)C1] | 524.3 | N-(1-(4-((4-([1,2,4]triazolo[1,5-a]pyridin-7-yloxy)-3-methylphenyl)amino)pyrrolo[2,1-f][1,2,4]triazin-5-yl)piperidin-3-yl)-N-methylacrylamide |
| 70 | 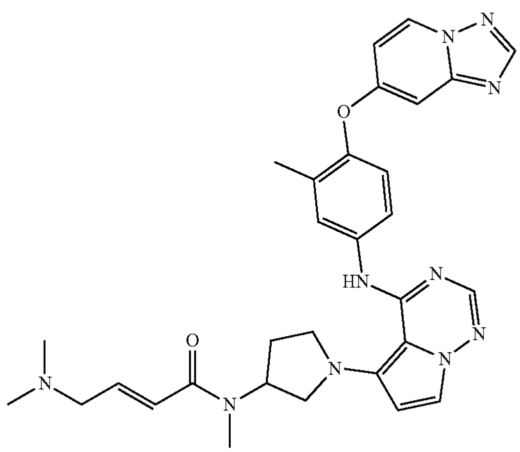 [SMILES: Cc1cc(Nc2ncnn3ccc(N4CCC(N(C)C(=O)/C=C/CN(C)C)C4)c23)ccc1Oc1ccn2ncnc2c1] | 567.3 | (E)-N-(1-(4-((4-([1,2,4]triazolo[1,5-a]pyridin-7-yloxy)-3-methylphenyl)amino)pyrrolo[2,1-f][1,2,4]triazin-5-yl)pyrrolidin-3-yl)-4-(dimethylamino)-N-methylbut-2-enamide |
| 71 | 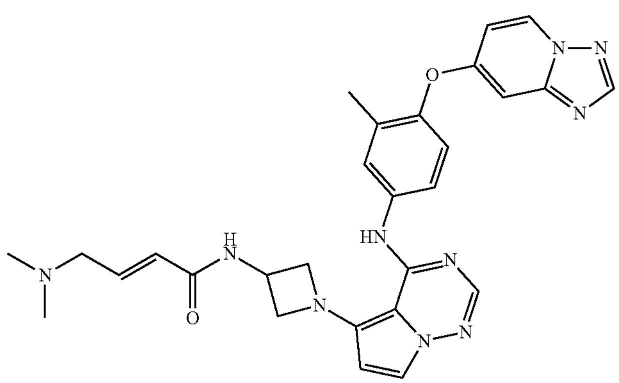 [SMILES: Cc1cc(Nc2ncnn3ccc(N4CC(NC(=O)/C=C/CN(C)C)C4)c23)ccc1Oc1ccn2ncnc2c1] | 539.3 | (E)-N-(1-(4-((4-([1,2,4]triazolo[1,5-a]pyridin-7-yloxy)-3-methylphenyl)amino)pyrrolo[2,1-f][1,2,4]triazin-5-yl)azetidin-3-yl)-4-(dimethylamino)but-2-enamide |
| 72 | 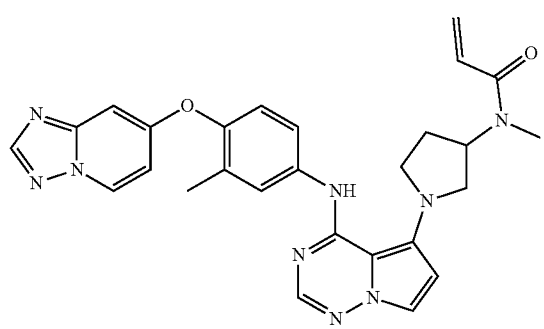 [SMILES: C=CC(=O)N(C)C1CCN(c2ccn3ncnc(Nc4ccc(Oc5ccn6ncnc6c5)c(C)c4)c23)C1] | 510.3 | N-(1-(4-((4-([1,2,4]triazolo[1,5-a]pyridin-7-yloxy)-3-methylphenyl)amino)pyrrolo[2,1-f][1,2,4]triazin-5-yl)pyrrolidin-3-yl)-N-methylacrylamide |

TABLE 1-continued

| E # | Structure | Mass Spec. M + H/1 | Name |
|---|---|---|---|
| 73 | 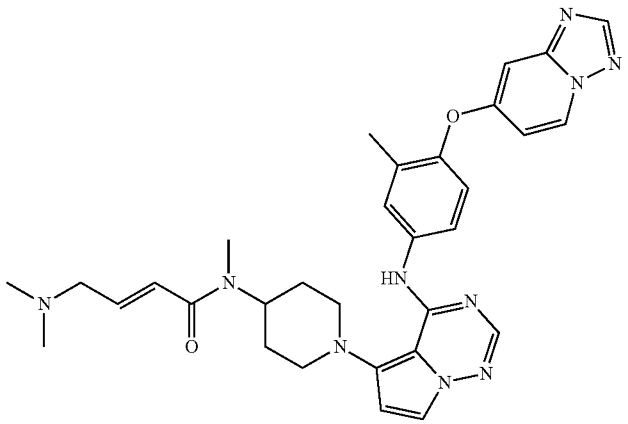 [SMILES: Cc1cc(Nc2ncnn3ccc(N4CCC(N(C)C(=O)/C=C/CN(C)C)CC4)c23)ccc1Oc1ccn2ncnc2c1] | 581.4 | (E)-N-(1-(4-((4-([1,2,4]triazolo[1,5-a]pyridin-7-yloxy)-3-methylphenyl)amino)pyrrolo[2,1-f][1,2,4]triazin-5-yl)piperidin-4-yl)-4-(dimethylamino)-N-methylbut-2-enamide |
| 74 | 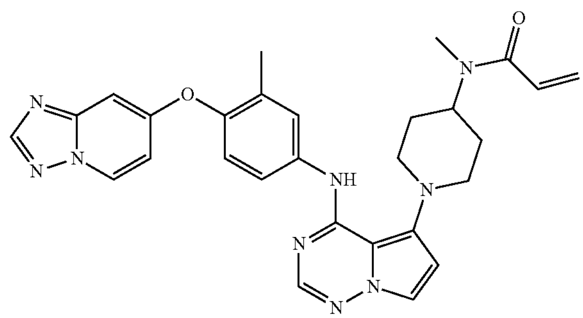 [SMILES: C=CC(=O)N(C)C1CCN(c2ccn3ncnc(Nc4ccc(Oc5ccn6ncnc6c5)c(C)c4)c23)CC1] | 524.3 | N-(1-(4-((4-([1,2,4]triazolo[1,5-a]pyridin-7-yloxy)-3-methylphenyl)amino)pyrrolo[2,1-f][1,2,4]triazin-5-yl)piperidin-4-yl)-N-methylacrylamide |
| 75 | 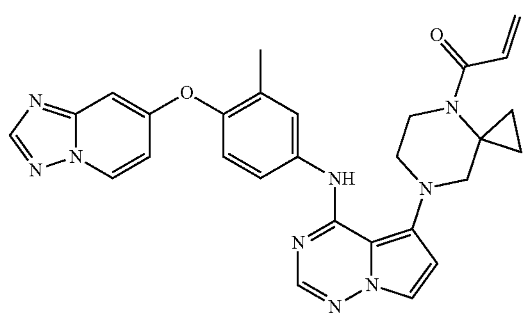 [SMILES: C=CC(=O)N1CCN(c2ccn3ncnc(Nc4ccc(Oc5ccn6ncnc6c5)c(C)c4)c23)CC12CC2] | 522.3 | 1-(7-(4-((4-([1,2,4]triazolo[1,5-a]pyridin-7-yloxy)-3-methylphenyl)amino)pyrrolo[2,1-f][1,2,4]triazin-5-yl)-4,7-diazaspiro[2.5]octan-4-yl)prop-2-en-1-one |
| 76 | 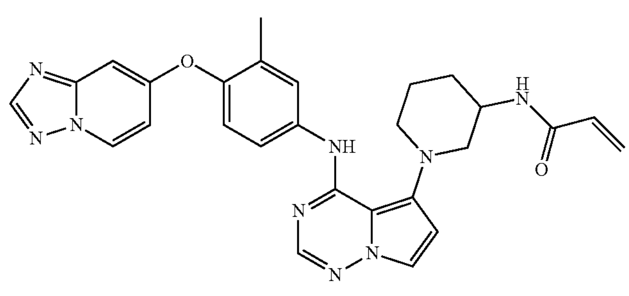 [SMILES: C=CC(=O)NC1CCCN(c2ccn3ncnc(Nc4ccc(Oc5ccn6ncnc6c5)c(C)c4)c23)C1] | 510.3 | N-(1-(4-((4-([1,2,4]triazolo[1,5-a]pyridin-7-yloxy)-3-methylphenyl)amino)pyrrolo[2,1-f][1,2,4]triazin-5-yl)piperidin-3-yl)acrylamide |
| 77 | 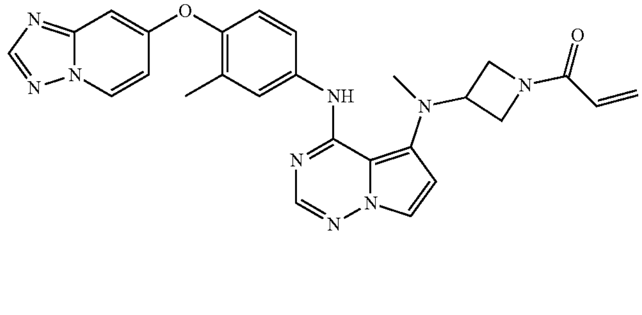 [SMILES: C=CC(=O)N1CC(N(C)c2ccn3ncnc(Nc4ccc(Oc5ccn6ncnc6c5)c(C)c4)c23)C1] | 496.2 | 1-(3-((4-((4-([1,2,4]triazolo[1,5-a]pyridin-7-yloxy)-3-methylphenyl)amino)pyrrolo[2,1-f][1,2,4]triazin-5-yl)(methyl)amino)azetidin-1-yl)prop-2-en-1-one |

TABLE 1-continued

| E # | Structure | Mass Spec. M + H/1 | Name |
|---|---|---|---|
| 78 | 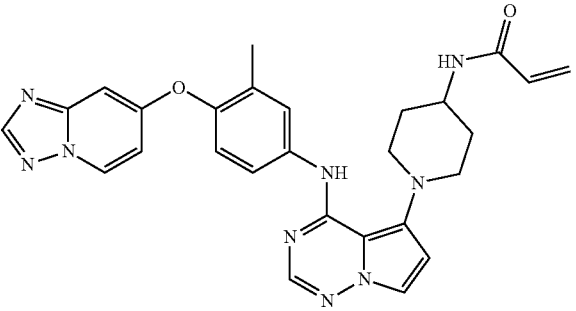 [SMILES: C=CC(=O)NC1CCN(c2ccn3ncnc(Nc4ccc(Oc5ccn6ncnc6c5)c(C)c4)c23)CC1] | 510.3 | N-(1-(4-((4-([1,2,4]triazolo[1,5-a]pyridin-7-yloxy)-3-methylphenyl)amino)pyrrolo[2,1-f][1,2,4]triazin-5-yl)piperidin-4-yl)acrylamide |
| 79 | 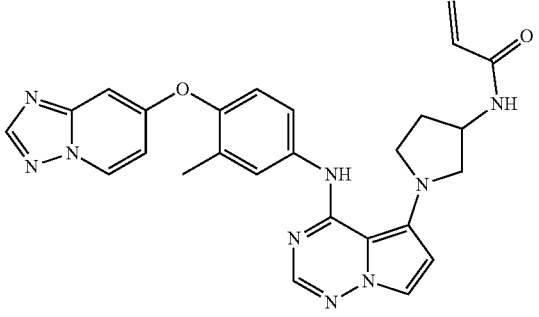 [SMILES: C=CC(=O)NC1CCN(c2ccn3ncnc(Nc4ccc(Oc5ccn6ncnc6c5)c(C)c4)c23)C1] | 496.2 | N-(1-(4-((4-([1,2,4]triazolo[1,5-a]pyridin-7-yloxy)-3-methylphenyl)amino)pyrrolo[2,1-f][1,2,4]triazin-5-yl)pyrrolidin-3-yl)acrylamide |
| 80 | 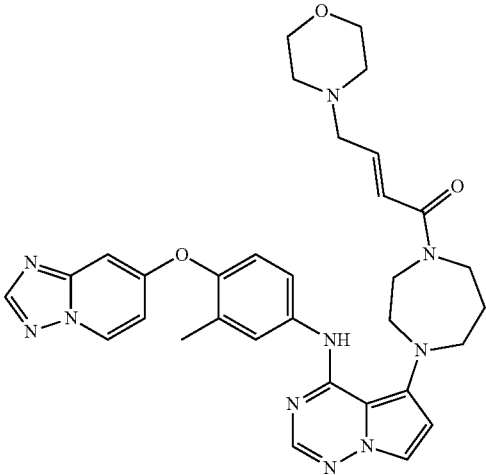 [SMILES: Cc1cc(Nc2ncnn3ccc(N4CCCN(C(=O)/C=C/CN5CCOCC5)CC4)c23)ccc1Oc1ccn2ncnc2c1] | 609.4 | (E)-1-(4-(4-((4-([1,2,4]triazolo[1,5-a]pyridin-7-yloxy)-3-methylphenyl)amino)pyrrolo[2,1-f][1,2,4]triazin-5-yl)-1,4-diazepan-1-yl)-4-morpholinobut-2-en-1-one |
| 81 | 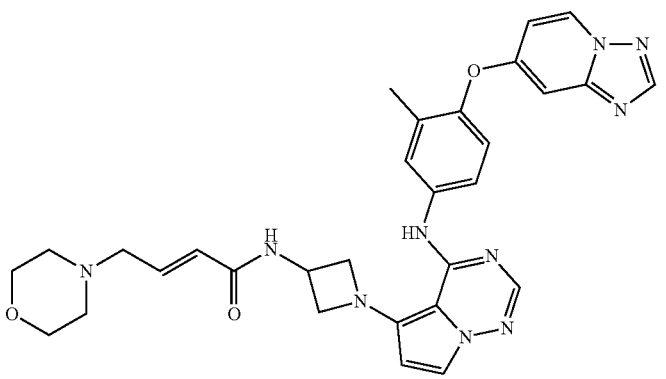 [SMILES: Cc1cc(Nc2ncnn3ccc(N4CC(NC(=O)/C=C/CN5CCOCC5)C4)c23)ccc1Oc1ccn2ncnc2c1] | 581.3 | (E)-N-(1-(4-((4-([1,2,4]triazolo[1,5-a]pyridin-7-yloxy)-3-methylphenyl)amino)pyrrolo[2,1-f][1,2,4]triazin-5-yl)azetidin-3-yl)-4-morpholinobut-2-enamide |

TABLE 1-continued

| E # | Structure | Mass Spec. M + H/1 | Name |
|---|---|---|---|
| 82 | 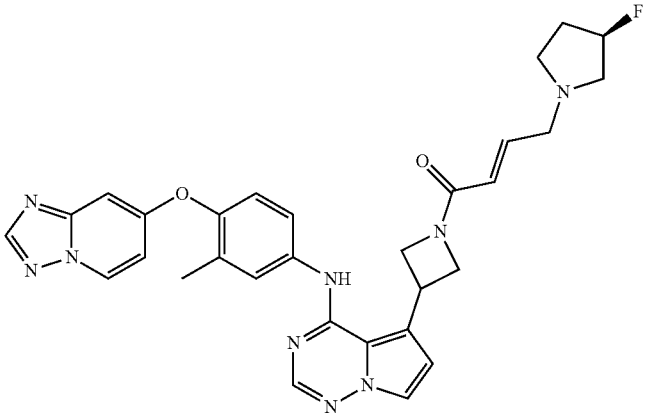 [SMILES: Cc1cc(Nc2ncnn3ccc(C4CN(C(=O)/C=C/CN5CC[C@@H](F)C5)C4)c23)ccc1Oc1ccn2ncnc2c1] | 568.3 | (R,E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(3-fluoropyrrolidin-1-yl)but-2-en-1-one |
| 83 | 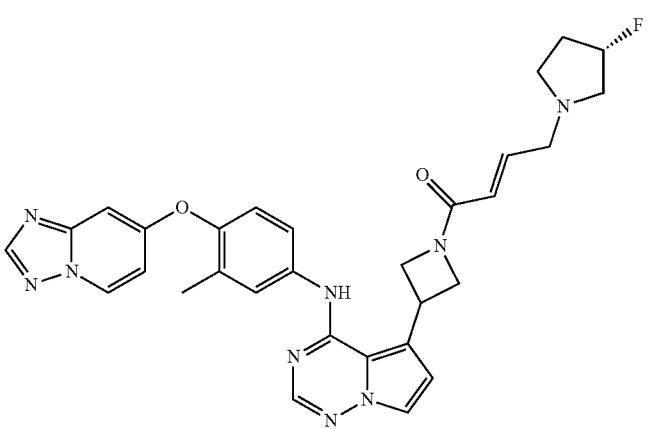 [SMILES: Cc1cc(Nc2ncnn3ccc(C4CN(C(=O)/C=C/CN5CC[C@H](F)C5)C4)c23)ccc1Oc1ccn2ncnc2c1] | 568.3 | (S,E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(3-fluoropyrrolidin-1-yl)but-2-en-1-one |
| 84 | 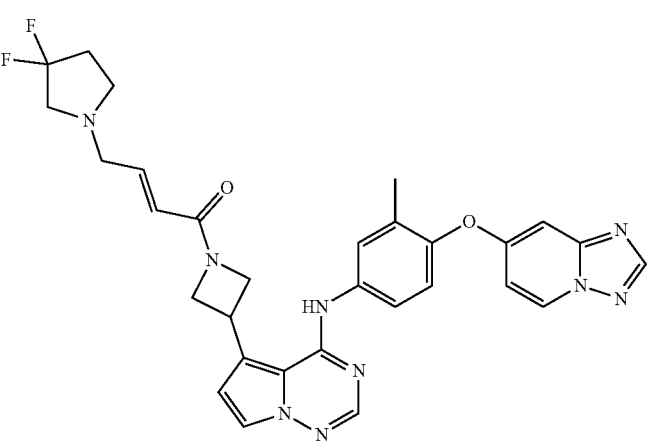 [SMILES: Cc1cc(Nc2ncnn3ccc(C4CN(C(=O)/C=C/CN5CCC(F)(F)C5)C4)c23)ccc1Oc1ccn2ncnc2c1] | 586.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(3,3-difluoropyrrolidin-1-yl)but-2-en-1-one |

TABLE 1-continued

| E # | Structure | Mass Spec. M + H/1 | Name |
|---|---|---|---|
| 85 | 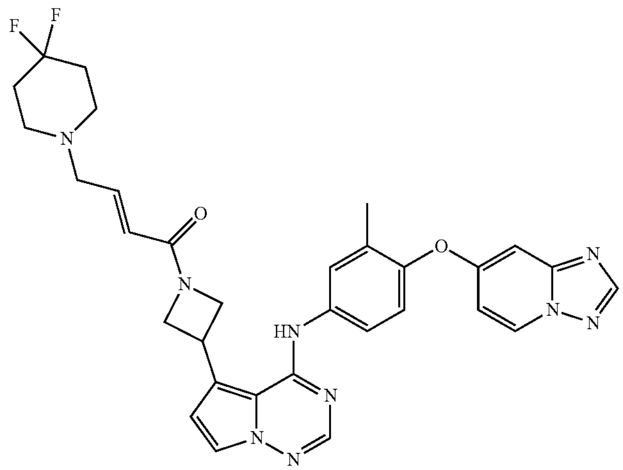 [SMILES: Cc1cc(Nc2ncnn3ccc(C4CN(C(=O)/C=C/CN5CCC(F)(F)CC5)C4)c23)ccc1Oc1ccn2ncnc2c1] | 600.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(4,4-difluoropiperidin-1-yl)but-2-en-1-one |
| 86 | 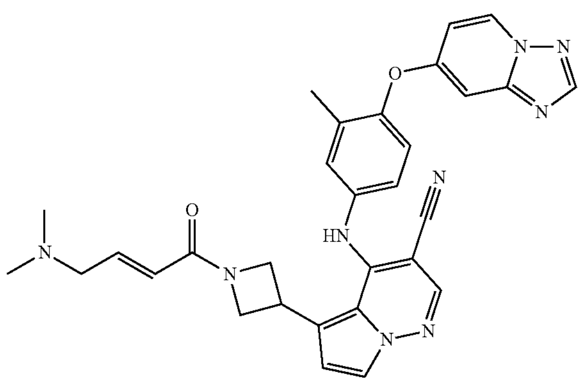 [SMILES: Cc1cc(Nc2c(C#N)cnn3ccc(C4CN(C(=O)/C=C/CN(C)C)C4)c23)ccc1Oc1ccn2ncnc2c1] | 548.1 | (E)-4-((4-([1,2,4]triazolo[1,5-a]pyridin-7-yloxy)-3-methylphenyl)amino)-5-(1-(4-(dimethylamino)but-2-enoyl)azetidin-3-yl)pyrrolo[1,2-b]pyridazine-3-carbonitrile |
| 87 | 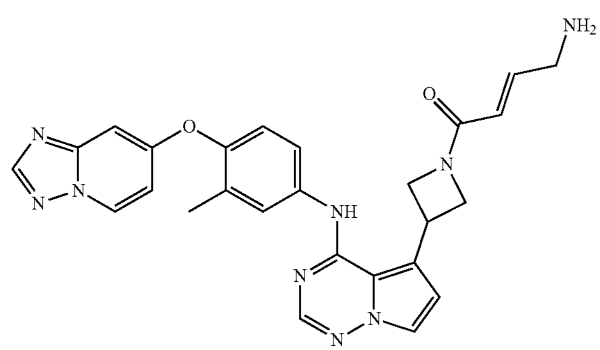 [SMILES: Cc1cc(Nc2ncnn3ccc(C4CN(C(=O)/C=C/CN)C4)c23)ccc1Oc1ccn2ncnc2c1] | 496.2 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-aminobut-2-en-1-one |

TABLE 1-continued

| E # | Structure | Mass Spec. M + H/1 | Name |
|---|---|---|---|
| 88 | 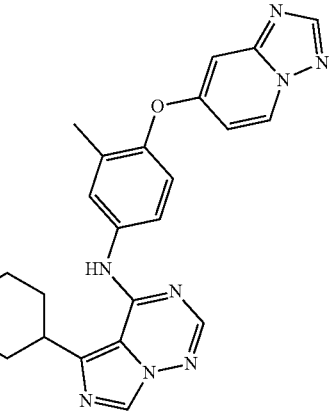 | 553.3 | (E)-1-(4-(4-((4-([1,2,4]triazolo[1,5-a]pyridin-7-yloxy)-3-methylphenyl)amino)imidazo[5,1-f][1,2,4]triazin-5-yl)piperidin-1-yl)-4-(dimethylamino)but-2-en-1-one |
| 89 | 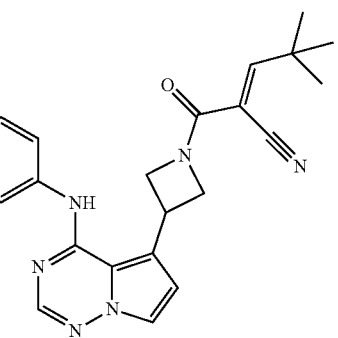 | 548.3 | (E)-2-(3-(4-((4-([1,2,4]triazolo[1,5-a]pyridin-7-yloxy)-3-methylphenyl)amino)pyrrolo[2,1-f][1,2,4]triazin-5-yl)azetidine-1-carbonyl)-4,4-dimethylpent-2-enenitrile |
| 90 | 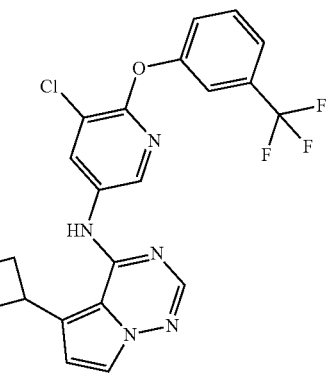 | 572.3 | (E)-1-(3-(4-((5-chloro-6-(3-(trifluoromethyl)phenoxy)pyridin-3-yl)amino)pyrrolo[2,1-f][1,2,4]triazin-5-yl)azetidin-1-yl)-4-(dimethylamino)but-2-en-1-one |
| 91 | 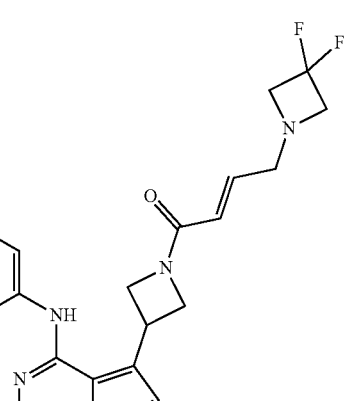 | 572.2 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(3,3-difluoroazetidin-1-yl)but-2-en-1-one |

TABLE 1-continued

| E # | Structure | Mass Spec. M + H/1 | Name |
|---|---|---|---|
| 92 | 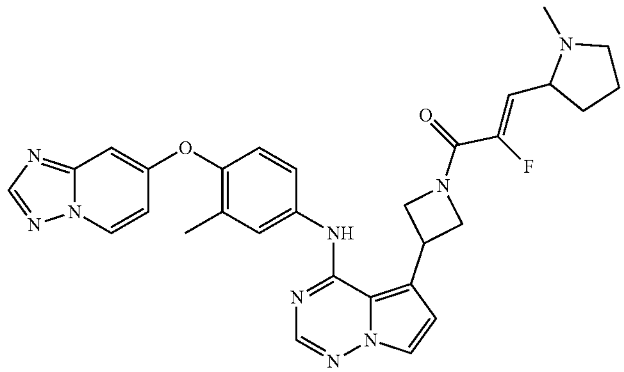 [SMILES: Cc1cc(Nc2ncnn3ccc(C4CN(C(=O)/C(F)=C/C5CCCN5C)C4)c23)ccc1Oc1ccn2ncnc2c1] | 568.4 | (Z)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-2-fluoro-3-(1-methylpyrrolidin-2-yl)prop-2-en-1-one |
| 93 | 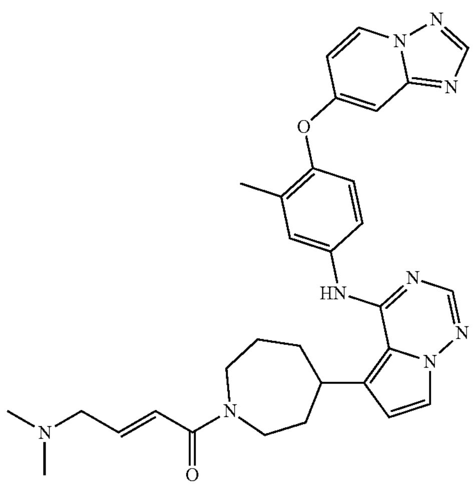 [SMILES: Cc1cc(Nc2ncnn3ccc(C4CCCN(C(=O)/C=C/CN(C)C)CC4)c23)ccc1Oc1ccn2ncnc2c1] | 566.4 | (E)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-4-(dimethylamino)but-2-en-1-one |
| 94 | 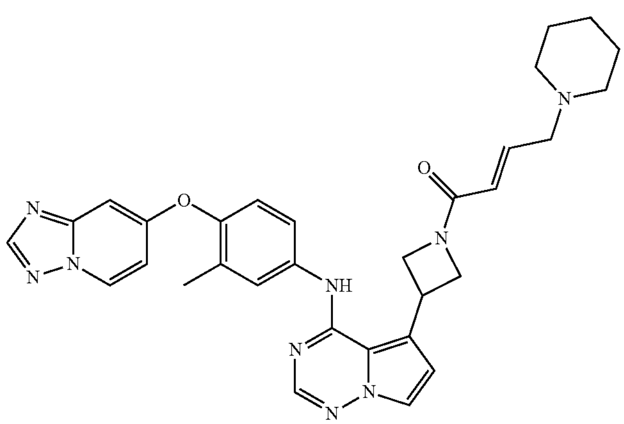 [SMILES: Cc1cc(Nc2ncnn3ccc(C4CN(C(=O)/C=C/CN5CCCCC5)C4)c23)ccc1Oc1ccn2ncnc2c1] | 564.6 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(piperidin-1-yl)but-2-en-1-one |

TABLE 1-continued

| E # | Structure | Mass Spec. M + H/1 | Name |
|---|---|---|---|
| 95 | 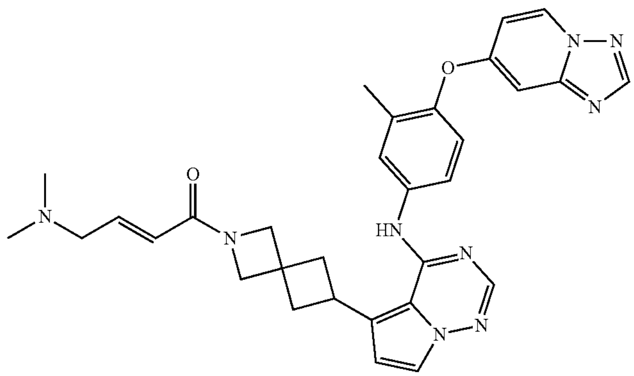 [SMILES: Cc1cc(Nc2ncnn3ccc(C4CC5(C4)CN(C(=O)/C=C/CN(C)C)C5)c23)ccc1Oc1ccn2ncnc2c1] | 564.4 | (E)-1-(6-(4-((4-([1,2,4]triazolo[1,5-a]pyridin-7-yloxy)-3-methylphenyl)amino)pyrrolo[2,1-f][1,2,4]triazin-5-yl)-2-azaspiro[3.3]heptan-2-yl)-4-(dimethylamino)but-2-en-1-one |
| 96 | 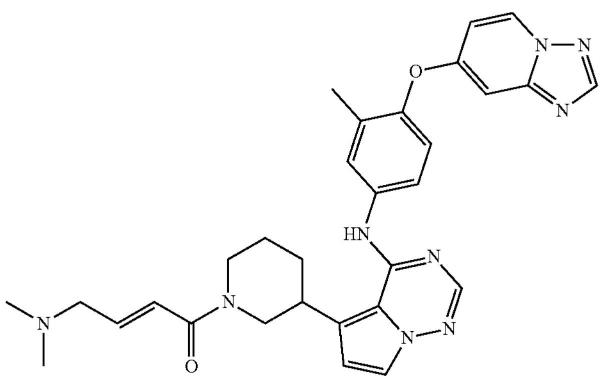 | 552.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(dimethylamino)but-2-en-1-one |
| 97 | 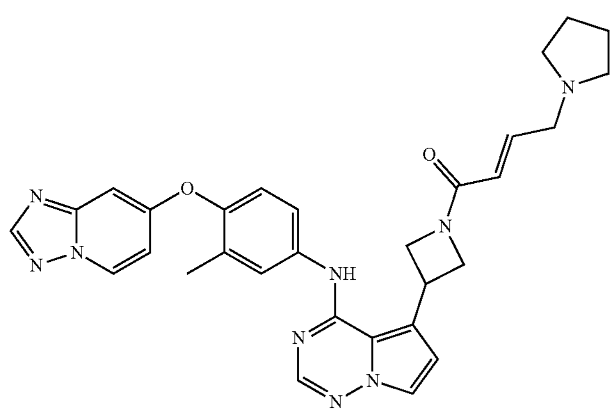 [SMILES: Cc1cc(Nc2ncnn3ccc(C4CN(C(=O)/C=C/CN5CCCC5)C4)c23)ccc1Oc1ccn2ncnc2c1] | 550.2 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(pyrrolidin-1-yl)but-2-en-1-one |

TABLE 1-continued

| E # | Structure | Mass Spec. M + H/1 | Name |
|---|---|---|---|
| 98 | 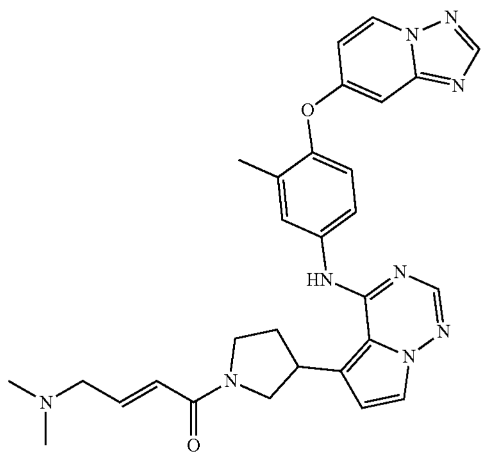 [SMILES: Cc1cc(Nc2ncnn3ccc(C4CCN(C(=O)/C=C/CN(C)C)C4)c23)ccc1Oc1ccn2ncnc2c1] | 538.2 | (E)-1-(3-(4-((4-([1,2,4]triazolo[1,5-a]pyridin-7-yloxy)-3-methylphenyl)amino)pyrrolo[2,1-f][1,2,4]triazin-5-yl)pyrrolidin-1-yl)-4-(dimethylamino)but-2-en-1-one |
| 99 | 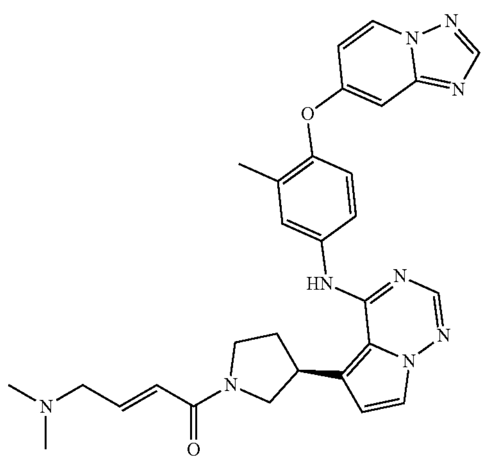 [SMILES: Cc1cc(Nc2ncnn3ccc([C@@H]4CCN(C(=O)/C=C/CN(C)C)C4)c23)ccc1Oc1ccn2ncnc2c1] | 538.2 | (S,E)-1-(3-(4-((4-([1,2,4]triazolo[1,5-a]pyridin-7-yloxy)-3-methylphenyl)amino)pyrrolo[2,1-f][1,2,4]triazin-5-yl)pyrrolidin-1-yl)-4-(dimethylamino)but-2-en-1-one |
| 100 | 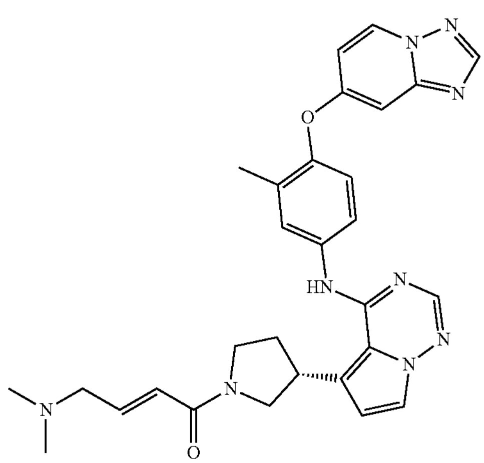 [SMILES: Cc1cc(Nc2ncnn3ccc([C@H]4CCN(C(=O)/C=C/CN(C)C)C4)c23)ccc1Oc1ccn2ncnc2c1] | 538.2 | (R,E)-1-(3-(4-((4-([1,2,4]triazolo[1,5-a]pyridin-7-yloxy)-3-methylphenyl)amino)pyrrolo[2,1-f][1,2,4]triazin-5-yl)pyrrolidin-1-yl)-4-(dimethylamino)but-2-en-1-one |

TABLE 1-continued

| E # | Structure | Mass Spec. M + H/1 | Name |
|---|---|---|---|
| 101 | 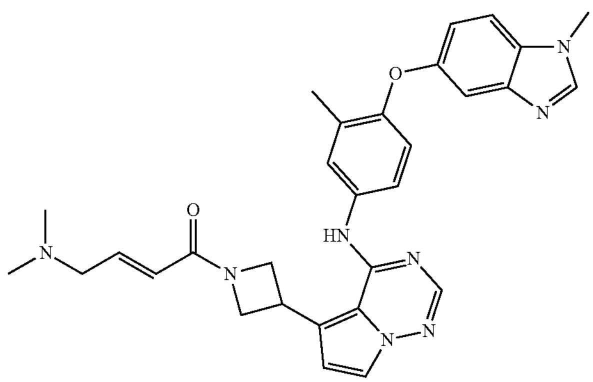 | 537.4 | (E)-4-(dimethylamino)-1-(3-(4-((3-methyl-4-((1-methyl-1H-benzo[d]imidazol-5-yl)oxy)phenyl)amino)pyrrolo[2,1-f][1,2,4]triazin-5-yl)azetidin-1-yl)but-2-en-1-one |
| 102 | 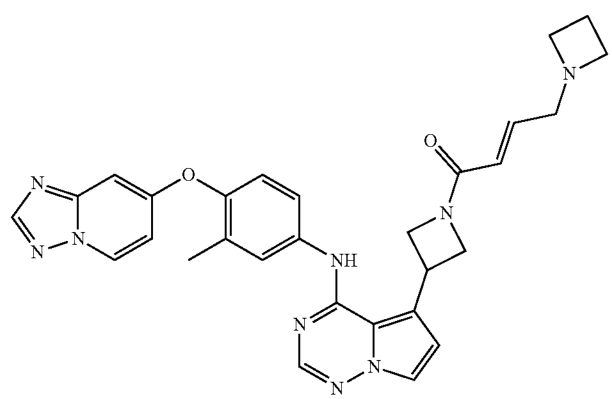 [SMILES: Cc1cc(Nc2ncnn3ccc(C4CN(C(=O)/C=C/CN5CCC5)C4)c23)ccc1Oc1ccn2ncnc2c1] | 536.1 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(azetidin-1-yl)but-2-en-1-one |
| 103 | 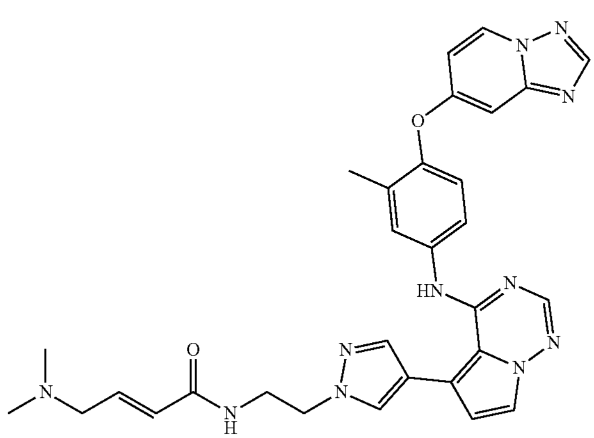 [SMILES: Cc1cc(Nc2ncnn3ccc(-c4cnn(CCNC(=O)/C=C/CN(C)C)c4)c23)ccc1Oc1ccn2ncnc2c1] | 578.2 | (E)-N-(2-(4-(4-((4-([1,2,4]triazolo[1,5-a]pyridin-7-yloxy)-3-methylphenyl)amino)pyrrolo[2,1-f][1,2,4]triazin-5-yl)-1H-pyrazol-1-yl)ethyl)-4-(dimethylamino)but-2-enamide |

TABLE 1-continued

| E # | Structure | Mass Spec. M + H/1 | Name |
|---|---|---|---|
| 104 | 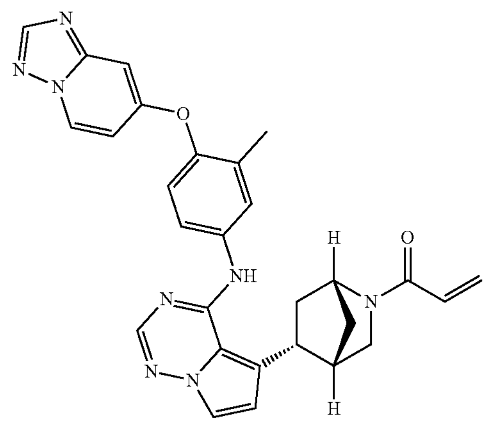 [SMILES: C=CC(=O)N1C[C@H]2C[C@@H]1C[C@H]2c1ccn2ncnc(Nc3ccc(Oc4ccn5ncnc5c4)c(C)c3)c12] | 507.3 | Rel-1-[(1S,4S,5R)-5-{4-[(3-methyl-4-{[1,2,4-triazolo[1,5-a]pyridin-7-yloxy}phenyl)amino]pyrrolo[2,1-f][1,2,4]triazin-5-yl}-2-azabicyclo[2.2.1]heptan-2-yl]prop-2-en-1-one |
| 105 | 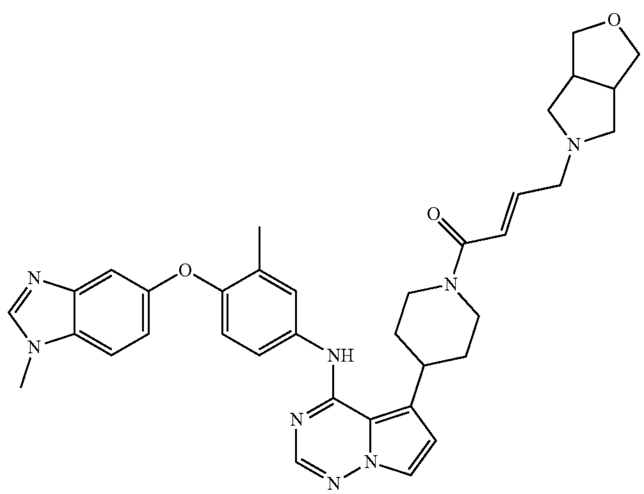 [SMILES: Cc1cc(Nc2ncnn3ccc(C4CCN(C(=O)/C=C/CN5CC6COCC6C5)CC4)c23)ccc1Oc1ccc2c(c1)ncn2C] | 633.5 | (E)-1-(4-(4-((3-methyl-4-((1-methyl-1H-benzo[d]imidazol-5-yl)oxy)phenyl)amino)pyrrolo[2,1-f][1,2,4]triazin-5-yl)piperdin-1-yl)-4-(tetrahydro-1H-furo[3,4-c]pyrrol-5(3H)-yl)but-2-en-1-one |
| 106 | Racemic mixture | 621.5 | (E)-4-(3-methoxypyrrolidin-1-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one |

TABLE 1-continued

| E # | Structure | Mass Spec. M + H/1 | Name |
|---|---|---|---|
| 107 | 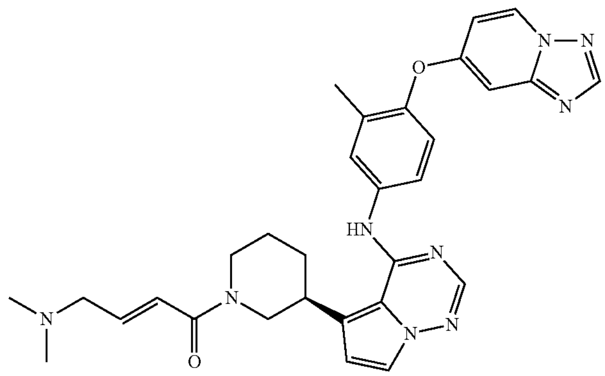 [SMILES: Cc1cc(Nc2ncnn3ccc([C@@H]4CCCN(C(=O)/C=C/CN(C)C)C4)c23)ccc1Oc1ccn2ncnc2c1] | 552.3 | (S,E)-1-(3-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(dimethylamino)but-2-en-1-one |
| 108 | 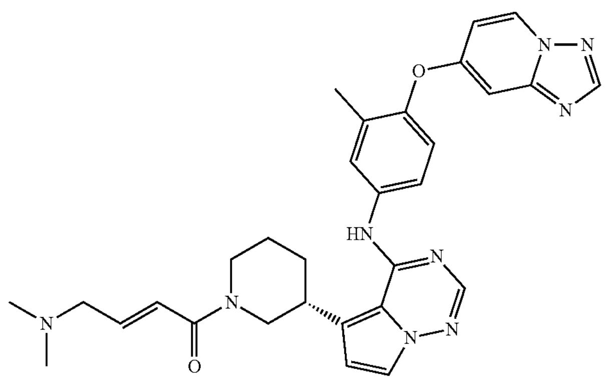 [SMILES: Cc1cc(Nc2ncnn3ccc([C@H]4CCCN(C(=O)/C=C/CN(C)C)C4)c23)ccc1Oc1ccn2ncnc2c1] | 552.3 | (R,E)-1-(3-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(dimethylamino)but-2-en-1-one |
| 109 | 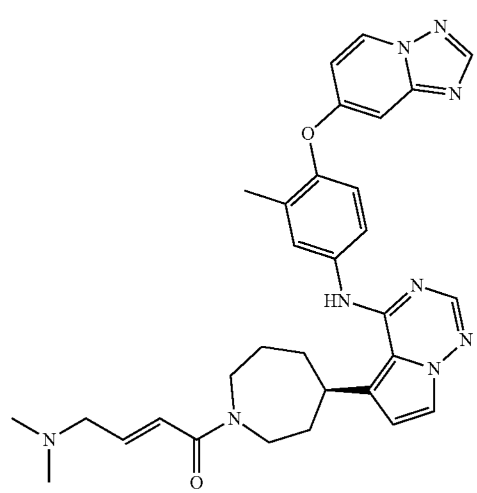 [SMILES: Cc1cc(Nc2ncnn3ccc([C@@H]4CCCN(C(=O)/C=C/CN(C)C)CC4)c23)ccc1Oc1ccn2ncnc2c1] | 566.4 | (R,E)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-4-(dimethylamino)but-2-en-1-one |

TABLE 1-continued

| E # | Structure | Mass Spec. M + H/1 | Name |
|---|---|---|---|
| 110 | 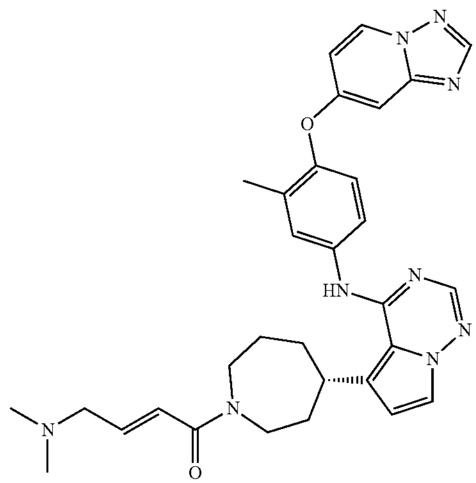 | 566.4 | (S,E)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-4-(dimethylamino)but-2-en-1-one |
| 111 | 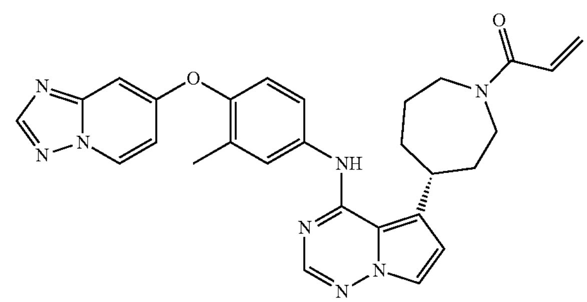 [SMILES: C=CC(=O)N1CCC[C@@H](c2ccn3ncnc(Nc4ccc(Oc5ccn6ncnc6c5)c(C)c4)c23)CC1] | 509.1 | (R)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)prop-2-en-1-one |
| 112 | 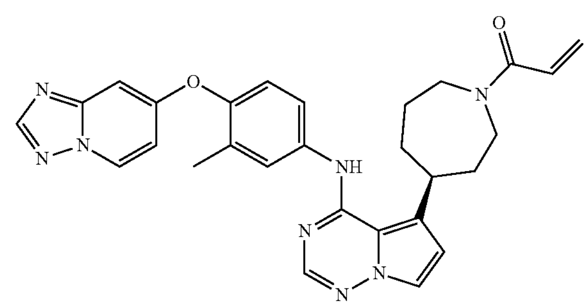 [SMILES: C=CC(=O)N1CCC[C@H](c2ccn3ncnc(Nc4ccc(Oc5ccn6ncnc6c5)c(C)c4)c23)CC1] | 509.1 | (S)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)prop-2-en-1-one |
| 113 | 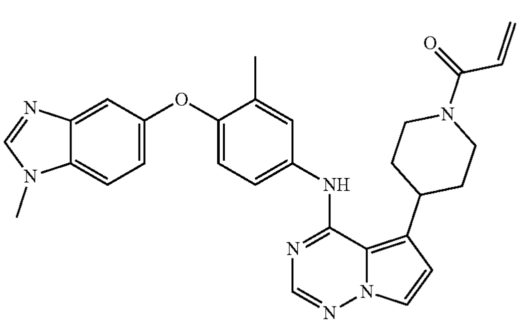 [SMILES: C=CC(=O)N1CCC(c2ccn3ncnc(Nc4ccc(Oc5ccc6c(c5)ncn6C)c(C)c4)c23)CC1] | 508.3 | 1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)prop-2-en-1-one |

TABLE 1-continued

| E # | Structure | Mass Spec. M + H/1 | Name |
|---|---|---|---|
| 114 | 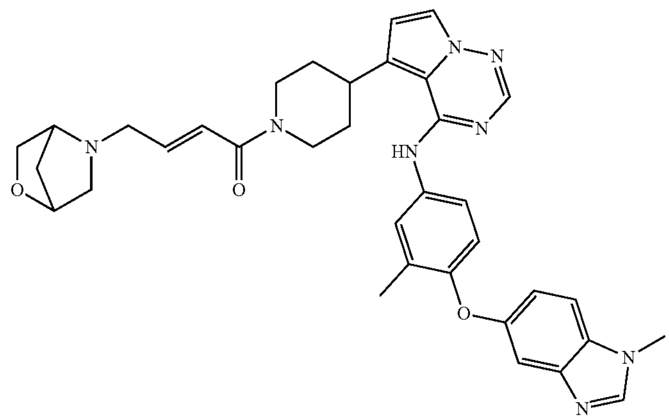 [SMILES: Cc1cc(Nc2ncnn3ccc(C4CCN(C(=O)/C=C/CN5CC6CC5CO6)CC4)c23)ccc1Oc1ccc2c(c1)ncn2C] | 619.3 | (E)-4-(2-oxa-5-azabicyclo[2.2.1]heptan-5-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one |
| 115 | 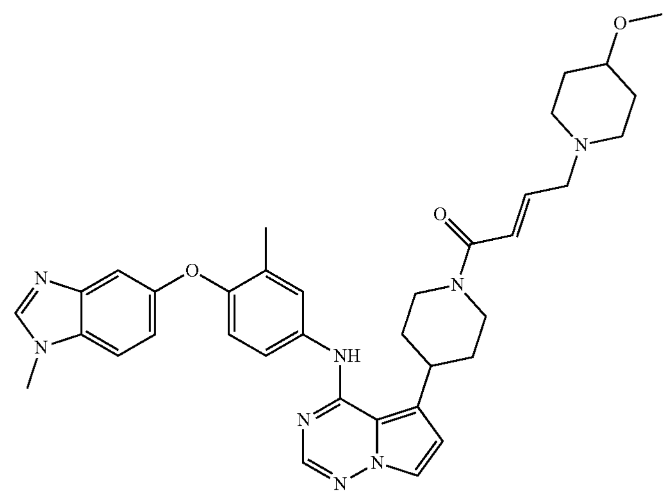 [SMILES: COC1CCN(C/C=C/C(=O)N2CCC(c3ccn4ncnc(Nc5ccc(Oc6ccc7c(c6)ncn7C)c(C)c5)c34)CC2)CC1] | 635.3 | (E)-4-(4-methoxypiperidin-1-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one |
| 117 | 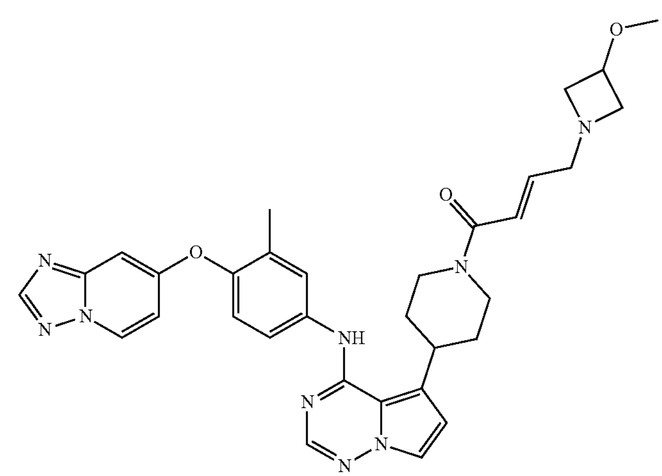 [SMILES: COC1CN(C/C=C/C(=O)N2CCC(c3ccn4ncnc(Nc5ccc(Oc6ccn7ncnc7c6)c(C)c5)c34)CC2)C1] | 594.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(3-methoxyazetidin-1-yl)but-2-en-1-one |

TABLE 1-continued

| E # | Structure | Mass Spec. M + H/1 | Name |
|---|---|---|---|
| 118 | 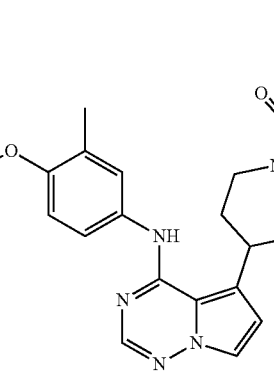 | 608.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(3-methoxypyrrolidin-1-yl)but-2-en-1-one |
| 119 | 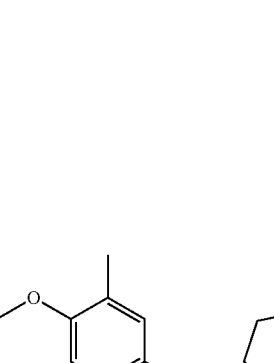 | 620.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(tetrahydro-1H-furo[3,4-c]pyrrol-5(3H)-yl)but-2-en-1-one |
| 120 | 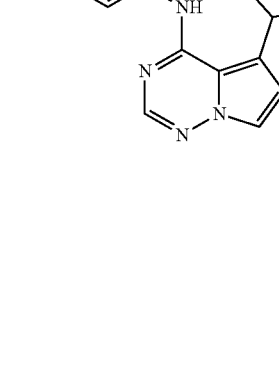 | 620.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(2-oxa-6-azaspiro[3.4]octan-6-yl)but-2-en-1-one |

TABLE 1-continued

| E # | Structure | Mass Spec. M + H/1 | Name |
|---|---|---|---|
| 121 | 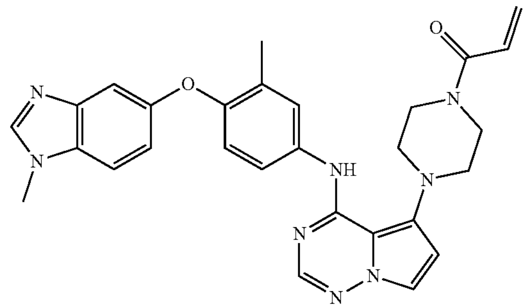 [SMILES: C=CC(=O)N1CCN(c2ccn3ncnc(Nc4ccc(Oc5ccc6c(c5)ncn6C)c(C)c4)c23)CC1] | 509.2 | 1-(4-(4-((3-methyl-4-((1-methyl-1H-benzo[d]imidazol-5-yl)oxy)phenyl)amino)pyrrolo[2,1-f][1,2,4]triazin-5-yl)piperazin-1-yl)prop-2-en-1-one |
| 122 | 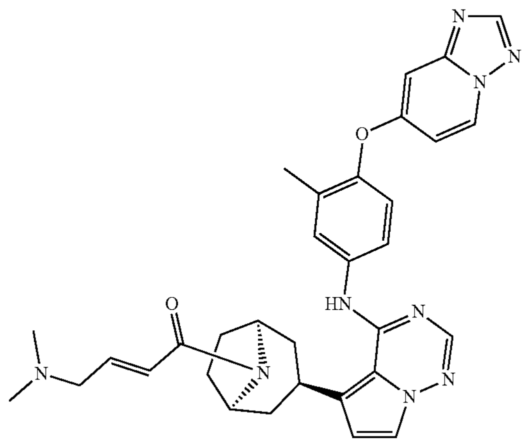 [SMILES: Cc1cc(Nc2ncnn3ccc([C@H]4C[C@H]5CC[C@@H](C4)N5C(=O)/C=C/CN(C)C)c23)ccc1Oc1ccn2ncnc2c1] | 578.3 | (E)-1-((1R,3r,5S)-3-(4-((4-([1,2,4]triazolo[1,5-a]pyridin-7-yloxy)-3-methylphenyl)amino)pyrrolo-[2,1-f][1,2,4]triazin-5-yl)-8-azabicyclo[3.2.1]octan-8-yl)-4-(dimethylamino)but-2-en-1-one |
| 123 | 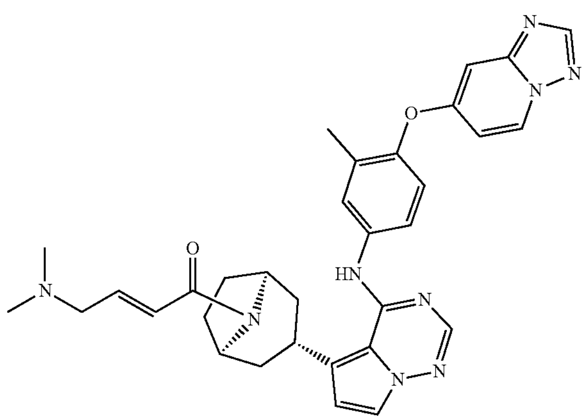 [SMILES: Cc1cc(Nc2ncnn3ccc([C@@H]4C[C@H]5CC[C@@H](C4)N5C(=O)/C=C/CN(C)C)c23)ccc1Oc1ccn2ncnc2c1] | 578.3 | (E)-1-((1R,3s,5S)-3-(4-((4-([1,2,4]triazolo[1,5-a]pyridin-7-yloxy)-3-methylphenyl)amino)pyrrolo-[2,1-f][1,2,4]triazin-5-yl)-8-azabicyclo[3.2.1]octan-8-yl)-4-(dimethylamino)but-2-en-1-one |
| 124 | 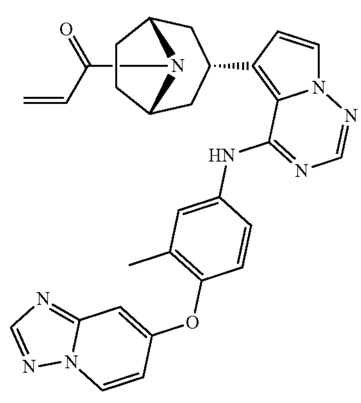 [SMILES: C=CC(=O)N1[C@@H]2CC[C@H]1C[C@@H](c1ccn3ncnc(Nc4ccc(Oc5ccn6ncnc6c5)c(C)c4)c13)C2] | 521.1 | 1-((1R,3r,5S)-3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)prop-2-en-1-one |

TABLE 1-continued

| E # | Structure | Mass Spec. M + H/1 | Name |
|---|---|---|---|
| 125 | 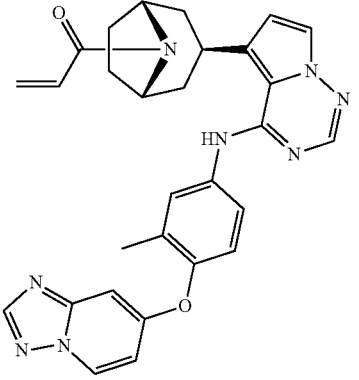 [SMILES: C=CC(=O)N1[C@@H]2CC[C@H]1C[C@H](c1ccn3ncnc(Nc4ccc(Oc5ccn6ncnc6c5)c(C)c4)c13)C2] | 521.2 | 1-((1R,3s,5S)-3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)prop-2-en-1-one |
| 126 | 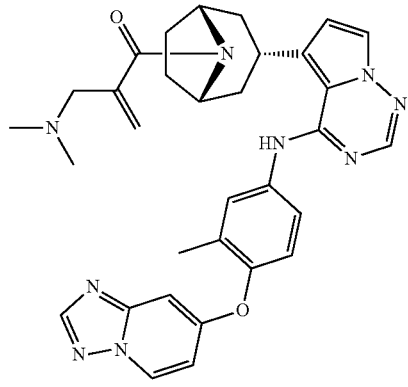 [SMILES: C=C(CN(C)C)C(=O)N1[C@@H]2CC[C@H]1C[C@@H](c1ccn3ncnc(Nc4ccc(Oc5ccn6ncnc6c5)c(C)c4)c13)C2] | 578.3 | 1-((1R,3r,5S)-3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-2-((dimethylamino)methyl)prop-2-en-1-one |
| 127 | 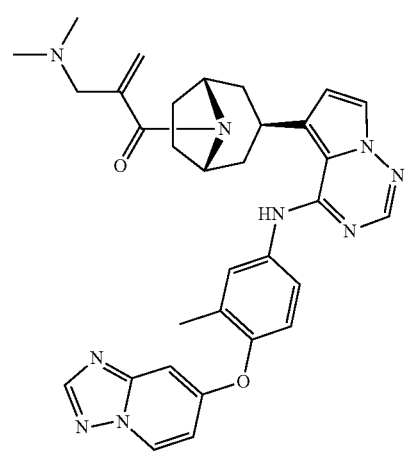 [SMILES: C=C(CN(C)C)C(=O)N1[C@@H]2CC[C@H]1C[C@H](c1ccn3ncnc(Nc4ccc(Oc5ccn6ncnc6c5)c(C)c4)c13)C2] | 578.3 | 1-((1R,3s,5S)-3-(4-((4-([1,2,4]triazolo[1,5-a]pyridin-7-yloxy)-3-methylphenyl)amino)pyrrolo[2,1-f][1,2,4]triazin-5-yl)-8-azabicyclo[3.2.1]octan-8-yl)-2-((dimethylamino)methyl)prop-2-en-1-one |

TABLE 1-continued

| E # | Structure | Mass Spec. M + H/1 | Name |
|---|---|---|---|
| 128 | 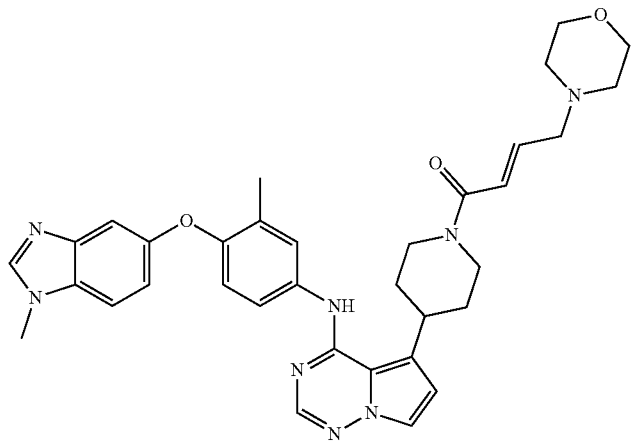 [SMILES: Cc1cc(Nc2ncnn3ccc(C4CCN(C(=O)/C=C/CN5CCOCC5)CC4)c23)ccc1Oc1ccc2c(c1)ncn2C] | 607.3 | (E)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)-4-morpholinobut-2-en-1-one |
| 129 | 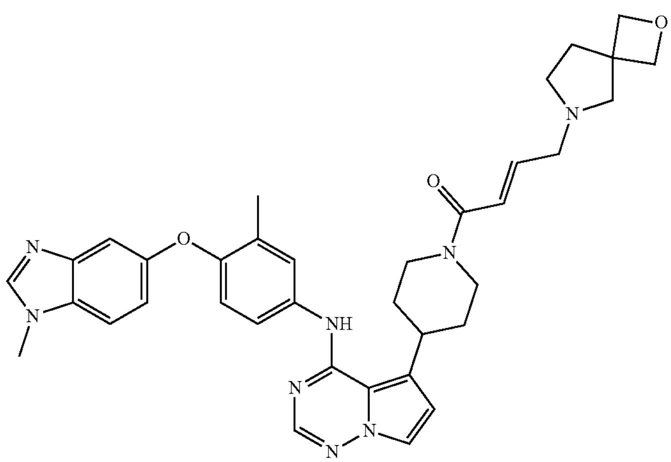 [SMILES: Cc1cc(Nc2ncnn3ccc(C4CCN(C(=O)/C=C/CN5CCC6(COC6)C5)CC4)c23)ccc1Oc1ccc2c(c1)ncn2C] | 633.3 | (E)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)-4-(2-oxa-6-azaspiro[3.4]octan-6-yl)but-2-en-1-one |
| 130 | 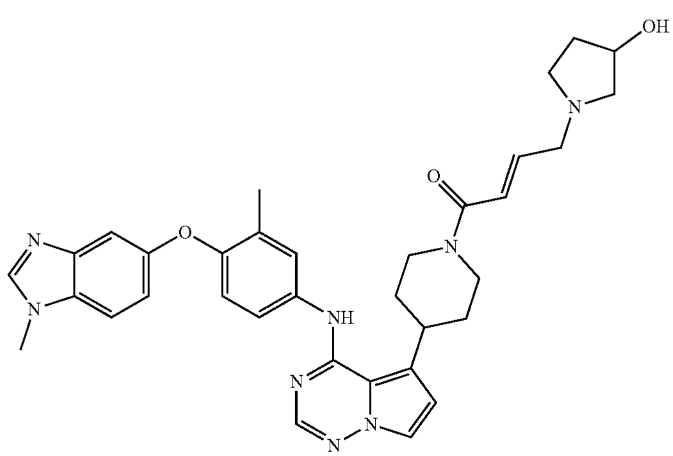 [SMILES: Cc1cc(Nc2ncnn3ccc(C4CCN(C(=O)/C=C/CN5CCC(O)C5)CC4)c23)ccc1Oc1ccc2c(c1)ncn2C] | 607.3 | (E)-4-(3-hydroxypyrrolidin-1-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one |

TABLE 1-continued

| E # | Structure | Mass Spec. M + H/1 | Name |
|---|---|---|---|
| 131 | 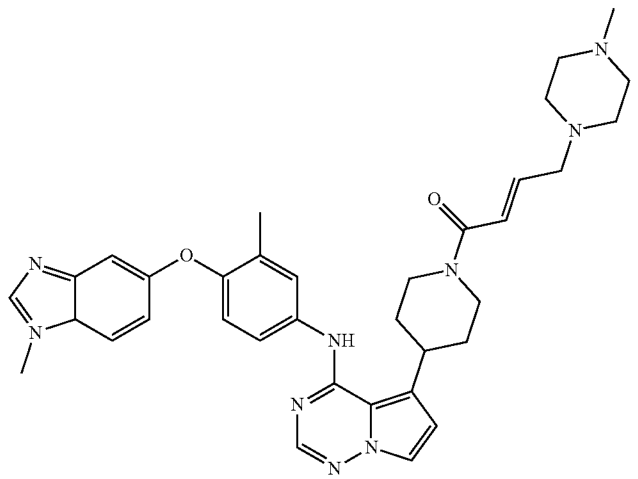 | 620.3 | (E)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)-4-(4-methylpiperazin-1-yl)but-2-en-1-one |
| 132 | 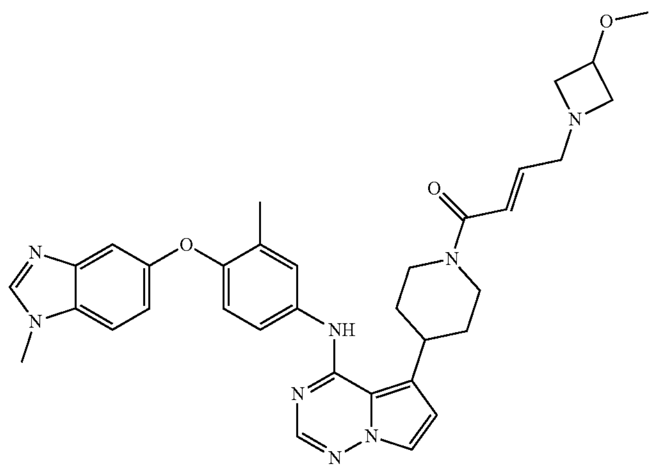 [SMILES: COC1CN(C/C=C/C(=O)N2CCC(c3ccn4ncnc(Nc5ccc(Oc6ccc7c(c6)ncn7C)c(C)c5)c34)CC2)C1] | 607.3 | (E)-4-(3-methoxyazetidin-1-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one |
| 133 | 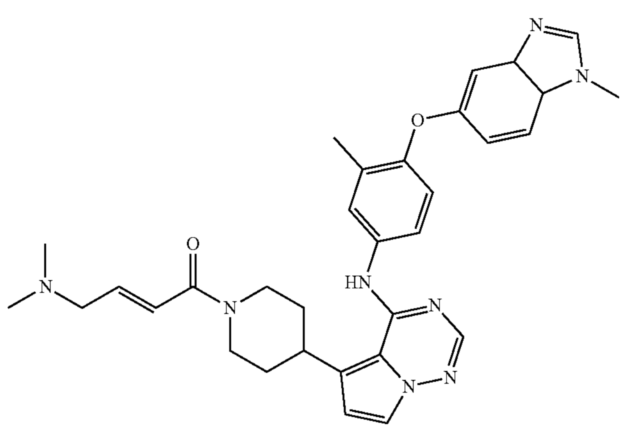 | 565.3 | (E)-4-(dimethylamino)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one |

TABLE 1-continued

| E # | Structure | Mass Spec. M + H/1 | Name |
|---|---|---|---|
| 134 | 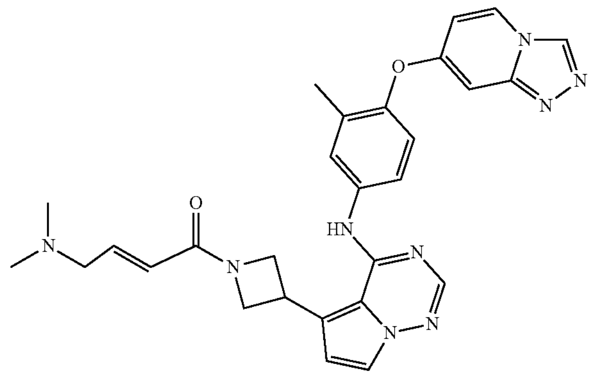 [SMILES: Cc1cc(Nc2ncnn3ccc(C4CN(C(=O)/C=C/CN(C)C)C4)c23)ccc1Oc1ccn2cnnc2c1] | 524.2 | (E)-1-(3-(4-((4-([1,2,4]triazolo[4,3-a]pyridin-7-yloxy)-3-methylphenyl)amino)pyrrolo[2,1-f][1,2,4]triazin-5-yl)azetidin-1-yl)-4-(dimethylamino)but-2-en-1-one |
| 135 | 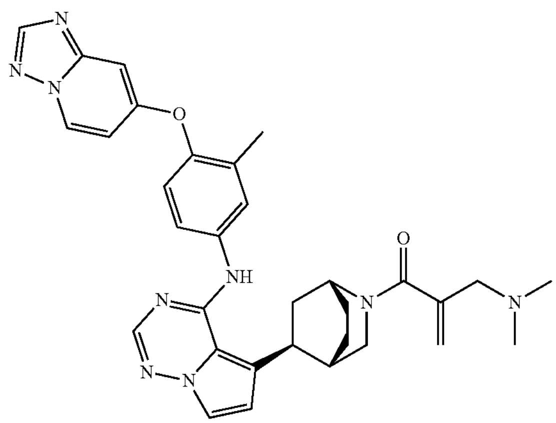 [SMILES: C=C(CN(C)C)C(=O)N1C[C@H]2CC[C@@H]1C[C@@H]2c1ccn2ncnc(Nc3ccc(Oc4ccn5ncnc5c4)c(C)c3)c12] | 578.3 | 1-((1R,4S,5S)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)-2-((dimethylamino)methyl)prop-2-en-1-one |
| 136 | 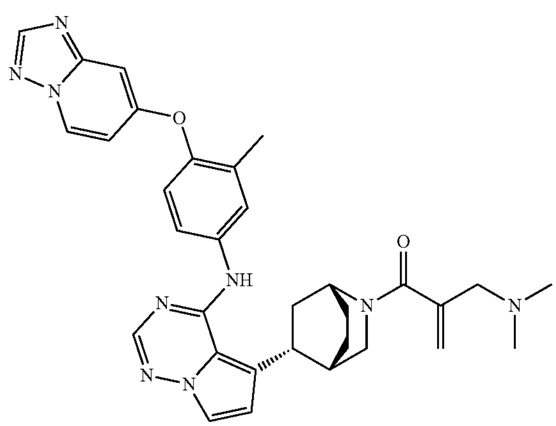 [SMILES: C=C(CN(C)C)C(=O)N1C[C@H]2CC[C@@H]1C[C@H]2c1ccn2ncnc(Nc3ccc(Oc4ccn5ncnc5c4)c(C)c3)c12] | 578.3 | 1-((1R,4S,5R)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)-2-((dimethylamino)methyl)prop-2-en-1-one |

TABLE 1-continued

| E # | Structure | Mass Spec. M + H/1 | Name |
|---|---|---|---|
| 137 | 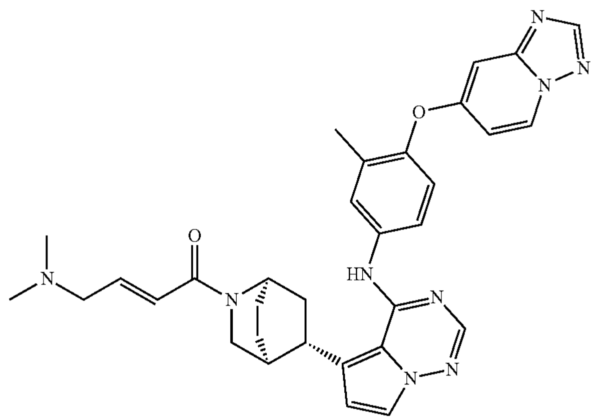 [SMILES: Cc1cc(Nc2ncnn3ccc([C@H]4C[C@H]5CC[C@@H]4CN5C(=O)/C=C/CN(C)C)c23)ccc1Oc1ccn2ncnc2c1] | 578.3 | (E)-1-((1R,4S,5S)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)-4-(dimethylamino)but-2-en-1-one |
| 138 | 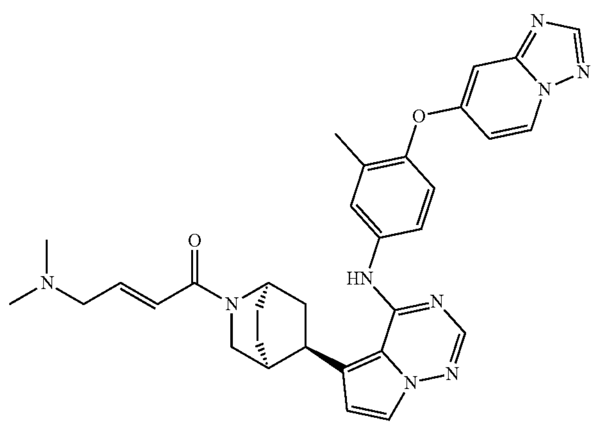 [SMILES: Cc1cc(Nc2ncnn3ccc([C@@H]4C[C@H]5CC[C@@H]4CN5C(=O)/C=C/CN(C)C)c23)ccc1Oc1ccn2ncnc2c1] | 578.3 | (E)-1-((1R,4S,5R)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)-4-(dimethylamino)but-2-en-1-one |
| 139 | 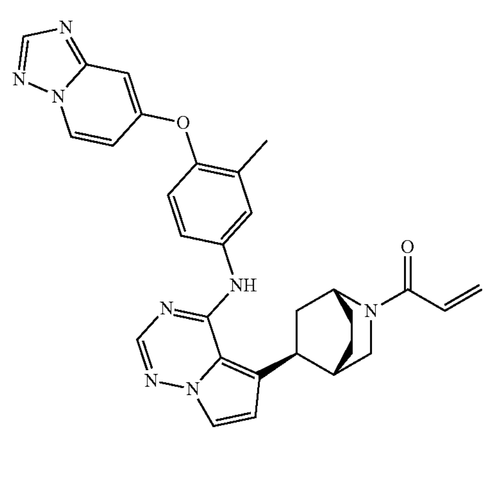 [SMILES: C=CC(=O)N1C[C@H]2CC[C@@H]1C[C@@H]2c1ccn2ncnc(Nc3ccc(Oc4ccn5ncnc5c4)c(C)c3)c12] | 521.2 | 1-((1R,4S,5S)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)prop-2-en-1-one |

TABLE 1-continued

| E # | Structure | Mass Spec. M + H/1 | Name |
|---|---|---|---|
| 140 | 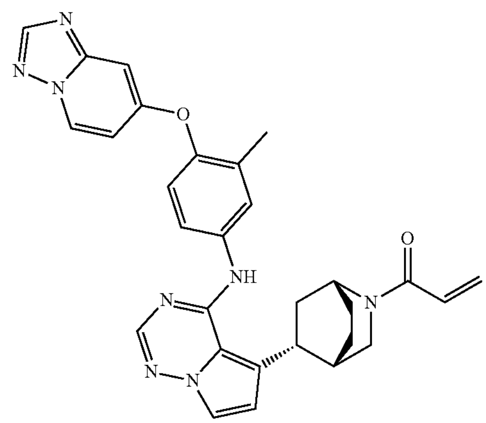 [SMILES: C=CC(=O)N1C[C@H]2CC[C@@H]1C[C@H]2c1ccn2ncnc(Nc3ccc(Oc4ccn5ncnc5c4)c(C)c3)c12] | 521.1 | 1-((1R,4S,5R)-5-(4-((4-([1,2,4]triazolo[1,5-a]pyridin-7-yloxy)-3-methylphenyl)amino)pyrrolo[2,1-f][1,2,4]triazin-5-yl)-2-azabicyclo[2.2.2]octan-2-yl)prop-2-en-1-one |
| 141 | 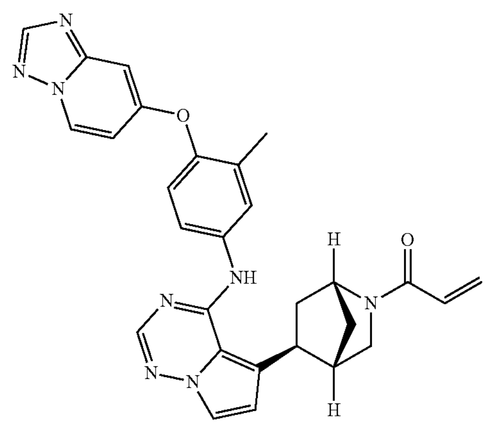 [SMILES: C=CC(=O)N1C[C@H]2C[C@@H]1C[C@@H]2c1ccn2ncnc(Nc3ccc(Oc4ccn5ncnc5c4)c(C)c3)c12] | 507.3 | 1-[(1S,4S,5S)-5-{4-[(3-methyl-4-{[1,2,4]triazolo[1,5-a]pyridin-7-yloxy}phenyl)amino]pyrrolo[2,1-f][1,2,4]triazin-5-yl}-2-azabicyclo[2.2.1]heptan-2-yl]prop-2-en-1-one |
| 142 | 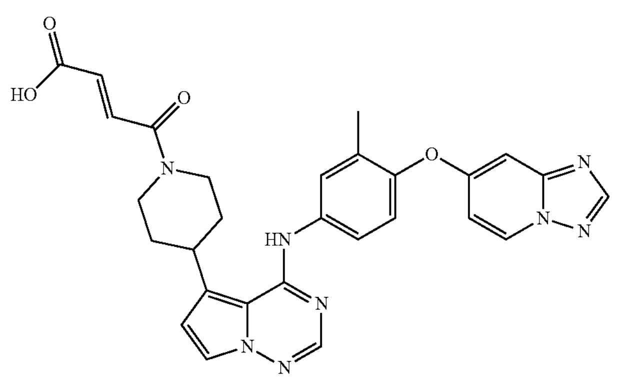 [SMILES: Cc1cc(Nc2ncnn3ccc(C4CCN(C(=O)/C=C/C(=O)O)CC4)c23)ccc1Oc1ccn2ncnc2c1] | 539.2 | (E)-4-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-oxobut-2-enoic acid |
| 143 | 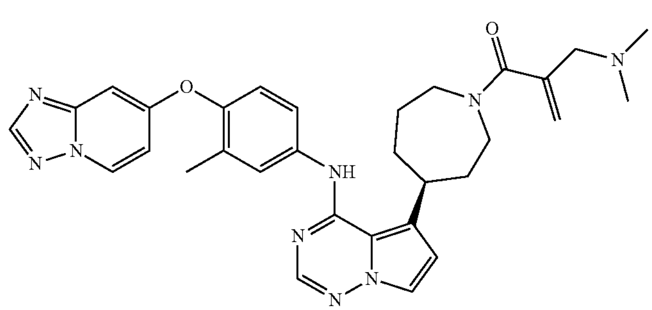 [SMILES: C=C(CN(C)C)C(=O)N1CCC[C@H](c2ccn3ncnc(Nc4ccc(Oc5ccn6ncnc6c5)c(C)c4)c23)CC1] | 566.3 | (S)-1-(4-(4-((4-([1,2,4]triazolo[1,5-a]pyridin-7-yloxy)-3-methylphenyl)amino)pyrrolo[2,1-f][1,2,4]triazin-5-yl)azetidin-1-yl)-2-((dimethylamino)methyl)prop-2-en-1-one |

TABLE 1-continued

| E # | Structure | Mass Spec. M + H/1 | Name |
|---|---|---|---|
| 144 | 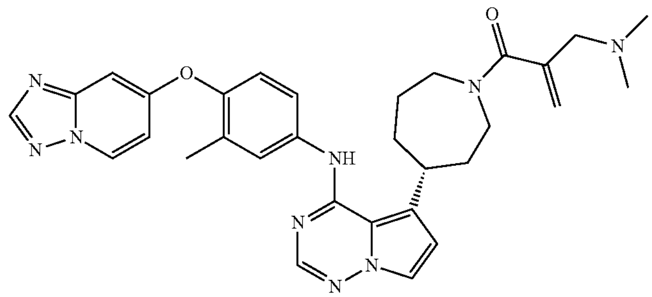 [SMILES: C=C(CN(C)C)C(=O)N1CCC[C@@H](c2ccn3ncnc(Nc4ccc(Oc5ccn6ncnc6c5)c(C)c4)c23)CC1] | 566.3 | (R)-1-(4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-((dimethylamino)methyl)prop-2-en-1-one |
| 145 | 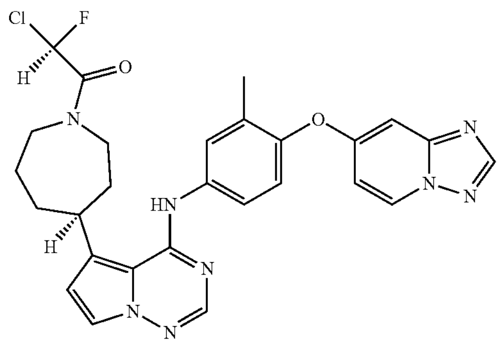 [SMILES: Cc1cc(Nc2ncnn3ccc([C@H]4CCCN(C(=O)[C@H](F)Cl)CC4)c23)ccc1Oc1ccn2ncnc2c1] | 549.2 | (R)-1-((S)-4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one |
| 146 | 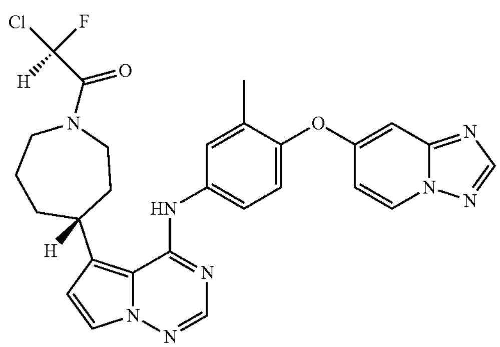 [SMILES: Cc1cc(Nc2ncnn3ccc([C@@H]4CCCN(C(=O)[C@H](F)Cl)CC4)c23)ccc1Oc1ccn2ncnc2c1] | 549.2 | (R)-1-((R)-4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one |
| 147 | 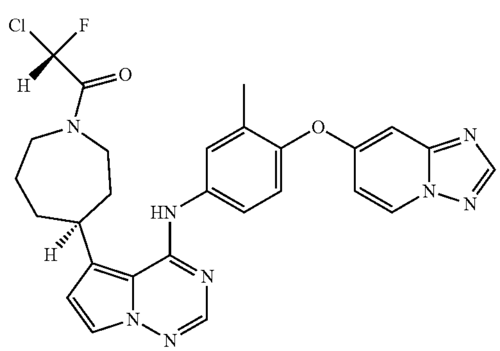 [SMILES: Cc1cc(Nc2ncnn3ccc([C@H]4CCCN(C(=O)[C@@H](F)Cl)CC4)c23)ccc1Oc1ccn2ncnc2c1] | 549.2 | (S)-1-((S)-4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one |

TABLE 1-continued

| E # | Structure | Mass Spec. M + H/1 | Name |
|---|---|---|---|
| 148 | 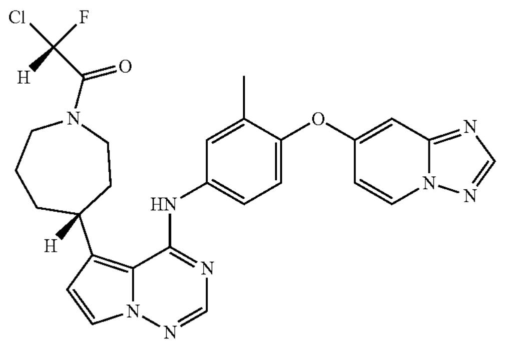 [SMILES: Cc1cc(Nc2ncnn3ccc([C@@H]4CCCN(C(=O)[C@@H](F)Cl)CC4)c23)ccc1Oc1ccn2ncnc2c1] | 549.2 | (S)-1-((R)-4-(4-((4-([1,2,4]triazolo[1,5-a]pyridin-7-yloxy)-3-methylphenyl)amino)pyrrolo[2,1-f][1,2,4]triazin-5-yl)azepan-1-yl)-2-chloro-2-fluoroethan-1-one |
| 149 | 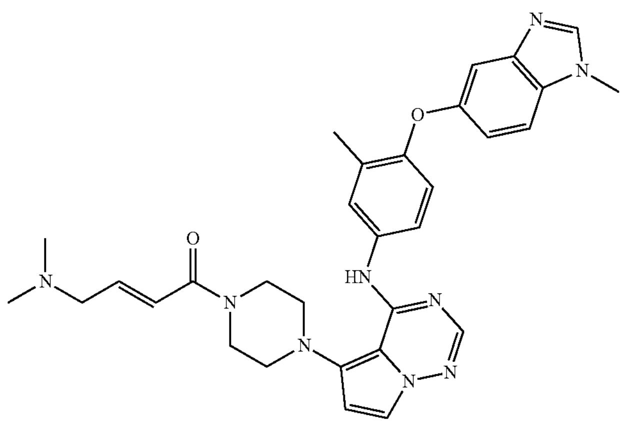 | 566.3 | (E)-4-(dimethylamino)-1-(4-(4-((3-methyl-4-((1-methyl-1H-benzo[d]imidazol-5-yl)oxy)phenyl)amino)pyrrolo[2,1-f][1,2,4]triazin-5-yl)piperazin-1-yl)but-2-en-1-one |
| 150 | 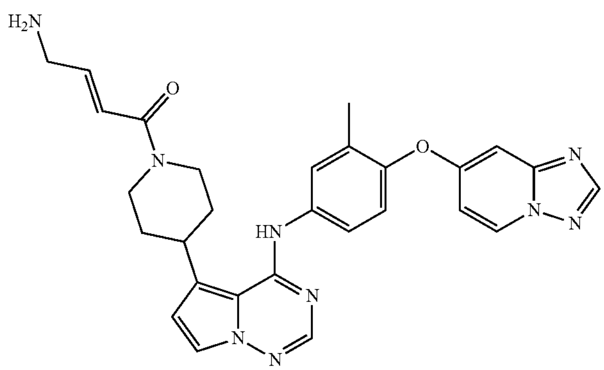 [SMILES: Cc1cc(Nc2ncnn3ccc(C4CCN(C(=O)/C=C/CN)CC4)c23)ccc1Oc1ccn2ncnc2c1] | 524.2 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-aminobut-2-en-1-one |
| 151 | 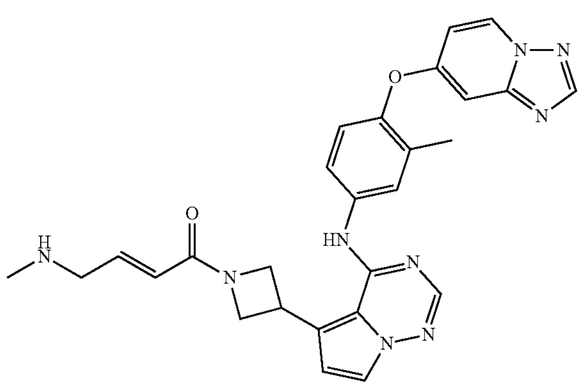 [SMILES: CNC/C=C/C(=O)N1CC(c2ccn3ncnc(Nc4ccc(Oc5ccn6ncnc6c5)c(C)c4)c23)C1] | 510.2 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-4-(methylamino)but-2-en-1-one |

TABLE 1-continued

| E # | Structure | Mass Spec. M + H/1 | Name |
|---|---|---|---|
| 152 | 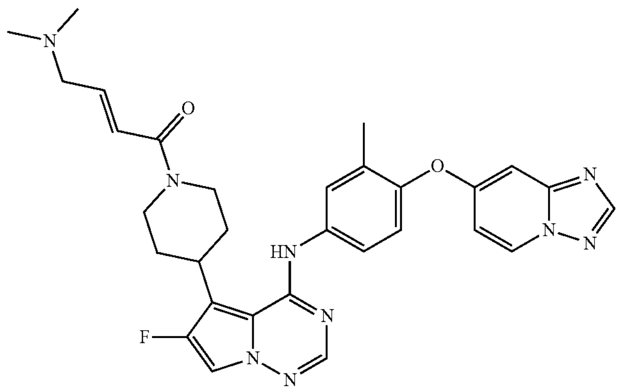 [SMILES: Cc1cc(Nc2ncnn3cc(F)c(C4CCN(C(=O)/C=C/CN(C)C)CC4)c23)ccc1Oc1ccn2ncnc2c1] | 570.3 | (E)-1-(4-(4-((4-([1,2,4]triazolo[1,5-a]pyridin-7-yloxy)-3-methylphenyl)amino)-6-fluoropyrrolo[2,1-f][1,2,4]triazin-5-yl)piperidin-1-yl)-4-(dimethylamino)but-2-en-1-one |
| 153 | 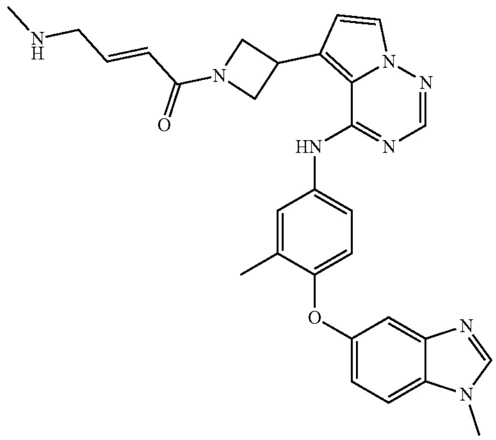 [SMILES: CNC/C=C/C(=O)N1CC(c2ccn3ncnc(Nc4ccc(Oc5ccc6c(c5)ncn6C)c(C)c4)c23)C1] | 523.6 | (E)-1-(3-(4-((3-methyl-4-((1-methyl-1H-benzo[d]imidazol-5-yl)oxy)phenyl)amino)pyrrolo[2,1-f][1,2,4]triazin-5-yl)azetidin-1-yl)-4-(methylamino)but-2-en-1-one |
| 154 | 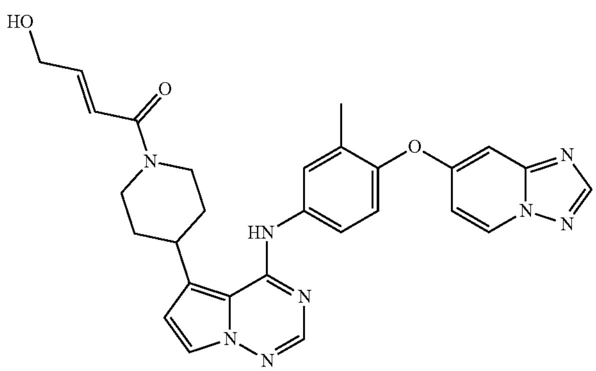 [SMILES: Cc1cc(Nc2ncnn3ccc(C4CCN(C(=O)/C=C/CO)CC4)c23)ccc1Oc1ccn2ncnc2c1] | 525.4 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-hydroxybut-2-en-1-one |
| 155 | 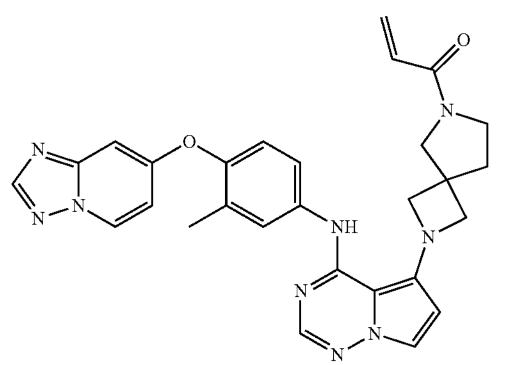 [SMILES: C=CC(=O)N1CCC2(C1)CN(c1ccn3ncnc(Nc4ccc(Oc5ccn6ncnc6c5)c(C)c4)c13)C2] | 522.3 | 1-(2-{4-[(3-methyl-4-{[1,2,4]triazolo[1,5-a]pyridin-7-yloxy}phenyl)amino]pyrrolo[2,1-f][1,2,4]triazin-5-yl}-2,6-diazaspiro[3.4]octan-6-yl)prop-2-en-1-one |

TABLE 1-continued

| E # | Structure | Mass Spec. M + H/1 | Name |
|---|---|---|---|
| 156 | 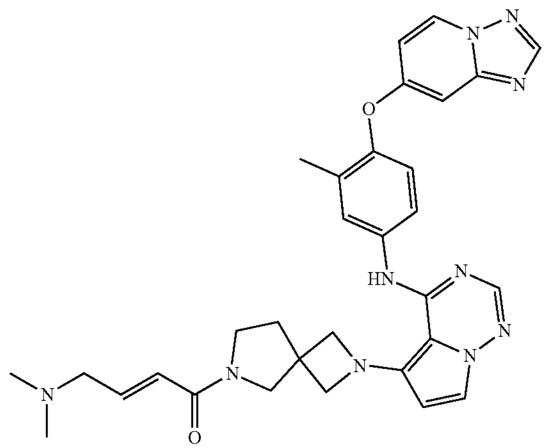 [SMILES: Cc1cc(Nc2ncnn3ccc(N4CC5(CCN(C(=O)/C=C/CN(C)C)C5)C4)c23)ccc1Oc1ccn2ncnc2c1] | 579.3 | (2E)-4-(dimethylamino)-1-(2-{4-[(3-methyl-4-{[1,2,4]triazolo[1,5-a]pyridin-7-yloxy}phenyl)amino]pyrrolo[2,1-f][1,2,4]triazin-5-yl}-2,6-diazaspiro[3.4]octan-6-yl)but-2-en-1-one |
| 157 | 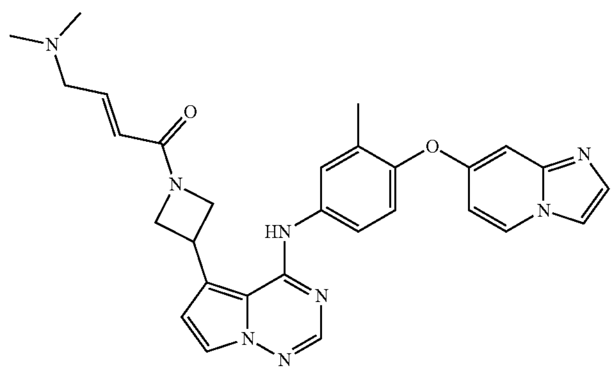 [SMILES: Cc1cc(Nc2ncnn3ccc(C4CN(C(=O)/C=C/CN(C)C)C4)c23)ccc1Oc1ccn2ccnc2c1] | 523.0 | (E)-4-(dimethylamino)-1-(3-(4-((4-(imidazo[1,2-a]pyridin-7-yloxy)-3-methylphenyl)amino)pyrrolo[2,1-f][1,2,4]triazin-5-yl)azetidin-1-yl)but-2-en-1-one |
| 158 | 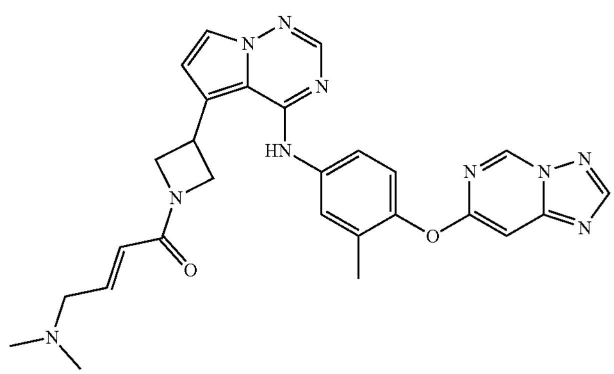 [SMILES: Cc1cc(Nc2ncnn3ccc(C4CN(C(=O)/C=C/CN(C)C)C4)c23)ccc1Oc1cc2ncnn2cn1] | 525.2 | (E)-1-(3-(4-((4-([1,2,4]triazolo[1,5-c]pyrimidin-7-yloxy)-3-methylphenyl)amino)pyrrolo[2,1-f][1,2,4]triazin-5-yl)azetidin-1-yl)-4-(dimethylamino)but-2-en-1-one |
| 159 | 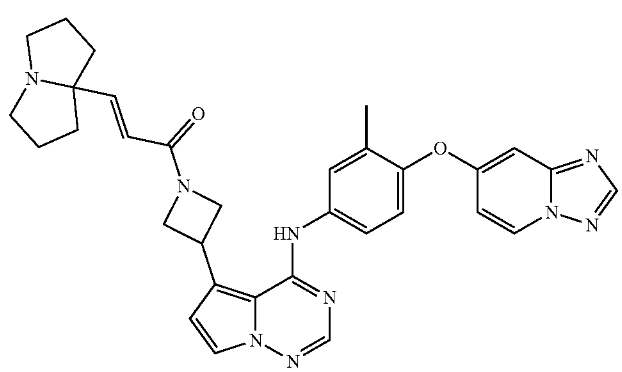 [SMILES: Cc1cc(Nc2ncnn3ccc(C4CN(C(=O)/C=C/C56CCCN5CCC6)C4)c23)ccc1Oc1ccn2ncnc2c1] | 576.3 | (E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(tetrahydro-1H-pyrrolizin-7a(5H)-yl)prop-2-en-1-one |

TABLE 1-continued

| E # | Structure | Mass Spec. M + H/1 | Name |
|---|---|---|---|
| 160 | 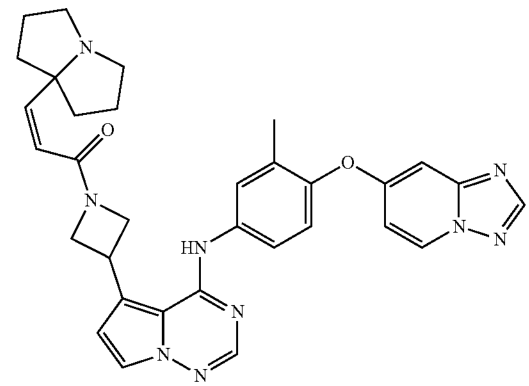 [SMILES: Cc1cc(Nc2ncnn3ccc(C4CN(C(=O)/C=C\C56CCCN5CCC6)C4)c23)ccc1Oc1ccn2ncnc2c1] | 576.3 | (Z)-1-(3-(4-((4-([1,2,4]triazolo[1,5-a]pyridin-7-yloxy)-3-methylphenyl)amino) pyrrolo[2,1-f][1,2,4]triazin-5-yl)azetidin-1-yl)-3-(tetrahydro-1H-pyrrolizin-7a(5H)-yl)prop-2-en-1-one |
| 161 | 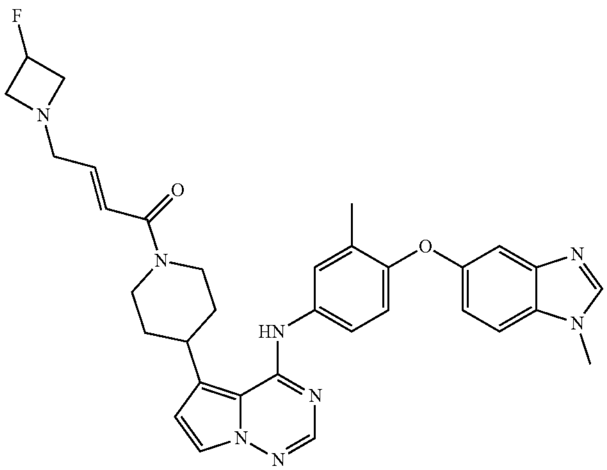 [SMILES: Cc1cc(Nc2ncnn3ccc(C4CCN(C(=O)/C=C/CN5CC(F)C5)CC4)c23)ccc1Oc1ccc2c(c1)ncn2C] | 567.3 | (E)-4-(3-fluoroazetidin-1-yl)-1-(3-(4-((3-methyl-4-((1-methyl-1H-benzo[d]imidazol-5-yl)oxy)phenyl)amino) pyrrolo[2,1-f][1,2,4]triazin-5-yl)azetidin-1-yl)but-2-en-1-one |
| 162 | 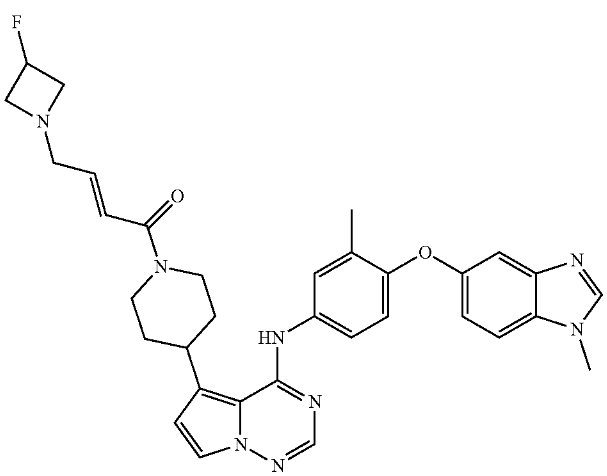 [SMILES: Cc1cc(Nc2ncnn3ccc(C4CCN(C(=O)/C=C/CN5CC(F)C5)CC4)c23)ccc1Oc1ccc2c(c1)ncn2C] | 595.5 | (E)-4-(3-fluoroazetidin-1-yl)-1-(4-(4-((3-methyl-4-((1-methyl-1H-benzo[d]imidazol-5-yl)oxy)phenyl)amino) pyrrolo[2,1-f][1,2,4]triazin-5-yl)piperidin-1-yl)but-2-en-1-one |

TABLE 1-continued

| E # | Structure | Mass Spec. M + H/1 | Name |
|---|---|---|---|
| 163 | 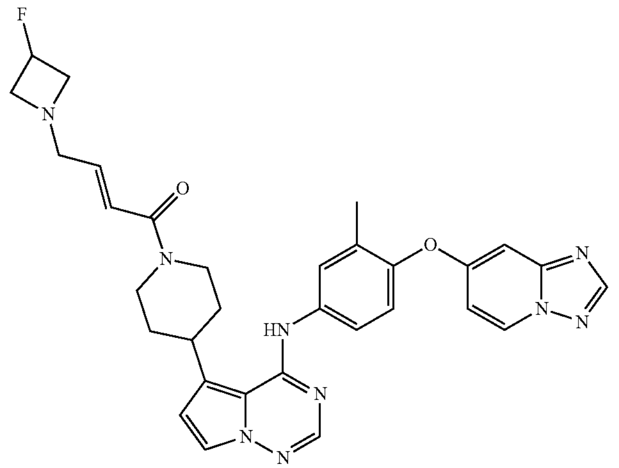 [SMILES: Cc1cc(Nc2ncnn3ccc(C4CCN(C(=O)/C=C/CN5CC(F)C5)CC4)c23)ccc1Oc1ccn2ncnc2c1] | 582.2 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(3-fluoroazetidin-1-yl)but-2-en-1-one |
| 164 | 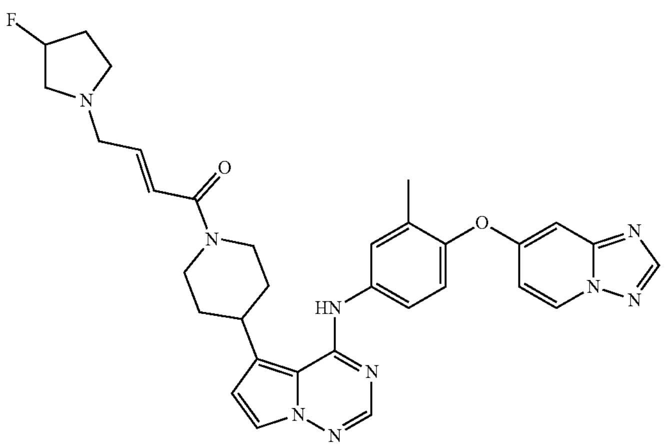 [SMILES: Cc1cc(Nc2ncnn3ccc(C4CCN(C(=O)/C=C/CN5CCC(F)C5)CC4)c23)ccc1Oc1ccn2ncnc2c1] | 596.5 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(3-fluoropyrrolidin-1-yl)but-2-en-1-one |
| 165 | 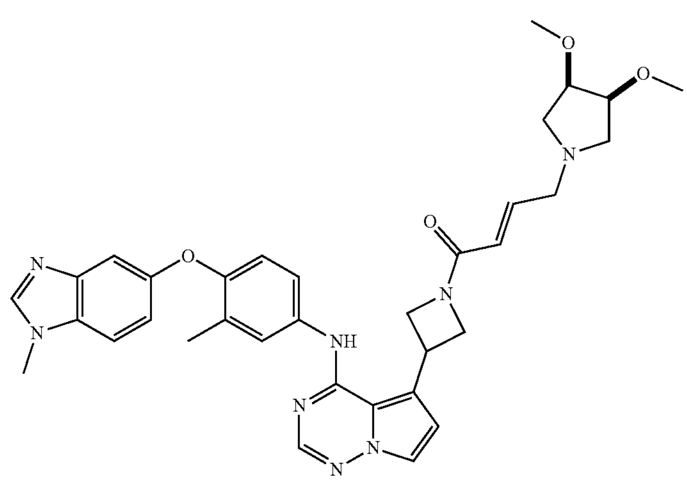 [SMILES: CO[C@H]1CN(C/C=C/C(=O)N2CC(c3ccn4ncnc(Nc5ccc(Oc6ccc7c(c6)ncn7C)c(C)c5)c34)C2)C[C@H]1OC] | 623.3 | (E)-4-((3R,4S)-3,4-dimethoxypyrrolidin-1-yl)-1-(3-(4-((3-methyl-4-((1-methyl-1H-benzo[d]imidazol-5-yl)oxy)phenyl)amino)pyrrolo[2,1-f][1,2,4]triazin-5-yl)azetidin-1-yl)but-2-en-1-one |

TABLE 1-continued

| E # | Structure | Mass Spec. M + H/1 | Name |
|---|---|---|---|
| 166 | 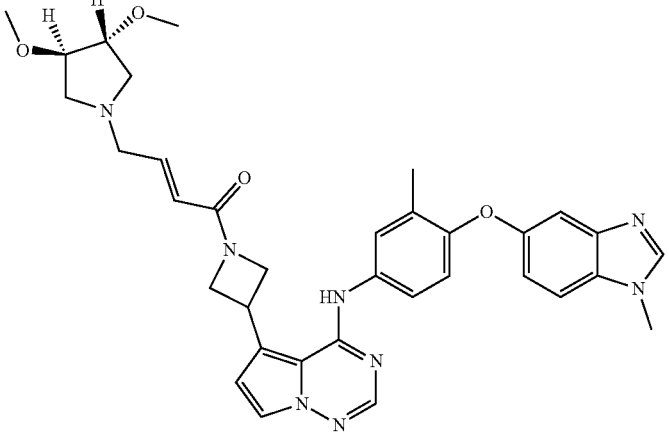 | 623.3 | (E)-4-((3R,4R)-3,4-dimethoxypyrrolidin-1-yl)-1-(3-(4-((3-methyl-4-((1-methyl-1H-benzo[d]imidazol-5-yl)oxy)phenyl)amino)pyrrolo[2,1-f][1,2,4]triazin-5-yl)azetidin-1-yl)but-2-en-1-one |
| 167 | 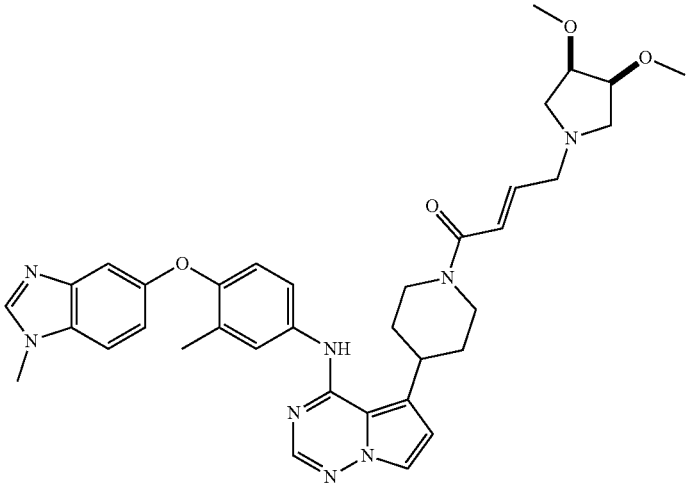 [SMILES: CO[C@H]1CN(C/C=C/C(=O)N2CCC(c3ccn4ncnc(Nc5ccc(Oc6ccc7c(c6)ncn7C)c(C)c5)c34)CC2)C[C@H]1OC] | 651.6 | (E)-4-((3R,4S)-3,4-dimethoxypyrrolidin-1-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one |
| 168 | 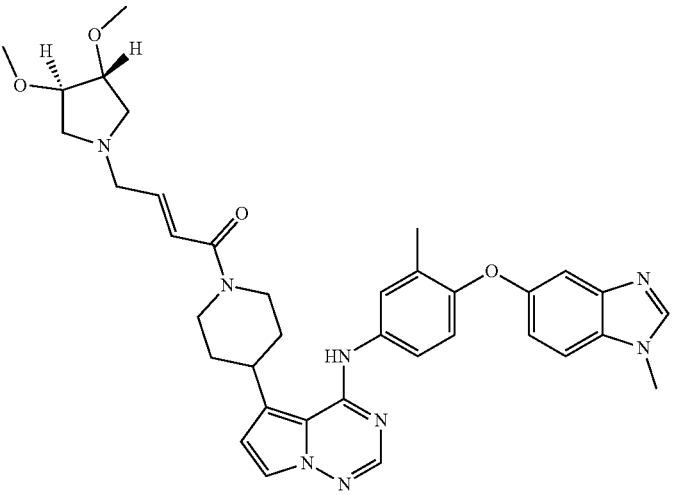 [SMILES: CO[C@@H]1CN(C/C=C/C(=O)N2CCC(c3ccn4ncnc(Nc5ccc(Oc6ccc7c(c6)ncn7C)c(C)c5)c34)CC2)C[C@H]1OC] | 651.6 | (E)-4-((3R,4R)-3,4-dimethoxypyrrolidin-1-yl)-1-(4-(4-((3-methyl-4-((1-methyl-1H-benzo[d]imidazol-5-yl)oxy)phenyl)amino)pyrrolo[2,1-f][1,2,4]triazin-5-yl)piperidin-1-yl)but-2-en-1-one |

TABLE 1-continued

| E # | Structure | Mass Spec. M + H/1 | Name |
|---|---|---|---|
| 169 | 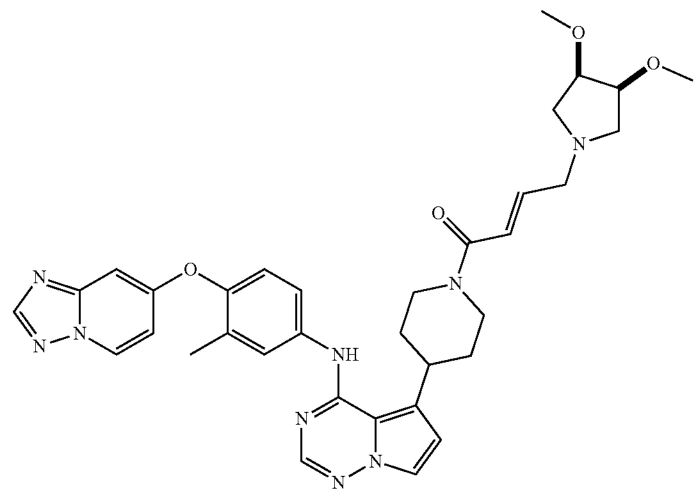 [SMILES: CO[C@H]1CN(C/C=C/C(=O)N2CCC(c3ccn4ncnc(Nc5ccc(Oc6ccn7ncnc7c6)c(C)c5)c34)CC2)C[C@H]1OC] | 638.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-((3R,4S)-3,4-dimethoxypyrrolidin-1-yl)but-2-en-1-one |
| 170 | 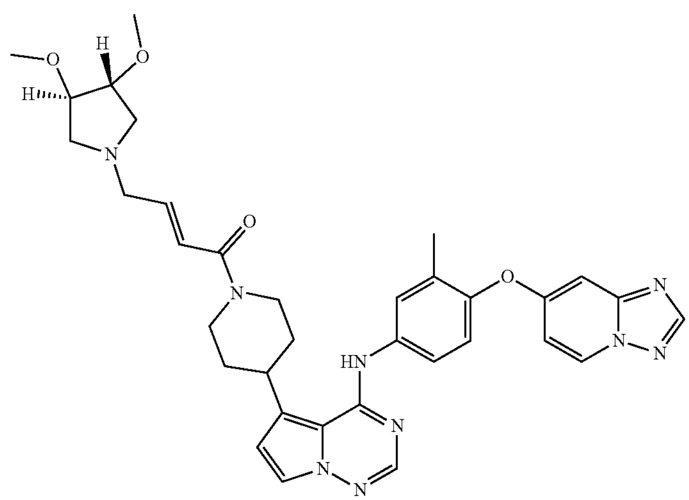 [SMILES: CO[C@@H]1CN(C/C=C/C(=O)N2CCC(c3ccn4ncnc(Nc5ccc(Oc6ccn7ncnc7c6)c(C)c5)c34)CC2)C[C@H]1OC] | 638.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-((3R,4R)-3,4-dimethoxypyrrolidin-1-yl)but-2-en-1-one |
| 171 | 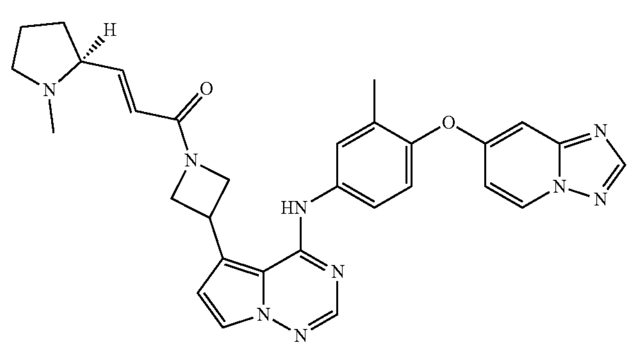 [SMILES: Cc1cc(Nc2ncnn3ccc(C4CN(C(=O)/C=C/[C@@H]5CCCN5C)C4)c23)ccc1Oc1ccn2ncnc2c1] | 550.4 | (R,E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(1-methylpyrrolidin-2-yl)prop-2-en-1-one |

TABLE 1-continued

| E # | Structure | Mass Spec. M + H/1 | Name |
|---|---|---|---|
| 172 | 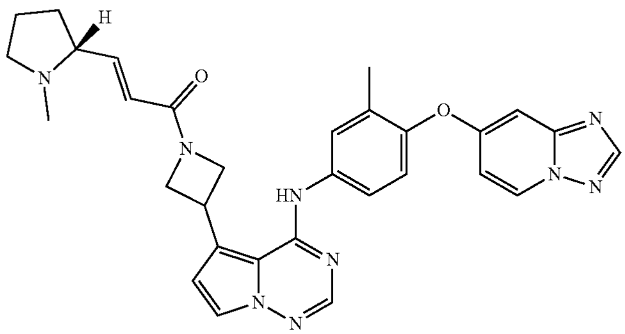 [SMILES: Cc1cc(Nc2ncnn3ccc(C4CN(C(=O)/C=C/[C@H]5CCCN5C)C4)c23)ccc1Oc1ccn2ncnc2c1] | 550.4 | (S,E)-1-(3-(4-((4-([1,2,4]triazolo[1,5-a]pyridin-7-yloxy)-3-methylphenyl)amino)pyrrolo[2,1-f][1,2,4]triazin-5-yl)azetidin-1-yl)-3-(1-methylpyrrolidin-2-yl)prop-2-en-1-one |
| 173 | 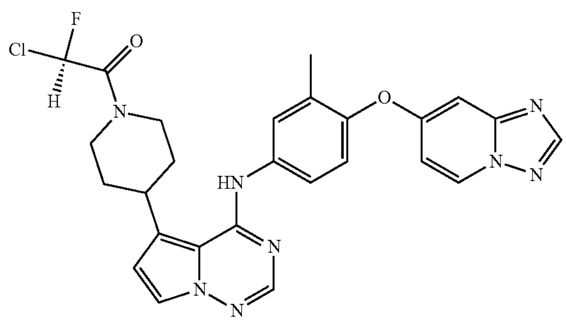 [SMILES: Cc1cc(Nc2ncnn3ccc(C4CCN(C(=O)[C@H](F)Cl)CC4)c23)ccc1Oc1ccn2ncnc2c1] | 535.2 | (R)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-2-chloro-2-fluoroethan-1-one |
| 174 | 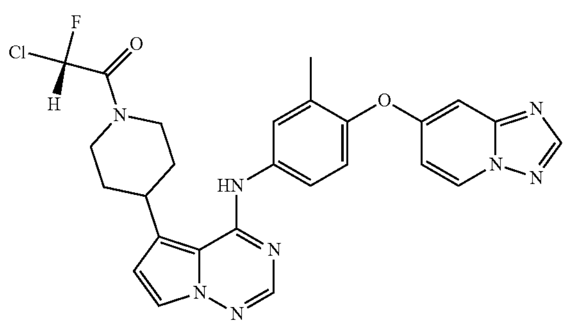 [SMILES: Cc1cc(Nc2ncnn3ccc(C4CCN(C(=O)[C@@H](F)Cl)CC4)c23)ccc1Oc1ccn2ncnc2c1] | 535.2 | (S)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-2-chloro-2-fluoroethan-1-one |
| 175 | 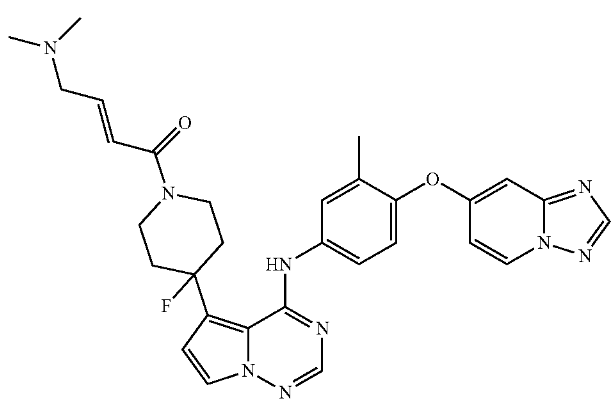 [SMILES: Cc1cc(Nc2ncnn3ccc(C4(F)CCN(C(=O)/C=C/CN(C)C)CC4)c23)ccc1Oc1ccn2ncnc2c1] | 570.4 | (E)-1-(4-(4-((4-([1,2,4]triazolo[1,5-a]pyridin-7-yloxy)-3-methylphenyl)amino)pyrrolo[2,1-f][1,2,4]triazin-5-yl)-4-fluoropiperidin-1-yl)-4-(dimethylamino)but-2-en-1-one |

TABLE 1-continued

| E # | Structure | Mass Spec. M + H/1 | Name |
|---|---|---|---|
| 176 | 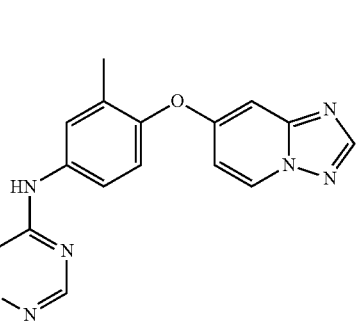 | 588.3 | (E)-1-(4-(4-((4-([1,2,4]triazolo[1,5-a]pyridin-7-yloxy)-3-methylphenyl)amino)pyrrolo[2,1-f][1,2,4]triazin-5-yl)-3,3-difluoropiperidin-1-yl)-4-(dimethylamino)but-2-en-1-one |
| 177 | 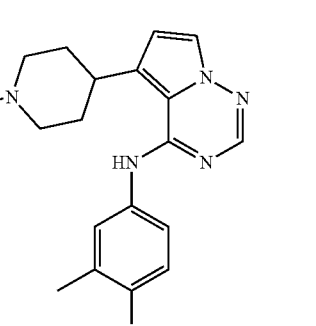 | 538.2 | (E)-1-(4-(4-((4-([1,2,4]triazolo[1,5-a]pyridin-7-yloxy)-3-methylphenyl)amino)pyrrolo[2,1-f][1,2,4]triazin-5-yl)piperidin-1-yl)-4-(methylamino)but-2-en-1-one |
| 178 | 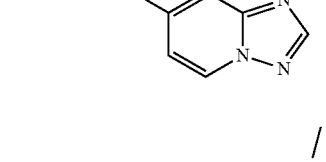 | 486.2 | 4-((4-([1,2,4]triazolo[1,5-a]pyridin-7-yloxy)-3-methylphenyl)amino)-N-(3-(dimethylamino)propyl)pyrrolo[2,1-f][1,2,4]triazine-5-carboxamide |
| 179 | 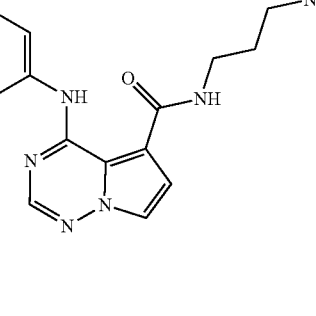 | 486.2 | 4-((4-([1,2,4]triazolo[1,5-a]pyridin-7-yloxy)-3-methylphenyl)amino)-N-(3-(dimethylamino)propyl)pyrrolo[2,1-f][1,2,4]triazine-5-carboxamide hydrochloride |

TABLE 1-continued

| E # | Structure | Mass Spec. M + H/1 | Name |
|---|---|---|---|
| 180 | 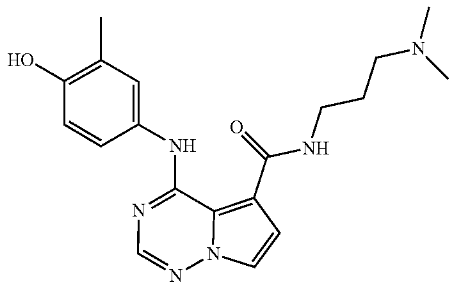 [SMILES: Cc1cc(Nc2ncnn3ccc(C(=O)NCCCN(C)C)c23)ccc1O] | 369.1 | N-(3-(dimethylamino)propyl)-4-((4-hydroxy-3-methylphenyl)amino)pyrrolo[2,1-f][1,2,4]triazine-5-carboxamide |
| 181 | 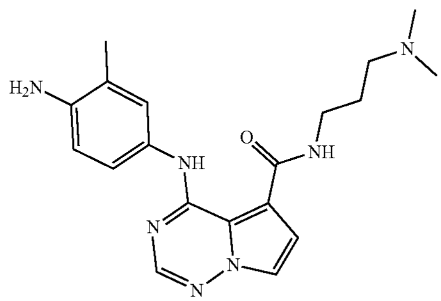 [SMILES: Cc1cc(Nc2ncnn3ccc(C(=O)NCCCN(C)C)c23)ccc1N] | 368.2 | 4-((4-amino-3-methylphenyl)amino)-N-(3-(dimethylamino)propyl)pyrrolo[2,1-f][1,2,4]triazine-5-carboxamide |

1H NMR for Compounds of TABLE 1

| E# | $^1$H NMR (ppm) |
|---|---|
| 1 | $^1$H NMR (400 MHz, DMSO-d$_6$) δ (ppm) 8.52 (d, J = 7.6 Hz, 1H), 8.25 (s, 1H), 8.02 (s, 1H), 7.65-7.59 (m, 3H), 7.12 (d, J = 8.4 Hz, 1H), 7.03-6.98 (m, 1H), 6.96-6.95 (m, 3H), 6.75-6.74 (m, 1H), 6.18-6.14 (m, 1H), 4.82-4.66 (m, 2H), 4.46-4.43 (m, 1H), 4.37-4.31 (m, 2H), 3.15-3.09 (m, 2H), 2.27-2.20 (m, 9H). |
| 2 | $^1$H NMR (400 MHz, DMSO-d$_6$) δ (ppm) 8.93 (d, J = 7.2 Hz, 1H), 8.38-8.29 (m, 2H), 8.13-8.07 (m, 2H), 7.88-7.79 (m, 2H), 7.64-7.59 (m, 2H), 7.18 (d, J = 8.8 Hz, 1H), 7.04-3.98 (m, 1H), 6.82-86.79 (m, 2H), 6.43-6.34 (m, 1H), 6.16-6.12 (m, 1H), 5.71-5.68 (m, 1H), 5.41-5.40 (m, 1H), 4.80-4.67 (m, 1H), 4.65-4.56 (m, 1H), 4.50-4.41 (m, 1H), 4.37-4.29 (m, 1H), 2.16 (s, 3H). |
| 3 | $^1$H NMR (499 MHz, CHLOROFORM-d) δ = 8.50 (d, J = 7.7 Hz, 1H), 8.26-8.21 (m, 1H), 8.03-7.93 (m, 1H), 7.67-7.49 (m, 3H), 7.10 (d, J = 8.5 Hz, 1H), 7.06-6.97 (m, 1H), 6.90 (dd, J = 2.6, 7.5 Hz, 1H), 6.85 (d, J = 2.5 Hz, 1H), 6.72 (br d, J = 1.9 Hz, 1H), 6.46-6.36 (m, 1H), 6.32-6.22 (m, 1H), 5.75 (dd, J = 1.6, 10.4 Hz, 1H), 4.82-4.74 (m, 1H), 4.73-4.63 (m, 1H), 4.47-4.40 (m, 1H), 4.32 (br t, J = 8.4 Hz, 2H), 2.24-2.22 (m, 3H). |
| 4 | $^1$H NMR (400 MHz, DMSO-d$_6$) δ (ppm) 12.87 (d, J = 8.5 Hz, 1H), 8.94 (dd, J = 7.5, 0.7 Hz, 1H), 8.50-8.37 (m, 2H), 8.20 (d, J = 2.1 Hz, 1H), 7.89-7.77 (m, 3H), 7.30-7.19 (m, 2H), 7.03 (dd, J = 7.5, 2.6 Hz, 1H), 6.81 (d, J = 2.4 Hz, 1H), 6.29-6.04 (m, 2H), 5.65-5.56 (m, 1H), 4.45-4.33 (m, 1H), 4.22-4.14 (m, 1H), 4.00-3.87 (m, 1H), 3.81-3.66 (m, 2H), 2.22-2.13 (m, 4H), 1.97-1.90 (m, 1H). |
| 5 | $^1$H NMR (400 MHz, DMSO-d$_6$) δ (ppm) 11.76 (s, 1H), 8.94 (d, J = 7.5 Hz, 1H), 8.39 (s, 1H), 8.21 (s, 1H), 8.14 (d, J = 7.6 Hz, 1H), 7.87 (dd, J = 3.0, 0.9 Hz, 1H), 7.76 (dd, J = 6.3, 2.7 Hz, 2H), 7.28-7.21 (m, 1H), 7.03 (dt, J = 5.2, 2.5 Hz, 2H), 6.81 (d, J = 2.6 Hz, 1H), 6.25-6.06 (m, 2H), 5.60 (dd, J = 10.0, 2.4 Hz, 1H), 4.40-4.29 (m, 2H), 4.04-3.94 (m, 1H), 3.40-3.36 (m, 2H), 2.21 (s, 3H), 1.92 (d, J = 12.6 Hz, 2H), 1.48 (q, J = 11.3 Hz, 2H). |
| 6 | $^1$H NMR (300 MHz, DMSO-d$_6$) δ 9.88 (s, 1H), 8.94 (d, J = 6.0 Hz, 1H), 8.39 (s, 1H), 8.01 (s, 1H), 7.91-7.93 (m, 2H), 7.72-7.74 (m, 1H), 7.30-7.1 (m, 1H), 7.08-7.01 (m, 1H), 6.98-6.71 (m, 3H), 6.28-6.12 (m, 1H), 5.81-5.68 (m, 1H), 3.61-4.25 (m, 3H), 3.38-3.41 (m, 1H), 3.01 (s, 4H), 2.21 (s, 3H). |
| 7 | $^1$H NMR (400 MHz, DMSO-d$_6$) δ (ppm) 8.53 (d, J = 6.8 Hz, 1H), 8.25 (s, 1H), 7.97 (s, 1H), 7.76-7.55(m, 3H), 7.13 (d, J = 8.8 Hz, 2H), 6.99-6.85 (m, 2H), 6.74-6.63 (m, 2H), 6.36-6.32 (m, 1H), 5.76-5.74 (m, 1H), 4.92-4.88 (m, 1H), 4.33-4.19 (m, 1H), 3.32-3.18 (m, 2H), 2.94-2.80 (m, 1H), 2.26 (s, 3H), 2.20-2.01 (m, 3H), 1.99-1.95 (m, 1H). |
| 8 | $^1$H NMR (400 MHz, DMSO-d$_6$) δ (ppm) 9.84 (d, J = 5.2 Hz, 1H), 8.94 (d, J = 7.6 Hz, 1H), 8.39 (s, 1H), 7.99 (d, J = 2.8 Hz, 1H), 7.94-7.81 (m, 1H), 7.75-7.67 (m, 1H), 7.67-7.64 (m, 1H), 7.22-7.19 (m, 1H), 7.04-7.01 (m, 1H), 6.98-6.81 (m, 1H), 6.80-6.77 (m, 2H), 6.22-6.14 (m, 1H), 5.75-5.65 (m, 1H), 3.88-3.80 (m, 4H), 3.30-3.24 (m, 2H), 3.18-3.12 (m, 2H), 2.20 (d, J = 8.0 Hz, 3H), 2.01-1.98 (m, 2H). |
| 9 | $^1$H NMR (400 MHz,DMSO-d$_6$) δ (ppm) 9.0 (s, 1H), 8.31-8.51 (m, 2H), 8 7.90 (s, 1H), 7.61-7.75 (m, 2H), 7.21 (s, 1H), 7.05 (s, 1H), 6.78-6.89 (m, 1H), 6.67 (s, 1H), 6.15-6.20 (m, 1H), 5.61-5.75 (m, 1H), 3.70-3.90 (m, 2H), 3.31-3.68 (m, 4H), 2.10-2.25 (m, 4H), 1.81-2.11(m, 3H), 1.65-1.81 (m, 2H). |
| 10 | $^1$H NMR (400 MHz, DMSO-d$_6$) δ (ppm) 12.48 (s, 1H), 8.94 (d, J = 7.6 Hz, 1H), 8.61 (d, |

| E# | ¹H NMR (ppm) |
|---|---|
|  | J = 2.8 Hz, 1H), 8.39 (s, 1H), 8.01 (s, 1H), 7.88 (d, J = 2.8 Hz, 1H), 7.83-7.79 (m, 1H), 7.70-7.65 (m, 1H), 7.27-7.23 (m, 1H), 7.22-7.16 (m, 1H), 7.07-7.01 (m, 1H), 6.86-6.83 (m, 1H), 6.83-6.79 (m, 1H), 6.36-6.24 (m, 1H), 6.12-6.04 (m, 1H), 5.68-5.59 (m, 1H), 4.74-4.65 (m, 1H), 4.46-4.33 (m, 2H), 4.24-4.13 (m, 1H), 4.12-1.04 (m, 1H), 2.23-2.19 (m, 3H). |
| 11 | ¹H NMR (400 MHz, DMSO-d₆) δ (ppm) 8.52 (d, J = 7.6 Hz, 1H), 8.24 (s, 1H), 8.00-7.99 (m, 1H), 7.62-7.55 (m, 3H), 7.28-7.10 (m, 2H), 6.92-6.85 (m, 2H), 6.63 (s, 1H), 6.54-6.42 (m, 2H), 5.77-5.75 (m, 1H), 4.19-4.09 (m, 1H), 3.93-3.73 (m, 4H), 2.58-2.47 (m, 2H), 2.38-2.24 (m, 3H). |
| 12 | ¹H NMR (300 MHz, DMSO-d₆) δ 8.93-8.95 (m, 1H), 8.38 (s, 1H), 7.57-7.90 (m, 3H), 7.21-7.33 (m, 1H), 7.16-7.18 (m, 1H), 7.03-7.05 (m, 1H), 6.59-6.94 (m, 3H), 5.96-6.23 (m, 1H), 5.29-5.76 (m, 1H), 4.49-4.70 (m, 1H), 4.01-4.30 (m, 1H), 3.56-3.71 (m, 1H), 3.11-3.32 (m, 1H), 2.89-3.01 (m, 1H), 2.61-2.83 (m, 1H), 2.11-2.35 (m, 3H), 2.01-2.10 (m, 1H), 1.80-1.98 (m, 1H), 1.41-1.78 (m, 2H). |
| 13 | ¹H NMR (400 MHz, methanol-d₄) δ (ppm) 8.73 (d, J = 7.6 Hz, 1H), 8.28 (s, 1H), 7.95-7.91 (m, 2H), 7.75 (s, 1H), 7.68 (d, J = 2.8 Hz, 2H), 7.60-7.57 (m, 1H), 7.12 (d, J = 8.8 Hz, 1H), 7.06-7.04 (m, 1H), 6.79 (d, J = 2.4 Hz, 1H), 6.71 (d, J = 2.4 Hz, 1H), 6.21-6.08 (m, 2H), 5.60-5.57 (m, 1H), 4.42-4.39 (m, 2H), 3.77-3.74 (m, 2H), 2.20 (s, 3H). |
| 14 | ¹H NMR (400 MHz, CDCl₃) δ (ppm) 9.48 (s, 1H), 8.52-8.51 (m, 1H), 8.48-8.24 (m, 1H), 8.05-7.93 (m, 1H), 7.89-7.65 (m, 2H), 7.55-7.40 (m, 1H), 7.28-7.08 (m, 1H), 7.03-6.80 (m, 2H), 6.64-6.52 (m, 1H), 6.50-6.10 (m, 2H), 5.70-5.67 (m, 1H), 5.09-4.60 (m, 2H), 4.32-4.16 (m, 2H), 3.90-3.73 (m, 2H), 2.34-2.20 (m, 3H). |
| 15 | ¹H NMR (300 MHz, DMSO-d₆) δ 8.91-9.02 (m, 1H), 8.66-8.69 (m, 1H), 8.48 (s, 1H), 8.34-8.39 (m, 1H), 7.81-7.83 (m, 1H), 7.54-7.70 (m, 2H), 7.12-7.15 (m, 1H), 6.41-6.81 (m,1H), 6.26-6.35 (m, 1H), 6.05-6.11 (m, 1H), 5.63-5.68 (m, 1H), 4.40-4.44 (m, 2H), 4.14-4.24 (m, 2H), 3.99-4.09 (m, 4H), 2.07 (s, 1H). |
| 16 | ¹H NMR (300 MHz, DMSO-d₆) δ 9.87(s,1H), 8.93-8.96 (m, 1H), 8.55 (s, 1H), 7.86-8.08 (m, 2H), 7.71-7.77 (m, 1H), 7.65-7.68 (m, 1H), 7.19-7.25 (m, 1H), 7.02-7.05 (m, 1H), 6.79-6.80 (m, 1H), 6.29-6.38 (m, 2H), 6.08-6.14 (m, 1H), 5.66-5.70 (m, 1H), 4.49 (s, 2H), 4.20-4.24 (m, 2H), 4.00 (s, 4H), 2.20 (s, 3H). |
| 17 | ¹H NMR (400 MHz, methanol-d₄) δ (ppm) 8.75 (d, J = 7.2 Hz, 1H), 8.30 (s, 1H), 7.80 (s, 1H), 7.68-7.60 (m, 3H), 7.20-7.10 (m, 1H), 7.09-7.07 (m, 1H), 6.86-6.85 (m, 1H), 6.75 (s, 1H), 6.36-6.26 (m, 2H), 5.80-5.74 (m, 1H), 4.50 (s, 1H), 4.26 (s, 2H), 4.18-4.02 (m, 2H), 3.66 (s, 1H), 2.80-2.78 (m, 2H), 2.55-2.46 (m, 2H), 2.25 (s, 3H). |
| 18 | ¹H NMR (400 MHz, methanol-d₄) δ (ppm) 8.75 (d, J = 7.6 Hz, 1H), 8.30 (s, 1H), 7.85-7.82 (m, 3H), 7.52-7.51 (m, 1H), 7.20-7.18 (m, 1H), 7.09-7.07 (m, 1H), 6.88 (d, J = 3.2 Hz, 1H), 6.81 (d, J = 2.4 Hz, 1H), 5.71-5.58 (m, 1H), 5.28-5.23 (m, 1H), 4.84-4.82 (m, 1H), 4.20-4.16 (m, 2H), 3.90-3.87 (m, 3H), 2.26 (s, 3H). |
| 19 | ¹H NMR (400 MHz, DMSO-d₆) δ (ppm) 8.94-8.92 (m, 1H), 8.59 (s, 1H), 8.38 (s, 1H), 8.31-8.24 (m, 1H), 8.14-8.07 (m, 1H), 7.88-7.86 (m, 2H), 7.64-7.62 (m, 2H), 7.19-7.16 (m, 1H), 7.03-6.99 (m, 1H), 6.80-6.76 (m, 2H), |

| E# | ¹H NMR (ppm) |
|---|---|
|  | 5.60-5.93 (m, 1H), 5.44-5.39 (m, 1H), 5.36-5.29 (m, 1H), 4.88-4.73 (m, 2H), 4.71-4.48 (m, 1H), 4.38-4.33 (m, 1H), 2.15 (s, 3H) |
| 21 | ¹H NMR (400 MHz, DMSO-d₆) δ (ppm) 8.96 (d, J = 7.4 Hz, 1H), 8.53 (s, 1H), 8.39 (s, 1H), 7.90 (s, 1H), 7.81-7.47 (m, 3H), 7.22 (d, J = 8.6 Hz, 1H), 7.05 (d, J = 7.5 Hz, 1H), 6.81 (s, 1H), 6.75-6.56 (m, 3H), 4.64-4.50 (m, 1H), 4.24-7.07 (m, 1H), 3.75-3.59 (m, 1H), 3.03 (d, J = 4.9 Hz, 2H), 2.91-2.77 (m, 1H), 2.26-2.10 (m, 10H), 2.04-1.91 (m, 2H), 1.67-1.45 (m, 2H). |
| 22 | ¹H NMR (400 MHz, DMSO-d₆) δ (ppm) 9.89 (s, 1H), 8.93 (d, J = 7.6 Hz,1H), 8.38 (s, 1H), 8.01 (s, 1H), 7.96-7.88 (m, 2H), 7.69-7.65 (m, 1H), 7.26-7.20 (m, 1H), 7.06-7.00 (m, 1H), 6.89-6.84 (m, 1H), 6.82-6.76 (m, 1H), 6.73-6.66 (m, 2H), 4.89-3.40 (m, 4H), 3.12-2.88 (m, 2H), 2.24-2.19 (m, 3H), 2.18-2.13 (m, 6H). |
| 23 | ¹H NMR (400 MHz, DMSO-d₆) δ (ppm) 8.95 (d, J = 7.5 Hz, 1H), 8.73-8.33 (m, 2H), 7.97-7.36 (m, 4H), 7.20 (d, J = 8.5 Hz, 1H), 7.08-7.00 (m, 1H), 6.87-6.75 (m, 1H), 6.62 (s, 1H), 4.63-4.47 (m, 1H), 4.09-3.86 (m, 1H), 3.73-3.57 (m, 1H), 3.27-3.15 (m, 1H), 3.07-2.85 (m, 1H), 2.78-2.64 (m, 1H), 2.35 (t, J = 7.4 Hz, 2H), 2.25-2.18 (m, 4H), 2.11 (s, 6H), 2.02-1.88 (m, 2H), 1.71-1.40 (m, 4H). |
| 37 | ¹H NMR (499 MHz, DMSO-d₆) δ = 8.94 (d, J = 7.4 Hz, 1H), 8.51 (s, 1H), 8.38 (s, 1H), 7.95 (s, 1H), 7.81 (d, J = 2.7 Hz, 1H), 7.70-7.64 (m, 2H), 7.21 (d, J = 8.5 Hz, 1H), 7.03 (dd, J = 2.6, 7.5 Hz, 1H), 6.97 (d, J = 2.7 Hz, 1H), 6.79 (d, J = 2.7 Hz, 1H), 6.63-6.57 (m, 1H), 6.20 (br d, J = 15.3 Hz, 1H), 4.74-4.64 (m, 2H), 4.41 (br t, J = 8.9 Hz, 1H), 4.27-4.20 (m, 1H), 4.02-3.95 (m, 1H), 3.57 (br s, 4H), 3.09 (br s, 2H), 2.42-2.29 (m, 4H), 2.19 (s, 3H) |
| 38 | ¹H NMR (400 MHz, Chloroform-d) δ 8.52 (s, 1H), 8.25 (s, 1H), 7.99 (s, 1H), 7.63 (s, 1H), 7.57 (s, 1H), 7.11 (s, 1H), 6.91-6.85 (m, 3H), 6.73 (s, 1H), 6.12 (d, J = 16.0 Hz, 1H), 4.78 (s, 1H), 4.66 (s, 1H), 4.43 (s, 1H), 4.33 (s, 2H), 3.85 (d, J = 14.7 Hz, 2H), 3.60 (s, 2H), 3.41 (s, 2H), 3.34 (s, 2H), 3.28 (s, 2H), 2.25 (s, 3H). |
| 42 | ¹H NMR (499 MHz, CHLOROFORM-d) δ = 8.50 (d, J = 7.4 Hz, 1H), 8.23 (s, 1H), 8.00 (s, 1H), 7.63 (d, J = 2.7 Hz, 1H), 7.60 (dd, J = 2.6, 8.6 Hz, 1H), 7.57 (d, J = 2.5 Hz, 1H), 7.10 (d, J = 8.5 Hz, 2H), 6.94 (td, J = 6.2, 15.3 Hz, 1H), 6.89 (dd, J = 2.7, 7.4 Hz, 1H), 6.85 (d, J = 2.5 Hz, 1H), 6.73 (d, J = 2.7 Hz, 1H), 6.11 (br d, J = 15.3 Hz, 1H), 4.83-4.72 (m, 1H), 4.65 (br t, J = 8.5 Hz, 1H), 4.46-4.37 (m, 1H), 4.37-4.25 (m, 2H), 3.33 (s, 3H), 3.23 (br d, J = 3.3 Hz, 1H), 3.21-3.14 (m, 2H), 2.74 (br s, 2H), 2.34-2.19 (m, 5H), 1.90 (br d, J = 12.0 Hz, 2H), 1.63 (br d, J = 8.8 Hz, 2H) |
| 49 | ¹H NMR (499 MHz, METHANOL-d4) δ ppm 8.71-8.79 (m, 1 H) 8.28 (s, 1 H) 7.95 (d, J-2.5 Hz, 1 H) 7.89 (s, 1 H) 7.72 (dd, J = 8.6, 2.6 Hz, 1 H) 7.48 (d, J = 3.0 Hz, 1 H) 7.19 (d, J-8.5 Hz, 1 H) 7.05-7.08 (m, 1 H) 6.78 (d, J = 2.5 Hz, 1 H) 6.58 (br d, J = 2.2 Hz, 1 H) 5.69 (br s, 1 H) 5.54 (br s, 1 H) 4.47 (br d, J-3.8 Hz, 1 H) 3.95-4.08 (m, 1 H) 3.58-3.86 (m, 4 H) 3.41-3.54 (m, 2 H) 2.51 (br s, 6 H) 2.25 (s, 6 H) 1.89 (br s, 2 H). |
| 50 | ¹H NMR (499 MHz, CHLOROFORM-d) δ ppm 11.22 (s, 1 H) 8.47 (d, J = 7.4 Hz, 1 H) 8.06 (s, 1 H) 7.99 (s, 1 H) 7.79 (d, J = 2.5 Hz, 1 H) |

| E# | $^1$H NMR (ppm) |
|---|---|
|  | 7.72 (dd, J = 8.6, 2.6 Hz, 1 H) 7.48 (d, J = 2.7 Hz, 1 H) 7.07 (d, J = 8.8 Hz, 1 H) 6.91 (dd, J = 7.5, 2.6 Hz, 1 H) 6.67-6.81 (m, 2 H) 6.43-6.53 (m, 2 H) 5.36 (br s, 1 H) 4.57 (br d, J = 11.8 Hz, 1 H) 3.92 (br d, J = 12.0 Hz, 1 H) 3.67 (br t, J = 12.5 Hz, 1 H) 3.23 (br t, J = 12.2 Hz, 1 H) 3.10 (br d, J = 6.0 Hz, 2 H) 2.27 (s, 6 H) 2.22 (s, 3 H) 1.89-2.19 (m, 4 H). |
| 51 | $^1$H NMR (499 MHz, CHLOROFORM-d) δ ppm 10.63 (s, 1 H) 8.48 (d, J = 7.4 Hz, 1 H) 8.13 (s, 1 H) 8.02 (s, 1 H) 7.78-7.82 (m, 1 H) 7.70-7.74 (m, 1 H) 7.52-7.57 (m, 1 H) 7.08 (d, J = 8.8 Hz, 1 H) 6.83-6.92 (m, 2 H) 6.75-6.80 (m, 1 H) 6.67 (d, J = 3.0 Hz, 1 H) 6.19-6.27 (m, 1 H) 4.52-4.66 (m, 3 H) 4.40 (br d, J = 11.0 Hz, 1 H) 3.26 (br d, J = 5.5 Hz, 2 H) 3.08 (s, 1 H) 2.29-2.38 (m, 6 H) 2.19-2.25 (m, 3 H). |
| 52 | $^1$H NMR (499 MHz, CHLOROFORM-d) δ ppm 10.54 (s, 1 H) 8.49 (d, J = 7.4 Hz, 1 H) 8.22 (s, 1 H) 8.04 (s, 1 H) 7.66-7.74 (m, 2 H) 7.54-7.59 (m, 1 H) 7.09 (d, J = 8.8 Hz, 1 H) 6.89 (dd, J = 7.4, 2.7 Hz, 1 H) 6.78-6.86 (m, 2 H) 6.56 (d, J = 2.7 Hz, 1 H) 4.51-4.72 (m, 2 H) 3.94-4.16 (m, 2 H) 3.36-3.75 (m, 4 H) 3.29 (s, 3 H) 3.16-3.25 (m, 1 H) 2.41-2.78 (m, 6 H) 2.32-2.40 (m, 2 H) 2.25 (s, 3 H). |
| 53 | $^1$H NMR (499 MHz, CHLOROFORM-d) δ ppm 8.48 (d, J = 7.7 Hz, 1 H) 8.21 (s, 1 H) 8.05 (s, 1 H) 7.79-8.01 (m, 1 H) 7.51-7.71 (m, 3 H) 7.00-7.14 (m, 1 H) 6.79-6.98 (m, 3 H) 6.50-6.64 (m, 2 H) 5.89-6.07 (m, 1 H) 4.33-4.54 (m, 2 H) 3.84-4.06 (m, 2 H) 3.15 (br s, 2 H) 2.68 (br d, J = 1.6 Hz, 2 H) 2.20-2.39 (m, 9 H). |
| 60 | $^1$H NMR (499 MHz, DMSO-d$_6$) δ = 8.97-8.91 (m, 1H), 8.52 (s, 1H), 8.42-8.36 (m, 1H), 7.95 (s, 1H), 7.81 (d, J = 2.7 Hz, 1H), 7.71-7.64 (m, 2H), 7.21 (d, J = 8.5 Hz, 1H), 7.03 (dd, J = 2.7, 7.4 Hz, 1H), 6.97 (d, J = 2.5 Hz, 1H), 6.79 (d, J = 2.7 Hz, 1H), 6.61-6.57 (m, 1H), 6.30-6.15 (m, 1H), 4.75-4.63 (m, 2H), 4.47-4.34 (m, 2H), 4.31-4.21 (m, 2H), 4.02-3.95 (m, 1H), 3.94-3.75 (m, 2H), 3.67-3.47 (m, 2H), 2.96-2.63 (m, 2H), 2.19 (s, 3H), 1.86-1.54 (m, 2H) |
| 61 | $^1$H NMR (499 MHz, DMSO-d$_6$) δ = 8.98-8.91 (m, 1H), 8.54 (s, 1H), 8.40-8.36 (m, 1H), 7.96 (s, 1H), 7.81 (d, J = 2.7 Hz, 1H), 7.72-7.64 (m, 2H), 7.21 (d, J = 8.8 Hz, 1H), 7.03 (dd, J = 2.6, 7.5 Hz, 1H), 6.97 (d, J = 2.2 Hz, 1H), 6.78 (d, J = 2.7 Hz, 1H), 6.66-6.58 (m, 1H), 6.42-6.25 (m, 1H), 4.77-4.66 (m, 2H), 4.47-4.36 (m, 3H), 4.32-4.21 (m, 2H), 4.09-4.04 (m, 1H), 3.95-3.85 (m, 1H), 3.64-3.52 (m, 2H), 3.08-2.75 (m, 2H), 2.19 (s, 3H), 1.94-1.65 (m, 2H) |
| 62 | $^1$H NMR (499 MHz, DMSO-d$_6$) δ = 8.94 (d, J = 7.4 Hz, 1H), 8.51 (s, 1H), 8.38 (s, 1H), 7.95 (s, 1H), 7.80 (d, J = 2.7 Hz, 1H), 7.72-7.61 (m, 2H), 7.20 (d, J = 8.5 Hz, 1H), 7.02 (dd, J = 2.6, 7.5 Hz, 1H), 6.97 (d, J = 2.7 Hz, 1H), 6.79 (d, J = 2.7 Hz, 1H), 6.62-6.54 (m, 1H), 6.24-6.13 (m, 1H), 4.74-4.58 (m, 3H), 4.45-4.37 (m, 1H), 4.33-4.23 (m, 1H), 4.03-3.97 (m, 1H), 3.17-3.04 (m, 2H), 2.63-2.52 (m, 1H), 2.48-2.41 (m, 1H), 2.30 (br d, J = 8.2 Hz, 2H), 2.18 (s, 3H), 1.91-1.79 (m, 2H), 1.70 (br s, 2H) |
| 65 | $^1$H NMR (499 MHz, DMSO-d$_6$) δ = 8.95 (d, J = 7.4 Hz, 1H), 8.51 (s, 1H), 8.40-8.38 (m, 1H), 7.92-7.88 (m, 1H), 7.72 (d, J = 2.7 Hz, 1H), 7.65 (d, J = 2.5 Hz, 1H), 7.63-7.58 (m, 1H), 7.22 (d, J = 8.5 Hz, 1H), 7.03 (dd, J = 2.6, 7.5 Hz, 1H), 6.79 (d, J = 2.5 Hz, 1H), 6.71 (d, J = 2.5 Hz, 1H), 6.65-6.59 (m, 1H), 6.51-6.43 (m, 1H), 4.63-4.51 (m, 1H), 4.22-4.09 (m, 1H), 3.73-3.62 (m, 1H), 3.04-2.98 (m, 1H), 2.92-2.79 (m, 1H), 2.77-2.70 (m, 1H), 2.21-2.19 (m, 3H), 2.18-2.15 (m, 3H), 2.02-1.89 (m, 4H), 1.79-1.67 (m, 2H), 1.62-1.45 (m, 4H) |
| 68 | $^1$H NMR (499 MHz, DMSO-d$_6$) δ = 9.97-9.74 (m, 1H), 8.93 (d, J = 7.4 Hz, 1H), 8.40-8.35 (m, 1H), 8.02-7.91 (m, 2H), 7.89-7.80 (m, 1H), 7.65 (d, J = 2.7 Hz, 1H), 7.25 (d, J = 8.5 Hz, 1H), 7.06-7.01 (m, 1H), 6.86-6.76 (m, 2H), 6.63-6.45 (m, 2H), 4.92-4.65 (m, 1H), 3.12-3.06 (m, 2H), 3.03-2.92 (m, 4H), 2.88-2.75 (m, 3H), 2.24-2.21 (m, 3H), 2.18-2.15 (m, 3H), 2.01-1.95 (m, 3H), 1.94-1.87 (m, 2H), 1.80-1.67 (m, 2H) |
| 70 | $^1$H NMR (499 MHz, DMSO-d$_6$) δ = 9.67-9.54 (m, 1H), 8.96-8.89 (m, 1H), 8.38-8.36 (m, 1H), 7.98-7.94 (m, 1H), 7.84-7.77 (m, 2H), 7.69-7.64 (m, 1H), 7.24-7.20 (m, 1H), 7.04-7.00 (m, 1H), 6.87-6.84 (m, 1H), 6.79-6.77 (m, 1H), 6.65-6.55 (m, 2H), 5.28 (br s, 1H), 3.21-2.91 (m, 9H), 2.19 (s, 9H), 2.14-2.02 (m, 4H) |
| 72 | $^1$H NMR (499 MHz, DMSO-d$_6$) δ = 9.67-9.57 (m, 1H), 8.93 (d, J = 7.4 Hz, 1H), 8.40-8.35 (m, 1H), 7.99-7.95 (m, 1H), 7.82-7.74 (m, 2H), 7.67 (d, J = 2.7 Hz, 1H), 7.26-7.20 (m, 1H), 7.04-6.99 (m, 1H), 6.87 (br s, 1H), 6.81-6.66 (m, 2H), 6.16-6.04 (m, 1H), 5.72-5.63 (m, 1H), 5.36-5.19 (m, 1H), 3.30-3.23 (m, 2H), 3.22-3.04 (m, 4H), 3.02-2.94 (m, 1H), 2.19 (s, 3H), 2.15-2.02 (m, 2H) |
| 73 | $^1$H NMR (499 MHz, DMSO-d$_6$) δ = 10.07-9.90 (m, 1H), 8.93 (d, J = 7.7 Hz, 1H), 8.38 (s, 1H), 7.99 (s, 1H), 7.94-7.80 (m, 2H), 7.65 (br s, 1H), 7.25 (d, J = 8.8 Hz, 1H), 7.03 (dd, J = 2.7, 7.4 Hz, 1H), 6.86-6.76 (m, 2H), 6.67-6.52 (m, 2H), 4.45 (br t, J = 11.8 Hz, 1H), 3.19 (br d, J = 11.5 Hz, 2H), 3.14-3.06 (m, 1H), 3.06-2.88 (m, 5H), 2.20 (s, 6H), 2.19 (br s, 3H), 2.16-2.03 (m, 2H), 1.83-1.63 (m, 2H) |
| 74 | $^1$H NMR (499 MHz, DMSO-d$_6$) δ = 10.09-9.82 (m, 1H), 8.95-8.92 (m, 1H), 8.48-8.31 (m, 1H), 7.99 (s, 1H), 7.95-7.83 (m, 2H), 7.65 (d, J = 2.7 Hz, 1H), 7.26 (d, J = 8.8 Hz, 1H), 7.06-7.01 (m, 1H), 6.93-6.83 (m, 1H), 6.82-6.72 (m, 1H), 6.17-6.06 (m, 1H), 5.73-5.64 (m, 1H), 4.55-4.35 (m, 1H), 3.19 (br d, J = 11.8 Hz, 2H), 3.08-2.94 (m, 4H), 2.93-2.87 (m, 1H), 2.24-2.17 (m, 3H), 2.17-2.04 (m, 2H), 1.83-1.64 (m, 2H) |
| 82 | $^1$H NMR (499 MHz, CHLOROFORM-d) δ = 8.51 (d, J = 7.4 Hz, 1H), 8.23 (s, 1H), 8.01 (s, 1H), 7.64 (d, J = 2.7 Hz, 1H), 7.63-7.57 (m, 2H), 7.11 (d, J = 8.5 Hz, 1H), 7.02 (br s, 1H), 6.94 (td, J = 5.9, 15.4 Hz, 1H), 6.89 (dd, J = 2.5, 7.4 Hz, 1H), 6.86 (d, J = 2.5 Hz, 1H), 6.74 (d, J = 2.7 Hz, 1H), 6.48-6.12 (m, 1H), 5.37-5.12 (m, 1H), 4.82 (br s, 1H), 4.72-4.61 (m, 1H), 4.46 (br s, 1H), 4.40-4.23 (m, 2H), 3.65-3.27 (m, 2H), 3.10-2.88 (m, 2H), 2.30-2.24 (m, 3H), 2.24-2.10 (m, 2H), 1.84-1.45 (m, 2H) |
| 83 | $^1$H NMR (499 MHz, CHLOROFORM-d) δ = 8.51 (d, J = 7.7 Hz, 1H), 8.24 (s, 1H), 8.01 (s, 1H), 7.64 (d, J = 2.7 Hz, 1H), 7.61 (dd, J = 2.6, 8.6 Hz, 1H), 7.58 (d, J = 2.5 Hz, 1H), 7.11 (d, J = 8.5 Hz, 1H), 7.07-7.03 (m, 1H), 6.96 (td, J = 5.7, 15.3 Hz, 1H), 6.89 (dd, J = 2.7, 7.4 Hz, 1H), 6.86 (d, J = 2.5 Hz, 1H), 6.73 (d, J = 3.0 Hz, 1H), 6.17 (br d, J = 15.6 Hz, 1H), 5.30-5.08 (m, 1H), 4.78 (br t, J = 7.7 Hz, 1H), 4.72-4.62 (m, 1H), 4.47-4.39 (m, 1H), 4.36-4.28 (m, 2H), 3.34 (br s, 2H), |

| E# | ¹H NMR (ppm) |
|---|---|
|  | 2.99-2.86 (m, 2H), 2.86-2.68 (m, 1H), 2.64-2.44 (m, 1H), 2.25 (s, 3H), 2.21-2.06 (m, 2H) |
| 84 | ¹H NMR (499 MHz, CHLOROFORM-d) δ = 8.51 (d, J = 7.4 Hz, 1H), 8.24 (s, 1H), 8.01 (s, 1H), 7.64 (d, J = 2.7 Hz, 1H), 7.62-7.56 (m, 2H), 7.11 (d, J = 8.5 Hz, 1H), 7.03 (s, 1H), 6.97-6.87 (m, 2H), 6.85 (d, J = 2.5 Hz, 1H), 6.74 (d, J = 2.7 Hz, 1H), 6.16 (br d, J = 15.3 Hz, 1H), 4.78 (br t, J = 7.9 Hz, 1H), 4.72-4.63 (m, 1H), 4.47-4.37 (m, 1H), 4.37-4.25 (m, 2H), 3.30 (br d, J = 5.7 Hz, 2H), 2.93 (br t, J = 13.0 Hz, 2H), 2.80 (br t, J = 6.8 Hz, 2H), 2.35-2.26 (m, 2H), 2.25 (s, 3H) |
| 85 | ¹H NMR (499 MHz, CHLOROFORM-d) δ = 8.51 (d, J = 7.7 Hz, 1H), 8.24 (s, 1H), 8.01 (s, 1H), 7.65 (d, J = 2.7 Hz, 1H), 7.62-7.56 (m, 2H), 7.11 (d, J = 8.5 Hz, 1H), 7.02 (s, 1H), 6.99-6.88 (m, 2H), 6.85 (d, J = 2.7 Hz, 1H), 6.74 (d, J = 2.7 Hz, 1H), 6.12 (br d, J = 14.2 Hz, 1H), 4.84-4.73 (m, 1H), 4.68 (br t, J = 11.4 Hz, 1H), 4.48-4.39 (m, 1H), 4.37-4.27 (m, 2H), 3.21 (br s, 2H), 2.57 (br s, 2H), 2.27-2.20 (m, 3H), 2.08-1.93 (m, 4H), 1.57 (br s, 2H) |
| 86 | ¹H NMR (400 MHz, Chloroform-d) δ (ppm) 8.51 (d, J = 7.5 Hz, 1H), 8.25 (s, 1H), 7.78 (s, 1H), 7.60-7.55 (m, 1H), 7.37 (d, J = 2.6 Hz, 1H), 7.35-7.28 (m, 1H), 7.19 (d, J = 8.4 Hz, 1H), 7.11 (d, J = 2.6 Hz, 1H), 6.95-6.90 (m, 1H), 6.83-6.80 (m, 1H), 6.62 (d, J = 2.6 Hz, 1H), 6.35 (s, 1H), 6.16 (d, J = 15.5 Hz, 1H), 4.14-4.10 (m, 1H), 3.85-3.80 (m, 2H), 3.68-3.65 (m, 2H), 3.35 (d, J = 6.3 Hz, 2H), 2.49 (s, 4H), 2.47-2.45 (m, 2H), 2.29 (s, 3H). |
| 87 | ¹H NMR (400 MHz, Chloroform-d) δ 8.51 (d, J = 7.6 Hz, 1H), 8.24 (s, 1H), 8.01 (s, 1H), 7.70-7.52 (m, 3H), 7.15-6.99 (m, 3H), 6.95-6.79 (m, 2H), 6.73 (d, J = 2.9 Hz, 1H), 6.13 (d, J = 15.1 Hz, 1H), 4.85-4.62 (m, 2H), 4.48-4.27 (m, 3H), 3.54 (dd, J = 4.9, 2.0 Hz, 2H), 2.25 (s, 3H), 1.70-1.68 (m, 2H). |
| 88 | ¹H NMR (400 MHz, DMSO-d₆) δ (ppm) 9.03 (s, 1H), 8.96-8.91 (m, 1H), 8.51 (s, 1H), 8.42-8.35 (m, 1H), 8.16-7.99 (m, 1H), 7.65-7.57 (m, 1H), 7.57-7.46 (m, 1H), 7.28-7.21 (m, 1H), 7.18-7.06 (m, 1H), 7.01-6.99 (m, 1H), 6.87-6.77 (m, 1H), 6.69-6.57 (m, 2H), 4.58-4.43 (m, 1H), 4.20-4.06 (m, 1H), 3.49 (s, 1H), 3.09-3.03 (m, 2H), 2.24-2.16 (m, 9H), 1.95-1.83 (m, 2H), 1.81-1.65 (m, 2H), 1.06-0.97 (m, 1H). |
| 89 | ¹H NMR (400 MHz, Chloroform-d) δ (ppm) 8.55-8.48 (m, 1H), 8.24 (s, 1H), 7.97 (s, 1H), 7.67-7.50 (m, 4H), 7.14-7.07 (m, 1H), 6.94-6.84 (m, 3H), 6.79-6.74 (m, 1H), 5.14-5.05 (m, 1H), 4.77-4.64 (m, 2H), 4.45-4.33 (m, 2H), 2.25 (s, 3H), 1.32 (s, 9H). |
| 90 | ¹H NMR (400 MHz, DMSO-d₆) δ 9.56 (s, 1H), 8.51 (t, J = 5.8 Hz, 1H), 8.36 (d, J = 2.4 Hz, 1H), 8.27 (d, J = 2.4 Hz, 1H), 7.93 (s, 1H), 7.76-7.68 (m, 2H), 7.68-7.62 (m, 2H), 7.56 (d, J = 7.9 Hz, 1H), 6.63 (d, J = 2.5 Hz, 1H), 6.58 (dt, J = 14.9, 7.2 Hz, 1H), 6.26 (d, J = 15.4 Hz, 1H), 4.20 (dd, J = 12.4, 4.9 Hz, 2H), 3.89 (dd, J = 12.6, 5.2 Hz, 3H), 2.76 (d, J = 4.1 Hz, 6H), 1.26 (dd, J = 6.7, 5.3 Hz, 2H). |
| 91 | ¹H NMR (400 MHz, Chloroform-d) δ (ppm) 8.55-8.53 (m, 1H), 8.28-8.23 (m, 1H), 8.03 (s, 1H), 7.66 (s, 1H), 7.63-7.58 (m, 2H), 7.29-7.30 (m, 2H), 7.13-7.14 (m, 1H), 7.04 (s, 1H), 6.96-6.84 (m, 1H), 6.88 (s, 2H), 6.76 (s, 1H), 6.17-6.07 (m, 1H), 4.79 (s, 1H), 4.68 (s, 1H), 4.45 (s, 1H), 4.34 (s, 1H), 3.71-3.59 (m, 2H), 3.63 (s, 2H), 3.41 (s, 1H), 3.19- |

| E# | ¹H NMR (ppm) |
|---|---|
|  | 3.21 (m, 1H), 2.30-2.23 (m, 1H), 1.84-1.86 (m, 1H). |
| 92 | ¹H NMR (400 MHz, DMSO-d₆) δ (ppm) 8.95 (s, 1H), 8.54 (s, 1H), 8.38 (s, 1H), 8.18 (s, 1H), 7.95 (s, 1H), 7.82 (s, 1H), 7.67-7.33 (m, 2H), 7.22-7.12 (m, 1H), 7.10-6.79 (m, 2H), 6.78-6.56 (m, 1H), 5.70-5.58 (m, 1H), 4.80-4.63 (m, 2H), 4.51-4.37 (m, 2H), 4.08-4.04 (m, 1H), 3.70-3.58 (m, 1H), 3.03-2.95 (m, 1H), 2.19-2.13 (m, 6H), 2.04-1.81 (m, 2H), 1.71 (s, 1H), 1.47 (s, 1H). |
| 93 | ¹H NMR (400 MHz, methanol-d₄) δ (ppm) 8.74 (s 1H), 8.32 (s, 2H), 7.72 (s, 1H), 7.62 (s, 1H), 7.56-7.41 (m, 2H), 7.19-7.17 (m, 1H), 7.10-7.06 (m, 1H), 6.95-6.88 (m, 1H), 6.84 (s, 1H), 6.77-6.70 (m, 1H), 6.64-6.62 (m, 1H), 3.96-3.61 (m, 6H), 3.55-3.39 (m, 1H), 2.82-2.73 (m, 6H), 2.35-2.30 (m, 1H), 2.24 (s, 5H), 1.98-1.73 (m, 3H). |
| 94 | ¹H NMR (400 MHz, Chloroform-d) δ (ppm) 8.56-8.49 (m, 1H), 8.28-8.21 (m, 1H), 8.06-7.98 (m, 1H), 7.65-7.67 (m, 1H), 7.62 (s, 2H), 7.60 (d, J = 2.5 Hz, 1H), 7.32-7.24 (m, 2H), 7.12 (d, J = 10.7 Hz, 2H), 6.99 (s, 1H), 6.90-7.00 (m, 2H), 6.75-6.82 (m, 1H), 6.12-6.14 (m, 1H), 4.79 (s, 1H), 4.68 (s, 1H), 4.44 (s, 1H), 4.33 (s, 3H), 3.16 (s, 2H), 2.43 (s, 1H), 2.29-2.22 (m, 3H), 2.04 (m, 3H), 1.45 (s, 2H). |
| 95 | ¹H NMR (400 MHz, DMSO-d₆) δ (ppm) 8.57-8.37 (m, 1H), 8.32-8.13 (m, 1H), 8.05-7.88 (m, 1H), 7.71-7.47 (m, 3H), 7.16-7.03 (m, 4H), 7.01-6.78 (m, 4H), 6.68-6.53 (m, 1H), 6.17-5.96 (m, 1H), 4.51-4.36 (m, 1H), 4.31-4.13 (m, 2H), 4.11-4.00 (m, 1H), 3.94-3.79 (m, 1H), 3.18-3.01 (m, 2H), 2.91-2.73 (m, 2H), 2.70-2.52 (m, 2H), 2.41-2.15 (m, 9H). |
| 96 | ¹H NMR (400 MHz, methanol-d₄) δ (ppm) 8.79-8.73 (m, 1H), 8.33-8.28 (m, 1H), 7.88-7.74 (m, 2H), 7.70-7.55 (m, 2H), 7.24-7.16 (m, 1H), 7.13-7.08 (m, 1H), 6.95-6.90 (m, 1H), 6.90-6.80 (m, 1H), 6.79-6.76 (m, 1H), 6.75-6.67 (m, 1H), 4.77-4.59 (m, 1H), 4.27-4.17 (m, 1H), 3.64-3.48 (m, 1H), 3.24-3.11 (m, 2H), 2.85-2.70 (m, 2H), 2.34-2.21 (m, 8H), 2.20-2.08 (m, 3H), 2.04-1.91 (m, 1H), 1.76-1.62 (m, 1H). |
| 97 | ¹H NMR (400 MHz, Chloroform-d) δ (ppm) 8.51 (dd, J = 7.3, 3.5 Hz, 1H), 8.22 (d, J = 1.8 Hz, 1H), 7.99 (s, 1H), 7.66-7.58 (m, 2H), 7.20 (s, 1H), 7.10 (d, J = 8.2 Hz, 1H), 6.94-6.83 (m, 3H), 6.76 (d, J = 2.9 Hz, 1H), 6.50 (d, J = 15.5 Hz, 1H), 4.89 (s, 1H), 4.63 (d, J = 8.8 Hz, 1H), 4.45-4.35 (m, 2H), 4.30-4.29 (m, 1H), 3.69-3.68 (m, 1H), 3.13-3.11 (m, 1H), 3.08 (s, 1H), 2.24 (s, 3H), 2.08-1.96 (m, 4H), 1.52-1.42 (m, 1H), 1.30-1.24 (m, 2H). |
| 98 | ¹H NMR (400 MHz, DMSO-d₆) δ (ppm) 8.98-8.91 (m, 1H), 8.66-8.59 (m, 1H), 8.41-8.36 (m, 1H), 7.94-7.90 (m, 1H), 7.80-7.74 (m, 1H), 7.66-7.55 (m, 2H), 7.25-7.19 (m, 1H), 7.07-7.01 (m, 1H), 6.85-6.75 (m, 2H), 6.70-6.58 (m, 1H), 6.48-6.37 (m, 1H), 4.29-4.04 (m, 2H), 3.73-3.59 (m, 2H), 3.57-3.42 (m, 1H), 3.08-2.98 (m, 2H), 2.22-2.08 (m, 11H). |
| 101 | ¹H NMR (400 MHz, DMSO-d₆) δ (ppm) 8.42(s, 1H), 8.18 (s, 1H), 7.91 (s, 1H), 7.78(d, J = 2.7 Hz, 1H), 7.61-7.52(m, 2H), 7.47(dd, J = 8.6, 2.6 Hz,1H), 7.10(d, J = 2.2 Hz, 1H), 7.00(dd, J = 8.7, 2.4 Hz, 1H), 6.95(d, J = 2.8 Hz, 1H), 6.86(d, J = 8.6 Hz, 1H), 6.61(dt, J = 15.4, 6.3 Hz, 1H), 4.69(d,J = 5.4 Hz, 2H), 4.41(t, J = 8.7 Hz, 1H), 4.27(s, 1H), 4.03(dd, J = 9.6, 5.0 Hz, 1H), 3.84(s, 3H), 3.20(s, 2H), 2.26-2.19(m, 10H). |

| E# | ¹H NMR (ppm) |
|---|---|
| 102 | ¹H NMR (400 MHz, Chloroform-d) δ (ppm) 8.52 (dd, J = 7.3, 0.9 Hz, 1H), 8.25 (s, 1H), 8.02 (s, 1H), 7.68-7.57 (m, 3H), 7.28 (d, J = 1.8 Hz, 1H), 7.12 (d, J = 8.6 Hz, 1H), 7.07 (s, 1H), 6.94-6.81 (m, 3H), 6.74 (d, J = 2.8 Hz, 1H), 6.15 (d, J = 15.4 Hz, 1H), 4.82 (d, J = 8.4 Hz, 1H), 4.68 (s, 1H), 4.45 (s, 1H), 4.33 (s, 2H), 3.36-3.27 (m, 3H), 2.28 (d, J = 8.7 Hz, 3H), 2.03 (d, J = 6.2 Hz, 1H), 1.34 (s, 1H), 1.28 (s, 2H). |
| 103 | ¹H NMR (400 MHz, DMSO-d₆) δ (ppm) 9.63 (s, 1H), 8.97 (d, J = 7.3 Hz, 1H), 8.45 (d, J = 10.9 Hz, 2H), 8.10 (s, 1H), 8.05 (s, 1H), 7.85 (s, 1H), 7.79 (s, 1H), 7.65 (s, 1H), 7.60 (s, 1H), 7.21 (d, J = 8.7 Hz, 1H), 7.06 (dd, J = 7.5, 2.6 Hz, 1H), 6.81 (d, J = 2.6 Hz, 1H), 6.76 (d, J = 2.7 Hz, 1H), 6.53 (m, J = 14.7, 7.2 Hz, 1H), 6.21 (m, J = 15.4, 1.3 Hz, 1H), 4.30 (t, J = 6.1 Hz, 2H), 3.83 (t, J = 5.8 Hz, 2H), 3.64 (q, J = 6.0 Hz, 2H), 2.72 (d, J = 4.3 Hz, 6H), 2.17 (s, 3H). |
| 104 | ¹H NMR (400 MHz, DMSO-d₆) δ 8.86 (d, J = 7.5 Hz, 1H), 8.32 (s, 1H), 7.92-7.82 (m, 1H), 7.72-7.50 (m, 3H), 7.17 (d, J = 8.4 Hz, 1H), 6.99 (dd, J = 7.4, 2.5 Hz, 1H), 6.87 (d, J = 2.2 Hz, 1H), 6.67 (dd, J = 15.3, 11.7 Hz, 2H), 6.15 (dd, J = 16.3, 4.7 Hz, 1H), 5.64 (d, J = 10.7 Hz, 1H), 4.60 (d, J = 20.7 Hz, 1H), 3.85 (dd, J = 8.7, 5.1 Hz, 1H), 3.57 (s, 1H), 3.47 (d, J = 14.1 Hz, 1H), 3.36 (d, J = 11.2 Hz, 1H), 2.80 (d, J = 13.1 Hz, 1H), 2.22 (s, 3H), 1.93-1.75 (m, 3H), 1.69 (d, J = 9.8 Hz, 1H). |
| 105 | ¹H NMR (400 MHz, DMSO-d₆) δ (ppm) 8.43 (s, 1H), 8.17 (s, 2H), 7.85 (s, 1H), 7.68 (d, J = 2.7 Hz, 1H), 7.57 (d, J = 8.7 Hz, 1H), 7.52 (d, J = 2.6 Hz, 1H), 7.40-7.35 (m, 1H), 7.10 (d, J = 2.3 Hz, 1H), 7.00-6.98 (m, 1H), 6.87 (d, J = 8.6 Hz, 1H), 6.70-6.60 (m, 3H), 4.57 (d, J = 12.6 Hz, 1H), 4.12 (s, 1H), 3.71 (s, 1H), 3.39-3.35 (m, 2H), 3.31 (d, J = 14.0 Hz, 1H), 2.84 (s, 1H), 2.70 (s, 2H), 2.53 (s, 2H), 2.47 (s, 4H), 2.33-2.35 (m, 2H), 2.30 (s, 1H), 2.25 (s, 3H), 1.96 (s, 2H), 1.55 (s, 3H). |
| 106 | ¹H NMR (400 MHz, DMSO-d₆) δ (ppm) 8.43 (s, 1H), 8.18 (d, J = 1.5 Hz, 2H), 7.85 (s, 1H), 7.68 (d, J = 2.7 Hz, 1H), 7.61-7.45 (m, 2H), 7.40 (dd, J = 8.7, 2.6 Hz, 1H), 7.10 (d, J = 2.3 Hz, 1H), 7.00-6.96 (m, 1H), 6.87-6.85 (m, 1H), 6.68 (d, J = 2.8 Hz, 1H), 6.65-6.59 (m, 2H), 4.57 (d, J = 12.6 Hz, 1H), 4.13 (d, J = 13.2 Hz, 1H), 3.91-3.83 (m, 1H), 3.70-3.59 (m, 1H), 3.34-3.23 (m, 1H), 3.19-3.17 (m, 2H), 3.16 (s, 3H), 2.84-2.80 (m, 1H), 2.68-2.65 (m, 1H), 2.57 (q, J = 7.7 Hz, 1H), 2.50-2.37 (m, 2H), 2.25 (s, 3H), 2.04-1.91 (m, 4H), 1.65-1.60 (m, 1H), 1.55 (s, 3H). |
| 107 | ¹H NMR (400 MHz, methanol-d₄) δ (ppm) 8.76-8.70 (m, 1H), 8.33-8.28 (m, 1H), 7.86-7.72 (m, 2H), 7.67-7.54 (m, 2H), 7.21-7.04 (m, 2H), 6.93-6.78 (m, 2H), 6.77-6.64 (m, 2H), 4.75-4.57 (m, 1H), 4.25-4.15 (m, 1H), 3.64-3.46 (m, 1H), 3.20-3.12 (m, 2H), 2.83-2.68 (m, 2H), 2.31-2.17 (m, 8H), 2.16-2.02 (m, 4H), 2.00-1.89 (m, 1H). |
| 108 | ¹H NMR (400 MHz, methanol-d₄) δ (ppm) 8.76-8.70 (m, 1H), 8.33-8.28 (m, 1H), 7.86-7.72 (m, 2H), 7.67-7.54 (m, 2H), 7.22-7.13 (m, 1H), 7.11-7.05 (m, 1H), 6.93-6.64 (m, 4H), 4.75-4.57 (m, 1H), 4.25-4.15 (m, 1H), 3.64-3.46 (m, 1H), 3.20-3.12 (m, 2H), 2.83-2.68 (m, 2H), 2.31-2.17 (m, 8H), 2.16-2.02 (m, 4H), 2.00-1.89 (m, 1H). |
| 109 | ¹H NMR (400 MHz, DMSO-d₆) δ 8.96-8.92 (m, 1H), 8.42 (s, 1H), 8.23 (s, 1H), 7.91-7.56 (m, 3H), 7.41-6.49 (m, 7H), 3.85-3.70 (m, 2H), 3.62-3.49 (m, 3H), 3.10-2.99 (m, 1H), 2.99 (s, 1H), 2.20 (s, 3H), 2.13 (s, 7H), 2.07-1.80 (m, 3H), 1.79-1.60 (m, 2H). |
| 110 | ¹H NMR (400 MHz, DMSO-d₆) δ (ppm) 8.96-8.92 (m, 1H), 8.48-8.25 (m, 2H), 7.92-7.54 (m, 3H), 7.41-6.44 (m, 7H), 3.87-3.67 (m, 2H), 3.65-3.40 (m, 3H), 3.05-2.89 (m, 1H), 2.99-2.89 (m, 1H), 2.20 (s, 3H), 2.14-2.05 (m, 7H), 2.06-1.82 (m, 3H), 1.80-1.60 (m, 2H). |
| 111 | ¹H NMR (400 MHz, DMSO-d₆) δ (ppm) 9.06-8.80 (m, 1H), 8.58-8.26 (m, 2H), 7.95-7.52 (m, 3H), 7.43-6.25 (m, 6H), 6.20-6.00 (m, 1H), 5.80-5.45 (m, 1H), 4.00-3.69 (m, 2H), 3.67-3.40 (m, 3H), 2.30-2.10 (m, 4H), 2.09-1.82 (m, 3H), 1.80-1.55 (m, 2H). |
| 112 | ¹H NMR (400 MHz, DMSO-d₆) δ (ppm) 9.06-8.80 (m, 1H), 8.58-8.26 (m, 2H), 7.95-7.52 (m, 3H), 7.43-6.25 (m, 6H), 6.20-6.00 (m, 1H), 5.80-5.45 (m, 1H), 4.00-3.69 (m, 2H), 3.67-3.40 (m, 3H), 2.30-2.10 (m, 4H), 2.09-1.82 (m, 3H), 1.80-1.55 (m, 2H). |
| 113 | ¹H NMR (400 MHz, DMSO-d₆) δ (ppm) 8.45 (s, 1H), 8.17 (s, 1H), 7.84 (s, 1H), 7.68 (s, 1H), 7.57 (d, J = 8.8 Hz, 1H), 7.51(s, 1H), 7.40 (d, J = 12.9 Hz, 1H), 7.10 (d, J = 2.3 Hz, 1H), 7.00 (dd, J = 8.7, 2.3 Hz, 1H), 6.91-6.79 (m, 2H), 6.67 (s, 1H), 6.11 (dd, J = 16.7, 2.5 Hz, 1H), 5.67 (dd, J = 10.4, 2.5 Hz, 1H), 4.57 (d, J = 12.9 Hz, 1H), 4.16 (d, J = 13.6 Hz, 1H), 3.84 (s, 3H), 3.66 (s, 1H), 3.31 (s, 1H), 2.85 (s, 1H), 2.24 (s, 3H), 1.96 (d, J = 12.6 Hz, 2H), 1.56 (s, 2H) |
| 114 | ¹H NMR (400 MHz, Chloroform-d) δ (ppm) 7.95 (s, 1H), 7.88 (s, 1H), 7.57 (d, J = 2.7 Hz, 1H), 7.50 (d, J = 2.7 Hz, 1H), 7.37 (t, J = 9.6 Hz, 1H), 7.36-7.31 (m, 1H), 7.09 (dd, J = 8.6, 2.2 Hz, 1H), 6.97 (s, 1H), 6.91 (d, J = 8.7 Hz, 1H), 6.84 (dd, J = 13.2, 7.3 Hz, 1H), 6.71 (s, 1H), 6.56 (d, J = 2.8 Hz, 1H), 4.89 (s, 1H), 4.51 (s, 1H), 4.26 (d, J = 13.3 Hz, 1H), 4.13 (d, J = 8.5 Hz, 1H), 3.87 (s, 3H), 3.72 (d, J = 8.7 Hz, 3H), 3.61 (s, 1H), 3.54 (s, 1H), 3.29 (s, 1H), 3.15 (s, 1H), 2.81 (s, 2H), 2.36 (s, 3H), 2.17 (d, J = 13.7 Hz, 2H), 2.05 (s, 1H), 1.89 (s, 2H), 1.83 (d, J = 12.3 Hz, 1H). |
| 115 | ¹H NMR (400 MHz, Chloroform-d) δ (ppm) 7.96 (s, 1H), 7.87 (s, 1H), 7.57 (d, J = 2.8 Hz, 1H), 7.51 (d, J = 2.7 Hz, 1H), 7.42-7.31 (m, 3H), 7.08 (dd, J = 8.7, 2.3 Hz, 1H), 6.97 (s, 1H), 6.91 (d, J = 8.6 Hz, 1H), 6.87 (s, 1H), 6.57 (d, J = 2.8 Hz, 1H), 4.90 (s, 1H), 4.29 (s, 1H), 3.87 (s, 3H), 3.35 (s, 3H), 3.30-3.25 (m, 5H), 3.15 (s, 3H), 2.85 (s, 3H), 2.36 (s, 3H), 2.17 (d, J = 13.8 Hz, 2H), 2.03-1.80 (m, 3H), 1.84 (d, J = 13.3 Hz, 3H). |
| 117 | ¹H NMR (400 MHz, Chloroform-d) δ(ppm) 8.50-8.45 (m, 1H), 8.23 (s, 1H), 7.97 (s, 1H), 7.59-7.50 (m, 3H), 7.12 (d, J = 8.6 Hz, 1H), 7.04 (s, 1H), 6.93-6.83 (m, 2H), 6.82-6.74 (m, 1H), 6.57 (d, J = 2.8 Hz, 1H), 4.89 (s, 1H), 4.33 (s, 1H), 4.15 (s, 1H), 3.90 (s, 1H), 3.45 (d, J = 7.1 Hz, 1H), 3.29 (s, 1H), 3.15 (s, 3H), 2.85 (s, 1H), 2.26 (s, 3H), 2.17-2.10 (m, 3H), 1.84-1.80 (m, 3H), 1.25 (s, 2H). |
| 118 | ¹H NMR (400 MHz, Chloroform-d) δ(ppm) 8.50-8.45 (m, 1H), 8.23 (s, 1H), 7.97 (s, 1H), 7.62 (d, J = 2.7 Hz, 1H), 7.60-7.53 (m, 2H), 7.12 (d, J = 8.6 Hz, 1H), 7.04 (s, 1H), 6.93-6.82 (m, 3H), 6.58 (d, J = 2.8 Hz, 1H), 4.89 (s, 1H), 4.33 (s, 1H), 3.98 (s, 1H), 3.30 (s, 3H), 3.14-3.10 (m, 4H), 2.85 (s, 3H), 2.26 (s, 3H), 2.17 (d, J = 14.5 Hz, 1H), 1.86-1.80 (m, 4H), 1.25 (s, 2H). |
| 119 | ¹H NMR (400 MHz, Chloroform-d) δ(ppm) 8.50-8.45 (m, 1H), 8.23 (s, 1H), 7.98 (s, 1H), 7.59-7.50 (m, 3H), 7.12 (d, J = 8.6 Hz, 1H), 7.05 (s, 1H), 6.96-6.86 (m, 2H), 6.84- |

| E# | ¹H NMR (ppm) |
|---|---|
| | 6.80 (m, 1H), 6.61-6.50 (m, 2H), 4.91 (s, 1H), 4.24 (s, 1H), 3.79 (dd, J = 8.9, 5.7 Hz, 2H), 3.61 (dd, J = 8.9, 2.7 Hz, 2H), 3.26-3.22 (m, 3H), 3.21-3.10 (m, 1H), 2.85 (s, 4H), 2.44-2.36 (m, 2H), 2.25 (s, 3H), 2.17 (d, J = 13.5 Hz, 2H), 1.84-1.80 (m, 3H). |
| 120 | ¹H NMR (400 MHz, Chloroform-d) δ(ppm) 8.50 (d, J = 7.4 Hz, 1H), 8.23 (s, 1H), 7.98 (s, 1H), 7.62 (d, J = 2.6 Hz, 1H), 7.61-7.53 (m, 2H), 7.12 (d, J = 8.6 Hz, 1H), 7.05 (s, 1H), 6.94-6.81 (m, 1H), 6.58 (d, J = 2.8 Hz, 1H), 4.91 (s, 1H), 4.64 (s, 4H), 4.26 (s, 1H), 3.30 (s, 3H), 3.16 (s, 1H), 2.89 (s, 3H), 2.63 (s, 2H), 2.25 (s, 3H), 2.17 (d, J = 12.8 Hz, 4H), 1.84 (d, J = 13.3 Hz, 2H), 1.25 (s, 1H). |
| 121 | ¹H NMR (400 MHz, Chloroform-d) δ(ppm) 9.63 (s, 1H), 8.22 (s, 1H), 7.97 (s, 1H), 7.70 (s, 1H), 7.54 (d, J = 8.6 Hz, 1H), 7.45 (d, J = 2.8 Hz, 1H), 7.41 (s, 1H), 7.15 (d, J = 8.7 Hz, 1H), 6.96 (d, J = 8.7 Hz, 1H), 6.65 (dd, J = 16.8, 10.5 Hz, 1H), 6.59 (d, J = 2.8 Hz, 1H), 6.43-6.34 (m, 1H), 5.79 (dd, J = 10.6, 1.9 Hz, 1H), 4.86 (s, 2H), 4.15 (s, 1H), 3.94 (s, 3H), 3.51 (s, 2H), 3.23 (s, 2H), 2.98 (s, 2H), 2.32 (s, 3H). |
| 128 | ¹H NMR (400 MHz, DMSO-d₆) δ (ppm) 7.96 (s, 1H), 7.88 (s, 1H), 7.59-7.56 (m, 1H), 7.53-7.50 (m, 1H), 7.41-7.31 (m, 3H), 7.12-7.09 (m, 1H), 7.09-7.07 (m, 1H), 6.97 (s, 1H), 6.93-6.89 (m, 1H), 6.89-6.84 (m, 1H), 6.59-6.55 (m, 1H), 4.91 (s, 1H), 4.25 (s, 1H), 3.88 (s, 3H), 3.82 (s, 1H), 3.29 (s, 3H), 3.18-3.10 (m, 1H), 2.85 (s, 1H), 2.62 (s, 4H), 2.36 (s, 3H), 2.24-2.11 (m, 2H), 1.94-1.46 (m, 2H). |
| 129 | ¹H NMR (400 MHz, DMSO-d₆) δ (ppm) 8.45 (s, 1H), 8.18 (s, 1H), 7.85 (s, 1H), 7.72-7.66 (m, 1H), 7.62-7.54 (m, 1H), 7.54-7.49 (m, 1H), 7.44-7.39 (m, 1H), 7.13-7.08 (m, 1H), 7.03-6.97 (m, 1H), 6.91-6.83(m, 1H), 6.72-6.57 (m, 3H), 4.62-4.53 (m, 1H), 4.47(s, 4H), 4.19-4.10 (m, 2H), 3.84 (s, 3H), 3.65 (s, 1H), 3.21-3.13 (m, 2H), 2.87-2.79 (m, 1H), 2.58-2.43 (m, 4H), 2.25 (s, 3H), 2.09-2.02 (m, 2H), 1.95 (s, 2H), 1.55 (s, 2H). |
| 130 | ¹H NMR (400 MHz, DMSO-d₆) δ (ppm) 8.45 (s, 1H), 8.18 (s, 1H), 7.85 (s, 1H), 7.71-7.67 (m, 1H), 7.60-7.55 (m, 1H), 7.53-7.50 (m, 1H), 7.43-7.37 (m, 1H), 7.12-7.08 (m, 1H), 7.04-7.98 (m, 1H), 6.89-6.83 (m, 1H), 6.71-6.66 (m, 1H), 6.65-6.59 (m, 2H), 4.73-4.68 (m, 1H), 4.62-4.52 (m, 1H), 4.23-4.09 (m, 2H), 3.84 (s, 3H), 3.71-3.62 (m, 1H), 3.21-3.16 (m, 2H), 2.88-2.79 (m, 1H), 2.70-2.65 (m, 1H), 2.61-2.56 (m, 1H), 2.41-2.38 (m, 2H), 2.36-2.29 (m, 1H), 2.27-2.22 (m, 3H), 2.04-1.89 (m, 3H), 1.64-1.45 (m, 3H). |
| 131 | ¹H NMR (400 MHz, DMSO-d₆) δ (ppm) 8.45 (s, 1H), 8.18 (s, 1H), 7.85 (s, 1H), 7.71-7.67 (m, 1H), 7.61-7.56 (m, 1H), 7.53-7.50 (m, 1H), 7.43-7.38 (m, 1H), 7.12-7.08 (m, 1H), 7.03-6.98 (m, 1H), 6.90-6.84 (m, 1H), 6.71-6.54 (m, 3H), 4.61-4.53 (m, 1H), 4.18-4.09 (m, 1H), 3.84 (s, 3H), 2.71-2.59 (m, 1H), 3.48-3.22 (m, 5H), 3.16-3.10 (m, 2H), 3.89-3.79 (m, 1H), 2.51-2.40 (m, 2H), 2.33-2.24 (m, 7H), 2.03-2.12 (m, 2H), 1.55 (s, 2H), 1.23 (s, 1H). |
| 132 | ¹H NMR (400 MHz, DMSO-d₆) δ (ppm) 8.45 (s, 1H), 8.27 (s, 1H), 8.18 (s, 1H), 7.85 (s, 1H), 7.70-7.67 (m, 1H), 7.59 (s, 1H), 7.54-7.50 (m, 1H), 7.43-7.31 (m, 1H), 7.13-7.09 (m, 1H), 7.03-6.97 (m, 1H), 6.86-6.84 (m, 1H), 6.69-6.65 (m, 1H), 6.58-6.52 (m, 1H), 4.18-4.07 (m, 1H), 3.84 (s, 3H), 3.65 (s, 2H), 3.55-3.49 (m, 2H), 3.35 (s, 4H), 3.14 (s, 3H), 2.89-2.77 (m, 3H), 2.25 (s, 3H), 1.95 (s, 2H), 1.54 (s, 2H). |
| 133 | ¹H NMR (400 MHz, DMSO-d₆) δ(ppm) 8.45 (s, 1H), 8.20-8.14 (m, 2H), 7.85 (s, 1H), 7.71-7.68 (m, 1H), 7.61-7.56 (m, 1H), 7.52-7.49 (m, 1H), 7.43-7.37 (m, 1H), 7.12-7.09 (m, 1H), 7.03-6.99 (m, 1H), 6.90-6.84 (m, 1H), 6.76-6.64 (m, 1H), 4.19-4.09 (m, 2H), 3.84 (s, 3H), 3.72-3.64 (m, 1H), 3.35-3.19 (m, 3H), 2.84 (s, 1H), 2.31 (s, 6H), 2.25 (s, 3H), 2.04-1.93 (m, 2H), 1.55 (s, 2H). |
| 134 | ¹H NMR (400 MHz, DMSO-d₆) δ (ppm) 8.97 (d, J = 7.4 Hz, 1H), 8.53 (s, 1H), 8.41 (s, 1H), 7.91 (s, 1H), 7.68 (d, J = 2.5 Hz, 1H), 7.56 (d, J = 2.7 Hz, 1H), 7.46 (dd, J = 8.7, 2.7 Hz, 1H), 7.26 (d, J = 8.7 Hz, 1H), 7.05 (dd, J = 7.5, 2.7 Hz, 1H), 6.82 (d, J = 2.7 Hz, 1H), 6.67-6.58 (m,2H), 6.22 (d, J = 15.5 Hz, 1H), 4.34-4.19 (m, 2H), 3.98-3.90 (m, 1H), 3.64-3.56 (m, 1H), 3.59-3.45 (m, 3H), 3.41-3.29 (m, 2H), 2.48 (s, 4H), 2.21 (s, 3H). |
| 135 | ¹H NMR (400 MHz, DMSO-d₆) δ (ppm) 9.08-8.85 (m, 1H), 8.50-8.30 (m, 2H), 7.99-7.86 (m, 1H), 7.85-7.70 (m, 2H), 7.69-7.61 (m, 1H), 7.48-7.21 (m, 1H), 7.20-6.99 (m, 1H), 6.92-6.70 (m, 2H), 5.58-5.09 (m, 2H), 4.20-3.99 (m, 2H), 3.30-3.20 (m, 1H), 3.18-2.99 (m, 3H), 2.28-2.10 (m, 11H), 2.08-1.95 (m, 1H), 1.94-1.67 (m, 4H). |
| 136 | ¹H NMR (400 MHz, Chloroform-d) δ (ppm) 8.50 (d, J = 7.4 Hz, 1H), 8.23 (s, 1H), 7.94 (s, 1H), 7.75-7.30 (m, 3H), 7.10 (d, J = 8.6 Hz, 1H), 6.96 (s, 1H), 6.90 (dd, J = 7.5, 2.3 Hz, 1H), 5.87 (s, 1H), 5.42 (s, 1H), 4.35 (s, 2H), 3.79 (d, J = 14.0 Hz, 1H), 3.69 (d, J = 13.9 Hz, 1H), 3.51 (s, 1H), 3.30 (s, 1H), 3.10 (s, 2H), 3.02 (s, 4H), 2.91 (s, 1H), 2.69-2.59 (m, 1H), 2.39-2.27 (m, 1H), 2.28-1.97 (m, 5H), 1.96-1.87 (m, 1H), 1.85-1.60 (m, 1H). |
| 137 | ¹H NMR (400 MHz, DMSO-d₆) δ (ppm) 9.00-8.80 (m, 1H), 8.52-8.40 (m, 1H), 8.39-8.25 (m, 1H), 8.03-7.60 (m, 3H), 7.48-6.86 (m, 3H), 6.84-6.25 (m, 4H), 4.62-4.12 (m, 1H), 4.11-3.85 (m, 1H), 3.60-3.35 (m, 1H), 3.30-3.10 (m, 1H), 3.09-2.89 (m, 2H), 2.30-1.95 (m, 13H), 1.93-1.60 (m, 3H). |
| 138 | ¹H NMR (400 MHz, DMSO-d₆) δ (ppm) 9.00-8.87 (m, 1H), 8.52-8.40 (m, 1H), 8.39-8.28 (m, 1H), 8.03-7.57 (m, 3H), 7.48-6.96 (m, 3H), 6.95-6.31 (m, 4H), 4.62-4.15 (m, 1H), 4.14-4.02 (m, 1H), 4.00-3.72 (m, 1H), 3.70-3.50 (m, 1H), 3.30-3.25 (m, 1H), 3.09-2.96 (m, 2H), 2.32-1.95 (m, 12H), 1.93-1.80 (m, 1H), 1.79-1.35 (m, 2H). |
| 139 | ¹H NMR (400 MHz, DMSO-d₆) δ (ppm) 9.10-8.80 (m, 1H), 8.55-8.40 (m, 1H), 8.39-8.28 (m, 1H), 8.06-7.86 (m, 1H), 7.83-7.30 (m, 3H), 7.29-7.12 (m, 1H), 7.11-6.95 (m, 1H), 6.94-6.75 (m, 2H), 6.73-6.43 (m, 1H), 6.35-6.05 (m, 1H), 5.80-5.50 (m, 1H), 4.68-4.20 (m, 1H), 4.19-3.90 (m, 1H), 3.60-3.39 (m, 1H), 3.30-3.10 (m, 1H), 2.32-2.11 (m, 5H), 2.10-1.95 (m, 2H), 1.93-1.55 (m, 3H). |
| 140 | ¹H NMR (400 MHz, DMSO-d₆) δ (ppm) 9.10-8.80 (m, 1H), 8.52-8.42 (m, 1H), 8.41-8.30 (m, 1H), 8.01-7.84 (m, 1H), 7.83-7.75 (m, 1H), 7.74-7.31 (m, 1H), 7.29-7.11 (m, 1H), 7.10-7.00 (m, 1H), 6.99-6.88 (m, 1H), 6.87-6.65 (m, 2H), 6.35-6.00 (m, 1H), 5.88-5.50 (m, 1H), 4.68-4.20 (m, 1H), 4.19-3.93 (m, 1H), 3.89-3.60 (m, 1H), 3.40-3.27 (m, 1H), 2.35-1.99 (m, 6H), 1.97-1.65 (m, 2H), 1.64-1.50 (m, 1H), 1.49-1.33 (m, 2H). |
| 141 | ¹H NMR (300 MHz, DMSO-d6) δ 8.95 (d, J = 7.4 Hz, 1H), 8.41 (d, J = 12.2 Hz, 2H), 7.91 (s, 1H), 7.75-7.65 (m, 2H), 7.58 (dt, J = 8.5, 2.1 Hz, 1H), 7.22 (d, J = 8.6 Hz, 1H), 7.03 (dd, J = 7.4, 2.4 Hz, 1H), 6.81 (d, |

| E# | ¹H NMR (ppm) |
|---|---|
|  | J = 2.4 Hz, 1H), 6.75 (dd, J = 5.7, 2.3 Hz, 1H), 6.16 (ddd, J = 16.7, 5.7, 2.4 Hz, 1H), 5.67 (td, J = 9.7, 2.4 Hz, 1H), 4.60 (d, J = 9.0 Hz, 1H), 3.88 (dd, J = 8.5, 5.2 Hz, 1H), 3.58 (s, 1H), 3.46 (d, J = 11.0 Hz, 1H), 2.79 (d, J = 8.1 Hz, 1H), 2.25-2.21 (m, 1H), 2.19 (s, 3H), 1.91-1.74 (m, 2H), 1.74-1.55 (m, 2H). |
| 142 | ¹H NMR (400 MHz, DMSO-d₆) δ (ppm) 12.97 (s, 1H), 8.95 (d, J = 7.5 Hz, 1H), 8.53 (s, 1H), 8.39 (s, 1H), 7.90 (s, 1H), 7.72 (d, J = 2.8 Hz, 1H), 7.68-7.57 (m, 2H), 7.44 (d, J = 15.4 Hz, 1H), 7.23 (d, J = 8.6 Hz, 1H), 7.17-7.00 (m, 1H), 6.80 (d, J = 2.6 Hz, 1H), 6.72 (d, J = 2.8 Hz, 1H), 6.52 (d, J = 15.4 Hz, 1H), 4.58 (d, J = 12.9 Hz, 1H), 4.09 (d, J = 13.5 Hz, 1H), 3.75-3.65 (m,1H), 3.45-3.29 (m, 1H), 2.96-2.84 (m, 1H), 2.20 (s, 3H), 2.04-1.91 (m, 2H), 1.74-1.45 (m, 2H). |
| 143 | ¹H NMR (400 MHz, DMSO-d₆) δ (ppm) 8.94 (d, J = 7.4 Hz, 1H), 8.37 (d, J = 7.8 Hz, 2H), 7.90 (s, 1H), 7.69 (d, J = 12.8 Hz, 2H), 7.22 (d, J = 8.5 Hz, 1H), 7.03 (d, J = 6.2 Hz, 1H), 6.78 (s, 1H), 6.62 (s, 1H), 5.33 (s, 1H), 5.27 (s, 1H), 3.84 (s, 1H), 3.57 (s, 3H), 3.12-2.95 (m, 2H), 2.18 (d, J = 10.6 Hz, 11H), 1.93 (s, 3H), 1.78 (d, J = 12.5 Hz, 2H), 1.24 (s, 1H). |
| 144 | ¹H NMR (400 MHz, DMSO-d6) δ (ppm) 8.95 (d, J = 7.4 Hz, 1H), 8.42 (s, 1H), 8.37 (d, J = 8.5 Hz, 1H), 7.90 (s, 1H), 7.74-7.65 (m, 2H), 7.29-7.18 (m, 1H), 7.03 (dd, J = 7.5, 2.6 Hz, 1H), 6.79 (d, J = 3.0 Hz, 1H), 6.62 (d, J = 2.7 Hz, 1H), 5.33 (s, 1H), 5.18 (d, J = 10.4 Hz, 1H), 3.84 (s, 1H), 3.55 (s, 3H), 3.00 (d, J = 12.2 Hz, 1H), 2.97-2.87 (m, 1H), 2.21-2.06 (m, 11H), 2.03-1.95 (m, 3H), 1.78 (d, J = 11.2 Hz, 1H), 1.74 (s, 1H), 1.24 (s, 1H). |
| 145 | ¹H NMR (400 MHz, Chloroform-d) δ (ppm) 8.52 (d, J = 7.2 Hz, 1H), 8.25 (s, 1H), 7.97 (s, 1H), 7.70 (d, J = 12.1 Hz, 1H), 7.61-7.56 (m, 2H), 7.12 (d, J = 8.5 Hz, 1H), 7.08 (s, 1H), 6.95-6.85 (m, 2H), 6.68-6.58 (m, 1H), 6.52 (d, J = 12.4 Hz, 1H), 3.99 (d, J = 17.2 Hz, 1H), 3.86-3.79 (m, 2H), 3.61 (s, 1H), 3.11 (s, 1H), 2.48 (s, 1H), 2.27 (d, J = 3.1 Hz, 4H), 2.20 (s, 1H), 2.04-1.81 (m, 3H). |
| 146 | ¹H NMR (400 MHz, Chloroform-d) δ (ppm) 8.52 (d, J = 7.4 Hz, 1H), 8.25 (s, 1H), 7.97 (s, 1H), 7.69 (s, 1H), 7.59 (d, J = 3.0 Hz, 2H), 7.12 (d, J = 8.5, 2.6 Hz, 2H), 6.95-6.87 (m, 2H), 6.62 (d, J = 12.9 Hz, 1H), 6.51 (d, J = 4.7 Hz, 1H), 4.07 (d, J = 16.8 Hz, 1H), 3.89-3.79 (m, 1H), 3.75 (s, 1H), 3.58 (s, 1H), 3.13 (s, 1H), 2.47 (d, J = 15.1 Hz, 1H), 2.32 (s, 2H), 2.21 (s, 1H), 2.17 (s, 1H), 2.00 (s, 2H), 1.89 (s, 2H). |
| 147 | ¹H NMR (400 MHz, Chloroform-d) δ (ppm) 8.53 (d, J = 7.3 Hz, 1H), 8.29 (s, 1H), 7.98 (s, 1H), 7.68 (s, 1H), 7.60 (s, 2H), 7.14 (d, J = 8.4 Hz, 2H), 6.91 (s, 2H), 6.64 (d, J = 10.9 Hz, 1H), 6.52 (s, 1H), 4.05 (d, J = 15.9 Hz, 1H), 3.86 (s, 1H), 3.75 (s, 1H), 3.58 (s, 1H), 3.16 (s, 1H), 2.49 (s, 1H), 2.27 (s, 1H), 2.18 (s, 1H), 2.01 (s, 4H). |
| 148 | ¹H NMR (400 MHz, Chloroform-d) δ (ppm) 8.52 (d, J = 7.2 Hz, 1H), 8.25 (s, 1H), 7.98 (s, 1H), 7.69 (s, 1H), 7.59 (s, 2H), 7.13 (d, J = 8.6 Hz, 1H), 6.96-6.87 (m, 1H), 6.64 (d, J = 21.6 Hz, 1H), 6.52 (d, J = 11.7 Hz, 2H), 3.99 (d, J = 17.1 Hz, 1H), 3.83 (d, J = 10.3 Hz, 1H), 3.76 (s, 1H), 3.61 (s, 1H), 3.12 (s, 1H), 2.48 (s, 1H), 2.31 (s, 1H), 2.19 (s, 3H), 2.01 (d, J = 12.3 Hz, 3H), 1.92-1.81 (m, 1H). |
| 149 | ¹H NMR (400 MHz, Chloroform-d) δ (ppm) 9.60 (s, 1H), 7.97 (s, 1H), 7.87 (s, 1H), 7.68 (s, 1H), 7.52 (d, J = 8.9 Hz, 1H), 7.44 (d, J = 2.9 Hz, 1H), 7.29 (d, J = 5.4 Hz, 1H), 7.11-7.04 (m, 2H), 6.92 (d, J = 11.9, 7.4 Hz, 1H), 6.58 (dd, J = 9.2, 6.3 Hz, 2H), 3.87 (s, 3H), 3.22 (d, J = 6.2 Hz, 4H), 2.97 (s, 3H), 2.36 (d, J = 8.7 Hz, 9H), 2.09 (s, 3H). |
| 150 | ¹H NMR (400 MHz, Methanol-d4) δ8.76 (d, J = 7.5 Hz, 1H), 8.31 (s, 1H), 7.82 (s, 1H), 7.64 (d, J = 15.9 Hz, 2H), 7.20 (d, J = 8.7 Hz, 1H), 7.10 (d, J = 7.4 Hz, 1H), 6.94-6.81 (m, 2H), 6.68-6.67 (m, 2H), 4.77-4.55 (m, 2H), 4.32-4.30 (m, 1H), 3.40-3.24 (m, 1H), 3.22-3.12 (m, 1H) 2.15 (s, 3H), 1.76-1.73 (m, 3H), 1.29-1.10(m, 4H). |
| 151 | ¹H NMR (400 MHz, DMSO-d₆) δ (ppm) 8.94 (d, J = 7.4 Hz, 1H), 8.56 (s, 1H), 8.38 (s, 1H), 7.95 (s, 1H), 7.81 (s, 1H), 7.68 (s, 2H), 7.20 (d, J = 8.5 Hz, 1H), 7.05-7.04 (m, 1H), 6.95 (s, 1H), 6.80 (s, 1H), 6.69-6.54 (m, 1H), 6.34 (d, J = 15.3 Hz, 1H), 4.70 (s, 3H), 4.42 (s, 1H), 4.26 (s, 1H), 4.05 (s, 1H), 3.61 (d, J = 5.9 Hz, 2H), 2.47 (s, 3H), 2.24-2.13 (s, 3H) |
| 152 | ¹H NMR (400 MHz, DMSO-d₆) δ (ppm) 8.95 (d, J = 7.6 Hz, 1H), 8.67 (s, 1H), 8.39 (s, 1H), 7.99 (s, 1H), 7.89 (s, 1H), 7.61 (s, 1H), 7.56 (d, J = 8.7 Hz, 1H), 7.23 (d, J = 8.7 Hz, 1H), 7.04 (d, J = 7.5 Hz, 1H), 6.79 (s, 1H), 6.65 (s, 1H), 6.60 (s, 1H), 4.57 (s, 1H), 4.17 (s, 1H), 3.62 (s, 1H), 3.04 (s, 2H), 2.18 (d, J = 16.2 Hz, 11H), 1.97 (s, 2H), 1.78 (s, 2H). |
| 153 | ¹H NMR (400 MHz, Chloroform-d) δ 7.97 (s, 1H), 7.86 (d, J = 4.3 Hz, 1H), 7.61 (s, 1H), 7.47 (s, 1H), 7.35 (d, J = 9.1 Hz, 3H), 7.12-7.03 (m, 2H), 6.87 (d, J = 8.7 Hz, 2H), 6.71 (s, 2H), 4.81 (d, J = 57.5 Hz, 1H), 4.55 (q, J = 9.8, 9.4 Hz, 1H), 4.29 (d, J = 39.0 Hz, 3H), 3.86 (s, 3H), 2.90 (s, 1H), 2.34 (d, J = 7.2 Hz, 8H). |
| 154 | ¹H NMR (400 MHz, DMSO-d₆) δ (ppm) 8.99 (d, J = 7.2 Hz, 1H), 8.47 (s, 1H), 8.05-7.72 (m, 2H), 7.69-7.40 (m, 2H), 7.39-7.02 (m, 2H), 6.89 (s, 1H), 6.77-6.73 (m, 2H), 6.64-6.60 (m, 1H), 6.52-4.80 (m, 2H), 4.58(s, 1H), 4.14 (s, 3H), 3.80-3.51 (m, 1H), 3.43-3.11 (m, 1H), 2.95-2.73 (m, 1H), 2.20 (s, 3H), 1.98 (s, 2H), 1.57 (s, 2H). |
| 155 | ¹H NMR (300 MHz, DMSO-d6) δ 9.66 (d, J = 10.8 Hz, 1H), 8.94 (d, J = 7.5 Hz, 1H), 8.38 (s, 1H), 7.94 (d, J = 1.2 Hz, 1H), 7.89-7.74 (m, 2H), 7.66 (dd, J = 2.9, 1.6 Hz, 1H), 7.25 (d, J = 8.6 Hz, 1H), 7.03 (dd, J = 7.5, 2.6 Hz, 1H), 6.89 (dd, J = 5.3, 2.9 Hz, 1H), 6.80 (t, J = 2.3 Hz, 1H), 6.61 (ddd, J = 16.8, 10.3, 8.4 Hz, 1H), 6.15 (dd, J = 16.8, 2.4 Hz, 1H), 5.68 (ddd, J = 10.3, 5.5, 2.4 Hz, 1H), 3.90 (s, 1H), 3.88-3.77 (m, 4H), 3.72 (s, 1H), 3.65 (t, J = 6.9 Hz, 1H), 3.47 (t, J = 7.0 Hz, 1H), 2.33 (t, J = 6.9 Hz, 1H), 2.26-2.17 (m, 4H). |
| 156 | ¹H NMR (300 MHz, DMSO-d6) δ 9.68 (d, J = 3.3 Hz, 1H), 8.94 (d, J = 7.5 Hz, 1H), 8.38 (s, 1H), 7.94 (s, 1H), 7.85 (d, J = 6.2 Hz, 1H), 7.66 (d, J = 2.8 Hz, 1H), 7.24 (dd, J = 8.7, 3.9 Hz, 1H), 7.03 (dd, J = 7.3, 2.6 Hz, 1H), 6.89 (d, J = 3.0 Hz, 1H), 6.80 (d, J = 2.6 Hz, 1H), 6.63 (dt, J = 15.3, 6.0 Hz, 1H), 6.39 (dd, J = 15.2, 9.5 Hz, 1H), 4.12-3.75 (m, 6H), 3.70 (s, 1H), 3.63 (t, J = 6.9 Hz, 1H), 3.45 (t, J = 7.0 Hz, 1H), 3.02 (t, J = 4.6 Hz, 2H), 2.39-2.17 (m, 5H), 2.14 (s, 3H), 2.12 (s, 3H). |
| 157 | ¹H NMR (400 MHz, DMSO-d₆) δ 8.55 (d, J = 7.4 Hz, 1H), 8.48 (s, 1H), 7.94 (s, 1H), 7.87-7.78 (m, 2H), 7.68-7.59 (m, 2H), 7.44 (d, J = 1.3 Hz, 1H), 7.14 (d, J = 8.5 Hz, 1H), 6.97 (d, J = 2.8 Hz, 1H), 6.81 (dd, J = 7.4, 2.5 Hz, 1H), 6.61 (dt, J = 15.4, 6.2 Hz, 1H), |

| E# | ¹H NMR (ppm) |
|---|---|
| | 6.54 (d, J = 2.5 Hz, 1H), 6.17 (dt, J = 15.5, 1.7 Hz, 1H), 4.69 (t, J = 7.1 Hz, 2H), 4.41 (t, J = 8.7 Hz, 1H), 4.26 (d, J = 13.1 Hz, 1H), 4.02 (dd, J = 10.0, 5.0 Hz, 1H), 3.02 (dd, J = 6.2, 1.6 Hz, 2H), 2.20 (s, 3H), 2.14 (d, J = 4.1 Hz, 6H). |
| 158 | ¹H NMR (400 MHz, Chloroform-d) δ 9.21 (d, J = 1.3 Hz, 1H), 8.35 (s, 1H), 8.01 (s, 1H), 7.68-7.61 (m, 2H), 7.59 (d, J = 2.7 Hz, 1H), 7.14 (d, J = 8.6 Hz, 1H), 7.09 (s, 1H), 7.01-6.90 (m, 2H), 6.74 (d, J = 2.8 Hz, 1H), 6.13 (dt, J = 15.4, 1.7 Hz, 1H), 4.77 (t, J = 8.1 Hz, 2H), 4.67 (s, 1H), 4.43 (s, 2H), 3.11 (dd, J = 6.0, 1.7 Hz, 2H), 2.27 (d, J = 3.0 Hz, 9H). |
| 159 | ¹H NMR (400 MHz, Chloroform-d) δ 8.48 (dd, J = 7.4, 0.7 Hz, 1H), 8.20 (s, 1H), 7.97 (s, 1H), 7.73-7.64 (m, 2H), 7.61 (d, J = 2.8 Hz, 1H), 7.11-7.01 (m, 3H), 6.87 (dd, J = 7.5, 2.6 Hz, 1H), 6.82 (d, J = 2.5 Hz, 1H), 6.77 (d, J = 2.8 Hz, 1H), 6.28 (d, J = 15.6 Hz, 1H), 4.96 (t, J = 8.3 Hz, 1H), 4.60 (t, J = 9.2 Hz, 1H), 4.53-4.45 (m, 1H), 4.45-4.37 (m, 1H), 4.27-4.19 (m, 1H), 3.96-3.81 (m, 2H), 3.11-3.14 (m, 2H), 2.33-2.43 (m, 2H), 2.20 (s, 3H), 2.08 (s, 1H), 2.14-2.01 (m, 1H), 1.25 (s, 3H), 0.86 (s, 1H). |
| 160 | ¹H NMR (400 MHz, Chloroform-d) δ 8.54-8.48 (m, 1H), 8.25 (s, 1H), 8.01 (s, 1H), 7.68-7.59 (m, 3H), 7.11-6.98 (m, 2H), 6.98 (d, J = 15.0 Hz, 1H), 6.92-6.85 (m, 2H), 6.75 (d, J = 2.8 Hz, 1H), 6.50-6.20(m, 2H), 4.90 (s, 1H), 4.66 (s, 1H), 4.49 (s, 2H), 3.19 (s, 2H), 2.69 (s, 2H), 2.26 (s, 3H), 1.88 (s, 7H). |
| 161 | ¹H NMR (400 MHz, Chloroform-d) δ 7.99 (s, 1H), 7.89 (s, 1H), 7.62 (d, J = 2.8 Hz, 1H), 7.48 (d, J = 2.7 Hz, 1H), 7.43-7.32 (m, 3H), 7.08 (dd, J = 8.7, 2.1 Hz, 1H), 6.93 (s, 1H), 6.92-6.81 (m, 2H), 6.72 (d, J = 2.8 Hz, 1H), 6.17 (d, J = 15.4 Hz, 1H), 5.19-5.22 (m, 1H), 4.78 (t, J = 7.9 Hz, 1H), 4.63 (d, J = 11.4 Hz, 1H), 4.42 (d, J = 8.0 Hz, 2H), 4.31-4.32(m, 3H), 3.88 (s, 2H), 3.42 (d, J = 5.0 Hz, 2H), 3.31 (d, J = 23.9 Hz, 3H), 2.35 (s, 3H). |
| 162 | ¹H NMR (400 MHz, Chloroform-d) δ (ppm) 8.54-8.49 (m, 1H), 8.24 (s, 1H), 7.99 (s, 1H), 7.65-7.54 (m, 3H), 7.16-7.10 (m, 1H), 7.04 (s, 1H), 6.93-6.85 (m, 3H), 6.62-6.58 (m, 1H), 5.46-5.22 (m, 1H), 4.92 (s, 1H), 4.52-4.33 (m, 1H), 4.12-3.70 (m, 2H), 3.45-2.81 (m, 5H), 2.28 (s, 5H), 2.24-2.16 (m, 2H), 1.93-1.82 (m, 2H), 1.57 (s, 3H), 1.27 (s, 1H). |
| 163 | ¹H NMR (400 MHz, DMSO-d₆) δ 8.95 (d, J = 7.4 Hz, 1H), 8.51 (s, 1H), 8.39 (s, 1H), 7.90 (s, 1H), 7.69 (dd, J = 23.5, 2.6 Hz, 2H), 7.64-7.57 (m, 1H), 7.23 (d, J = 8.6 Hz, 1H), 7.04 (dd, J = 7.5, 2.6 Hz, 1H), 6.80 (d, J = 2.6 Hz, 1H), 6.71 (d, J = 2.8 Hz, 1H), 6.55 (dd, J = 10.0, 5.5 Hz, 2H), 5.17 (dt, J = 57.5, 5.0 Hz, 1H), 4.57 (s, 1H), 4.14 (s, 1H), 3.70-3.47 (m, 4H), 3.24 (d, J = 4.7 Hz, 2H), 3.20-3.07 (m, 2H), 2.84 (s, 1H), 2.20 (s, 3H), 1.98 (s, 2H), 1.56 (s, 2H). |
| 164 | ¹H NMR (400 MHz, DMSO-d₆) δ 8.95 (d, J = 7.4 Hz, 1H), 8.51 (s, 1H), 8.39 (s, 1H), 7.90 (s, 1H), 7.72 (d, J = 2.7 Hz, 1H), 7.66 (s, 1H), 7.61 (d, J = 9.3 Hz, 1H), 7.23 (d, J = 8.6 Hz, 1H), 7.04 (dd, J = 7.5, 2.6 Hz, 1H), 6.80 (d, J = 2.6 Hz, 1H), 6.71 (d, J = 2.7 Hz, 1H), 6.67-6.60 (m, 2H), 5.20 (d, J = 55.4 Hz, 1H), 4.58 (s, 1H), 4.14 (s, 1H), 3.67 (s, 4H), 2.97-2.72 (m, 2H), 2.72-2.56 (m, 2H), 2.36 (d, J = 7.7 Hz, 2H), 2.20 (s, 3H), 2.18-1.86 (m, 3H), 1.57 (s, 2H). |
| 165 | ¹H NMR (400 MHz, Chloroform-d) δ 7.98 (s, 1H), 7.88 (s, 1H), 7.62 (d, J = 2.8 Hz, 1H), 7.49 (s, 1H), 7.41 (d, J = 8.9 Hz, 1H), 7.38-7.32 (m, 1H), 7.29 (s, 2H), 7.08 (d, J = 8.6 Hz, 1H), 6.93-6.86 (m, 3H), 6.73 (d, J = 2.8 Hz, 1H), 4.82 (s, 1H), 4.65 (s, 1H), 4.45 (s, 1H), 4.32 (s, 2H), 3.94 (s, 2H), 3.88-3.82 (m, 3H), 3.50 (s, 3H), 3.45-3.42 (m, 7H), 2.77 (s, 2H), 2.36 (s, 3H). |
| 166 | ¹H NMR (400 MHz, Chloroform-d) δ 7.98 (s, 1H), 7.88 (s, 1H), 7.62 (d, J = 2.7 Hz, 1H), 7.48 (d, J = 2.6 Hz, 1H), 7.41 (d, J = 8.9 Hz, 1H), 7.36 (d, J = 5.3 Hz, 2H), 7.07 (dd, J = 8.9, 2.1 Hz, 1H), 7.00-6.86 (m, 3H), 6.72 (d, J = 2.7 Hz, 1H), 6.19 (d, J = 15.1 Hz, 1H), 4.77 (s, 1H), 4.65 (s, 1H), 4.42 (s, 1H), 4.31 (s, 2H), 3.87 (s, 3H), 3.80 (d, J = 5.8 Hz, 2H), 3.38-3.36 (m, 8H), 2.97 (s, 2H), 2.67 (s, 2H), 2.35 (s, 3H). |
| 167 | ¹H NMR (400 MHz, Chloroform-d) δ (ppm) 7.95 (s, 1H), 7.89 (s, 1H), 7.59-7.56 (m, 1H), 7.52-7.49 (m, 1H), 7.41-7.32 (m, 3H), 7.20 (s, 1H), 7.12-7.06 (m, 1H), 6.97 (s, 1H), 6.94-6.88 (m, 1H), 6.83 (s, 1H), 6.59-6.55 (m, 1H), 4.90 (s, 1H), 4.27 (s, 1H), 3.99-3.82 (m, 5H), 3.45 (s, 8H), 3.28 (s, 1H), 3.21-3.19 (m, 2H), 2.93-2.66 (m, 3H), 2.36 (s, 3H), 2.22-2.12 (m, 2H), 1.83 (s, 2H), 0.86 (s, 1H). |
| 168 | ¹H NMR (400 MHz, Chloroform-d) δ (ppm) 7.95 (s, 1H), 7.88 (s, 1H), 7.58-7.56 (m, 1H), 7.52-7.49 (m, 1H), 7.41-7.33 (m, 3H), 7.11-7.06 (m, 1H), 6.97 (s, 1H), 6.92 (s, 2H), 6.90 (s, 1H), 6.58-6.56 (m, 1H), 4.89 (s, 1H), 4.31 (s, 1H), 3.87 (s, 5H), 3.40 (s, 8H), 3.29 (s, 1H), 3.18-3.09 (m, 3H), 2.84 (s, 2H), 2.36 (s, 3H), 2.22-2.11 (m, 2H), 1.90-1.74 (s, 2H), 1.32-1.24 (s, 1H). |
| 169 | ¹H NMR (400 MHz, DMSO-d₆) δ 8.95 (d, J = 7.5 Hz, 1H), 8.51 (s, 1H), 8.39 (s, 1H), 7.90 (s, 1H), 7.72 (d, J = 2.8 Hz, 1H), 7.69-7.58 (m, 2H), 7.23 (d, J = 8.6 Hz, 1H), 7.17-7.00 (m, 1H), 6.80 (d, J = 2.6 Hz, 1H), 6.71 (d, J = 2.8 Hz, 1H), 6.68-6.57 (m, 2H), 4.58 (s, 1H), 4.14 (s, 1H), 3.78 (t, J = 4.0 Hz, 2H), 3.66 (s, 3H), 3.27 (s, 9H), 2.92 (dd, J = 9.2, 5.0 Hz, 3H), 2.85 (s, 1H), 2.50-2.43 (m, 1H), 2.20 (s, 3H), 1.98 (s, 2H), 1.58-1.55 (m, 2H). |
| 170 | ¹H NMR (400 MHz, DMSO-d₆) δ 8.94 (d, J = 7.2 Hz, 1H), 8.51 (s, 1H), 8.38 (d, J = 5.0 Hz, 1H), 7.90 (s, 1H), 7.72 (d, J = 2.8 Hz, 1H), 7.66 (d, J = 2.6 Hz, 1H), 7.61 (dd, J = 8.6, 2.6 Hz, 1H), 7.23 (d, J = 8.6 Hz, 1H), 7.04 (dd, J = 7.5, 2.7 Hz, 1H), 6.80 (d, J = 2.6 Hz, 1H), 6.71 (d, J = 2.8 Hz, 1H), 6.66-6.56 (m, 2H), 4.58 (d, J = 13.3 Hz, 1H), 4.14 (s, 1H), 3.76-3.63 (m, 3H), 3.24-3.22 (m, 9H), 2.89-2.73 (m, 3H), 2.44-2.41 (m, 2H), 2.20 (s, 3H), 1.98-1.97 (m, 2H), 1.57-1.55 (m, 2H). |
| 175 | ¹H NMR (400 MHz, Chloroform-d) δ 8.28-8.19 (m, 2H), 8.07 (s, 1H), 7.66 (s, 3H), 7.12 (s, 2H), 6.87 (s, 2H), 6.81 (s, 1H), 6.75 (s, 1H), 6.67 (s, 1H), 4.80 (s, 1H), 4.17 (s, 1H), 3.63 (s, 1H), 3.49 (s, 2H), 3.17 (s, 3H), 2.62-2.53 (m, 6H), 2.30-2.23 (m, 3H), 2.01 (s, 2H). |
| 176 | ¹H NMR (400 MHz, Methanol-d₄) δ (ppm) 8.75 (d, J = 7.6 Hz, 1H), 8.30 (s, 1H), 7.85 (s, 1H), 7.68 (s, 1H), 7.59 (s, 1H), 7.53 (s, 1H), 7.20 (d, J = 8.7 Hz, 1H), 7.12-7.05 (m, 1H), 6.96-6.75 (m, 4H), 5.05-4.91 (m, 1H), 4.56-4.11 (m, 3H), 3.72-3.41 (m, 4H), 2.60 (d, J = 8.3 Hz, 6H), 2.25 (s, 3H), 2.22-2.11 (m, 2H). |
| 177 | ¹H NMR (400 MHz, Chloroform-d) δ (ppm) 8.52 (d, J = 7.4 Hz, 1H), 8.24 (s, 1H), 7.99 (s, 1H), 7.67-7.54 (m, 3H), 7.16-7.07 (m, 2H), 6.95-6.87 (m, 2H), 6.86-6.74 (m, 2H), |

-continued

| E# | ¹H NMR (ppm) |
|---|---|
| | 6.59 (d, J = 2.8 Hz, 1H), 4.94-4.80 (m, 1H), 4.36-4.33 (m, 1H), 3.61 (s, 2H), 3.40-3.24 (m, 1H), 3.22-3.12 (m, 1H), 2.96-2.81 (m, 1H), 2.64 (s, 3H), 2.27 (s, 3H), 2.22-2.12 (m, 2H), 1.92-1.77 (m, 2H), 1.39-1.30 (m, 1H). |

IX. Biological Examples

Biological Test Methods
Her2 Biochemistry Assay

The purpose of the wtERBB2, ERBB2-A775_G776insYVMA (ERBB2YVMA), wtEGFR biochemical assay was to evaluate the inhibition (% inhibition and $IC_{50}$ values) of the small molecule inhibitors by using the "HotSpot" radiometric kinase activity assay. HotSpot assays monitor the production of kinase substrate by the radioactive gamma phosphate of adenosine triphosphate (33P-ATP) during biochemical reactions. HotSpot assays was performed in steps upon completion of the kinase reaction: deposition of a reaction mixture aliquot onto P81 ion exchange paper, extensive washing of the aforementioned P81 paper using phosphoric acid to remove unbound radiolabeled 33P-ATP from the P81 paper, and finally visualization and quantification of the dried P81 paper utilizing a phosphoimager. The radioactive signal generated from the aliquot of buffer solution was proportional to the amount of radiolabeled substrate produced, and which is generally reflective of kinase activity. wtERBB2 was purchased from Reaction Biology (Cat: Kin-21-497), ERBB2-A775_G776insYVMA was purchased from SignalChem (Cat: E27-13BG), and wt EGFR was purchased from Invitrogen (Cat: PR7295B). Typical reaction solutions (10 µL final reaction volume) contained the following buffer conditions: 20 mM Hepes (pH 7.5), 10 mM $MgCl_2$, 1 mM EGTA, 0.01% Brij35, 0.02 mg/mL BSA, 0.1 mM $Na_3VO_4$, 2 mM DTT, 1% DMSO. The assay was primed by preparing a fresh 0.2 mg/mL solution of pEY (Sigma Cat: P7244) substrate in the reaction buffer and supplementing that solution with 2 mN of $MnCl_2$ as substrate cofactor (Sigma Cat: M9522). The kinase of interest was then added to the solution at the appropriate concentration (30 nM wtERBB2 from, or 20 nM ERBB2YVMA, or 4 nM wtEGFR) and gently mixed prior to delivery of compound in 100% DMSO by acoustic dispensing (Beckman Echo550). Compound, Kinase, and substrate were allowed to incubate for 20 min at room temperature prior to the initiation of the reaction by addition of 33P-ATP (PerkinElmer Cat: NEG602, final conc 10 µM). The reaction was allowed to run for 2 hours at room temperature and was then spotted onto P81 ion exchange paper, washed with a 0.75% Phosphoric acid solution, and imaged to quantify the amount of radioactivity. $IC_{50}$ determinations were made from a plot of kinase activity as a function of inhibitor concentration fit to the 4-parameter $IC_{50}$ equation with the enzyme concentration held constant using GraphPad Prism (San Diego). Table 2 provides biochemical activity of various compounds in this disclosure against Her2 WT, Her2 YVMA and EGFR WT kinases in HotSpot assay.

Cell Growth Inhibition Assay

BaF3_RTK (BaF3 HER2WT, BaF3-HER2YVMA and BaF3_EGFRWT) cells were used to evaluate the potency and selectivity of the HER2 inhibitors. BaF3_HER2WT and YVMA cells were maintained in RPMI media supplemented with 10% fetal bovine serum. BaF3_EGFRWT cells were maintained in RPMI media+10% FBS+80 ng/mL recombinant human EGF. For cell growth inhibition assay, HER2 inhibitors in DMSO solution were dispensed with HP D300e (Tecan) into 384-well plates (Corning #3765) and the 384-well plates were UV-sterilized prior to the assay. The inhibitors were tested in the 10-10,000 nM or 0.316-316 nM concentration range with half-log serial dilutions. BaF3_RTK cells (750 cells/30 uL/well) were added to each well using Multidrop Combi (ThermoFisher) and the treatment duration was 3 days. To counter screen against non-specific activities, 10 ng/mL IL-3 was supplemented to BaF3_HER2WT cells during the compound treatment. BaF3_HER2 WT cells were no longer susceptible to HER2 inhibition in the presence of IL-3. Any remaining cell growth inhibition is likely due to non-target related activities. Equal volume of CellTiterGlo 2.0 (Promega) was added to each well at the end of the 3-day treatment and ClarioStar (BMG) was used to read the luminescent signal. The % cell growth inhibition (% CGI) was calculated using the following formula % CGI=100−100*$luminescence_{sample}$/$luminescence_{control}$. The half maximal inhibitory concentration ($IC_{50}$) was determined by nonlinear curve fitting (four parameters, variable slope). Table 3 provides cell growth inhibition activity of selected examples against BaF3_HER2 WT, BaF3_HER2 YVMA and BaF3 EGFR WT cells of various compounds in this disclosure. The following Tables 2 and 3 provide data indicating biochemical in Table 2 and and cell inhibitory activity in Table 3 for exemplary compounds as described in Table 1. In Tables 2 and 3 below, activity is provided as follows:

TABLE 2

Biochemical activity of selected examples against Her2 WT, Her2 YVMA and EGFR WT kinases in HotSpot assay in nM

| EXAMPLE # | HER2-YVMA $IC_{50}$ (nM) | HER2 WT $IC_{50}$ (nM) | EGFR WT $IC_{50}$ (nM) |
|---|---|---|---|
| 1 | ++++ | ++++ | ++++ |
| 2 | ++++ | ++++ | ++++ |
| 4 | ++++ | ++++ | + |
| 5 | +++ | ++++ | + |
| 6 | ++++ | ++++ | ++++ |
| 7 | ++++ | ++++ | ++++ |
| 8 | ++++ | ++++ | ++++ |
| 10 | ++++ | ++++ | ++++ |
| 11 | ++++ | ++++ | ++ |
| 12 | ++++ | ++++ | ++++ |
| 13 | ++++ | ++++ | + |
| 14 | ++++ | ++++ | +++ |
| 16 | ++++ | ++++ | + |
| 18 | ++++ | ++++ | + |
| 19 | +++ | ++++ | + |
| 21 | ++++ | ++++ | +++ |
| 22 | ++++ | ++++ | ++ |
| 23 | ++++ | ++++ | ++ |
| 86 | + | + | + |
| 87 | ++++ | ++++ | +++ |
| 88 | ++ | +++ | + |
| 90 | + | + | + |
| 91 | ++++ | ++++ | ++ |
| 93 | ++++ | ++++ | +++ |
| 94 | ++++ | ++++ | ++++ |
| 95 | ++++ | ++++ | +++ |
| 96 | ++++ | ++++ | ++ |
| 97 | ++++ | ++++ | ++++ |
| 98 | ++++ | ++++ | ++++ |
| 99 | ++++ | ++++ | ++++ |
| 100 | ++++ | ++++ | + |
| 101 | ++++ | ++++ | ++++ |
| 102 | ++++ | ++++ | + |

TABLE 2-continued

Biochemical activity of selected examples against Her2 WT, Her2 YVMA and EGFR WT kinases in HotSpot assay in nM.

| EXAMPLE # | HER2-YVMA IC$_{50}$ (nM) | HER2 WT IC$_{50}$ (nM) | EGFR WT IC$_{50}$ (nM) |
|---|---|---|---|
| 103 | +++ | ++++ | + |
| 105 | ++++ | ++++ | ++++ |
| 106 | ++++ | ++++ | ++++ |
| 107 | ++++ | ++++ | ++ |
| 108 | ++++ | ++++ | + |
| 109 | ++++ | ++++ | ++++ |
| 110 | ++++ | ++++ | +++ |
| 111 | ++++ | ++++ | ++++ |
| 112 | ++++ | ++++ | ++++ |
| 113 | ++++ | ++++ | ++++ |
| 155 | ++++ | ++++ | + |
| 156 | ++++ | ++++ | ++ |
| 178 | ++++ | ++++ | ++ |

++++ = IC$_{50}$ < 200 nM;
+++ = 200 nM < IC$_{50}$ < 500 nM;
++ = 500 nM < IC50 < 1500 nM;
+ = 1500 nM < IC50 < 5000 nM;
X = IC50 > 5000 nM

TABLE 3

Cell growth inhibition activity of selected examples against BaF3_HER2WT, BaF3_HER2YVMA and BaF3_EGFRWT cells in nM.

| EXAMPLE # | HER2-YVMA | HER2 WT | EGFR WT |
|---|---|---|---|
| 1 | ++++ | ++++ | + |
| 2 | ++++ | ++++ | + |
| 3 | ++++ | ++++ | ++ |
| 4 | ++++ | ++++ | + |
| 5 | +++ | ++++ | + |
| 6 | ++++ | ++++ | ++ |
| 7 | ++++ | ++++ | +++ |
| 8 | ++++ | ++++ | ++ |
| 9 | ++++ | ++++ | +++ |
| 10 | ++ | +++ | + |
| 11 | ++++ | ++++ | + |
| 12 | ++++ | ++++ | + |
| 13 | +++ | ++++ | + |
| 14 | ++++ | ++++ | + |
| 15 | X | + | + |
| 16 | ++ | +++ | + |
| 17 | ++++ | ++++ | + |
| 18 | ++ | +++ | + |
| 19 | ++ | +++ | + |
| 20 | + | + | + |
| 21 | ++++ | ++++ | + |
| 22 | ++++ | ++++ | + |
| 23 | + | ++ | + |
| 24 | ++ | ++++ | + |
| 25 | ++++ | ++++ | + |
| 26 | + | +++ | + |
| 27 | + | ++ | + |
| 28 | ++ | ++++ | + |
| 29 | + | ++++ | + |
| 30 | ++++ | ++++ | + |
| 32 | ++++ | ++++ | +++ |
| 33 | +++ | ++++ | + |
| 35 | ++++ | ++++ | + |
| 36 | + | + | + |
| 37 | ++++ | ++++ | + |
| 38 | ++++ | ++++ | + |
| 39 | ++ | ++++ | + |
| 39 | ++++ | ++++ | + |
| 40 | +++ | +++ | + |
| 41 | ++++ | ++++ | + |
| 42 | ++++ | ++++ | + |
| 43 | +++ | ++++ | + |
| 44 | ++++ | ++++ | + |
| 45 | ++++ | ++++ | + |
| 46 | ++++ | ++++ | +++ |
| 47 | ++++ | ++++ | + |
| 48 | + | +++ | + |
| 49 | ++++ | ++++ | + |
| 50 | ++ | +++ | + |
| 51 | ++++ | ++++ | + |
| 52 | ++ | +++ | + |
| 53 | ++++ | ++++ | + |
| 54 | + | ++ | + |
| 55 | ++ | ++++ | + |
| 56 | ++++ | ++++ | + |
| 57 | ++++ | ++++ | + |
| 58 | ++ | ++++ | + |
| 59 | +++ | ++++ | + |
| 62 | ++++ | ++++ | + |
| 63 | ++ | ++ | + |
| 64 | ++++ | ++++ | +++ |
| 65 | ++++ | ++++ | + |
| 66 | ++++ | ++++ | + |
| 67 | ++++ | ++++ | ++ |
| 68 | ++++ | ++++ | + |
| 69 | +++ | ++++ | + |
| 70 | ++++ | ++++ | + |
| 71 | +++ | ++++ | + |
| 72 | ++++ | ++++ | + |
| 73 | ++ | ++++ | + |
| 74 | ++ | ++++ | + |
| 75 | ++++ | ++++ | ++ |
| 76 | ++ | ++++ | + |
| 77 | + | +++ | + |
| 78 | +++ | ++++ | + |
| 79 | +++ | ++++ | + |
| 80 | + | ++++ | + |
| 81 | + | +++ | + |
| 84 | +++ | ++++ | + |
| 85 | ++++ | ++++ | + |
| 86 | X | + | + |
| 87 | + | + | + |
| 88 | + | ++ | + |
| 89 | + | + | + |
| 90 | + | + | + |
| 91 | ++ | ++++ | + |
| 92 | ++++ | ++++ | + |
| 93 | ++++ | ++++ | + |
| 94 | ++++ | ++++ | + |
| 95 | ++ | +++ | + |
| 96 | ++ | ++++ | + |
| 97 | ++++ | ++++ | + |
| 98 | +++ | ++++ | + |
| 101 | ++++ | ++++ | + |
| 102 | + | ++ | + |
| 103 | + | + | + |
| 104 | + | ++ | + |
| 105 | ++++ | ++++ | + |
| 106 | ++++ | ++++ | + |
| 113 | ++++ | ++++ | ++ |
| 114 | ++++ | ++++ | + |
| 115 | ++++ | ++++ | + |
| 117 | ++++ | ++++ | + |
| 118 | ++++ | ++++ | + |
| 119 | ++++ | ++++ | + |
| 120 | ++++ | ++++ | + |
| 121 | ++++ | ++++ | ++ |
| 128 | ++++ | ++++ | + |
| 129 | ++++ | ++++ | + |
| 130 | ++++ | ++++ | + |
| 131 | ++++ | ++++ | + |
| 132 | ++++ | ++++ | + |
| 133 | ++++ | ++++ | + |
| 134 | + | +++ | + |
| 141 | ++ | +++ | + |
| 142 | + | + | + |
| 150 | + | ++ | + |

TABLE 3-continued

Cell growth inhibition activity of selected examples against BaF3_HER2WT, BaF3_HER2YVMA and BaF3_EGFRWT cells in nM.

| EXAMPLE # | HER2-YVMA | HER2 WT | EGFR WT |
|---|---|---|---|
| 151 | ++++ | ++++ | + |
| 152 | ++++ | ++++ | + |
| 153 | + | + | + |
| 154 | ++++ | ++++ | + |
| 155 | +++ | ++++ | + |
| 156 | + | +++ | + |
| 157 | ++++ | ++++ | + |
| 158 | ++++ | ++++ | ++ |
| 159 | ++++ | ++++ | + |
| 160 | ++++ | ++++ | + |
| 161 | ++++ | ++++ | + |
| 162 | ++ | +++ | + |
| 163 | ++++ | ++++ | + |
| 164 | ++++ | ++++ | + |
| 165 | ++++ | ++++ | + |
| 166 | ++++ | ++++ | + |
| 167 | ++++ | ++++ | + |
| 168 | ++++ | ++++ | + |
| 169 | ++++ | ++++ | + |
| 170 | ++++ | ++++ | + |
| 175 | + | + | + |
| 176 | ++++ | ++++ | + |
| 177 | ++++ | ++++ | + |
| 178 | + | +++ | X |
| 179 | + | +++ | X |
| 181 | X | + | X |

++++ = IC$_{50}$ < 200 nM;
+++ = 200 nM < IC50 < 500 nM;
++ = 500 nM < IC50 < 1500 nM;
+ = 1500 nM < IC50 < 5000 nM;
X = IC50 > 5000 nM

The compounds of this disclosure are highly selective inhibitors of HER2 wild-type and HER2 mutants and can thus be effective agents for treating HER2 wild-type and/or HER mutant-driven cancers such as the cancers described within this disclosure by way of example. Efficacious exposure and tumor distribution for the compounds of this disclosure can be measured using certain models such as H1781/HER2-VC (e.g., H1781 human lung cancer xenografts in mice) and Baf3/HER2-YVMA xenograft models.

In certain embodiments of this disclosure, at least one of the compounds in Table 1 has a tumor-plasma ratio in a HER2 wild-type and/or HER mutant-driven cancer of greater than 10 over a period of about 12 hours.

In other embodiments of this disclosure, at least one of the compounds in Table 1 has a tumor-plasma ratio in a HER2 wild-type and/or HER mutant-driven cancer of greater than 20 over a period of about 12 hours.

In other embodiments of this disclosure, at least one of the compounds in Table 1 has a tumor-plasma ratio in a HER2 wild-type and/or HER mutant-driven cancer of greater than 30 over a period of about 12 hours.

In other embodiments of this disclosure, at least one of the compounds in Table 1 has a tumor-plasma ratio in a HER2 wild-type and/or HER mutant-driven cancer of greater than 40 over a period of about 12 hours.

In other embodiments of this disclosure, at least one of the compounds in Table 1 has a tumor-plasma ratio in a HER2 wild-type and/or HER mutant-driven cancer of greater than 50 over a period of about 12 hours.

In other embodiments of this disclosure, at least one of the compounds in Table 1 has a tumor-plasma ratio in a HER2 wild-type and/or HER mutant-driven cancer of greater than 60 over a period of about 12 hours.

In other embodiments of this disclosure, at least one of the compounds in Table 1 has a tumor-plasma ratio in a HER2 wild-type and/or HER mutant-driven cancer of greater than 1 over a period of about 4 hours.

In other embodiments of this disclosure, at least one of the compounds in Table 1 has a tumor-plasma ratio in a HER2 wild-type and/or HER mutant-driven cancer of greater than 2 over a period of about 4 hours.

In other embodiments of this disclosure, at least one of the compounds in Table 1 has a tumor-plasma ratio in a HER2 wild-type and/or HER mutant-driven cancer of greater than 2.5 over a period of about 4 hours.

All patents and other references cited herein are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of the embodiments described herein are exemplary and are not intended as limitations on the scope of the disclosure. Changes therein and other uses will occur to those skilled in the art, which are encompassed within the spirit of the disclosure, are defined by the scope of the claims.

It will be readily apparent to one skilled in the art that varying substitutions and modifications may be made to the present disclosure described herein without departing from the scope and spirit of the disclosure. For example, variations can be made to provide additional compounds of the compounds of this disclosure and/or various methods of administration can be used. Thus, such additional embodiments are within the scope of the present disclosure and the following claims.

The present disclosure illustratively described herein suitably may be practiced in the absence of any element or elements, limitation or limitations which is not specifically described herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically described by the embodiments and optional features, modification and variation of the concepts herein described may be resorted to by those skilled in the art, and that such modifications and variations are considered to be within the scope of this disclosure as defined by the appended claims.

In addition, where features or aspects of the disclosure are described in terms grouping of alternatives, those skilled in the art will recognize that the disclosure is also thereby described in terms of any individual member or subgroup of members of the groups described herein.

Also, unless indicated to the contrary, where various numerical values are provided for embodiments, additional embodiments are described by taking any 2 different values as the endpoints of a range. Such ranges are also within the scope of the present disclosure. Thus, additional embodiments are within the scope of the disclosure and within the following claims.

What is claimed is:
1. A compound of Formula (I):

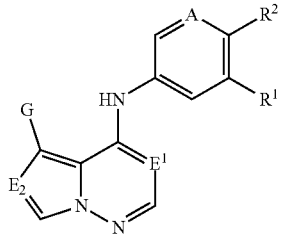

or a pharmaceutically acceptable salt, a tautomer, a stereoisomer, or a deuterated analog thereof, wherein:
A is N or CH;
$E^1$ is N or C(CN);
$E^2$ is C($R^4$) or N;
$R^1$ is alkyl, haloalkyl or halogen;
$R^2$ is —O-alkyl, —O-aryl, —O-heteroaryl, —O-cycloalkyl, —O-heterocycloalkyl, —O— heteroaryl-alkylene-aryl, —NH-alkyl, —NH-aryl, or —NH-heteroaryl, wherein each of the alkyl, aryl, heteroaryl, cycloalkyl or heterocycloalkyl moieties are optionally substituted with 1-4 groups;
G is -$L^1$-$R^3$ or —W—X—Y;
$L^1$ is a bond, —C(O)—, —S(O)$_2$—, —N($R^c$)—, alkylene, aryl, heteroaryl, heterocycloalkyl, or cycloalkyl, wherein the alkylene, aryl, heteroaryl, heterocycloalkyl, or cycloalkyl are each optionally substituted with 1-4 $J^2$ groups, provided that when $L^1$ is CH$_2$, $L^1$ is not attached to carbon or nitrogen of a saturated ring;
$R^3$ is a 4-9 membered heterocyclic ring containing at least one nitrogen ring atom, wherein $R^3$ is optionally substituted with 1-4 $J^3$ groups, and wherein one nitrogen atom of $R^3$ is substituted with -$L^2$-R; or $R^3$ is a 7-11 membered spirocyclic group containing at least one nitrogen ring atom, wherein the 7-11 membered spirocyclic group containing at least one nitrogen ring atom is optionally substituted with 1-4 $J^3$ groups, and wherein one nitrogen atom of the 7-11 membered spirocyclic group is substituted with -$L^2$-R;
W is a bond, —C(O)— or —S(O)$_2$—;
X is aryl, heteroaryl, heterocycloalkyl, or cycloalkyl, each of which is optionally substituted with 1-4 $J^2$ groups;
Y is —C$_0$-C$_4$alkylene-N($R^d$)-$L^2$-R, —C(O)-4-7 membered heterocycloalkyl containing at least one nitrogen atom and substituted with 1-2 oxo groups, -4-7 membered heterocycloalkyl-$L^2$R, —C$_0$-C$_4$alkylene-1-yl-1H-pyrrole-2,5-dione, —C$_0$-C$_4$alkylene-C(H)═C(O)—NH$_2$, —C$_0$-C$_4$alkylene-C(H)═C(H)—C(O)—O-alkyl, —C$_0$-C$_4$alkylene-ethynylene-C(O)—O-alkyl, —C$_0$-C$_4$alkylene-C(H)═C(H)—CN, —C$_0$-C$_4$alkylene-N═C═S, —C$_0$-C$_4$-etheyny, —C$_0$-C$_4$alkylene-ethynyl, —C$_0$-C$_4$alkylene-CN, —C$_0$-C$_4$alkylene-C(H)═N—N(H)Boc, —C$_0$-C$_4$alkylene-C(O)—CH$_2$—Br, —C$_0$-C$_4$alkylene-CH$_2$—Cl, —C$_0$-C$_4$alkylene-oxiranyl, —C$_0$-C$_4$alkylene-SH, —C$_0$-C$_4$alkylene-F, and —C$_0$-C$_4$alkylene-C(H)═O, wherein the C$_0$-C$_4$alkylene moiety is optionally substituted with 1-4 groups independently selected from halogen, cycloalkyl, alkoxy alkoxyalkyl, or hydroxy;
$R^4$ is H, halo, alkyl, or —O-alkyl;
$L^2$ is —SO$_2$— or —C(O)—;
R is ethenyl optionally substituted with 1-3 Q groups, ethynyl optionally substituted with Q, C$_1$-C$_4$ alkylene-NR$^a$R$^b$, —CH$_2$—CN, or haloalkyl wherein one halogen of haloalkyl is on the carbon atom adjacent to $L^2$,
each Q is independently selected from the group consisting of halogen, haloalkyl, alkyl, alkene, alkyne, —C$_1$-C$_6$alkylene-NR$^a$R$^b$, —C$_1$-C$_6$alkylene-OR$^c$, cyano, hydroxyalkyl, —C$_0$-C$_6$alkylene-C(O)OH, —C$_1$-C$_6$alkylene-C(O)O-alkyl, alkoxyalkyl, —C$_0$-C$_4$alkylene-cycloalkyl optionally substituted with 1-3 $J^4$ groups, —C$_0$-C$_4$alkylene-cycloalkenyl optionally substituted with 1-3 $J^4$ groups, —C$_0$-C$_4$alkylene-7-11 membered spirocyclic cycloalkyl, optionally substituted with 1-3 $J^4$ groups, —C$_0$-C$_4$alkylene-7-11 membered spirocyclic heterocycloalkyl optionally substituted with 1-3 $J^4$ groups, —C$_0$-C$_4$alkylene-heterocycloalkyl optionally substituted with 1-3 $J^4$ groups, and —C$_0$-C$_4$alkylene-heterocycloalkenyl optionally substituted with 1-3 $J^4$ groups;
or -$L^2$-R is —C═N—OH;
each J is independently selected from the group consisting of halogen, alkyl, haloalkyl, hydroxy, hydroxyalkyl, —C$_0$-C$_4$alkylene-N(H)R$^c$, alkoxy, and alkoxyalkyl;
each $J^2$ is independently selected from the group consisting of halogen, alkyl, haloalkyl, hydroxy, hydroxyalkyl, alkoxy, and alkoxyalkyl;
each $J^3$ is attached to a carbon atom and is independently selected from the group consisting of halogen, haloalkyl, CN, alkyl, hydroxy, hydroxyalkyl, alkoxy, and alkoxyalkyl, or two of the optional 1-4 $J^3$ groups form an oxo group or a 3-6 membered spiro group, or two of the optional 1-4 $J^3$ groups are on different ring carbon and join to form a 1-3 carbon bridge;
each $J^4$ is independently selected from the group consisting of halogen, alkyl, haloalkyl, hydroxy, hydroxyalkyl, alkoxy, alkoxyalkyl, oxo, and —C$_0$-C$_4$alkylene-NR$^a$R$^b$, provided that $J^4$ groups can only include up to two oxo groups and up to one —C$_0$-C$_4$alkylene-NR$^a$R$^b$ group;
$R^a$ and $R^b$ each are independently selected from the group consisting of H, alkyl, alkenyl, alkynyl, haloalkyl, hydroxyalkyl, alkoxyalkyl, and —C$_0$-C$_3$alkylene-alkynyl optionally substituted with alkyl, alkenyl, alkynyl, haloalkyl, hydroxyalkyl, or alkoxyalkyl; and
$R^c$ is selected from the group consisting of H, alkyl, haloalkyl, hydroxyalkyl, alkoxyalkyl, cycloalkyl, heterocycloalkyl, aryl, and heteroaryl, wherein the cycloalkyl, heterocycloalkyl, aryl, and heteroaryl groups are each optionally substituted with 1-3 groups selected from the group consisting of halogen, alkyl, alkoxy and alkoxyalkyl; and
$R^d$ is selected from the group consisting of H, alkyl, and haloalkyl.
2. The compound according to claim 1, wherein:
$R^1$ is C$_1$-C$_4$alkyl, C$_1$-C$_4$haloalkyl or halogen;
$R^2$ is —O-(5-10 membered) aryl, —O-(5-10 membered) heteroaryl, —O-(4-7 membered) cycloalkyl, —O-(4-7 membered) heterocycloalkyl, —O-(5-10 membered) heteroaryl-C$_1$-C$_4$alkylene-phenyl, —NH-(5-10 membered) aryl, or —NH-(5-10 membered) heteroaryl, wherein each of the aryl, heteroaryl, cycloalkyl and heterocycloalkyl moieties are optionally substituted with 1-3 $J^1$ groups;
G is -$L^1$-$R^3$ or —W—X—Y;
$L^1$ is a bond, —C(O)—, —S(O)$_2$, —N(H)—, —N(C$_1$-C$_6$alkyl)-, C$_1$-C$_3$alkylene, 5-10 membered aryl, 5-10 membered heteroaryl, 4-7 membered heterocycloalkyl, or 4-7 membered cycloalkyl, wherein $C_1$-$C_3$alkylene, 5-10 membered aryl, 5-10 membered heteroaryl, 5-7 membered heterocycloalkyl, and 5-7 membered cycloalkyl are each optionally substituted with 1-3 $J^2$ groups, provided that when $L^1$ is $CH_2$, $L^1$ is not attached to carbon or nitrogen of a saturated ring;

$R^3$ is a 4-7 membered heterocyclic ring containing at least one nitrogen ring atom, wherein the 4-7 membered heterocyclic ring containing at least one nitrogen ring atom is optionally substituted with 1-4 $J^3$ groups, and wherein one nitrogen atom of the 4-7 membered heterocyclic ring is substituted with -$L^2$-R;

or $R^3$ is a 7-11 membered spirocyclic group containing at least one nitrogen ring atom, wherein the 7-11 membered spirocyclic group is optionally substituted with 1-4 $J^3$ groups, and wherein one nitrogen atom of $R^3$ is substituted with -$L^2$-R;

W is 9a bond, —C(O)— or —S(O)$_2$—;

X is 5-10 membered aryl, 5-10 membered heteroaryl, 5-7 membered heterocycloalkyl, or 5-7 membered cycloalkyl, wherein the -10 membered aryl, 5-10 membered heteroaryl, 5-7 membered heterocycloalkyl, and 5-7 membered cycloalkyl are optionally substituted with 1-3 $J^2$ groups;

Y is —$C_0$-$C_4$alkylene-N($R^d$)-$L^2$-R, —C(O)-4-6 membered heterocycloalkyl containing one nitrogen atom and substituted with 1-2 oxo groups, -4-7 membered heterocycloalkyl-$L^2$R, —$C_0$-$C_4$alkylene-1-yl-1H-pyrrole-2,5-dione, —$C_0$-$C_4$alkylene-C(H)=C(O)—NH$_2$, —$C_0$-$C_4$alkylene-C(H)=C(H)—C(O)—O-alkyl, —$C_0$-$C_4$alkylene-ethynylene-C(O)—O-alkyl, —$C_0$-$C_4$alkylene-C(H)=C(H)—CN, —$C_0$-$C_4$alkylene-N=C=S, —$C_0$-$C_4$-etheyny, —$C_0$-$C_4$alkylene-ethynyl, —$C_0$-$C_4$alkylene-CN, —$C_0$-$C_4$alkylene-C(H)=N—N(H)Boc, —$C_0$-$C_4$alkylene-C(O)—CH$_2$—Br, —$C_0$-$C_4$alkylene-CH$_2$—Cl, —$C_0$-$C_4$alkylene-oxiranyl, —$C_0$-$C_4$alkylene-SH, —$C_0$-$C_4$alkylene-F, and —$C_0$-$C_4$alkylene-C(H)=O, wherein the —$C_0$-$C_4$alkylene moiety is optionally substituted with 1-4 groups independently selected from the group consisting of halogen, $C_3$-$C_6$cycloalkyl, $C_1$-$C_6$alkoxy-$C_1$-$C_6$alkyl-$C_1$-$C_6$alkoxy, or hydroxy;

$R^4$ is H, halo, $C_0$-$C_4$alkyl, or —O—$C_0$-$C_4$alkyl;

$L^2$ is —SO$_2$— or —C(O)—;

R is ethenyl optionally substituted with 1-3 Q groups, ethynyl optionally substituted with Q, $C_1$-$C_4$ alkylene-NR$^a$R$^b$, —CH$_2$—CN, or $C_1$-$C_6$haloalkyl, wherein one halogen of $C_1$-$C_6$haloalkyl is on the carbon atom adjacent to $L^2$;

each Q is independently selected from the group consisting of halogen, $C_1$-$C_6$haloalkyl, $C_1$-$C_6$alkyl, —$C_1$-$C_4$alkylene-NR$^a$R$^b$, cyano, $C_1$-$C_6$hydroxyalkyl, —$C_1$-$C_6$alkylene-C(O)OH, —$C_1$-$C_6$alkylene-C(O)O—$C_1$-$C_6$alkyl, —$C_1$-$C_4$alkylene-$C_1$-$C_6$alkoxy, —$C_0$-$C_4$alkylene-$C_3$-$C_7$cycloalkyl optionally substituted with 1-3 $J^4$ groups, —$C_0$-$C_4$alkylene-$C_3$-$C_7$cycloalkenyl optionally substituted with 1-3 $J^4$ groups, —$C_0$-$C_4$alkylene-7-11 membered spirocyclic heterocycloalkyl optionally substituted with 1-3 $J^4$ groups, —$C_0$-$C_4$alkylene-4-7 membered heterocycloalkyl optionally substituted with 1-3 $J^4$ groups, and —$C_0$-$C_4$alkylene-4-7 membered heterocycloalkenyl optionally substituted with 1-3 $J^4$ groups;

or -$L^2$-R is —C=N—OH;

each J is independently selected from the group consisting of halogen, $C_1$-$C_6$alkyl, $C_1$-$C_6$haloalkyl, hydroxy, $C_1$-$C_6$hydroxyalkyl, —$C_0$-$C_4$alkylene-N(H)R$^c$, $C_1$-$C_6$alkoxy, and —$C_1$-$C_6$alkyl-$C_1$-$C_6$alkoxy;

each $J^2$ is independently selected from the group consisting of halogen, $C_1$-$C_6$alkyl, $C_1$-$C_6$haloalkyl, hydroxy, $C_1$-$C_6$hydroxyalkyl, $C_1$-$C_6$alkoxy, and —$C_1$-$C_6$alkyl-$C_1$-$C_6$alkoxy;

each $J^3$ is attached to a carbon atom of $R^3$ and is independently selected from the group consisting of halogen, —$C_1$-$C_6$haloalkyl, CN, $C_1$-$C_6$alkyl, hydroxy, $C_1$-$C_6$hydroxyalkyl, $C_1$-$C_6$alkoxy, and —$C_1$-$C_6$alkyl-$C_1$-$C_6$alkoxy, or two of the optional 1-4 $J^3$ groups form an oxo group or a 3-6 membered spiro group, or two of the optional 1-4 $J^3$ groups are on different ring carbon and join to form a 1-3 carbon bridge;

each $J^4$ is independently selected from the group consisting of halogen, $C_1$-$C_6$alkyl, $C_1$-$C_6$haloalkyl, hydroxy, $C_1$-$C_6$hydroxyalkyl, $C_1$-$C_6$alkoxy, —$C_1$-$C_6$alkyl-$C_1$-$C_6$alkoxy, oxo, and —$C_0$-$C_4$alkylene-NR$^a$R$^b$, provided that $J^4$ groups can only include up to two oxo groups and up to one —$C_0$-$C_4$alkylene-NR$^a$R$^b$ group;

$R^a$ and $R^b$ each are independently selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, and $C_0$-$C_3$alkylene-$C_2$-$C_6$alkynyl optionally substituted with alkyl, $C_1$-$C_6$haloalkyl, $C_1$-$C_6$hydroxyalkyl, or —$C_1$-$C_6$alkoxy-$C_1$-$C_6$alkyl; and $R^c$ is selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, $C_3$-$C_7$cycloalkyl, 4-7 membered heterocycloalkyl, 6-10 membered aryl, and 5-10 membered heteroaryl, wherein the $C_3$-$C_7$cycloalkyl, 4-7 membered heterocycloalkyl, 6-10 membered aryl, and 5-10 membered heteroaryl groups are each optionally substituted with 1-3 groups selected from the group consisting of halogen, $C_1$-$C_6$alkyl, $C_1$-$C_6$alkoxy and $C_1$-$C_6$alkoxy-$C_1$-$C_6$alkyl; and $R^d$ is selected from the group consisting of H, $C_1$-$C_6$alkyl, and $C_1$-$C_6$haloalkyl.

3. The compound according to claim 1 having one of the following formulae:

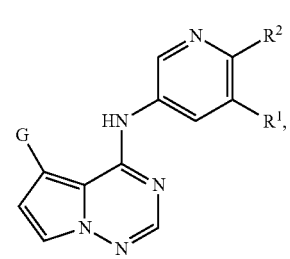

(IIa)

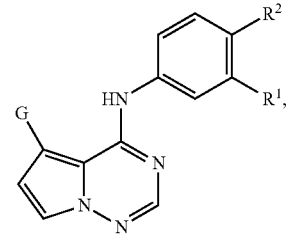

(IIb)

-continued

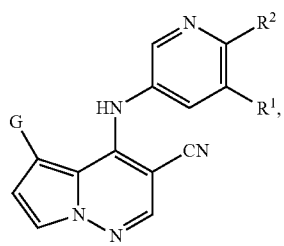
(IIc)

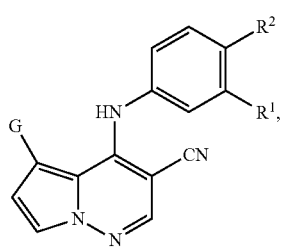
(IId)

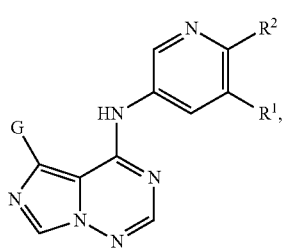
(IIe)

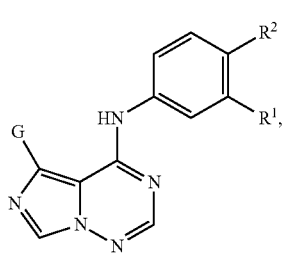
(IIf)

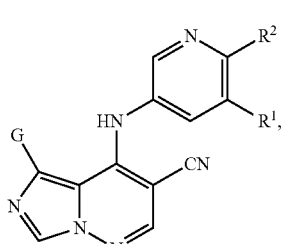
(IIg)

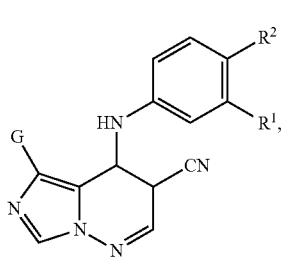
(IIh)

or a pharmaceutically acceptable salt, a tautomer, a stereoisomer, or a deuterated analog of any of the above compounds.

4. The compound according to claim 3 having Formula (IIa) or (IIb), or a pharmaceutically acceptable salt, a tautomer, a stereoisomer, or a deuterated analog of Formula (IIa) or (IIb).

5. The compound according to claim 1 having one of the following formulae:

(IIIa)

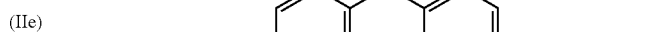
(IIIb)

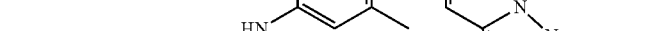
(IIIc)

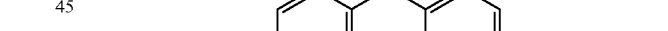
(IIId)

(IIIe)

-continued (IIIf)

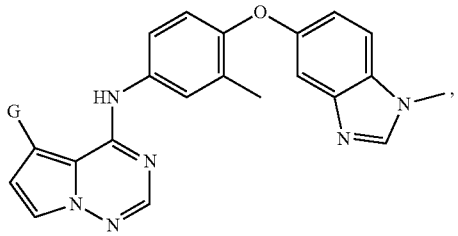

or a pharmaceutically acceptable salt, a tautomer, a stereoisomer, or a deuterated analog of any of the above compounds.

6. The compound according to claim 1, wherein G is -L$^1$-R$^3$.

7. The compound according to claim 1, wherein G is

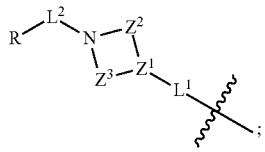

wherein:
L$^1$ is a bond, —C(O)—, —S(O)$_2$—, C$_1$-C$_3$alkylene, phenyl, 5-6 membered heteroaryl, 4-6 membered heterocycloalkyl, or 4-6 membered cycloalkyl, wherein C$_1$-C$_2$alkylene, phenyl, 5-6 membered heteroaryl, 4-6 membered heterocycloalkyl, or 4-6 membered cycloalkyl are each optionally substituted with 1-2 J$^2$ groups, provided that when L$^1$ is CH$_2$, Z$^1$ is not CH$_2$ or N;
L$^2$ is —SO$_2$— or —C(O)—;
Z$^1$ is —N(H)—, —C(R$^5$)—, or a 4-7 membered spiro group optionally containing 1-2 nitrogen atoms;
R$^5$ is H, halogen, C$_1$-C$_3$alkyl or CN;
Z$^2$ and Z$^3$ are each independently —C$_1$-C$_3$alkylene or —C$_2$-C$_3$alkenylene, wherein —C$_1$-C$_3$alkylene and —C$_2$-C$_3$alkenylene are each optionally substituted with 1-4 J$^3$ groups;
R is ethenyl optionally substituted with 1-3 Q groups, ethynyl optionally substituted with Q groups, C$_1$-C$_4$ alkylene-NR$^a$R$^b$, —CH$_2$—CN, or C$_1$-C$_4$haloalkyl, wherein one halogen of C$_1$-C$_4$haloalkyl is on the carbon atom adjacent to L$^2$;
each Q is independently selected from the group consisting of halogen, C$_1$-C$_4$haloalkyl, C$_1$-C$_4$alkyl, —C$_1$-C$_4$alkylene-NR$^a$R$^b$, —C$_1$-C$_4$alkylene-cyano, C$_1$-C$_4$hydroxyalkyl, —C$_1$-C$_4$alkylene-C(O)OH, —C$_1$-C$_4$alkylene-C(O)O—C$_1$-C$_4$alkyl, —C$_1$-C$_3$alkylene-C$_1$-C$_4$alkoxy, —C$_0$-C$_4$alkylene-C$_3$-C$_7$cycloalkyl optionally substituted with 1-3 J$^4$ groups, —C$_0$-C$_4$alkylene-C$_3$-C$_7$cycloalkenyl optionally substituted with 1-3 J$^4$ groups, —C$_0$-C$_4$alkylene-7-11 membered spirocyclic heterocycloalkyl optionally substituted with 1-3 J$^4$ groups, —C$_0$-C$_4$alkylene-4-7 membered heterocycloalkyl optionally substituted with 1-3 J$^4$ groups, and —C$_0$-C$_4$alkylene-4-7 membered heterocycloalkenyl optionally substituted with 1-3 J$^4$ groups;
each J$^2$ is independently selected from the group consisting of halogen, C$_1$-C$_4$alkyl, C$_1$-C$_4$haloalkyl, hydroxy, C$_1$-C$_4$hydroxyalkyl, C$_1$-C$_4$alkoxy, and —C$_1$-C$_4$alkyl-C$_1$-C$_4$alkoxy;
each J$^3$ is independently selected from the group consisting of halogen, —C$_1$-C$_4$haloalkyl, CN, C$_1$-C$_4$alkyl, hydroxy, C$_1$-C$_4$hydroxyalkyl, C$_1$-C$_4$alkoxy, and —C$_1$-C$_4$alkyl-C$_1$-C$_4$alkoxy, or two of the optional 1-4 J$^3$ groups form an oxo group or a 3-6 membered spiro group, or two of the optional 1-4 J$^3$ groups are on different ring carbon atoms and join to form a 1-3 carbon bridge; and
each J$^4$ is independently selected from the group consisting of halogen, C$_1$-C$_4$alkyl, C$_1$-C$_4$haloalkyl, hydroxy, C$_1$-C$_4$hydroxyalkyl, C$_1$-C$_4$alkoxy, —C$_1$-C$_4$alkyl-C$_1$-C$_4$alkoxy, oxo, and —C$_0$-C$_4$alkylene-NR$^a$R$^b$, provided that J$^4$ groups can only include up to two oxo groups and up to one —C$_0$-C$_4$alkylene-NR$^a$R$^b$ group.

8. The compound according to claim 1, wherein G is

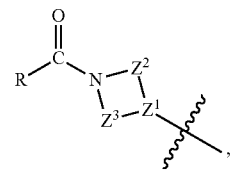

wherein:
Z$^1$ is —N(H)—, —C(R$^5$)—, or a 4-6 membered spiro group optionally containing 1-2 nitrogen atoms;
R$^5$ is H, halogen, C$_1$-C$_3$alkyl or CN;
Z$^2$ is —C$_1$-C$_3$alkylene or —C$_2$-C$_3$alkenylene, each of which is optionally substituted with 1-2 J$^3$ groups;
Z$^3$ is —C$_1$-C$_2$alkylene optionally substituted with 1-2 J$^3$ groups;
R is ethenyl optionally substituted with 1-3 Q groups, ethynyl optionally substituted with Q, C$_1$-C$_4$ alkylene-NR$^a$R$^b$, —CH$_2$—CN, or C$_1$-C$_3$haloalkyl, wherein one halogen of C$_1$-C$_3$haloalkyl is on the carbon atom adjacent to —C(O)—;
each Q is independently selected from the group consisting of halogen, C$_1$-C$_3$haloalkyl, C$_1$-C$_3$alkyl, —C$_1$-C$_3$alkylene-NR$^a$R$^b$, —C$_1$-C$_3$alkylene-cyano, C$_1$-C$_3$hydroxyalkyl, —C(O)OH, —C$_1$-C$_3$alkylene-C(O)O—C$_1$-C$_3$alkyl, —C$_0$-C$_3$alkylene-C$_1$-C$_3$alkoxy, —C$_0$-C$_3$alkylene-C$_3$-C$_6$cycloalkyl optionally substituted with 1-3 J$^4$ groups, —C$_0$-C$_3$alkylene-C$_3$-C$_6$cycloalkenyl optionally substituted with 1-3 J$^4$ groups, —C$_0$-C$_4$alkylene-7-11 membered spirocyclic heterocycloalkyl optionally substituted with 1-3 J$^4$ groups, —C$_0$-C$_3$alkylene-4-6 membered heterocycloalkyl optionally substituted with 1-3 J$^4$ groups, and —C$_0$-C$_3$alkylene-4-6 membered heterocycloalkenyl optionally substituted with 1-3 J$^4$ groups;
each J$^2$ is independently selected from the group consisting of halogen, C$_1$-C$_3$alkyl, C$_1$-C$_3$haloalkyl, hydroxy, C$_1$-C$_3$hydroxyalkyl, C$_1$-C$_3$alkoxy, and —C$_1$-C$_3$alkyl-C$_1$-C$_3$alkoxy;
each J$^3$ is independently selected from the group consisting of halogen, —C$_1$-C$_3$haloalkyl, CN, C$_1$-C$_3$alkyl, hydroxy, C$_1$-C$_3$hydroxyalkyl, C$_1$-C$_3$alkoxy, and —C$_1$-C$_3$alkyl-C$_1$-C$_3$alkoxy, or two of the optional J$^3$ groups are on different ring carbon atoms and join to form a 1-2 carbon bridge; and
each J$^4$ is independently selected from the group consisting of halogen, C$_1$-C$_3$alkyl, C$_1$-C$_3$haloalkyl, hydroxy, C$_1$-C$_3$hydroxyalkyl, C$_1$-C$_3$alkoxy, —C$_1$-C$_3$alkyl-C$_1$-C$_3$alkoxy, oxo, and —C$_0$-C$_3$alkylene-NR$^a$R$^b$, provided that J⁴ groups can only include up to two oxo groups and up to one —C₀-C₃alkylene-NRᵃRᵇ group.

9. The compound according to claim 1, wherein R³ is

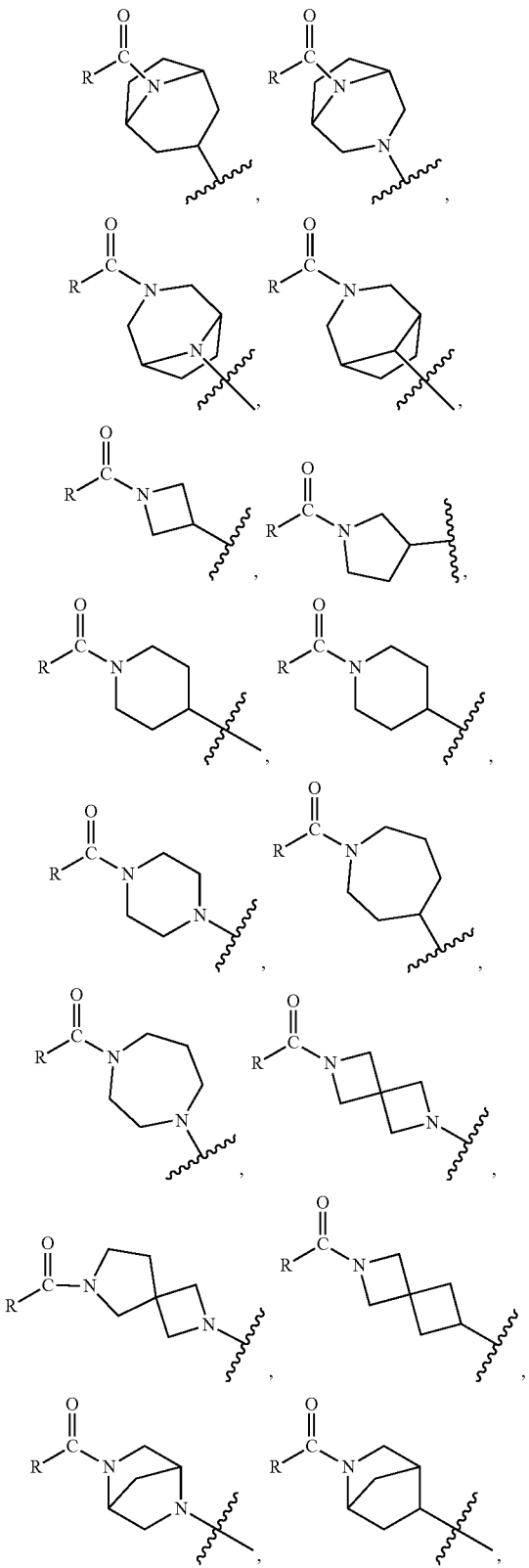

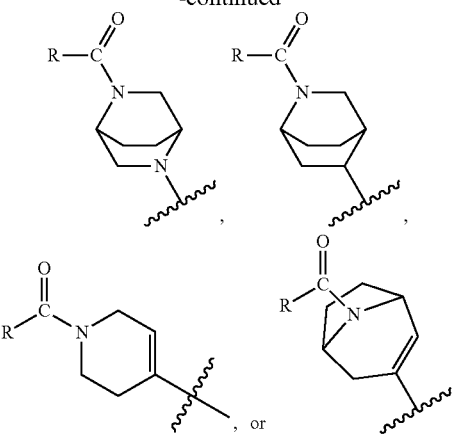

, or wherein the heterocyclic ring containing at least one nitrogen ring atom of R³ is optionally substituted with 1-3 J³ groups; and each J³ is independently selected from the group consisting of halogen, —C₁-C₃haloalkyl, CN, C₁-C₃alkyl, hydroxy, C₁-C₃hydroxyalkyl, C₁-C₃alkoxy, and —C₁-C₃alkyl-C₁-C₃alkoxy.

10. The compound according to claim 1, wherein G is —X—Y.

11. The compound according to claim 10 wherein X is a 5-10 membered heteroaryl optionally substituted with 1-3 J² groups and Y is —C₀-C₄alkylene-N(H)-L²-R.

12. The compound according to claim 1, wherein R is ethenyl optionally substituted with 1-2 groups independently selected from the group consisting of halogen, C₁-C₃haloalkyl, C₁-C₃alkyl, —C₁-C₃alkylene-NRᵃRᵇ, —C₁-C₃alkylene-cyano, C₁-C₃hydroxyalkyl, —C₁-C₃alkylene-C(O)O—C₁-C₃alkyl, —C₁-C₃alkylene-C₁-C₃alkoxy, —C₁-C₃alkylene-C₃-C₆cycloalkyl optionally substituted with 1-3 J⁴ groups, —C₁-C₃alkylene-C₃-C₆cycloalkenyl optionally substituted with 1-3 J⁴ groups, —C₁-C₃alkylene-4-6 membered heterocycloalkyl optionally substituted with 1-3 J⁴ groups, and
—C₁-C₃alkylene-4-6 membered heterocycloalkenyl optionally substituted with 1-3 J⁴ groups.

13. The compound according to claim 1, wherein R is

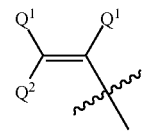

wherein:
each Q¹ is independently selected from the group consisting of H, F, and Cl; and
Q² is selected from the group consisting of H, C₁-C₆haloalkyl, C₁-C₆alkyl, —C₁-C₄alkylene-NRᵃRᵇ, —C₀-C₄alkylene-4-7 membered heterocycloalkyl optionally substituted with 1-3 J⁴ groups, and —C₀-C₄alkylene-4-7 membered heterocycloalkenyl optionally substituted with 1-3 J⁴ groups.

14. The compound according to claim 1, wherein R² is —O-heteroaryl, —O— heterocycloalkyl, —NH-heteroaryl or, —N(H)-heterocycloalkyl, wherein the heteroaryl or heterocycloalkyl moieties are optionally substituted with 1-3 J¹ groups.

15. The compound according to claim 1, wherein $R^2$ is

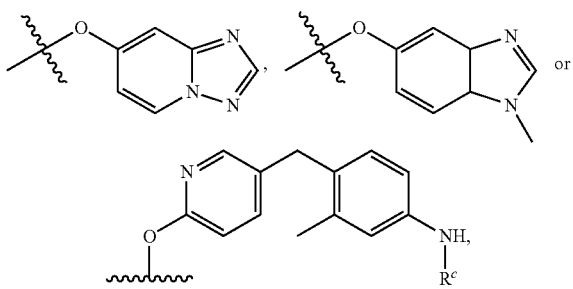

each of which is optionally substituted with 1-2 $J^1$ groups.

16. The compound according to claim 15, wherein $R^2$ is

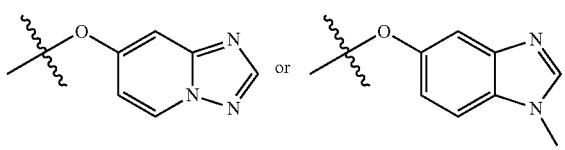 [SMILES: *Oc1ccn2ncnc2c1 ; *Oc1ccc2c(c1)ncn2C]

each of which is optionally substituted with 1-2 $J^1$ groups, wherein:

each J is independently selected from the group consisting of halogen, $C_1$-$C_3$alkyl, $C_1$-$C_3$haloalkyl, hydroxy, $C_1$-$C_3$hydroxyalkyl, —$C_0$-$C_3$alkylene-N(H)$R^c$, $C_1$-$C_6$alkoxy, and —$C_1$-$C_6$alkyl-$C_1$-$C_6$alkoxy; and $R^c$ is selected from the group consisting of H, $C_1$-$C_6$alkyl, $C_1$-$C_6$haloalkyl, $C_1$-$C_6$hydroxyalkyl, —$C_1$-$C_6$alkyl-$C_1$-$C_6$alkoxy, $C_3$-$C_7$cycloalkyl, 4-7 membered heterocycloalkyl, 6-10 membered aryl, and 5-10 membered heteroaryl, wherein the $C_3$-$C_7$cycloalkyl, 4-7 membered heterocycloalkyl, 6-10 membered aryl, and 5-10 membered heteroaryl groups are each optionally substituted with 1-3 groups selected from the group consisting of halogen, $C_1$-$C_6$alkyl, $C_1$-$C_6$alkoxy and $C_1$-$C_6$alkoxy-$C_1$-$C_6$alkyl.

17. The compound according to claim 16, wherein $R^2$ is

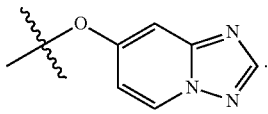 [SMILES: *Oc1ccn2ncnc2c1]

18. The compound according to claim 1 having one of the following formulae:

(IVa)

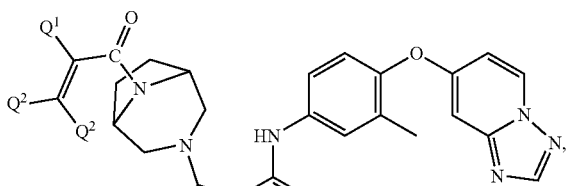

(IVb)

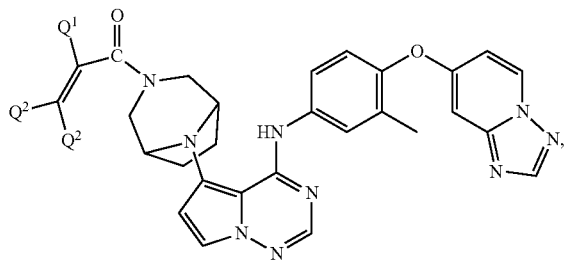

(IVc)

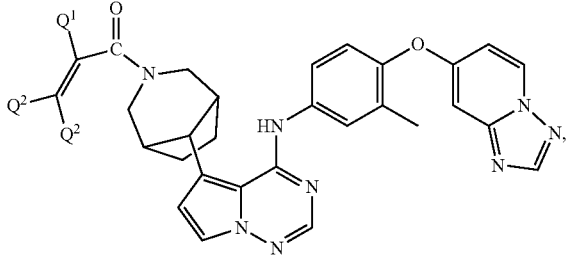

(IVd)

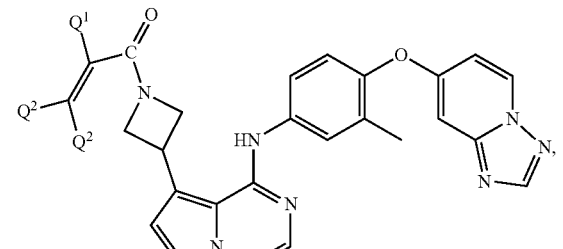

(IVe)

(IVf)

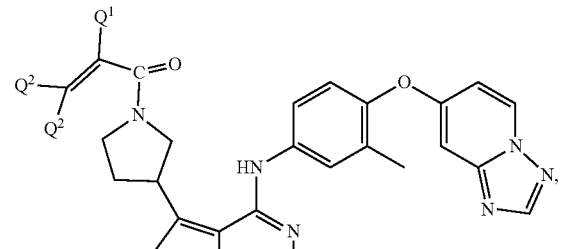

525
-continued (IVg)
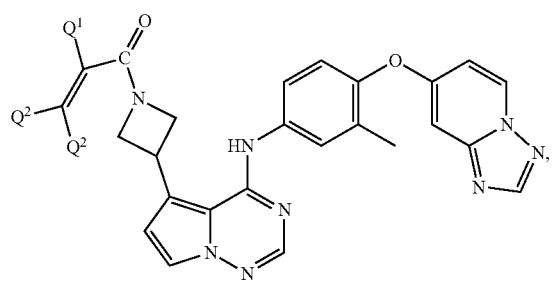

(IVh)

(IVi)

(IVj)

(IVk)

526
-continued (IVl)
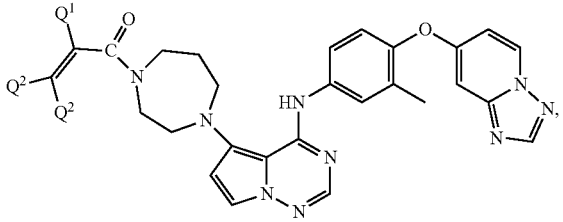

(IVm)
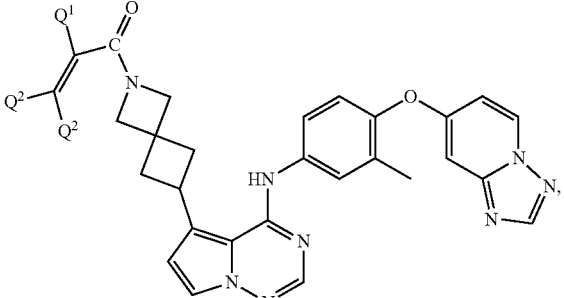

(IVn)
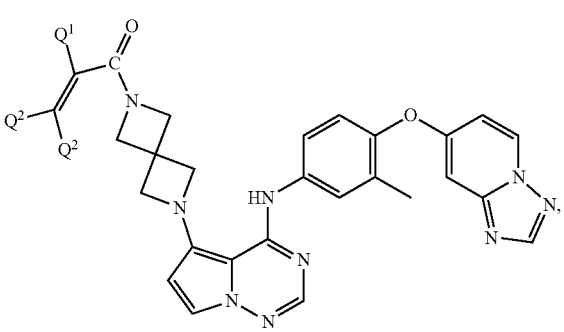

(IVo)
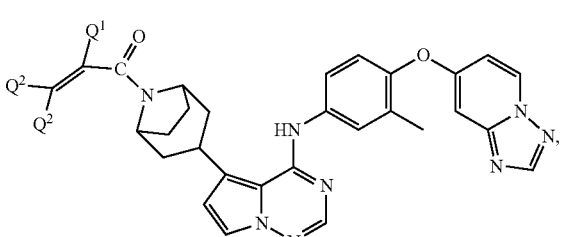

(IVp)
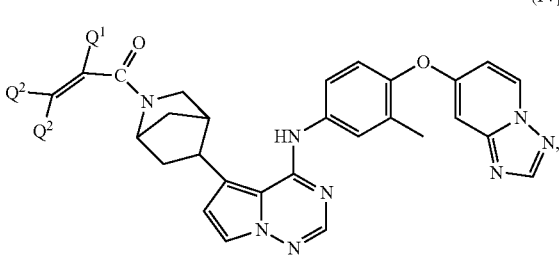

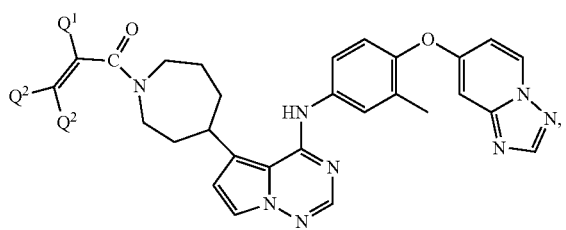

or a pharmaceutically acceptable salt, a tautomer, a stereoisomer, or a deuterated analog thereof wherein:
each $Q^1$ is independently selected from the group consisting of H, F, and Cl; and
$Q^2$ is independently selected from the group consisting of H, $C_1$-$C_6$haloalkyl, $C_1$-$C_6$alkyl, —$C_1$-$C_3$alkylene-$NR^aR^b$, —$C_0$-$C_3$alkylene-4-7 membered heterocycloalkyl optionally substituted with 1-3 $J^4$ groups, and —$C_0$-$C_3$alkylene-4-7 membered heterocycloalkenyl optionally substituted with 1-3 $J^4$ groups, or a pharmaceutically acceptable salt, a tautomer, a stereoisomer, or a deuterated analog thereof, wherein each $Q^1$ is independently selected from the group consisting of H, F, and Cl; and $Q^2$ is independently selected from the group consisting of H, $C_1$-$C_6$haloalkyl, $C_1$-$C_6$alkyl, —$C_1$-$C_3$alkylene-$NR^aR^b$, —$C_0$-$C_3$alkylene-4-7 membered heterocycloalkyl optionally substituted with 1-3 $J^4$ groups, and —$C_0$-$C_3$alkylene-4-7 membered heterocycloalkenyl optionally substituted with 1-3 $J^4$ groups.

19. The compound according to claim 1 having one of the following formulae:

(Va)

(Vb)

(Vc)

(Vd)

(Ve)

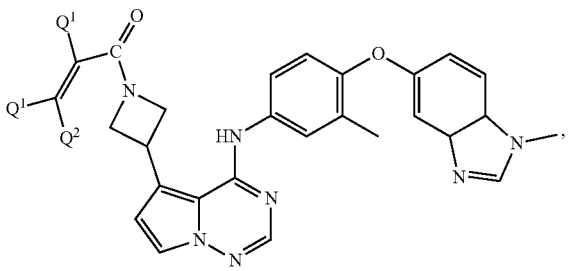

(Vf)

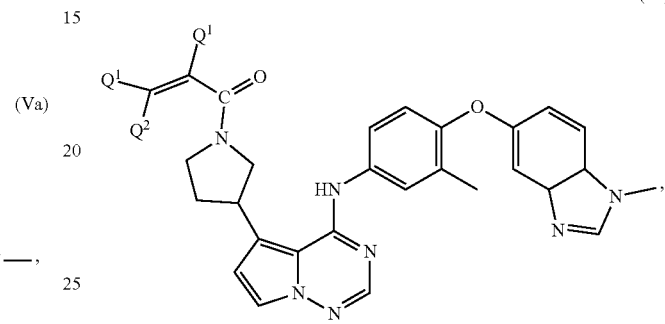

(Vg)

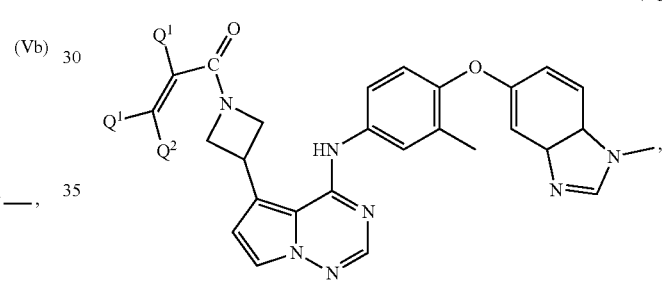

(Vh)

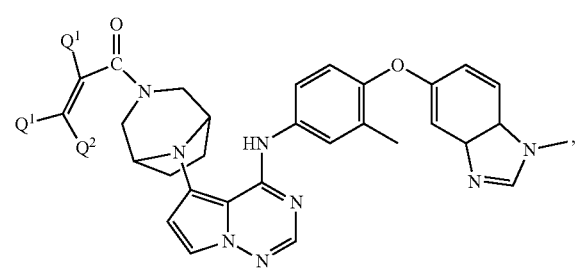
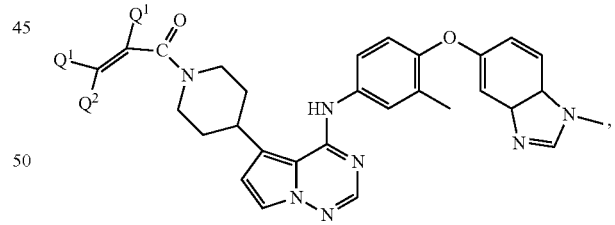
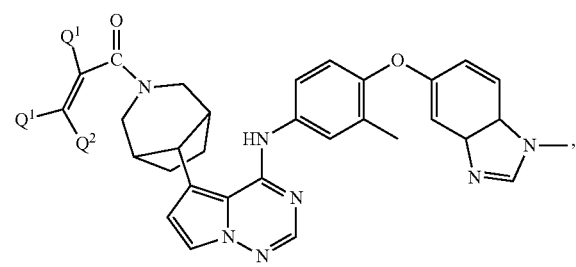
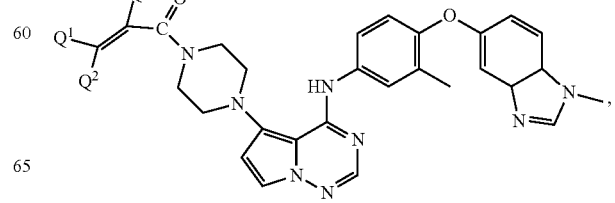

(Vi)

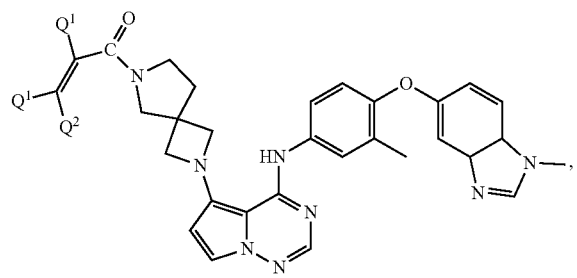
(Vj)
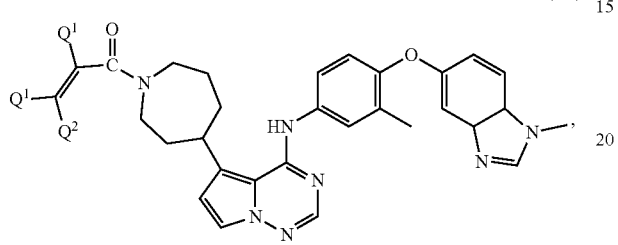
(Vk)
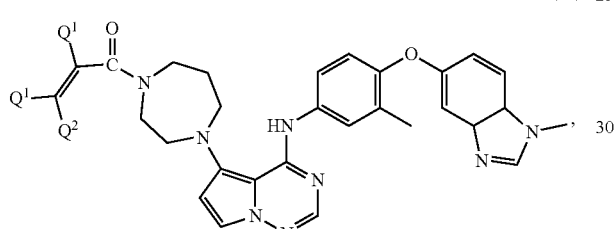
(Vl)
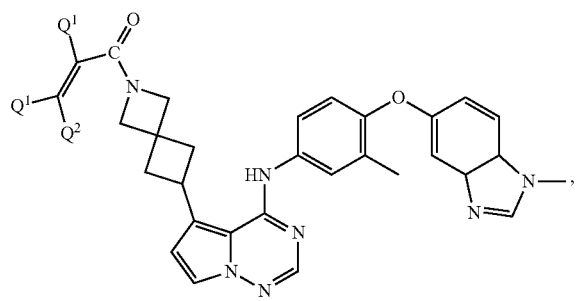
(Vm)
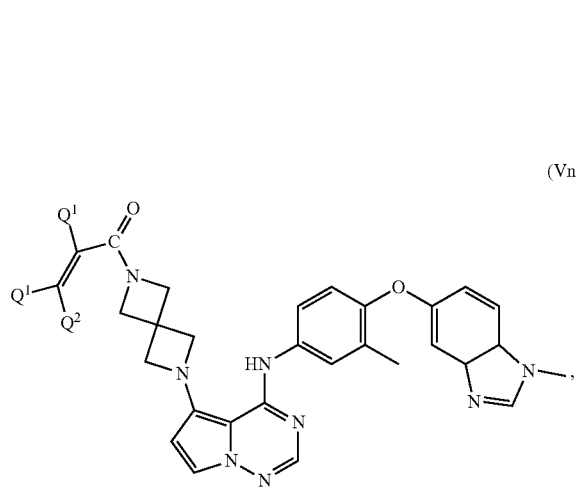
(Vn)
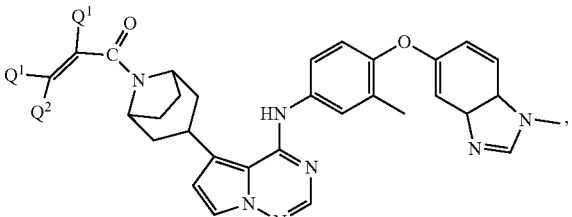
(Vo)
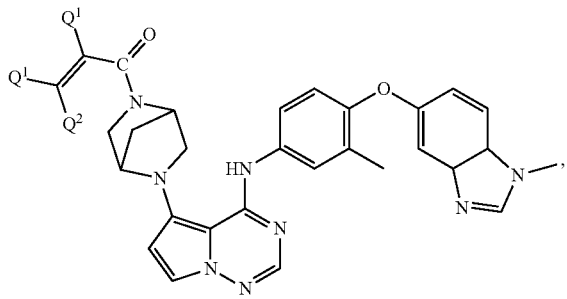
(Vp)
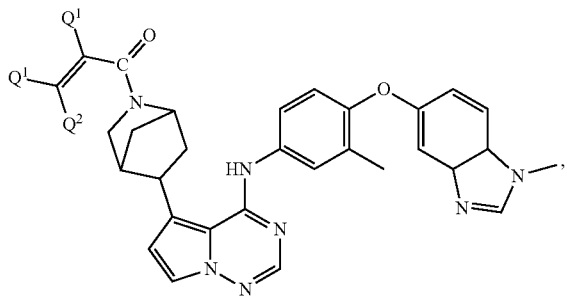
(Vq)
(Vr)
(Vs)

or a pharmaceutically acceptable salt, a tautomer, a stereoisomer, or a deuterated analog thereof, wherein:

each $Q^1$ is independently selected from the group consisting of H, F, and Cl; and $Q^2$ is selected from the group consisting of H, $C_1$-$C_6$haloalkyl, $C_1$-$C_6$alkyl, —$C_1$-$C_3$alkylene-$NR^aR^b$, —$C_0$-$C_3$alkylene-4-7 membered heterocycloalkyl optionally substituted with 1-3 $J^4$ groups, and —$C_0$-$C_3$alkylene-4-7 membered heterocycloalkenyl optionally substituted with 1-3 $J^4$ groups.

20. The compound according to claim 19, wherein at least one $Q^2$ is H, —$C_1$-$C_3$alkylene-$NR^aR^b$, or $C_0$-$C_3$alkylene-4-7 membered heterocycloalkyl optionally substituted with 1-3 $J^4$ groups.

21. The compound according to claim 1, wherein the compound is

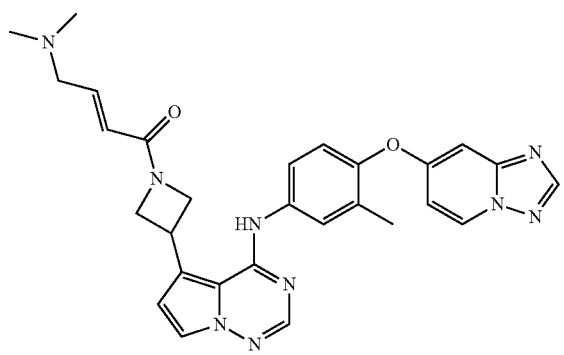 [SMILES: Cc1cc(Nc2ncnn3ccc(C4CN(C(=O)/C=C/CN(C)C)C4)c23)ccc1Oc1ccn2ncnc2c1]

or a pharmaceutically acceptable salt thereof.

22. The compound according to claim 1, wherein the compound is

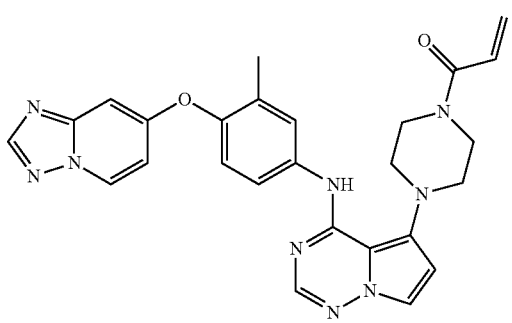 [SMILES: C=CC(=O)N1CCN(c2ccn3ncnc(Nc4ccc(Oc5ccn6ncnc6c5)c(C)c4)c23)CC1]

or a pharmaceutically acceptable salt thereof.

23. The compound according to claim 1, wherein the compound is

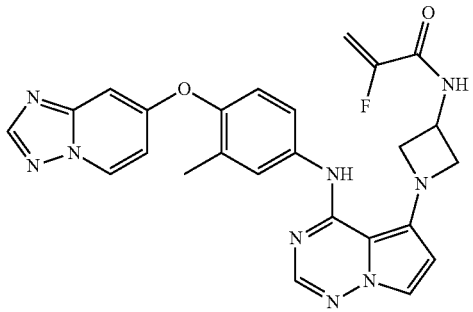 [SMILES: C=C(F)C(=O)NC1CN(c2ccn3ncnc(Nc4ccc(Oc5ccn6ncnc6c5)c(C)c4)c23)C1]

or a pharmaceutically acceptable salt thereof.

24. The compound according to claim 1, wherein the compound is

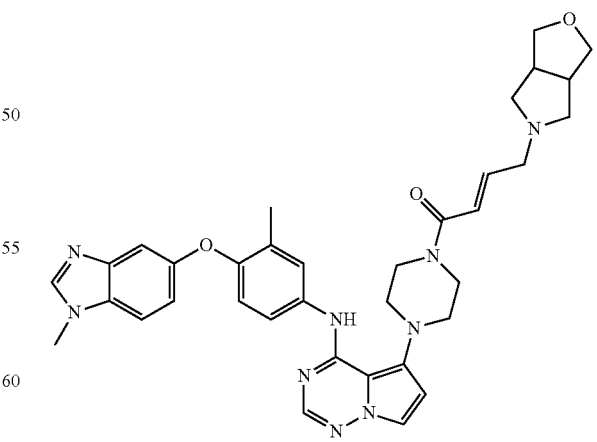

or a pharmaceutically acceptable salt thereof.

25. The compound according to claim 1, wherein the compound is or a pharmaceutically acceptable salt thereof.

26. The compound according to claim 1, wherein the compound is
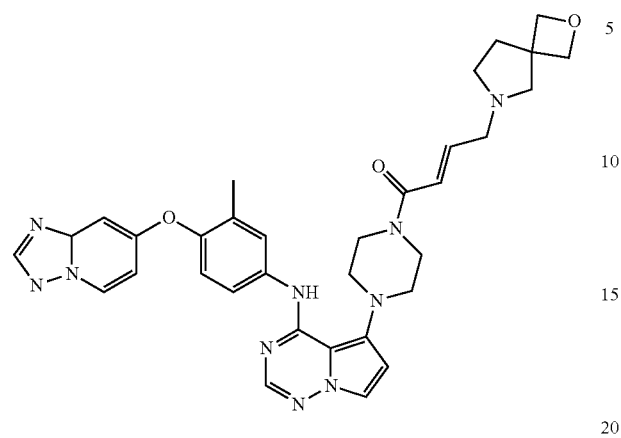
or a pharmaceutically acceptable salt thereof.
27. A pharmaceutical composition comprising the compound of claim 1, and a pharmaceutically acceptable carrier.
* * * * *

UNITED STATES PATENT AND TRADEMARK OFFICE
CERTIFICATE OF CORRECTION

Page 1 of 2

PATENT NO. : 12,145,948 B2
APPLICATION NO. : 18/526935
DATED : November 19, 2024
INVENTOR(S) : Svitlana Kulyk et al.

It is certified that error appears in the above-identified patent and that said Letters Patent is hereby corrected as shown below:

In the Claims

Column 513, Line 28, Claim 1, please replace:
"with 1-4 groups"

With:
--with 1-4 $J^1$ groups--

Column 514, Line 21, Claim 1, please replace:
"each J is independently selected from the group consisting"

With:
--each $J^1$ is independently selected from the group consisting--

Column 514, Line 32, Claim 1, please replace:
"the optional 1-4 $J^3$ groups are on different ring carbon"

With:
--the optional 1-4 $J^3$ groups are on different ring carbons--

Column 515, Line 19, Claim 2, please replace:
"W is 9a bond, -C(O)- or -S(O)$_2$-;"

With:
--W is a bond, -C(O)- or -S(O)$_2$-;--

Column 515, Line 66, Claim 2, please replace:
"each J is independently selected from the group consisting"

Signed and Sealed this
Eighth Day of April, 2025

Coke Morgan Stewart
*Acting Director of the United States Patent and Trademark Office*

CERTIFICATE OF CORRECTION (continued)
U.S. Pat. No. 12,145,948 B2

With:
--each $J^1$ is independently selected from the group consisting--

Column 516, Line 14, Claim 2, please replace:
"the optional 1-4 $J^3$ groups are on different ring carbon"

With:
--the optional 1-4 $J^3$ groups are on different ring carbons--

Column 523, Line 29, Claim 16, please replace:
"each J is independently selected from the group consisting"

With:
--each $J^1$ is independently selected from the group consisting--

Column 527, Lines 3 to 13, Claim 18, please replace:
"optionally substituted with 1-3 $J^4$ groups, or a pharmaceutically acceptable salt, a tautomer, a stereoisomer, or a deuterated analog thereof, wherein each $Q^1$ is independently selected from the group consisting of H, F, and Cl; and $Q^2$ is independently selected from the group consisting of H, $C_1$-$C_6$haloalkyl, $C_1$-$C_6$alkyl, -$C_1$-$C_3$alkylene-$NR^aR^b$, -$C_0$-$C_3$alkylene-4-7 membered heterocycloalkyl optionally substituted with 1-3 $J^4$ groups, and -$C_0$-$C_3$alkylene-4-7 membered heterocycloalkenyl optionally substituted with 1-3 $J^4$ groups."

With:
--optionally substituted with 1-3 $J^4$ groups.--